(12) United States Patent
Nonnenmacher et al.

(10) Patent No.: US 12,419,969 B2
(45) Date of Patent: Sep. 23, 2025

(54) AAV CAPSID VARIANTS AND USES THEREOF

(71) Applicant: VOYAGER THERAPEUTICS, INC., Lexington, MA (US)

(72) Inventors: Mathieu Emmanuel Nonnenmacher, Boston, MA (US); Tyler Christopher Moyer, Boston, MA (US); Jiangyu Li, Watertown, MA (US); Dan Richard Laks, Cambridge, MA (US)

(73) Assignee: VOYAGER THERAPEUTICS, INC., Lexington, MA (US)

( * ) Notice: Subject to any disclaimer, the term of this patent is extended or adjusted under 35 U.S.C. 154(b) by 0 days.

(21) Appl. No.: 19/097,114

(22) Filed: Apr. 1, 2025

(65) Prior Publication Data

US 2025/0228967 A1  Jul. 17, 2025

Related U.S. Application Data

(60) Division of application No. 18/757,141, filed on Jun. 27, 2024, now Pat. No. 12,296,025, which is a continuation of application No. 18/703,166, filed as application No. PCT/US2022/079060 on Nov. 1, 2022.

(60) Provisional application No. 63/339,711, filed on May 9, 2022, provisional application No. 63/274,806, filed on Nov. 2, 2021.

(51) Int. Cl.
| | |
|---|---|
| A61K 47/64 | (2017.01) |
| A61K 9/00 | (2006.01) |
| A61K 48/00 | (2006.01) |
| C07K 7/06 | (2006.01) |
| C07K 14/005 | (2006.01) |
| C12N 15/86 | (2006.01) |

(52) U.S. Cl.
CPC ........ *A61K 48/0041* (2013.01); *A61K 9/0019* (2013.01); *A61K 47/64* (2017.08); *A61K 48/0058* (2013.01); *A61K 48/0075* (2013.01); *C07K 7/06* (2013.01); *C07K 14/005* (2013.01); *C12N 15/86* (2013.01); *C12N 2750/14122* (2013.01); *C12N 2750/14141* (2013.01); *C12N 2830/50* (2013.01)

(58) Field of Classification Search
None
See application file for complete search history.

(56) References Cited

U.S. PATENT DOCUMENTS

| | | | |
|---|---|---|---|
| 9,409,953 B2 | 8/2016 | Asokan et al. | |
| 9,585,971 B2 | 3/2017 | Deverman et al. | |
| 9,644,205 B2 | 5/2017 | Brunicardi et al. | |
| 9,938,541 B2 | 4/2018 | Nishie et al. | |
| 10,081,659 B2 | 9/2018 | Chiorini et al. | |
| 10,265,417 B2 | 4/2019 | Wilson et al. | |
| 10,485,993 B2 | 11/2019 | Goer et al. | |
| 10,695,441 B2 | 6/2020 | Wilson et al. | |
| 10,973,928 B2 | 4/2021 | Wilson et al. | |
| 11,149,256 B2 | 10/2021 | Gradinaru et al. | |
| 11,459,558 B2 | 10/2022 | Nakai et al. | |
| 11,572,637 B2 | 2/2023 | Nakai et al. | |
| 11,821,009 B2 | 11/2023 | Crystal et al. | |
| 11,859,200 B2 | 1/2024 | Nonnenmacher et al. | |
| 11,981,967 B2 | 5/2024 | McGovern et al. | |
| 12,296,025 B2 | 5/2025 | Nonnenmacher et al. | |
| 2004/0132042 A1 | 7/2004 | Frankard et al. | |
| 2005/0148076 A1 | 7/2005 | Allen | |
| 2010/0186103 A1 | 7/2010 | Gao et al. | |
| 2013/0035472 A1 | 2/2013 | Horlick et al. | |
| 2013/0296409 A1 | 11/2013 | Miller et al. | |
| 2016/0333375 A1 | 11/2016 | Chen | |
| 2017/0166926 A1 | 6/2017 | Deverman et al. | |
| 2017/0204144 A1 | 7/2017 | Deverman et al. | |
| 2018/0230186 A1 | 8/2018 | Deverman et al. | |
| 2018/0265571 A1 | 9/2018 | Esteves et al. | |
| 2020/0165576 A1 | 5/2020 | Gradinaru et al. | |
| 2020/0237799 A1 | 7/2020 | Sah et al. | |
| 2020/0239912 A1 | 7/2020 | Sah et al. | |
| 2020/0316221 A1 | 10/2020 | Gao et al. | |
| 2021/0163985 A1 | 6/2021 | Sah et al. | |
| 2021/0207167 A1 | 7/2021 | Hou et al. | |
| 2021/0214749 A1 | 7/2021 | Hou et al. | |
| 2021/0230632 A1 | 7/2021 | Sah et al. | |
| 2021/0269825 A1 | 9/2021 | Chamberlain | |
| 2021/0277418 A1 | 9/2021 | Sah et al. | |
| 2021/0371470 A1 | 12/2021 | Murlidharan et al. | |
| 2021/0380969 A1 | 12/2021 | Nonnenmacher et al. | |
| 2021/0393713 A1 | 12/2021 | Hordeaux et al. | |
| 2022/0042044 A1 | 2/2022 | Nonnenmacher et al. | |
| 2022/0064675 A1 | 3/2022 | McCoy et al. | |
| 2022/0186256 A1 | 6/2022 | Danos et al. | |
| 2023/0119163 A1 | 4/2023 | Nakai et al. | |
| 2023/0131352 A1 | 4/2023 | Nonnenmacher et al. | |

(Continued)

FOREIGN PATENT DOCUMENTS

| | | |
|---|---|---|
| CN | 106032540 A | 10/2016 |
| CN | 106884014 A | 6/2017 |

(Continued)

OTHER PUBLICATIONS

U.S. Appl. No. 18/998,358, filed Jan. 24, 2025, Mathieu Emmanuel Nonnenmacher et al.

(Continued)

*Primary Examiner* — Robert M Kelly
(74) *Attorney, Agent, or Firm* — K&L Gates LLP

(57) ABSTRACT

The disclosure relates to compositions and methods for the preparation, use, and/or formulation of adeno-associated virus capsid protein variants.

30 Claims, No Drawings

Specification includes a Sequence Listing.

(56) References Cited

U.S. PATENT DOCUMENTS

| | | |
|---|---|---|
| 2023/0203102 A1 | 6/2023 | Nonnenmacher et al. |
| 2024/0141377 A1 | 5/2024 | Nguyen et al. |
| 2024/0200097 A1 | 6/2024 | Nonnenmacher et al. |
| 2024/0374756 A1 | 11/2024 | Nonnenmacher et al. |
| 2024/0391988 A1 | 11/2024 | Liu et al. |
| 2025/0001012 A1 | 1/2025 | Nonnenmacher et al. |
| 2025/0011372 A1 | 1/2025 | Nonnenmacher et al. |
| 2025/0034559 A1 | 1/2025 | Nonnenmacher et al. |
| 2025/0049955 A1 | 2/2025 | Nonnenmacher et al. |
| 2025/0161485 A1 | 5/2025 | Nonnenmacher et al. |

FOREIGN PATENT DOCUMENTS

| | | |
|---|---|---|
| CN | 108330147 A | 7/2018 |
| WO | 2004096993 A2 | 11/2004 |
| WO | 2005033321 A2 | 4/2005 |
| WO | 2010138263 A2 | 12/2010 |
| WO | 2011133890 A1 | 10/2011 |
| WO | 2012109570 A1 | 8/2012 |
| WO | 2012145601 A2 | 10/2012 |
| WO | 2015038958 A1 | 3/2015 |
| WO | 2015121501 A1 | 8/2015 |
| WO | 2015164757 A1 | 10/2015 |
| WO | 2016065001 A1 | 4/2016 |
| WO | 2016073693 A2 | 5/2016 |
| WO | 2016081811 A1 | 5/2016 |
| WO | 2016126857 A1 | 8/2016 |
| WO | 2016164642 A1 | 10/2016 |
| WO | 2017058892 A2 | 4/2017 |
| WO | 2017100671 A1 | 6/2017 |
| WO | 2017143100 A1 | 8/2017 |
| WO | 2018022905 A2 | 2/2018 |
| WO | 2018035213 A1 | 2/2018 |
| WO | 2018119330 A2 | 6/2018 |
| WO | 2018226785 A1 | 12/2018 |
| WO | 2019006043 A1 | 1/2019 |
| WO | 2019006418 A2 | 1/2019 |
| WO | 2019028306 A2 | 2/2019 |
| WO | 2019060454 A2 | 3/2019 |
| WO | 2019068854 A1 | 4/2019 |
| WO | 2019169132 A1 | 9/2019 |
| WO | 2019213668 A1 | 11/2019 |
| WO | 2019222329 A1 | 11/2019 |
| WO | 2019222441 A1 | 11/2019 |
| WO | 2019222444 A2 | 11/2019 |
| WO | 2020014471 A1 | 1/2020 |
| WO | 2020028751 A2 | 2/2020 |
| WO | 2020068990 A1 | 4/2020 |
| WO | 2020072683 A1 | 4/2020 |
| WO | 2020077165 A1 | 4/2020 |
| WO | 2020154324 A1 | 7/2020 |
| WO | 2020160337 A1 | 8/2020 |
| WO | 2020160508 A1 | 8/2020 |
| WO | 2020191300 A1 | 9/2020 |
| WO | 2020193799 A1 | 10/2020 |
| WO | 2020205889 A1 | 10/2020 |
| WO | 2020206189 A1 | 10/2020 |
| WO | 2020210655 A1 | 10/2020 |
| WO | 2020219933 A1 | 10/2020 |
| WO | 2020219988 A2 | 10/2020 |
| WO | 2020223280 A1 | 11/2020 |
| WO | 2021025995 A1 | 2/2021 |
| WO | 2021073568 A1 | 4/2021 |
| WO | 2021113512 A1 | 6/2021 |
| WO | 2021202651 A1 | 10/2021 |
| WO | 2021216456 A2 | 10/2021 |
| WO | 2021222831 A2 | 11/2021 |
| WO | 2021226008 A1 | 11/2021 |
| WO | 2021230987 A1 | 11/2021 |
| WO | 2021242909 A1 | 12/2021 |
| WO | 2022040527 A2 | 2/2022 |
| WO | 2022076750 A2 | 4/2022 |
| WO | 2022187548 A1 | 9/2022 |
| WO | 2022221400 A2 | 10/2022 |
| WO | 2022221404 A2 | 10/2022 |
| WO | 2022221420 A2 | 10/2022 |
| WO | 2022221421 A2 | 10/2022 |
| WO | 2022235702 A1 | 11/2022 |
| WO | 2023/004416 A1 | 1/2023 |
| WO | 2023/044306 A1 | 3/2023 |
| WO | 2023/049710 A1 | 3/2023 |
| WO | 2023044483 A2 | 3/2023 |
| WO | 2023/091934 A1 | 5/2023 |
| WO | 2023081648 A1 | 5/2023 |
| WO | 2023091948 A1 | 5/2023 |
| WO | 2023091949 A2 | 5/2023 |
| WO | 2023092002 A2 | 5/2023 |
| WO | 2023092004 A1 | 5/2023 |
| WO | 2023154693 A1 | 8/2023 |
| WO | 2023/168333 A1 | 9/2023 |
| WO | 2023/183582 A2 | 9/2023 |
| WO | 2023/183583 A2 | 9/2023 |
| WO | 2023201207 A1 | 10/2023 |
| WO | 2023/215546 A2 | 11/2023 |
| WO | 2023/225508 A2 | 11/2023 |
| WO | 2023220695 A2 | 11/2023 |
| WO | 2023/244919 A1 | 12/2023 |
| WO | 2023/244920 A2 | 12/2023 |
| WO | 2023235791 A1 | 12/2023 |
| WO | 2023240236 A1 | 12/2023 |
| WO | 2023250388 A1 | 12/2023 |
| WO | 2024006741 A1 | 1/2024 |
| WO | 2024011112 A1 | 1/2024 |
| WO | 2024030976 A2 | 2/2024 |
| WO | 2024059739 A1 | 3/2024 |
| WO | 2024/086628 A2 | 4/2024 |
| WO | 2024086747 A1 | 4/2024 |
| WO | 2024/092164 A1 | 5/2024 |
| WO | 2024100633 A1 | 5/2024 |
| WO | 2024191778 A1 | 9/2024 |
| WO | 2024226761 A2 | 10/2024 |
| WO | 2024226790 A1 | 10/2024 |
| WO | 2024228943 A1 | 11/2024 |
| WO | 2024229125 A2 | 11/2024 |
| WO | 2024229161 A1 | 11/2024 |
| WO | 2024229163 A1 | 11/2024 |
| WO | 2024229164 A2 | 11/2024 |
| WO | 2024229167 A1 | 11/2024 |
| WO | 2024229173 A2 | 11/2024 |
| WO | 2024229389 A1 | 11/2024 |
| WO | 2024229425 A1 | 11/2024 |
| WO | 2024238579 A2 | 11/2024 |
| WO | 2024238684 A1 | 11/2024 |
| WO | 2025038430 A1 | 2/2025 |
| WO | 2025038795 A1 | 2/2025 |
| WO | 2025038796 A1 | 2/2025 |
| WO | 2025038800 A1 | 2/2025 |
| WO | 2025038802 A1 | 2/2025 |
| WO | 2025038805 A1 | 2/2025 |

OTHER PUBLICATIONS

U.S. Appl. No. 18/862,369, filed Nov. 1, 2024, Dan Richard Laks et al.

Abeliovich, A. et al. "Gene Therapy for Parkinson's Disease Associated with GBA1 Mutations." Journal of Parkinson's Disease vol. 11,s2 (2021): S183-S188.

Adachi et al. "A new recombinant adeno-associated virus (AAV)-based random peptide display library system: infection-defective AAV1.9-3 as a novel detargeted platform for vector evolution," Gene Therapy and Regulation (2010) vol. 5, pp. 31-55.

Adachi et al., "Drawing a high-resolution functional map of adeno-associated virus capsid by massively parallel sequencing," Nature Communications (2014) vol. 5, article 3075, 14 pages.

Adachi, M. et al. "A segment of the Mecp2 promoter is sufficient to drive expression in neurons." Human Molecular Genetics vol. 14,23 (2005): 3709-22.

Albright et al. "Modulation of sialic acid dependence influences the central nervous system transduction profile of adeno-associated viruses," Journal of Virology, 2019, vol. 93, Issue 11, pp. 1-15.

Anonymous: "capsid-associated protein VP80 [Spodoptera littoralis nucleopolyhedrovirus]—Protein—NCBI", (Feb. 15, 2013), pp. 1-1,

(56) References Cited

OTHER PUBLICATIONS

Retrieved from the Internet: URL:https://www.ncbi.nlm.nih.gov/protein/AGE89944 [retrieved on Mar. 6, 2023].
Anonymous: "toxin-antitoxin system YwqK family antitoxin [*Campylobacter* sp. CCUG 57310]—Protein—NCBI", (Jun. 7, 2020), Retrieved from the Internet: URL:https://www.ncbi.nlm.nih.gov/protein/WP_173030534 [retrieved on Mar. 7, 2023].
Bryant et al. "Deep diversification of an AAV capsid protein by machine learning," Nature Biotechnology, 2021, vol. 39, pp. 691-696.
Büning, H. & Srivastava, A. "Capsid Modifications for Targeting and Improving the Efficacy of AAV Vectors." Molecular Therapy—Methods & Clinical Development vol. 12 (2019): 248-265.
Challis et al. "Systemic AAV vectors for widespread and targeted gene delivery in rodents," Nature Protocols (2019) vol. 14, pp. 379-414.
Chen et al. "Efficient Gene Delivery and Expression in Pancreas and Pancreatic Tumors by Capsid-Optimized AAV8 Vectors," Human Gene Therapy Methods (2017) vol. 28, No. 1, pp. 49-59.
Chen et al. "Targeting the Rodent Peripheral Nervous System Efficiently and with Greater Specificity through Intravenous Delivery of AAV Capsids Evolved by Multiplexed-CREATE," Molecular Therapy (2020) vol. 28, No. 4S1, pp. 252-253, Abstract 571.
Child, M.A. et al. "High-resolution Quantitative Analysis of Multiple AAV Capsids in Rodent and Primate Models Using Multiplexed Reporter Protein Tagging Platform." Voyager Therapeutics. ASGCT 27th Annual Meeting 2024, May 7-11, 2024, Baltimore, MD, USA.
Choi et al., "AAV Hybrid Serotypes: Improved Vectors for Gene Delivery," Current Gene Therapy (2005) vol. 5, No. 3, pp. 209-210.
Davidsson et al. "A systematic capsid evolution approach performed in vivo for the design of AAV vectors with tailored properties and tropism," PNAS, 2019, vol. 116, No. 52, pp. 27053-27062.
Deverman et al. "Cre-dependent selection yields AAV variants for widespread gene transfer to the adult brain," Nat Biotechnol. (2016) vol. 34, No. 2, pp. 204-209.
Dimattia et al., "Structural Insight into the Unique Properties of Adeno-Associated Virus Serotype 9," J Virol (2012) vol. 86, No. 12, pp. 6947-6958.
Fischell, J.M. and Fishman, P.S. "A Multifaceted Approach to Optimizing AAV Delivery to the Brain for the Treatment of Neurodegenerative Diseases." Frontiers in Neuroscience vol. 15, article 747726 (2021).
Flytzanis et al. "Broad gene expression throughout the mouse and marmoset brain after intravenous delivery of engineered AAV capsids," bioRxiv Preprint Server (2020) Doi: https://doi.org/10.1101/2020.06.16.152975, 21 pages.
Gao, G. et al. "Clades of Adeno-associated viruses are widely disseminated in human tissues," Journal of Virology vol. 78,12 (2004): 6381-8.
Gessler et al., "Intravenous infusion of AAV for widespread gene delivery to the nervous system," Methods Mol. Biol., 2019, vol. 1950, pp. 143-163.
Goertsen et al. "AAV capsid variants with brain-wide transgene expression and decreased liver targeting after intravenous delivery in mouse and marmoset," Nature Neuroscience, 2022, vol. 25, pp. 106-115.
Goertsen et al. "Transduction Profiles of Engineered Adeno-Associated Viral Capsids in Mouse and Marmoset," Molecular Therapy (2020) vol. 28, No. 4S1, pp. 269-270, Abstract 609.
Grannan, M.D. et al. "Intravenous Delivery of AAV Gene Therapy for the Treatment of SOD1-ALS Provides Broad SOD1 Lowering in NHP." Molecular Therapy, vol. 32 No 4S1 (2024): 769-770, Abstract 1647.
Grannan, M.D. et al. "Intravenous Delivery of AAV Gene Therapy for the Treatment of SOD1-ALS Provides Broad SOD1 Lowering in NHP." Voyager Therapeutics. ASGCT 27th Annual Meeting 2024, May 7-11, 2024, Baltimore, MD, USA.
Gray, S.J. et al. "Optimizing promoters for recombinant adeno-associated virus-mediated gene expression in the peripheral and central nervous system using self-complementary vectors." Human Gene Therapy vol. 22,9 (2011): 1143-53.
Hanlon et al. "Selection of an efficient AAV vector for robust CNS transgene expression," Molecular Therapy: Methods & Clinical Development, 2019, vol. 15, pp. 320-332.
Hoffman, B. et al. "Identification and Characterization of a Highly Conserved Cell Surface Receptor Utilized by Engineered BBB-Penetrant AAV Capsids with Enhanced Brain Tropism in Non-Human Primates and Mice." Voyager Therapeutics. ASGCT 27th Annual Meeting 2024, May 7-11, 2024, Baltimore, MD, USA.
Hoffman, B. et al. "Identification and Characterization of a Highly Conserved Cell Surface Receptor Utilized by Engineered BBB-Penetrant AAV Capsids with Enhanced Brain Tropism in Non-Human Primates and Mice." Molecular Therapy, vol. 32 No 4S1 (2024): 475, Abstract 975.
Hoffman, B. et al. "Identification of a cell surface receptor utilized by an engineered BBB-penetrant capsid family with enhanced brain tropism in non-human primates and mice." Human Gene Therapy vol. 33: A2-A212 (Dec. 2022), A32, Abstract P024.
Hoffman, B.A. et al. "Discovery and Characterization of Novel Cross-Species BBB-Penetrant Capsids." Voyager Therapeutics. ASGCT 26th Annual Meeting 2023, May 16-20, 2023, Los Angeles, CA, USA.
Hoffman, B.A. et al. "Identification of a Cell Surface Receptor Utilized by an Engineered BBB-Penetrant Capsid Family with Enhanced Brain Tropism in Non-Human Primates and Mice." Voyager Therapeutics. ESGCT—29th Congress, Oct. 11-14, 2022, Edinburgh, Scotland, UK.
Huang et al. "Cell Type-Specific TRAnscriptionDependent Directed Evolution (TRADE) Identifies Novel AAV Capsids Capable of Enhanced Neuronal Transduction in Mice and Non-Human Primates," Molecular Therapy (2019) vol. 27, No. 4S1, pp. 24-25, Abstract 44.
Huang et al. "Delivering genes across the blood-brain barrier: LY6A, a novel cellular receptor for AAV-PHP.B capsids," PLOS One (2019) vol. 14, No. 11, e0225206, pp. 1-17.
Ibe, M.et al. "Role of strong anchor residues in the effective binding of 10-mer and 11-mer peptides to HLA-A*2402 molecules," Immunogenetics vol. 44, 4, (1996): 233-241.
International Search Report and Written Opinion for International Application No. PCT/US2021/025061 dated Sep. 20, 2021.
International Search Report and Written Opinion for International Patent Application No. PCT/US2021/025072 dated Jul. 26, 2021.
International Search Report and Written Opinion from International Patent Application No. PCT/US2019/054345 dated Jan. 24, 2020.
International Search Report and Written Opinion in International Patent Application No. PCT/US2022/079060 dated Mar. 6, 2023.
International Search Report and Written Opinion in International Patent Application No. PCT/US2022/079963 dated May 9, 2023.
International Search Report and Written Opinion in International Patent Application No. PCT/US2022/080035 dated Apr. 3, 2023.
International Search Report and Written Opinion in International Patent Application No. PCT/US2022/080040 dated Mar. 1, 2023.
International Search Report and Written Opinion in International Patent Application No. PCT/US2023/067749 dated Sep. 29, 2023.
International Search Report and Written Opinion of International Patent Application No. PCT/US2022/079964 dated Jun. 9, 2023.
Invitation to Pay Additional Fees and Partial Search Report from International Application No. PCT/US2021/025061 dated Jul. 27, 2021.
Ishan, S. et al. "Establishment of a Predictive Transcytosis Model to Recapitulate Capsid-Receptor Interaction and Phenotype of BBB-penetrant AAV Variant." Voyager Therapeutics. ASGCT 27th Annual Meeting 2024, May 7-11, 2024, Baltimore, MD, USA.
Ising, C. et al. "AAV-mediated expression of anti-tau scFvs decreases tau accumulation in a mouse model of tauopathy." The Journal of Experimental Medicine vol. 214, 5 (2017): 1227-1238.
Khalid, A. et al. "Evaluation of Cross-species Expression Across Four Species and Cellular Tropism of VCAP-102, an Engineered Blood-brain Barrier-penetrating AAV Derived Capsid from TRACER

(56) References Cited

OTHER PUBLICATIONS

Platform Screens." Voyager Therapeutics. ASGCT 27th Annual Meeting 2024, May 7-11, 2024, Baltimore, MD, USA.

Khalid, H. et al. "Evaluation of Cross-Species Expression Across Four Species and Cellular Tropism of VCAP-102, an Engineered Blood-Brain Barrier-Penetrating AAV." Molecular Therapy, vol. 32 No 4S1 (2024): 685, Abstract 1452.

Kienle et al. "Secrets to finding the ideal mate: New insights into parameters that govern successful Adeno-associated virus (AAV) vector evolution," Dissertation, University Heidelberg (2014) pp. 1-194.

Kotchey, N. M. et al. "A potential role of distinctively delayed blood clearance of recombinant adeno-associated virus serotype 9 in robust cardiac transduction." Molecular Therapy : The Journal of the American Society of Gene Therapy vol. 19,6 (2011): 1079-89.

Kotterman et al. "4D-C102, a novel muscle-tropic AAV variant demonstrates superior gene delivery in cardiac and skeletal muscle tissues versus wild-type AAV in human cells and non-human primates."

Kotterman et al. "Engineering adeno-associated viruses for clinical gene therapy," Nature Reviews Genetics (2014) vol. 15, pp. 445-451.

Kotterman et al., "Directed evolution of AAV targeting lung epithelia using aerosol delivery identifies 4D-A101, a variant demonstrating robust gene delivery in non-human primates" Abstract 1336, 31 pages.

Kumar et al. "Evolution and Investigation of Engineered AAV Capsids Exhibiting Enhanced Transduction of the Central Nervous System with or without Murine Strain Specificity," Molecular Therapy (2020) vol. 28, No. 4S1, pp. 11-12, Abstract 22.

Kumar et al. "Multiplexed Cre-dependent selection yields systemic AAVs for targeting distinct brain cell types," Nature Methods (2020) vol. 17, No. 5, pp. 541-550.

Li et al. "A Novel AAV Capsid with a Potential of Crossing NHP Blood-Brain Barrier," Molecular Therapy (2020) vol. 28, No. 4S1, pp. 253, Abstract 572.

Liu, W. et al. "AAV Gene Delivery of the Anti-Tau Antibody PHF1 Reduces Brain Tau Pathology in P301L Mice," Molecular Therapy vol. 23, Supplement 1 (2015): S237, Abstract 596.

Liu, W. et al. "Efficacy of a vectorized anti-tau antibody using systemic dosing of a blood brain barrier penetrant AAV capsid in mouse models of tauopathies." Alzheimer's & Dementia vol. 17, No. S9 (2021): e053341.

Marsic et al. "High-accuracy biodistribution analysis of adeno-associated virus variants by double barcode sequencing," Molecular Therapy—Methods & Clinical Development (2015) vol. 2, 15041.

Marsic, D. et al. "Vector design Tour de Force: integrating combinatorial and rational approaches to derive novel adeno-associated virus variants." Molecular Therapy : The Journal of the American Society of Gene Therapy vol. 22,11 (2014): 1900-9.

Maura, D. et al. "Discovery of TRACER AAV Capsids Escaping Pre-Existing Neutralizing Antibodies." Molecular Therapy, vol. 32 No 4S1 (2024): 475, Abstract 973.

Maura, D. et al. "Discovery of TRACER AAV Capsids Escaping Pre-existing Neutralizing Antibodies." Voyager Therapeutics. ASGCT 27th Annual Meeting 2024, May 7-11, 2024, Baltimore, MD, USA.

Moyer, T. "Continued directed evolution of VCAP-101 and VCAP-102 identifies second generation capsids with increased brain tropism in non-human primates and mice (#119)." Voyager Therapeutics. ASGCT 27th Annual Meeting. ASGCT 27th Annual Meeting 2024, May 7-11, 2024, Baltimore, MD, USA. Breaking Barriers to the CNS via AAV Capsid Engineering, Wednesday May 8, 2024.

Moyer, T. "Directed Evolution of AAV9 Peptide Display Libraries Identifies a Family of Cross-Species Variants With Enhanced Brain Tropism in Non-Human Primates and Mice Following Systemic Administration." Voyager Therapeutics. SGCT 2022—Novel AAV Capsids for the Brain, Eye, and Kidney, May 19, 2022.

Moyer, T. "Directed Evolution of an AAV9 Library Identifies a Capsid Variant with Enhanced Brain Tropism and Liver Detargeting in Non-Human Primates and Mice Following Systemic Administration." Voyager Therapeutics. AAV Engineering for CNS Targeting, Thursday, May 18, 2023, Abstract #105.

Moyer, T. et al. "Continued Directed Evolution of VCAP-101 and VCAP-102 Identifies Second Generation Capsid Variants with Increased Brain Tropism and in Non-Human Primates and Mice." Molecular Therapy, vol. 32 No 4S1 (2024): 64, Abstract 119.

Moyer, T. et al. "Directed Evolution of AAV9 Peptide Display Libraries Identifies a Family of Cross-Species Variants with Enhanced Brain Tropism in Non-Human Primates and Mice Following Systemic Administration." Molecular Therapy, vol. 30 No 4S1 (2022): 556, Abstract 1198.

Moyer, T. et al. "Directed Evolution of an AAV9 Library Identifies a Capsid Variant with Enhanced Brain Tropism and Liver De-Targeting in Non-Human Primates and Mice Following Systemic Administration." Molecular Therapy, vol. 31 No 4S1 (2023): 57, Abstract 105.

Moyer, T.C. et al. "Highly conserved brain vascular receptor ALPL mediates transport of engineered viral vectors across the blood-brain barrier," bioRxiv 2024.03.12.584703.

Nonnenmacher et al. "RNA-Driven Evolution of AAV Capsid Libraries Identifies Variants with High Transduction Efficiency in Non-Human Primate Central Nervous System," Molecular Therapy (2021) vol. 29, No. 4S1, pp. 25-26, Abstract 51.

Nonnenmacher et al. "Targeted In Vivo Biopanning of AAV Capsid Libraries Using Cell Type-Specific RNA Expression," Molecular Therapy (2019) vol. 27, No. 4S1, pp. 27, Abstract 48.

Nonnenmacher et al., "Dose-response evaluation of 9P801, an engineered AAV capsid with high BBB penetration and CNS transduction in non-human primates," ESGCT 29th Annual Congress in collaboration with BSGCT Edinburgh, UK Oct. 11-14, 2022 Abstract P015.Human Gene Therapy. Dec. 2022.

Nonnenmacher, M. "Iterative Evolution of Cross-Species BBB-Penetrant Capsids." Voyager Therapeutics. In Vivo Gene Therapy & Genome Editing Summit, Oct. 30-Nov. 2, 2023, Miami, FL, USA, talk was on Oct. 31, 2023.

Nonnenmacher, M. "TracerTM capsid discovery platform." Voyager Therapeutics. In Vivo Gene Therapy & Genome Editing Summit, Oct. 31-Nov. 2, 2022, Miami, FL, USA.

Nonnenmacher, M. et al. "Rapid evolution of blood-brain-barrier-penetrating AAV capsids by RNA-driven biopanning." Molecular Therapy: Methods & Clinical Development, vol. 20 (2021): 366-378.

Nonnenmacher. "RNA-driven Evolution of AAV Capsid Libraries Identifies Variants with High Transduction Efficiency in Non-Human Primate Central Nervous System," American Society of Cell + Gene Therapy Annual Meeting, 2021, 17 pages.

Ogden et al. "Comprehensive AAV capsid fitness landscape reveals a viral gene and enables machine-guided design," Science, 2019, 366(6469), pp. 1139-1143.

Pekrun et al. "Screening of Barcoded Capsid Shuffled AAV Libraries Results in the Selection of Capsids with Enhanced Transduction Efficiency for Human Islets," Molecular Therapy (2019) vol. 26, No. 5S1, pp. 41, Abstract 82.

Puglisi, M. et al. "Targeting astrocytes by non-invasive viral vectors and probing the influence of age and inducibile expression of the reprogramming factors in vivo." Presented at Cell State Conversions, Cold Spring Harbor Laboratory, New York, USA, Oct. 10-14, 2023.

Qiao, C. et al. "Liver-specific microRNA-122 target sequences incorporated in AAV vectors efficiently inhibits transgene expression in the liver." Gene Therapy vol. 18,4 (2011): 403-10.

Rees, H. A. and Liu, D. R. "Base editing: precision chemistry on the genome and transcriptome of living cells." Nature Reviews. Genetics vol. 19,12 (2018): 770-788.

Ren, X. et al. "Establishment of a Predictive Transcytosis Model to Recapitulate Capsid-Receptor Interaction and Phenotype of BBB Penetrant AAV Variants." Molecular Therapy, vol. 32 No 4S1 (2024): 476, Abstract 976.

Song et al. "Strong Alpha Cell Preference of the AAV Strains That Best Transduce Human Pancreatic Islets in Vitro," Molecular Therapy (2017) vol. 25, No. 5S1, pp. 47, Abstract 98.

(56) References Cited

OTHER PUBLICATIONS

Stanton, A. C. et al. "Systemic administration of novel engineered AAV capsids facilitates enhanced transgene expression in the macaque CNS." Med vol. 4, 1 (2023): 31-50.e8. Epub: Nov. 22, 2022.
Stoica, L. and Sena-Esteves, M. "Adeno Associated Viral Vector Delivered RNAi for Gene Therapy of SOD1 Amyotrophic Lateral Sclerosis." Frontiers in Molecular Neuroscience vol. 9 article 56 (2016).
Voyager Therapeutics, "Intravenous Delivery of Novel AAV Capsids", Oct. 20, 2017, Retrieved from the Internet: URL:https://www.voyagertherapeutics.com/wp-content/uploads/2017/10/ESGCT_slides.pdf [retrieved on Oct. 9, 2019].
Wang et al. "Adeno-associated virus vector as a platform for gene therapy delivery," Nat Rev Drug Discov., 2019, vol. 18, 5, pp. 358-378.
Yan et al., "Two-Amino Acid Molecular Switch in an Epithelial Morphogen That Regulates Binding to Two Distinct Receptors," Science (2000) vol. 290, pp. 523-527.
Yin, Z. et al., "Research Advances on Increasing the Transduction Efficiency of Recombinant Adeno-associated Viral Vectors." Biotechnology Bulletin vol. 31, 9 (2015): 49-59.
Afione, S. et al. "Identification and mutagenesis of the adeno-associated virus 5 sialic acid binding region." Journal of Virology vol. 89,3 (2015): 1660-72.
Almeida, C F et al. "Promising AAV. U7snRNAs vectors targeting DMPK improve DM1 hallmarks in patient-derived cell lines." Frontiers in Cell and Developmental Biology vol. 11 1181040. Jun. 15, 2023.
Bremel, R. et al. "Bioinformatic Processes for Determination of Peptide Binding", GS_PROT_ALERT:WO20130401421 Mar. 2013 (Mar. 21, 2013), retrieved from WO2013040142, Database Accession No. GS_PROT_ALERT:WO2013040142.974324.
Choudhury, S. et al. "Peptide Grafting Yields Novel AAV Vectors Capable of Enhanced Neuronal Transduction in Adult Mouse Brain." Molecular Therapy vol. 22, Supplement 1 (2014): S109-S110, Abstract 285.
Govindasamy, L. et al. "Structural insights into adeno-associated virus serotype 5." Journal of Virology vol. 87,20 (2013): 11187-99.
Hida, K. et al. "Sites in the AAV5 capsid tolerant to deletions and tandem duplications." Archives of Biochemistry and Biophysics vol. 496, 1 (2010): 1-8.
International Search Report and Written Opinion in International Patent Application No. PCT/US2023/062101 dated Jul. 24, 2023.
International Search Report and Written Opinion in International Patent Application No. PCT/US2023/069146 dated Nov. 9, 2023.
International Search Report and Written Opinion in International Patent Application No. PCT/US2023/069621 dated Oct. 16, 2023.
International Search Report and Written Opinion in International Patent Application No. PCT/US2024/041668 dated Dec. 3, 2024.
International Search Report and Written Opinion in International Patent Application No. PCT/US2024/042395 dated Dec. 2, 2024.
International Search Report and Written Opinion in International Patent Application No. PCT/US2024/042397 dated Dec. 3, 2024.
International Search Report and Written Opinion in International Patent Application No. PCT/US2024/042405 dated Dec. 2, 2024.
International Search Report and Written Opinion in International Patent Application No. PCT/US2024/042407 dated Dec. 2, 2024.
International Search Report and Written Opinion in International Patent Application No. PCT/US2024/042411 dated Dec. 2, 2024.
Jose, A. et al. "High-Resolution Structural Characterization of a New Adeno-associated Virus Serotype 5 Antibody Epitope toward Engineering Antibody-Resistant Recombinant Gene Delivery Vectors." Journal of Virology vol. 93,1e01394-18. Dec. 10, 2018.
Lin, J. et al. "An Evolved AAV Variant with Enhanced Brain and Spinal Cord Tropism and Translation across Primate Species," Molecular Therapy vol. 31 No. 4S1, Apr. 2023, Abstract 1393.
Lin, J. et al. "An Evolved AAV Variant with Enhanced Brain and Spinal Cord Tropism and Translation across Primate Species." Voyager Therapeutics. ASGCT Annual Meeting 2023, May 16-May 20, 2023, Los Angeles, CA, USA, (#1393).
Maura, D. et al. "Stepwise Evolution of the AAV5-Derived Capsid VCAP-100 Identifies Novel Variants with Improved CNS Transduction and Liver Detargeting Following Systemic Injection," Molecular Therapy vol. 31 No. 4S1, Apr. 2023, Abstract 464.
Maura, D. et al. "Stepwise evolution of the AAV5-derived capsid VCAP-100 identifies novel variants with improved CNS transduction and liver detargeting following systemic injection." Voyager Therapeutics. ASGCT Annual Meeting 2023, May 16-May 20, 2023, Los Angeles, CA, USA, (#464).
Medici, G. et al., "Expression of a Secretable, Cell-Penetrating CDKL5 Protein Enhances the Efficacy of AAV Vector-Mediated Gene Therapy for CDKL5 Deficiency Disorder," Dec. 17, 2021 (Dec. 17, 2021), p. 1-25, Retrieved from the Internet: URL:https://www.biorxiv.org/content/10.1101/2021.07.26.453746v2.full.pdf.
Nonnenmacher, M. et al. "Directed Evolution of an AAV5 Capsid Library Identifies a Variant with Enhanced Transduction in Non-Human Primate and Rodent Brain Following Systemic Administration," Molecular Therapy vol. 30 No. 4S1, Apr. 2022, Abstract 129.
Nonnenmacher, M. et al. "Directed Evolution of an AAV5 Capsid Library Identifies a Variant with Enhanced Transduction in Non-Human Primate and Rodent Brain Following Systemic Administration." Voyager Therapeutics. ASGCT 2022 Annual Meeting, May 16-19, 2022, Washington, DC, USA (#129).
Qian, R. et al. "Directed Evolution of AAV Serotype 5 for Increased Hepatocyte Transduction and Retained Low Humoral Seroreactivity." Molecular Therapy. Methods & Clinical Development vol. 20 122-132. Oct. 20, 2020.
Shah, I. et al. "Establishment of a Predictive Transcytosis Model to Recapitulate Capsid-Receptor Interaction and Phenotype of BBB-penetrant AAV Variant." Voyager Therapeutics. ASGCT 27th Annual Meeting 2024, May 7-11, 2024, Baltimore, MD, USA.
Walters, R. W. et al. "Structure of adeno-associated virus serotype 5." Journal of Virology vol. 78,7 (2004): 3361-71.
Zhang, X. et al. "Blood-brain barrier shuttle peptides enhance AAV transduction in the brainadministration." Biomaterials vol. 176 (2018): 71-83.

AAV CAPSID VARIANTS AND USES THEREOF

RELATED APPLICATIONS

This application is a divisional of U.S. patent application Ser. No. 18/757,141 filed Jun. 27, 2024, which is a continuation of U.S. patent application Ser. No. 18/703,166 filed Apr. 19, 2024, which is a U.S. National Phase Application under 35 U.S.C. § 371 of International Application No. PCT/US2022/079060, filed Nov. 1, 2022, which claims priority to U.S. Provisional Application No. 63/274,806 filed on Nov. 2, 2021 and U.S. Provisional Application No. 63/339,711 filed on May 9, 2022; the entire contents of each of which are hereby incorporated by reference in their entirety.

SEQUENCE LISTING

The instant application contains a Sequence Listing which has been submitted electronically in XML format and is hereby incorporated by reference in its entirety. Said XML copy, created on Mar. 27, 2025, is named V2071-1125USDIV1FT_SL.xml and is 5,455,506 bytes in size.

FIELD OF THE DISCLOSURE

The disclosure relates to compositions and methods for the preparation, use, and/or formulation of adeno-associated virus capsid proteins and variants thereof.

BACKGROUND

Gene delivery to the adult central nervous system (CNS) remains a significant challenge in gene therapy. Engineered adeno-associated virus (AAV) capsids with improved brain tropism represent an attractive solution to the limitations of CNS delivery.

AAV-derived vectors are promising tools for clinical gene transfer because of their non-pathogenic nature, their low immunogenic profile, low rate of integration into the host genome and long-term transgene expression in non-dividing cells. However, the transduction efficiency of AAV natural variants in certain organs is too low for clinical applications, and capsid neutralization by pre-existing neutralizing antibodies may prevent treatment of a large proportion of patients. For these reasons, considerable efforts have been devoted to obtaining capsid variants with enhanced properties. Of many approaches tested so far, significant advances have resulted from directed evolution of AAV capsids using in vitro or in vivo selection of capsid variants created by capsid sequence randomization using either error-prone PCR, shuffling of various parent serotypes, or insertion of fully randomized short peptides at defined positions.

Attempts at providing AAV capsids with improved properties, e.g., improved tropism to a target cell or tissue upon systemic administration, have met with limited success. As such, there is a need for improved methods of producing AAV capsids and resulting AAV capsids for delivery of a payload of interest to a target cell or tissue, e.g., a CNS cell or tissue, or a muscle cell or tissue.

SUMMARY OF THE DISCLOSURE

The present disclosure pertains at least in part, to compositions and methods for the production and use of an AAV particle comprising an AAV capsid polypeptide, e.g., an AAV capsid variant. In some embodiments, the AAV capsid variant has an enhanced tropism for a tissue or a cell, e.g., a CNS tissue or a CNS cell. Said tropism can be useful for delivery of a payload, e.g., a payload described herein to a cell or tissue, for the treatment of a disorder, e.g., a neurological or a neurodegenerative disorder, a muscular or a neuromuscular disorder, or a neuro-oncological disorder.

Accordingly, in one aspect, the present disclosure provides an AAV capsid variant, comprising an amino acid sequence having the following formula: [N1]-[N2]-[N3], wherein: (i) optionally [N1] comprises X1, X2, and X3, wherein at least one of X1, X2, or X3 is G; (ii) [N2] comprises the amino acid sequence of SPH; (ii) [N3] comprises X4, X5, and X6, wherein at least one of X4, X5, or X6 is a basic amino acid, e.g., a K or R. In some embodiments, position X4 of [N3] is K. In some embodiments, position X5 of [N3] is K. In some embodiments, [N3] is or comprises SKA. In some embodiments [N3] is or comprises KSG. In some embodiments, [N2]-[N3] is present immediately subsequent to position 455, numbered according to SEQ ID NO: 138, 981 or 982. In some embodiments, [N1] is present immediately subsequent to position 452, relative to a reference sequence numbered according to the amino acid sequence of SEQ ID NO: 138, 981, or 982. In some embodiments, [N1] replaces positions 453-455 (e.g., G453, S454, and G455), relative to a reference sequence numbered according to SEQ ID NO: 138. In some embodiments, the AAV capsid variant comprises H at position 454 and D at position 455, numbered according to SEQ ID NO: 138 or 982. In some embodiments, the AAV capsid variant comprises S at position 454 and G at position 455, numbered according to SEQ ID NO: 138 or 981. In some embodiments, an insert of 8 amino acids replaces the SG at positions 454-455, numbered according to SEQ ID NO: 138. In some embodiments, an insert of 6 amino acids is present immediately subsequent to position 455, numbered according to SEQ ID NO: 138, 981, or 982.

In another aspect, the present disclosure provides an AAV capsid variant comprising [A][B](SEQ ID NO: 4694), wherein: (i) [A] comprises the amino acid sequence of GSGSPH (SEQ ID NO: 4695); and (ii) [B] comprises X1 X2 X3 X4 X5 X6 X7, wherein: (a) position X1 is S, C, F, or V; (b) position X2 is K, L, R, I, E, Y, V, or S; (c) position X3 is A, R, L, G, I, Y, S, F, or W; (d) position X4 is W, Q, R, G, L, V, S, or F; (e) position X5 is N, Y, R, C, K, or L; (f) position X6 is Q, G, K, R, T, L, or Y; and (g) position X7 is Q, L, R, or V.

In yet another aspect, the present disclosure provides an AAV capsid variant comprising [A][B](SEQ ID NO: 4699) wherein: (i) [A] comprises X1 X2 X3 X4 X5 X6, wherein (a) position X1 is T, M, A, C, I, R, L, D, F, V, Q, N, or H; (b) position X2 is I, P, E, N, D, S, A, T, M, or Q; (c) position X3 is N, E, G, Y, W, M, T, I, K, Q, F, S, V, A, or L; (d) position X4 is G, D, R, or E; (e) position X5 is H, Q, N, or D; (f) position X6 is D or R; and (ii) [B] comprises SPHKSG (SEQ ID NO: 946).

In yet another aspect, the present disclosure provides an AAV capsid variant comprising an amino acid sequence having the following formula: [N1]-[N2]-[N3](SEQ ID NO: 6407), wherein: (i) [N1] comprises positions X1, X2, and X3, wherein position X2 is S and position X3 is G; (ii) [N2] comprises the amino acid sequence SPH; and (iii) [N3] comprises positions X4, X5, and X6, wherein position X5 is K. In some embodiments, [N1]-[N2]-[N3] is present immediately subsequent to position 452 and replaces positions 453-455, numbered according to SEQ ID NO: 138 or 982.

In some embodiments, [N1]-[N2]-[N3] is or comprises GSGSPHSKA (SEQ ID NO: 4697).

In another aspect, the present disclosure provides an AAV capsid variant comprising an amino acid sequence having the following formula: [N1]-[N2]-[N3](SEQ ID NO: 6408), wherein: (i) [N1] comprises positions X1, X2, and X3, wherein position X2 is an amino acid other than S and position X3 is an amino acid other than G; (ii) [N2] comprises the amino acid sequence SPH; and (iii) [N3] comprises positions X4, X5, and X6, wherein position X4 is K. In some embodiments, [N1]-[N2]-[N3] is present immediately subsequent to position 452 and replaces positions 453-455, numbered according to SEQ ID NO: 138 or 982. In some embodiments, [N1]-[N2]-[N3] is or comprises GHDSPHKSG (SEQ ID NO: 4698).

In yet another aspect, the present disclosure provides an AAV capsid variant comprising the formula [A]-[B](SEQ ID NO: 4696), wherein: (i) [A] comprises GSGSPH (SEQ ID NO: 4695); and (ii) [B] comprises X1 X2, X3, X4, and X5, wherein: (a) position X1 is S, I, F, V, C, Y, W, R, P, L, Q, M, K, or G; (b) position X2 is K, M, R, F, V, C, P, Y, L, W, G, N, S, T, I, or A; (c) position X3 is A, Y, L, R, W, C, T, F, H, I, P, M, K, S, V, G, Q, or N; (d) position X4 is Q, M, F, K, H, R, C, W, P, V, L, G, S, Y, I, A, T, D, N, or E; and (e) position X5 is A, N, Y, R, K, L, I, M, Q, S, C, W, F, T, G, V, or P; optionally wherein the AAV capsid variant comprises an amino acid modification, e.g., a conservative substitution, of any of the aforesaid amino acids in (a)-(e). In some, embodiments, [A]-[B] is present immediately subsequent to position 452, and wherein [A]-[B] replaces positions 453-457 (e.g., G453, S454, G455, Q456, N457), relative to a reference sequence numbered according to the amino acid sequence of SEQ ID NO: 138. In some embodiments, the AAV capsid variant has increased tropism for a liver cell or tissue, relative to the tropism of a reference sequence comprising the amino acid sequence of SEQ ID NO: 138. In some embodiments, the AAV capsid shows preferential transduction in the liver relative to transduction in the brain and/or dorsal root ganglia (DRG), e.g., as compared to SEQ ID NO: 138.

In another aspect, the present disclosure provides an AAV capsid variant comprising (a) the amino acid sequence of any of the sequences provided in Tables 1, 2A, 2B, 13-19; (b) an amino acid sequence comprising at least 3, 4, 5, 6, 7, 8, 9, 10, 11, 12, 13, 14, 15, 16, or 17, consecutive amino acids from any one of the sequences provided in Tables 1, 2A, 2B, 13-19; (c) an amino acid sequence comprising at least one, two, or three, but no more than four different amino acids, relative to any one of the sequences provided in Tables 1, 2A, 2B, 13-19; or (d) an amino acid sequence comprising at least one, two, or three but no more than four modifications, e.g., substitutions (e.g., conservative substitutions), relative to the amino acid sequence of any one of the sequences provided in Tables 1, 2A, 2B, 13-19. In some embodiments, the amino acid sequence is present in loop IV. In some embodiments, the amino acid sequence is present immediately subsequent to position 448, 4 52, 453, 455, relative to a reference sequence numbered according to the amino acid sequence of SEQ ID NO: 138.

In yet another aspect, the present disclosure provides an AAV capsid variant comprising (a) the amino acid sequence of any of SEQ ID NOs: 945-980 or 985-986; (b) an amino acid sequence comprising at least 3, 4, or 5 consecutive amino acids from any one of SEQ ID NOs: 945-980 or 985-986; (c) an amino acid sequence comprising at least one, two, or three but no more than four different amino acids, relative to the amino acid sequence of any one of SEQ ID NOs: 945-980 or 985-986; (d) an amino acid sequence comprising at least one, two, or three but no more than four modifications, e.g., substitutions (e.g., conservative substitutions), relative to the amino acid sequence of any one of SEQ ID NOs: 945-980 or 985-986. In some embodiments, the amino acid sequence is present in loop IV. In some embodiments, the amino acid sequence is present immediately subsequent to position 448, 452, 453, 455, relative to a reference sequence numbered according to the amino acid sequence of SEQ ID NO: 138.

In yet another aspect, the present disclosure provides an AAV capsid variant comprising (a) the amino acid sequence of any of SEQ ID NOs: 2, 200, 201, 941, 943, 204, 208, 404, or 903-909; (b) an amino acid sequence comprising at least 3, 4, 5, 6, 7, 8, 9, 10, 11, 12, or 13 consecutive amino acids from any one of SEQ ID NOs: 2, 200, 201, 941, 943, 204, 208, 404, or 903-909; (c) an amino acid sequence comprising at least one, two, or three, but no more than four different amino acids, relative to the amino acid sequence of any one of SEQ ID NOs: 2, 200, 201, 941, 943, 204, 208, 404, or 903-909; or (d) an amino acid sequence comprising at least one, two, or three but no more than four modifications, e.g., substitutions (e.g., conservative substitutions), relative to the amino acid sequence of any one of SEQ ID NOs: 2, 200, 201, 941, 943, 204, 208, 404, or 903-909. In some embodiments, the amino acid sequence is present in loop IV. In some embodiments, the amino acid sequence is present immediately subsequent to position 448, 452, 453, 455, relative to a reference sequence numbered according to the amino acid sequence of SEQ ID NO: 138.

In yet another aspect, the present disclosure provides a polynucleotide encoding an AAV capsid variant described herein. In some embodiments, the polynucleotide comprises (i) a nucleotide sequence comprising at least one, two, three, four, five, six, or seven modifications, e.g., substitutions (e.g., conservative substitutions), but no more than ten modifications, e.g., substitutions (e.g., conservative substitutions), relative to the nucleotide sequences of SEQ ID NO: 3 or 942; (ii) a nucleotide sequence comprising at least one, two, three, four, five, six, or seven, but no more than ten different nucleotides, relative to the nucleotide sequences of SEQ ID NO: 3 or 942; or (iii) the nucleotide sequence of SEQ ID NOs: 3 or 942, or nucleotide sequence substantially identical (e.g., having at least 70%, 75%, 80%, 85%, 90%, 92%, 95%, 97%, 98%, or 99% sequence identity) thereto.

In yet another aspect, present disclosure provides an AAV capsid variant comprising an amino acid sequence comprising at least 3, 4, 5, or 6 consecutive amino acids from the amino acid sequence of SPHSKA (SEQ ID NO: 941), wherein: (i) the 3 consecutive amino acids comprise SPH; (ii) the 4 consecutive amino acids comprise SPHS (SEQ ID NO: 4700); (iii) the 5 consecutive amino acids comprise SPHSK (SEQ ID NO: 4701); or (iv) the 6 consecutive amino acids comprise SPHSKA (SEQ ID NO: 941); wherein the AAV capsid variant comprises: (a) a VP1 protein comprising the amino acid sequence of SEQ ID NO: 138 or SEQ ID NO: 981; (b) a VP2 protein comprising the amino acid sequence of positions 138-736 of SEQ ID NO: 138 or positions 138-742 of SEQ ID NO: 981; (c) a VP3 protein comprising the amino acid sequence of positions 203-736 of SEQ ID NO: 138 or positions 203-742 of SEQ ID NO: 981; or (d) an amino acid sequence with at least 90% (e.g., at least about 95, 96, 97, 98, or 99%) sequence identity to any of the amino acid sequences in (a)-(c). In some embodiments, the amino acid sequence is present immediately subsequent to positions 455, numbered according to SEQ ID NO: 138 or 981.

In yet another aspect, the present disclosure provides an AAV capsid variant comprising one or two, but no more than three substitutions relative to the amino acid sequence of SPHSKA (SEQ ID NO: 941), wherein the AAV capsid variant comprises: (a) a VP1 protein comprising the amino acid sequence of SEQ ID NO: 138 or SEQ ID NO: 981; (b) a VP2 protein comprising the amino acid sequence of positions 138-736 of SEQ ID NO: 138 or positions 138-742 of SEQ ID NO: 981; (c) a VP3 protein comprising the amino acid sequence of positions 203-736 of SEQ ID NO: 138 or positions 203-742 of SEQ ID NO: 981; or (d) an amino acid sequence with at least 90% (e.g., at least about 95, 96, 97, 98, or 99%) sequence identity to any of the amino acid sequences in (a)-(c). In some embodiments, the amino acid sequence is present immediately subsequent to positions 455, numbered according to SEQ ID NO: 138 or 981.

In another aspect, the present disclosure provides an AAV capsid variant comprising at least 3, 4, 5, or 6 consecutive amino acids from the amino acid sequence of HDSPHK (SEQ ID NO: 2), wherein: (i) the 3 consecutive amino acids comprise HDS; (ii) the 4 consecutive amino acids comprise HDSP (SEQ ID NO: 4702); (iii) the 5 consecutive amino acids comprise HDSPH (SEQ ID NO: 4703); and/or (iv) the 6 consecutive amino acids comprise HDSPHK (SEQ ID NO: 2); wherein the AAV capsid variant comprises: (a) a VP1 protein comprising the amino acid sequence of SEQ ID NO: 138 or SEQ ID NO: 982; (b) a VP2 protein comprising the amino acid sequence of positions 138-736 of SEQ ID NO: 138 or positions 138-742 of SEQ ID NO: 982; (c) a VP3 protein comprising the amino acid sequence of positions 203-736 of SEQ ID NO: 138 or positions 203-742 of SEQ ID NO: 982; or (d) an amino acid sequence with at least 90% (e.g., at least about 95, 96, 97, 98, or 99%) sequence identity to any of the amino acid sequences in (a)-(c). In some embodiments, the amino acid sequence is present immediately subsequent to positions 453, numbered according to SEQ ID NO: 138 or 982.

In another aspect, the present disclosure provides an AAV capsid variant comprising one or two, but no more than three substitutions relative to the amino acid sequence of HDSPHK (SEQ ID NO: 2), wherein the AAV capsid variant comprises: (a) a VP1 protein comprising the amino acid sequence of SEQ ID NO: 138 or SEQ ID NO: 982; (b) a VP2 protein comprising the amino acid sequence of positions 138-736 of SEQ ID NO: 138 or positions 138-742 of SEQ ID NO: 982; (c) a VP3 protein comprising the amino acid sequence of positions 203-736 of SEQ ID NO: 138 or positions 203-742 of SEQ ID NO: 982; or (d) an amino acid sequence with at least 90% (e.g., at least about 95, 96, 97, 98, or 99%) sequence identity to any of the amino acid sequences in (a)-(c).

In yet another aspect, the present disclosure provides a peptide comprising: (a) the amino acid sequence of any of the sequences provided in Tables 1, 2A, 2B, 13-19; (b) an amino acid sequence comprising at least 3, 4, 5, 6, 7, 8, 9, 10, 11, 12, 13, 14, 15, 16, or 17 consecutive amino acids from any one of the sequences provided in Tables 1, 2A, 2B, 13-19; (c) an amino acid sequence comprising at least one, two, or three, but no more than four different amino acids relative to the amino acid sequence of any one of the sequences provided in Tables 1, 2A, 2B, 13-19; or (d) an amino acid sequence comprising at least one, two, or three but no more than four modifications, e.g., substitutions (e.g., conservative substitutions), relative to the amino acid sequence of any one of the sequences provided in Tables 1, 2A, 2B, 13-19.

In another aspect, the present disclosure provides a peptide comprising (a) the amino acid sequence of any of SEQ ID NOs: 945-980 or 985-986; (b) an amino acid sequence comprising at least 3, 4, or 5 consecutive amino acids from any one of SEQ ID NOs: 945-980 or 985-986; (c) an amino acid sequence comprising at least one, two, or three, but no more than four different amino acids relative to the amino acid sequence of any one of SEQ ID NOs: 945-980 or 985-986; or (d) an amino acid sequence comprising at least one, two, or three but no more than four modifications, e.g., substitutions (e.g., substitutions), relative to the amino acid sequence of any one of SEQ ID NOs: 945-980 or 985-986.

In another aspect, the present disclosure provides a peptide comprising: (a) the amino acid sequence of any of SEQ ID NOs: 2, 200, 201, 941, 943, 204, 208, 404, or 903-909; (b) an amino acid sequence comprising at least 3, 4, 5, 6, 7, 8, 9, 10, 11, 12, or 13 consecutive amino acids from any one of SEQ ID NOs: 2, 200, 201, 941, 943, 204, 208, 404, or 903-909; or (c) an amino acid sequence comprising at least one, two, or three but no more than four different amino acids relative to the amino acid sequence of any one of SEQ ID NOs: 2, 200, 201, 941, 943, 204, 208, 404, or 903-909; or (d) an amino acid sequence comprising at least one, two, or three but no more than four modifications, e.g., substitutions (conservative substitutions), relative to the amino acid sequence of any one of SEQ ID NOs: 2, 200, 201, 941, 943, 204, 208, 404, or 903-909.

In yet another aspect, the present disclosure provides a peptide comprising: (i) the amino acid sequence of SPHSKA (SEQ ID NO: 941); (ii) an amino acid sequence comprising at least one, two, or three, but no more than four different amino acids relative to the amino acid sequence of SPHSKA (SEQ ID NO: 941); (iii) an amino acid sequence comprising at least one, two, or three modifications, e.g., substitutions (e.g., conservative substitutions), but no more than four modifications, e.g., substitutions (e.g., conservative substitutions), relative to the amino acid sequence of SPHSKA (SEQ ID NO: 941); or (iv) at least 3, 4, or 5 consecutive amino acids from the amino acid sequence of SPHSKA (SEQ ID NO: 941).

In yet another aspect, the present disclosure provides a peptide encoded by (i) the nucleotide sequence of SEQ ID NO: 942, or a nucleotide sequence substantially identical (e.g., having at least 70%, 75%, 80%, 85%, 90%, 92%, 95%, 97%, 98%, or 99% sequence identity) thereto; or (ii) a nucleotide sequence comprising at least one, two, three, four, five, six, or seven, but no more than ten different nucleotides relative to the nucleotide sequence of SEQ ID NO: 942; or (iii) a nucleotide sequence comprising at least one, two, three, four, five, six, or seven modifications, e.g., substitutions (e.g., conservative substitutions), but no more than ten modifications, e.g., substitutions (e.g., conservative substitutions), relative to the nucleotide sequence of SEQ ID NO: 942.

In yet another aspect, the present disclosure provides a peptide, wherein the nucleotide sequence encoding the peptide comprises (i) the nucleotide sequence of SEQ ID NO: 942, or a nucleotide sequence substantially identical (e.g., having at least 70%, 75%, 80%, 85%, 90%, 92%, 95%, 97%, 98%, or 99% sequence identity) thereto; (ii) a nucleotide sequence comprising at least one, two, three, four, five, six, or seven, but not more than 10 different nucleotides, relative to the nucleotide sequence of SEQ ID NO: 942; or (iii) a nucleotide sequence comprising at least one, two, three, four, five, six, or seven modifications, e.g., substitutions (e.g., conservative substitutions), but no more than ten modifications, e.g., substitutions (e.g., conservative substitutions), relative to the nucleotide sequence of SEQ ID NO: 942.

In another aspect, the present disclosure provides a peptide comprising: (i) the amino acid sequence of HDSPHK (SEQ ID NO: 2); (ii) an amino acid sequence comprising at least one, two, or three, but no more than four different amino acids, relative to the amino acid sequence of HDSPHK (SEQ ID NO: 2); (iii) an amino acid sequence comprising at least one, two, or three modifications, e.g., substitutions (e.g., conservative substitutions), but no more than four modifications, e.g., substitutions (e.g., conservative substitutions), relative to the amino acid sequence of HDSPHK (SEQ ID NO: 2); or (iv) at least 3, 4, or 5 consecutive amino acids from the amino acid sequence of HDSPHK (SEQ ID NO: 2).

In yet another aspect, the present disclosure provides a peptide encoded by (i) the nucleotide sequence of SEQ ID NO: 3, or a nucleotide sequence substantially identical (e.g., having at least 70%, 75%, 80%, 85%, 90%, 92%, 95%, 97%, 98%, or 99% sequence identity) thereto; (ii) a nucleotide sequence comprising at least one, two, three, four, five, six, or seven, but no more than ten different nucleotides, relative to the nucleotide sequence of SEQ ID NO: 3; (iii) a nucleotide sequence comprising at least one, two, three, four, five, six, or seven modifications, e.g., substitutions (e.g., conservative substitutions), but no more than ten modifications, e.g., substitutions (e.g., conservative substitutions), relative to the nucleotide sequence of SEQ ID NO: 3.

In another aspect, the present disclosure provides a peptide wherein the nucleotide sequence encoding the peptide comprises: (i) the nucleotide sequence of SEQ ID NO: 3, or a nucleotide sequence substantially identical (e.g., having at least 70%, 75%, 80%, 85%, 90%, 92%, 95%, 97%, 98%, or 99% sequence identity) thereto; (ii) a nucleotide sequence comprising at least one, two, three, four, five, six, or seven, but no more than ten different nucleotides relative to the nucleotide sequence of SEQ ID NO: 3; or (iii) a nucleotide sequence comprising at least one, two, three, four, five, six, or seven modifications, e.g., substitutions (e.g., conservative substitutions), but no more than ten modifications, e.g., substitutions (e.g., conservative substitutions), relative to the nucleotide sequence of SEQ ID NO: 3.

In yet another aspect, the present disclosure provides a polynucleotide encoding an AAV capsid variant comprising: (a) the amino acid sequence of any of the sequences provided in Tables 1, 2A, 2B, 13-19; (b) an amino acid sequence comprising at least 3, 4, 5, 6, 7, 8, 9, 10, 11, 12, 13, 14, 15, 16, or 17 consecutive amino acids from any one of the sequences provided in Tables 1, 2A, 2B, 13-19; (c) an amino a sequence comprising at least one, two, or three but no more than four different amino acids, relative to the amino acid sequence of any one of the sequences provided in Tables 1, 2A, 2B, 13-19; or (d) an amino acid sequence comprising at least one, two, or three but no more than four modifications, e.g., substitutions (conservative substitutions), relative to the amino acid sequence of any one of the sequences provided in Tables 1, 2A, 2B, 13-19. In some embodiments, the amino acid sequence of (a), (b), (c), and/or (d) is present immediately subsequent to position 448, 449, 450, 451, 452, 453, 454, or 455, relative to a reference sequence numbered according to the amino acid sequence of SEQ ID NO: 138.

In yet another aspect, the present disclosure provides a polynucleotide encoding an AAV capsid variant, wherein the AAV capsid variant comprises: (i) the amino acid sequence of SPHSKA (SEQ ID NO: 941); (ii) an amino acid sequence comprising at least one, two, or three, but no more than four different amino acids, relative to the amino acid sequence of SPHSKA (SEQ ID NO: 941); (iii) an amino acid sequence comprising at least one, two, or three modifications, e.g., substitutions (e.g., conservative substitutions), but no more than four modifications, e.g., substitutions (e.g., conservative substitutions), relative to the amino acid sequence of SPHSKA (SEQ ID NO: 941); or (iv) at least 3, 4, 5, 6, 7, 8, or 9 consecutive amino acids from the amino acid sequence of SPHSKA (SEQ ID NO: 941). In some embodiments, the amino acid sequence of (i), (ii), (iii), and/or (iv) is present immediately subsequent to position 455, relative to a reference sequence numbered according to the amino acid sequence of SEQ ID NO: 138.

In another aspect, the present disclosure provides a polynucleotide encoding an AAV capsid variant, wherein the AAV capsid variant comprises: (i) the amino acid sequence of HDSPHK (SEQ ID NO: 2); (ii) an amino acid sequence comprising at least one, two, or three, but no more than four different amino acids, relative to the amino acid sequence of HDSPHK (SEQ ID NO: 2); (iii) an amino acid sequence comprising at least one, two, or three modifications, e.g., substitutions (e.g., conservative substitutions), but no more than four modifications, e.g., substitutions (e.g., conservative substitutions), relative to the amino acid sequence of HDSPHK (SEQ ID NO: 2); or (iv) at least 3, 4, 5, or 6 consecutive amino acids from the amino acid sequence of HDSPHK (SEQ ID NO: 2). In some embodiments, the amino acid sequence of (i), (ii), (iii), and/or (iv) is present immediately subsequent to position 453, relative to a reference sequence numbered according to the amino acid sequence of SEQ ID NO: 138.

In yet another aspect, the present disclosure provides an AAV capsid variant comprising the amino acid sequence of SPH, wherein the amino acid sequence is present immediately subsequent to position 455, numbered according to the amino acid sequence of any one of SEQ ID NOs: 36-59, 138, 981, or 982.

In yet another aspect, the present disclosure provides an AAV capsid variant comprising the amino acid sequence of SPHSKA (SEQ ID NO: 941), wherein the amino acid sequence is present immediately subsequent to position 455, numbered according to the amino acid sequence of SEQ ID NO: 138.

In yet another aspect, the present disclosure provides an AAV capsid variant comprising the amino acid sequence of SPHSKA (SEQ ID NO: 941), wherein the amino acid sequence is present immediately subsequent to position 455, numbered according to the amino acid sequence of SEQ ID NO: 981.

In yet another aspect, the present disclosure provides an AAV capsid variant comprising the amino acid sequence of HDSPHK (SEQ ID NO: 2), wherein the amino acid sequence is present immediately subsequent to position 453, numbered according to the amino acid sequence of SEQ ID NO: 138.

In yet another aspect, the present disclosure provides an AAV capsid variant comprising the amino acid sequence of HDSPHK (SEQ ID NO: 2), wherein the amino acid sequence is present immediately subsequent to position 453, numbered according to the amino acid sequence of SEQ ID NO: 982.

In yet another aspect, the present disclosure provides an AAV capsid variant comprising the amino acid sequence of SPHSKA (SEQ ID NO: 941), wherein the amino acid sequence is present in loop IV, relative to a reference sequence of SEQ ID NO: 138. In some embodiments, loop IV comprises positions 449-460, numbered according to SEQ ID NO: 138.

In yet another aspect, the present disclosure provides an AAV capsid variant comprising the amino acid sequence of HDSPHK (SEQ ID NO: 2), wherein the amino acid sequence is present in loop IV, relative to a reference sequence of SEQ ID NO: 138. In some embodiments, loop IV comprises positions 449-460, numbered according to SEQ ID NO: 138.

In yet another aspect, the present disclosure provides an AAV particle comprising an AAV capsid variant, described herein. In some embodiments, the AAV particle comprises a nucleic acid sequence encoding a payload. In some embodiments, the AAV particle further comprises a viral genome comprising a promoter operably linked to the nucleic acid encoding the payload.

In yet another aspect, the present disclosure provides a method of making an AAV particle comprising an AAV capsid variant described herein. The method comprises providing a host cell comprising a viral genome and incubating the host cell under conditions suitable to enclose the viral genome in the AAV capsid variant, e.g., an AAV capsid variant described herein, thereby making the AAV particle.

In yet another aspect, the present disclosure provides a method of delivering a payload to a cell or tissue (e.g., a CNS cell, a CNS tissue, a liver cell, or a liver tissue). The method comprising administering an effective amount of an AAV particle comprising an AAV capsid variant described herein.

In yet another aspect, the present disclosure provides a method of treating a subject having or diagnosed with having a genetic disorder, e.g., a monogenic disorder or a polygenic disorder. The method comprising administering to the subject an effective amount an AAV particle comprising an AAV capsid variant described herein.

In yet another aspect, the present disclosure provides a method of treating a subject having or diagnosed with having neurological, e.g., a neurodegenerative, disorder. The method comprising administering an effective amount of an AAV particle comprising an AAV capsid variant described herein.

In yet another aspect, the present disclosure provides a method of treating a subject having or diagnosed with having a neuro-oncological disorder. The method comprising administering an effective amount of an AAV particle comprising an AAV capsid variant described herein.

Those skilled in the art will recognize or be able to ascertain using no more than routine experimentation, many equivalents to the specific embodiments of the invention described herein. Such equivalents are intended to be encompassed by the following enumerated embodiments.

ENUMERATED EMBODIMENTS

1. An AAV capsid variant, comprising an amino acid sequence having the following formula: [N1]-[N2]-[N3], wherein:
   (i) optionally [N1] comprises X1, X2, and X3, wherein at least one of X1, X2, or X3 is G;
   (ii) [N2] comprises the amino acid sequence of SPH;
   (ii) [N3] comprises X4, X5, and X6, wherein at least one of X4, X5, or X6 is a basic amino acid, e.g., a K or R.
2. The AAV capsid variant of embodiment 1, wherein X4, X5, or both of [N3] is a K.
3. The AAV capsid variant of embodiment 1 or 2, wherein X4, X5, or X6 of [N3] is an R.

4. The AAV capsid variant of any one of embodiments 1-3, wherein:
   (a) position X4 of [N3] is: K, S, A, V, T, G, F, W, V, N, or R;
   (b) position X5 of [N3] is: S, K, T, F, I, L, Y, H, M, or R; and/or
   (c) position X6 of [N3] is: G, A, R, M, I, N, T, Y, D, P, V, L, E, W, N, Q, K, or S;
   optionally wherein the AAV capsid variant comprises an amino acid modification, e.g., a conservative substitution, of any of the aforesaid amino acids in (a)-(c).
5. The AAV capsid variant of any one of embodiments 1-4, wherein [N3] comprises SK, KA, KS, AR, RM, VK, AS, SR, VK, KR, KK, KN, VR, RS, RK, KT, TS, KF, FG, KI, IG, KL, LG, TT, TY, KY, YG, KD, KP, TR, RG, VR, GA, SL, SS, FL, WK, SA, RA, LR, KW, RR, GK, TK, NK, AK, KV, KG, KH, KM, TG, SE, SV, SW, SN, HG, SQ, LW, MG, MA, or SG.
6. The AAV capsid variant of any one of embodiments 1-5, wherein [N3] is or comprises SKA, KSG, ARM, VKS, ASR, VKI, KKN, VRM, RKA, KTS, KFG, KIG, KLG, KTT, KTY, KYG, SKD, SKP, TRG, VRG, KRG, GAR, KSA, KSR, SKL, SRA, SKR, SLR, SRG, SSR, FLR, SKW, SKS, WKA, VRR, SKV, SKT, SKG, GKA, TKA, NKA, SKL, SKN, AKA, KTG, KSL, KSE, KSV, KSW, KSN, KHG, KSQ, KSK, KLW, WKG, KMG, KMA, or RSG.
7. The AAV capsid variant of any one of embodiments 1-6, wherein [N2]-[N3] comprises SPHSK (SEQ ID NO: 4701), SPHKS (SEQ ID NO: 4704), SPHAR (SEQ ID NO: 4705), SPHVK (SEQ ID NO: 4706), SPHAS (SEQ ID NO: 4707), SPHKK (SEQ ID NO: 4708), SPHVR (SEQ ID NO: 4709), SPHRK (SEQ ID NO: 4710), SPHKT (SEQ ID NO: 4711), SPHKF (SEQ ID NO: 4712), SPHKI (SEQ ID NO: 4713), SPHKL (SEQ ID NO: 4714), SPHKY (SEQ ID NO: 4715), SPHTR (SEQ ID NO: 4716), SPHKR (SEQ ID NO: 4717), SPHGA (SEQ ID NO: 4718), SPHSR (SEQ ID NO: 4719), SPHSL (SEQ ID NO: 4720), SPHSS (SEQ ID NO: 4721), SPHFL (SEQ ID NO: 4722), SPHWK (SEQ ID NO: 4723), SPHGK (SEQ ID NO: 4724), SPHTK (SEQ ID NO: 4725), SPHNK (SEQ ID NO: 4726), SPHAK (SEQ ID NO: 4727), SPHKH (SEQ ID NO: 4728), SPHKM (SEQ ID NO: 4729), or SPHRS (SEQ ID NO: 4730).
8. The AAV capsid variant of any one of embodiments 1-7, wherein [N2]-[N3] is or comprises:

(i)
SPHSKA, (SEQ ID NO: 941)

SPHKSG, (SEQ ID NO: 946)

SPHARM, (SEQ ID NO: 947)

SPHVKS, (SEQ ID NO: 948)

SPHASR, (SEQ ID NO: 949)

SPHVKI, (SEQ ID NO: 950)

SPHKKN (SEQ ID NO: 954)

SPHVRM, (SEQ ID NO: 955)

-continued

SPHRKA, (SEQ ID NO: 956)

SPHKFG, (SEQ ID NO: 957)

SPHKIG, (SEQ ID NO: 958)

SPHKLG, (SEQ ID NO: 959)

SPHKTS, (SEQ ID NO: 963)

SPHKTT, (SEQ ID NO: 964)

SPHKTY, (SEQ ID NO: 965)

SPHKYG, (SEQ ID NO: 966)

SPHSKD, (SEQ ID NO: 967)

SPHSKP, (SEQ ID NO: 968)

SPHTRG, (SEQ ID NO: 972)

SPHVRG, (SEQ ID NO: 973)

SPHKRG, (SEQ ID NO: 974)

SPHGAR, (SEQ ID NO: 975)

SPHKSA, (SEQ ID NO: 977)

SPHKSR, (SEQ ID NO: 951)

SPHSKL, (SEQ ID NO: 960)

SPHSRA, (SEQ ID NO: 969)

SPHSKR, (SEQ ID NO: 978)

SPHSLR, (SEQ ID NO: 952)

SPHSRG, (SEQ ID NO: 961)

SPHSSR, (SEQ ID NO: 970)

SPHFLR, (SEQ ID NO: 979)

SPHSKW, (SEQ ID NO: 953)

SPHSKS, (SEQ ID NO: 962)

SPHWKA, (SEQ ID NO: 971)

SPHVRR, (SEQ ID NO: 980)

-continued

SPHSKT, (SEQ ID NO: 4731)

SPHSKG, (SEQ ID NO: 4732)

SPHGKA, (SEQ ID NO: 4733)

SPHNKA, (SEQ ID NO: 4734)

SPHSKN, (SEQ ID NO: 4735)

SPHAKA, (SEQ ID NO: 4736)

SPHSKV, (SEQ ID NO: 4737)

SPHKTG, (SEQ ID NO: 4738)

SPHTKA, (SEQ ID NO: 4739)

SPHKSL, (SEQ ID NO: 4740)

SPHKSE, (SEQ ID NO: 4741)

SPHKSV, (SEQ ID NO: 4742)

SPHKSW, (SEQ ID NO: 4743)

SPHKSN, (SEQ ID NO: 4744)

SPHKHG, (SEQ ID NO: 4745)

SPHKSQ, (SEQ ID NO: 4746)

SPHKSK, (SEQ ID NO: 4747)

SPHKLW, (SEQ ID NO: 4748)

SPHWKG, (SEQ ID NO: 4749)

SPHKMG, (SEQ ID NO: 4750)

SPHKMA, (SEQ ID NO: 4751)
or

SPHRSG; (SEQ ID NO: 976)

(ii) an amino acid sequence comprising any portion of an amino acid sequence in (i), e.g., any 2, 3, 4, or 5 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

9. The AAV capsid variant of any one of embodiments 1-8, which comprises an amino acid other than G at position 453

(e.g., V, R, D, E, M, T, I, S, A, N, L, K, H, P, W, or C), an amino acid other than S at position 454 (V, L, N, D, H, R, P, G, T, I, A, E, Y, M, or Q), and/or a G at position 455 (e.g., C, L, D, E, Y, H, V, A, N, P, or S), numbered according to any one of SEQ ID NOs: 36-59, 138, 981, 982.

10. The AAV capsid variant of any one of embodiments 1-8, which comprises the amino acid G at position 453, the amino acid S at position 454, and the amino acid G at position 455, numbered according to SEQ ID NO: 138 or 981.

11. The AAV capsid variant of any one of embodiments 1-9, which comprises the amino acid G at position 453, the amino acid H at position 454, and the amino acid D at position 455, numbered according to SEQ ID NO: 138 or 982.

12. The AAV capsid variant of any one of embodiments 1-11, wherein [N1] comprises X1, X2, and X3, wherein at least one of X1, X2, or X3 is G.

13. The AAV capsid variant of any one of embodiments 1-12, wherein:
   (a) position X1 of [N1] is: G, V, R, D, E, M, T, I, S, A, N, L, K, H, P, W, or C;
   (b) position X2 of [N1] is: S, V, L, N, D, H, R, P, G, T, I, A, E, Y, M, or Q; and/or
   (c) position X3 of [N1] is: G, C, L, D, E, Y, H, V, A, N, P, or S;
   optionally wherein the AAV capsid variant comprises an amino acid modification, e.g., a conservative substitution, of any of the aforesaid amino acids in (a)-(c).

14. The AAV capsid variant of any one of embodiments 1-13, wherein [N1] comprises GS, SG, GH, HD, GQ, QD, VS, CS, GR, RG, QS, SH, MS, RN, TS, IS, GP, ES, SS, GN, AS, NS, LS, GG, KS, GT, PS, RS, GI, WS, DS, ID, GL, DA, DG, ME, EN, KN, KE, AI, NG, PG, TG, SV, IG, LG, AG, EG, SA, YD, HE, HG, RD, ND, PD, MG, QV, DD, HN, HP, GY, GM, GD, or HS.

15. The AAV capsid variant of any one of embodiments 1-14, wherein [N1] is or comprises GSG, GHD, GQD, VSG, CSG, GRG, CSH, GQS, GSH, RVG, GSC, GLL, GDD, GHE, GNY, MSG, RNG, TSG, ISG, GPG, ESG, SSG, GNG, ASG, NSG, LSG, GGG, KSG, HSG, GTG, PSG, GSV, RSG, GIG, WSG, DSG, IDG, GLG, DAG, DGG, MEG, ENG, GSA, KNG, KEG, AIG, GYD, GHG, GRD, GND, GPD, GMG, GQV, GHN, GHP, or GHS.

16. The AAV capsid variant of any one of embodiments 1-15, wherein [N1]-[N2] comprises:

(i)
SGSPH,      (SEQ ID NO: 4752)
HDSPH,      (SEQ ID NO: 4703)
QDSPH,      (SEQ ID NO: 4753)
RGSPH,      (SEQ ID NO: 4754)
SHSPH,      (SEQ ID NO: 4755)
QSSPH,      (SEQ ID NO: 4756)
DDSPH,      (SEQ ID NO: 4757)
HESPH,      (SEQ ID NO: 4758)
NYSPH,      (SEQ ID NO: 4759)
VGSPH,      (SEQ ID NO: 4760)
SCSPH,      (SEQ ID NO: 4761)
LLSPH,      (SEQ ID NO: 4762)
NGSPH,      (SEQ ID NO: 4763)
PGSPH,      (SEQ ID NO: 4764)
GGSPH,      (SEQ ID NO: 4765)
TGSPH,      (SEQ ID NO: 4766)
SVSPH       (SEQ ID NO: 4767)
IGSPH,      (SEQ ID NO: 4768)
DGSPH,      (SEQ ID NO: 4769)
LGSPH,      (SEQ ID NO: 4770)
AGSPH,      (SEQ ID NO: 4771)
EGSPH,      (SEQ ID NO: 4772)
SASPH,      (SEQ ID NO: 4773)
YDSPH,      (SEQ ID NO: 4774)
HGSPH,      (SEQ ID NO: 4775)
RDSPH,      (SEQ ID NO: 4776)
NDSPH       (SEQ ID NO: 4777)
PDSPH,      (SEQ ID NO: 4778)
MGSPH,      (SEQ ID NO: 4779)
QVSPH,      (SEQ ID NO: 4780)
HNSPH,      (SEQ ID NO: 4781)
HPSPH,      (SEQ ID NO: 4782)
or
HSSPH;      (SEQ ID NO: 4783)

(ii) an amino acid sequence comprising any portion of an amino acid sequence in (i), e.g., any 2, 3, or 4 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or
(iv) an amino acid sequence comprising one, two, or three but no more than four different amino acids, relative to any one of the amino acid sequences in (i).

17. The AAV capsid variant of any one of embodiments 1-16, wherein [N1]-[N2] is or comprises:

(i)
GSGSPH, (SEQ ID NO: 4695)
GHDSPH, (SEQ ID NO: 4784)
GQDSPH, (SEQ ID NO: 4785)
VSGSPH, (SEQ ID NO: 4786)
CSGSPH, (SEQ ID NO: 4787)
GRGSPH, (SEQ ID NO: 4788)
CSHSPH, (SEQ ID NO: 4789)
GQSSPH, (SEQ ID NO: 4790)
GSHSPH, (SEQ ID NO: 4791)
GDDSPH, (SEQ ID NO: 4792)
GHESPH, (SEQ ID NO: 4793)
GNYSPH, (SEQ ID NO: 4794)
RVGSPH, (SEQ ID NO: 4795)
GSCSPH, (SEQ ID NO: 4796)
GLLSPH, (SEQ ID NO: 4797)
MSGSPH, (SEQ ID NO: 4798)
RNGSPH, (SEQ ID NO: 4799)
TSGSPH, (SEQ ID NO: 4800)
ISGSPH, (SEQ ID NO: 4801)
GPGSPH, (SEQ ID NO: 4802)
ESGSPH, (SEQ ID NO: 4803)
SSGSPH, (SEQ ID NO: 4804)
GNGSPH, (SEQ ID NO: 4805)
ASGSPH, (SEQ ID NO: 4806)
NSGSPH, (SEQ ID NO: 4807)
LSGSPH, (SEQ ID NO: 4808)
GGGSPH, (SEQ ID NO: 4809)
KSGSPH, (SEQ ID NO: 4810)
HSGSPH, (SEQ ID NO: 4811)
GTGSPH, (SEQ ID NO: 4812)
PSGSPH, (SEQ ID NO: 4813)
GSVSPH, (SEQ ID NO: 4814)
RSGSPH, (SEQ ID NO: 4815)
GIGSPH, (SEQ ID NO: 4816)
WSGSPH, (SEQ ID NO: 4817)
DSGSPH, (SEQ ID NO: 4818)
IDGSPH, (SEQ ID NO: 4819)
GLGSPH, (SEQ ID NO: 4820)
DAGSPH, (SEQ ID NO: 4821)
DGGSPH, (SEQ ID NO: 4822)
MEGSPH, (SEQ ID NO: 4823)
ENGSPH, (SEQ ID NO: 4824)
GSASPH, (SEQ ID NO: 4825)
KNGSPH, (SEQ ID NO: 4826)
KEGSPH, (SEQ ID NO: 4827)
AIGSPH, (SEQ ID NO: 4828)
GYDSPH, (SEQ ID NO: 4829)
GHGSPH, (SEQ ID NO: 4830)
GRDSPH, (SEQ ID NO: 4831)

-continued

GNDSPH, (SEQ ID NO: 4832)

GPDSPH, (SEQ ID NO: 4833)

GMGSPH, (SEQ ID NO: 4834)

GQVSPH, (SEQ ID NO: 4835)

GHNSPH, (SEQ ID NO: 4836)

GHPSPH, or (SEQ ID NO: 4837)

GHSSPH; (SEQ ID NO: 4838)

(ii) an amino acid sequence comprising any portion of an amino acid sequence in (i), e.g., any 2, 3, 4, or 5 amino acids, e.g., consecutive amino acids, thereof;
(iii) an amino acid sequence comprising one, two, or three but no more than four modifications, e.g., substitutions (e.g., conservative substitutions), insertions, or deletions, relative to any of the amino acid sequences in (i); or
(iv) an amino acid sequence comprising one, two, or three but no more than four different amino acids, relative to any one of the amino acid sequences in (i).

18. The AAV capsid variant of any one of embodiments 1-17, wherein [N1]-[N2]-[N3] comprises:

(i)

SGSPHSK, (SEQ ID NO: 4839)

HDSPHKS, (SEQ ID NO: 4840)

SGSPHAR, (SEQ ID NO: 4841)

SGSPHVK, (SEQ ID NO: 4842)

QDSPHKS, (SEQ ID NO: 4843)

SGSPHKK, (SEQ ID NO: 4844)

SGSPHVR, (SEQ ID NO: 4845)

SGSPHAS, (SEQ ID NO: 4846)

SGSPHRK, (SEQ ID NO: 4847)

SGSPHKT, (SEQ ID NO: 4848)

SHSPHKS, (SEQ ID NO: 4849)

QSSPHRS, (SEQ ID NO: 4850)

RGSPHAS, (SEQ ID NO: 4851)

RGSPHSK, (SEQ ID NO: 4852)

SGSPHKF, (SEQ ID NO: 4853)

SGSPHKI, (SEQ ID NO: 4854)

SGSPHKL, (SEQ ID NO: 4855)

SGSPHKY, (SEQ ID NO: 4856)

SGSPHTR, (SEQ ID NO: 4857)

SHSPHKR, (SEQ ID NO: 4858)

SGSPHGA, (SEQ ID NO: 4859)

HDSPHKR, (SEQ ID NO: 4860)

DDSPHKS, (SEQ ID NO: 4861)

HESPHKS, (SEQ ID NO: 4862)

NYSPHKI, (SEQ ID NO: 4863)

SGSPHSR, (SEQ ID NO: 4864)

SGSPHSL, (SEQ ID NO: 4865)

SGSPHSS, (SEQ ID NO: 4866)

VGSPHSK, (SEQ ID NO: 4867)

SCSPHRK, (SEQ ID NO: 4868)

SGSPHFL, (SEQ ID NO: 4869)

LLSPHWK, (SEQ ID NO: 4870)

NGSPHSK, (SEQ ID NO: 4871)

PGSPHSK, (SEQ ID NO: 4872)

GGSPHSK, (SEQ ID NO: 4873)

TGSPHSK, (SEQ ID NO: 4874)

SVSPHGK, (SEQ ID NO: 4875)

SGSPHTK, (SEQ ID NO: 4876)

IGSPHSK, (SEQ ID NO: 4877)

DGSPHSK, (SEQ ID NO: 4878)

| | |
|---|---|
| SGSPHNK, | (SEQ ID NO: 4879) |
| LGSPHSK, | (SEQ ID NO: 4880) |
| AGSPHSK, | (SEQ ID NO: 4881) |
| EGSPHSK, | (SEQ ID NO: 4882) |
| SASPHSK, | (SEQ ID NO: 4883) |
| SGSPHAK, | (SEQ ID NO: 4884) |
| HDSPHKI, | (SEQ ID NO: 4885) |
| YDSPHKS, | (SEQ ID NO: 4886) |
| HDSPHKT, | (SEQ ID NO: 4887) |
| RGSPHKR, | (SEQ ID NO: 4888) |
| HGSPHSK, | (SEQ ID NO: 4889) |
| RDSPHKS, | (SEQ ID NO: 4890) |
| NDSPHKS, | (SEQ ID NO: 4891) |
| QDSPHKI, | (SEQ ID NO: 4892) |
| PDSPHKI, | (SEQ ID NO: 4893) |
| PDSPHKS, | (SEQ ID NO: 4894) |
| MGSPHSK, | (SEQ ID NO: 4895) |
| HDSPHKH, | (SEQ ID NO: 4896) |
| QVSPHKS, | (SEQ ID NO: 4897) |
| HNSPHKS, | (SEQ ID NO: 4898) |
| NGSPHKR, | (SEQ ID NO: 4899) |
| HDSPHKY, | (SEQ ID NO: 4900) |
| NDSPHKI, | (SEQ ID NO: 4901) |
| HDSPHKL, | (SEQ ID NO: 4902) |
| HPSPHWK, | (SEQ ID NO: 4903) |
| HDSPHKM, or | (SEQ ID NO: 4904) |
| HSSPHRS; | (SEQ ID NO: 4905) |

(ii) an amino acid sequence comprising any portion of an amino acid sequence in (i), e.g., any 2, 3, 4, 5, or 6 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

19. The AAV capsid variant of any one of embodiments 1-18, wherein [N1]-[N2]-[N3] is or comprises:

(i)

| | |
|---|---|
| GSGSPHSKA, | (SEQ ID NO: 4697) |
| GHDSPHKSG, | (SEQ ID NO: 4698) |
| GSGSPHARM | (SEQ ID NO: 4906) |
| GSGSPHVKS, | (SEQ ID NO: 4907) |
| GQDSPHKSG, | (SEQ ID NO: 4908) |
| GSGSPHASR, | (SEQ ID NO: 4909) |
| GSGSPHVKI, | (SEQ ID NO: 4910) |
| GSGSPHKKN, | (SEQ ID NO: 4911) |
| GSGSPHVRM, | (SEQ ID NO: 4912) |
| VSGSPHSKA, | (SEQ ID NO: 4913) |
| CSGSPHSKA, | (SEQ ID NO: 4914) |
| GSGSPHRKA, | (SEQ ID NO: 4915) |
| CSGSPHKTS, | (SEQ ID NO: 4916) |
| CSHSPHKSG, | (SEQ ID NO: 4917) |
| GQSSPHRSG, | (SEQ ID NO: 4918) |
| GRGSPHASR, | (SEQ ID NO: 4919) |
| GRGSPHSKA, | (SEQ ID NO: 4920) |
| GSGSPHKFG, | (SEQ ID NO: 4921) |
| GSGSPHKIG, | (SEQ ID NO: 4922) |
| GSGSPHKLG, | (SEQ ID NO: 4923) |
| GSGSPHKTS, | (SEQ ID NO: 4924) |

GSGSPHKTT, (SEQ ID NO: 4925)

GSGSPHKTY, (SEQ ID NO: 4926)

GSGSPHKYG, (SEQ ID NO: 4927)

GSGSPHSKD, (SEQ ID NO: 4928)

GSGSPHSKP, (SEQ ID NO: 4929)

GSGSPHTRG, (SEQ ID NO: 4930)

GSGSPHVRG, (SEQ ID NO: 4931)

GSHSPHKRG, (SEQ ID NO: 4932)

GSHSPHKSG, (SEQ ID NO: 4933)

VSGSPHASR, (SEQ ID NO: 4934)

VSGSPHGAR, (SEQ ID NO: 4935)

VSGSPHKFG, (SEQ ID NO: 4936)

GHDSPHKRG, (SEQ ID NO: 4937)

GDDSPHKSG, (SEQ ID NO: 4938)

GHESPHKSA, (SEQ ID NO: 4939)

GHDSPHKSA, (SEQ ID NO: 4940)

GNYSPHKIG, (SEQ ID NO: 4941)

GHDSPHKSR, (SEQ ID NO: 4942)

GSGSPHSKL, (SEQ ID NO: 4943)

GSGSPHSRA, (SEQ ID NO: 4944)

GSGSPHSKR, (SEQ ID NO: 4945)

GSGSPHSLR, (SEQ ID NO: 4946)

GSGSPHSRG, (SEQ ID NO: 4947)

GSGSPHSSR, (SEQ ID NO: 4948)

RVGSPHSKA, (SEQ ID NO: 4949)

GSCSPHRKA, (SEQ ID NO: 4950)

GSGSPHFLR, (SEQ ID NO: 4951)

GSGSPHSKW, (SEQ ID NO: 4952)

GSGSPHSKS, (SEQ ID NO: 4953)

GLLSPHWKA, (SEQ ID NO: 4954)

GSGSPHVRR, (SEQ ID NO: 4955)

GSGSPHSKV, (SEQ ID NO: 4956)

MSGSPHSKA, (SEQ ID NO: 4957)

RNGSPHSKA, (SEQ ID NO: 4958)

TSGSPHSKA, (SEQ ID NO: 4959)

ISGSPHSKA, (SEQ ID NO: 4960)

GPGSPHSKA, (SEQ ID NO: 4961)

GSGSPHSKT (SEQ ID NO: 4962)

ESGSPHSKA, (SEQ ID NO: 4963)

SSGSPHSKA, (SEQ ID NO: 4964)

GNGSPHSKA, (SEQ ID NO: 4965)

ASGSPHSKA, (SEQ ID NO: 4966)

NSGSPHSKA, (SEQ ID NO: 4967)

LSGSPHSKA, (SEQ ID NO: 4968)

GGGSPHSKA, (SEQ ID NO: 4969)

KSGSPHSKA (SEQ ID NO: 4970)

GGGSPHSKS, (SEQ ID NO: 4971)

GSGSPHSKG, (SEQ ID NO: 4972)

HSGSPHSKA, (SEQ ID NO: 4973)

GTGSPHSKA, (SEQ ID NO: 4974)

PSGSPHSKA, (SEQ ID NO: 4975)

GSVSPHGKA, (SEQ ID NO: 4976)

RSGSPHSKA, (SEQ ID NO: 4977)

GSGSPHTKA, (SEQ ID NO: 4978)

GIGSPHSKA, (SEQ ID NO: 4979)

WSGSPHSKA, (SEQ ID NO: 4980)

DSGSPHSKA, (SEQ ID NO: 4981)

IDGSPHSKA, (SEQ ID NO: 4982)

GSGSPHNKA, (SEQ ID NO: 4983)

GLGSPHSKS, (SEQ ID NO: 4984)

DAGSPHSKA, (SEQ ID NO: 4985)

DGGSPHSKA, (SEQ ID NO: 4986)

MEGSPHSKA, (SEQ ID NO: 4987)

ENGSPHSKA, (SEQ ID NO: 4988)

GSASPHSKA, (SEQ ID NO: 4989)

GNGSPHSKS, (SEQ ID NO: 4990)

KNGSPHSKA, (SEQ ID NO: 4991)

KEGSPHSKA, (SEQ ID NO: 4992)

AIGSPHSKA, (SEQ ID NO: 4993)

GSGSPHSKN (SEQ ID NO: 4994)

GSGSPHAKA, (SEQ ID NO: 4995)

GHDSPHKIG, (SEQ ID NO: 4996)

GYDSPHKSG, (SEQ ID NO: 4997)

GHESPHKSG, (SEQ ID NO: 4998)

GHDSPHKTG, (SEQ ID NO: 4999)

GRGSPHKRG, (SEQ ID NO: 5000)

GQDSPHKSG, (SEQ ID NO: 4908)

GHDSPHKSL (SEQ ID NO: 5001)

GHGSPHSKA, (SEQ ID NO: 5002)

GHDSPHKSE, (SEQ ID NO: 5003)

VSGSPHSKA, (SEQ ID NO: 4913)

GRDSPHKSG, (SEQ ID NO: 5004)

GNDSPHKSV, (SEQ ID NO: 5005)

GQDSPHKIG, (SEQ ID NO: 5006)

GHDSPHKSV, (SEQ ID NO: 5007)

GPDSPHKIG, (SEQ ID NO: 5008)

GPDSPHKSG, (SEQ ID NO: 5009)

GHDSPHKSW, (SEQ ID NO: 5010)

GHDSPHKSN, (SEQ ID NO: 5011)

GMGSPHSKT, (SEQ ID NO: 5012)

GHDSPHKHG, (SEQ ID NO: 5013)

GQVSPHKSG, (SEQ ID NO: 5014)

GDDSPHKSV, (SEQ ID NO: 5015)

GHNSPHKSG, (SEQ ID NO: 5016)

GNGSPHKRG, (SEQ ID NO: 5017)

GHDSPHKYG, (SEQ ID NO: 5018)

GHDSPHKSQ, (SEQ ID NO: 5019)

GNDSPHKIG, (SEQ ID NO: 5020)

GHDSPHKSK, (SEQ ID NO: 5021)

GHDSPHKLW, (SEQ ID NO: 5022)

GHPSPHWKG, (SEQ ID NO: 5023)

GHDSPHKMG, (SEQ ID NO: 5024)

GHDSPHKMA, (SEQ ID NO: 5025)
or

GHSSPHRSG; (SEQ ID NO: 5026)

(ii) an amino acid sequence comprising any portion of an amino acid sequence in (i), e.g., any 2, 3, 4, 5, 6, 7, or 8 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

20. The AAV capsid variant of any one of embodiments 1-19, wherein [N3] comprises SK, KA, KS, or SG.
21. The AAV capsid variant of any one of embodiments 1-20, wherein [N3] is or comprises SKA, KSG, or KYG.
22. The AAV capsid variant of any one of embodiments 1-21, wherein [N2]-[N3] comprises SPHSK (SEQ ID NO: 4701), SPHKS (SEQ ID NO: 4704), or SPHKY (SEQ ID NO: 4715).
23. The AAV capsid variant of any one of embodiments 1-22, wherein [N2]-[N3] is or comprises SPHSKA (SEQ ID NO: 941).
24. The AAV capsid variant of any one of embodiments 1-22, wherein [N2]-[N3] is or comprises SPHKSG (SEQ ID NO: 946).
25. The AAV capsid variant of any one of embodiments 1-22, wherein [N2]-[N3] is or comprises SPHKYG (SEQ ID NO: 966).
26. The AAV capsid variant of any one of embodiments 1-25, wherein [N1] comprises GS, SG, GH, or HD.
27. The AAV capsid variant of any one of embodiments 1-26, wherein [N1] is or comprises GSG.
28. The AAV capsid variant of any one of embodiments 1-26, wherein [N1] is or comprises GHD.
29. The AAV capsid variant of any one of embodiments 1-23 or 26-27, wherein [N1]-[N2]-[N3] comprises SGSPHSK (SEQ ID NO: 4839).
30. The AAV capsid variant of any one of embodiments 1-22, 24, 26, or 28, wherein [N1]-[N2]-[N3] comprises HDSPHKS (SEQ ID NO: 4840).
31. The AAV capsid variant of any one of embodiments 1-22 or 25-27, wherein [N1]-[N2]-[N3] comprises SGSPHKYG (SEQ ID NO: 5027).
32. The AAV capsid variant of any one of embodiments 1-8, 10, 12-23, 26-27, or 29, wherein [N1]-[N2]-[N3] is or comprises GSGSPHSKA (SEQ ID NO: 4697).
33. The AAV capsid variant of any one of embodiments 1-9, 11-22, 24, 26, 28, or 30, wherein [N1]-[N2]-[N3] is or comprises GHDSPHKSG (SEQ ID NO: 4698).
34. The AAV capsid variant of any one of embodiments 1-8, 10, 12-22, 25-27, or 31, wherein [N1]-[N2]-[N3] is or comprises GSGSPHKYG (SEQ ID NO: 4927).
35. The AAV capsid variant of any one of embodiments 1-34, wherein [N1]-[N2]-[N3] replaces positions 453-455, numbered according to the amino acid sequence of SEQ ID NO: 138.
36. The AAV capsid variant of any one of embodiments 1-35, which comprises an amino acid other than Q at position 456 (e.g., W, K, R, G, L, V, S, P, H, K, I, M, A, E, or F), an amino acid other than N at position 457 (e.g., Y, C, K, T, H, R, D, V, S, P, G, W, E, F, A, I, M, Q, or L), an amino acid other than Q at position 458 (e.g., G, K, H, R, T, L, D, A, P, I, F, V, M, W, Y, S, E, N, or Y), and/or an amino acid other than Q at position 459 (e.g., H, L, R, W, K, A, P, E, M, I, S, G, N, Y, C, V, T, D, or V), relative to a reference sequence numbered according to SEQ ID NO: 138.
37. The AAV capsid variant of any one of embodiments 1-36, which comprises an amino acid other than Q at position 462 (e.g., W, K, R, G, L, V, S, P, H, K, I, M, A, E, or F), an amino acid other than N at position 463 (e.g., Y, C, K, T, H, R, D, V, S, P, G, W, E, F, A, I, M, Q, or L), an amino acid other than Q at position 464 (e.g., G, K, H, R, T, L, D, A, P, I, F, V, M, W, Y, S, E, N, or Y), and/or an amino acid other than Q at position 465 (e.g., H, L, R, W, K, A, P, E, M, I, S, G, N, Y, C, V, T, D, or V), relative to a reference sequence numbered according to SEQ ID NO: 981, 982, 36, 37, 39, 40, 42-46, 48, 49, 50, 52, 53, 56, or 57.
38. The AAV capsid variant of any one of embodiments 1-37, which comprises:
    (a) the amino acid Q at position 456, the amino acid N at position 457, the amino acid Q at position 458, and/or the amino acid Q at position 459, relative to a reference sequence numbered according to SEQ ID NO: 138; or
    (b) the amino acid Q at position 462, the amino acid N at position 463, the amino acid Q at position 464, and/or the amino acid Q at position 465, relative to a reference sequence numbered according to SEQ ID NO: 981, 982, 36, 37, 39, 40, 42-46, 48, 49, 50, 52, 53, 56, or 57.
39. The AAV capsid variant of any one of embodiments 1-38, which further comprises [N4], wherein [N4] comprises X7 X8 X9 X10, and wherein:
    (a) position X7 is: Q, W, K, R, G, L, V, S, P, H, K, I, M, A, E, or F;
    (b) position X8 is: N, Y, C, K, T, H, R, D, V, S, P, G, W, E, F, A, I, M, Q, or L;
    (c) position X9 is: Q, G, K, H, R, T, L, D, A, P, I, F, V, M, W, Y, S, E, N, or Y; and
    (d) position X10 is: Q, H, L, R, W, K, A, P, E, M, I, S, G, N, Y, C, V, T, D, or V;
    optionally wherein the AAV capsid variant comprises an amino acid modification, e.g., a conservative substitution, of any of the aforesaid amino acids in (a)-(d).
40. The AAV capsid variant of embodiment 39, wherein:
    (a) position X7 of [N4] is Q or R;
    (b) position X8 of [N4] is N or R;
    (c) position X9 of [N4] is Q or R; and
    (d) position X10 of [N4] is Q, L, or R.
41. The AAV capsid variant of embodiment 39 or 40, wherein [N4] is or comprises:

(i)

QNQQ, (SEQ ID NO: 5028)

WNQQ, (SEQ ID NO: 5029)

QYYV, (SEQ ID NO: 5030)

RRQQ, (SEQ ID NO: 5031)

GCGQ, (SEQ ID NO: 5032)

LRQQ, (SEQ ID NO: 5033)

RNQQ, (SEQ ID NO: 5034)

VNQQ, (SEQ ID NO: 5035)

FRLQ, (SEQ ID NO: 5036)

FNQQ, (SEQ ID NO: 5037)

LLQQ, (SEQ ID NO: 5038)

SNQQ, (SEQ ID NO: 5039)

RLQQ, (SEQ ID NO: 5040)

LNQQ, (SEQ ID NO: 5041)

QRKL, (SEQ ID NO: 5042)

LRRQ, (SEQ ID NO: 5043)

QRLR, (SEQ ID NO: 5044)

QRRL, (SEQ ID NO: 5045)

RRLQ, (SEQ ID NO: 5046)

RLRQ, (SEQ ID NO: 5047)

SKRQ, (SEQ ID NO: 5048)

QLYR, (SEQ ID NO: 5049)

QLTV, (SEQ ID NO: 5050)

QNKQ, (SEQ ID NO: 5051)

KNQQ, (SEQ ID NO: 5052)

QKQQ, (SEQ ID NO: 5053)

QTQQ, (SEQ ID NO: 5054)

QNHQ, (SEQ ID NO: 5055)

QHQQ, (SEQ ID NO: 5056)

QNQH, (SEQ ID NO: 5057)

QHRQ, (SEQ ID NO: 5058)

LTQQ, (SEQ ID NO: 5059)

QNQW, (SEQ ID NO: 5060)

QNTH, (SEQ ID NO: 5061)

RRRQ, (SEQ ID NO: 5062)

QYQQ, (SEQ ID NO: 5063)

QNDQ, (SEQ ID NO: 5064)

QNRH, (SEQ ID NO: 5065)

RDQQ, (SEQ ID NO: 5066)

PNLQ, (SEQ ID NO: 5067)

HVRQ, (SEQ ID NO: 5068)

PNQH, (SEQ ID NO: 5069)

HNQQ, (SEQ ID NO: 5070)

QSQQ, (SEQ ID NO: 5071)

QPAK, (SEQ ID NO: 5072)

QNLA, (SEQ ID NO: 5073)

QNQL, (SEQ ID NO: 5074)

QGQQ, (SEQ ID NO: 5075)

LNRQ, (SEQ ID NO: 5076)

QNPP, (SEQ ID NO: 5077)

QNLQ, (SEQ ID NO: 5078)

QDQE, (SEQ ID NO: 5079)

QDQQ, (SEQ ID NO: 5080)

HWQQ, (SEQ ID NO: 5081)

PNQQ, (SEQ ID NO: 5082)

PEQQ, (SEQ ID NO: 5083)

QRTM, (SEQ ID NO: 5084)

LHQH, (SEQ ID NO: 5085)

QHRI, (SEQ ID NO: 5086)

QYIH, (SEQ ID NO: 5087)

QKFE, (SEQ ID NO: 5088)

QFPS, (SEQ ID NO: 5089)

QNPL, (SEQ ID NO: 5090)

QAIK, (SEQ ID NO: 5091)

QNRQ, (SEQ ID NO: 5092)

QYQH, (SEQ ID NO: 5093)

-continued

QNPQ, (SEQ ID NO: 5094)

QHQL, (SEQ ID NO: 5095)

QSPP, (SEQ ID NO: 5096)

QAKL, (SEQ ID NO: 5097)

KSQQ, (SEQ ID NO: 5098)

QDRP, (SEQ ID NO: 5099)

QNLG, (SEQ ID NO: 5100)

QAFH, (SEQ ID NO: 5101)

QNAQ, (SEQ ID NO: 5102)

HNQL, (SEQ ID NO: 5103)

QKLN, (SEQ ID NO: 5104)

QNVQ, (SEQ ID NO: 5105)

QAQQ, (SEQ ID NO: 5106)

QTPP, (SEQ ID NO: 5107)

QPPA, (SEQ ID NO: 5108)

QERP, (SEQ ID NO: 5109)

QDLQ, (SEQ ID NO: 5110)

QAMH, (SEQ ID NO: 5111)

QHPS, (SEQ ID NO: 5112)

PGLQ, (SEQ ID NO: 5113)

QGIR, (SEQ ID NO: 5114)

QAPA, (SEQ ID NO: 5115)

QIPP, (SEQ ID NO: 5116)

QTQL, (SEQ ID NO: 5117)

QAPS, (SEQ ID NO: 5118)

QNTY, (SEQ ID NO: 5119)

QDKQ, (SEQ ID NO: 5120)

-continued

QNHL, (SEQ ID NO: 5121)

QIGM, (SEQ ID NO: 5122)

LNKQ, (SEQ ID NO: 5123)

PNQL, (SEQ ID NO: 5124)

QLQQ, (SEQ ID NO: 5125)

QRMS, (SEQ ID NO: 5126)

QGIL, (SEQ ID NO: 5127)

QDRQ, (SEQ ID NO: 5128)

RDWQ, (SEQ ID NO: 5129)

QERS, (SEQ ID NO: 5130)

QNYQ, (SEQ ID NO: 5131)

QRTC, (SEQ ID NO: 5132)

QIGH, (SEQ ID NO: 5133)

QGAI, (SEQ ID NO: 5134)

QVPP, (SEQ ID NO: 5135)

QVQQ, (SEQ ID NO: 5136)

LMRQ, (SEQ ID NO: 5137)

QYSV, (SEQ ID NO: 5138)

QAIT, (SEQ ID NO: 5139)

QKTL, (SEQ ID NO: 5140)

QLHH, (SEQ ID NO: 5141)

QNII, (SEQ ID NO: 5142)

QGHH, (SEQ ID NO: 5143)

QSKV, (SEQ ID NO: 5144)

QLPS, (SEQ ID NO: 5145)

IGKQ, (SEQ ID NO: 5146)

QAIH, (SEQ ID NO: 5147)

-continued

QHGL, (SEQ ID NO: 5148)

QFMC, (SEQ ID NO: 5149)

QNQM, (SEQ ID NO: 5150)

QHLQ, (SEQ ID NO: 5151)

QPAR, (SEQ ID NO: 5152)

QSLQ, (SEQ ID NO: 5153)

QSQL, (SEQ ID NO: 5154)

HSQQ, (SEQ ID NO: 5155)

QMPS, (SEQ ID NO: 5156)

QGSL, (SEQ ID NO: 5157)

QVPA, (SEQ ID NO: 5158)

HYQQ, (SEQ ID NO: 5159)

QVPS, (SEQ ID NO: 5160)

RGEQ, (SEQ ID NO: 5161)

PGQQ, (SEQ ID NO: 5162)

LEQQ, (SEQ ID NO: 5163)

QNQS, (SEQ ID NO: 5164)

QKVI, (SEQ ID NO: 5165)

QNND, (SEQ ID NO: 5166)

QSVH, (SEQ ID NO: 5167)

QPLG, (SEQ ID NO: 5168)

HNQE, (SEQ ID NO: 5169)

QIQQ, (SEQ ID NO: 5170)

QVRN, (SEQ ID NO: 5171)

PSNQ, (SEQ ID NO: 5172)

QVGH, (SEQ ID NO: 5173)

QRDI, (SEQ ID NO: 5174)

-continued

QMPN, (SEQ ID NO: 5175)

RGLQ, (SEQ ID NO: 5176)

PSLQ, (SEQ ID NO: 5177)

QRDQ, (SEQ ID NO: 5178)

QAKG, (SEQ ID NO: 5179)

QSAH, (SEQ ID NO: 5180)

QSTM, (SEQ ID NO: 5181)

QREM, (SEQ ID NO: 5182)

QYRA, (SEQ ID NO: 5183)

QRQQ, (SEQ ID NO: 5184)

QWQQ, (SEQ ID NO: 5185)

QRMN, (SEQ ID NO: 5186)

GDSQ, (SEQ ID NO: 5187)

QKIS, (SEQ ID NO: 5188)

PSMQ, (SEQ ID NO: 5189)

SPRQ, (SEQ ID NO: 5190)

MEQQ, (SEQ ID NO: 5191)

QYQN, (SEQ ID NO: 5192)

QIRQ, (SEQ ID NO: 5193)

QSVQ, (SEQ ID NO: 5194)

RSQQ, (SEQ ID NO: 5195)

QNKL, (SEQ ID NO: 5196)

QIQH, (SEQ ID NO: 5197)

PRQQ, (SEQ ID NO: 5198)

HTQQ, (SEQ ID NO: 5199)

QRQH, (SEQ ID NO: 5200)

RNQE, (SEQ ID NO: 5201)

-continued

QSKQ, (SEQ ID NO: 5202)

QNQP, (SEQ ID NO: 5203)

QSPQ, (SEQ ID NO: 5204)

QTRQ, (SEQ ID NO: 5205)

QNLH, (SEQ ID NO: 5206)

QNQE, (SEQ ID NO: 5207)

LNQP, (SEQ ID NO: 5208)

QNQD, (SEQ ID NO: 5209)

QNLL, (SEQ ID NO: 5210)

QLVI, (SEQ ID NO: 5211)

RTQE, (SEQ ID NO: 5212)

QTHQ, (SEQ ID NO: 5213)

QDQH, (SEQ ID NO: 5214)

QSQH, (SEQ ID NO: 5215)

VRQQ, (SEQ ID NO: 5216)

AWQQ, (SEQ ID NO: 5217)

QSVP, (SEQ ID NO: 5218)

QNIQ, (SEQ ID NO: 5219)

LDQQ, (SEQ ID NO: 5220)

PDQQ, (SEQ ID NO: 5221)

ESQQ, (SEQ ID NO: 5222)

QRQL, (SEQ ID NO: 5223)

QIIV, (SEQ ID NO: 5224)

QKQS, (SEQ ID NO: 5225)

QSHQ, (SEQ ID NO: 5226)

QFVV, (SEQ ID NO: 5227)

QSQP, (SEQ ID NO: 5228)

QNEQ, (SEQ ID NO: 5229)

INQQ, (SEQ ID NO: 5230)

RNRQ, (SEQ ID NO: 5231)

RDQK, (SEQ ID NO: 5232)

QWKR, (SEQ ID NO: 5233)

ENRQ, (SEQ ID NO: 5234)

QTQP, (SEQ ID NO: 5235)

QKQL, (SEQ ID NO: 5236)

RNQL, (SEQ ID NO: 5237)

ISIQ, (SEQ ID NO: 5238)

QTVC, (SEQ ID NO: 5239)

QQIM, (SEQ ID NO: 5240)

LNHQ, (SEQ ID NO: 5241)

QNQA, (SEQ ID NO: 5242)

QMIH, (SEQ ID NO: 5243)

RNHQ, (SEQ ID NO: 5244)
or

QKMN; (SEQ ID NO: 5245)

(ii) an amino acid sequence comprising any portion of an amino acid sequence in (i), e.g., any 2, or 3 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

42. The AAV capsid variant of any one of embodiments 39-41, wherein [N1]-[N2]-[N3]-[N4] is or comprises:

(i) the amino acid sequence of any of SEQ ID NOs: 1800-2241;

(ii) an amino acid sequence comprising any portion of an amino acid sequence in (i), e.g., any 2, 3, 4, 5, 6, 7, 8, 9, 10, 11, or 12 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

43. The AAV capsid variant of any one of embodiments 39-42, wherein [N1]-[N2]-[N3]-[N4] is or comprises GSGSPHSKAQNQQ (SEQ ID NO: 1801).

44. The AAV capsid variant of any one of embodiments 39-42, wherein [N1]-[N2]-[N3]-[N4] is or comprises GHDSPHKSGQNQQ (SEQ ID NO: 1800).

45. The AAV capsid variant of any one of embodiments 39-42, wherein [N1]-[N2]-[N3]-[N4] is or comprises GSGSPHKYGQNQQT (SEQ ID NO: 910).

46. The AAV capsid variant of any one of embodiments 1-45, which comprises an amino acid other than T at position 450 (e.g., S, Y, M, A, C, I, R, L, D, F, V, Q, N, H, E, or G), an amino acid other than I at position 451 (e.g., M, P, E, N, D, S, A, T, G, Q, F, V, L, C, H, R, W, or L), and/or an amino acid other than N at position 452 (e.g., M, E, G, Y, W, T, I, Q, F, V, A, L, I, P, K, R, H, S, D, or S), relative to a reference sequence numbered according to any one of SEQ ID NOs: 36-59, 138, 981, or 982.

47. The AAV capsid variant of any one of embodiments 1-46, which comprises the amino acid T at position 450, the amino acid I at position 451, and/or the amino acid N at position 452, relative to a reference sequence numbered according to any one of SEQ ID NOs: 138, 981, or 982.

48. The AAV capsid variant of any one of embodiments 1-47, which further comprises [N0], wherein [N0] comprises XA XB and XC, and wherein:
   (a) position XA is: T, S, Y, M, A, C, I, R, L, D, F, V, Q, N, H, E, or G;
   (b) position XB is: I, M, P, E, N, D, S, A, T, G, Q, F, V, L, C, H, R, W, or L; and
   (c) position XC is: N, M, E, G, Y, W, T, I, Q, F, V, A, L, I, P, K, R, H, S, D, or S; and optionally wherein the AAV capsid variant comprises an amino acid modification, e.g., a conservative substitution, of any of the aforesaid amino acids in (a)-(c).

49. The AAV capsid variant of embodiment 48, wherein [N0] is or comprises TIN, SMN, TIM, YLS, GLS, MPE, MEG, MEY, AEW, CEW, ANN, IPE, ADM, IEY, ADY, IET, MEW, CEY, RIN, MEI, LEY, ADW, IEI, DIM, FEQ, MEF, CDQ, LPE, IEN, MES, AEI, VEY, IIN, TSN, IEV, MEM, AEV, MDA, VEW, AEQ, LEW, MEL, MET, MEA, IES, MEV, CEI, ATN, MDG, QEV, ADQ, NMN, IEM, ISN, TGN, QQQ, HDW, IEG, TII, TFP, TEK, EIN, TVN, TFN, SIN, TER, TSY, ELH, AIN, SVN, TDN, TFH, TVH, TEN, TSS, TID, TCN, NIN, TEH, AEM, AIK, TDK, TFK, SDQ, TEI, NTN, TET, SIK, TEL, TEA, TAN, TIY, TFS, TES, TTN, TED, TNN, EVH, TIS, TVR, TDR, TIK, NHI, TIP, ESD, TDL, TVP, TVI, AEH, NCL, TVK, NAD, TIT, NCV, TIR, NAL, VIN, TIQ, TEF, TRE, QGE, SEK, NVN, GGE, EFV, SDK, TEQ, EVQ, TEY, NCW, TDV, SDI, NSI, NSL, EVV, TEP, SEL, TWQ, TEV, AVN, GVL, TLN, TEG, TRD, NAI, AEN, AET, ETA, NNL, or any dipeptide thereof.

50. The AAV capsid variant of embodiment 48 or 49, wherein [N0]-[N1]-[N2]-[N3]-[N4] is or comprises:
   (i) the amino acid sequence of any one of SEQ ID NOs: 2242-2886;
   (ii) an amino acid sequence comprising any portion of an amino acid sequence in (i), e.g., any 2, 3, 4, 5, 6, 7, 8, 9, 10, 11, 12, 13, 14, or 15 amino acids, e.g., consecutive amino acids, thereof;
   (iii) an amino acid sequence comprising one, two, or three but no more than four modifications, e.g., substitutions (e.g., conservative substitutions), insertions, or deletions, relative to any of the amino acid sequences in (i); or
   (iv) an amino acid sequence comprising one, two, or three but no more than four different amino acids, relative to any one of the amino acid sequences in (i).

51. The AAV capsid variant of any one of embodiments 48-50, wherein [N0]-[N1]-[N2]-[N3]-[N4] is or comprises TINGSGSPHSKAQNQQ (SEQ ID NO: 2242).

52. The AAV capsid variant of any one of embodiments 48-50, wherein [N0]-[N1]-[N2]-[N3]-[N4] is or comprises TINGHDSPHKSGQNQQ (SEQ ID NO: 2243).

53. The AAV capsid variant of any one of embodiments 48-52, wherein [N0]-[N1]-[N2]-[N3]-[N4] is or comprises TINGSGSPHKYGQNQQT (SEQ ID NO: 5246).

54. The AAV capsid variant of any one of embodiments 1-53, wherein [N1]-[N2]-[N3] is present in loop IV.

55. The AAV capsid variant of any one of embodiments 48-54, wherein [N0] and [N4] are present in loop IV.

56. The AAV capsid variant of any one of embodiments 48-55, wherein [N0] is present immediately subsequent to position 449, relative to a reference sequence numbered according to the amino acid sequence of SEQ ID NO: 138.

57. The AAV capsid variant of any one of embodiments 48-56, wherein [N0] is present immediately subsequent to position 449, relative to a reference sequence numbered according to the amino acid sequence of any one of SEQ ID NOs: 36-59, 981, or 982.

58. The AAV capsid variant of any one of embodiments 48-57, wherein [N0] replaces positions 450, 451, and 452 (e.g., T450, I451, and N452), relative to a reference sequence numbered according to SEQ ID NO: 138.

59. The AAV capsid variant of any one of embodiments 48-58, wherein [N0] replaces positions 450-452 (e.g., T450, I451, and N452), relative to a reference sequence numbered according to any one of SEQ ID NOs: 36-59, 981, or 982.

60. The AAV capsid variant of any one of embodiments 48-59, wherein [N0] corresponds to positions 450-452 of any one of SEQ ID NOs: 36-59, 138, 981 or 982.

61. The AAV capsid variant of any one of embodiments 48-60, wherein [N0] is present immediately subsequent to position 449 and wherein [N0] replaces positions 450-452 (e.g., T450, I451, and N452), relative to a reference sequence numbered according to SEQ ID NO: 138.

62. The AAV capsid variant of any one of embodiments 48-61, wherein [N0] is present immediately subsequent to position 449 and wherein [N0] replaces positions 450-452 (e.g., T450, I451, and N452), relative to a reference sequence numbered according to any one of SEQ ID NOs: 36-59, 981, or 982.

63. The AAV capsid variant of any one of embodiments 1-62, wherein [N1] is present immediately subsequent to position 452, relative to a reference sequence numbered according to the amino acid sequence of SEQ ID NO: 138.

64. The AAV capsid variant of any one of embodiments 1-63, wherein [N1] is present immediately subsequent to position 452, relative to a reference sequence numbered according to the amino acid sequence of SEQ ID NO: 981 or 982.

65. The AAV capsid variant of any one of embodiments 1-61, wherein [N1] replaces positions 453-455 (e.g., G453, S454, and G455), relative to a reference sequence numbered according to SEQ ID NO: 138.

66. The AAV capsid variant of any one of embodiments 1-64, wherein [N1] replaces positions 453 (e.g., G453), relative to a reference sequence numbered according to SEQ ID NO: 138.

67. The AAV capsid variant of any one of embodiments 1-65, wherein [N1] replaces positions 453-455 (e.g., G453, S454, and G455), relative to a reference sequence numbered according to SEQ ID NO: 981.

68. The AAV capsid variant of any one of embodiments 1-65 or 67, wherein [N1] replaces positions 453-455, relative to a reference sequence numbered according to SEQ ID NO: 982.

69. The AAV capsid variant of any one of embodiments 1-65, 67, or 68, wherein [N1] is present immediately subsequent to position 452 and wherein [N1] replaces positions 453-455 (e.g., G453, S454, and G455), relative to a reference sequence numbered according to SEQ ID NO: 138.

70. The AAV capsid variant of any one of embodiments 1-64 or 66, wherein [N1] is present immediately subsequent to position 452 and wherein [N1] replaces positions 453 (e.g., G453), relative to a reference sequence numbered according to SEQ ID NO: 138.

71. The AAV capsid variant of any one of embodiments 1-64, 66 or 70, wherein [N1] is present immediately subsequent to position 452 and wherein [N1] replaces positions 453-455, relative to a reference sequence numbered according to SEQ ID NO: 981 or 982.

72. The AAV capsid variant of any one of embodiments 1-71, wherein [N1] corresponds to positions 453-455 of any one of SEQ ID NOs: 36-59, 981 or 982.

73. The AAV capsid variant of any one of embodiment 1-72, which comprises an amino acid other than S at position 454 and/or an amino acid other than G at position 455, numbered according to SEQ ID NO: 138, 981, or 982.

74. The AAV capsid variant of any one of embodiments 1-73, which comprises the amino acid H at position 454 and the amino acid D at position 455, numbered according to SEQ ID NO: 138 or 982.

75. The AAV capsid variant of any one of embodiments 1-74, which comprises a substitution at position 454 (e.g., S454H) and/or a substitution at position 455 (e.g., G455D), numbered according to SEQ ID NO: 138.

76. The AAV capsid variant of any one of embodiments 1-75, which comprises the amino acid H at position 454 and the amino acid D at position 455, and further comprises the amino acid sequence SPHSKA (SEQ ID NO: 941) immediately subsequent to position 455, relative to a reference sequence numbered according to SEQ ID NO: 138.

77. The AAV capsid variant of any one of embodiments 1-76, which comprises the amino acid H at position 454 and the amino acid D at position 455, relative to a reference sequence numbered according to SEQ ID NO: 982.

78. The AAV capsid variant of any one of embodiments 1-77, which comprises the amino acid H at position 454 and the amino acid D at position 455, and further comprises the amino acid sequence SPHSKA (SEQ ID NO: 941) immediately subsequent to position 455, relative to a reference sequence numbered according to SEQ ID NO: 982.

79. The AAV capsid variant of any one of embodiments 1-72, which comprises the amino acid S at position 454 and the amino acid G at position 455, relative to a reference sequence numbered according to SEQ ID NO: 138.

80. The AAV capsid variant of any one of embodiments 1-72 or 79, which comprises the amino acid S at position 454 and the amino acid G at position 455, and further comprises the amino acid sequence SPHSKA (SEQ ID NO: 941) immediately subsequent to position 455, relative to a reference sequence numbered according to SEQ ID NO: 138.

81. The AAV capsid variant of any one of embodiments 1-72, 79, or 80, which comprises the amino acid S at position 454 and the amino acid G at position 455, relative to a reference sequence numbered according to SEQ ID NO: 981.

82. The AAV capsid variant of any one of embodiments 1-72 or 79-81, which comprises the amino acid S at position 454 and the amino acid G at position 455, and further comprises the amino acid sequence SPHSKA (SEQ ID NO: 941) immediately subsequent to position 455, relative to a reference sequence numbered according to SEQ ID NO: 981.

83. The AAV capsid variant of any one of embodiments 1-82, wherein [N2] is present immediately subsequent to position 455, relative to a reference sequence numbered according to the amino acid sequence of SEQ ID NO: 138.

84. The AAV capsid variant of any one of embodiments 1-83, wherein [N2] corresponds to positions 456-458 (e.g., S456, P457, H458) of SEQ ID NO: 981 or 982.

85. The AAV capsid variant of any one of embodiments 1-83, wherein [N2] corresponds to positions 456-458 (e.g., S456, P457, H458) of any one of SEQ ID NOs: 36-59.

86. The AAV capsid variant of any one of embodiments 1-85, wherein [N2]-[N3] is present immediately subsequent to position 455, relative to a reference sequence numbered according to the amino acid sequence of SEQ ID NO: 138.

87. The AAV capsid variant of any one of embodiments 1-86, wherein [N2] is present immediately subsequent to position 455, relative to a reference sequence numbered according to the amino acid sequence of SEQ ID NO: 981 or 982.

88. The AAV capsid variant of any one of embodiments 1-87, wherein [N2]-[N3] is present immediately subsequent to position 455, relative to a reference sequence numbered according to the amino acid sequence of SEQ ID NO: 981 or 982.

89. The AAV capsid variant of any one of embodiments 1-88, wherein [N2]-[N3] corresponds to positions 456-461 (e.g., S456, P457, H458, S459, K460, A461) of SEQ ID NO: 981.

90. The AAV capsid variant of any one of embodiments 1-88, wherein [N2]-[N3] corresponds to positions 456-461 (e.g., S456, P457, H458, K459, S460, G461) of SEQ ID NO: 982.

91. The AAV capsid variant of any one of embodiments 1-90, wherein [N2] is present immediately subsequent to [N1].

92. The AAV capsid variant of any one of embodiments 1-64, 66, 70, or 71, wherein [N3] is present immediately subsequent to [N2] and replaces positions 454 and 455 (e.g., S454 and G455), numbered according to SEQ ID NO: 138.

93. The AAV capsid variant of any one of embodiments 1-1-64, 66, 70, 71, or 92, wherein [N3] is present immediately subsequent to [N1]-[N2] and replaces positions 454 and 455 (e.g., S454 and G455), numbered according to SEQ ID NO: 138.

94. The AAV capsid variant of any one of embodiments 39-93, wherein [N4] is present immediately subsequent to position 455, relative to a reference sequence numbered according to the amino acid sequence of SEQ ID NO: 138.

95. The AAV capsid variant of any one of embodiments 39-94, wherein [N4] replaces positions 456-459 (e.g., Q456, N457, Q458, and Q459), relative to a reference sequence numbered according to the amino acid sequence of SEQ ID NO: 138.

96. The AAV capsid variant of any one of embodiments 39-95, wherein [N4] corresponds to positions 462-465 (e.g., Q462, N463, Q464, Q465) of SEQ ID NO: 981 or 982.

97. The AAV capsid variant of any one of embodiments 39-96, wherein [N2]-[N3]-[N4] replaces positions 456-459

(e.g., Q456, N457, Q458, and Q459), relative to a reference sequence numbered according to the amino acid sequence of SEQ ID NO: 138.

98. The AAV capsid variant of any one of embodiments 39-97, wherein [N2]-[N3]-[N4] is present immediately subsequent to position 455, and wherein [N2]-[N3]-[N4] replaces positions 456-459 (e.g., Q456, N457, Q458, and Q459), relative to a reference sequence numbered according to the amino acid sequence of SEQ ID NO: 138.

99. The AAV capsid variant of any one of embodiments 39-98, wherein [N2]-[N3]-[N4] corresponds to positions 456-465 (e.g., S456, P457, H458, S459, K460, A461, Q462, N463, Q464, Q465) of SEQ ID NO: 981.

100. The AAV capsid variant of any one of embodiments 39-98, wherein [N2]-[N3]-[N4] corresponds to positions 456-465 (e.g., S456, P457, H458, K459, S460, G461, Q462, N463, Q464, Q465) of SEQ ID NO: 982.

101. The AAV capsid variant of any one of embodiments 39-98, wherein [N2]-[N3]-[N4] corresponds to positions 456-465 of any one of SEQ ID NOs: 36-59.

102. The AAV capsid variant of any one of embodiments 39-101, wherein [N1]-[N2]-[N3]-[N4] replaces positions 453-459 (e.g., G453, S454, G455, Q456, N457, Q458, and Q459), relative to a reference sequence numbered according to the amino acid sequence of SEQ ID NO: 138.

103. The AAV capsid variant of any one of embodiments 39-102, wherein [N1]-[N2]-[N3]-[N4] is present immediately subsequent to position 452, and wherein [N1]-[N2]-[N3]-[N4] replaces positions 453-459 (e.g., G453, S454, G455, Q456, N457, Q458, and Q459), relative to a reference sequence numbered according to the amino acid sequence of SEQ ID NO: 138.

104. The AAV capsid variant of any one of embodiments 39-99, 102,103, wherein [N1]-[N2]-[N3]-[N4] corresponds to positions 453-465 (e.g., G453, S454, G455, S456, P457, H458, S459, K460, A461, Q462, N463, Q464, Q465) of SEQ ID NO: 981.

105. The AAV capsid variant of any one of embodiments 39-98, 100, 102, or 103, wherein [N1]-[N2]-[N3]-[N4] corresponds to positions 453-465 (e.g., G453, H454, D455, S456, P457, H458, K459, S460, G461, Q462, N463, Q464, Q465) of SEQ ID NO: 982.

106. The AAV capsid variant of any one of embodiments 39-98, 102, or 103, wherein [N1]-[N2]-[N3]-[N4] corresponds to positions 453-465 of any one of SEQ ID NOs: 36-59.

107. The AAV capsid variant of any one of embodiments 1-99 or 102-104, wherein [N1]-[N2]-[N3] corresponds to positions 453-461 (e.g., G453, S454, G455, S456, P457, H458, S459, K460, A461) of SEQ ID NO: 981.

108. The AAV capsid variant of any one of embodiments 1-98, 100, 102, 103, or 105, wherein [N1]-[N2]-[N3] corresponds to positions 453-461 (e.g., G453, H454, D455, S456, P457, H458, K459, S460, G461) of SEQ ID NO: 982.

109. The AAV capsid variant of any one of embodiments 39-98, 102, 103, or 106, wherein [N1]-[N2]-[N3] corresponds to positions 453-461 of any one of SEQ ID NOs: 36-59.

110. The AAV capsid variant of any one of embodiments 48-109, wherein [N0]-[N1]-[N2]-[N3]-[N4] replaces positions 450-459 (e.g., T450, I451, N452, G453, S454, G455, Q456, N457, Q458, and Q459), relative to a reference sequence numbered according to the amino acid sequence of SEQ ID NO: 138.

111. The AAV capsid variant of any one of embodiments 48-110, wherein [N0]-[N1]-[N2]-[N3]-[N4] is present immediately subsequent to position 449, and wherein [N0]-[N1]-[N2]-[N3]-[N4] replaces positions 450-459 (e.g., T450, I451, N452, G453, S454, G455, Q456, N457, Q458, and Q459), relative to a reference sequence numbered according to the amino acid sequence of SEQ ID NO: 138.

112. The AAV capsid variant of any one of embodiments 48-99, 102-104, or 106, wherein [N0]-[N1]-[N2]-[N3]-[N4] corresponds to positions 450-465 (e.g., T450, I451, N452, G453, S454, G455, S456, P457, H458, S459, K460, A461, Q462, N463, Q464, Q465) of SEQ ID NO: 981.

113. The AAV capsid variant of any one of embodiments 48-98, 100, 102, 103, 105, or 108, wherein [N0]-[N1]-[N2]-[N3]-[N4] corresponds to positions 450-465 (e.g., T450, I451, N452, G453, H454, D455, S456, P457, H458, K459, S460, G461, Q462, N463, Q464, Q465) of SEQ ID NO: 982.

114. The AAV capsid variant of any one of embodiments 48-98, 102, 103, 106, or 109, wherein [N0]-[N1]-[N2]-[N3]-[N4] corresponds to positions 450-465 of any one of SEQ ID NOs: 36-59.

115. The AAV capsid variant of any one of embodiments 39-114, wherein [N4] replaces positions 462-465 (e.g., Q462, N463, Q464, and Q465), relative to a reference sequence numbered according to the amino acid sequence of SEQ ID NO: 981 or 982.

116. The AAV capsid variant of any one of embodiments 39-115, wherein [N2]-[N3]-[N4] replaces positions 462-465 (e.g., Q462, N463, Q464, and Q465), relative to a reference sequence numbered according to the amino acid sequence of SEQ ID NO: 981 or 982.

117. The AAV capsid variant of any one of embodiments 39-116, wherein [N2]-[N3]-[N4] is present immediately subsequent to position 455, and wherein [N2]-[N3]-[N4] replaces positions 462-465 (e.g., Q462, N463, Q464, and Q465), relative to a reference sequence numbered according to the amino acid sequence of SEQ ID NO: 981 or 982.

118. The AAV capsid variant of any one of embodiments 1-117, wherein [N3] is present immediately subsequent to [N2].

119. The AAV capsid variant of any one of embodiments 1-118, which comprises from N-terminus to C-terminus, [N2]-[N3].

120. The AAV capsid variant of any one of embodiments 1-119, which comprises from N-terminus to C-terminus, [N1]-[N2]-[N3].

121. The AAV capsid variant of any one of embodiments 48-120, which comprises from N-terminus to C-terminus, [N0]-[N1]-[N2]-[N3].

122. The AAV capsid variant of any one of embodiments 39-121, which comprises from N-terminus to C-terminus, [N1]-[N2]-[N3]-[N4].

123. The AAV capsid variant of any one of embodiments 48-122, which comprises from N-terminus to C-terminus, [N0]-[N1]-[N2]-[N3]-[N4].

124. The AAV capsid variant of any one of the preceding embodiments, which comprises an amino acid other T at position 460 (e.g., N, I, C, H, R, L, D, Y, A, M, Q, I, E, K, P, G or S), numbered according to the amino acid sequence of SEQ ID NO: 138.

125. The AAV capsid variant of any one of the preceding embodiments, which comprises the amino acid N, I, C, H, R, L, D, Y, A, M, Q, I, E, K, P, G or S at position 460, numbered according to the amino acid sequence of SEQ ID NO: 138.

126. The AAV capsid variant of any one of the preceding embodiments, which comprises an amino acid other T at position 466 (e.g., N, I, C, H, R, L, D, Y, A, M, Q, I, E, K, P, G or S), numbered according to the amino acid sequence of any one of SEQ ID NOs: 36-59, 981, or 982.

127. The AAV capsid variant of any one of the preceding embodiments, which comprises the amino acid N, I, C, H, R, L, D, Y, A, M, Q, I, E, K, P, G or S at position 466, numbered according to the amino acid sequence of any one of SEQ ID NOs: 36-59, 981 or 982.

128. The AAV capsid variant of any one of the preceding embodiments, which comprises an amino acid other K at position 449 (e.g., an E, an N, or a T), numbered according to the amino acid sequence of any one of SEQ ID NOs: 36-59, 138, 981, or 982.

129. The AAV capsid variant of any one of the preceding embodiments, which comprises the amino E, N, or T at position 449, numbered according to the amino acid sequence of any one of SEQ ID NOs: 36-59, 138, 981 or 982.

130. An AAV capsid variant, comprising [A][B](SEQ ID NO: 4694), wherein:
  (i) [A] comprises the amino acid sequence of GSGSPH (SEQ ID NO: 4695); and
  (ii) [B] comprises X1 X2 X3 X4 X5 X6 X7, wherein:
    (a) position X1 is: S, C, F, or V;
    (b) position X2 is: K, L, R, I, E, Y, V, or S;
    (c) position X3 is: A, R, L, G, I, Y, S, F, or W;
    (d) position X4 is: W, Q, R, G, L, V, S, or F;
    (e) position X5 is: N, Y, R, C, K, or L;
    (f) position X6 is: Q, G, K, R, T, L, or Y; and
    (g) position X7 is: Q, L, R, or V;
  optionally wherein the AAV capsid variant comprises an amino acid modification, e.g., a conservative substitution, of any of the aforesaid amino acids in (a)-(g).

131. The AAV capsid variant of embodiment 130, wherein
  (a) position X1 is S;
  (b) position X2 is K or L;
  (c) position X3 is: A, R, or L;
  (d) position X4 is: Q or R;
  (e) position X5 is: N or R;
  (f) position X6 is: Q or R; and
  (g) position X7 is: Q, L, or R.

132. The AAV capsid variant of embodiment 130 or 131, wherein [B] comprises:

(i)
SLLWNQQ, (SEQ ID NO: 5247)
SKAQYYV, (SEQ ID NO: 5248)
SKLRRQQ, (SEQ ID NO: 5249)
SIWQNQQ, (SEQ ID NO: 5250)
SKAGCGQ, (SEQ ID NO: 5251)
SRAQNQQ, (SEQ ID NO: 5252)
SKRLRQQ, (SEQ ID NO: 5253)
SLRRNQQ, (SEQ ID NO: 5254)
SRGRNQQ, (SEQ ID NO: 5255)
SEIVNQQ, (SEQ ID NO: 5256)
SSRRNQQ, (SEQ ID NO: 5257)
CLLQNQQ, (SEQ ID NO: 5258)
SKAFRLQ, (SEQ ID NO: 5259)
CLAQNQQ, (SEQ ID NO: 5260)
FLRQNQQ, (SEQ ID NO: 5261)
SLRFNQQ, (SEQ ID NO: 5262)
SYLRNQQ, (SEQ ID NO: 5263)
CSLQNQQ, (SEQ ID NO: 5264)
VLWQNQQ, (SEQ ID NO: 5265)
SKWLLQQ, (SEQ ID NO: 5266)
SLWSNQQ, (SEQ ID NO: 5267)
SKRRLQQ, (SEQ ID NO: 5268)
SVYLNQQ, (SEQ ID NO: 5269)
SLWLNQQ, (SEQ ID NO: 5270)
SKAQRKL, (SEQ ID NO: 5271)
SKALRRQ, (SEQ ID NO: 5272)
SKAQRLR, (SEQ ID NO: 5273)
SKAQNQQ, (SEQ ID NO: 5274)
SKAQRRL, (SEQ ID NO: 5275)
SKARRQQ, (SEQ ID NO: 5276)
SKARRLQ, (SEQ ID NO: 5277)
SKSRRQQ, (SEQ ID NO: 5278)
SKARLRQ, (SEQ ID NO: 5279)
SKASKRQ, (SEQ ID NO: 5280)
VRRQNQQ, (SEQ ID NO: 5281)
SKAQLYR, (SEQ ID NO: 5282)

-continued

```
                              (SEQ ID NO: 5283)
SLFRNQQ, (SEQ ID NO: 5284)
SKAQLTV;
```

(ii) an amino acid sequence comprising any portion of an amino acid sequence in (i), e.g., any 2, 3, 4, 5, or 6 amino acids, e.g., consecutive amino acids, thereof;
(iii) an amino acid sequence comprising one, two, or three but no more than four modifications, e.g., substitutions (e.g., conservative substitutions), insertions, or deletions, relative to any of the amino acid sequences in (i); or
(iv) an amino acid sequence comprising one, two, or three but no more than four different amino acids, relative to any one of the amino acid sequences in (i).

133. The AAV capsid variant of any one of embodiments 130-132, wherein [A][B] comprises:

(i)
```
                              (SEQ ID NO: 5285)
GSGSPHSLLWNQQ, (SEQ ID NO: 2060)
GSGSPHSKAQYYV, (SEQ ID NO: 2061)
GSGSPHSKLRRQQ, (SEQ ID NO: 5286)
GSGSPHSIWQNQQ, (SEQ ID NO: 2062)
GSGSPHSKAGCGQ, (SEQ ID NO: 2063)
GSGSPHSRAQNQQ, (SEQ ID NO: 2064)
GSGSPHSKRLRQQ, (SEQ ID NO: 2065)
GSGSPHSLRRNQQ, (SEQ ID NO: 2066)
GSGSPHSRGRNQQ, (SEQ ID NO: 5287)
GSGSPHSEIVNQQ, (SEQ ID NO: 2067)
GSGSPHSSRRNQQ, (SEQ ID NO: 5288)
GSGSPHCLLQNQQ, (SEQ ID NO: 2068)
GSGSPHSKAFRLQ, (SEQ ID NO: 5289)
GSGSPHCLAQNQQ, (SEQ ID NO: 2070)
GSGSPHFLRQNQQ, (SEQ ID NO: 2071)
GSGSPHSLRFNQQ, (SEQ ID NO: 5290)
GSGSPHSYLRNQQ, (SEQ ID NO: 5291)
GSGSPHCSLQNQQ, (SEQ ID NO: 5292)
GSGSPHVLWQNQQ, (SEQ ID NO: 2072)
GSGSPHSKWLLQQ, (SEQ ID NO: 5293)
GSGSPHSLWSNQQ, (SEQ ID NO: 2073)
GSGSPHSKRRLQQ, (SEQ ID NO: 5294)
GSGSPHSVYLNQQ, (SEQ ID NO: 5295)
GSGSPHSLWLNQQ, (SEQ ID NO: 2074)
GSGSPHSKAQRKL, (SEQ ID NO: 2075)
GSGSPHSKALRRQ, (SEQ ID NO: 2076)
GSGSPHSKAQRLR, (SEQ ID NO: 1801)
GSGSPHSKAQNQQ, (SEQ ID NO: 2077)
GSGSPHSKAQRRL, (SEQ ID NO: 2078)
GSGSPHSKARRQQ, (SEQ ID NO: 2079)
GSGSPHSKARRLQ, (SEQ ID NO: 2080)
GSGSPHSKSRRQQ, (SEQ ID NO: 2082)
GSGSPHSKARLRQ, (SEQ ID NO: 2083)
GSGSPHSKASKRQ, (SEQ ID NO: 2084)
GSGSPHVRRQNQQ, (SEQ ID NO: 2085)
GSGSPHSKAQLYR, (SEQ ID NO: 5296)
GSGSPHSLFRNQQ, (SEQ ID NO: 2086)
GSGSPHSKAQLTV; .
```

(ii) an amino acid sequence comprising any portion of an amino acid sequence in (i), e.g., any 2, 3, 4, 5, 6, 7, 8, 9, 10, 11, or 12 amino acids, e.g., consecutive amino acids, thereof;
(iii) an amino acid sequence comprising one, two, or three but no more than four modifications, e.g., substitutions (e.g., conservative substitutions), insertions, or deletions, relative to any of the amino acid sequences in (i); or
(iv) an amino acid sequence comprising one, two, or three but no more than four different amino acids, relative to any one of the amino acid sequences in (i)

134. The AAV capsid variant of any one of embodiments 130-133, which further comprises one, two, or all of an amino acid other than T at position 450 (e.g., S, Y, or G), an amino acid other than I at position 451 (e.g., M or L), and/or an amino acid other than N at position 452 (e.g., S), relative to a reference sequence numbered according to the amino acid sequence of SEQ ID NO: 138.

135. The AAV capsid variant of any one of embodiments 130-134, which further comprises an S at position 450 and an M at position 451, relative to a reference sequence numbered according to the amino acid sequence of SEQ ID NO: 138.
136. The AAV capsid variant of any one of embodiments 130-134, which further comprises a Y at position 450, an L at position 451, and an S at position 452, relative to a reference sequence numbered according to the amino acid sequence of SEQ ID NO: 138.
137. The AAV capsid variant of any one of embodiments 130-134, which further comprises a G at position 450, an L at position 451, and an S at position 452, relative to a reference sequence numbered according to the amino acid sequence of SEQ ID NO: 138.
138. The AAV capsid variant of any one of embodiments 130-137, wherein [A][B] is present in loop IV.
139. The AAV capsid variant of any one of embodiments 130-138, wherein [A] is present immediately subsequent to position 452, relative to a reference sequence numbered according to the amino acid sequence of SEQ ID NO: 138.
140. The AAV capsid variant of any one of embodiments 130-139, wherein [A] replaces positions 453-455 (e.g., G453, S454, G455), relative to a reference sequence numbered according to the amino acid sequence of SEQ ID NO: 138.
141. The AAV capsid variant of any one of embodiments 130-140, wherein [A] is present immediately subsequent to position 452, and wherein [A] replaces positions 453-455 (e.g., G453, S454, G455), relative to a reference sequence numbered according to the amino acid sequence of SEQ ID NO: 138.
142. The AAV capsid variant of any one of embodiments 130-141, wherein [B] is present immediately subsequent to [A].
143. The AAV capsid variant of any one of embodiments 130-142, wherein [B] replaces positions 456-459 (e.g., Q456, N457, Q458, Q459), relative to a reference sequence numbered according to the amino acid sequence of SEQ ID NO: 138.
144. The AAV capsid variant of any one of embodiments 130-143, wherein [A][B] replaces positions 453-459 (e.g., G453, S454, G455, Q456, N457, Q458, Q459), relative to a reference sequence numbered according to the amino acid sequence of SEQ ID NO: 138.
145. The AAV capsid variant of any one of embodiments 130-144, wherein [A][B] is present immediately subsequent to position 452, and wherein [A][B] replaces positions 453-459 (e.g., G453, S454, G455, Q456, N457, Q458, Q459), relative to a reference sequence numbered according to the amino acid sequence of SEQ ID NO: 138.
146. The AAV capsid variant of any one of embodiments 130-145, which comprises from N-terminus to C-terminus, [A][B].
147. An AAV capsid comprising [A][B] (SEQ ID NO: 4699), wherein:
(i) [A] comprises X1 X2 X3 X4 X5 X6, wherein
(a) position X1 is T, M, A, C, I, R, L, D, F, V, Q, N, or H;
(b) position X2 is I, P, E, N, D, S, A, T, M, or Q;
(c) position X3 is N, E, G, Y, W, M, T, I, K, Q, F, S, V, A, or L;
(d) position X4 is G, D, R, or E;
(e) position X5 is H, Q, N, or D;
(f) position X6 is D or R;

optionally wherein the AAV capsid variant comprises an amino acid modification, e.g., a conservative substitution, of any of the aforesaid amino acids in (a)-(f); and
(ii) [B] comprises SPHKSG (SEQ ID NO: 946).
148. The AAV capsid of embodiment 147, wherein
(a) position X1 is: T, M, A, or I;
(b) position X2 is: E, I or D;
(c) position X3 is: N, Q, Y, I, M, or V;
(d) position X4 is G;
(e) position X5 is H; and
(f) position X6 is D.
149. The AAV capsid variant of embodiment 147 or 148, wherein [A] comprises:

(i)
TINGHD, (SEQ ID NO: 5297)

MPEGHD, (SEQ ID NO: 5298)

MEGGHD, (SEQ ID NO: 5299)

MEYGHD, (SEQ ID NO: 5300)

AEWGHD, (SEQ ID NO: 5301)

CEWGHD, (SEQ ID NO: 5302)

ANNGQD, (SEQ ID NO: 5303)

IPEGHD, (SEQ ID NO: 5304)

ADMGHD, (SEQ ID NO: 5305)

IEYGHD, (SEQ ID NO: 5306)

ADYGHD, (SEQ ID NO: 5307)

IETGHD, (SEQ ID NO: 5308)

MEWGHD, (SEQ ID NO: 5309)

CEYGHD, (SEQ ID NO: 5310)

RINGHD, (SEQ ID NO: 5311)

MEIGHD, (SEQ ID NO: 5312)

LEYGHD, (SEQ ID NO: 5313)

ADWGHD, (SEQ ID NO: 5314)

IEIGHD, (SEQ ID NO: 5315)

TIKDND, (SEQ ID NO: 5316)

DIMGHD, (SEQ ID NO: 5317)

FEQGHD, (SEQ ID NO: 5318)

MEFGHD, (SEQ ID NO: 5319)

CDQGHD, (SEQ ID NO: 5320)

LPEGHD, (SEQ ID NO: 5321)

IENGHD, (SEQ ID NO: 5322)

MESGHD, (SEQ ID NO: 5323)

AEIGHD, (SEQ ID NO: 5324)

VEYGHD, (SEQ ID NO: 5325)

TSNGDD, (SEQ ID NO: 5326)

IEVGHD, (SEQ ID NO: 5327)

MEMGHD, (SEQ ID NO: 5328)

AEVGHD, (SEQ ID NO: 5329)

MDAGHD, (SEQ ID NO: 5330)

VEWGHD, (SEQ ID NO: 5331)

AEQGHD, (SEQ ID NO: 5332)

LEWGHD, (SEQ ID NO: 5333)

MELGHD, (SEQ ID NO: 5334)

METGHD, (SEQ ID NO: 5335)

MEAGHD, (SEQ ID NO: 5336)

TINRQR, (SEQ ID NO: 5337)

IESGHD, (SEQ ID NO: 5338)

TAKDHD, (SEQ ID NO: 5339)

MEVGHD, (SEQ ID NO: 5340)

CEIGHD, (SEQ ID NO: 5341)

ATNGHD, (SEQ ID NO: 5342)

MDGGHD, (SEQ ID NO: 5343)

QEVGHD, (SEQ ID NO: 5344)

ADQGHD, (SEQ ID NO: 5345)

NMNGHD, (SEQ ID NO: 5346)

TPWEHD, (SEQ ID NO: 5347)

IEMGHD, (SEQ ID NO: 5348)

TANEHD, (SEQ ID NO: 5349)

QQQGHD, (SEQ ID NO: 5350)

TPQDHD, (SEQ ID NO: 5351)

HDWGHD, (SEQ ID NO: 5352)

IEGGHD, (SEQ ID NO: 5353)

(ii) an amino acid sequence comprising any portion of an amino acid sequence in (i), e.g., any 2, 3, 4, or 5 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

150. The AAV capsid variant of any one of embodiments 147-149, wherein [A][B] comprises:

(i)

TINGHDSPHKR, (SEQ ID NO: 5354)

MPEGHDSPHKS, (SEQ ID NO: 5355)

MEGGHDSPHKS, (SEQ ID NO: 5356)

MEYGHDSPHKS, (SEQ ID NO: 5357)

AEWGHDSPHKS, (SEQ ID NO: 5358)

CEWGHDSPHKS, (SEQ ID NO: 5359)

ANNGQDSPHKS, (SEQ ID NO: 5360)

IPEGHDSPHKS, (SEQ ID NO: 5361)

ADMGHDSPHKS, (SEQ ID NO: 5362)

IEYGHDSPHKS, (SEQ ID NO: 5363)

ADYGHDSPHKS, (SEQ ID NO: 5364)

IETGHDSPHKS, (SEQ ID NO: 5365)
MEWGHDSPHKS, (SEQ ID NO: 5366)
CEYGHDSPHKS, (SEQ ID NO: 5367)
RINGHDSPHKS, (SEQ ID NO: 5368)
MEIGHDSPHKS, (SEQ ID NO: 5369)
LEYGHDSPHKS, (SEQ ID NO: 5370)
ADWGHDSPHKS, (SEQ ID NO: 5371)
IEIGHDSPHKS, (SEQ ID NO: 5372)
TIKDNDSPHKS, (SEQ ID NO: 5373)
DIMGHDSPHKS, (SEQ ID NO: 5374)
FEQGHDSPHKS, (SEQ ID NO: 5375)
MEFGHDSPHKS, (SEQ ID NO: 5376)
CDQGHDSPHKS, (SEQ ID NO: 5377)
LPEGHDSPHKS, (SEQ ID NO: 5378)
IENGHDSPHKS, (SEQ ID NO: 5379)
MESGHDSPHKS, (SEQ ID NO: 5380)
AEIGHDSPHKS, (SEQ ID NO: 5381)
VEYGHDSPHKS, (SEQ ID NO: 5382)
TSNGDDSPHKS, (SEQ ID NO: 5383)
IEVGHDSPHKS, (SEQ ID NO: 5384)
MEMGHDSPHKS, (SEQ ID NO: 5385)
AEVGHDSPHKS, (SEQ ID NO: 5386)
MDAGHDSPHKS, (SEQ ID NO: 5387)
VEWGHDSPHKS, (SEQ ID NO: 5388)
AEQGHDSPHKS, (SEQ ID NO: 5389)
LEWGHDSPHKS, (SEQ ID NO: 5390)
MELGHDSPHKS, (SEQ ID NO: 5391)
METGHDSPHKS, (SEQ ID NO: 5392)
MEAGHDSPHKS, (SEQ ID NO: 5393)
TINRQRSPHKS, (SEQ ID NO: 5394)
IESGHDSPHKS, (SEQ ID NO: 5395)
TAKDHDSPHKS, (SEQ ID NO: 5396)
MEVGHDSPHKS, (SEQ ID NO: 5397)
CEIGHDSPHKS, (SEQ ID NO: 5398)
ATNGHDSPHKS, (SEQ ID NO: 5399)
MDGGHDSPHKS, (SEQ ID NO: 5400)
QEVGHDSPHKS, (SEQ ID NO: 5401)
ADQGHDSPHKS, (SEQ ID NO: 5402)
NMNGHDSPHKS, (SEQ ID NO: 5403)
TPWEHDSPHKS, (SEQ ID NO: 5404)
IEMGHDSPHKS, (SEQ ID NO: 5405)
TANEHDSPHKS, (SEQ ID NO: 5406)
TINGHDSPHKS, (SEQ ID NO: 5407)
QQQGHDSPHKS, (SEQ ID NO: 5408)
TPQDHDSPHKS, (SEQ ID NO: 5409)
HDWGHDSPHKS, (SEQ ID NO: 5410)
IEGGHDSPHKS (SEQ ID NO: 5411)

(ii) an amino acid sequence comprising any portion of an amino acid sequence in (i), e.g., any 2, 3, 4, 5, 6, 7, 8, 9, or 10 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

151. The AAV capsid variant of any one of embodiments 147-150, which further comprises one, two, three, four, or all of an amino acid other than Q at position 456 (e.g., R or L), N at position 457 (e.g., H, K, or R), Q at position 458 (e.g., R or T), Q at position 459 (H), and/or T at position 460 (N or S), relative to a reference sequence numbered according to the amino acid sequence of SEQ ID NO: 138.

152. The AAV capsid variant of any one of embodiments 147-151, which further comprises an R at position 456, relative to a reference sequence numbered according to the amino acid sequence of SEQ ID NO: 138.

153. The AAV capsid variant of any one of embodiments 147-151, which further comprises an L at position 456, relative to a reference sequence numbered according to the amino acid sequence of SEQ ID NO: 138.

154. The AAV capsid variant of any one of embodiments 147-153, which further comprises an H at position 457 and an R at position 458, relative to a reference sequence numbered according to the amino acid sequence of SEQ ID NO: 138.

155. The AAV capsid variant of any one of embodiments 147-153, which further comprises a K at position 457 and an N at position 460, relative to a reference sequence numbered according to the amino acid sequence of SEQ ID NO: 138.

156. The AAV capsid variant of any one of embodiments 147-153, which further comprises a T at position 458, an H at position 459, and an S at position 460, relative to a reference sequence numbered according to the amino acid sequence of SEQ ID NO: 138.

157. The AAV capsid variant of any one of embodiments 147-151, which further comprises an R at position 456, an R at position 457, and an R at position 458, relative to a reference sequence numbered according to the amino acid sequence of SEQ ID NO: 138.

158. The AAV capsid variant of any one of embodiments 147-157, wherein [A][B] is present in loop IV.

159. The AAV capsid variant of any one of embodiments 147-158, wherein [A] is present immediately subsequent to position 449, relative to a reference sequence numbered according to the amino acid sequence of SEQ ID NO: 138.

160. The AAV capsid variant of any one of embodiments 147-159, wherein [A] replaces positions 450-453 (e.g., T450, I451, N452, G453), relative to a reference sequence numbered according to the amino acid sequence of SEQ ID NO: 138.

161. The AAV capsid variant of any one of embodiments 147-160, wherein [A] is present immediately subsequent to position 449, and wherein [A] replaces positions 450-453 (e.g., T450, I451, N452, G453), relative to a reference sequence numbered according to the amino acid sequence of SEQ ID NO: 138.

162. The AAV capsid variant of any one of embodiments 147-161, wherein [A][B] replaces positions 450-455 (e.g., T450, I451, N452, G453, S454, G455), relative to a reference sequence numbered according to the amino acid sequence of SEQ ID NO: 138.

163. The AAV capsid variant of any one of embodiments 147-162, wherein [A][B] is present immediately subsequent to position 449, and wherein [A][B] replaces positions 450-455 (e.g., T450, I451, N452, G453, S454, G455), relative to a reference sequence numbered according to the amino acid sequence of SEQ ID NO: 138.

164. The AAV capsid variant of any one of embodiments 147-163, wherein [B] is present immediately subsequent [A], and replaces positions 454 and 455 (e.g., S454 and G455), relative to a reference sequence numbered according to the amino acid sequence of SEQ ID NO: 138.

165. The AAV capsid variant of any one of embodiments 147-164, wherein [B] is present immediately subsequent to position 455, relative to a reference sequence numbered according to the amino acid sequence of SEQ ID NO: 982.

166. The AAV capsid variant of any one of embodiments 147-165, wherein [B] is present immediately subsequent to [A].

167. The AAV capsid variant of any one of embodiments 147-166, which comprises from N-terminus to C-terminus, [A][B].

168. An AAV capsid variant comprising an amino acid sequence having the following formula: [N1]-[N2]-[N3] (SEQ ID NO: 6407), wherein:
(i) [N1] comprises positions X1, X2, and X3, wherein position X2 is S and position X3 is G;
(ii) [N2] comprises the amino acid sequence SPH; and
(iii) [N3] comprises positions X4, X5, and X6, wherein position X5 is K.

169. The AAV capsid variant of embodiment 168, wherein:
(i) X4 of [N3] is S, T, N, or A; and
(ii) X5 of [N3] is A, V, T, S, G, R, L, or N;
optionally wherein the AAV capsid variant comprises an amino acid modification, e.g., a conservative substitution, of any of the aforesaid amino acids in (i) or (ii).

170. The AAV capsid variant of embodiment 168 or 169, wherein X4 is S and/or X5 is A.

171. The AAV capsid variant of any one of embodiments 168-170, wherein [N3] comprises SK, TK, NK, AK, KA, KV, KT, KS, KG, KR, KL, or KN.

172. The AAV capsid variant of any one of embodiments 168-171, wherein [N3] is or comprises SKA, SKV, SKT, SKS, SKG, SKR, TKA, NKA, SKL, SKN, or AKA.

173. The AAV capsid variant of any one of embodiments 168-172, wherein [N3] is or comprises SKA.

174. The AAV capsid variant of any one of embodiments 168-173, wherein [N2]-[N3] comprises SPHSK (SEQ ID NO: 4701), SPHTK (SEQ ID NO: 4725), SPHNK (SEQ ID NO: 4726), or SPHAK (SEQ ID NO: 4727).

175. The AAV capsid variant of any one of embodiments 168-174, wherein [N2]-[N3] is or comprises:

(i)

SPHSKA, (SEQ ID NO: 941)

SPHSKV, (SEQ ID NO: 4737)

SPHSKT, (SEQ ID NO: 4731)

SPHSKS, (SEQ ID NO: 962)

SPHSKG, (SEQ ID NO: 4732)

SPHSKR, (SEQ ID NO: 978)

SPHTKA, (SEQ ID NO: 4739)

SPHNKA, (SEQ ID NO: 4734)

SPHSKL, (SEQ ID NO: 960)

SPHSKN, (SEQ ID NO: 4735)
or

SPHAKA; (SEQ ID NO: 4736)

(ii) an amino acid sequence comprising any portion of an amino acid sequence in (i), e.g., any 2, 3, 4, or 5 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

176. The AAV capsid variant of any one of embodiments 168-175, wherein [N2]-[N3] is or comprises SPHSKA (SEQ ID NO: 941).

177. The AAV capsid variant of any one of embodiments 168-176, which comprises an amino acid other than G at position 453 (e.g., M, T, I, E, S, A, N, V, L, K, H, P, R, W, or D), numbered according to SEQ ID NO: 138 or 981.

178. The AAV capsid variant of any one of embodiments 168-177, which comprises the amino acid G at position 453, numbered according to SEQ ID NO: 138 or 981.

179. The AAV capsid variant of any one of embodiments 168-178, wherein X1 of [N1] is chosen from: G, M, T, I, E, S, A, N, V, L, K, H, P, R, W, or D; optionally wherein the AAV capsid variant comprises an amino acid modification, e.g., a conservative substitution, of any of the aforesaid amino acids.

180. The AAV capsid variant of any one of embodiments 168-179, wherein [N1] comprises SG, GS, MS, TS, IS, ES, SS, AS, NS, VS, LS, KS, HS, PS, RS, WS, or DS.

181. The AAV capsid variant of any one of embodiments 168-180, wherein [N1] is or comprises: GSG, MSG, TSG, ISG, ESG, SSG, ASG, NSG, VSG, LSG, KSG, HSG, PSG, RSG, WSG, or DSG.

182. The AAV capsid variant of any one of embodiments 168-181, wherein [N1] is or comprises GSG.

183. The AAV capsid variant of any one of embodiments 168-182, wherein [N1]-[N2] comprises SGSPH (SEQ ID NO: 4752).

184. The AAV capsid variant of any one of embodiments 168-183, wherein [N1]-[N2] is or comprises:

(i)

GSGSPH, (SEQ ID NO: 4695)

MSGSPH, (SEQ ID NO: 4798)

TSGSPH, (SEQ ID NO: 4800)

ISGSPH, (SEQ ID NO: 4801)

ESGSPH, (SEQ ID NO: 4803)

SSGSPH, (SEQ ID NO: 4804)

ASGSPH, (SEQ ID NO: 4806)

NSGSPH, (SEQ ID NO: 4807)

VSGSPH, (SEQ ID NO: 4786)

LSGSPH, (SEQ ID NO: 4808)

KSGSPH, (SEQ ID NO: 4810)

HSGSPH, (SEQ ID NO: 4811)

PSGSPH, (SEQ ID NO: 4813)

RSGSPH, (SEQ ID NO: 4815)

WSGSPH, (SEQ ID NO: 4817)

DSGSPH; (SEQ ID NO: 4818)

(ii) an amino acid sequence comprising any portion of an amino acid sequence in (i), e.g., any 2, 3, 4, or 5 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

185. The AAV capsid variant of any one of embodiments 168-184, wherein [N1]-[N2]-[N3] is or comprises:

(i)

GSGSPHSKA, (SEQ ID NO: 4697)

GSGSPHSKV, (SEQ ID NO: 4956)

MSGSPHSKA, (SEQ ID NO: 4957)

TSGSPHSKA, (SEQ ID NO: 4959)

ISGSPHSKA, (SEQ ID NO: 4960)

GSGSPHSKT, (SEQ ID NO: 4962)

ESGSPHSKA, (SEQ ID NO: 4963)

SSGSPHSKA, (SEQ ID NO: 4964)

GSGSPHSKS, (SEQ ID NO: 4953)

ASGSPHSKA, (SEQ ID NO: 4966)

NSGSPHSKA, (SEQ ID NO: 4967)

VSGSPHSKA, (SEQ ID NO: 4913)

LSGSPHSKA, (SEQ ID NO: 4968)

-continued

| | |
|---|---|
| KSGSPHSKA, | (SEQ ID NO: 4970) |
| GSGSPHSKG, | (SEQ ID NO: 4972) |
| GSGSPHSKR, | (SEQ ID NO: 4945) |
| HSGSPHSKA, | (SEQ ID NO: 4973) |
| PSGSPHSKA, | (SEQ ID NO: 4975) |
| RSGSPHSKA, | (SEQ ID NO: 4977) |
| GSGSPHTKA, | (SEQ ID NO: 4978) |
| WSGSPHSKA, | (SEQ ID NO: 4980) |
| DSGSPHSKA, | (SEQ ID NO: 4981) |
| GSGSPHNKA, | (SEQ ID NO: 4983) |
| GSGSPHSKL, | (SEQ ID NO: 4943) |
| GSGSPHSKN, or | (SEQ ID NO: 4994) |
| GSGSPHAKA; | (SEQ ID NO: 4995) |

(ii) an amino acid sequence comprising any portion of an amino acid sequence in (i), e.g., any 2, 3, 4, 5, 6, 7, 8, or 9 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

186. The AAV capsid variant of any one of embodiments 168-185, wherein [N1]-[N2]-[N3] is or comprises GSGSPHSKA (SEQ ID NO: 4697).

187. The AAV capsid variant of any one of embodiments 168-186, which comprises an amino acid other than Q at position 456 (e.g., R, P, H, L, K, I, G, S, M, or E), an amino acid other than N at position 457 (e.g., D, V, S, P, T, G, Y, W, E, R, H, K, F, A, I, L, or M), an amino acid other than Q at position 458 (e.g., R, L, A, P, H, T, I, F, K, V, M, G, W, Y, S, E, N, or D), an amino acid other than Q at position 459 (e.g., H, K, A, L, P, E, M, I, S, N, R, Y, C, V, T, W, D, G), and/or an amino acid other than T at position 460 (e.g., I, N, S, H, R, L, D, Y, A, or Q), relative to a reference sequence numbered according to SEQ ID NO: 138.

188. The AAV capsid variant of any one of embodiments 168-187, which comprises an amino acid other than Q at position 462 (e.g., R, P, H, L, K, I, G, S, M, or E), an amino acid other than N at position 463 (e.g., D, V, S, P, T, G, Y, W, E, R, H, K, F, A, I, L, or M), an amino acid other than Q at position 464 (e.g., R, L, A, P, H, T, I, F, K, V, M, G, W, Y, S, E, N, or D), an amino acid other than Q at position 465 (e.g., H, K, A, L, P, E, M, I, S, N, R, Y, C, V, T, W, D, G), and/or an amino acid other than T at position 466 (e.g., I, N, S, H, R, L, D, Y, A, or Q), relative to a reference sequence numbered according to SEQ ID NO: 981.

189. The AAV capsid variant of any one of embodiments 168-188, which comprises the amino acid Q at position 456, the amino acid N at position 457, the amino acid Q at position 458, the amino acid Q at position 459, and/or the amino acid T at position 460, relative to a reference sequence numbered according to SEQ ID NO: 138.

190. The AAV capsid variant of any one of embodiments 168-189, which comprises the amino acid Q at position 462, the amino acid N at position 463, the amino acid Q at position 464, the amino acid Q at position 465, and/or the amino acid T at position 466, numbered according to SEQ ID NO: 981

191. The AAV capsid variant of any one of embodiments 168-190, further comprising [N4] wherein [N4] comprises X7, X8, X9, X10, and X11, wherein:

(a) X7 is Q, R, P, H, L, K, I, G, S, M, or E;
(b) X8 is N, D, V, S, P, T, G, Y, W, E, R, H, K, F, A, I, L, or M;
(c) X9 is Q, R, L, A, P, H, T, I, F, K, V, M, G, W, Y, S, E, N, D;
(d) X10 is Q, H, K, A, L, P, E, M, I, S, N, R, Y, C, V, T, W, D, G; and
(e) X1I is T, I, N, S, H, R, L, D, Y, A, Q;
optionally wherein the AAV capsid variant comprises an amino acid modification, e.g., a conservative substitution, of any of the aforesaid amino acids in (a)-(e).

192. The AAV capsid variant of embodiment 191, wherein [N4] is or comprises:

(i)

| | |
|---|---|
| QNQQT, | (SEQ ID NO: 5412) |
| QNRHT, | (SEQ ID NO: 5413) |
| RDQQT, | (SEQ ID NO: 5414) |
| PNLQT, | (SEQ ID NO: 5415) |
| HVRQT, | (SEQ ID NO: 5416) |
| PNQHT, | (SEQ ID NO: 5417) |
| QSQQT, | (SEQ ID NO: 5418) |
| QNQQI, | (SEQ ID NO: 5419) |
| QPAKT, | (SEQ ID NO: 5420) |
| QTQQN, | (SEQ ID NO: 5421) |
| QNLAT, | (SEQ ID NO: 5422) |
| QNQLT, | (SEQ ID NO: 5423) |
| QGQQT, | (SEQ ID NO: 5424) |

-continued

LNRQS, (SEQ ID NO: 5425)

HNQQT, (SEQ ID NO: 5426)

QNPPT, (SEQ ID NO: 5427)

QNLQT, (SEQ ID NO: 5428)

QYQQT, (SEQ ID NO: 5429)

QDQET, (SEQ ID NO: 5430)

QNHQT, (SEQ ID NO: 5431)

QDQQT, (SEQ ID NO: 5432)

HWQQT, (SEQ ID NO: 5433)

PNQQT, (SEQ ID NO: 5434)

QNQLI, (SEQ ID NO: 5435)

PEQQT, (SEQ ID NO: 5436)

QRTMT, (SEQ ID NO: 5437)

QNQQH, (SEQ ID NO: 5438)

LHQHT, (SEQ ID NO: 5439)

QHRIT, (SEQ ID NO: 5440)

QYIHT, (SEQ ID NO: 5441)

QKFET, (SEQ ID NO: 5442)

QFPST, (SEQ ID NO: 5443)

HNQQR, (SEQ ID NO: 5444)

QAIKT, (SEQ ID NO: 5445)

QNRQT, (SEQ ID NO: 5446)

QYQHT, (SEQ ID NO: 5447)

QNPQS, (SEQ ID NO: 5448)

QHQLT, (SEQ ID NO: 5449)

QSPPT, (SEQ ID NO: 5450)

QAKLT, (SEQ ID NO: 5451)

-continued

KSQQT, (SEQ ID NO: 5452)

QDRPT, (SEQ ID NO: 5453)

QSQQL, (SEQ ID NO: 5454)

QAFHT, (SEQ ID NO: 5455)

QKQQD, (SEQ ID NO: 5456)

QNAQT, (SEQ ID NO: 5457)

HNQLT, (SEQ ID NO: 5458)

QNQQY, (SEQ ID NO: 5459)

QKLNT, (SEQ ID NO: 5460)

QNVQT, (SEQ ID NO: 5461)

QAQQT, (SEQ ID NO: 5462)

QNLQA, (SEQ ID NO: 5463)

QTPPT, (SEQ ID NO: 5464)

QYQHA, (SEQ ID NO: 5465)

QGQQA, (SEQ ID NO: 5466)

QPPAT, (SEQ ID NO: 5467)

QERPT, (SEQ ID NO: 5468)

QDLQT, (SEQ ID NO: 5469)

QAMHT, (SEQ ID NO: 5470)

LNQQT, (SEQ ID NO: 5471)

QHPST, (SEQ ID NO: 5472)

PGLQT, (SEQ ID NO: 5473)

QGIRT, (SEQ ID NO: 5474)

QAPAT, (SEQ ID NO: 5475)

QSQQI, (SEQ ID NO: 5476)

QIPPT, (SEQ ID NO: 5477)

QTQLT, (SEQ ID NO: 5478)

-continued

QAPST, (SEQ ID NO: 5479)

QNTYA, (SEQ ID NO: 5480)

QNQHI, (SEQ ID NO: 5481)

QNHLT, (SEQ ID NO: 5482)

QIGMT, (SEQ ID NO: 5483)

LNKQT, (SEQ ID NO: 5484)

QLQQT, (SEQ ID NO: 5485)

QRMST, (SEQ ID NO: 5486)

QGILT, (SEQ ID NO: 5487)

QDRQT, (SEQ ID NO: 5488)

RDWQT, (SEQ ID NO: 5489)

QNTHD, (SEQ ID NO: 5490)

PNLQI, (SEQ ID NO: 5491)

QERST, (SEQ ID NO: 5492)

QNYQT, (SEQ ID NO: 5493)

QRTCT, (SEQ ID NO: 5494)

QIGHT, (SEQ ID NO: 5495)

QGAIT, (SEQ ID NO: 5496)

QVPPT, (SEQ ID NO: 5497)

QVQQI, (SEQ ID NO: 5498)

LMRQT, (SEQ ID NO: 5499)

QYSVT, (SEQ ID NO: 5500)

QAITT, (SEQ ID NO: 5501)

QKTLT, (SEQ ID NO: 5502)

QNQWT, (SEQ ID NO: 5503)

QLHHT, (SEQ ID NO: 5504)

QNIII, (SEQ ID NO: 5505)

-continued

QGHHT, (SEQ ID NO: 5506)

QSKVT, (SEQ ID NO: 5507)

QLPST, (SEQ ID NO: 5508)

IGKQT, (SEQ ID NO: 5509)

QAIHT, (SEQ ID NO: 5510)

QHGLT, (SEQ ID NO: 5511)

QFMCT, (SEQ ID NO: 5512)

QHLQT, (SEQ ID NO: 5513)

QNHQN, (SEQ ID NO: 5514)

QPART, (SEQ ID NO: 5515)

QSLQT, (SEQ ID NO: 5516)

QSQLT, (SEQ ID NO: 5517)

QDRQS, (SEQ ID NO: 5518)

QMPST, (SEQ ID NO: 5519)

QGSLT, (SEQ ID NO: 5520)

QVPAT, (SEQ ID NO: 5521)

QDKQT, (SEQ ID NO: 5522)

HYQQT, (SEQ ID NO: 5523)

QVPST, (SEQ ID NO: 5524)

RGEQT, (SEQ ID NO: 5525)

PGQQT, (SEQ ID NO: 5526)

QSLQI, (SEQ ID NO: 5527)

LEQQT, (SEQ ID NO: 5528)

QNQST, (SEQ ID NO: 5529)

QKVIT, (SEQ ID NO: 5530)

QNNDQ, (SEQ ID NO: 5531)

QSVHT, (SEQ ID NO: 5532)

QPLGT, (SEQ ID NO: 5533)

HNQET, (SEQ ID NO: 5534)

QNLQI, (SEQ ID NO: 5535)

QIQQT, (SEQ ID NO: 5536)

QVRNT, (SEQ ID NO: 5537)

PSNQT, (SEQ ID NO: 5538)

QVGHT, (SEQ ID NO: 5539)

QRDIT, (SEQ ID NO: 5540)

QMPNT, (SEQ ID NO: 5541)

RGLQT, (SEQ ID NO: 5542)

QKQQT, (SEQ ID NO: 5543)

PSLQT, (SEQ ID NO: 5544)

QRDQT, (SEQ ID NO: 5545)

QAKGT, (SEQ ID NO: 5546)

QSAHT, (SEQ ID NO: 5547)

QSTMT, (SEQ ID NO: 5548)

QREMT, (SEQ ID NO: 5549)

QYRAT, (SEQ ID NO: 5550)

QWQQT, (SEQ ID NO: 5551)

QRMNT, (SEQ ID NO: 5552)

GDSQT, (SEQ ID NO: 5553)

QKIST, (SEQ ID NO: 5554)

PSMQT, (SEQ ID NO: 5555)

SPRQT, (SEQ ID NO: 5556)

MEQQT, (SEQ ID NO: 5557)

QYQNT, (SEQ ID NO: 5558)

QHQQT, (SEQ ID NO: 5559)

INQQT, (SEQ ID NO: 5560)

PNQQH, (SEQ ID NO: 5561)

ENRQT, (SEQ ID NO: 5562)

QTQQA, (SEQ ID NO: 5563)
or

QNQAT; (SEQ ID NO: 5564)

(ii) an amino acid sequence comprising any portion of an amino acid sequence in (i), e.g., any 2, 3, or 4 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

193. The AAV capsid variant of embodiment 191 or 192, wherein [N1]-[N2]-[N3]-[N4] is or comprises:

(i) the amino acid sequence of any of SEQ ID NOs: 200 or 2887-3076;

(ii) an amino acid sequence comprising any portion of an amino acid sequence in (i), e.g., any 2, 3, 4, 5, 6, 7, 8, 9, 10, 11, 12, or 13 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

194. The AAV capsid variant of any one of embodiments 191-193, wherein [N1]-[N2]-[N3]-[N4] is or comprises GSGSPHSKAQNQQT (SEQ ID NO: 200).

195. The AAV capsid variant of any one of embodiments 191-193, wherein [N1]-[N2]-[N3]-[N4] is or comprises VSGSPHSKAQNQQT (SEQ ID NO: 903).

196. The AAV capsid variant of any one of embodiments 168-195, which comprises an amino acid other than K at position 449 (e.g., T, E, or N), T at position 450 (e.g., S, E, A, N, V, Q, or G), an amino acid other than I at position 451 (e.g., F, E, V, L, D, S, C, T, A, N, H, R, G, or W), and/or an amino acid other than N at position 452 (e.g., I, P, K, R, H, S, M, Q, D, T, L, A, Y, V, F, E, W, or G), relative to a reference sequence numbered according to SEQ ID NO: 138 or 981.

197. The AAV capsid variant of any one of embodiments 168-196, which comprises the amino acid K at position 449, the amino acid T at position 450, the amino acid I at position 451, and/or the amino acid N at position 452, relative to a reference sequence numbered according to SEQ ID NO: 138 or 981.

198. The AAV capsid variant of any one of embodiments 168-197, which further comprises [N0], wherein [N0] comprises $X_A$, $X_B$, $X_C$, and $X_D$, wherein:

(a) $X_A$ is K, T, E, or N;
(b) $X_b$ is T, S, E, A, N, V, Q, or G;

(c) $X_C$ is I, F, E, V, L, D, S, C, T, A, N, H, R, G, or W; and
(d) $X_D$ is N, I, P, K, R, H, S, M, Q, D, T, L, A, Y, V, F, E, W, or G;

optionally wherein the AAV capsid variant comprises an amino acid modification, e.g., a conservative substitution, of any of the aforesaid amino acids in (a)-(d).

199. The AAV capsid variant of embodiment 198, wherein [N0] is or comprises:

(i)

KTII, (SEQ ID NO: 5565)

KTFP, (SEQ ID NO: 5566)

KTEK, (SEQ ID NO: 5567)

KTVN, (SEQ ID NO: 5568)

KTFN, (SEQ ID NO: 5569)

KTIN, (SEQ ID NO: 5570)

TTIN, (SEQ ID NO: 5571)

KSIN, (SEQ ID NO: 5572)

KTER, (SEQ ID NO: 5573)

KELH, (SEQ ID NO: 5574)

KAIN, (SEQ ID NO: 5575)

KTDN, (SEQ ID NO: 5576)

KTFH, (SEQ ID NO: 5577)

KTSN, (SEQ ID NO: 5578)

ETIN, (SEQ ID NO: 5579)

NTIN, (SEQ ID NO: 5580)

KTEN, (SEQ ID NO: 5581)

KTSS, (SEQ ID NO: 5582)

KTCN, (SEQ ID NO: 5583)

KTEH, (SEQ ID NO: 5584)

KAEM, (SEQ ID NO: 5585)

KATN, (SEQ ID NO: 5586)

KAIK, (SEQ ID NO: 5587)

-continued

KTDK, (SEQ ID NO: 5588)

KTFK, (SEQ ID NO: 5589)

KSDQ, (SEQ ID NO: 5590)

KTEI, (SEQ ID NO: 5591)

KTID, (SEQ ID NO: 5592)

KNTN, (SEQ ID NO: 5593)

KTET, (SEQ ID NO: 5594)

KTEL, (SEQ ID NO: 5595)

KNIN, (SEQ ID NO: 5596)

KTEA, (SEQ ID NO: 5597)

KTAN, (SEQ ID NO: 5598)

NTIY, (SEQ ID NO: 5599)

KTFS, (SEQ ID NO: 5600)

KTES, (SEQ ID NO: 5601)

KTTN, (SEQ ID NO: 5602)

KTED, (SEQ ID NO: 5603)

KTNN, (SEQ ID NO: 5604)

KEVH, (SEQ ID NO: 5605)

KTIS, (SEQ ID NO: 5606)

KTVR, (SEQ ID NO: 5607)

KTDR, (SEQ ID NO: 5608)

ETIK, (SEQ ID NO: 5609)

KNHI, (SEQ ID NO: 5610)

KESD, (SEQ ID NO: 5611)

KTIK, (SEQ ID NO: 5612)

KTDL, (SEQ ID NO: 5613)

KTVP, (SEQ ID NO: 5614)

KTVI, (SEQ ID NO: 5615)

KAEH, (SEQ ID NO: 5616)

KNCL, (SEQ ID NO: 5617)

KTVK, (SEQ ID NO: 5618)

KNAD, (SEQ ID NO: 5619)

KTIT, (SEQ ID NO: 5620)

KNCV, (SEQ ID NO: 5621)

KNAL, (SEQ ID NO: 5622)

KVIN, (SEQ ID NO: 5623)

KTEF, (SEQ ID NO: 5624)

KTRE, (SEQ ID NO: 5625)

KQGE, (SEQ ID NO: 5626)

KSEK, (SEQ ID NO: 5627)

KNVN, (SEQ ID NO: 5628)

KGGE, (SEQ ID NO: 5629)

KEFV, (SEQ ID NO: 5630)

KSDK, (SEQ ID NO: 5631)

KTEQ, (SEQ ID NO: 5632)

KEVQ, (SEQ ID NO: 5633)

KTEY, (SEQ ID NO: 5634)

KNCW, (SEQ ID NO: 5635)

KTDV, (SEQ ID NO: 5636)

KSDI, (SEQ ID NO: 5637)

KNSI, (SEQ ID NO: 5638)

KNSL, (SEQ ID NO: 5639)

KEVV, (SEQ ID NO: 5640)

KTEP, (SEQ ID NO: 5641)

KSEL, (SEQ ID NO: 5642)

KTWQ, (SEQ ID NO: 5643)

KTEV, (SEQ ID NO: 5644)

KAVN, (SEQ ID NO: 5645)

KGVL, (SEQ ID NO: 5646)

KTEG, (SEQ ID NO: 5647)

KTRD, (SEQ ID NO: 5648)

KTGN, (SEQ ID NO: 5649)

KNAI, (SEQ ID NO: 5650)

KAEN, (SEQ ID NO: 5651)

KAET, (SEQ ID NO: 5652)

KTVH, (SEQ ID NO: 5653)

KETA, (SEQ ID NO: 5654)

KNNL, (SEQ ID NO: 5655)

EAIN, (SEQ ID NO: 5656)

KSLN, (SEQ ID NO: 5657)

KTIP, (SEQ ID NO: 5658)
or

KTIH; (SEQ ID NO: 5659)

(ii) an amino acid sequence comprising any portion of an amino acid sequence in (i), e.g., any 2, or 3 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

200. The AAV capsid variant of embodiment 198 or 199, wherein [N0]-[N1]-[N2]-[N3]-[N4] is or comprises:

(i) the amino acid sequence of any one of SEQ ID NOs: 3239-3526 or 3591-3605;

(ii) an amino acid sequence comprising any portion of an amino acid sequence in (i), e.g., any 2, 3, 4, 5, 6, 7, 8, 9, 10, 11, 12, 13, 14, 15, 16, or 17 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

201. The AAV capsid variant of any one of embodiments 198-200, wherein [N0]-[N1]-[N2]-[N3]-[N4] is or comprises KTINGSGSPHSKAQNQQT (SEQ ID NO: 5660).

202. The AAV capsid variant of any one of embodiments 198-200, wherein [N0]-[N1]-[N2]-[N3]-[N4] is or comprises KTERVSGSPHSKAQNQQT (SEQ ID NO: 3589).

203. An AAV capsid variant comprising an amino acid sequence having the following formula: [N1]-[N2]-[N3] (SEQ ID NO: 6408), wherein:
  (i) [N1] comprises positions X1, X2, and X3, wherein position X2 is an amino acid other than S and position X3 is an amino acid other than G;
  (ii) [N2] comprises the amino acid sequence SPH; and
  (iii) [N3] comprises positions X4, X5, and X6, wherein position X4 is K.

204. The AAV capsid variant of embodiment 203, wherein:
  (i) X5 of [N3] is S, I, T, R, H, Y, L, or M; and
  (ii) X6 of [N3] is G, A, L, E, V, R, W, N, Q, or K;
  optionally wherein the AAV capsid variant comprises an amino acid modification, e.g., a conservative substitution, of any of the aforesaid amino acids in (i) or (ii).

205. The AAV capsid variant of embodiment 203 or 204, wherein X5 is S and/or $X_6$ is G.

206. The AAV capsid variant of any one of embodiments 203-205, wherein [N3] comprises KS, KI, KT, KR, KH, KY, KL, KM, SG, IG, TG, RG, SA, SL, SE, SV, SR, SW, SN, HG, YG, SQ, IV, SK, LW, MG, or MA.

207. The AAV capsid variant of any one of embodiments 203-206, wherein [N3] is or comprises KSG, KIG, KTG, KRG, KSA, KSL, KSE, KSV, KSR, KSW, KSN, KHG, KYG, KSQ, KIV, KSK, KLW, KMG, or KMA.

208. The AAV capsid variant of any one of embodiments 203-207, wherein [N3] is or comprises KSG.

209. The AAV capsid variant of any one of embodiments 203-208, wherein [N2]-[N3] comprises SPHKS (SEQ ID NO: 4704), SPHKI (SEQ ID NO: 4713), SPHKT (SEQ ID NO: 4711), SPHKR (SEQ ID NO: 4717), NPHKS (SEQ ID NO: 5661), SPHKH (SEQ ID NO: 4728), SPHKY (SEQ ID NO: 4715), SPHKL (SEQ ID NO: 4714), or SPHKM (SEQ ID NO: 4729).

210. The AAV capsid variant of any one of embodiments 203-209, wherein [N2]-[N3] is or comprises:

(i)
```
SPHKSG,    (SEQ ID NO: 946)
SPHKIG,    (SEQ ID NO: 958)
SPHKTG,    (SEQ ID NO: 4738)
SPHKRG,    (SEQ ID NO: 974)
NPHKSG,    (SEQ ID NO: 5662)
SPHKSA,    (SEQ ID NO: 977)
SPHKSL,    (SEQ ID NO: 4740)
SPHKSE,    (SEQ ID NO: 4741)
SPHKSV,    (SEQ ID NO: 4742)
SPHKSR,    (SEQ ID NO: 951)
SPHKSW,    (SEQ ID NO: 4743)
SPHKSN,    (SEQ ID NO: 4744)
SPHKHG,    (SEQ ID NO: 4745)
SPHKYG,    (SEQ ID NO: 966)
SPHKSQ,    (SEQ ID NO: 4746)
SPHKIV,    (SEQ ID NO: 5663)
SPHKSK,    (SEQ ID NO: 4747)
SPHKLW,    (SEQ ID NO: 4748)
SPHKMG,    (SEQ ID NO: 4750)
or
SPHKMA;    (SEQ ID NO: 4751)
```

(ii) an amino acid sequence comprising any portion of an amino acid sequence in (i), e.g., any 2, 3, 4, or 5 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

211. The AAV capsid variant of any one of embodiments 203-210, wherein [N2]-[N3] is or comprises SPHKSG (SEQ ID NO: 946).

212. The AAV capsid variant of any one of embodiments 203-211, which comprises an amino acid other than G at position 453 (e.g., A, K, W, R, L, I, M, N, T, E, Q, Y, H, F, or V), numbered according to SEQ ID NO: 138 or 981.

213. The AAV capsid variant of any one of embodiments 203-212, which comprises the amino acid G at position 453, numbered according to SEQ ID NO: 138 or 981.

214. The AAV capsid variant of any one of embodiments 203-214, wherein:
  (i) position X1 of [N1] is G, A, K, W, R, L, I, M, N, T, E, Q, Y, H, F, or V;
  (ii) position X2 of [N1] is H, Y, R, Q, N, P, or D;
  (iii) position X3 of [N1] is D, E, G, V, or N;
  optionally wherein the AAV capsid variant comprises an amino acid modification, e.g., a conservative substitution, of any of the aforesaid amino acids in (i), (ii), or (iii).

215. The AAV capsid variant of any one of embodiments 203-214, wherein position X2 of [N1] is H and position X3 of [N1] is D.
216. The AAV capsid variant of any one of embodiments 203-215, wherein position X1 of [N1] is G, position X2 of [N1] is H and position X3 of [N1] is D.
217. The AAV capsid variant of any one of embodiments 203-216, wherein [N1] comprises GH, HD, GY, GR, GQ, AH, GN, KH, GP, WH, RH, LH, JH, MH, GD, NH, TH, EH, QH, YH, HH, FH, VH, YD, HE, RG, QD, RD, ND, PD, QV, DD, HN, or NG 218. The AAV capsid variant of any one of embodiments 203-217, wherein [N1] is or comprises GHD, GYD, GHE, GRG, GQD, GRD, AHD, GND, KHD, GPD, WHD, RHD, LHD, GQV, IHD, MHD, GDD, GHN, NHD, THD, GNG, EHD, QHD, YHD, HHD, FHD, or VHD.
219. The AAV capsid variant of any one of embodiments 203-218, wherein [N1] is or comprises GHD.
220. The AAV capsid variant of any one of embodiments 203-219, wherein [N1]-[N2] comprises HDSPH (SEQ ID NO: 4703).
221. The AAV capsid variant of any one of embodiments 203-220, wherein [N1]-[N2] is or comprises:

(i)

GHDSPH, (SEQ ID NO: 4784)

GYDSPH, (SEQ ID NO: 4829)

GHESPH, (SEQ ID NO: 4793)

GRGSPH, (SEQ ID NO: 4788)

GHDNPH, (SEQ ID NO: 5664)

GQDSPH, (SEQ ID NO: 4785)

GRDSPH, (SEQ ID NO: 4831)

AHDSPH, (SEQ ID NO: 5665)

GNDSPH, (SEQ ID NO: 4832)

KHDSPH, (SEQ ID NO: 5666)

GPDSPH, (SEQ ID NO: 4833)

WHDSPH, (SEQ ID NO: 5667)

RHDSPH, (SEQ ID NO: 5668)

LHDSPH, (SEQ ID NO: 5669)

GQVSPH, (SEQ ID NO: 4835)

IHDSPH, (SEQ ID NO: 5670)

MHDSPH, (SEQ ID NO: 5671)

-continued

GDDSPH, (SEQ ID NO: 4792)

GHNSPH, (SEQ ID NO: 4836)

NHDSPH, (SEQ ID NO: 5672)

THDSPH, (SEQ ID NO: 5673)

GNGSPH, (SEQ ID NO: 4805)

EHDSPH, (SEQ ID NO: 5674)

QHDSPH, (SEQ ID NO: 5675)

YHDSPH, (SEQ ID NO: 5676)

HHDSPH, (SEQ ID NO: 5677)

FHDSPH, (SEQ ID NO: 5678)

or

VHDSPH; (SEQ ID NO: 5679)

(ii) an amino acid sequence comprising any portion of an amino acid sequence in (i), e.g., any 2, 3, 4, or 5 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

222. The AAV capsid variant of any one of embodiments 203-221, wherein [N1]-[N2]-[N3] is or comprises:

(i)

GHDSPHKSG, (SEQ ID NO: 4698)

GHDSPHKIG, (SEQ ID NO: 4996)

GYDSPHKSG, (SEQ ID NO: 4997)

GHESPHKSG, (SEQ ID NO: 4998)

GHDSPHKTG, (SEQ ID NO: 4999)

GRGSPHKRG, (SEQ ID NO: 5000)

GHDNPHKSG, (SEQ ID NO: 5680)

GQDSPHKSG, (SEQ ID NO: 4908)

GHDSPHKSA, (SEQ ID NO: 4940)

GHDSPHKSL, (SEQ ID NO: 5001)

GHDSPHKSE, (SEQ ID NO: 5003)

GRDSPHKSG, (SEQ ID NO: 5004)

AHDSPHKSG, (SEQ ID NO: 5681)

GNDSPHKSV, (SEQ ID NO: 5005)

AHDSPHKIG, (SEQ ID NO: 5682)

GHESPHKSA, (SEQ ID NO: 4939)

GQDSPHKIG, (SEQ ID NO: 5006)

GHDSPHKSV, (SEQ ID NO: 5007)

GHDSPHKSR, (SEQ ID NO: 4942)

KHDSPHKSG, (SEQ ID NO: 5683)

GPDSPHKIG, (SEQ ID NO: 5008)

GPDSPHKSG, (SEQ ID NO: 5009)

GHDSPHKSW, (SEQ ID NO: 5010)

WHDSPHKSG, (SEQ ID NO: 5684)

RHDSPHKSG, (SEQ ID NO: 5685)

GHDSPHKSN, (SEQ ID NO: 5011)

GHDSPHKRG, (SEQ ID NO: 4937)

GHDSPHKHG, (SEQ ID NO: 5013)

LHDSPHKSG, (SEQ ID NO: 5686)

GQVSPHKSG, (SEQ ID NO: 5014)

IHDSPHKSG, (SEQ ID NO: 5687)

MHDSPHKSG, (SEQ ID NO: 5688)

GDDSPHKSV, (SEQ ID NO: 5015)

GHNSPHKSG, (SEQ ID NO: 5016)

NHDSPHKSG, (SEQ ID NO: 5689)

THDSPHKSG, (SEQ ID NO: 5690)

GNGSPHKRG, (SEQ ID NO: 5017)

EHDSPHKSG, (SEQ ID NO: 5691)

GHDSPHKYG, (SEQ ID NO: 5018)

GHDSPHKSQ, (SEQ ID NO: 5019)

QHDSPHKSG, (SEQ ID NO: 5692)

RHDSPHKIV, (SEQ ID NO: 5693)

YHDSPHKSG, (SEQ ID NO: 5694)

GNDSPHKIG, (SEQ ID NO: 5020)

HHDSPHKSG, (SEQ ID NO: 5695)

GHDSPHKSK, (SEQ ID NO: 5021)

FHDSPHKSG, (SEQ ID NO: 5696)

GHDSPHKLW, (SEQ ID NO: 5022)

VHDSPHKSG, (SEQ ID NO: 5697)

GHDSPHKMG, (SEQ ID NO: 5024)

GHDSPHKMA, (SEQ ID NO: 5025)
or

GDDSPHKSG; (SEQ ID NO: 4938)

(ii) an amino acid sequence comprising any portion of an amino acid sequence in (i), e.g., any 2, 3, 4, 5, 6, 7, 8, or 9 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

223. The AAV capsid variant of any one of embodiments 203-222, wherein [N1]-[N2]-[N3] is or comprises GHDSPHKSG (SEQ ID NO: 4698).

224. The AAV capsid variant of any one of embodiments 203-223, which comprises an amino acid other than Q at position 456 (e.g., R, P, H, K, L, V, A, E, or I), an amino acid other than N at position 457 (e.g., I, K, S, H, R, T, D, Y, L, W, F, A, Q, or M), an amino acid other than Q at position 458 (e.g., R, V, K, P, Y, H, L, I, E, or M), an amino acid other than Q at position 459 (e.g., H, L, E, P, W, D, I, V, S, K, R, C, M, or N), and/or an amino acid other than T at position 460 (e.g., A, E, K, S, I, P, G, or N), relative to a reference sequence numbered according to SEQ ID NO: 138.

225. The AAV capsid variant of any one of embodiments 203-224, which comprises an amino acid other than Q at position 462 (e.g., R, P, H, K, L, V, A, E, or I), an amino acid other than N at position 463 (e.g., I, K, S, H, R, T, D, Y, L, W, F, A, Q, or M), an amino acid other than Q at position 464 (e.g., R, V, K, P, Y, H, L, I, E, or M), an amino acid other than Q at position 465 (e.g., H, L, E, P, W, D, I, V, S, K, R, C, M, or N), and/or an amino acid other than T at position 466 (e.g., A, E, K, S, I, P, G, or N), relative to a reference sequence numbered according to SEQ ID NO: 982.

226. The AAV capsid variant of any one of embodiments 203-225, which comprises the amino acid Q at position 456, the amino acid N at position 457, the amino acid Q at position 458, the amino acid Q at position 459, and/or the amino acid T at position 460, relative to a reference sequence numbered according to SEQ ID NO: 138.

227. The AAV capsid variant of any one of embodiments 203-226, which comprises the amino acid Q at position 462, the amino acid N at position 463, the amino acid Q at position 464, the amino acid Q at position 465, and/or the amino acid T at position 466, relative to a reference sequence numbered according to SEQ ID NO: 138.

228. The AAV capsid variant of any one of embodiments 203-227, further comprising [N4] wherein [N4] comprises X7, X8, X9, X10, and X11, wherein:
  (a) X7 is Q, R, P, H, L, K, I, G, S, M, or E;
  (b) X8 is N, D, V, S, P, T, G, Y, W, E, R, H, K, F, A, I, L, or M;
  (c) X9 is Q, R, L, A, P, H, T, I, F, K, V, M, G, W, Y, S, E, N, D;
  (d) X10 is Q, H, K, A, L, P, E, M, I, S, N, R, Y, C, V, T, W, D, G; and
  (e) X11 is T, I, N, S, H, R, L, D, Y, A, Q;
  optionally wherein the AAV capsid variant comprises an amino acid modification, e.g., a conservative substitution, of any of the aforesaid amino acids in (a)-(e).

229. The AAV capsid variant of embodiment 228, wherein [N4] is or comprises:

(i)
QNQQT, (SEQ ID NO: 5412)
QIRQT, (SEQ ID NO: 5698)
QNQHA, (SEQ ID NO: 5699)
QKQQT, (SEQ ID NO: 5543)
QSVQT, (SEQ ID NO: 5700)
RSQQT, (SEQ ID NO: 5701)
QNKLE, (SEQ ID NO: 5702)
QNQQK, (SEQ ID NO: 5703)
QHQQA, (SEQ ID NO: 5704)
QIQHT, (SEQ ID NO: 5705)

-continued

PRQQT, (SEQ ID NO: 5706)
HTQQT, (SEQ ID NO: 5707)
QRQHT, (SEQ ID NO: 5708)
QSQQT, (SEQ ID NO: 5418)
QNQQS, (SEQ ID NO: 5709)
RNQET, (SEQ ID NO: 5710)
QTQLT, (SEQ ID NO: 5478)
KNQQT, (SEQ ID NO: 5711)
QDQQT, (SEQ ID NO: 5432)
HNQQT, (SEQ ID NO: 5426)
QNQLT, (SEQ ID NO: 5423)
QTQQT, (SEQ ID NO: 5712)
QTQQI, (SEQ ID NO: 5713)
QSKQA, (SEQ ID NO: 5714)
QNQPP, (SEQ ID NO: 5715)
QSPQT, (SEQ ID NO: 5716)
QNYQT, (SEQ ID NO: 5493)
QNHQT, (SEQ ID NO: 5431)
QNRQT, (SEQ ID NO: 5446)
QNQQG, (SEQ ID NO: 5717)
QNHLT, (SEQ ID NO: 5482)
QYQHT, (SEQ ID NO: 5447)
QNQWT, (SEQ ID NO: 5503)
QNQHT, (SEQ ID NO: 5718)
QTRQT, (SEQ ID NO: 5719)
QNLHT, (SEQ ID NO: 5720)
LNQQT, (SEQ ID NO: 5471)

QNQET, (SEQ ID NO: 5721)

QHLQT, (SEQ ID NO: 5513)

LNQPT, (SEQ ID NO: 5722)

QNQDT, (SEQ ID NO: 5723)

RNQQT, (SEQ ID NO: 5724)

QNLLT, (SEQ ID NO: 5725)

QLVIT, (SEQ ID NO: 5726)

RTQET, (SEQ ID NO: 5727)

QTHQT, (SEQ ID NO: 5728)

QNQPA, (SEQ ID NO: 5729)

QDQHT, (SEQ ID NO: 5730)

QSQHT, (SEQ ID NO: 5731)

RNQQI, (SEQ ID NO: 5732)

VRQQT, (SEQ ID NO: 5733)

QNQHS, (SEQ ID NO: 5734)

AWQQT, (SEQ ID NO: 5735)

QSVPT, (SEQ ID NO: 5736)

QNIQP, (SEQ ID NO: 5737)

QNHLN, (SEQ ID NO: 5738)

LDQQT, (SEQ ID NO: 5739)

PDQQS, (SEQ ID NO: 5740)

ESQQT, (SEQ ID NO: 5741)

QNKQT, (SEQ ID NO: 5742)

QRQLT, (SEQ ID NO: 5743)

QIIVT, (SEQ ID NO: 5744)

QKQST, (SEQ ID NO: 5745)

QSHQT, (SEQ ID NO: 5746)

QFVVT, (SEQ ID NO: 5747)

QNLQT, (SEQ ID NO: 5428)

QNQQI, (SEQ ID NO: 5419)

QSQPT, (SEQ ID NO: 5748)

QNEQT, (SEQ ID NO: 5749)

QSLQT, (SEQ ID NO: 5516)

RNRQT, (SEQ ID NO: 5750)

QSKQT, (SEQ ID NO: 5751)

QNPLT, (SEQ ID NO: 5752)

RDQKT, (SEQ ID NO: 5753)

HNQQN, (SEQ ID NO: 5754)

QWKRT, (SEQ ID NO: 5755)

QSQQI, (SEQ ID NO: 5476)

QAQQT, (SEQ ID NO: 5462)

QNHQI, (SEQ ID NO: 5756)

QNQQA, (SEQ ID NO: 5757)

QNQLN, (SEQ ID NO: 5758)

QTQPT, (SEQ ID NO: 5759)

INQQT, (SEQ ID NO: 5560)

QKQLT, (SEQ ID NO: 5760)

RNQLA, (SEQ ID NO: 5761)

RNQQS, (SEQ ID NO: 5762)

ISIQT, (SEQ ID NO: 5763)

QNQQN, (SEQ ID NO: 5764)

QSQQS, (SEQ ID NO: 5765)

QTVCT, (SEQ ID NO: 5766)

QYQQI, (SEQ ID NO: 5767)

-continued

| | |
|---|---|
| QQIMT, | (SEQ ID NO: 5768) |
| QNEQS, | (SEQ ID NO: 5769) |
| LNHQT, | (SEQ ID NO: 5770) |
| QMIHT, | (SEQ ID NO: 5771) |
| RNHQS, | (SEQ ID NO: 5772) |
| QKMNT, | (SEQ ID NO: 5773) |
| QSQQN, | (SEQ ID NO: 5774) |
| QYQHA; | (SEQ ID NO: 5465) |

(ii) an amino acid sequence comprising any portion of an amino acid sequence in (i), e.g., any 2, 3, or 4 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

230. The AAV capsid variant of embodiment 228 or 229, wherein [N1]-[N2]-[N3]-[N4] is or comprises:
(i) the amino acid sequence of any of SEQ ID NOs: 201 or 3160-3237;
(ii) an amino acid sequence comprising any portion of an amino acid sequence in (i), e.g., any 2, 3, 4, 5, 6, 7, 8, 9, 10, 11, 12, or 13 amino acids, e.g., consecutive amino acids, thereof;
(iii) an amino acid sequence comprising one, two, or three but no more than four modifications, e.g., substitutions (e.g., conservative substitutions), insertions, or deletions, relative to any of the amino acid sequences in (i); or
(iv) an amino acid sequence comprising one, two, or three but no more than four different amino acids, relative to any one of the amino acid sequences in (i).

231. The AAV capsid variant of any one of embodiments 228-230, wherein [N1]-[N2]-[N3]-[N4] is or comprises GHDSPHKSGQNQQT (SEQ ID NO: 201).

232. The AAV capsid variant of any one of embodiments 203-231, which comprises an amino acid other than K at position 449 (e.g., T), T at position 450 (e.g., A, S, I, V, N, E, Y, C, G, W, or Q), an amino acid other than I at position 451 (e.g., E, V, S, T, N, D, C, G, Q, L, P, A), and/or an amino acid other than N at position 452 (e.g., S, Y, I, K, F, T, D, E, G, V, L, A, M, Q, H, P, or R), relative to a reference sequence numbered according to SEQ ID NO: 138 or 982.

233. The AAV capsid variant of any one of embodiments 203-232, which comprises the amino acid K at position 449, the amino acid T at position 450, the amino acid I at position 451, and/or the amino acid N at position 452, relative to a reference sequence numbered according to SEQ ID NO: 138 or 982.

234. The AAV capsid variant of any one of embodiments 203-233, which further comprises [N0], wherein [N0] comprises $X_A$, $X_B$, $X_C$, and $X_D$, wherein:
(a) $X_A$ is K or T;
(b) $X_b$ is T, A, S, I, V, N, E, Y, C, G, W, or Q;
(c) $X_C$ is I, E, V, S, T, N, D, C, G, Q, L, P, A; and
(d) $X_D$ is N, S, Y, I, K, F, T, D, E, G, V, L, A, M, Q, H, P, or R;
optionally wherein the AAV capsid variant comprises an amino acid modification, e.g., a conservative substitution, of any of the aforesaid amino acids in (a)-(d).

235. The AAV capsid variant of embodiment 234, wherein [N0] is or comprises:

(i)

| | |
|---|---|
| KAIN, | (SEQ ID NO: 5575) |
| KTIN, | (SEQ ID NO: 5570) |
| KTES, | (SEQ ID NO: 5601) |
| TTIN, | (SEQ ID NO: 5571) |
| KSIN, | (SEQ ID NO: 5572) |
| KTVN, | (SEQ ID NO: 5568) |
| KSIY, | (SEQ ID NO: 5775) |
| KTSN, | (SEQ ID NO: 5578) |
| KTTN, | (SEQ ID NO: 5602) |
| KIIN, | (SEQ ID NO: 5776) |
| KTIS, | (SEQ ID NO: 5606) |
| KAII, | (SEQ ID NO: 5777) |
| KTIK, | (SEQ ID NO: 5612) |
| KTEF, | (SEQ ID NO: 5624) |
| KTIT, | (SEQ ID NO: 5620) |
| KTNN, | (SEQ ID NO: 5604) |
| KTID, | (SEQ ID NO: 5592) |
| KAIS, | (SEQ ID NO: 5778) |
| KTVD, | (SEQ ID NO: 5779) |
| KTIE, | (SEQ ID NO: 5780) |
| KTEG, | (SEQ ID NO: 5647) |

-continued

KVIN, (SEQ ID NO: 5623)

KAVN, (SEQ ID NO: 5645)

KTIY, (SEQ ID NO: 5781)

KTDN, (SEQ ID NO: 5576)

KTCN, (SEQ ID NO: 5583)

KNVV, (SEQ ID NO: 5782)

KTEL, (SEQ ID NO: 5595)

KTDA, (SEQ ID NO: 5783)

KTEV, (SEQ ID NO: 5644)

KSEL, (SEQ ID NO: 5642)

KTEM, (SEQ ID NO: 5784)

KTEQ, (SEQ ID NO: 5632)

KTII, (SEQ ID NO: 5565)

KIVN, (SEQ ID NO: 5785)

KTEK, (SEQ ID NO: 5567)

KTEN, (SEQ ID NO: 5581)

KIGN, (SEQ ID NO: 5786)

KEVM, (SEQ ID NO: 5787)

KYQV, (SEQ ID NO: 5788)

KTEA, (SEQ ID NO: 5597)

KATN, (SEQ ID NO: 5586)

KTEH, (SEQ ID NO: 5584)

KTVE, (SEQ ID NO: 5789)

KAID, (SEQ ID NO: 5790)

KTIM, (SEQ ID NO: 5791)

KEVG, (SEQ ID NO: 5792)

KSEM, (SEQ ID NO: 5793)

-continued

KAQQ, (SEQ ID NO: 5794)

KCGE, (SEQ ID NO: 5795)

KASN, (SEQ ID NO: 5796)

KTET, (SEQ ID NO: 5594)

KTIG, (SEQ ID NO: 5797)

KTDP, (SEQ ID NO: 5798)

KELV, (SEQ ID NO: 5799)

KELM, (SEQ ID NO: 5800)

KNEI, (SEQ ID NO: 5801)

KTPN, (SEQ ID NO: 5802)

KITN, (SEQ ID NO: 5803)

KTDI, (SEQ ID NO: 5804)

KTDQ, (SEQ ID NO: 5805)

KGIN, (SEQ ID NO: 5806)

KSEI, (SEQ ID NO: 5807)

KSEK, (SEQ ID NO: 5627)

KWSA, (SEQ ID NO: 5808)

KELA, (SEQ ID NO: 5809)

KQTQ, (SEQ ID NO: 5810)

KGAD, (SEQ ID NO: 5811)

KVGE, (SEQ ID NO: 5812)

KANE, (SEQ ID NO: 5813)

KTDT, (SEQ ID NO: 5814)

KTCI, (SEQ ID NO: 5815)

KELR, (SEQ ID NO: 5816)

KCQI, (SEQ ID NO: 5817)

KGVM, (SEQ ID NO: 5818)

-continued

| | |
|---|---|
| KACD, | (SEQ ID NO: 5819) |
| KNEL, | (SEQ ID NO: 5820) |
| KAAE, | (SEQ ID NO: 5821) |
| KGQN, | (SEQ ID NO: 5822) |
| KNEF, | (SEQ ID NO: 5823) |
| KTSI, | (SEQ ID NO: 5824) |
| KAEH, | (SEQ ID NO: 5616) |
| KCDQ, | (SEQ ID NO: 5825) |
| KEIL, | (SEQ ID NO: 5826) |
| KTER, | (SEQ ID NO: 5573) |
| KNAI, | (SEQ ID NO: 5650) |
| KTDK, | (SEQ ID NO: 5588) |
| KTPD, | (SEQ ID NO: 5827) |
| KTIH, or | (SEQ ID NO: 5659) |
| KTEI; | (SEQ ID NO: 5591) |

(ii) an amino acid sequence comprising any portion of an amino acid sequence in (i), e.g., any 2, or 3 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

236. The AAV capsid variant of embodiment 234 or 235, wherein [N0]-[N1]-[N2]-[N3]-[N4] is or comprises:

(i) the amino acid sequence of any one of SEQ ID NOs: 3606-3836;

(ii) an amino acid sequence comprising any portion of an amino acid sequence in (i), e.g., any 2, 3, 4, 5, 6, 7, 8, 9, 10, 11, 12, 13, 14, 15, 16, or 17 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i).

237. The AAV capsid variant of any one of embodiments 234-236, wherein [N0]-[N1]-[N2]-[N3]-[N4] is or comprises KTINGHDSPHKSGQNQQT (SEQ ID NO: 5828).

238. The AAV capsid variant of any one of embodiments 234-236, wherein [N0]-[N1]-[N2]-[N3]-[N4] is or comprises KAEIGHDSPHKSGQNQQT (SEQ ID NO: 1754).

239. The AAV capsid variant of any one of embodiments 234-236, wherein [N0]-[N1]-[N2]-[N3]-[N4] is or comprises KTEKMSGSPHSKAQNQQT (SEQ ID NO: 3241).

240. The AAV capsid variant of any one of embodiments 168-239, wherein [N1]-[N2]-[N3] is present in loop IV.

241. The AAV capsid variant of any one of embodiments 198-202 or 234-240, wherein [N0] and [N4] are present in loop IV.

242. The AAV capsid variant of any one of embodiments 198-202 or 234-241, wherein [N0] is present immediately subsequent to position 448, relative to a reference sequence numbered according to the amino acid sequence of SEQ ID NO: 138, 981, or 982.

243. The AAV capsid variant of any one of embodiments 198-202 or 234-242, wherein [N0] replaces positions 449-452 (e.g., K449, T450, I451, and N452), relative to a reference sequence numbered according to SEQ ID NO: 138, 981, or 982.

244. The AAV capsid variant of any one of embodiments 198-202 or 234-243, wherein [N0] is present immediately subsequent to position 448 and wherein [N0] replaces positions 449-452 (e.g., K449, T450, 1451, and N452), relative to a reference sequence numbered according to SEQ ID NO: 138, 981, or 982.

245. The AAV capsid variant of any one of embodiments 198-202 or 234-244, wherein [N0] corresponds to positions 449-452 (e.g., K449, T450, I451, and N452) of any one of SEQ ID NOs: 138, 981, or 982.

246. The AAV capsid variant of any one of embodiments 168-245, wherein [N1] is present immediately subsequent to position 452, relative to a reference sequence numbered according to the amino acid sequence of SEQ ID NO: 138, 981, or 982.

247. The AAV capsid variant of any one of embodiments 168-246, wherein [N1] replaces positions 453-455 (e.g., G453, S454, and G455), relative to a reference sequence numbered according to SEQ ID NO: 138, 981, or 982.

248. The AAV capsid variant of any one of embodiments 168-246, wherein [N1] replaces position 453 (e.g., G453), relative to a reference sequence numbered according to SEQ ID NO: 138, 981, or 982.

249. The AAV capsid variant of any one of embodiments 168-177, 179-181, 183-185, 187-193, 195-200, 202, or 240-246, wherein:

(i) position X1 of [N1] replaces position 453 (e.g., G453);
(ii) position X2 of [N1] corresponds to position 454 (e.g., S454); and
(iii) position X3 of [N1] corresponds to position 455 (e.g., G455),
wherein (i), (ii), and (iii) are numbered according to SEQ ID NO: 138 or SEQ ID NO: 981.

250. The AAV capsid variant of any one of embodiments 168-176, 178-201, or 240-246, wherein:

(i) position X1 of [N1] corresponds to position 453 (e.g., G453);
(ii) position X2 of [N1] corresponds to position 454 (e.g., S454); and
(iii) position X3 of [N1] corresponds to position 455 (e.g., G455),
wherein (i), (ii), and (iii) are numbered according to SEQ ID NO: 138 or SEQ ID NO: 981.

251. The AAV capsid variant of any one of embodiments 203-248, wherein:
  (i) position X1 of [N1] corresponds to position 453 (e.g., G453);
  (ii) position X2 of [N1] replaces position 454 (e.g., S454); and
  (iii) position X3 of [N1] replaces position 455 (e.g., G455),
    wherein (i), (ii), and (iii) are numbered according to SEQ ID NO: 138 or SEQ ID NO: 982.

252. The AAV capsid variant of any one of embodiments 203-248 or 251, wherein [N1] corresponds to positions 453-455 (e.g., G453, H454, D455) of SEQ ID NO 982.

253. The AAV capsid variant of any one of embodiments 168-176, 178-201, 240-247, or 250, wherein [N1] corresponds to positions 453-455 (e.g., G453, S454, G455) of SEQ ID NO: 138, or 981.

254. The AAV capsid variant of any one of embodiments 168-253, wherein [N2] is present immediately subsequent to position 455, relative to a reference sequence numbered according to the amino acid sequence of SEQ ID NO: 138, 981, or 982.

255. The AAV capsid variant of any one of embodiments 168-254, wherein [N2] corresponds to positions 456-458 (e.g., S456, P457, and H458) of SEQ ID NO: 981 or 982.

256. The AAV capsid variant of any one of embodiments 168-254, wherein [N2] corresponds to positions 456-458 (e.g., S456, P457, and H458) of any one of SEQ ID NOs: 36-59.

257. The AAV capsid variant of any one of embodiments 168-256, wherein [N2] is present immediately subsequent to [N1].

258. The AAV capsid variant of any one of embodiments 168-202, 240-247, 249-257, wherein [N3] corresponds to positions 459-460 (e.g., S459, K460, A461) of SEQ ID NO: 981.

259. The AAV capsid variant of any one of embodiments 168-202, 240-247, 249-257, wherein [N3] corresponds to positions 459-460 (e.g., S459, K460, A461) of SEQ ID NO: 36, 38, 39, 40, 41, 42, 43, 44, 45, 46, 47, 48, 49, 50, 51, 52, 53, 54, 55, 57, or 59.

260. The AAV capsid variant of any one of embodiments 168-259, wherein [N2]-[N3] is present immediately subsequent to position 455, relative to a reference sequence numbered according to the amino acid sequence of any one of SEQ ID NOs: 138, 981, or 982.

261. The AAV capsid variant of any one of embodiments 168-259, wherein [N2]-[N3] is present immediately subsequent to position 455, relative to a reference sequence numbered according to the amino acid sequence of SEQ ID NO: 981.

262. The AAV capsid variant of any one of embodiments 168-261, wherein [N2]-[N3] corresponds to positions 456-461 (e.g., S456, P457, H458, S459, K460, A461) of SEQ ID NO: 981.

263. The AAV capsid variant of any one of embodiments 168-262, wherein [N2]-[N3] corresponds to positions 456-461 (e.g., S456, P457, H458, S459, K460, A461) of any one of SEQ ID NOs: 36, 38, 39, 40, 41, 42, 43, 44, 45, 46, 47, 48, 49, 50, 51, 52, 53, 54, 55, 57, or 59.

264. The AAV capsid variant of any one of embodiments 203-257 or 259-261, wherein [N3] corresponds to positions 459-460 (e.g., K459, S460, G461) of SEQ ID NO: 982.

265. The AAV capsid variant of any one of embodiments 203-257 or 259-261, wherein [N3] corresponds to positions 459-460 (e.g., K459, S460, G461) of SEQ ID NO: 37.

266. The AAV capsid variant of any one of embodiments 203-265, wherein [N2]-[N3] is present immediately subsequent to position 455, relative to a reference sequence numbered according to the amino acid sequence of SEQ ID NO: 982.

267. The AAV capsid variant of any one of embodiments 203-246, 248, 252, 255, 257, 260, 263-266, wherein [N3] replaces positions 454 and 455 (e.g., S454 and G455), numbered according to SEQ ID NO: 138.

268. The AAV capsid variant of any one of embodiments 203-246, 248, 252, 255, 257, 260, 263-267, wherein [N3] is present immediately subsequent to [N2] and replaces positions 454 and 455 (e.g., S454 and G455), numbered according to SEQ ID NO: 138.

269. The AAV capsid variant of any one of embodiments 203-246, 248, 252, 255, 257, 260, 263-268, wherein [N3] is present immediately subsequent to [N1]-[N2] and replaces positions 454 and 455 (e.g., S454 and G455), numbered according to SEQ ID NO: 138.

270. The AAV capsid variant of any one of embodiments 203-257, 260, 264-269, wherein [N2]-[N3] corresponds to positions 456-461 (e.g., S456, P457, H458, K459, S460, G461) of SEQ ID NO: 982.

271. The AAV capsid variant of any one of embodiments 203-257, 260, 264-270, wherein [N2]-[N3] corresponds to positions 456-461 (e.g., S456, P457, H458, K459, S460, G461) of SEQ ID NO: 37.

272. The AAV capsid variant of any one of embodiments 191-202 or 228-271, wherein [N4] is present immediately subsequent to position 455, relative to a reference sequence numbered according to the amino acid sequence of SEQ ID NO: 138.

273. The AAV capsid variant of any one of embodiments 191-202 or 228-272, wherein [N4] replaces positions 456-460 (e.g., Q456, N457, Q458, Q459, and T460), relative to a reference sequence numbered according to the amino acid sequence of SEQ ID NO: 138.

274. The AAV capsid variant of any one of embodiments 191-202 or 228-273, wherein [N4] corresponds to positions 462-466 (e.g., Q462, N463, Q464, Q465, and T466) of SEQ ID NO: 981 or 982.

275. The AAV capsid variant of any one of embodiments 191-202 or 228-273, wherein [N4] corresponds to positions 462-466 of any one of SEQ ID NOs: 36-59.

276. The AAV capsid variant of any one of embodiments 191-202 or 228-274, wherein [N4] corresponds to positions 456-460 (e.g., Q456, N457, Q458, Q459, and T460) of SEQ ID NO: 138.

277. The AAV capsid variant of any one of embodiments 191-202 or 228-276, wherein [N2]-[N3]-[N4] replaces positions 456-460 (e.g., Q456, N457, Q458, Q459, and T460), relative to a reference sequence numbered according to the amino acid sequence of SEQ ID NO: 138.

278. The AAV capsid variant of any one of embodiments 191-202 or 228-277, wherein [N2]-[N3]-[N4] is present immediately subsequent to position 455, and wherein [N2]-[N3]-[N4] replaces positions 456-460 (e.g., Q456, N457, Q458, Q459, and T460), relative to a reference sequence numbered according to the amino acid sequence of SEQ ID NO: 138.

279. The AAV capsid variant of any one of embodiments 191-202 or 228-278, wherein [N1]-[N2]-[N3]-[N4] replaces positions 453-460 (e.g., G453, S454, G455, Q456, N457, Q458, Q459, and T460), relative to a reference sequence numbered according to the amino acid sequence of SEQ ID NO: 138.

280. The AAV capsid variant of any one of embodiments 191-202 or 228-279, wherein [N1]-[N2]-[N3]-[N4] is present immediately subsequent to position 452, and wherein [N1]-[N2]-[N3]-[N4] replaces positions 453-460 (e.g., G453, S454, G455, Q456, N457, Q458, Q459, and T460), relative to a reference sequence numbered according to the amino acid sequence of SEQ ID NO: 138.

281. The AAV capsid variant of any one of embodiments 191-202, 240-247, 249, 250, 253-263, 266, or 272-280, wherein [N1]-[N2]-[N3]-[N4] corresponds to positions 453-466 (e.g., G453, S454, G455, S456, P457, H458, S459, K460, A461, Q462, N463, Q464, Q465, and T466) of SEQ ID NO: 981.

282. The AAV capsid variant of any one of embodiments 168-202, 240-247, 249, 250, 253-263, 266, or 272-280, wherein [N1]-[N2]-[N3] corresponds to positions 453-461 (e.g., G453, S454, G455, S456, P457, H458, S459, K460, A461) of SEQ ID NO: 981.

283. The AAV capsid variant of any one of embodiments 228-257, 260, 261, 264-282, wherein [N1]-[N2]-[N3]-[N4] corresponds to positions 453-466 (e.g., G453, H454, D455, S456, P457, H458, K459, S460, G461, Q462, N463, Q464, Q465, T466) of SEQ ID NO: 982.

284. The AAV capsid variant of any one of embodiments 203-257, 260, 261, 264-283, wherein [N1]-[N2]-[N3] corresponds to positions 453-461 (e.g., G453, H454, D455, S456, P457, H458, K459, S460, G461) of SEQ ID NO: 982.

285. The AAV capsid variant of any one of embodiments 228-257, 260, 261, 264-282, wherein [N1]-[N2]-[N3]-[N4] corresponds to positions 453-466 of any one of SEQ ID NOs: 36-59.

286. The AAV capsid variant of any one of embodiments 198-202 or 234-286, wherein [N0]-[N1]-[N2]-[N3]-[N4] replaces positions 449-460 (e.g., K449, T450, I451, N452, G453, S454, G455, Q456, N457, Q458, Q459, and T460), relative to a reference sequence numbered according to the amino acid sequence of SEQ ID NO: 138.

287. The AAV capsid variant of any one of embodiments 198-202 or 234-286, wherein [N0]-[N1]-[N2]-[N3]-[N4] is present immediately subsequent to position 449, and wherein [N0]-[N1]-[N2]-[N3]-[N4] replaces positions 449-460 (e.g., K449, T450, I451, N452, G453, S454, G455, Q456, N457, Q458, Q459, and T460), relative to a reference sequence numbered according to the amino acid sequence of SEQ ID NO: 138.

288. The AAV capsid variant of any one of embodiments 198-202, 240-247, 249, 250, 253-263, 266, 272-281, 286, or 287, wherein [N0]-[N1]-[N2]-[N3]-[N4] corresponds to positions 449-466 (e.g., K449, T450, I451, N452, G453, S454, G455, S456, P457, H458, S459, K460, A461, Q462, N463, Q464, Q465, T466) of SEQ ID NO: 981.

289. The AAV capsid variant of any one of embodiments 234-257, 260, 261, 264-284, 286, or 287, wherein [N0]-[N1]-[N2]-[N3]-[N4] corresponds to positions 449-466 (e.g., K449, T450, I451, N452, G453, H454, D455, S456, P457, H458, K459, S460, G461, Q462, N463, Q464, Q465, T466) of SEQ ID NO: 982.

290. The AAV capsid variant of any one of embodiments 234-257, 260, 261, 264-284, 286, or 287, wherein [N0]-[N1]-[N2]-[N3]-[N4] corresponds to positions 449-466 of any one of SEQ ID NOs: 36-59.

291. The AAV capsid variant of any one of embodiments 191-202 or 228-290, wherein [N4] is present immediately subsequent to position 461, relative to a reference sequence numbered according to the amino acid sequence of SEQ ID NO: 981 or 982.

292. The AAV capsid variant of any one of embodiments 191-202 or 228-291, wherein [N4] replaces positions 462-466 (e.g., Q462, N463, Q464, Q465, and T466), relative to a reference sequence numbered according to the amino acid sequence of SEQ ID NO: 981 or 982.

293. The AAV capsid variant of any one of embodiments 191-202 or 228-292, wherein [N2]-[N3]-[N4] replaces positions 462-466 (e.g., Q462, N463, Q464, Q465, and T466), relative to a reference sequence numbered according to the amino acid sequence of SEQ ID NO: 981 or 982.

294. The AAV capsid variant of any one of embodiments 191-202 or 228-293, wherein [N2]-[N3]-[N4] is present immediately subsequent to position 455, and wherein [N2]-[N3]-[N4] replaces positions 462-466 (e.g., Q462, N463, Q464, Q465, and T466), relative to a reference sequence numbered according to the amino acid sequence of SEQ ID NO: 981 or 982.

295. The AAV capsid variant of any one of embodiments 168-294, which comprises from N-terminus to C-terminus, [N2]-[N3].

296. The AAV capsid variant of any one of embodiments 168-295, which comprises from N-terminus to C-terminus, [N1]-[N2]-[N3].

297. The AAV capsid variant of any one of embodiments 168-296, which comprises from N-terminus to C-terminus, [N0]-[N1]-[N2]-[N3].

298. The AAV capsid variant of any one of embodiments 168-297, which comprises from N-terminus to C-terminus, [N1]-[N2]-[N3]-[N4].

299. The AAV capsid variant of any one of embodiments 168-298, which comprises from N-terminus to C-terminus, [N0]-[N1]-[N2]-[N3]-[N4].

300. An AAV capsid variant comprising the formula [A]-[B](SEQ ID NO: 4696), wherein:
   (i) [A] comprises GSGSPH (SEQ ID NO: 4695); and
   (ii) [B] comprises X1 X2, X3, X4, and X5, wherein:
      (a) position X1 is S, I, F, V, C, Y, W, R, P, L, Q, M, K, or G;
      (b) position X2 is K, M, R, F, V, C, P, Y, L, W, G, N, S, T, I, or A;
      (c) position X3 is A, Y, L, R, W, C, T, F, H, I, P, M, K, S, V, G, Q, or N;
      (d) position X4 is Q, M, F, K, H, R, C, W, P, V, L, G, S, Y, I, A, T, D, N, or E; and
      (e) position X5 is A, N, Y, R, K, L, I, M, Q, S, C, W, F, T, G, V, or P; optionally wherein the AAV capsid variant comprises an amino acid modification, e.g., a conservative substitution, of any of the aforesaid amino acids in (a)-(e).

301. The AAV capsid variant of embodiment 300, wherein:
   (a) position X1 is S, L, R, V, or P;
   (b) position X2 is K, C, F, L, P, R, S, or V;
   (c) position X3 is A, C, F, I, K, L, M, P, R, T, W, or Y;
   (d) position X4 is Q, R, S, T, C, F, K, L, P or Y; and
   (e) position X5 is N, R, S, T, K, M, Q or Y;
   optionally wherein the AAV capsid variant comprises an amino acid modification, e.g., a conservative substitution, of any of the aforesaid amino acids in (a)-(e).

302. The AAV capsid variant of embodiment 300 or 301, wherein [B] comprises SKA, SMY, SKL, SKR, SKW, SRC, SFT, SKF, IVW, SKY, SCH, FPW, SKI, VYY, SLY, SKP, SRF, SRM, SVK, SWA, SLW, SFR, SKK, SYA, SCS, SGA, SFP, SFF, SMC, SKT, SGK, FYR, CRV, YGI, VNC, SLA, WSY, RWL, PSC, SSW, SKG, VPW, SGC, STT, PKR, SKC, WVP, SFW, RIK, SKM, LRW, LPT, SYM, LLC, RCC, LCV, SYL, QGC, MAF, SFQ, SLC, RPW, RPR, SCP, SVR, SLP, VYH, SYT, LVY, YRY, SWL, CPA, SPP, RWT, PRK, PFV, SKS, WVA, SKV, CAL, SSC, SKN, LCT, STC, SKQ, KSG, SYY, SLT, SCQ, FPF, SVF, GRY, AQA, AQN, YMN, AFY, LKR, RHR, AQK, WRL, CRN, TCN, FFI, AQY, WQN, YFM, ARQ, HQN, IRR, YQN, YWN, AFS, FWN, AQC, MRN, KKN, APN, WKN, ARW, RPN, KVF, AFN, ACS, RLW, SRN, CPN, ACN, FRQ, PFN, FGN, CQN, LFW, TRK, KRN, RQN, VQN, IQN, AQR, PFR, AWN, RSY, LQN, WLN, RRA, AQT, GCT, RYT, TPN, ARM, CFL, PQN, WSN, FKN, KQN, APR, RYN, MIC, TQN, WKS, AAR, LTR, IRG, LVN, FQN, ACQ, WGL, ILR, QIN, ACI, ALR, AHA, CLN, AFV, AQF, RCN, MPC, KTS, PYN, AQS, TRN, LKN, AQM, CTN, PDN, RNY, ACR, CSV, ARI, LPK, SEQ, VRM, NSR, RKR, ARN, QRP, RVV, GQN, YSN, QSN, AKG, CTS, FEN, AKK, KAQ, MYM, KAF, KLK, KRH, KWR, RCR, FTC, KFF, VWQ, KYF, KAR, CHQ, PWQ, KIR, YYQ, LYW, KPK, RFW, RMR, VKK, WAP, LWK, FRP, KKV, YAF, KAC, KRL, CSR, RCP, GAC, KFR, FFG, MCQ, KLF, KTR, GKR, YRQ, RVQ, GIQ, NCQ, KPF, LAW, KRS, SYQ, WLQ, KRR, KGC, KRY, GCQ, FTP, TTC, KRQ, KCF, VPQ, FWS, KFK, IKQ, KAP, FRY, KMI, RWQ, PTQ, KWK, YMR, KAA, LCQ, CCQ, CVQ, KLT, KLC, YLV, AFQ, KWG, KIL, FQI, KAL, KAH, LCL, PRQ, CPQ, VRY, VRC, KMP, KKT, LPY, YHQ, YTR, VYQ, RYQ, WLK, PAQ, MCT, PPD, WTQ, RKQ, KCS, FVQ, KLP, KSE, VAQ, LYQ, KVR, ALQ, SCT, KNS, KRK, CTQ, TCL, YAR, KQR, KRV, SGQ, YYS, LTC, CQS, KAK, KPQ, PFQ, KCT, or VFE.

303. The AAV capsid variant of any one of embodiments 300-302, wherein [B] comprises (SEQ ID NO: 5829), SMYM (SEQ ID NO: 5830), SKAF (SEQ ID NO: 5831), SKLK (SEQ ID NO: 5832), SKRH (SEQ ID NO: 5833), SKWR (SEQ ID NO: 5834), SRCR (SEQ ID NO: 5835), SFTC (SEQ ID NO: 5836), SKFF (SEQ ID NO: 5837), IVWQ (SEQ ID NO: 5838), SKYF (SEQ ID NO: 5839), SKAR (SEQ ID NO: 5840), SCHQ (SEQ ID NO: 5841), FPWQ (SEQ ID NO: 5842), SKIR (SEQ ID NO: 5843), VYYQ (SEQ ID NO: 5844), SLYW (SEQ ID NO: 5845), SKPK (SEQ ID NO: 5846), SRFW (SEQ ID NO: 5847), SRMR (SEQ ID NO: 5848), SVKK (SEQ ID NO: 5849), SWAP (SEQ ID NO: 5850), SLWK (SEQ ID NO: 5851), SFRP (SEQ ID NO: 5852), SKKV (SEQ ID NO: 5853), SYAF (SEQ ID NO: 5854), SKAC (SEQ ID NO: 5855), SKRL (SEQ ID NO: 5856), SCSR (SEQ ID NO: 5857), SRCP (SEQ ID NO: 5858), SGAC (SEQ ID NO: 5859), SKFR (SEQ ID NO: 5860), SFPF (SEQ ID NO: 5861), SFFG (SEQ ID NO: 5862), SMCQ (SEQ ID NO: 5863), SKLF (SEQ ID NO: 5864), SKTR (SEQ ID NO: 5865), SGKR (SEQ ID NO: 5866), FYRQ (SEQ ID NO: 5867), CRVQ (SEQ ID NO: 5868), YGIQ (SEQ ID NO: 5869), VNCQ (SEQ ID NO: 5870), SKPF (SEQ ID NO: 5871), SLAW (SEQ ID NO: 5872), SKRS (SEQ ID NO: 5873), WSYQ (SEQ ID NO: 5874), RWLQ (SEQ ID NO: 5875), PSCQ (SEQ ID NO: 5876), SSWL (SEQ ID NO: 5877), SKRR (SEQ ID NO: 5878), SKGC (SEQ ID NO: 5879), VPWQ (SEQ ID NO: 5880), SKRY (SEQ ID NO: 5881), SGCQ (SEQ ID NO: 5882), SFTP (SEQ ID NO: 5883), STTC (SEQ ID NO: 5884), PKRQ (SEQ ID NO: 5885), SKCF (SEQ ID NO: 5886), WVPQ (SEQ ID NO: 5887), SFWS (SEQ ID NO: 5888), SKFK (SEQ ID NO: 5889), RIKQ (SEQ ID NO: 5890), SKAP (SEQ ID NO: 5891), SFRY (SEQ ID NO: 5892), SKMI (SEQ ID NO: 5893), LRWQ (SEQ ID NO: 5894), LPTQ (SEQ ID NO: 5895), SKWK (SEQ ID NO: 5896), SYMR (SEQ ID NO: 5897), SKAA (SEQ ID NO: 5898), LLCQ (SEQ ID NO: 5899), RCCQ (SEQ ID NO: 5900), LCVQ (SEQ ID NO: 5901), SKLT (SEQ ID NO: 5902), SKLC (SEQ ID NO: 5903), SYLV (SEQ ID NO: 5904), QGCQ (SEQ ID NO: 5905), MAFQ (SEQ ID NO: 5906), SKWG (SEQ ID NO: 5907), SKIL (SEQ ID NO: 5908), SFQI (SEQ ID NO: 5909), SKAL (SEQ ID NO: 5910), SKAH (SEQ ID NO: 5911), SLCL (SEQ ID NO: 5912), RPWQ (SEQ ID NO: 5913), RPRQ (SEQ ID NO: 5914), SCPQ (SEQ ID NO: 5915), SVRY (SEQ ID NO: 5916), SVRC (SEQ ID NO: 5917), SKMP (SEQ ID NO: 5918), SKKT (SEQ ID NO: 5919), SLPY (SEQ ID NO: 5920), VYHQ (SEQ ID NO: 5921), SYTR (SEQ ID NO: 5922), LVYQ (SEQ ID NO: 5923), YRYQ (SEQ ID NO: 5924), SWLK (SEQ ID NO: 5925), CPAQ (SEQ ID NO: 5926), SMCT (SEQ ID NO: 5927), SPPD (SEQ ID NO: 5928), SKRN (SEQ ID NO: 5929), RWTQ (SEQ ID NO: 5930), PRKQ (SEQ ID NO: 5931), SKCS (SEQ ID NO: 5932), PFVQ (SEQ ID NO: 5933), SKLP (SEQ ID NO: 5934), SKSE (SEQ ID NO: 5935), WVAQ (SEQ ID NO: 5936), SLYQ (SEQ ID NO: 5937), SKVR (SEQ ID NO: 5938), CALQ (SEQ ID NO: 5939), SSCT (SEQ ID NO: 5940), SKNS (SEQ ID NO: 5941), SKRK (SEQ ID NO: 5942), LCTQ (SEQ ID NO: 5943), STCL (SEQ ID NO: 5944), SYAR (SEQ ID NO: 5945), SKQR (SEQ ID NO: 5946), SKRV (SEQ ID NO: 5947), KSGQ (SEQ ID NO: 5948), SYYS (SEQ ID NO: 5949), SLTC (SEQ ID NO: 5950), SCQS (SEQ ID NO: 5951), SKAK (SEQ ID NO: 5952), SKPQ (SEQ ID NO: 5953), FPFQ (SEQ ID NO: 5954), SKCT (SEQ ID NO: 5955), SVFE (SEQ ID NO: 5956), GRYQ (SEQ ID NO: 5957), KAQA (SEQ ID NO: 5958), KAQN (SEQ ID NO: 5959), MYMN (SEQ ID NO: 5960), KAFY (SEQ ID NO: 5961), KLKR (SEQ ID NO: 5962), KRHR (SEQ ID NO: 5963), KAQK (SEQ ID NO: 5964), KWRL (SEQ ID NO: 5965), RCRN (SEQ ID NO: 5966), FTCN (SEQ ID NO: 5967), KFFI (SEQ ID NO: 5968), KAQY (SEQ ID NO: 5969), VWQN (SEQ ID NO: 5970), KYFM (SEQ ID NO: 5971), KARQ (SEQ ID NO: 5972), CHQN (SEQ ID NO: 5973), PWQN (SEQ ID NO: 5974), KIRR (SEQ ID NO: 5975), YYQN (SEQ ID NO: 5976), LYWN (SEQ ID NO: 5977), KPKR (SEQ ID NO: 5978), KAFS (SEQ ID NO: 5979), RFWN (SEQ ID NO: 5980), KAQC (SEQ ID NO: 5981), RMRN (SEQ ID NO: 5982), VKKN (SEQ ID NO: 5983), WAPN (SEQ ID NO: 5984), LWKN (SEQ ID NO: 5985), KARW (SEQ ID NO: 5986), FRPN (SEQ ID NO: 5987), KKVF (SEQ ID NO: 5988), YAFN (SEQ ID NO: 5989), KACS (SEQ ID NO: 5990), KRLW (SEQ ID NO: 5991), CSRN (SEQ ID NO: 5992), RCPN (SEQ ID NO: 5993), GACN (SEQ ID NO: 5994), KFRQ (SEQ ID NO: 5995), FPFN (SEQ ID NO: 5996), FFGN (SEQ ID NO: 5997), MCQN (SEQ ID NO: 5998), KLFW (SEQ ID NO: 5999), KTRK (SEQ ID NO: 6000), GKRN (SEQ ID NO: 6001), YRQN (SEQ ID NO: 6002), RVQN (SEQ ID NO: 6003), GIQN (SEQ ID NO: 6004), KAQR (SEQ ID NO: 6005), NCQN (SEQ ID NO: 6006), KPFR (SEQ ID NO: 6007), LAWN (SEQ ID NO: 6008), KRSY (SEQ ID NO: 6009), SYQN (SEQ ID NO: 6010), WLQN (SEQ ID NO: 6011), SCQN (SEQ ID NO: 6012), SWLN (SEQ ID NO: 6013), KRRA (SEQ ID NO: 6014), KAQT (SEQ ID NO: 6015), KGCT (SEQ ID NO: 6016), KRYT (SEQ ID NO: 6017), GCQN (SEQ ID NO: 6018), FTPN (SEQ ID NO: 6019), TTCN (SEQ ID NO: 6020), KARM (SEQ ID NO: 6021), KRQN (SEQ ID NO: 6022), KCFL (SEQ ID NO: 6023), VPQN (SEQ ID NO: 6024), FWSN (SEQ ID NO: 6025), KFKN (SEQ ID NO: 6026), IKQN (SEQ ID NO: 6027), KAPR (SEQ ID NO: 6028), FRYN (SEQ ID NO: 6029), KMIC (SEQ ID NO: 6030), RWQN (SEQ ID NO: 6031), PTQN (SEQ ID NO: 6032), KWKS (SEQ ID NO: 6033), YMRN (SEQ ID NO: 6034), KAAR (SEQ ID NO: 6035), LCQN (SEQ ID NO: 6036), CCQN (SEQ ID NO: 6037), CVQN (SEQ ID NO: 6038), KLTR (SEQ ID NO: 6039), KLCT (SEQ ID NO: 6040), KIRG (SEQ ID NO: 6041), YLVN (SEQ ID NO: 6042), AEQN (SEQ ID NO: 6043), KACQ (SEQ ID NO: 6044), KWGL (SEQ ID NO: 6045), KILR (SEQ ID NO: 6046), FQIN (SEQ ID NO: 6047), KACI (SEQ ID NO: 6048), KALR (SEQ ID NO: 6049), KAHA (SEQ ID NO: 6050), LCLN (SEQ ID NO: 6051), KAFV (SEQ ID NO: 6052), PRQN (SEQ ID NO: 6053), CPQN (SEQ ID NO: 6054), KAQF (SEQ ID NO: 6055), VRYN (SEQ ID NO: 6056), VRCN (SEQ ID NO: 6057), KMPC (SEQ ID NO: 6058), KKTS (SEQ ID NO: 6059), LPYN (SEQ ID NO: 6060), YHQN (SEQ ID NO: 6061), KAQS (SEQ ID NO: 6062), YTRN (SEQ ID NO: 6063), VYQN (SEQ ID NO: 6064), RYQN (SEQ ID NO: 6065), WLKN (SEQ ID NO: 6066), KAQM (SEQ ID NO: 6067), PAQN (SEQ ID NO: 6068), MCTN (SEQ ID NO: 6069), PPDN (SEQ ID NO: 6070), KRNY (SEQ ID NO: 6071), WTQN (SEQ ID NO: 6072), KACR (SEQ ID NO: 6073), RKQN (SEQ ID NO: 6074), KCSV (SEQ ID NO: 6075), KARI (SEQ ID NO: 6076), FVQN (SEQ ID NO: 6077), KLPK (SEQ ID NO: 6078), KSEQ (SEQ ID NO: 6079), VAQN (SEQ ID NO: 6080), LYQN (SEQ ID NO: 6081), KVRM (SEQ ID NO: 6082), ALQN (SEQ ID NO: 6083), SCTN (SEQ ID NO: 6084), KNSR (SEQ ID NO: 6085), KRKR (SEQ ID NO: 6086), CTQN (SEQ ID NO: 6087), TCLN (SEQ ID NO: 6088), YARN (SEQ ID NO: 6089), KQRP (SEQ ID NO: 6090), KRVV (SEQ ID NO: 6091), SGQN (SEQ ID NO: 6092), YYSN (SEQ ID NO: 6093), LTCN (SEQ ID NO: 6094), CQSN (SEQ ID NO: 6095), KAKG (SEQ ID NO: 6096), KPQN (SEQ ID NO: 6097), PFQN (SEQ ID NO: 6098), KCTS (SEQ ID NO: 6099), VFEN (SEQ ID NO: 6100), or KAKK (SEQ ID NO: 6101).

304. The AAV capsid variant of any one of embodiments 300-303, wherein [B] is or comprises:

(i)
SKAQA, (SEQ ID NO: 6102)
SKAQN, (SEQ ID NO: 6103)
SMYMN, (SEQ ID NO: 6104)
SKAFY, (SEQ ID NO: 6105)
SKLKR, (SEQ ID NO: 6106)
SKRHR, (SEQ ID NO: 6107)
SKAQK, (SEQ ID NO: 6108)
SKWRL, (SEQ ID NO: 6109)
SRCRN, (SEQ ID NO: 6110)
SFTCN, (SEQ ID NO: 6111)
SKFFI, (SEQ ID NO: 6112)
SKAQY, (SEQ ID NO: 6113)
IVWQN, (SEQ ID NO: 6114)
SKYFM, (SEQ ID NO: 6115)
SKARQ, (SEQ ID NO: 6116)
SCHQN, (SEQ ID NO: 6117)
FPWQN, (SEQ ID NO: 6118)
SKIRR, (SEQ ID NO: 6119)
VYYQN, (SEQ ID NO: 6120)
SLYWN, (SEQ ID NO: 6121)
SKPKR, (SEQ ID NO: 6122)
SKAFS, (SEQ ID NO: 6123)
SRFWN, (SEQ ID NO: 6124)
SKAQC, (SEQ ID NO: 6125)
SRMRN, (SEQ ID NO: 6126)
SVKKN, (SEQ ID NO: 6127)
SWAPN, (SEQ ID NO: 6128)
SLWKN, (SEQ ID NO: 6129)
SKARW, (SEQ ID NO: 6130)
SFRPN, (SEQ ID NO: 6131)
SKKVF, (SEQ ID NO: 6132)
SYAFN, (SEQ ID NO: 6133)
SKACS, (SEQ ID NO: 6134)
SKRLW, (SEQ ID NO: 6135)
SCSRN, (SEQ ID NO: 6136)
SRCPN, (SEQ ID NO: 6137)
SGACN, (SEQ ID NO: 6138)
SKFRQ, (SEQ ID NO: 6139)
SFPFN, (SEQ ID NO: 6140)

SFFGN, (SEQ ID NO: 6141)

SMCQN, (SEQ ID NO: 6142)

SKLFW, (SEQ ID NO: 6143)

SKTRK, (SEQ ID NO: 6144)

SGKRN, (SEQ ID NO: 6145)

FYRQN, (SEQ ID NO: 6146)

CRVQN, (SEQ ID NO: 6147)

YGIQN, (SEQ ID NO: 6148)

SKAQR, (SEQ ID NO: 6149)

VNCQN, (SEQ ID NO: 6150)

SKPFR, (SEQ ID NO: 6151)

SLAWN, (SEQ ID NO: 6152)

SKRSY, (SEQ ID NO: 6153)

WSYQN, (SEQ ID NO: 6154)

RWLQN, (SEQ ID NO: 6155)

PSCQN, (SEQ ID NO: 6156)

SSWLN, (SEQ ID NO: 6157)

SKRRA, (SEQ ID NO: 6158)

SKAQT, (SEQ ID NO: 6159)

SKGCT, (SEQ ID NO: 6160)

VPWQN, (SEQ ID NO: 6161)

SKRYT, (SEQ ID NO: 6162)

SGCQN, (SEQ ID NO: 6163)

SFTPN, (SEQ ID NO: 6164)

STTCN, (SEQ ID NO: 6165)

SKARM, (SEQ ID NO: 6166)

PKRQN, (SEQ ID NO: 6167)

SKCFL, (SEQ ID NO: 6168)

WVPQN, (SEQ ID NO: 6169)

SFWSN, (SEQ ID NO: 6170)

SKFKN, (SEQ ID NO: 6171)

RIKQN, (SEQ ID NO: 6172)

SKAPR, (SEQ ID NO: 6173)

SFRYN, (SEQ ID NO: 6174)

SKMIC, (SEQ ID NO: 6175)

LRWQN, (SEQ ID NO: 6176)

LPTQN, (SEQ ID NO: 6177)

SKWKS, (SEQ ID NO: 6178)

SYMRN, (SEQ ID NO: 6179)

SKAAR, (SEQ ID NO: 6180)

LLCQN, (SEQ ID NO: 6181)

RCCQN, (SEQ ID NO: 6182)

LCVQN, (SEQ ID NO: 6183)

SKLTR, (SEQ ID NO: 6184)

SKLCT, (SEQ ID NO: 6185)

SKIRG, (SEQ ID NO: 6186)

SYLVN, (SEQ ID NO: 6187)

QGCQN, (SEQ ID NO: 6188)

MAFQN, (SEQ ID NO: 6189)

SKACQ, (SEQ ID NO: 6190)

SKWGL, (SEQ ID NO: 6191)

SKILR, (SEQ ID NO: 6192)

SFQIN, (SEQ ID NO: 6193)

SKACI, (SEQ ID NO: 6194)

-continued

SKALR, (SEQ ID NO: 6195)

SKAHA, (SEQ ID NO: 6196)

SLCLN, (SEQ ID NO: 6197)

SKAFV, (SEQ ID NO: 6198)

RPWQN, (SEQ ID NO: 6199)

RPRQN, (SEQ ID NO: 6200)

SCPQN, (SEQ ID NO: 6201)

SKAQF, (SEQ ID NO: 6202)

SVRYN, (SEQ ID NO: 6203)

SVRCN, (SEQ ID NO: 6204)

SKMPC, (SEQ ID NO: 6205)

SKKTS, (SEQ ID NO: 6206)

SLPYN, (SEQ ID NO: 6207)

VYHQN, (SEQ ID NO: 6208)

SKAQS, (SEQ ID NO: 6209)

SYTRN, (SEQ ID NO: 6210)

LVYQN, (SEQ ID NO: 6211)

YRYQN, (SEQ ID NO: 6212)

SWLKN, (SEQ ID NO: 6213)

SKAQM, (SEQ ID NO: 6214)

CPAQN, (SEQ ID NO: 6215)

SMCTN, (SEQ ID NO: 6216)

SPPDN, (SEQ ID NO: 6217)

SKRNY, (SEQ ID NO: 6218)

RWTQN, (SEQ ID NO: 6219)

SKACR, (SEQ ID NO: 6220)

PRKQN, (SEQ ID NO: 6221)

SKCSV, (SEQ ID NO: 6222)

SKARI, (SEQ ID NO: 6223)

PFVQN, (SEQ ID NO: 6224)

SKLPK, (SEQ ID NO: 6225)

SKSEQ, (SEQ ID NO: 6226)

WVAQN, (SEQ ID NO: 6227)

SLYQN, (SEQ ID NO: 6228)

SKVRM, (SEQ ID NO: 6229)

CALQN, (SEQ ID NO: 6230)

SSCTN, (SEQ ID NO: 6231)

SKNSR, (SEQ ID NO: 6232)

SKRKR, (SEQ ID NO: 6233)

LCTQN, (SEQ ID NO: 6234)

STCLN, (SEQ ID NO: 6235)

SYARN, (SEQ ID NO: 6236)

SKQRP, (SEQ ID NO: 6237)

SKRVV, (SEQ ID NO: 6238)

KSGQN, (SEQ ID NO: 6239)

SYYSN, (SEQ ID NO: 6240)

SLTCN, (SEQ ID NO: 6241)

SCQSN, (SEQ ID NO: 6242)

SKAKG, (SEQ ID NO: 6243)

SKPQN, (SEQ ID NO: 6244)

FPFQN, (SEQ ID NO: 6245)

SKCTS, (SEQ ID NO: 6246)

SVFEN, (SEQ ID NO: 6247)

SKAKK, (SEQ ID NO: 6248)
or

GRYQN; (SEQ ID NO: 6249)

(ii) an amino acid sequence comprising any portion of an amino acid sequence in (i), e.g., any 2, 3, or 4 amino acids, e.g., consecutive amino acids, thereof;
(iii) an amino acid sequence comprising one, two, or three but no more than four modifications, e.g., substitutions (e.g., conservative substitutions), insertions, or deletions, relative to any of the amino acid sequences in (i); or
(iv) an amino acid sequence comprising one, two, or three but no more than four different amino acids, relative to any one of the amino acid sequences in (i).

305. The AAV capsid variant of any one of embodiments 300-304, wherein [A]-[B] is or comprises:

(i)

GSGSPHSKAQA, (SEQ ID NO: 6250)

GSGSPHSKAQN, (SEQ ID NO: 6251)

GSGSPHSMYMN, (SEQ ID NO: 6252)

GSGSPHSKAFY, (SEQ ID NO: 6253)

GSGSPHSKLKR, (SEQ ID NO: 6254)

GSGSPHSKRHR, (SEQ ID NO: 6255)

GSGSPHSKAQK, (SEQ ID NO: 6256)

GSGSPHSKWRL, (SEQ ID NO: 6257)

GSGSPHSRCRN, (SEQ ID NO: 6258)

GSGSPHSFTCN, (SEQ ID NO: 6259)

GSGSPHSKFFI, (SEQ ID NO: 6260)

GSGSPHSKAQY, (SEQ ID NO: 6261)

GSGSPHIVWQN, (SEQ ID NO: 6262)

GSGSPHSKYFM, (SEQ ID NO: 6263)

GSGSPHSKARQ, (SEQ ID NO: 6264)

GSGSPHSCHQN, (SEQ ID NO: 6265)

GSGSPHFPWQN, (SEQ ID NO: 6266)

GSGSPHSKIRR, (SEQ ID NO: 6267)

GSGSPHVYYQN, (SEQ ID NO: 6268)

GSGSPHSLYWN, (SEQ ID NO: 6269)

GSGSPHSKPKR, (SEQ ID NO: 6270)

GSGSPHSKAFS, (SEQ ID NO: 6271)

GSGSPHSRFWN, (SEQ ID NO: 6272)

GSGSPHSKAQC, (SEQ ID NO: 6273)

GSGSPHSRMRN, (SEQ ID NO: 6274)

GSGSPHSVKKN, (SEQ ID NO: 6275)

GSGSPHSWAPN, (SEQ ID NO: 6276)

GSGSPHSLWKN, (SEQ ID NO: 6277)

GSGSPHSKARW, (SEQ ID NO: 6278)

GSGSPHSFRPN, (SEQ ID NO: 6279)

GSGSPHSKKVF, (SEQ ID NO: 6280)

GSGSPHSYAFN, (SEQ ID NO: 6281)

GSGSPHSKACS, (SEQ ID NO: 6282)

GSGSPHSKRLW, (SEQ ID NO: 6283)

GSGSPHSCSRN, (SEQ ID NO: 6284)

GSGSPHSRCPN, (SEQ ID NO: 6285)

GSGSPHSGACN, (SEQ ID NO: 6286)

GSGSPHSKFRQ, (SEQ ID NO: 6287)

GSGSPHSFPFN, (SEQ ID NO: 6288)

GSGSPHSFFGN, (SEQ ID NO: 6289)

GSGSPHSMCQN, (SEQ ID NO: 6290)

GSGSPHSKLFW, (SEQ ID NO: 6291)

GSGSPHSKTRK, (SEQ ID NO: 6292)

GSGSPHSGKRN, (SEQ ID NO: 6293)

GSGSPHFYRQN, (SEQ ID NO: 6294)

GSGSPHCRVQN, (SEQ ID NO: 6295)

GSGSPHYGIQN, (SEQ ID NO: 6296)

GSGSPHSKAQR, (SEQ ID NO: 6297)

GSGSPHVNCQN, (SEQ ID NO: 6298)

GSGSPHSKPFR, (SEQ ID NO: 6299)

GSGSPHSLAWN, (SEQ ID NO: 6300)

GSGSPHSKRSY, (SEQ ID NO: 6301)

GSGSPHWSYQN, (SEQ ID NO: 6302)

GSGSPHRWLQN, (SEQ ID NO: 6303)

GSGSPHPSCQN, (SEQ ID NO: 6304)

GSGSPHSSWLN, (SEQ ID NO: 6305)

GSGSPHSKRRA, (SEQ ID NO: 6306)

GSGSPHSKAQT, (SEQ ID NO: 6307)

GSGSPHSKGCT, (SEQ ID NO: 6308)

GSGSPHVPWQN, (SEQ ID NO: 6309)

GSGSPHSKRYT, (SEQ ID NO: 6310)

GSGSPHSGCQN, (SEQ ID NO: 6311)

GSGSPHSFTPN, (SEQ ID NO: 6312)

GSGSPHSTTCN, (SEQ ID NO: 6313)

GSGSPHSKARM, (SEQ ID NO: 6314)

GSGSPHPKRQN, (SEQ ID NO: 6315)

GSGSPHSKCFL, (SEQ ID NO: 6316)

GSGSPHWVPQN, (SEQ ID NO: 6317)

GSGSPHSFWSN, (SEQ ID NO: 6318)

GSGSPHSKFKN, (SEQ ID NO: 6319)

GSGSPHRIKQN, (SEQ ID NO: 6320)

GSGSPHSKAPR, (SEQ ID NO: 6321)

GSGSPHSFRYN, (SEQ ID NO: 6322)

GSGSPHSKMIC, (SEQ ID NO: 6323)

GSGSPHLRWQN, (SEQ ID NO: 6324)

GSGSPHLPTQN, (SEQ ID NO: 6325)

GSGSPHSKWKS, (SEQ ID NO: 6326)

GSGSPHSYMRN, (SEQ ID NO: 6327)

GSGSPHSKAAR, (SEQ ID NO: 6328)

GSGSPHLLCQN, (SEQ ID NO: 6329)

GSGSPHRCCQN, (SEQ ID NO: 6330)

GSGSPHLCVQN, (SEQ ID NO: 6331)

GSGSPHSKLTR, (SEQ ID NO: 6332)

GSGSPHSKLCT, (SEQ ID NO: 6333)

GSGSPHSKIRG, (SEQ ID NO: 6334)

GSGSPHSYLVN, (SEQ ID NO: 6335)

GSGSPHQGCQN, (SEQ ID NO: 6336)

GSGSPHMAFQN, (SEQ ID NO: 6337)

GSGSPHSKACQ, (SEQ ID NO: 6338)

GSGSPHSKWGL, (SEQ ID NO: 6339)

GSGSPHSKILR, (SEQ ID NO: 6340)

GSGSPHSFQIN, (SEQ ID NO: 6341)

GSGSPHSKACI, (SEQ ID NO: 6342)

GSGSPHSKALR, (SEQ ID NO: 6343)

GSGSPHSKAHA, (SEQ ID NO: 6344)

GSGSPHSLCLN, (SEQ ID NO: 6345)

GSGSPHSKAFV, (SEQ ID NO: 6346)

GSGSPHRPWQN, (SEQ ID NO: 6347)

GSGSPHRPRQN, (SEQ ID NO: 6348)

GSGSPHSCPQN, (SEQ ID NO: 6349)

GSGSPHSKAQF, (SEQ ID NO: 6350)

GSGSPHSVRYN, (SEQ ID NO: 6351)

GSGSPHSVRCN, (SEQ ID NO: 6352)

GSGSPHSKMPC, (SEQ ID NO: 6353)

GSGSPHSKKTS, (SEQ ID NO: 6354)

GSGSPHSLPYN, (SEQ ID NO: 6355)

GSGSPHVYHQN, (SEQ ID NO: 6356)

GSGSPHSKAQS, (SEQ ID NO: 6357)

GSGSPHSYTRN, (SEQ ID NO: 6358)

GSGSPHLVYQN, (SEQ ID NO: 6359)

GSGSPHYRYQN, (SEQ ID NO: 6360)

GSGSPHSWLKN, (SEQ ID NO: 6361)

GSGSPHSKAQM, (SEQ ID NO: 6362)

GSGSPHCPAQN, (SEQ ID NO: 6363)

GSGSPHSMCTN, (SEQ ID NO: 6364)

GSGSPHSPPDN, (SEQ ID NO: 6365)

GSGSPHSKRNY, (SEQ ID NO: 6366)

GSGSPHRWTQN, (SEQ ID NO: 6367)

GSGSPHSKACR, (SEQ ID NO: 6368)

GSGSPHPRKQN, (SEQ ID NO: 6369)

GSGSPHSKCSV, (SEQ ID NO: 6370)

GSGSPHSKARI, (SEQ ID NO: 6371)

GSGSPHPFVQN, (SEQ ID NO: 6372)

GSGSPHSKLPK, (SEQ ID NO: 6373)

GSGSPHSKSEQ, (SEQ ID NO: 6374)

GSGSPHWVAQN, (SEQ ID NO: 6375)

GSGSPHSLYQN, (SEQ ID NO: 6376)

GSGSPHSKVRM, (SEQ ID NO: 6377)

GSGSPHCALQN, (SEQ ID NO: 6378)

GSGSPHSSCTN, (SEQ ID NO: 6379)

GSGSPHSKNSR, (SEQ ID NO: 6380)

GSGSPHSKRKR, (SEQ ID NO: 6381)

GSGSPHLCTQN, (SEQ ID NO: 6382)

GSGSPHSTCLN, (SEQ ID NO: 6383)

GSGSPHSYARN, (SEQ ID NO: 6384)

GSGSPHSKQRP, (SEQ ID NO: 6385)

GSGSPHSKRVV, (SEQ ID NO: 6386)

GSGSPHKSGQN, (SEQ ID NO: 6387)

GSGSPHSYYSN, (SEQ ID NO: 6388)

GSGSPHSLTCN, (SEQ ID NO: 6389)

GSGSPHSCQSN, (SEQ ID NO: 6390)

GSGSPHSKAKG, (SEQ ID NO: 6391)

GSGSPHSKPQN, (SEQ ID NO: 6392)

GSGSPHFPFQN, (SEQ ID NO: 6393)

GSGSPHSKCTS, (SEQ ID NO: 6394)

GSGSPHSVFEN, (SEQ ID NO: 6395)

GSGSPHSKAKK, (SEQ ID NO: 6396)
or

GSGSPHGRYQN; (SEQ ID NO: 6397)

(ii) an amino acid sequence comprising any portion of an amino acid sequence in (i), e.g., any 2, 3, 4, 5, 6, 7, 8, 9, or 10 amino acids, e.g., consecutive amino acids, thereof;

(iii) an amino acid sequence comprising one, two, or three but no more than four modifications, e.g., substitutions (e.g., conservative substitutions), insertions, or deletions, relative to any of the amino acid sequences in (i); or (iv) an amino acid sequence comprising one, two, or three but no more than four different amino acids, relative to any one of the amino acid sequences in (i)

306. The AAV capsid of any one of embodiments 300-305, wherein [A]-[B] does not comprise the amino acid sequence of GSGSPHSKAQN (SEQ ID NO: 6251).

307. The AAV capsid variant of any one of embodiments 300-306, which comprises one, two, or all of an amino acid other than Q at position 458 (e.g., R, C, S, W, L, F, Y, H, I, V, A, or P), an amino acid other than Q at position 459 (e.g., K, I, R, L or S), and/or an amino acid other than T at position 460 (e.g., R), numbered relative to SEQ ID NO: 138.

308. The AAV capsid variant of any one of embodiments 300-307, which comprises:
  (i) the amino acid R at position 458;
  (ii) the amino acid W at position 458;
  (iii) the amino acid Y at position 458;
  (iv) the amino acid F at position 458;
  (v) the amino acid S at position 458;
  (vi) the amino acid C at position 458;
  (vii) the amino acid I at position 458;
  (viii) the amino acid L at position 458;
  (ix) the amino acid P at position 458;
  (x) the amino acid I at position 459;
  (xi) the amino acid H at position 458; or
  (xii) the amino acid V at position 458;
  wherein (i)-(xii) are numbered according to SEQ ID NO: 138.

309. The AAV capsid variant of any one of embodiments 300-307, which comprises:
  (i) the amino acid R at position 458 and the amino acid K at position 459;
  (ii) the amino acid C at position 458 and the amino acid I at position 459;
  (iii) the amino acid S at position 458 and the amino acid R at position 459';
  (iv) the amino acid L at position 458 and the amino acid K at position 459;
  (v) the amino acid F at position 458 and the amino acid K at position 459;
  (vi) the amino acid C at position 458 and the amino acid R at position 459;
  (vii) the amino acid H at position 458 and the amino acid R at position 459;
  (viii) the amino acid I at position 458 and the amino acid L at position 459;
  (ix) the amino acid V at position 458 and the amino acid R at position 459;
  (x) the amino acid A at position 458 and the amino acid K at position 459;
  (xi) the amino acid I at position 458 and the amino acid K at position 459;
  (xii) the amino acid C at position 458 and the amino acid S at position 459; or
  (xiii) the amino acid C at position 458 and the amino acid L at position 459
  wherein (i)-(xiii) are numbered according to SEQ ID NO: 138.

310. The AAV capsid variant of any one of embodiments 300-307, which comprises the amino acid F at position 458, the amino acid K at position 459, and the amino acid R at position 460, numbered relative to SEQ ID NO: 138.

311. The AAV capsid variant of any one of embodiments 300-310, which comprises one, two, or all of an amino acid other than T at position 450 (e.g., Y, P, W, R, K, S, or F), an amino acid other than I at position 451 (e.g., R, S, Y, L, V, H, P, A, or F), and/or an amino acid other than N at position 452 (e.g., V, W, A, T, F, Y, L, R, H, S, or M), numbered relative to SEQ ID NO: 138.

312. The AAV capsid variant of any one of embodiments 300-311, which comprises the amino acid V at position 452, numbered according to SEQ ID NO: 138.

313. The AAV capsid variant of any one of embodiments 300-312, which comprises the amino acid Y at position 450 and the amino acid V at position 452, numbered according to SEQ ID NO: 138.

314. The AAV capsid variant of any one of embodiments 300-312, which comprises the amino acid R at position 450 and the amino acid Y at position 451, numbered according to SEQ ID NO: 138.

315. The AAV capsid variant of any one of embodiments 300-311, which comprises:
  (i) the amino acid P at position 450, the amino acid R at position 451, and the amino acid W at position 452;
  (ii) the amino acid Y at position 450, the amino acid S at position 451, and the amino acid A at position 452;
  (iii) the amino acid Y at position 450, the amino acid Y at position 451, and the amino acid T at position 452;
  (iv) the amino acid P at position 450, the amino acid R at position 451, and the amino acid F at position 452;
  (v) the amino acid W at position 450, the amino acid L at position 451, and the amino acid T at position 452;
  (vi) the amino acid R at position 450, the amino acid S at position 451, and the amino acid Y at position 452;
  (vii) the amino acid Y at position 450, the amino acid V at position 451, and the amino acid F at position 452;
  (viii) the amino acid K at position 450, the amino acid H at position 451, and the amino acid L at position 452;
  (ix) the amino acid P at position 450, the amino acid P at position 451, and the amino acid L at position 452;
  (x) the amino acid P at position 450, the amino acid A at position 451, and the amino acid R at position 452;
  (xi) the amino acid S at position 450, the amino acid R at position 451, and the amino acid R at position 452;
  (xii) the amino acid F at position 450, the amino acid F at position 451, and the amino acid H at position 452;
  (xiii) the amino acid R at position 450, the amino acid F at position 451, and the amino acid S at position 452;
  (xiv) the amino acid Y at position 450, the amino acid S at position 451, and the amino acid M at position 452; or
  (xv) the amino acid P at position 450, the amino acid F at position 451, and the amino acid L at position 452;
  wherein (i)-(xv) is numbered according to SEQ ID NO: 138.

316. The AAV capsid variant of any one of embodiments 300-315, which comprises:
  (i) the amino acid sequence of any one of SEQ ID NOs: 3849-3982, 2984-4010, 4681-4693;
  (ii) an amino acid sequence comprising any portion of an amino acid sequence in (i), e.g., any 2, 3, 4, 5, 6, 7, 8, 9, 10, 11, 12, 13, 14, 15, 16, or 17 amino acids, e.g., consecutive amino acids, thereof;
  (iii) an amino acid sequence comprising one, two, or three but no more than four modifications, e.g., substitutions (e.g., conservative substitutions), insertions, or deletions, relative to any of the amino acid sequences in (i); or
  (iv) an amino acid sequence comprising one, two, or three but no more than four different amino acids, relative to any one of the amino acid sequences in (i).

317. The AAV capsid variant of any one of embodiments 300-316, which does not comprise the amino acid sequence of GSGSPHSKAQNQQ (SEQ ID NO: 1801) or GSGSPHS-KAQNQQT (SEQ ID NO: 200).

318. The AAV capsid variant of any one of embodiments 300-317, wherein [A]-[B] is present in loop IV.

319. The AAV capsid variant of any one of embodiments 300-318, wherein [A] is present immediately subsequent to position 452, relative to a reference sequence numbered according to the amino acid sequence of SEQ ID NO: 138 or 981.

320. The AAV capsid variant of any one of embodiments 300-319, wherein [A] replaces positions 453-455 (e.g., G453, S454, G455), relative to a reference sequence numbered according to the amino acid sequence of SEQ ID NO: 138 or 981.

321. The AAV capsid variant of any one of embodiments 300-320, wherein [A] is present immediately subsequent to position 452, and wherein [A] replaces positions 453-455 (e.g., G453, S454, G455), relative to a reference sequence numbered according to the amino acid sequence of SEQ ID NO: 138 or 981.

322. The AAV capsid variant of any one of embodiments 300-321, wherein [B] is present immediately subsequent to [A].

323. The AAV capsid variant of any one of embodiments 300-322, wherein [B] replaces positions 456 and 457 (e.g., Q456, N457), numbered relative to SEQ ID NO: 138.

324. The AAV capsid variant of any one of embodiments 300-323, wherein [A]-[B] replaces positions 453-457 (e.g., G453, S454, G455, Q456, N457), relative to a reference sequence numbered according to the amino acid sequence of SEQ ID NO: 138.

325. The AAV capsid variant of any one of embodiments 300-324, wherein [A]-[B] is present immediately subsequent to position 452, and wherein [A]-[B] replaces positions 453-457 (e.g., G453, S454, G455, Q456, N457), relative to a reference sequence numbered according to the amino acid sequence of SEQ ID NO: 138.

326. The AAV capsid variant of any one of embodiments 300-325, which comprises from N-terminus to C-terminus, [A][B].

327. The AAV capsid variant of any one of the preceding embodiments, which comprises at least one, two, three or four (e.g., from 1-4 to 1-5) charged amino acid residues (e.g., acidic and/or basic amino acid residues) relative to SEQ ID NO: 138, which is present N-terminal to the amino acid sequence of SPH (e.g., within 1, 2, 3, 4, 5, or 6 amino acids from the start of the SPH amino acid sequence (e.g., within positions 450-455 numbered according to SEQ ID NO: 138)), optionally wherein the amino acid sequence of SPH is present at positions 456-458 numbered according to any one of SEQ ID NOs: 36-59, 981, or 982.

328. The AAV capsid variant of embodiment 327, wherein the amino acid sequence of SPH is present at positions 456-458 numbered according to any one of SEQ ID NOs: 36-59, 981, or 982.

329. The AAV capsid variant of embodiment 327 or 328, which comprises less than four, less than three, less than two (e.g., two or one) charged amino acid residues (e.g., acidic and/or basic amino acid residues) relative to SEQ ID NO: 138.

330. The AAV capsid variant of any one of embodiments 327-329, which comprises one charged amino acid residues (e.g., an acidic or basic amino acid residue) relative to SEQ ID NO: 138, optionally at any one of positions 450-455 numbered relative to SEQ ID NO: 138.

331. The AAV capsid variant of any one of embodiments 327-330, wherein the charged amino acid residue is an acidic amino acid (e.g., D or E).

332. The AAV capsid variant of any one of embodiments 327-331, wherein the charged amino acid residue is a negatively charged amino acid (e.g., D or E).

333. The AAV capsid variant of any one of embodiments 327-332, wherein the charged amino acid residue is D.

334. The AAV capsid variant of any one of embodiments 327-333, wherein the charged amino acid residue is E.

335. The AAV capsid variant of any one of embodiments 327-334, wherein the charged amino acid residue is a basic amino acid (e.g., K, R, or H).

336. The AAV capsid variant of any one of embodiments 327-335, wherein the charged amino acid residue is a positively charged amino acid (e.g., K, R, or H).

337. The AAV capsid variant of any one of embodiments 327-336, wherein the charged amino acid residue is H.

338. The AAV capsid variant of any one of embodiments 327-337, wherein the charged amino acid residue is R.

339. The AAV capsid variant of any one of embodiments 327-338, wherein the charged amino acid residue is K.

340. The AAV capsid variant of any one of embodiments 327-339, wherein the AAV capsid variant comprises an acidic amino acid (e.g., E or D) and a basic amino acid (e.g., R, K, or H).

341. The AAV capsid variant of any one of embodiments 327-340, at least one, two, three or four charged amino acid residues is present within 1, 2, 3, 4, 5, or 6 (e.g., 1-6) amino acids from the start of the SPH amino acid sequence.

342. The AAV capsid variant of any one of embodiments 327-341, which comprises two charged amino acid residue immediately preceding the amino acid sequence of SPH (e.g., at positions 454 and 455, numbered according to SEQ ID NO: 138 or SEQ ID NO: 982).

343. The AAV capsid variant of any one of embodiments 327-342, which comprises a charged amino acid residue (e.g., E) within 1, 2, 3, 4, 5 (e.g., 5) amino acids from the start of the SPH amino acid sequence.

344. The AAV capsid variant of any one of embodiments 327-343, which comprises a charged amino acid residue (e.g., E) at position 451, numbered according to any one of SEQ ID NO: 138, 981, or 982.

345. The AAV capsid variant of any one of embodiments 327-344, which comprises E at position 451, numbered according to any one of SEQ ID NOs: 138, 981, or 982.

346. The AAV capsid variant of any one of embodiments 327-345, which comprises a charged amino acid residue (e.g., R or K) at position 452, numbered according to any one of SEQ ID NOs: 138, 981, or 982.

347. The AAV capsid variant of any one of embodiments 327-346, which comprises R at position 452, numbered according to SEQ ID NO: 138 or SEQ ID NO: 982.

348. The AAV capsid variant of any one of embodiments 327-347, which comprises E at position 451 and R at position 452, numbered according to SEQ ID NO: 138 or SEQ ID NO: 982.

349. The AAV capsid variant of any one of embodiments 327-348, which has decreased tropism for a liver cell or tissue, relative to the tropism of a reference sequence comprising the amino acid sequence of SEQ ID NO: 138 or SEQ ID NO: 981.

350. The AAV capsid variant of any one of the preceding embodiments, which comprises at least one, two, three or four (e.g., from 1-4 to 1-5) charged amino acid residues (e.g., basic amino acid residues) relative to SEQ ID NO: 138, which is present C-terminal to the amino acid sequence of SPH (e.g., within 1, 2, 3, 4, 5, 6, or 7 amino acids from the end of the SPH amino acid sequence (e.g., within positions 459-465 numbered according to any one of SEQ ID NOs: 36-59, or 981)), optionally wherein the amino acid sequence of SPH is present at positions 456-458 numbered according to any one of SEQ ID NOs: 36-59, 981, or 982.

351. The AAV capsid variant of embodiment 350, wherein the amino acid sequence of SPH is present at positions 456-458 numbered according to any one of SEQ ID NOs: 36-59, 981, or 982.

352. The AAV capsid variant of embodiment 350 or 351, which comprises less than four, less than three, less than two (e.g., two or one) charged amino acid residues (e.g., basic amino acid residues) relative to SEQ ID NO: 138.

353. The AAV capsid variant of any one of embodiments 350-352, which comprises one charged amino acid residues (e.g., an basic amino acid residue) relative to SEQ ID NO: 138, optionally at any one of positions 456-460 numbered relative to SEQ ID NO: 138 or at positions 462-466 numbered according to any one of SEQ ID NOs: 36-59, 981, or 982.

354. The AAV capsid variant of any one of embodiments 350-353, wherein the charged amino acid residue is a basic amino acid (e.g., R or K).

355. The AAV capsid variant of any one of embodiments 350-354, wherein the charged amino acid residue is a positively charged amino acid (e.g., R or K).

356. The AAV capsid variant of any one of embodiments 350-355, wherein the charged amino acid residue is R.

357. The AAV capsid variant of any one of embodiments 350-355, wherein the charged amino acid residue is K.

358. The AAV capsid variant of any one of embodiments 350-357, at least one, two, three or four charged amino acid residues is present within 1, 2, 3, 4, 5, 6, 7 (e.g., 1-7) amino acids from the end of the SPH amino acid sequence.

359. The AAV capsid variant of any one of embodiments 350-358, which comprises a charged amino acid residue (e.g., K or R) immediately after the SPH sequence (e.g., at position 459 numbered according to SEQ ID NO: 981).

360. The AAV capsid variant of any one of embodiments 350-359, which comprises a charged amino acid residue (e.g., K or R) at position 459, numbered according to SEQ ID NO: 138 or SEQ ID NO: 982.

361. The AAV capsid variant of any one of embodiments 350-360, which comprises K at position 459, numbered according to SEQ ID NO: 981.

362. The AAV capsid variant of any one of embodiments 350-360, which comprises R at position 459, numbered according to SEQ ID NO: 981.

363. The AAV capsid variant of any one of embodiments 350-362, which comprises a charged amino acid residue (e.g., R or K) at one, two three, four, five, or all of positions 460, 461, 462, 463, 464, and/or 465, numbered according to SEQ ID NO: 138 or 981.

364. The AAV capsid variant of any one of embodiments 300-326 or 350-363, which has increased tropism for a liver cell or tissue, relative to the tropism of a reference sequence comprising the amino acid sequence of SEQ ID NO: 138.

365. The AAV capsid variant of any one of embodiments 300-326 or 350-364, which is enriched at least about 10, 15, 20, 25, 30, 35, 40, 45, 50, 55, 60, 65, 70, 75, 80, 85, 90, 95, 100, 105, 110, 115, 120, 125, 130, 135, 140, 150, 160, 170, 180, 190, or 200-fold, in the liver compared to a reference sequence of SEQ ID NO: 138, e.g., when measured by an assay as described in Example 4.

366. The AAV capsid variant of any one of embodiments 300-326, 364, or 365, which has reduced tropism for a CNS cell or tissue, e.g., a brain cell, brain tissue, spinal cord cell, or spinal cord tissue, relative to the tropism of a reference sequence comprising the amino acid sequence of SEQ ID NO: 138.

367. The AAV capsid variant of any one of embodiments 300-326 or 364-366, which shows preferential transduction in a liver region relative to the transduction in the brain and/or dorsal root ganglia (DRG).

368. The AAV capsid variant of any one of embodiments 300-326 or 364-367, which shows preferential transduction in a liver region relative to the transduction in the heart and/or muscle (e.g., quadriceps).

369. An AAV capsid variant comprising:
(a) the amino acid sequence of any of the sequences provided in Tables 1, 2A, 2B, 13-19;
(b) an amino acid sequence comprising at least 3, 4, 5, 6, 7, 8, 9, 10, 11, 12, 13, 14, 15, 16, or 17 consecutive amino acids from any one of the sequences provided in Tables 1, 2A, 2B, 13-19; or
(c) an amino acid sequence comprising at least one, two, or three but no more than four different amino acids, relative to any one of the sequences provided in Tables 1, 2A, 2B, 13-19; or
(d) an amino acid sequence comprising at least one, two, or three but no more than four modifications, e.g., substitutions (e.g., conservative substitutions), relative to the amino acid sequence of any one of the sequences provided in Tables 1, 2A, 2B, 13-19.

370. An AAV capsid variant comprising:
(a) the amino acid sequence of any of SEQ ID NOs: 945-980 or 985-986;
(b) an amino acid sequence comprising at least 3, 4, or 5 consecutive amino acids from any one of SEQ ID NOs: 945-980 or 985-986; or
(c) an amino acid sequence comprising at least one, two, or three but no more than four different amino acids, relative to the amino acid sequence of any one of SEQ ID NOs: 945-980 or 985-986;
(d) an amino sequence comprising at least one, two, or three but no more than four modifications, e.g., substitutions (e.g., conservative substitutions), relative to the amino acid sequence of any one of SEQ ID NOs: 945-980 or 985-986.

371. An AAV capsid variant comprising:
(a) the amino acid sequence of any of SEQ ID NOs: 2, 200, 201, 941, 943, 204, 208, 404, or 903-909;
(b) an amino acid sequence comprising at least 3, 4, 5, 6, 7, 8, 9, 10, 11, 12, or 13 consecutive amino acids from any one of SEQ ID NOs: 2, 200, 201, 941, 943, 204, 208, 404, or 903-909;
(c) an amino acid sequence comprising at least one, two, or three but no more than four different amino acids, relative to the amino acid sequence of any one of SEQ ID NOs: 2, 200, 201, 941, 943, 204, 208, 404, or 903-909; or
(d) an amino acid sequence comprising at least one, two, or three but no more than four modifications, e.g., substitutions (e.g., conservative substitutions), relative to the amino acid sequence of any one of SEQ ID NOs: 2, 200, 201, 941, 943, 204, 208, 404, or 903-909.

372. An AAV capsid variant comprising:
(a) the amino acid sequence of any of SEQ ID NOs: 3849-4051 or 4681-4693;
(b) an amino acid sequence comprising at least 3, 4, 5, 6, 7, 8, 9, 10, 11, 12, 13, 14, 15, 16 or 17 consecutive amino acids from any one of SEQ ID NOs: 3849-4051 or 4681-4693;

(c) an amino acid sequence comprising at least one, two, or three but no more than four different amino acids, relative to the amino acid sequence of any one of SEQ ID NOs: 3849-4051 or 4681-4693; or (d) an amino acid sequence comprising at least one, two, or three but no more than four modifications, e.g., substitutions (e.g., conservative substitutions), relative to the amino acid sequence of any one of SEQ ID NOs: 3849-4051 or 4681-4693.

373. An AAV capsid variant comprising:
  (a) the amino acid sequence of any of SEQ ID NOs: 4052-4092;
  (b) an amino acid sequence comprising at least 3, 4, 5, 6, 7, 8, 9, 10, 11, 12, 13, 14, 15, 16 or 17 consecutive amino acids from any one of SEQ ID NOs: 4052-4092;
  (c) an amino acid sequence comprising at least one, two, or three but no more than four different amino acids, relative to the amino acid sequence of any one of SEQ ID NOs: 4052-4092; or
  (d) an amino acid sequence comprising at least one, two, or three but no more than four modifications, e.g., substitutions (e.g., conservative substitutions), relative to the amino acid sequence of any one of SEQ ID NOs: 4052-4092.

374. An AAV capsid variant comprising:
  (a) the amino acid sequence of any of SEQ ID NOs: 4056, 4058, 4059, 4062-4064, 4066, 4067, 4080, 4084, 4090, or 4095-4097;
  (b) an amino acid sequence comprising at least 3, 4, 5, 6, 7, 8, 9, 10, 11, 12, 13, 14, 15, 16 or 17 consecutive amino acids from any one of SEQ ID NOs: 4056, 4058, 4059, 4062-4064, 4066, 4067, 4080, 4084, 4090, or 4095-4097;
  (c) an amino acid sequence comprising at least one, two, or three but no more than four different amino acids, relative to the amino acid sequence of any one of SEQ ID NOs: 4056, 4058, 4059, 4062-4064, 4066, 4067, 4080, 4084, 4090, or 4095-4097; or
  (d) an amino acid sequence comprising at least one, two, or three but no more than four modifications, e.g., substitutions (e.g., conservative substitutions), relative to the amino acid sequence of any one of SEQ ID NOs: 4056, 4058, 4059, 4062-4064, 4066, 4067, 4080, 4084, 4090, or 4095-4097.

375. The AAV capsid variant of embodiment 369 or 371, comprising an amino acid sequence comprising at least 4, 5, 6, 7, 8, 9, 10, 11, 12, or 13 consecutive amino acids from any one of SEQ ID NOs: 2, 200, 201, 941, 943, 204, 208, 404, or 903-909.

376. The AAV capsid variant of any one of embodiments 369-375, wherein the 3 consecutive amino acids comprise SPH.

377. The AAV capsid variant of any one of embodiments 369-371 or 376, wherein the 4 consecutive amino acids comprise SPHS (SEQ ID NO: 4700).

378. The AAV capsid variant of any one of embodiments 369-371, 376, or 377, wherein the 5 consecutive amino acids comprise SPHSK (SEQ ID NO: 4701).

379. The AAV capsid variant of any one of embodiments 369-371 or 376-378, wherein the 6 consecutive amino acids comprise SPHSKA (SEQ ID NO: 941).

380. The AAV capsid variant of embodiment 369-371, wherein the 3 consecutive amino acids comprise HDS.

381. The AAV capsid variant of any one of embodiments 369-371 or 380, wherein the 4 consecutive amino acids comprise HDSP (SEQ ID NO: 4702).

382. The AAV capsid variant of any one of embodiments 369-371, 380, or 381, wherein the 5 consecutive amino acids comprise HDSPH (SEQ ID NO: 4703).

383. The AAV capsid variant of any one of embodiments 369-371 or 380-382, wherein the 6 consecutive amino acids comprise HDSPHK (SEQ ID NO: 2).

384. The AAV capsid variant of any one of embodiments 369-371, wherein:
  (i) the 3 consecutive amino acids comprise SPH; (ii) the 4 consecutive amino acids comprise SPHK (SEQ ID NO: 6398);
  (iii) the 5 consecutive amino acids comprise SPHKY (SEQ ID NO: 4715); and/or
  (iv) the 6 consecutive amino acids comprise SPHKYG (SEQ ID NO: 966).

385. The AAV capsid variant of embodiment 369 or 371, which comprises an amino acid sequence comprising at least one, two, or three but no more than four modifications, e.g., substitutions (e.g., conservative substitutions), relative to the amino acid sequence of any one of SEQ ID NOs: 2, 200, 201, 941, 943, 204, 208, 404, or 903-909.

386. The AAV capsid variant of any one of embodiments 369,371, or 385, which comprises an amino acid sequence comprising at least one, two, or three but no more than four modifications, e.g., substitutions (e.g., conservative substitutions), relative to the amino acid sequence of SPHSKA (SEQ ID NO: 941).

387. The AAV capsid variant of any one of embodiments 369, 371, or 385, which comprises an amino acid sequence comprising at least one, two, or three but no more than four modifications, e.g., substitutions (e.g., conservative substitutions), relative to the amino acid sequence of HDSPHK (SEQ ID NO: 2).

388. The AAV capsid variant of any one of embodiments 369-371, 384, or 385, which comprises an amino acid sequence comprising at least one, two, or three but no more than four modifications, e.g., substitutions (e.g., conservative substitutions), relative to the amino acid sequence of SPHKYG (SEQ ID NO: 966).

389. The AAV capsid variant of embodiment 370, which comprises:
  (i) an amino acid sequence comprising at least one, two, or three but no more than four modifications, e.g., substitutions (e.g., conservative substitutions), relative to the amino acid sequence of KTERVSGSPHSKAQNQQT (SEQ ID NO: 3589);
  (ii) an amino acid sequence comprising at least one, two, or three but no more than four modifications, e.g., substitutions (e.g., conservative substitutions), relative to the amino acid sequence of KAEIGHDSPHKSGQNQQT (SEQ ID NO: 1754)
  (iii) an amino acid sequence comprising at least one, two, or three but no more than four modifications, e.g., substitutions (e.g., conservative substitutions), relative to the amino acid sequence of KTEKMSGSPHSKAQNQQT (SEQ ID NO: 3241);
  (iv) an amino acid sequence comprising at least one, two, or three but no more than four modifications, e.g., substitutions (e.g., conservative substitutions), relative to the amino acid sequence of KTINGHDSPHSKAQNLQT (SEQ ID NO: 4100); or
  (v) an amino acid sequence comprising at least one, two, or three but no more than four modifications, e.g., substitutions (e.g., conservative substitutions), relative to the amino acid sequence of KTVNGHDSPHSKAQNQQT (SEQ ID NO: 4062).

390. The AAV capsid variant of embodiment 369 or 371, which comprises an amino acid sequence comprising at least one, two, or three but no more than four different amino acids relative to the amino acid sequence of any one of SEQ ID NOs: 2, 200, 201, 941, 943, 204, 208, 404, or 903-909.

391. The AAV capsid variant of any one of embodiments 369, 371, or 390, which comprises an amino acid sequence comprising at least one, two, or three but no more than four different amino acids relative to the amino acid sequence of SPHSKA (SEQ ID NO: 941).

392. The AAV capsid variant of any one of embodiments 369, 371, or 390, which comprises an amino acid sequence comprising at least one, two, or three but no more than four different amino acids relative to the amino acid sequence of HDSPHK (SEQ ID NO: 2).

393. The AAV capsid variant of any one of embodiments 369, 371, 384, or 390, which comprises an amino acid sequence comprising at least one, two, or three but no more than four different amino acids relative to the amino acid sequence of SPHKYG (SEQ ID NO: 966).

394. The AAV capsid variant of embodiment 369, which comprises:
(i) an amino acid sequence comprising at least one, two, or three but no more than four different amino acids relative to the amino acid sequence of KTERVSGSPHSKAQNQQT (SEQ ID NO: 3589);
(ii) an amino acid sequence comprising at least one, two, or three but no more than four different amino acids relative to the amino acid sequence of KAEIGHDSPHKSGQNQQT (SEQ ID NO: 1754);
(iii) an amino acid sequence comprising at least one, two, or three but no more than four different amino acids relative to the amino acid sequence of KTEKMSGSPHSKAQNQQT (SEQ ID NO: 3241);
(iv) an amino acid sequence comprising at least one, two, or three but no more than four different amino acids relative to the amino acid sequence of KTINGHDSPHSKAQNLQT (SEQ ID NO: 4100); or
(v) an amino acid sequence comprising at least one, two, or three but no more than four different amino acids relative to the amino acid sequence of KTVNGHDSPHSKAQNQQT (SEQ ID NO: 4062).

395. The AAV capsid variant of any one of embodiments 1-129, 269, 271, 375-388, or 390-394, which comprises the amino acid sequence of any of SEQ ID NOs: 2, 200, 201, 941, 943, 204, 208, 404, or 903-909.

396. The AAV capsid variant of any one of embodiments 295-297, 301-305, 313, 314, 318, 319, or 323, which comprises the amino acid sequence of ERVSGSPHSKA (SEQ ID NO: 6399), optionally wherein the amino acid sequence is present immediately subsequent to position 450 and replaces positions 451-455 (e.g., 1451, N542, G453, S454, G455), numbered according to SEQ ID NO: 138.

397. The AAV capsid variant of any one of embodiments 369-371, 375-379, 385, 386, 389-391, or 394-396, which comprises the amino acid sequence of KTERVSGSPHSKAQNQQT (SEQ ID NO: 3589), optionally wherein the amino acid sequence is present immediately subsequent to position 448 and replaces positions 449-460 (e.g., K449, T450, 1451, N452, G453, S454, G455, Q456, N457, Q458, Q459, T460), numbered according to SEQ ID NO: 138.

398. The AAV capsid variant of any one of embodiments 269-371, 375, 380-383, 385, 387, 389, 390, 393, or 394, which comprises the amino acid sequence of AEIGHDSPHKSG (SEQ ID NO: 6400), optionally wherein the amino acid sequence is present immediately subsequent to position 449 and replaces positions 450-455 (e.g., T450, 1451, N452, G453, S454, G455), numbered according to SEQ ID NO: 138.

399. The AAV capsid variant of any one of embodiments 369-371, 375, 380-383, 385, 387, 389, 390, 393, 394, or 398, which comprises the amino acid sequence of KAEIGHDSPHKSGQNQQT (SEQ ID NO: 1754), optionally wherein the amino acid sequence is present immediately subsequent to position 448 and replaces positions 449-460 (e.g., K449, T450, 1451, N452, G453, S454, G455, Q456, N457, Q458, Q459, T460), numbered according to SEQ ID NO: 138.

400. The AAV capsid variant of any one of embodiments 369-371, 375-379, 390, 391, or 395, which comprises the amino acid sequence of EKMSGSPHSKA (SEQ ID NO: 6401), optionally wherein the amino acid sequence is present immediately subsequent to position 450 and replaces positions 451-455 (e.g., 1451, N452, G453, S454, G455), numbered according to SEQ ID NO: 138.

401. The AAV capsid variant of any one of embodiments 369-371, 375-379, 390, 391, or 395, which comprises the amino acid sequence of KTEKMSGSPHSKAQNQQT (SEQ ID NO: 3241), optionally wherein the amino acid sequence is present immediately subsequent to position 448 and replaces positions 449-460 (e.g., K449, T450, 1451, N452, G453, S454, G455, Q456, N457, Q458, Q459, T460), numbered according to SEQ ID NO: 138.

402. The AAV capsid variant of any one of embodiments 369-371, 375-379, 390, 391, or 395, which comprises the amino acid sequence of HDSPHSKAQNL (SEQ ID NO: 6402), optionally wherein the amino acid sequence is present immediately subsequent to position 453 and replaces positions 456-458 (e.g., Q456, N457, Q458), numbered according to SEQ ID NO: 138.

403. The AAV capsid variant of any one of embodiments 369-371, 375-379, 390, 391, or 395, which comprises the amino acid sequence of KTINGHDSPHSKAQNLQT (SEQ ID NO: 4100), optionally wherein the amino acid sequence is present immediately subsequent to position 448 and replaces positions 449-460 (e.g., K449, T450, 1451, N452, G453, S454, G455, Q456, N457, Q458, Q459, T460), numbered according to SEQ ID NO: 138.

404. The AAV capsid variant of any one of embodiments 369-371, 375-379, 390, 391, or 395, which comprises the amino acid sequence of VNGHDSPHSKA (SEQ ID NO: 6403), optionally wherein the amino acid sequence is present immediately subsequent to position 450 and replaces positions 451-455 (e.g., 1451, N452, G453, S454, G455), numbered according to SEQ ID NO: 138.

405. The AAV capsid variant of any one of embodiments 369-371, 375-379, 390, 391, or 395, which comprises the amino acid sequence of KTVNGHDSPHSKAQNQQT (SEQ ID NO: 4062), optionally wherein the amino acid sequence is present immediately subsequent to position 448 and replaces positions 449-460 (e.g., K449, T450, 1451, N452, G453, S454, G455, Q456, N457, Q458, Q459, T460), numbered according to SEQ ID NO: 138.

406. The AAV capsid variant of any one of embodiments 1-23, 26-29, 32, 35-43, 46-51, 54-72, 69-89, 91, 94-99, 102-104, 107, 110-112, 115-129, 168-202, 02, 240-247, 249, 250, 253-263, 266, 272-281, 286, 288, 291-299, 327-363, 369-371, 375-379, 385, 386, 390, 391, or 395, comprising an amino acid sequence encoded by: the nucleotide sequence of SEQ ID NO: 942; a nucleotide sequence comprising at least one, two, three, four, five, six, or seven modifications, e.g., substitutions (e.g., conservative substitutions), but no more than ten modifications, e.g., substitutions (e.g., conservative substitutions), relative to the nucleotide sequence of SEQ ID NO: 942; or a nucleotide sequence comprising at least one, two, three, four, five, six, or seven, but no more than ten different nucleotides relative to the nucleotide sequence of SEQ ID NO: 942.

407. The AAV capsid variant of any one of embodiments 1-9, 11, 12-22, 24, 26, 28, 30, 33, 35-42, 44, 46-50, 52, 54-77, 83-88, 90-97, 100-103, 105, 110, 111, 113-129, 203-248, 251, 252, 254-257, 260, 261, 264-280, 283-287, 289-299, 327-363, 369, 369, 371, 380-383, 385, 386, 390, 392, or 395, comprising an amino acid sequence encoded by: the nucleotide sequence of SEQ ID NO: 3; a nucleotide sequence comprising at least one, two, three, four, five, six, or seven modifications, e.g., substitutions (e.g., conservative substitutions), but no more than ten modifications, e.g., substitutions (e.g., conservative substitutions), relative to the nucleotide sequence of SEQ ID NO: 3; or a nucleotide sequence comprising at least one, two, three, four, five, six, or seven, but no more than ten different nucleotides relative to the nucleotide sequence of SEQ ID NO: 3.

408. The AAV capsid variant of any one of embodiments 1-23, 26-29, 32, 35-43, 46-51, 54-72, 69-89, 91, 94-99, 102-104, 107, 110-112, 115-129, 168-202, 02, 240-247, 249, 250, 253-263, 266, 272-281, 286, 288, 291-299, 327-363, 369-371, 375-379, 385, 386, 390, 391, 395, or 406, wherein the nucleotide sequence encoding the capsid variant comprises the nucleotide sequence of SEQ ID NO: 942; a nucleotide sequence comprising at least one, two, three, four, five, six, or seven modifications, e.g., substitutions (e.g., conservative substitutions), but no more than ten modifications, e.g., substitutions (e.g., conservative substitutions), relative to the nucleotide sequence of SEQ ID NO: 942; or a nucleotide sequence comprising at least one, two, three, four, five, six, or seven, but no more than ten different nucleotides relative to the nucleotide sequence of SEQ ID NO: 942.

409. The AAV capsid variant of any one of embodiments 1-9, 11, 12-22, 24, 26, 28, 30, 33, 35-42, 44, 46-50, 52, 54-77, 83-88, 90-97, 100-103, 105, 110, 111, 113-129, 203-248, 251, 252, 254-257, 260, 261, 264-280, 283-287, 289-299, 327-363, 369, 369, 371, 380-383, 385, 386, 390, 392, 395, or 407, wherein the nucleotide sequence encoding the capsid variant comprises the nucleotide sequence of SEQ ID NO: 3; a nucleotide sequence comprising at least one, two, three, four, five, six, or seven modifications, e.g., substitutions (e.g., conservative substitutions), but no more than ten modifications, e.g., substitutions (e.g., conservative substitutions), relative to the nucleotide sequence of SEQ ID NO: 3; or a nucleotide sequence comprising at least one, two, three, four, five, six, or seven, but no more than ten different nucleotides relative to the nucleotide sequence of SEQ ID NO: 3.

410. The AAV capsid variant of any one of embodiments 369-409, wherein the amino acid sequence is present in loop IV.

411. The AAV capsid variant of any one of embodiments 369-410, wherein the amino acid sequence is present immediately subsequent to position 448, 449, 450, 451, 452, 453, 454, or 455, relative to a reference sequence numbered according to the amino acid sequence of SEQ ID NO: 138.

412. The AAV capsid variant of any one of embodiments 369-411, wherein the amino acid sequence replaces amino acids 449, 450, 451, 452, 453, 454, 455, 456, 457, 458, 459, and/or 460 (e.g., K449, T450, I451, N452, G453, S454, G455, Q456, N457, Q458, Q459, and/or T460), numbered according to the amino acid sequence of SEQ ID NO: 138.

413. The AAV capsid variant of any one of embodiments 369-412, wherein the amino acid sequence is present immediately subsequent to position 455, relative to a reference sequence numbered according to the amino acid sequence of SEQ ID NO: 138.

414. The AAV capsid variant of any one of embodiments 369-413, wherein the amino acid sequence is present immediately subsequent to position 453, relative to a reference sequence numbered according to the amino acid sequence of SEQ ID NO: 138.

415. The AAV capsid variant of any one of embodiments 1-23, 26-29, 32, 35-43, 46-51, 54-72, 69-89, 91, 94-99, 102-104, 107, 110-112, 115-129, 168-202, 02, 240-247, 249, 250, 253-263, 266, 272-281, 286, 288, 291-299, 327-363, 369-371, 375-379, 385, 386, 390, 391, 395, 406, 408, or 410-413, comprising the amino acid sequence of SPHSKA (SEQ ID NO: 941), wherein the amino acid sequence is present immediately subsequent to position 455, relative to a reference sequence numbered according to the amino acid sequence of SEQ ID NO: 138.

416. The AAV capsid variant of any one of embodiments 1-23, 26-29, 32, 35-43, 46-51, 54-72, 69-89, 91, 94-99, 102-104, 107, 110-112, 115-129, 168-202, 02, 240-247, 249, 250, 253-263, 266, 272-281, 286, 288, 291-299, 327-363, 369-371, 375-379, 385, 386, 390, 391, 395, 406, 408, 410-413, or 415, comprising the amino acid sequence of SPHSKA (SEQ ID NO: 941), wherein the amino acid sequence is present immediately subsequent to position 455, relative to a reference sequence numbered according to the amino acid sequence of SEQ ID NO: 981.

417. The AAV capsid variant of embodiment 415 or 416, which further comprises an amino acid other than I at position 451, an amino acid other than N at position 452, and an amino acid other than G at position 453, numbered according to any one of SEQ ID NOs: 36, 138, or 981.

418. The AAV capsid variant of any one of embodiments 415-417, which further comprises E at position 451, R at position 452, and V at position 453, numbered according to any one of SEQ ID NOs: 36, 138, or 981.

419. The AAV capsid variant of any one of embodiments 415-418, which further comprises the substitutions I451E, N452R, and G453V, numbered according to any one of SEQ ID NOs: 36, 138, or 981.

420. The AAV capsid variant of any one of embodiments 415-419, which comprises:
  (i) E at position 451, R at position 452, and V at position 453, numbered according to any one of SEQ ID NOs: 36, 138, or 981; and
  (ii) the amino acid sequence of SPHSKA (SEQ ID NO: 941), wherein the amino acid sequence is present immediately subsequent to position 455, numbered according to any one of SEQ ID NOs: 36, 138, or 981.

421. The AAV capsid variant of embodiment 415 or 416, which further comprises an amino acid other than I at position 451, an amino acid other than N at position 452, and/or G at position 453, numbered according to SEQ ID NO: 39 or 138.

422. The AAV capsid variant of any one of embodiments 415, 416, or 421, which further comprises E at position 451, K at position 452, and/or M at position 453, numbered according to SEQ ID NO: 138 or 39.

423. The AAV capsid variant of any one of embodiments 415, 416, 421, or 422, which further comprises the substitutions I451E, N452K, and G453M, numbered according to SEQ ID NO: 39 or 138.

424. The AAV capsid variant of any one of embodiments 415, 416, or 421-423, which comprises:

(i) E at position 451, K at position 452, and M at position 453, numbered according to SEQ ID NO: 39 or 138; and (ii) the amino acid sequence of SPHSKA (SEQ ID NO: 941), wherein the amino acid sequence is present immediately subsequent to position 455, numbered according to SEQ ID NO: 39 or 138.

425. The AAV capsid variant of embodiment 415 or 416, which further comprises an amino acid other than S at position 454, an amino acid other than G at position 455, and/or Q at position 458, numbered according to SEQ ID NO: 138.

426. The AAV capsid variant of any one of embodiments 415, 416, or 425, which further comprises H at position 454, D at position 455, and/or L at position 458, numbered according to SEQ ID NO: 138.

427. The AAV capsid variant of any one of embodiments 415, 416, 425, or 426, which further comprises the substitutions S454H, G455D, and Q458L, numbered according to SEQ ID NO: 138.

428. The AAV capsid variant of any one of embodiments 415, 416, or 425-427, which comprises:
  (i) H at position 454, D at position 455, and/or L at position 458, numbered according to SEQ ID NO: 138; and
  (ii) the amino acid sequence of SPHSKA (SEQ ID NO: 941), wherein the amino acid sequence is present immediately subsequent to position 455, numbered according to SEQ ID NO: 138.

429. The AAV capsid variant of embodiment 415 or 416, which further comprises an amino acid other than I at position 451, an amino acid other than S at position 454, and/or an amino acid other than G at position 455, numbered according to SEQ ID NO: 52 or 138.

430. The AAV capsid variant of any one of embodiments 415, 416, or 429, which further comprises V at position 451, H at position 454, and/or D at position 455, numbered according to SEQ ID NO: 52 or 138.

431. The AAV capsid variant of any one of embodiments 415, 416, 429, or 430, which further comprises the substitutions I451V, S454H, and/or G455D, numbered according to SEQ ID NO: 52 or 138.

432. The AAV capsid variant of any one of embodiments 415, 416, or 429-431, which comprises:
  (i) V at position 451, H at position 454, and/or D at position 455, numbered according to SEQ ID NO: 52 or 138; and
  (ii) the amino acid sequence of SPHSKA (SEQ ID NO: 941), wherein the amino acid sequence is present immediately subsequent to position 455, numbered according to SEQ ID NO: 52 or 138.

433. The AAV capsid variant of any one of embodiments 1-9, 11, 12-22, 24, 26, 28, 30, 33, 35-42, 44, 46-50, 52, 54-77, 83-88, 90-97, 100-103, 105, 110, 111, 113-129, 203-248, 251, 252, 254-257, 260, 261, 264-280, 283-287, 289-299, 327-363, 369, 369, 371, 380-383, 385, 386, 390, 392, 395, 407, 409-412, or 414, comprising the amino acid sequence of HDSPHK (SEQ ID NO: 2), wherein the amino acid sequence is present immediately subsequent to position 453, numbered according to the amino acid sequence of SEQ ID NO: 138.

434. The AAV capsid variant of any one of embodiments 1-9, 11, 12-22, 24, 26, 28, 30, 33, 35-42, 44, 46-50, 52, 54-77, 83-88, 90-97, 100-103, 105, 110, 111, 113-129, 203-248, 251, 252, 254-257, 260, 261, 264-280, 283-287, 289-299, 327-363, 369, 369, 371, 380-383, 385, 386, 390, 392, 395, 407, 409-412, 414, or 433, comprising the amino acid sequence of HDSPHK (SEQ ID NO: 2), wherein the amino acid sequence is present immediately subsequent to position 453, numbered according to the amino acid sequence of SEQ ID NO: 982.

435. The AAV capsid variant of any one of embodiments 1-9, 11, 12-22, 24, 26, 28, 30, 33, 35-42, 44, 46-50, 52, 54-77, 83-88, 90-97, 100-103, 105, 110, 111, 113-129, 203-248, 251, 252, 254-257, 260, 261, 264-280, 283-287, 289-299, 327-363, 369, 369, 371, 380-383, 385, 386, 390, 392, 395, 407, 409-412, 414, 433, or 434, comprising the amino acid sequence of SPHKSG (SEQ ID NO: 946), wherein the amino acid sequence is present immediately subsequent to position 455, numbered relative to a reference sequence numbered according to the amino acid sequence of SEQ ID NO: 982.

436. The AAV capsid variant of any one of embodiments 369-435, which comprises:
  (i) the amino acid sequence of HDSPHSKA (SEQ ID NO: 4486), which is present immediately subsequent to position 453; and
  (ii) a deletion of amino acids SG at position 454 and 455; wherein (i) and (ii) are numbered according to SEQ ID NO: 138.

437. The AAV capsid variant of any one of embodiments 369-436, which comprises the amino acids HD at position 454 and 455, and further comprises the amino acid sequence of SPHSKA (SEQ ID NO: 941), which is present immediately subsequent to position 455, numbered relative to SEQ ID NO: 138.

438. The AAV capsid variant of any one of embodiments 433-435, which further comprises an amino acid other than T at position 450, an amino acid other than I at position 451, and an amino acid other than N at position 452, numbered according to SEQ ID NO: 138 or 982.

439. The AAV capsid variant of any one of embodiments 433-435 or 438, which further comprises A at position 450, E at position 451, and I at position 452, numbered according to SEQ ID NO: 138 or 982.

440. The AAV capsid variant of any one of embodiments 433-435, 438, or 439, which further comprises the substitutions T450A, I451E, and N452I, numbered according to SEQ ID NO: 138 or 982.

441. The AAV capsid variant of any one of embodiments 433, 434, or 438-440, which comprises:
  (i) A at position 450, E at position 451, and I at position 452, numbered according to SEQ ID NO: 138 or 982; and
  (ii) the amino acid sequence of HDSPHK (SEQ ID NO: 2), which is present immediately subsequent to positions 453, numbered according to SEQ ID NO: 138 or 982.

442. The AAV capsid variant of any one of embodiments 1-22, 25-27, 31, 34-42, 45-50, 53-63, 69, 79, 83-86, 91-98, 102, 103, 110, 111, 118-129, 369-371, 384, 385, 390, 393, 395, 410-413, comprising the amino acid sequence of SPHKYG (SEQ ID NO: 966), wherein the amino acid sequence is present immediately subsequent to position 455, relative to a reference sequence numbered according to the amino acid sequence of SEQ ID NO: 138.

443. An AAV capsid variant comprising the amino acid sequence of HDSPHK (SEQ ID NO: 2), wherein the amino acid sequence is present immediately subsequent to position 453, numbered according to the amino acid sequence of SEQ ID NO: 982.

444. An AAV capsid variant comprising the amino acid sequence of SPHSKA (SEQ ID NO: 941), wherein the amino acid sequence is present immediately subsequent to position 455, numbered according to the amino acid sequence of SEQ ID NO: 981.

445. An AAV capsid variant comprising the amino acid sequence of HDSPHK (SEQ ID NO: 2), wherein the amino acid sequence is present immediately subsequent to position 453, numbered according to the amino acid sequence of SEQ ID NO: 37, and optionally further comprising:
- (i) one, two, or all of an amino acid other than T at position 450, an amino acid other than I at position 541, and/or an amino acid other than N at position 452, numbered according to SEQ ID NO: 138 or 37;
- (ii) one, two, or all of A at position 450, E at position 451, and/or I at position 452, numbered according to SEQ ID NO: 138 or 37.

446. An AAV capsid variant comprising the amino acid sequence of SPHSKA (SEQ ID NO: 941), wherein the amino acid sequence is present immediately subsequent to position 455, numbered according to the amino acid sequence of any one of SEQ ID NO: 36, 38-55, 57, or 59.

447. The AAV capsid variant of any one of the preceding embodiments, which further comprises:
- (i) a modification, e.g., an insertion, substitution (e.g., conservative substitution), and/or deletion, in loop I, II, VI and/or VIII; and/or
- (ii) a substitution at position K449, e.g., a K449R substitution, numbered according to SEQ ID NO: 138.

448. The AAV capsid variant of any one of the preceding embodiments, which comprises an amino acid sequence comprising at least one, two or three modifications, e.g., substitutions (e.g., conservative substitutions), but not more than 30, 20 or 10 modifications, e.g., substitutions (e.g., conservative substitutions), relative to the amino acid sequence of SEQ ID NO: 138.

449. The AAV capsid variant of any one of the preceding embodiments, which comprises an amino acid sequence comprising at least one, two or three, but no more than 30, 20 or 10 different amino acids relative to the amino acid sequence of SEQ ID NO: 138.

450. The AAV capsid variant of any one of the preceding embodiments, which comprises the amino acid sequence of SEQ ID NO: 138, or an amino acid sequence with at least 80% (e.g., at least about 85, 90, 95, 96, 97, 98, or 99%) sequence identity thereto.

451. The AAV capsid variant of any one of the preceding embodiments, which comprises the amino acid sequence of SEQ ID NO: 138.

452. The AAV capsid variant of any one of the preceding embodiments, which comprises an amino acid sequence encoded by the nucleotide sequence of SEQ ID NO: 137, or a sequence with at least 80% (e.g., at least about 85, 90, 95, 96, 97, 98, or 99%) sequence identity thereto.

453. The AAV capsid variant of any one of the preceding embodiments, wherein the nucleotide sequence encoding the capsid variant comprises the nucleotide sequence of SEQ ID NO: 137, or a sequence with at least 80% (e.g., at least about 85, 90, 95, 96, 97, 98, or 99%) sequence identity thereto.

454. The AAV capsid variant of any one of the preceding embodiments, which comprises a VP1 protein, a VP2 protein, a VP3 protein, or a combination thereof.

455. The AAV capsid variant of any one of embodiments 1-454, which comprises the amino acid sequence corresponding to positions 138-742, e.g., a VP2, of SEQ ID NO: 981 or 982, or a sequence with at least 80% (e.g., at least about 85, 90, 95, 96, 97, 98, or 99%) sequence identity thereto.

456. The AAV capsid variant of any one of embodiments 1-455, which comprises the amino acid sequence corresponding to positions 203-742, e.g., a VP3, of SEQ ID NO: 981 or 982, or a sequence with at least 80% (e.g., at least about 85, 90, 95, 96, 97, 98, or 99%) sequence identity thereto.

457. The AAV capsid variant of any one of embodiments 1-456, which comprises the amino acid sequence corresponding to positions 138-736, e.g., a VP2, of SEQ ID NO: 138, or a sequence with at least 80% (e.g., at least about 85, 90, 95, 96, 97, 98, or 99%) sequence identity thereto.

458. The AAV capsid variant of any one of embodiments 1-457, which comprises the amino acid sequence corresponding to positions 203-736, e.g., a VP3, of SEQ ID NO: 138, or a sequence with at least 80% (e.g., at least about 85, 90, 95, 96, 97, 98, or 99%) sequence identity thereto.

459. The AAV capsid variant of any one of embodiments 1-23, 26-29, 32, 35-43, 46-51, 54-72, 69-89, 91, 94-99, 102-104, 107, 110-112, 115-129, 168-202, 02, 240-247, 249, 250, 253-263, 266, 272-281, 286, 288, 291-299, 327-363, 369-371, 375-379, 385, 386, 390, 391, 395, 406, 408, 410-413, 415-432, 444, or 446-458, comprising an amino acid sequence comprising at least 3, 4, 5, or 6 consecutive amino acids from the amino acid sequence of SPHSKA (SEQ ID NO: 941), wherein:
- (i) the 3 consecutive amino acids comprise SPH;
- (ii) the 4 consecutive amino acids comprise SPHS (SEQ ID NO: 4700);
- (iii) the 5 consecutive amino acids comprise SPHSK (SEQ ID NO: 4701); or
- (iv) the 6 consecutive amino acids comprise SPHSKA (SEQ ID NO: 941);
wherein the AAV capsid variant comprises: (a) a VP1 protein comprising the amino acid sequence of SEQ ID NO: 138 or SEQ ID NO: 981; (b) a VP2 protein comprising the amino acid sequence of positions 138-736 of SEQ ID NO: 138 or positions 138-742 of SEQ ID NO: 981; (c) a VP3 protein comprising the amino acid sequence of positions 203-736 of SEQ ID NO: 138 or positions 203-742 of SEQ ID NO: 981; or (d) an amino acid sequence with at least 90% (e.g., at least about 95, 96, 97, 98, or 99%) sequence identity to any of the amino acid sequences in (a)-(c).

460. The AAV capsid variant of any one of embodiments 1-23, 26-29, 32, 35-43, 46-51, 54-72, 69-89, 91, 94-99, 102-104, 107, 110-112, 115-202, 02, 240-247, 249, 250, 253-263, 266, 272-281, 286, 288, 291-299, 327-363, 369-371, 375-379, 385, 386, 390, 391, 395, 406, 408, 410-413, 415-432, 444, or 446-459, comprising an amino acid sequence comprising at least 3, 4, 5, or 6 consecutive amino acids from the amino acid sequence of SPHSKA (SEQ ID NO: 941), wherein:
- (i) the 3 consecutive amino acids comprise SPH;
- (ii) the 4 consecutive amino acids comprise SPHS (SEQ ID NO: 4700);
- (iii) the 5 consecutive amino acids comprise SPHSK (SEQ ID NO: 4701); or
- (iv) the 6 consecutive amino acids comprise SPHSKA (SEQ ID NO: 941);
wherein the AAV capsid variant comprises an amino acid sequence at least 90% (e.g., at least about 95, 96, 97, 98, or 99%) identical to the amino acid sequence of SEQ ID NO: 981.

461. The AAV capsid variant of any one of embodiments 1-23, 26-29, 32, 35-43, 46-51, 54-72, 69-89, 91, 94-99, 102-104, 107, 110-112, 115-129, 168-202, 02, 240-247, 249, 250, 253-263, 266, 272-281, 286, 288, 291-299, 327-363, 369-371, 375-379, 385, 386, 390, 391, 395, 406, 408, 410-413, 415-432, 444, or 446-460, comprising one or two, but no more than three substitutions relative to the amino acid sequence of SPHSKA (SEQ ID NO: 941), wherein the AAV capsid variant comprises:
- (a) a VP1 protein comprising the amino acid sequence of SEQ ID NO: 138 or SEQ ID NO: 981;
- (b) a VP2 protein comprising the amino acid sequence of positions 138-736 of SEQ ID NO: 138 or positions 138-742 of SEQ ID NO: 981;
- (c) a VP3 protein comprising the amino acid sequence of positions 203-736 of SEQ ID NO: 138 or positions 203-742 of SEQ ID NO: 981; or
- (d) an amino acid sequence with at least 90% (e.g., at least about 95, 96, 97, 98, or 99%) sequence identity to any of the amino acid sequences in (a)-(c).

462. The AAV capsid variant of any one of embodiments 1-23, 26-29, 32, 35-43, 46-51, 54-72, 69-89, 91, 94-99, 102-104, 107, 110-112, 115-129, 168-202, 02, 240-247, 249, 250, 253-263, 266, 272-281, 286, 288, 291-299, 327-363, 369-371, 375-379, 385, 386, 390, 391, 395, 406, 408, 410-413, 415-432, 444, or 446-461, comprising one or two, but no more than three substitutions relative to the amino acid sequence of SPHSKA (SEQ ID NO: 941), wherein the AAV capsid variant comprises an amino acid sequence at least 90% (e.g., at least about 95, 96, 97, 98, or 99%) identical to the amino acid sequence of SEQ ID NO: 138 or SEQ ID NO: 981.

463. The AAV capsid variant of any one of embodiments 459-462, wherein the amino acid sequence is present immediately subsequent to position 455, numbered according to SEQ ID NO: 138 or 981.

464. The AAV capsid variant of any one of embodiments 1-9, 11, 12-22, 24, 26, 28, 30, 33, 35-42, 44, 46-50, 52, 54-77, 83-88, 90-97, 100-103, 105, 110, 111, 113-129, 203-248, 251, 252, 254-257, 260, 261, 264-280, 283-287, 289-299, 327-363, 369, 369, 371, 380-383, 385, 386, 390, 392, 395, 407, 409-412, 414, 433-435, 438-441, 443, 445, or 447-458, comprising an amino acid sequence comprising at least 3, 4, 5, or 6 consecutive amino acids from the amino acid sequence of HDSPHK (SEQ ID NO: 2), wherein:
- (i) the 3 consecutive amino acids comprise HDS;
- (ii) the 4 consecutive amino acids comprise HDSP (SEQ ID NO: 4702);
- (iii) the 5 consecutive amino acids comprise HDSPH (SEQ ID NO: 4703); or
- (iv) the 6 consecutive amino acids comprise HDSPHK (SEQ ID NO: 2);

wherein the AAV capsid variant comprises: (a) a VP1 protein comprising the amino acid sequence of SEQ ID NO: 138 or SEQ ID NO: 982; (b) a VP2 protein comprising the amino acid sequence of positions 138-736 of SEQ ID NO: 138 or positions 138-742 of SEQ ID NO: 982; (c) a VP3 protein comprising the amino acid sequence of positions 203-736 of SEQ ID NO: 138 or positions 203-742 of SEQ ID NO: 982; or (d) an amino acid sequence with at least 90% (e.g., at least about 95, 96, 97, 98, or 99%) sequence identity to any of the amino acid sequences in (a)-(c).

465. The AAV capsid variant of any one of embodiments 1-9, 11, 12-22, 24, 26, 28, 30, 33, 35-42, 44, 46-50, 52, 54-77, 83-88, 90-97, 100-103, 105, 110, 111, 113-129, 203-248, 251, 252, 254-257, 260, 261, 264-280, 283-287, 289-299, 327-363, 369, 369, 371, 380-383, 385, 386, 390, 392, 395, 407, 409-412, 414, 433-435, 438-441, 443, 445, 447-458, or 464, comprising an amino acid sequence comprising at least 3, 4, 5, or 6 consecutive amino acids from the amino acid sequence of HDSPHK (SEQ ID NO: 2), wherein:
- (i) the 3 consecutive amino acids comprise HDS;
- (ii) the 4 consecutive amino acids comprise HDSP (SEQ ID NO: 4702);
- (iii) the 5 consecutive amino acids comprise HDSPH (SEQ ID NO: 4703); or
- (iv) the 6 consecutive amino acids comprise HDSPHK (SEQ ID NO: 2);
- wherein the AAV capsid variant comprises an amino acid sequence at least 90% (e.g., at least about 95, 96, 97, 98, or 99%) identical to the amino acid sequence of SEQ ID NO: 982.

466. The AAV capsid variant of any one of embodiments 1-9, 11, 12-22, 24, 26, 28, 30, 33, 35-42, 44, 46-50, 52, 54-77, 83-88, 90-97, 100-103, 105, 110, 111, 113-129, 203-248, 251, 252, 254-257, 260, 261, 264-280, 283-287, 289-299, 327-363, 369, 369, 371, 380-383, 385, 386, 390, 392, 395, 407, 409-412, 414, 433-435, 438-441, 443, 445, 447-458, 464, or 465, comprising one or two, but no more than three substitutions relative to the amino acid sequence of HDSPHK (SEQ ID NO: 2), wherein the AAV capsid variant comprises:
- (a) a VP1 protein comprising the amino acid sequence of SEQ ID NO: 138 or SEQ ID NO: 982;
- (b) a VP2 protein comprising the amino acid sequence of positions 138-736 of SEQ ID NO: 138 or positions 138-742 of SEQ ID NO: 982;
- (c) a VP3 protein comprising the amino acid sequence of positions 203-736 of SEQ ID NO: 138 or positions 203-742 of SEQ ID NO: 982; or
- (d) an amino acid sequence with at least 90% (e.g., at least about 95, 96, 97, 98, or 99%) sequence identity to any of the amino acid sequences in (a)-(c).

467. The AAV capsid variant of any one of embodiments 1-9, 11, 12-22, 24, 26, 28, 30, 33, 35-42, 44, 46-50, 52, 54-77, 83-88, 90-97, 100-103, 105, 110, 111, 113-129, 203-248, 251, 252, 254-257, 260, 261, 264-280, 283-287, 289-299, 327-363, 369, 369, 371, 380-383, 385, 386, 390, 392, 395, 407, 409-412, 414, 433-435, 438-441, 443, 445, 447-458, or 464-466, comprising one or two, but no more than three substitutions relative to the amino acid sequence of HDSPHK (SEQ ID NO: 2), wherein the AAV capsid variant comprises an amino acid sequence at least 90% (e.g., at least about 95, 96, 97, 98, or 99%) identical to the amino acid sequence of SEQ ID NO: 982.

468. The AAV capsid variant of any one of embodiments 464-468, wherein the amino acid sequence is present immediately subsequent to position 453, numbered according to SEQ ID NO: 138 or 982.

469. The AAV capsid variant of any one of embodiments 1-468, which comprises the amino acid sequence of any one of SEQ ID NO: 981 or 982, or an amino acid sequence with at least 80% (e.g., at least about 85, 90, 95, 96, 97, 98, or 99%) sequence identity thereto.

470. The AAV capsid variant of any one of embodiments 1-469, which comprises an amino acid sequence comprising at least one, two or three modifications, e.g., substitutions (e.g., conservative substitutions), but not more than 30, 20 or 10 modifications, e.g., substitutions (e.g., conservative substitutions), relative to the amino acid sequence of SEQ ID NO: 981 or 982.

471. The AAV capsid variant of any one of embodiments, 1-470, which comprises an amino acid sequence comprising at least one, two or three, but not more than 30, 20 or 10 different amino acids, relative to the amino acid sequence of SEQ ID NO: 981 or 982.

472. The AAV capsid variant of any one of embodiments 1-23, 26-29, 32, 35-43, 46-51, 54-72, 69-89, 91, 94-99, 102-104, 107, 110-112, 115-129, 168-202, 02, 240-247, 249, 250, 253-263, 266, 272-281, 286, 288, 291-299, 327-363, 369-371, 375-379, 385, 386, 390, 391, 395, 406, 408, 410-413, 415-432, 444, 446-463, or 469-471, which comprises the amino acid sequence of SEQ ID NO: 981, or an amino acid sequence with at least 80% (e.g., at least about 85, 90, 95, 96, 97, 98, or 99%) sequence identity thereto.

473. The AAV capsid variant of any one of embodiments 1-23, 26-29, 32, 35-43, 46-51, 54-72, 69-89, 91, 94-99, 102-104, 107, 110-112, 115-129, 168-202, 02, 240-247, 249, 250, 253-263, 266, 272-281, 286, 288, 291-299, 327-363, 369-371, 375-379, 385, 386, 390, 391, 395, 406, 408, 410-413, 415-432, 444, 446-463, or 469-472, which comprises an amino acid sequence comprising at least one, two or three modifications, e.g., substitutions (e.g., conservative substitutions), but not more than 30, 20 or 10 modifications, e.g., substitutions (e.g., conservative substitutions), relative to the amino acid sequence of SEQ ID NO: 981.

474. The AAV capsid variant of any one of embodiments 1-23, 26-29, 32, 35-43, 46-51, 54-72, 69-89, 91, 94-99, 102-104, 107, 110-112, 115-129, 168-202, 02, 240-247, 249, 250, 253-263, 266, 272-281, 286, 288, 291-299, 327-363, 369-371, 375-379, 385, 386, 390, 391, 395, 406, 408, 410-413, 415-432, 444, 446-463, or 469-473, which comprises an amino acid sequence comprising at least one, two or three, but not more than 30, 20 or 10 different amino acids, relative to the amino acid sequence of SEQ ID NO: 981.

475. The AAV capsid variant of any one of embodiments 1-9, 11, 12-22, 24, 26, 28, 30, 33, 35-42, 44, 46-50, 52, 54-77, 83-88, 90-97, 100-103, 105, 110, 111, 113-129, 203-248, 251, 252, 254-257, 260, 261, 264-280, 283-287, 289-299, 327-363, 369, 369, 371, 380-383, 385, 386, 390, 392, 395, 407, 409-412, 414, 433-435, 438-441, 443, 445, 447-458, or 464-471, which comprises the amino acid sequence of SEQ ID NO: 982, or an amino acid sequence with at least 80% (e.g., at least about 85, 90, 95, 96, 97, 98, or 99%) sequence identity thereto.

476. The AAV capsid variant of any one of embodiments 1-9, 11, 12-22, 24, 26, 28, 30, 33, 35-42, 44, 46-50, 52, 54-77, 83-88, 90-97, 100-103, 105, 110, 111, 113-129, 203-248, 251, 252, 254-257, 260, 261, 264-280, 283-287, 289-299, 327-363, 369, 369, 371, 380-383, 385, 386, 390, 392, 395, 407, 409-412, 414, 433-435, 438-441, 443, 445, 447-458, 464-471, or 475, which comprises an amino acid sequence comprising at least one, two or three modifications, e.g., substitutions (e.g., conservative substitutions), but not more than 30, 20 or 10 modifications, e.g., substitutions (e.g., conservative substitutions), relative to the amino acid sequence of SEQ ID NO: 982.

477. The AAV capsid variant of any one of embodiments 1-9, 11, 12-22, 24, 26, 28, 30, 33, 35-42, 44, 46-50, 52, 54-77, 83-88, 90-97, 100-103, 105, 110, 111, 113-129, 203-248, 251, 252, 254-257, 260, 261, 264-280, 283-287, 289-299, 327-363, 369, 369, 371, 380-383, 385, 386, 390, 392, 395, 407, 409-412, 414, 433-435, 438-441, 443, 445, 447-458, 464-471, 475, or 476, which comprises an amino acid sequence comprising at least one, two or three, but not more than 30, 20 or 10 different amino acids, relative to the amino acid sequence of SEQ ID NO: 982.

478. The AAV capsid variant of any one of embodiments 1-477, which comprises an amino acid sequence encoded by the nucleotide sequence of SEQ ID NO: 983 or 984, or a nucleotide sequence with at least 80% (e.g., at least about 85, 90, 95, 96, 97, 98, or 99%) sequence identity thereto.

479. The AAV capsid variant of any one of the preceding embodiments 1-478, wherein the nucleotide sequence encoding the capsid variant comprises the nucleotide sequence of SEQ ID NOs: 983 or 984, or a nucleotide sequence with at least 80% (e.g., at least about 85, 90, 95, 96, 97, 98, or 99%) sequence identity thereto.

480. The AAV capsid variant of any one of the preceding embodiments 1-23, 26-29, 32, 35-43, 46-51, 54-72, 69-89, 91, 94-99, 102-104, 107, 110-112, 115-129, 168-202, 02, 240-247, 249, 250, 253-263, 266, 272-281, 286, 288, 291-299, 327-363, 369-371, 375-379, 385, 386, 390, 391, 395, 406, 408, 410-413, 415-432, 444, 446-463, 469-474, 478, or 479, wherein the nucleotide sequence encoding the capsid variant comprises the nucleotide sequence of SEQ ID NO: 983, or a nucleotide sequence with at least 80% (e.g., at least about 85, 90, 95, 96, 97, 98, or 99%) sequence identity thereto.

481. The AAV capsid variant of any one of the preceding embodiments 1-9, 11, 12-22, 24, 26, 28, 30, 33, 35-42, 44, 46-50, 52, 54-77, 83-88, 90-97, 100-103, 105, 110, 111, 113-129, 203-248, 251, 252, 254-257, 260, 261, 264-280, 283-287, 289-299, 327-363, 369, 369, 371, 380-383, 385, 386, 390, 392, 395, 407, 409-412, 414, 433-435, 438-441, 443, 445, 447-458, 464-471, or 475-479, wherein the nucleotide sequence encoding the capsid variant comprises the nucleotide sequence of SEQ ID NO: 984, or a nucleotide sequence with at least 80% (e.g., at least about 85, 90, 95, 96, 97, 98, or 99%) sequence identity thereto.

482. The AAV capsid variant of any one of the preceding embodiments, wherein the nucleotide sequence encoding the capsid variant is codon optimized.

483. An AAV capsid variant, comprising the amino acid sequence of any one of embodiments 1-23, 26-29, 32, 35-43, 46-51, 54-72, 69-89, 91, 94-99, 102-104, 107, 110-112, 115-129, 168-202, 02, 240-247, 249, 250, 253-263, 266, 272-281, 286, 288, 291-299, 327-363, 369-371, 375-379, 385, 386, 390, 391, 395, 406, 408, 410-413, 415-432, 444, 446-463, 469-474, 478-480, or 482, and further comprising an amino acid sequence at least 95% identical to SEQ ID NO: 981.

484. An AAV capsid variant comprising the amino acid sequence of SEQ ID NO: 981.

485. The AAV capsid variant of embodiment 483 or 484, wherein the nucleotide sequence encoding the AAV capsid variant comprises the nucleotide sequence of SEQ ID NO: 983, or a nucleotide sequence at least 90%, 95%, or 99% identical thereto.

486. An AAV capsid variant, comprising the amino acid sequence of any one of embodiments 1-9, 11, 12-22, 24, 26, 28, 30, 33, 35-42, 44, 46-50, 52, 54-77, 83-88, 90-97, 100-103, 105, 110, 111, 113-129, 203-248, 251, 252, 254-257, 260, 261, 264-280, 283-287, 289-299, 327-363, 369, 369, 371, 380-383, 385, 386, 390, 392, 395, 407, 409-412, 414, 433-435, 438-441, 443, 445, 447-458, 464-471, 475-479, 481, or 482, and further comprising an amino acid sequence at least 95% identical to SEQ ID NO: 982.

487. An AAV capsid variant comprising the amino acid sequence of SEQ ID NO: 982.

488. The AAV capsid variant of embodiment 486 or 487, wherein the nucleotide sequence encoding the AAV capsid variant comprises the nucleotide sequence of SEQ ID NO: 984, or a nucleotide sequence at least 90%, 95%, or 99% identical thereto.

489. An AAV capsid variant comprising an amino acid sequence encoded by the nucleotide sequence of SEQ ID NOs: 983 or 984, or a nucleotide sequence at least 95% identical thereto.

490. An AAV capsid variant comprising the amino acid sequence of any one of SEQ ID NOs: 36-59.

491. An AAV capsid variant comprising an amino acid sequence encoded by the nucleotide sequence of any one of SEQ ID NOs: 12-35, or a nucleotide sequence at least 95% identical thereto.

492. The AAV capsid variant of 490 or 491, wherein the nucleotide sequence encoding the AAV capsid variant comprises the nucleotide sequence of any one of SEQ ID NOs: 12-35, or a nucleotide sequence at least 95% identical thereto.

493. The AAV capsid variant of any one of embodiments 1-299, 369-371, or 375-492, which has an increased tropism for a CNS cell or tissue, e.g., a brain cell, brain tissue, spinal cord cell, or spinal cord tissue, relative to the tropism of a reference sequence comprising the amino acid sequence of SEQ ID NO: 138.

494. The AAV capsid variant of any one of embodiments 1-129, 168-299, 369-371, or 375-493, which transduces a brain region, e.g., a midbrain region (e.g., the hippocampus, or thalamus) or the brain stem, optionally wherein the level of transduction is at least 5, 10, 15, 20, 25, 30, 35, 40, 45, 50, 55, 60, or 65-fold greater as compared to a reference sequence of SEQ ID NO: 138, e.g., when measured by an assay, e.g., an immunohistochemistry assay or a qPCR assay, e.g., as described in Example 2.

495. The AAV capsid variant of any one of embodiments 1-129, 168-299, 369-371, or 375-494, which transduces a brain region, e.g., a midbrain region (e.g., the hippocampus, or thalamus) or the brain stem, optionally wherein the level of transduction is at least 30, 35, 40, 45, 50, 55, 60, or 65-fold greater as compared to a reference sequence of SEQ ID NO: 138, e.g., when measured by an assay, e.g., an immunohistochemistry assay or a qPCR assay, e.g., as described in Example 2.

496. The AAV capsid variant of any one of embodiments 1-129, 168-299, 369-371, or 375-495, which is enriched at least about 3, 4, 5, 6, 7, 8, 9, or 10-fold, in the brain compared to a reference sequence of SEQ ID NO: 138, e.g., when measured by an assay as described in Example 1.

497. The AAV capsid variant of any one of embodiments 1-129, 168-299, 369-371, or 375-496, which is enriched at least about 20, 25, 30, 35, 40, 45, 50, 55, 60, 65, 70, 75, 80 or 85-fold, in the brain compared to a reference sequence of SEQ ID NO: 138, e.g., when measured by an assay as described in Example 1.

498. The AAV capsid variant of any one of embodiments 1-129, 168-299, 369-371, or 375-497, which is enriched in the brain of at least two to three species, e.g., a non-human primate and rodent (e.g., mouse), e.g., as compared to a reference sequence of SEQ ID NO: 138.

499. The AAV capsid variant of any one of embodiments 1-129, 168-299, 369-371, or 375-498, which is enriched at least about 10, 15, 20, 25, 30, 35, 40, 45, 50, 55, 60, 65, 70, 75, 80, 85, 90, 95, 100, 105, 115, 120, 125, 130, 135, 140, 145, 150, 155, 160, 165, 170, 175, 180, 190, 200, 205, or 210-fold, in the brain of at least two to three species, e.g., a non-human primate and rodent (e.g., mouse), compared to a reference sequence of SEQ ID NO: 138, e.g., when measured by an assay as described in Example 1 or 5.

500. The AAV capsid variant of embodiment 498 or 499, wherein the at least two to three species are *Macaca fascicularis, Chlorocebus sabaeus, Callithrix jacchus*, and/or mouse (e.g., BALB/c mice, C57Bl/6 mice, and/or CD-1 outbred mice).

501. The AAV capsid variant of any one of embodiments 130-146, 369, 410-414, 447-454, 457, 458, 482, or 493, which is enriched at least about 2, 2.5, 3, 3.5, 4, 4.5, 5, 5.5, 6, 6.5, 7, 7.5, or 8-fold, in the brain compared to a reference sequence of SEQ ID NO: 981, e.g., when measured by an assay as described in Example 3.

502. The AAV capsid variant of any one of embodiments 147-167, 369, 410-414, 447-454, 457, 458, 482, or 493, which is enriched at least about 2, 2.5, 3, 3.5, 4, 4.5, 5, or 5.5-fold, in the brain compared to a reference sequence of SEQ ID NO: 982, e.g., when measured by an assay as described in Example 3.

503. The AAV capsid variant of any one of embodiments 1-129, 168-299, 369-371, or 375-500, which delivers an increased level of a payload to a brain region, optionally wherein the level of the payload is increased by at least 10, 12, 15, 20, 25, 30, 35, 40, 45, 50, 55, 60, 65, or 70-fold, as compared to a reference sequence of SEQ ID NO: 138, e.g., when measured by an assay, e.g., a qRT-PCR or a qPCR assay (e.g., as described in Example 2 or 8).

504. The AAV capsid variant of any one of embodiments 1-129, 168-299, 369-371, 375-500, or 503, which delivers an increased level of viral genomes to a brain region, optionally wherein the level of viral genomes is increased by at least 5, 10, 15, 17, 18, 19, 20, 25, 30, 35, 40, 45, or 50-fold, as compared to a reference sequence of SEQ ID NO: 138, e.g., when measured by an assay, e.g., a qRT-PCR or a qPCR assay (e.g., as described in Example 2 or 8).

505. The AAV capsid variant of embodiment 504 or 504, wherein the brain region is a midbrain region (e.g., the hippocampus or thalamus), frontal cortex, temporal cortex, motor cortex, cerebral cortex, caudate, putamen, dentate nucleus, substantia nigra, or the brainstem.

506. The AAV capsid variant of any one of embodiments 1-129, 168-299, 369-371, 375-500, or 503-505, which is enriched at least about 4, 5, 10, 15, 20, 25, 30, or 35-fold, in the spinal cord compared to a reference sequence of SEQ ID NO: 138, e.g., when measured by an assay as described in Example 1 or 8, optionally wherein the region of the spinal cord is a thoracic spinal cord region, cervical spinal cord region, C5 ventral horn region, lumbar spinal cord region, or L5 ventral horn region.

507. The AAV capsid variant of any one of embodiments 1-129, 168-299, 369-371, 375-500, or 503-506, which shows preferential transduction in a brain region relative to the transduction in the dorsal root ganglia (DRG).

508. The AAV capsid variant of any one of embodiments 1-129, 168-299, 369-371, 375-500, or 503-507, which shows preferential transduction in a brain region relative to the liver.

509. The AAV capsid variant of any one of embodiments 1-129, 168-299, 369-371, 375-500, or 503-508, which shows preferential transduction in a brain region relative to the transduction in the heart.

510. The AAV capsid variant of any one of embodiments 1-129, 168-299, 369-371, 375-500, or 503-509, which shows preferential transduction in a brain region relative to the transduction in the dorsal root ganglia (DRG) and the heart.

511. The AAV capsid variant of any one of the preceding embodiments, which is capable of transducing non-neuronal cells, e.g., glial cells (e.g., oligodendrocytes or astrocytes).

512. The AAV capsid variant of embodiment 511, wherein the non-neuronal cells comprise glial cells, oligodendrocytes (e.g., Olig2 positive oligodendrocytes), or astrocytes (e.g., Olig2 positive astrocytes).

513. The AAV capsid variant of any one of the preceding embodiments, which is capable of transducing Olig2 positive cells, e.g., Olig2 positive astrocytes or Olig2 positive oligodendrocytes.

514. The AAV capsid variant of any one of embodiments 369, 373, 447-454, 457, 458, or 482, which has increased tropism for a heart cell or tissue, e.g., a heart ventricle or heart atrium, relative to the tropism of a reference sequence of SEQ ID NO: 138.

515. The AAV capsid variant of any one of embodiments 369, 373, 447-454, 457, 458, 482, or 514, which is enriched at least about 4, 5, 8, 10, 11, 12, 13, 14, 18, 19, 20, 21, 22, 24, 25, 27, 31, 33, or 34-fold, in the heart compared to a reference sequence of SEQ ID NO: 138, e.g., when measured by an assay as described in Example 4.

516. The AAV capsid variant of any one of embodiments 369, 374, 447-454, 457, 458, 482, which has an increased tropism for a muscle cell or tissue (e.g., a quadriceps cell or a quadriceps tissue), relative to the tropism of a reference sequence comprising the amino acid sequence of SEQ ID NO: 138.

517. The AAV capsid variant of any one of embodiments 369, 374, 447-454, 457, 458, 482, which is enriched at least about 4, 5, 8, 12, 17, 18, 20, 26, 27, 28, 30, or 36-fold, in the muscle compared to a reference sequence of SEQ ID NO: 138, e.g., when measured by an assay as described in Example 4.

518. The AAV capsid variant of embodiment 516 or 517, wherein the muscle cell or tissue is a heart muscle (e.g., a heart ventricle or a heart atrium, or both), a quadriceps muscle, or both.

519. The AAV capsid variant of any one of the preceding embodiments, which is isolated, e.g., recombinant.

520. A polynucleotide encoding the AAV capsid variant of any one of embodiments 1-519.

521. The polynucleotide of embodiment 520, which comprises:
    (i) a nucleotide sequence comprising at least one, two, three, four, five, six, or seven modifications, e.g., substitutions (e.g., conservative substitutions), but no more than ten modifications, e.g., substitutions (e.g., conservative substitutions), relative to the nucleotide sequences of SEQ ID NO: 3 or 942;
    (ii) a nucleotide sequence comprising at least one, two, three, four, five, six, or seven, but no more than ten different nucleotides, relative to the nucleotide sequences of SEQ ID NO: 3 or 942; or
    (iii) the nucleotide sequence of SEQ ID NOs: 3 or 942, or nucleotide sequence substantially identical (e.g., having at least 70%, 75%, 80%, 85%, 90%, 92%, 95%, 97%, 98%, or 99% sequence identity) thereto.

522. The polynucleotide of embodiment 520 or 521, which comprises the nucleotide sequence of SEQ ID NO: 983 or 984, or a nucleotide sequence with at least 80% (e.g., at least about 85, 90, 95, 96, 97, 98, or 99%) sequence identity thereto.

523. The polynucleotide of any one of embodiments 520-522, which comprises a nucleotide sequence that is codon optimized.

524. A peptide comprising an amino acid sequence having the following formula: [N1]-[N2]-[N3] according to any one of embodiments 1-8, 12-35, 39-45, 48-53, 91, or 118-123.

525. A peptide comprising an amino acid sequence having the following formula: [A][B] according to any one of embodiments 130-133, 142, or 146.

526. A peptide comprising an amino acid sequence having the following formula: [A][B] according to any one of embodiments 147-150, 166, or 167.

527. A peptide comprising an amino acid sequence having the following formula: [N1]-[N2]-[N3] according to any one of embodiments 168-176, 179-186, 191-195, 198-202, or 295-299.

528. A peptide comprising an amino acid sequence having the following formula: [N1]-[N2]-[N3] according to any one of embodiments 203-211, 214-223, 228-231, 234-239, or 295-299.

529. A peptide comprising an amino acid sequence having the following formula: [A]-[B], according to any one of embodiments 300-306, 316, 317, 322, or 326.

530. A peptide comprising:
    (a) the amino acid sequence of any of the sequences provided in Tables 1, 2A, 2B, 13-19;
    (b) an amino acid sequence comprising at least 3, 4, 5, 6, 7, 8, 9, 10, 11, 12, 13, 14, 15, 16, or 17 consecutive amino acids from any one of the sequences provided in Tables 1, 2A, 2B, 13-19;
    (c) an amino acid sequence comprising at least one, two, or three but no more than four different amino acids relative to the amino acid sequence of any one of the sequences provided in Tables 1, 2A, 2B, 13-19; or
    (d) an amino acid sequence comprising at least one, two, or three but no more than four modifications, e.g., substitutions (e.g., conservative substitutions), relative to the amino acid sequence of any one of the sequences provided in Tables 1, 2A, 2B, 13-19.

531. A peptide comprising:
    (a) the amino acid sequence of any of SEQ ID NOs: 3849-4051 or 4681-4693;
    (b) an amino acid sequence comprising at least 3, 4, 5, 6, 7, 8, 9, 10, 11, 12, 13, 14, 15, 16, or 17 consecutive amino acids from any one of SEQ ID NOs: 3849-4051 or 4681-4693;
    (c) an amino acid sequence comprising at least one, two, or three but no more than four different amino acids relative to the amino acid sequence of any one of SEQ ID NOs: 3849-4051 or 4681-4693; or
    (d) an amino acid sequence comprising at least one, two, or three but no more than four modifications, e.g., substitutions (e.g., conservative substitutions), relative to the amino acid sequence of any one of SEQ ID NOs: 3849-4051 or 4681-4693.

532. A peptide comprising:
    (a) the amino acid sequence of any of SEQ ID NOs: 4052-4092;
    (b) an amino acid sequence comprising at least 3, 4, 5, 6, 7, 8, 9, 10, 11, 12, 13, 14, 15, 16, or 17 consecutive amino acids from any one of SEQ ID NOs: 4052-4092;
    (c) an amino acid sequence comprising at least one, two, or three but no more than four different amino acids relative to the amino acid sequence of any one of SEQ ID NOs: 4052-4092; or
    (d) an amino acid sequence comprising at least one, two, or three but no more than four modifications, e.g., substitutions (e.g., conservative substitutions), relative to the amino acid sequence of any one of SEQ ID NOs: 4052-4092.

533. A peptide comprising:
    (a) the amino acid sequence of any of SEQ ID NOs: 4056, 4058, 4059, 4062-4064, 4066, 4067, 4080, 4084, 4090, or 4095-4097;
    (b) an amino acid sequence comprising at least 3, 4, 5, 6, 7, 8, 9, 10, 11, 12, 13, 14, 15, 16, or 17 consecutive amino acids from any one of SEQ ID NOs: 4056, 4058, 4059, 4062-4064, 4066, 4067, 4080, 4084, 4090, or 4095-4097;

(c) an amino acid sequence comprising at least one, two, or three but no more than four different amino acids relative to the amino acid sequence of any one of SEQ ID NOs: 4056, 4058, 4059, 4062-4064, 4066, 4067, 4080, 4084, 4090, or 4095-4097; or (d) an amino acid sequence comprising at least one, two, or three but no more than four modifications, e.g., substitutions (e.g., conservative substitutions), relative to the amino acid sequence of any one of SEQ ID NOs: 4056, 4058, 4059, 4062-4064, 4066, 4067, 4080, 4084, 4090, or 4095-4097.

534. A peptide comprising:
  (a) the amino acid sequence of any of SEQ ID NOs: 945-980 or 985-986;
  (b) an amino acid sequence comprising at least 3, 4, or 5 consecutive amino acids from any one of SEQ ID NOs: 945-980 or 985-986;
  (c) an amino acid sequence comprising at least one, two, or three but no more than four different amino acids relative to the amino acid sequence of any one of SEQ ID NOs: 945-980 or 985-986; or
  (d) an amino acid sequence comprising at least one, two, or three but no more than four modifications, e.g., substitutions (e.g., conservative substitutions), relative to the amino acid sequence of any one of SEQ ID NOs: 945-980 or 985-986.

535. A peptide comprising:
  (a) the amino acid sequence of any of SEQ ID NOs: 2, 200, 201, 941, 943, 204, 208, 404, or 903-909;
  (b) an amino acid sequence comprising at least 3, 4, 5, 6, 7, 8, 9, 10, 11, 12, or 13 consecutive amino acids from any one of SEQ ID NOs: 2, 200, 201, 941, 943, 204, 208, 404, or 903-909;
  (c) an amino acid sequence comprising at least one, two, or three but no more than four different amino acids relative to the amino acid sequence of any one of SEQ ID NOs: 2,200, 201, 941, 943, 204, 208, 404, or 903-909; or
  (d) an amino acid sequence comprising at least one, two, or three but no more than four modifications, e.g., substitutions (e.g., conservative substitutions), relative to the amino acid sequence of any one of SEQ ID NOs: 2, 200, 201, 941, 943, 204, 208, 404, or 903-909.

536. A peptide comprising:
  (i) the amino acid sequence of SPHSKA (SEQ ID NO: 941);
  (ii) an amino acid sequence comprising at least one, two, or three, but no more than four different amino acids relative to the amino acid sequence of SPHSKA (SEQ ID NO: 941);
  (iii) an amino acid sequence comprising at least one, two, or three modifications, e.g., substitutions (e.g., conservative substitutions), but no more than four modifications, e.g., substitutions (e.g., conservative substitutions), relative to the amino acid sequence of SPHSKA (SEQ ID NO: 941); or
  (iv) at least 3, 4, or 5 consecutive amino acids from the amino acid sequence of SPHSKA (SEQ ID NO: 941).

537. A peptide encoded by:
  (i) the nucleotide sequence of SEQ ID NO: 942, or a nucleotide sequence substantially identical (e.g., having at least 70%, 75%, 80%, 85%, 90%, 92%, 95%, 97%, 98%, or 99% sequence identity) thereto;
  (ii) a nucleotide sequence comprising at least one, two, three, four, five, six, or seven, but no more than ten different nucleotides relative to the nucleotide sequence of SEQ ID NO: 942; or
  (iii) a nucleotide sequence comprising at least one, two, three, four, five, six, or seven modifications, e.g., substitutions (e.g., conservative substitutions), but no more than ten modifications, e.g., substitutions (e.g., conservative substitutions), relative to the nucleotide sequence of SEQ ID NO: 942.

538. A peptide wherein the nucleotide sequence encoding the peptide comprises:
  (i) the nucleotide sequence of SEQ ID NO: 942, or a nucleotide sequence substantially identical (e.g., having at least 70%, 75%, 80%, 85%, 90%, 92%, 95%, 97%, 98%, or 99% sequence identity) thereto;
  (ii) a nucleotide sequence comprising at least one, two, three, four, five, six, or seven, but not more than 10 different nucleotides, relative to the nucleotide sequence of SEQ ID NO: 942; or
  (iii) a nucleotide sequence comprising at least one, two, three, four, five, six, or seven modifications, e.g., substitutions (e.g., conservative substitutions), but no more than ten modifications, e.g., substitutions (e.g., conservative substitutions), relative to the nucleotide sequence of SEQ ID NO: 942.

539. A peptide comprising:
  (i) the amino acid sequence of HDSPHK (SEQ ID NO: 2);
  (ii) an amino acid sequence comprising at least one, two, or three, but no more than four different amino acids, relative to the amino acid sequence of HDSPHK (SEQ ID NO: 2);
  (iii) an amino acid sequence comprising at least one, two, or three modifications, e.g., substitutions (e.g., conservative substitutions), but no more than four modifications, e.g., substitutions (e.g., conservative substitutions), relative to the amino acid sequence of HDSPHK (SEQ ID NO: 2); or
  (iv) at least 3, 4, or 5 consecutive amino acids from the amino acid sequence of HDSPHK (SEQ ID NO: 2).

540. A peptide encoded by:
  (i) the nucleotide sequence of SEQ ID NO: 3, or a nucleotide sequence substantially identical (e.g., having at least 70%, 75%, 80%, 85%, 90%, 92%, 95%, 97%, 98%, or 99% sequence identity) thereto; or
  (ii) a nucleotide sequence comprising at least one, two, three, four, five, six, or seven, but no more than ten different nucleotides, relative to the nucleotide sequence of SEQ ID NO: 3
  (iii) a nucleotide sequence comprising at least one, two, three, four, five, six, or seven modifications, e.g., substitutions (e.g., conservative substitutions), but no more than ten modifications, e.g., substitutions (e.g., conservative substitutions), relative to the nucleotide sequence of SEQ ID NO: 3.

541. A peptide wherein the nucleotide sequence encoding the peptide comprises:
  (i) the nucleotide sequence of SEQ ID NO: 3, or a nucleotide sequence substantially identical (e.g., having at least 70%, 75%, 80%, 85%, 90%, 92%, 95%, 97%, 98%, or 99% sequence identity) thereto;
  (ii) a nucleotide sequence comprising at least one, two, three, four, five, six, or seven, but no more than ten different nucleotides relative to the nucleotide sequence of SEQ ID NO: 3; or
  (iii) a nucleotide sequence comprising at least one, two, three, four, five, six, or seven modifications, e.g., substitutions (e.g., conservative substitutions), but no more than ten modifications, e.g., substitutions (e.g., conservative substitutions), relative to the nucleotide sequence of SEQ ID NO: 3.

542. A peptide comprising:
(i) the amino acid sequence of KTERVSGSPHSKAQNQQT (SEQ ID NO: 3589);
(ii) an amino acid sequence comprising at least one, two, or three, but no more than four different amino acids, relative to the amino acid sequence of KTERVSGSPHSKAQNQQT (SEQ ID NO: 3589);
(iii) an amino acid sequence comprising at least one, two, or three modifications, e.g., substitutions (e.g., conservative substitutions), but no more than four modifications, e.g., substitutions (e.g., conservative substitutions), relative to the amino acid sequence of KTERVSGSPHSKAQNQQT (SEQ ID NO: 3589); or
(iv) at least 3, 4, 5, 6, 7, 8, 9, 10, 11, 12, 13, 14, 15, 16 or 17 consecutive amino acids from the amino acid sequence of KTERVSGSPHSKAQNQQT (SEQ ID NO: 3589).

543. A peptide comprising:
(i) the amino acid sequence of KAEIGHDSPHKSGQNQQT (SEQ ID NO: 1754);
(ii) an amino acid sequence comprising at least one, two, or three, but no more than four different amino acids, relative to the amino acid sequence of KAEIGHDSPHKSGQNQQT (SEQ ID NO: 1754);
(iii) an amino acid sequence comprising at least one, two, or three modifications, e.g., substitutions (e.g., conservative substitutions), but no more than four modifications, e.g., substitutions (e.g., conservative substitutions), relative to the amino acid sequence of KAEIGHDSPHKSGQNQQT (SEQ ID NO: 1754); or
(iv) at least 3, 4, 5, 6, 7, 8, 9, 10, 11, 12, 13, 14, 15, 16 or 17 consecutive amino acids from the amino acid sequence of KAEIGHDSPHKSGQNQQT (SEQ ID NO: 1754).

544. The peptide of any one of embodiments 524-543, which is fused or coupled, e.g., conjugated, to an active agent, e.g., a therapeutic agent or a diagnostic agent.

545. The peptide of any one of embodiments 524-544, wherein at least 1-5, e.g., at least 1, 2, 3, 4, or 5, peptides are fused or coupled, e.g., conjugated, to an active agent, e.g., a therapeutic agent or a diagnostic agent.

546. The peptide of embodiment 545, wherein the at least 1-5, e.g., at least 1, 2, 3, 4, or 5, peptides comprise the same amino acid sequence.

547. The peptide of embodiment 454, wherein the at least 1-5, e.g., at least 1, 2, 3, 4, or 5, peptides comprise different amino acid sequences.

548. The peptide of any one of embodiments 545-547, wherein the at least 1-5, e.g., at least 1, 2, 3, 4, or 5, peptides are present in tandem (e.g., connected directly or indirectly via a linker) or in a multimeric configuration.

549. The peptide of any one of embodiments 524-548, wherein the peptide comprises an amino acid sequence of at least 3, 4, 5, 6, 7, 8, 9, 10, 11, 12, 15, 20, 25, 30, or 35 amino acids in length.

550. The peptide of any one of embodiments 544-549, wherein the active agent is or comprises a therapeutic agent chosen from a protein (e.g., an enzyme), an antibody molecule, a nucleic acid molecule (e.g., an RNAi agent), or a small molecule.

551. The peptide of any one of embodiments 544-549, wherein the active agent is or comprises a ribonucleic acid complex (e.g., a Cas9/gRNA complex), a plasmid, a closed-end DNA, a circ-RNA, or an mRNA.

552. The peptide of any one of embodiments 544-549, wherein the active agent is an RNAi agent.

553. The peptide of embodiment 552, wherein the RNAi agent is a dsRNA, a siRNA, a shRNA, a pre-miRNA, a pri-miRNA, a miRNA, a stRNA, a lncRNA, a piRNA, an antisense oligonucleotide agent (ASO), or a snoRNA, optionally wherein the RNAi agent is an siRNA or an ASO, which further optionally comprises at least one modified nucleotide.

554. The peptide of any one of embodiments 544-553, wherein the active agent modulates, e.g., inhibits, decreases or increases, expression of, a CNS related gene, mRNA, and/or protein.

555. The peptide of any one of embodiments 544-449, wherein the active agent is a diagnostic agent is or comprises an imaging agent (e.g., a protein or small molecule compound coupled to a detectable moiety).

556. The peptide of any one of embodiments 544-555, wherein the peptide covalently linked, e.g., directly or indirectly via a linker, to the active agent.

557. The peptide of any one of embodiments 544-556, wherein the peptide is conjugated to the active agent via a linker.

558. The peptide of embodiment 557, wherein the linker is a cleavable linker or a non-cleavable linker.

559. The peptide of embodiment 558, wherein the cleavable linker is a pH sensitive linker or an enzyme sensitive linker.

560. The peptide of embodiment 558 or 559, wherein:
(i) the pH sensitive linker comprises a hydrazine/hydrazone linker or a disulfide linker;
(ii) the enzyme sensitive linker comprises a peptide based linker, e.g., a peptide linker sensitive to a protease (e.g., a lysosomal protease); or a beta-glucuronide linker; or
(iii) the non-cleavable linker is a linker comprising a thioether group or a maleimidocaproyl group.

561. The peptide of any one of embodiments 544-560, wherein:
(i) the peptide and the active agent are fused or coupled post-translationally, e.g., using click chemistry; or
(ii) the peptide and the active agent are fused or couple via chemically induced dimerization.

562. The peptide of any one of embodiments 544-561, wherein the peptide is present N-terminal relative to the active agent.

563. The peptide of any one of embodiments 544-561, wherein the peptide is present C-terminal relative to the active agent.

564. The peptide of any one of embodiment 544-549, 554, or 556-563, wherein the peptide is present or coupled to a carrier, e.g., an exosome, a microvesicle, or a lipid nanoparticle (LNP), optionally, wherein the carrier comprises a therapeutic agent (e.g., an RNAi agent (e.g., an dsRNA, a siRNA, a shRNA, a pre-miRNA, a pri-miRNA, a miRNA, a stRNA, a lncRNA, a piRNA, an antisense oligonucleotide agent (ASO), or a snoRNA), an mRNA, a ribonucleoprotein complex (e.g., a Cas9/gRNA complex), or a circRNA).

565. The peptide of embodiment 564, wherein the peptide is present on the surface of the carrier, optionally wherein at least 10%, 20%, 30%, 40%, 50%, 60%, 70%, or 80% of the surface of the carrier comprises at least 1-5, e.g., at least 1, 2, 3, 4, or 5 peptides according to any one of embodiments 422-436.

566. An AAV capsid variant, comprising the peptide of any one of embodiments 524-543.

567. A polynucleotide encoding an AAV capsid variant comprising:
(a) the amino acid sequence of any of the sequences provided in Tables 1, 2A, 2B, 13-19;

(b) an amino acid sequence comprising at least 3, 4, 5, 6, 7, 8, 9, 10, 11, 12, 13, 14, 15, 16, or 17 consecutive amino acids from any one of the sequences provided in Tables 1, 2A, 2B, 13-19;
(c) an amino a sequence comprising at least one, two, or three but no more than four different amino acids, relative to the amino acid sequence of any one of the sequences provided in Tables 1, 2A, 2B, 13-19; or
(d) an amino acid sequence comprising at least one, two, or three but no more than four modifications, e.g., substitutions (conservative substitutions), relative to the amino acid sequence of any one of the sequences provided in Tables 1, 2A, 2B, 13-19;
optionally wherein the amino acid sequence of (a), (b), (c), and/or (d) is present immediately subsequent to position 448, 449, 450, 451, 452, 453, 454, or 455, relative to a reference sequence numbered according to the amino acid sequence of SEQ ID NO: 138, 981, or 982.

568. A polynucleotide encoding an AAV capsid variant, wherein the AAV capsid variant comprises:
(i) the amino acid sequence of SPHSKA (SEQ ID NO: 941);
(ii) an amino acid sequence comprising at least one, two, or three, but no more than four different amino acids, relative to the amino acid sequence of SPHSKA (SEQ ID NO: 941);
(iii) an amino acid sequence comprising at least one, two, or three modifications, e.g., substitutions (e.g., conservative substitutions), but no more than four modifications, e.g., substitutions (e.g., conservative substitutions), relative to the amino acid sequence of SPHSKA (SEQ ID NO: 941); or
(iv) at least 3, 4, 5, 6, 7, 8, or 9 consecutive amino acids from the amino acid sequence of SPHSKA (SEQ ID NO: 941);
optionally wherein the amino acid sequence of (i), (ii), (iii), and/or (iv) is present immediately subsequent to position 455, relative to a reference sequence numbered according to the amino acid sequence of SEQ ID NO: 138.

569. The polynucleotide of embodiment 567 or 568, which comprises:
(i) the nucleotide sequence of SEQ ID NO: 942, or a nucleotide sequence substantially identical (e.g., having at least 70%, 75%, 80%, 85%, 90%, 92%, 95%, 97%, 98%, or 99% sequence identity) thereto;
(ii) a nucleotide sequence comprising at least one, two, three, four, five, six, or seven modifications, e.g., substitutions (e.g., conservative substitutions), but no more than ten modifications, e.g., substitutions (e.g., conservative substitutions), relative to the nucleotide sequence of SEQ ID NO: 942;
(iii) a nucleotide sequence comprising at least one, two, three, four, five, six, or seven modifications, e.g., substitutions (e.g., conservative substitutions), but no more than ten modifications, e.g., substitutions (e.g., conservative substitutions), relative to the nucleotide sequence of SEQ ID NO: 942.

570. A polynucleotide encoding an AAV capsid variant, wherein the AAV capsid variant comprises:
(i) the amino acid sequence of HDSPHK (SEQ ID NO: 2);
(ii) an amino acid sequence comprising at least one, two, or three but no more than four different amino acids, relative to the amino acid sequence of HDSPHK (SEQ ID NO: 2);
(iii) an amino acid sequence comprising at least one, two, or three modifications, e.g., substitutions (e.g., conservative substitutions), but no more than four modifications, e.g., substitutions (e.g., conservative substitutions), relative to the amino acid sequence of HDSPHK (SEQ ID NO: 2); or
(iv) at least 3, 4, or 5 consecutive amino acids from the amino acid sequence of HDSPHK (SEQ ID NO: 2);
optionally wherein the amino acid sequence of (i), (ii), (iii), and/or (iv) is present immediately subsequent to position 453, relative to a reference sequence numbered according to the amino acid sequence of SEQ ID NO: 138.

571. The polynucleotide of any one of embodiments 567 or 570, which comprises:
(i) the nucleotide sequence of SEQ ID NO: 3, or a nucleotide sequence substantially identical (e.g., having at least 70%, 75%, 80%, 85%, 90%, 92%, 95%, 97%, 98%, or 99% sequence identity) thereto;
(ii) a nucleotide sequence comprising at least one, two, three, four, five, six, or seven, but no more than ten different nucleotides, relative to the nucleotide sequence of SEQ ID NO: 3; or
(iii) a nucleotide sequence comprising at least one, two, three, four, five, six, or seven modifications, e.g., substitutions (e.g., conservative substitutions), but no more than ten modifications, e.g., substitutions (e.g., conservative substitutions), relative to the nucleotide sequence of SEQ ID NO: 3.

572. The polynucleotide of any one of embodiments 567-571, wherein the AAV capsid variant comprises:
(i) the amino acid sequence of SEQ ID NO: 981 or 982, or an amino acid sequence with at least 80% (e.g., at least about 85, 90, 95, 96, 97, 98, or 99%) sequence identity thereto;
(ii) an amino acid sequence having at least one, two or three, but no more than four different amino acids, relative to the amino acid sequence of SEQ ID NO: 981 or 982; or
(iii) an amino acid sequence having at least one, two or three modifications, e.g., substitutions (e.g., conservative substitutions), but not more than 30, 20 or 10 modifications, e.g., substitutions (e.g., conservative substitutions), relative to the amino acid sequence of SEQ ID NO: 981 or 982.

573. The polynucleotide of any one of embodiments 567-572, comprising the nucleotide sequence of SEQ ID NO: 983 or 984, or a nucleotide sequence with at least 80% (e.g., at least about 85, 90, 95, 96, 97, 98, or 99%) sequence identity thereto.

574. The polynucleotide, peptide, or AAV capsid variant, of any one of embodiments 1-573, which is isolated, e.g., recombinant.

575. An AAV particle comprising the AAV capsid variant of any one of embodiments 1-519, 566, or 574.

576. The AAV particle of embodiment 575, which comprises a nucleotide sequence encoding a payload.

577. The AAV particle of embodiment 576, wherein the encoded payload comprises a therapeutic protein or functional variant thereof; an antibody or antibody fragment; an enzyme; a component of a gene editing system; an RNAi agent (e.g., a dsRNA, siRNA, shRNA, pre-miRNA, pri-miRNA, miRNA, stRNA, lncRNA, piRNA, or snoRNA); or a combination thereof.

578. The AAV particle of embodiment 577, wherein the therapeutic protein or functional variant thereof, e.g., a recombinant protein, is associated with (e.g., aberrantly expressed in) a neurological or neurodegenerative disorder, a muscular or neuromuscular disorder, or a neuro-oncological disorder.

579. The AAV particle of embodiment 577 or 578, the therapeutic protein or functional variant thereof is chosen from apolipoprotein E (APOE) (e.g., ApoE2, ApoE3 and/or ApoE4); human survival of motor neuron (SMN) 1 or SMN2; glucocerebrosidase (GBA1); aromatic L-amino acid decarboxylase (AADC); aspartoacylase (ASPA); tripeptidyl peptidase I (CLN2); beta-galactosidase (GLB1); N-sulphoglucosamine sulphohydrolase (SGSH); N-acetyl-alpha-glucosaminidase (NAGLU); iduronate 2-sulfatase (IDS); intracellular cholesterol transporter (NPC1); gigaxonin (GAN); or a combination thereof.

580. The AAV particle of embodiment 577, wherein the antibody or antibody binding fragment binds to:
   (i) a CNS related target, e.g., an antigen associated with a neurological or neurodegenerative disorder, e.g., β-amyloid, APOE, tau, SOD1, TDP-43, huntingtin (HTT), and/or synuclein;
   (ii) a muscular or neuromuscular related target, e.g., an antigen associated with a muscular or neuromuscular disorder; or
   (iii) a neuro-oncology related target, e.g., an antigen associated with a neuro-oncological disorder, e.g., HER2, or EGFR (e.g., EGFRvIII).

581. The AAV particle of embodiment 577, wherein the enzyme comprises a meganuclease, a zinc finger nuclease, a TALEN, a recombinase, integrase, a base editor, a Cas9, or a fragment thereof.

582. The AAV particle of embodiment 577, wherein the component of a gene editing system comprises one or more components of a CRISPR-Cas system.

583. The AAV particle of embodiment 582, wherein the one or more components of the CRISPR-Cas system comprises a Cas9, e.g., a Cas9 ortholog or a Cpf1, and a single guide RNA (sgRNA), optionally wherein:
   (i) the sgRNA is located upstream (5') of the cas9 enzyme; or
   (ii) the sgRNA is located downstream (3') of the cas9 enzyme.

584. The AAV particle of embodiment 577, wherein the RNAi agent (e.g., a dsRNA, siRNA, shRNA, pre-miRNA, pri-miRNA, miRNA, stRNA, lncRNA, piRNA, or snoRNA), modulates, e.g., inhibits, expression of, a CNS related gene, mRNA, and/or protein.

585. The AAV particle of embodiment 584, wherein the CNS related gene is chosen from SOD1, MAPT, APOE, HTT, C90RF72, TDP-43, APP, BACE, SNCA, ATXN1, ATXN3, ATXN7, SCN1A-SCN5A, SCN8A-SCN11A, or a combination thereof.

586. The AAV particle of any one of embodiments 575-585, which comprises a viral genome comprising a promoter operably linked to the nucleic acid sequence encoding the payload.

587. The AAV particle of embodiment 586, wherein the promoter is chosen from human elongation factor 1α-subunit (EF1α), cytomegalovirus (CMV) immediate-early enhancer and/or promoter, chicken β-actin (CBA) and its derivative CAG, β glucuronidase (GUSB), or ubiquitin C (UBC), neuron-specific enolase (NSE), platelet-derived growth factor (PDGF), platelet-derived growth factor B-chain (PDGF-β), intercellular adhesion molecule 2 (ICAM-2), synapsin (Syn), methyl-CpG binding protein 2 (MeCP2), Ca2+/calmodulin-dependent protein kinase II (CaMKII), metabotropic glutamate receptor 2 (mGluR2), neurofilament light (NFL) or heavy (NFH), β-globin minigene nβ2, preproenkephalin (PPE), enkephalin (Enk) and excitatory amino acid transporter 2 (EAAT2), glial fibrillary acidic protein (GFAP), myelin basic protein (MBP), a cardiovascular promoter (e.g., αMHC, cTnT, and CMV-MLC2k), a liver promoter (e.g., hAAT, TBG), a skeletal muscle promoter (e.g., desmin, MCK, C512) or a fragment, e.g., a truncation, or a functional variant thereof.

588. The AAV particle of embodiment 586 or 587, wherein the promoter is an EF-1a promoter variant, e.g., a truncated EF-1a promoter.

589. The AAV particle of any one of embodiments 586-588, wherein the promoter comprises the nucleotide sequence of any one of SEQ ID NOs: 987, 988, 990, 991, 995, 996, 998-1007 or any one of the sequences provided in Table 8, a nucleotide sequence comprising at least one, two, or three but no more than four modifications, e.g., substitutions (e.g., conservative substitutions), relative to the nucleotide sequence of SEQ ID NOs: 987, 988, 990, 991, 995, 996, 998-1007 or any one of the sequences provided in Table 8, or a nucleotide sequence with at least 80% (e.g., 85%, 90%, 95%, 96%, 97%, 98%, or 99%) sequence identity to any one of SEQ ID NOs: 987, 988, 990, 991, 995, 996, 998-1007 or any one of the sequences provided in Table 8.

590. The AAV particle of any one of embodiments 586-589 wherein the viral genome further comprises a polyA signal sequence.

591. The AAV particle of any one of embodiments 586-590, wherein the viral genome further comprises an inverted terminal repeat (ITR) sequence.

592. The AAV particle of any one of embodiments 586-591, wherein the viral genome comprises an ITR sequence positioned 5' relative to the encoded payload.

593. The AAV particle of any one of embodiments 586-592, wherein the viral genome comprises an ITR sequence positioned 3' relative to the encoded payload.

594. The AAV particle of any one of embodiments 586-593, wherein the viral genome comprises an ITR sequence positioned 5' relative to the encoded payload and an ITR sequence positioned 3' relative to the encoded payload.

595. The AAV particle of any one of embodiments 586-594, wherein the viral genome further comprises an enhancer, a Kozak sequence, an intron region, and/or an exon region.

596. The AAV particle of any one of embodiments 586-594, wherein the viral genome further comprises a nucleotide sequence encoding a miR binding site, e.g., a miR binding site that modulates, e.g., reduces, expression of the antibody molecule encoded by the viral genome in a cell or tissue where the corresponding miRNA is expressed.

597. The AAV particle of embodiment 596, wherein the encoded miRNA binding site is complementary, e.g., fully complementary or partially complementary, to a miRNA expressed in a cell or tissue of the DRG, liver, heart, hematopoietic, or a combination thereof.

598. The AAV particle of embodiment 596 or 597, wherein the encoded miR binding site modulates, e.g., reduces, expression of the encoded antibody molecule in a cell or tissue of the DRG, liver, heart, hematopoietic lineage, or a combination thereof.

599. The AAV particle of any one of embodiments 586-598, wherein the viral genome comprises at least 1-5 copies of the encoded miR binding site, e.g., at least 1, 2, 3, 4, or 5 copies.

600. The AAV particle of any one of embodiments 586-599, wherein the viral genome comprises at least 3 copies of an encoded miR binding sites, optionally wherein all three copies comprise the same miR binding site, or at least one, two, three, or all of the copies comprise a different miR binding site.

601. The AAV particle of embodiment 600, wherein the 3 copies of the encoded miR binding sites are continuous (e.g., not separated by a spacer), or are separated by a spacer, optionally wherein the spacer comprises the nucleotide sequence of GATAGTTA, or a nucleotide sequence having at least one, two, or three modifications, e.g., substitutions (e.g., conservative substitutions), but no more than four modifications, e.g., substitutions (e.g., conservative substitutions), relative to the nucleotide sequence of GATAGTTA.

602. The AAV particle of any one of embodiments 586-601, wherein the viral genome comprises at least 4 copies of an encoded miR binding site, optionally wherein all four copies comprise the same miR binding site, or at least one, two, three, or all of the copies comprise a different miR binding site.

603. The AAV particle of embodiment 602, wherein the 4 copies of the encoded miR binding sites are continuous (e.g., not separated by a spacer), or are separated by a spacer, optionally wherein the spacer comprises the nucleotide sequence of GATAGTTA, or a nucleotide sequence having at least one, two, or three modifications, e.g., substitutions (e.g., conservative substitutions), but no more than four modifications, e.g., substitutions (e.g., conservative substitutions), relative to the nucleotide sequence of GATAGTTA.

604. The AAV particle of any one of embodiments 596-603, wherein the encoded miR binding site comprises a miR122 binding site, a miR183 binding site, a miR-1 binding site, a miR-142-3p, or a combination thereof, optionally wherein:
- (i) the encoded miR122 binding site comprises the nucleotide sequence of SEQ ID NO: 4673, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, e.g., substitutions (e.g., conservative substitutions), but no more than ten modifications, e.g., substitutions (e.g., conservative substitutions), relative to SEQ ID NO: 4673;
- (ii) the encoded miR183 binding site comprises the nucleotide sequence of SEQ ID NO: 4676, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, e.g., substitutions (e.g., conservative substitutions), but no more than ten modifications, e.g., substitutions (e.g., conservative substitutions), relative to SEQ ID NO: 4676;
- (iii) the encoded miR-1 binding site comprises the nucleotide sequence of SEQ ID NO: 4679, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, e.g., substitutions (e.g., conservative substitutions), but no more than ten modifications, e.g., substitutions (e.g., conservative substitutions), relative to SEQ ID NO: 4679; and/or
- (iv) the encoded miR-142-3p binding site comprises the nucleotide sequence of SEQ ID NO: 4675, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, e.g., substitutions (e.g., conservative substitutions), but no more than ten modifications, e.g., substitutions (e.g., conservative substitutions), relative to SEQ ID NO: 4675.

605. The AAV particle of any one of embodiments 586-604, wherein the viral genome comprises an encoded miR122 binding site.

606. The AAV particle of any one of embodiments 586-605, wherein the viral genome comprises at least 1-5 copies, e.g., 1, 2, or 3 copies of a miR122 binding site, optionally wherein each copy is continuous (e.g., not separated by a spacer), or each copy is separated by a spacer, optionally wherein the spacer comprises the nucleotide sequence of GATAGTTA, or a nucleotide sequence having at least one, two, or three modifications, e.g., substitutions (e.g., conservative substitutions), but no more than four modifications, e.g., substitutions (e.g., conservative substitutions), relative to the nucleotide sequence of GATAGTTA.

607. The AAV particle of embodiment 605 or 606, wherein the encoded miR122 binding site comprises the nucleotide sequence of SEQ ID NO: 4673, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, e.g., substitutions (e.g., conservative substitutions), but no more than ten modifications, e.g., substitutions (e.g., conservative substitutions), relative to SEQ ID NO: 4673.

608. The AAV particle of any one of embodiments 586-607, wherein the viral genome comprises:
- (A) (i) a first encoded miR122 binding site comprising the nucleotide sequence of SEQ ID NO: 4673, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, e.g., substitutions (e.g., conservative substitutions), but no more than ten modifications, e.g., substitutions (e.g., conservative substitutions), relative to SEQ ID NO: 4673;
  - (ii) a first spacer comprising the nucleotide sequence of GATAGTTA, or a nucleotide sequence having at least one, two, or three modifications, e.g., substitutions (e.g., conservative substitutions), but no more than four modifications, e.g., substitutions (e.g., conservative substitutions), relative to the nucleotide sequence of GATAGTTA; and
  - (iii) a second encoded miR122 binding site comprising the nucleotide sequence of SEQ ID NO: 4673, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, e.g., substitutions (e.g., conservative substitutions), but no more than ten modifications, e.g., substitutions (e.g., conservative substitutions), relative to SEQ ID NO: 4673; or
- (B) (i) a first encoded miR122 binding site comprising the nucleotide sequence of SEQ ID NO: 4673, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, e.g., substitutions (e.g., conservative substitutions), but no more than ten modifications, e.g., substitutions (e.g., conservative substitutions), relative to SEQ ID NO: 4673;

(ii) a first spacer comprising the nucleotide sequence of GATAGTTA, or a nucleotide sequence having at least one, two, or three modifications, e.g., substitutions (e.g., conservative substitutions), but no more than four modifications, e.g., substitutions (e.g., conservative substitutions), relative to the nucleotide sequence of GATAGTTA;
(iii) a second encoded miR122 binding site comprising the nucleotide sequence of SEQ ID NO: 4673, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, e.g., substitutions (e.g., conservative substitutions), but no more than ten modifications, e.g., substitutions (e.g., conservative substitutions), relative to SEQ ID NO: 4673;
(iv) a second spacer comprising the nucleotide sequence of GATAGTTA, or a nucleotide sequence having at least one, two, or three modifications, e.g., substitutions (e.g., conservative substitutions), but no more than four modifications, e.g., substitutions (e.g., conservative substitutions), relative to the nucleotide sequence of GATAGTTA; and
(v) a third encoded miR122 binding site comprising the nucleotide sequence of SEQ ID NO: 4673, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, e.g., substitutions (e.g., conservative substitutions), but no more than ten modifications, e.g., substitutions (e.g., conservative substitutions), relative to SEQ ID NO: 4673.

609. The AAV particle of any one of embodiments 586-608, wherein the viral genome comprises an encoded miR183 binding site.

610. The AAV particle of any one of embodiments 586-609, wherein the viral genome comprises at least 1-5 copies, e.g., 1, 2, or 3 copies of a miR183 binding site, optionally wherein each copy is continuous (e.g., not separated by a spacer), or each copy is separated by a spacer, optionally wherein the spacer comprises the nucleotide sequence of GATAGTTA, or a nucleotide sequence having at least one, two, or three modifications, e.g., substitutions (e.g., conservative substitutions), but no more than four modifications, e.g., substitutions (e.g., conservative substitutions), relative to the nucleotide sequence of GATAGTTA.

611. The AAV particle of embodiment 609 or 610, wherein the encoded miR183 binding site comprises the nucleotide sequence of SEQ ID NO: 4673, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, e.g., substitutions (e.g., conservative substitutions), but no more than ten modifications, e.g., substitutions (e.g., conservative substitutions), relative to SEQ ID NO: 4673.

612. The AAV particle of any one of embodiments 586-611, wherein the viral genome comprises:
(A) (i) a first encoded miR183 binding site comprising the nucleotide sequence of SEQ ID NO: 4676, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, e.g., substitutions (e.g., conservative substitutions), but no more than ten modifications, e.g., substitutions (e.g., conservative substitutions), relative to SEQ ID NO: 4676;
(ii) a first spacer comprising the nucleotide sequence of GATAGTTA, or a nucleotide sequence having at least one, two, or three modifications, e.g., substitutions (e.g., conservative substitutions), but no more than four modifications, e.g., substitutions (e.g., conservative substitutions), relative to the nucleotide sequence of GATAGTTA; and
(iii) a second encoded miR183 binding site comprising the nucleotide sequence of SEQ ID NO: 4676, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, e.g., substitutions (e.g., conservative substitutions), but no more than ten modifications, e.g., substitutions (e.g., conservative substitutions), relative to SEQ ID NO: 4676; or
(B) (i) a first encoded miR183 binding site comprising the nucleotide sequence of SEQ ID NO: 4676, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, e.g., substitutions (e.g., conservative substitutions), but no more than ten modifications, e.g., substitutions (e.g., conservative substitutions), relative to SEQ ID NO: 4676;
(ii) a first spacer comprising the nucleotide sequence of GATAGTTA, or a nucleotide sequence having at least one, two, or three modifications, e.g., substitutions (e.g., conservative substitutions), but no more than four modifications, e.g., substitutions (e.g., conservative substitutions), relative to GATAGTTA;
(iii) a second encoded miR183 binding site comprising the nucleotide sequence of SEQ ID NO: 4676, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, e.g., substitutions (e.g., conservative substitutions), but no more than ten modifications, e.g., substitutions (e.g., conservative substitutions), relative to SEQ ID NO: 4676;
(iv) a second spacer comprising the nucleotide sequence of GATAGTTA, or a nucleotide sequence having at least one, two, or three modifications, e.g., substitutions (e.g., conservative substitutions), but no more than four modifications, e.g., substitutions (e.g., conservative substitutions), relative to the nucleotide sequence of GATAGTTA; and
(v) a third encoded miR183 binding site comprising the nucleotide sequence of SEQ ID NO: 4676, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, e.g., substitutions (e.g., conservative substitutions), but no more than ten modifications, e.g., substitutions (e.g., conservative substitutions), relative to SEQ ID NO: 4676.

613. The AAV particle of any one of embodiments 586-612, wherein the viral genome comprises an encoded miR122 binding site and a miR-1 binding site.

614. The AAV particle of any one of embodiments 586-613, wherein the viral genome is single stranded.

615. The AAV particle of any one of embodiments 586-613, wherein the viral genome self-complementary.

616. The AAV particle of any one of embodiments 586-615, wherein the viral genome further comprises a nucleotide sequence encoding a Rep protein, e.g., a non-structural protein, wherein the Rep protein comprises a Rep78 protein, a Rep68, Rep52 protein, and/or a Rep40 protein (e.g., a Rep78 and a Rep52 protein).

617. The AAV particle of any one of embodiments 586-615, wherein the AAV particle further comprises a nucleotide sequence encoding a Rep protein, e.g., a non-structural protein, wherein the Rep protein comprises a Rep78 protein, a Rep68, Rep52 protein, and/or a Rep40 protein (e.g., a Rep78 and a Rep52 protein).

618. The AAV particle of embodiment 616 or 617, wherein the Rep78 protein, the Rep68 protein, the Rep52 protein, and/or the Rep40 protein are encoded by at least one Rep gene.

619. The AAV particle of any one of embodiments 586-618, wherein the viral genome further comprises a nucleic acid sequence encoding the AAV capsid variant of any one of embodiments 1-519, 566, or 574.

620. The AAV particle of any one of embodiments 575-519, which is isolated, e.g., recombinant.

621. A vector comprising a polynucleotide encoding the AAV capsid variant of any one of embodiments 1-519, 566, or 574, the polynucleotide of any one of embodiments 520-523 or 567-574, or a polynucleotide encoding the peptide of any one of embodiments 524-543 or 574.

622. A cell, e.g., a host cell, comprising the AAV capsid variant of any one of embodiments 1-519, 566, or 574, the polynucleotide of any one of embodiments 520-523 or 567-574, the peptide of any one of embodiments 524-565 or 574, the AAV particle of any one of embodiments 575-620, or the vector of embodiment 621.

623. The cell of embodiment 622, wherein the cell is a mammalian cell or an insect cell.

624. The cell of embodiment 622 or 623, wherein the cell is a cell of a brain region or a spinal cord region, optionally a cell of the brain stem, hippocampus, or thalamus.

625. The cell of any one of embodiments 622-624, wherein the cell is a neuron, a sensory neuron, a motor neuron, an astrocyte, a glial cell, oligodendrocyte, or a muscle cell (e.g., a cell of the heart, diaphragm, or quadriceps).

626. The cell of embodiment 622 or 623, wherein the cell is a liver cell.

627. A method of making an AAV particle, comprising
  (i) providing a host cell comprising a viral genome; and
  (ii) incubating the host cell under conditions suitable to enclose the viral genome in the AAV capsid variant of any one of embodiments 1-519, 566, or 574 or an AAV capsid variant encoded by the polynucleotide of any one of embodiments 520-523 or 567-574;
  thereby making the AAV particle.

628. The method of embodiment 627, further comprising, prior to step (i), introducing a first nucleic acid molecule comprising the viral genome into the host cell.

629. The method of embodiment 628, wherein the host cell comprises a second nucleic acid encoding the capsid variant.

630. The method of embodiment 629, wherein the second nucleic acid molecule is introduced into the host cell prior to, concurrently with, or after the first nucleic acid molecule.

631. A pharmaceutical composition comprising the AAV particle of any one of embodiments 575-620, an AAV particle comprising the capsid variant of any one of embodiments 1-519, 566, or 574, an AAV particle comprising the peptide of any one of embodiments 524-543 or 574, and a pharmaceutically acceptable excipient.

632. A method of delivering a payload to a cell or tissue (e.g., a CNS cell, CNS tissue, a liver cell, or a liver tissue), comprising administering an effective amount of the pharmaceutical composition of embodiment 631, the AAV particle of any one of embodiments 575-620, an AAV particle comprising the capsid variant of any one of embodiments 1-519, 566, or 574, or an AAV particle comprising the peptide of any one of embodiments 524-543 or 574.

633. The method of embodiment 632, wherein the cell is a cell of a brain region or a spinal cord region, optionally a cell of the frontal cortex, sensory cortex, motor cortex, caudate, cerebellar cortex, cerebral cortex, brain stem, hippocampus, or thalamus.

634. The method of embodiment 632 or 633, wherein the cell is a neuron, a sensory neuron, a motor neuron, an astrocyte, a glial cell, or an oligodendrocyte.

635. The method of embodiment 632, wherein the cell is a liver cell.

636. The method of any one of embodiments 632-635, wherein the cell or tissue is within a subject.

637. The method of embodiment 636, wherein the subject has, has been diagnosed with having, or is at risk of having a genetic disorder, e.g., a monogenic disorder or a polygenic disorder.

638. The method of embodiment 636 or 637, wherein the subject has, has been diagnosed with having, or is at risk of having a neurological, e.g., a neurodegenerative disorder.

639. The method of embodiment 636 or 637, wherein the subject has, has been diagnosed with having, or is at risk of having a neuro-oncological disorder.

640. The method of embodiment 636 or 637, wherein the subject has, has been diagnosed with having, or is at risk of having a muscular disorder or a neuromuscular disorder.

641. A method of treating a subject having or diagnosed with having a genetic disorder, e.g., a monogenic disorder or a polygenic disorder, comprising administering to the subject an effective amount of the pharmaceutical composition of embodiment 631, the AAV particle of any one of embodiments 575-620, an AAV particle comprising the capsid variant of any one of embodiments 1-519, 566, or 574, or an AAV particle comprising the peptide of any one of embodiments 524-543 or 574.

642. A method of treating a subject having or diagnosed with having a neurological disorder, e.g., a neurodegenerative disorder, comprising administering to the subject an effective amount of the pharmaceutical composition of embodiment 631, the AAV particle of any one of embodiments 575-620, an AAV particle comprising the capsid variant of any one of embodiments 1-519, 566, or 574, or an AAV particle comprising the peptide of any one of embodiments 524-543 or 574.

643. A method of treating a subject having or diagnosed with having a muscular disorder or a neuromuscular disorder, comprising administering to the subject an effective amount of the pharmaceutical composition of embodiment 631, the AAV particle of any one of embodiments 575-620, an AAV particle comprising the capsid variant of any one of embodiments 1-519, 566, or 574, or an AAV particle comprising the peptide of any one of embodiments 524-543 or 574.

644. A method of treating a subject having or diagnosed with having a neuro-oncological disorder, comprising administering to the subject an effective amount of the pharmaceutical composition of embodiment 631, the AAV particle of any one of embodiments 575-620, an AAV particle comprising the capsid variant of any one of embodiments 1-519, 566, or 574, or an AAV particle comprising the peptide of any one of embodiments 524-543 or 574.

645. The method of any one of embodiments 637-645, wherein the genetic disorder, neurological disorder, neurodegenerative disorder, muscular disorder, neuromuscular disorder, or neuro-oncological disorder is Huntington's Disease, Amyotrophic Lateral Sclerosis (ALS), Gaucher Disease, Dementia with Lewy Bodies, Parkinson's disease, Spinal Muscular Atrophy, Alzheimer's Disease, a leukodystrophy (e.g., Alexander disease, autosomal dominant leukodystrophy with autonomic diseases (ADLD), Canavan disease, cerebrotendinous xanthomatosis (CTX), metachromatic leukodystrophy (MLD), Pelizaeus-Merzbacher disease, or Refsum disease), or a cancer (e.g., a HER2/neu positive cancer or a glioblastoma)'.

646. The method of any one of embodiments 641-645, where treating comprises prevention of progression of the disease or disorder in the subject.

647. The method of embodiment 636-646, wherein the subject is a human.

648. The method of any one of embodiments 636-647, wherein the AAV particle is administered to the subject intravenously, via intra-cisterna magna injection (ICM), intracerebrally, intrathecally, intracerebroventricularly, via intraparenchymal administration, intraarterially, or intramuscularly.

649. The method of any one of embodiments 636-648, wherein the AAV particle is administered to the subject via focused ultrasound (FUS), e.g., coupled with the intravenous administration of microbubbles (FUS-MB), or MRI-guided FUS coupled with intravenous administration.

650. The method of any one of embodiments 636-649, wherein the AAV particle is administered to the subject intravenously.

651. The method of any one of embodiments 636-650, wherein the AAV particle is administered to the subject via intra-cisterna magna injection (ICM).

652. The method of any one of embodiments 636-651, wherein the AAV particle is administered to the subject intraarterially.

653. The method of any one of embodiments 648-652, wherein administration of the AAV particle results in a decreased presence, level, and/or activity of a gene, mRNA, protein, or combination thereof.

654. The method of any one of embodiments 648-652, wherein administration of the AAV particle results in an increased presence, level, and/or activity of a gene, mRNA, protein, or a combination thereof.

655. The pharmaceutical composition of embodiment 631, the AAV particle of any one of embodiments 575-620, an AAV particle comprising the capsid variant of any one of embodiments 1-519, 566, or 574, or an AAV particle comprising the peptide of any one of embodiments 524-543 or 574, for use in a method of delivering a payload to a cell or tissue.

656. The pharmaceutical composition of embodiment 631, the AAV particle of any one of embodiments 575-620, an AAV particle comprising the capsid variant of any one of embodiments 1-519, 566, or 574, or an AAV particle comprising the peptide of any one of embodiments 524-543 or 574, for use in a method of treating a genetic disorder, a neurological disorder, a neurodegenerative disorder, a muscular disorder, a neuromuscular disorder, or a neuro-oncological disorder.

657. The pharmaceutical composition of embodiment 631, the AAV particle of any one of embodiments 575-620, an AAV particle comprising the capsid variant of any one of embodiments 1-519, 566, or 574, or an AAV particle comprising the peptide of any one of embodiments 524-543 or 574, for use in the manufacture of a medicament.

658. Use of the pharmaceutical composition of embodiment 631, the AAV particle of any one of embodiments 575-620, an AAV particle comprising the capsid variant of any one of embodiments 1-519, 566, or 574, or an AAV particle comprising the peptide of any one of embodiments 524-543 or 574, in the manufacture of a medicament.

659. Use of the pharmaceutical composition of embodiment 631, the AAV particle of any one of embodiments 575-620, an AAV particle comprising the capsid variant of any one of embodiments 1-519, 566, or 574, or an AAV particle comprising the peptide of any one of embodiments 524-543 or 574, in the manufacture of a medicament for treating a genetic disorder, a neurological disorder, a neurodegenerative disorder, a muscular disorder, a neuromuscular disorder, or a neuro-oncological disorder.

The details of one or more embodiments of the disclosure are set forth in the accompanying description below. Other features, objects and advantages of the disclosure will be apparent from the description. In the description, the singular forms also include the plural unless the context clearly dictates otherwise. Certain terms are defined in the Definition section and throughout.

DETAILED DESCRIPTION OF THE DISCLOSURE

Described herein, inter alia, are compositions comprising an AAV capsid variant, e.g., an AAV capsid variant described herein, and methods of making and using the same. Generally, the AAV capsid variant has enhanced tropism for a cell or tissue, e.g., for the delivery of a payload to said cell or tissue, for example a CNS tissue or a CNS cell or a liver cell or liver tissue.

As demonstrated in the Examples herein below, certain AAV capsid variants described herein show multiple advantages over wild-type AAV9, including (i) increased penetrance through the blood brain barrier following intravenous administration, (ii) wider distribution throughout the multiple brain regions, e.g., frontal cortex, sensory cortex, motor cortex, putamen, thalamus, cerebellar cortex, dentate nucleus, caudate, and/or hippocampus, and/or (iii) elevated payload expression in multiple brain regions. Without wishing to be being bound by theory, it is believed that these advantages may be due, in part, to the dissemination of the AAV capsid variants through the brain vasculature. In some embodiments, the AAV capsids described herein enhance the delivery of a payload to multiple regions of the brain including for example, the frontal cortex, sensory cortex, motor cortex, putamen, thalamus, cerebellar cortex, dentate nucleus, caudate, and/or hippocampus.

Several approaches have been used previously to produce AAV capsids with enhanced tropism for a cell or tissue, e.g., a CNS cell or tissue. One approach used co-infection of cultured cells (Grimm et al. In vitro and in vivo gene therapy vector evolution via multispecies interbreeding and retargeting of adeno-associated viruses. J. Virol. 2008 June 82(12):5887-5911, the contents of which are herein incorporated by reference in its entirety) or in situ animal tissue (Lisowski et al. Selection and evaluation of clinically relevant AAV variants in a xenograft liver model. Nature 2014 506:382-386, the contents of which are herein incorporated by reference in its entirety) with adenovirus, in order to trigger exponential replication of infectious AAV DNA. Another approach involved the use of cell-specific CRE transgenic mice (Deverman et al. Cre-dependent selection yields AAV variants for widespread gene transfer to the adult brain. Nat Biotechnol. 2016 February 34(2)204-209; the contents of which are herein incorporated by reference in its entirety) allowing viral DNA recombination specifically in astrocytes, followed by recovery of CRE-recombined capsid variants. Other approaches apply high throughput DNA synthesis, multiplexing, sequencing technologies, and machine learning to evaluate sequencing reads of viral DNA in different tissues to engineer variant capsids. These approaches are different from the approach disclosed herein.

There are some limitations to the art-known capsid generation methods. For example, the transgenic CRE system used by Deverman et al. (2016) has limited tractable in other animal species and AAV variants selected by directed evolution in mouse tissue do not show similar properties in large animals. Previously described transduction-specific approaches are not amenable to large animal studies because: 1) many tissues of interest (e.g., CNS) are not readily accessible to adenovirus co-infection, 2) the specific adenovirus tropism itself would bias the library distribution, and 3) large animals are typically not amenable to transgenesis or genetic engineering to express CRE recombinase in defined cell types.

To address these limitations, a broadly-applicable functional AAV capsid library screening platform for cell type-specific biopanning in non-transgenic animals has been developed and is described in the appended Examples. In the TRACER (Tropism Redirection of AAV by Cell type-specific Expression of RNA) platform system, the capsid gene is placed under the control of a cell type-specific promoter to drive capsid mRNA expression in the absence of helper virus co-infection. Without wishing to be bound by theory, it is believed that this RNA-driven screen increases the selective pressure in favor of capsid variants which transduce a specific cell type. The TRACER platform allows for generation of AAV capsid libraries whereby specific recovery and subcloning of capsid mRNA expressed in transduced cells is achieved with no need for transgenic animals or helper virus co-infection. Without wishing to be bound by theory, it is believed that since mRNA transcription is a hallmark of full transduction, the methods disclosed herein allow identification of fully infectious AAV capsid mutants, and in addition to its higher stringency, this method allows identification of capsids with high tropism for particular cell types using libraries designed to express CAP mRNA under the control of any cell-specific promoter such as, but not limited to, synapsin-1 promoter (neurons), GFAP promoter (astrocytes), TBG promoter (liver), CAMK promoter (skeletal muscle), MYH6 promoter (cardiomyocytes). Described herein are novel AAV capsid variants generated using the TRACER method which demonstrate enhance tropism in for example a CNS cell, a CNS tissue, a liver cell, a liver tissue, a muscle cell, or a muscle tissue.

In some embodiments, an AAV capsid variant disclosed herein comprises a modification in loop IV of AAV9, e.g., at positions between 449-460, e.g., at position 454 and/or 455, numbered relative to SEQ ID NO: 138, 981, or 982. In some embodiments, loop (e.g., loop IV) is used interchangeably herein with the term variable region (e.g., variable region IV), or VR (e.g., VR-IV). In some embodiments loop IV comprises positions 449-475 (e.g., amino acids KTINGSGQNQQTLKFSVAGPSNMAVQG (SEQ ID NO: 6404)), numbered according to SEQ ID NO: 138. In some embodiments loop IV comprises positions 449-460 (e.g., amino acids KTINGSGQNQQT (SEQ ID NO: 6405)), numbered according to SEQ ID NO: 138. In some embodiments, loop IV or variable region IV (VR-IV) is as described in DiMattia et al. "Structural Insights into the Unique Properties of the Adeno-Associated Virus Serotype 9," *Journal of Virology*, 12(86):6947-6958 (the contents of which are hereby incorporated by reference in their entirety), e.g., comprising positions 452-460 (e.g., NGSGQNQQT (SEQ ID NO: 4487)), numbered according to SEQ ID NO: 138.

The AAV particles and payloads of the disclosure may be delivered to one or more target cells, tissues, organs, or organisms. In some embodiments, the AAV particles of the disclosure demonstrate enhanced tropism for a target cell type, tissue or organ. As a non-limiting example, the AAV particle may have enhanced tropism for cells and tissues of the central or peripheral nervous systems (CNS and PNS, respectively). In some embodiments, an AAV particle of the disclosure may, in addition, or alternatively, have decreased tropism for a cell-type, tissue or organ.

In some embodiments, an AAV comprises a small non-enveloped icosahedral capsid virus of the Parvoviridae family and is characterized by a single stranded DNA viral genome. Parvoviridae family viruses consist of two subfamilies: Parvovirinae, which infect vertebrates, and Densovirinae, which infect invertebrates. The Parvoviridae family comprises the Dependovirus genus which includes AAV, capable of replication in vertebrate hosts including, but not limited to, human, primate, bovine, canine, equine, and ovine species.

The parvoviruses and other members of the Parvoviridae family are generally described in Kenneth I. Berns, "Parvoviridae: The Viruses and Their Replication," Chapter 69 in FIELDS VIROLOGY (3d Ed. 1996), the contents of which are incorporated by reference in their entirety.

In some embodiments, AAV are used as a biological tool due to a relatively simple structure, their ability to infect a wide range of cells (including quiescent and dividing cells) without integration into the host genome and without replicating, and their relatively benign immunogenic profile. The genome of the virus may be manipulated to contain a minimum of components for the assembly of a functional recombinant virus, or viral particle, which is loaded with or engineered to target a particular tissue and express or deliver a desired payload.

In some embodiments, the AAV, is a naturally occurring (e.g., wild-type) AAV or a recombinant AAV. In some embodiments, the wild-type AAV vector genome is a linear, single-stranded DNA (ssDNA) molecule approximately 5,000 nucleotides (nt) in length. In some embodiments, inverted terminal repeats (ITRs) cap the viral genome at both the 5' and the 3' end, providing origins of replication for the viral genome. In some embodiments, an AAV viral genome typically comprises two ITR sequences. These ITRs have a characteristic T-shaped hairpin structure defined by a self-complementary region (145nt in wild-type AAV) at the 5' and 3' ends of the ssDNA which form an energetically stable double stranded region. The double stranded hairpin structures comprise multiple functions including, but not limited to, acting as an origin for DNA replication by functioning as primers for the endogenous DNA polymerase complex of the host viral replication cell.

In some embodiments, the wild-type AAV viral genome further comprises nucleotide sequences for two open reading frames, one for the four non-structural Rep proteins (Rep78, Rep68, Rep52, Rep40, encoded by Rep genes) and one for the three capsid, or structural, proteins (VP1, VP2, VP3, encoded by capsid genes or Cap genes). The Rep proteins are used for replication and packaging, while the capsid proteins are assembled to create the protein shell of the AAV, or AAV capsid polypeptide, e.g., an AAV capsid variant. Alternative splicing and alternate initiation codons and promoters result in the generation of four different Rep proteins from a single open reading frame and the generation of three capsid proteins from a single open reading frame. Though it varies by AAV serotype, as a non-limiting example, for AAV9/hu.14 (SEQ ID NO: 123 of U.S. Pat. No. 7,906,111, the contents of which are herein incorporated by reference in their entirety) VP1 refers to amino acids 1-736, VP2 refers to amino acids 138-736, and VP3 refers to amino acids 203-736. In some embodiments, for any one of the amino acid sequences of SEQ ID NO: 981 or 982, VP1 comprises amino acids 1-742, VP2 comprises amino acids 138-742, and VP3 comprises amino acids 203-742. In other words, VP1 is the full-length capsid sequence, while VP2 and VP3 are shorter components of the whole. As a result, changes in the sequence in the VP3 region, are also changes to VP1 and VP2, however, the percent difference as compared to the parent sequence will be greatest for VP3 since it is the shortest sequence of the three. Though described here in relation to the amino acid sequence, the nucleic acid sequence encoding these proteins can be similarly described. Together, the three capsid proteins assemble to create the AAV capsid protein. While not wishing to be bound by theory, the AAV capsid protein typically comprises a molar ratio of 1:1:10 of VP1:VP2:VP3.

AAV vectors of the present disclosure may be produced recombinantly and may be based on adeno-associated virus (AAV) reference sequences. In addition to single stranded AAV viral genomes (e.g., ssAAVs), the present disclosure also provides for self-complementary AAV (scAAVs) viral genomes. scAAV vector genomes contain DNA strands which anneal together to form double stranded DNA. By skipping second strand synthesis, scAAVs allow for rapid expression in the transduced cell. In some embodiments, the AAV particle of the present disclosure is an scAAV. In some embodiments, the AAV particle of the present disclosure is an ssAAV.

Methods for producing and/or modifying AAV particles are disclosed in the art such as pseudotyped AAV vectors (PCT Patent Publication Nos. WO200028004; WO200123001; WO2004112727; WO2005005610; and WO2005072364, the content of each of which is incorporated herein by reference in its entirety).

As described herein, the AAV particles of the disclosure comprising an AAV capsid variant, and a viral genome, have enhanced tropism for a cell-type or a tissue, e.g., a CNS cell-type, region, or tissue.

Peptides

Disclosed herein are peptides, and associated AAV particles comprising an AAV capsid variant and a peptide for enhanced or improved transduction of a target tissue (e.g., cells of the CNS or PNS). In some, embodiments, the peptide is an isolated, e.g., recombinant, peptide. In some embodiments, the nucleic acid encoding the peptide, is an isolated, e.g., recombinant nucleic acid.

In some embodiments, the peptide may increase distribution of an AAV particle to a cell, region, or tissue of the CNS. The cell of the CNS may be, but is not limited to, neurons (e.g., excitatory, inhibitory, motor, sensory, autonomic, sympathetic, parasympathetic, Purkinje, Betz, etc.), glial cells (e.g., microglia, astrocytes, oligodendrocytes) and/or supporting cells of the brain such as immune cells (e.g., T cells). The tissue of the CNS may be, but is not limited to, the cortex (e.g., frontal, parietal, occipital, and/or temporal), thalamus, hypothalamus, striatum, putamen, caudate nucleus, hippocampus, entorhinal cortex, basal ganglia, or deep cerebellar nuclei.

In some embodiments, the peptide may increase distribution of an AAV particle to a cell, region, or tissue of the PNS. The cell or tissue of the PNS may be, but is not limited to, a dorsal root ganglion (DRG).

In some embodiments, the peptide may increase distribution of an AAV particle to the CNS (e.g., the cortex) after intravenous administration. In some embodiments, the peptide may increase distribution of an AAV particle to the CNS (e.g., the cortex) following focused ultrasound (FUS), e.g., coupled with the intravenous administration of microbubbles (FUS-MB), or MRI-guided FUS coupled with intravenous administration.

In some embodiments, the peptide may increase distribution of an AAV particle to the PNS (e.g., DRG) after intravenous administration. In some embodiments, the peptide may increase distribution of an AAV particle to the PNS (e.g., DRG) following focused ultrasound (FUS), e.g., coupled with the intravenous administration of microbubbles (FUS-MB), or MRI-guided FUS coupled with intravenous administration.

In some embodiments, the peptide may increase distribution of an AAV particle to a cell, region, or tissue of a muscle. In some embodiments, the muscle is a heart muscle, e.g., a heart atrium or a heart ventricle. In some embodiments, the peptide may direct an AAV particle to a muscle cell, region, or tissue after intravenous administration.

In some embodiments, the peptide may increase distribution of an AAV particle to a cell, region, or tissue of the liver.

A peptide may vary in length. In some embodiments, the peptide is about 3 to about 20 amino acids in length. As non-limiting examples, the peptide may be 3, 4, 5, 6, 7, 8, 9, 10, 11, 12, 13, 14, 15, 16, 17, 18, 19, 20 or 3-5, 3-8, 3-10, 3-12, 3-15, 3-18, 3-20, 5-10, 5-15, 5-20, 10-12, 10-15, 10-20, 12-20, or 15-20 amino acids in length. In some embodiments, a peptide comprises about 6 to 12 amino acids in length, e.g., about 9 amino acids in length. In some embodiments, a peptide comprises about 5 to 10 amino acids in length, e.g., about 7 amino acids in length. In some embodiments, a peptide comprises about 7 to 11 amino acids in length, e.g., about 8 amino acids in length. In some embodiments, a peptide comprises about 4 to 9 amino acids in length, e.g., about 6 amino acids in length.

In some embodiments a peptide may comprise a sequence as set forth in Table 1 (e.g., comprising the amino acid sequence of any one of SEQ ID NOs: 200-940, 1800-2241, 2242-2886, or 2887-3076). In some embodiments a peptide may comprise a sequence as set forth in Table 2A or 2B. In some embodiments, the peptide may comprise a sequence set forth in Table 13 or 14. In some embodiments, the peptide may comprise a sequence as set forth in Table 15. In some embodiments, the peptide may comprise a sequence as set forth in Table 16. In some embodiments, the peptide may comprise a sequence as set forth in Table 17. In some embodiments, the peptide may comprise a sequence as set forth in Table 18. In some embodiments, the peptide may comprise a sequence as set forth in Table 19. In some embodiments, the peptide is isolated, e.g., recombinant.

TABLE 1

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| GSGSPHSKAQNQQT | 200 | GSLHHDNHGQNQQT | 385 | GSVFGVPSGQNQQT | 570 | GSIAMTSHGQNQQT | 755 |
| GHDSPHKSGQNQQT | 201 | GIMARDSSGQNQQT | 386 | GSGLPDRNLQNQQT | 571 | GSPGVSPSGQNQQT | 756 |
| GSGSPHARMQNQQT | 202 | GVVHITNSGQNQQT | 387 | GSGTHNSAIQNQQT | 572 | GSGQNQQTGSSSRV | 757 |
| GSGSPHVKSQNQQT | 203 | GSGQNQHSAPFNQT | 388 | GSGMIIASMQNQQT | 573 | GSGQHLPLLGNQQT | 758 |
| GQDSPHKSGQNQQT | 204 | GSGQTSGLKQNQQT | 389 | GGITWTDSGQNQQT | 574 | GSDHSHRGGQNQQT | 759 |
| GSGSPHASRQNQQT | 205 | GSGQNQQTSLSNTA | 390 | GSGQNQQASGRQQT | 575 | GSGIVTKLGQNQQT | 760 |
| GSGSPHASRQNKQT | 206 | GSGQNQAVHNKSQT | 391 | GSGQNQQPHLKSLT | 576 | GSGQDVTKTGNQQT | 761 |
| GSGSPHVKIQNQQT | 207 | GVHTHLPSGQNQQT | 392 | GPPQHMTSGQNQQT | 577 | GSGQNQQSHGRIGT | 762 |
| GSGSPHSKAKNQQT | 208 | GHLTMHNSGQNHQT | 393 | GSGQNQQASLPSRT | 578 | GSGQNQQINHRSPT | 763 |
| GSGSPHKKNQNQQT | 209 | GSGSSSRPYQNQQT | 394 | GSGQIVSTQTNQQT | 579 | GSGDDSRVGQNQQT | 764 |
| GSGSPHVRMQNQQT | 210 | GILLATPSGQNQQT | 395 | GSGKGHSAGQNQQT | 580 | GSGQSTLKRINQQT | 765 |
| GSGSPHASRQKQQT | 211 | GSGQNAGSFPNQQT | 396 | GSGQNTRLQLGQQT | 581 | GSGSQHSKAQNQQT | 766 |
| GHSSPHRSGQNQQT | 212 | GSRDGHTVGQNQQT | 397 | GSVGSRPVGQNQQT | 582 | GSGQNQQHASSNNT | 767 |
| GMRTYHLSGQNQQT | 213 | GSLLISTSGQNQQT | 398 | GSSHTLALGQNQQT | 583 | GSRTYQVSGQNQQT | 768 |
| GSGSPHTRGQNQQT | 214 | GSGAMPSHGQNQQT | 399 | GMYEYSQSGQNQQT | 584 | GSGQNQGLLSSPQT | 769 |
| GSGIIPVSSQNQQT | 215 | GALVSPISGQNQQT | 400 | GNGQNQQHSILHGT | 585 | GSGGGLQHNQNQQT | 770 |
| GSEYGHKSGQNQQT | 216 | GSLSSHGVGQNQQT | 401 | GSGYNQPHLQNQQT | 586 | GSGQNQQTTAATRM | 771 |
| GRGQNVSSVHRQQT | 217 | GSGQNQQASLAMRT | 402 | GPLVNASSGQNQQT | 587 | GSGQNQRASILVQT | 772 |
| GSSHRFYGGQNQQT | 218 | GPGLGSHSGQNQQT | 403 | GSGQNQQVLTTART | 588 | GSGQNLGLLGAQQT | 773 |
| GYFVAAWSGQNQQT | 219 | GHDSQHKSGQNQQT | 404 | GSGQNQHSVHNDQT | 589 | GSLDLGRSGQNQQT | 774 |
| GSVLHSHAAQNQQT | 220 | GSGLTLSATQNQQT | 405 | GAGLIMHSGQNQQT | 590 | GNSQVKVSGQNQQT | 775 |
| GSGDLVVSTQNQQT | 221 | GSGQVVAHVGNQQT | 406 | GMGRHSASGQNQQT | 591 | GSSGSHQYGQNQQT | 776 |
| GSYGMAASGQNQQT | 222 | GSGLRTMTTQNQQT | 407 | GSHSQSGHGQNQQT | 592 | GSGQNQQQRDGTLT | 777 |
| GLNHFGASGQNQQT | 223 | GSGQVGRLLQNQQT | 408 | GSSTTIVSGQNHQT | 593 | GRGQHVSVANNQQT | 778 |
| GSTGSHSAGQNQHT | 224 | GSGQLSHQSVNQQT | 409 | GRHLVTASGQNQQT | 594 | GDSSRISGQNQQT | 779 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| GLAGHTVSGQNQQT | 225 | GSGDRYQTLQNQQT | 410 | GSGQNQQHANLNQT | 595 | GSGQNQQHSLSSQT | 780 |
| GIILGASSGQNQQT | 226 | GSGQNQQLKSSAQT | 411 | GSGSTHSKAQNQQT | 596 | GSLMDVHRGQNQQT | 781 |
| GSGVSTYNIQNQQT | 227 | GSGQNQYSIPVAQT | 412 | GSGQNKQMLSGNTT | 597 | GSIQYQSSGQNQQT | 782 |
| GSLVSVQTGQNQQT | 228 | GSGERLHLTQNQQT | 413 | GSGQVHNPTQNQQT | 598 | GLGSKNPSGQNQQT | 783 |
| GQSSPHRSGQNQQT | 229 | GSGHNQQVRTAPNT | 414 | GSGQNQQIPHVHQT | 599 | GSGQLVLTLQNQQT | 784 |
| GREYGHKSGQNQQT | 230 | GGLSHVMSGQNQQT | 415 | GSLHAGLSGQNQQT | 600 | GSGQNQQTSQPLPG | 785 |
| GHTLTLSSGQNQQT | 231 | GSGQSHRDVLNQQT | 416 | GPAQHGTSGQNQQT | 601 | GSGQNQQNLGKLNT | 786 |
| GSITLIPSGQNQQT | 232 | GSGQNLAGRMDQQT | 417 | GEKAVTSSGQNQQT | 602 | GTTAHPSGQNQQT | 787 |
| GSNGFTALGQNQQT | 233 | GSGQNQQTNRGNPM | 418 | GSGQNQQTMANGQR | 603 | GSGQNRAQIGTQQT | 788 |
| GSGHSSHSVQNQQT | 234 | GSGQSYQRDHNQQT | 419 | GSGSPHSKDQNQQT | 604 | GSGQYVHVSSNQQT | 789 |
| GSGIPQRSGKNQQT | 235 | GSLLSAGMGQNQHT | 420 | GSFSMGYGGQNQQT | 605 | GSGQNQQTAHAFNI | 790 |
| GSGDTLHMLQNQQT | 236 | GSGQNQQTAIYRNI | 421 | GSGTHLVSLQNQQT | 606 | GSGQNQRTMVATQT | 791 |
| GERHTVLSGQNQQT | 237 | GSGQNQQTSGTTNC | 422 | GSGQMPHVQNQQT | 607 | GSGQNPIRGAMQQT | 792 |
| GSGMPQSHIQNQQT | 238 | GMTSHSVSGQNQQT | 423 | GSGQNQQVAGLNNT | 608 | GSGYVITGSQNQQT | 793 |
| GSGQLSGIGGNQQT | 239 | GSSQSTGYQPNQQT | 424 | GSSQNQQHDMRLRT | 609 | GRGPKQSNIQNQQT | 794 |
| GSGQNRKPASFAQT | 240 | GSLKPTTLGQNQQT | 425 | GPASLPISGQNQQT | 610 | GSGQNQQTMLGKPC | 795 |
| GSGSVSQLGQNQQT | 241 | GRMFSLGSGQNQQT | 426 | GSGQNQQPPLATRT | 611 | GSGQNQQVGSTVRT | 796 |
| GSDFLGTHGQNQQT | 242 | GSGQNQQTALGVKC | 427 | GSSRVPVSGQNQQT | 612 | GNVTTQKSGQNQQT | 797 |
| GQIVQNPSGQNQQT | 243 | GAMVSHSSGQNQQT | 428 | GSGQNQQTNLGHTT | 613 | GSGNPVSHLQNQQT | 798 |
| GSGTQIPSQQNQQT | 244 | GSGQNQQRNSDSVT | 429 | GSGQNQQLVSRVQT | 614 | GSLSHMESGQNQQT | 799 |
| GSGQNQQSAREGLT | 245 | GSGQSMTLHLNQQT | 430 | GPNSYPVSGQKQQT | 615 | GRAPTNLSGQNQQT | 800 |
| GSGLGMSTGQNQQT | 246 | GSGQVHQAEVNQQT | 431 | GHAHYQASGQNQQT | 616 | GSGQNQQTVMTARA | 801 |
| GSGLPVLSGQNQQT | 247 | GSGQNQSQNHLQQT | 432 | GSGQALLSTGNQQT | 617 | GSGMPASRLQNQQT | 802 |
| GSGHSIRTDQNQQT | 248 | GSLLTTASGQNQQT | 433 | GSGQLPRQMTNQQT | 618 | GVVRNHQSGQNQQT | 803 |

TABLE 1-continued

Exemplary Peptide Sequences

| Peptide Sequence | SEQ ID NO: | Peptide Sequence | SEQ ID NO: | Peptide Sequence | SEQ ID NO: |
|---|---|---|---|---|---|
| GSGQSVQTVVNQQT | 249 | GSGLIRTAAQNQQT | 434 | GSGFPKSTEQNQQT | 619 | GSGQNHSVQVRQT | 804 |
| GSGQNRAQSRFQQT | 250 | GSGQNQQTVSRQST | 435 | GSRETSLSGQNQQT | 620 | GSGQNTGHLTMQQT | 805 |
| GGGDLGRSSQNQQT | 251 | GSGQYANHGINQQT | 436 | GSGQNQQGTGVSHT | 621 | GSGQNQQYAGKILT | 806 |
| GGGTKMDSGQNQQT | 252 | GSRSTGPSGQNQQT | 437 | GSRTVPVYGQNQQT | 622 | GSGNPHVRNQNQQT | 807 |
| GSGSPHPSRQNQQT | 253 | GRGVQQKLQQNQQT | 438 | GSNAQSAHGQNQQT | 623 | GSGQNGGSSNRQQT | 808 |
| GSGQFTNAGMNQQT | 254 | GSGQNQQVHLSTGT | 439 | GAFHLAASGQNQQT | 624 | GSGQRLSQGVNHQT | 809 |
| GGRNGHTVGQNQQT | 255 | GSGQNQQLSAKSST | 440 | GSGQYRSSSDNQQT | 625 | GSGQNAHAKEGQQT | 810 |
| GSGFGPQTGQNQQT | 256 | GSGYKAARPQNQQT | 441 | GSGQVYISTPNQQT | 626 | GSSPAPNSGQNQQT | 811 |
| GRTDSHTSGQNQQT | 257 | GSAGISPSGQNQQT | 442 | GSGVSTQLLQNQQT | 627 | GLAHKTSSGQNQQT | 812 |
| GYEVLGSSGQNQQT | 258 | GSGQNRAHAFLQQT | 443 | GSGQLGLSVTNQQT | 628 | GSGQNQQTPGAHKT | 813 |
| GSVHLSVTGQNQQT | 259 | GSGLSGITMQNQQT | 444 | GSGSNMRLSQNQQT | 629 | GSGQNQQSLSGSFT | 814 |
| GFMSYKGSGQNQQT | 260 | GPGSAHSSGQNQQT | 445 | GSGQNLHSGLPQQT | 630 | GSGQNQQSTGTSRT | 815 |
| GNIAGSVSGQNQQT | 261 | GSSHTQALGQNQQT | 446 | GSSHTALGQNKQT | 631 | GSGQNQQTVQSNLV | 816 |
| GSGSHRDVSQNQQT | 262 | GSGVHGVSSQNQQT | 447 | GSGQNHSLPAHRT | 632 | GSGQNQQLGSRQCT | 817 |
| GGLGSMSSGQNQQT | 263 | GSSGRDMGGQNQQT | 448 | GSGQNQGTVYPNQT | 633 | GSGQNQYLRLELQT | 818 |
| GSGHLPQSAQNQQT | 264 | GERAFPTSGQNQQT | 449 | GSGQNQQPSLRQST | 634 | GSGQNQQTSPRLQT | 819 |
| GGVLVGGSGQNQQT | 265 | GGRIVSLSGQNQQT | 450 | GSGQNARLKDNQQT | 635 | GSGQNQQTTSSNMT | 820 |
| GTHPYTSSGQNQQT | 266 | GSGQNSYSHTSQQT | 451 | GHAGSTGSGQNQQT | 636 | GTASTYNSGQNQQT | 821 |
| GSGQNQQLKENRST | 267 | GLGYPGSSGQNQQT | 452 | GSGQALSSSGNQQT | 637 | GSGQNQQTMPQHKI | 822 |
| GSGQNQQTSPHNHT | 268 | GSGPQSHTGQNQQT | 453 | GSGASESHRQNQQT | 638 | GSGQSHLHTGNQQT | 823 |
| GSGTLYPQSQNQQT | 269 | GSGQNQQLSRDAST | 454 | GVGVITSSGQNQQT | 639 | GVKGVGHSGQNQQT | 824 |
| GSGQNQQSNWITKT | 270 | GSGQILHSVPNQQT | 455 | GSLYGQSLGQNQQT | 640 | GSGKVTKQSQNQQT | 825 |
| GSGYTSLFLQNQQT | 271 | GSGFHTDSRQNQQT | 456 | GSGMSDVHGNQQT | 641 | GSGQNQQTALEKSL | 826 |
| GSGVMTHVLQNQQT | 272 | GSGQSHSLATNQQT | 457 | GSGQNQQHSSKATT | 642 | GSGYKDTYGQNQQT | 827 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| GSVSDVRAGQNQQT | 273 | GSGQNQQTLSKPWT | 458 | GSGQNQQTSVSQQT | 643 | GSGQNQQSGTFLST | 828 |
| GSGQSHMATLNQQT | 274 | GSGHAAISQQNQQT | 459 | GSGQKMWKLDNQQT | 644 | GSGQNTGQHMMQQT | 829 |
| GSGLSVHLAQNQQT | 275 | GSGQNQQQIGGNST | 460 | GSGQNVSMQVNQQT | 645 | GSGKNQQRPGLDQT | 830 |
| GSGLSHATQQNQQT | 276 | GGGPMAGSGQNQQT | 461 | GSGQNQRATLSNQT | 646 | GSGQSREISLNQQT | 831 |
| GSGLSVQSGQNQQT | 277 | GMRMEYQSGQNQQT | 462 | GSGQASSKSANQQT | 647 | GTPTSPSSGQNQQT | 832 |
| GSGHMTYREKNQQT | 278 | GSGQNQQGTLLHQT | 463 | GSGKNQTPIPKGQT | 648 | GKPAGGLSGQNQQT | 833 |
| GSKGVPTPGQNQQT | 279 | GSGQNQRSSGGVQT | 464 | GSGQNQQTRQEGST | 649 | GSGQNHRSADMQQT | 834 |
| GSGLLPLSSQNQQT | 280 | GSGQNQRGALATQT | 465 | GASSLATSGQNQQT | 650 | GSGQNQQTLPSLSL | 835 |
| GNGLYAVSGQNQQT | 281 | GSGTVHAATQNQQT | 466 | GSGQRGSLTENQQT | 651 | GSPYMGATGQNQQT | 836 |
| GFNGSPSSGQNQQT | 282 | GSRMTQQFGQNQQT | 467 | GSEQTRQRGQNQQT | 652 | GSGHAKAVGQNQQT | 837 |
| GSGQIRHSDQNQQT | 283 | GSSSPGASGQNQQT | 468 | GSGQNQQTLTASKE | 653 | GHMKGVTSGQNQQT | 838 |
| GGQVAPSSGQNQQT | 284 | GHPSPHVSGQNQQT | 469 | GSGTSGKTGKNQQT | 654 | GSGQNQKILTLDQT | 839 |
| GSFSMHTHGQNQQT | 285 | GSGSHHASRQNQQT | 470 | GQLVTFTSGQNQQT | 655 | GSGQNQQTKVGHSA | 840 |
| GSGQNQQVIQGSNT | 286 | GAVGHSYSGQNQQT | 471 | GSGQNQQSANKILT | 656 | GIARTTISGQNQQT | 841 |
| GRVLHSHAGQNQQT | 287 | GSRSQYDIGQNQQT | 472 | GSGQNQQHHSSHTT | 657 | GSGQNQQTSVGFRT | 842 |
| GSGQNQQTSLQDQT | 288 | GSGQGPQERGNQQT | 473 | GSGQNQKGMQPNQT | 658 | GSGQNQQTMIANIR | 843 |
| GSGLGRAPVQNQQT | 289 | GSIAHVGTGQNQQT | 474 | GSGQLVSGLYNQQT | 659 | GDMTRSSSGQNQQT | 844 |
| GNGFSSASGQNQQT | 290 | GSGQNQQKQNHGNT | 475 | GSSVGVPSGQNQQT | 660 | GSGHMSDLRQNQQT | 845 |
| GSGQMASRESNQQT | 291 | GSGQNQQALGSQRT | 476 | GSGQNQQWDSRRQT | 661 | GRGAVMASGQNQQT | 846 |
| GPGLPNHSGQNQQT | 292 | GSGAITHMPQNQQT | 477 | GSEQTRQSGQNQQT | 662 | GSGQNQQLSGKSVT | 847 |
| GNIQWQGSGQNQQT | 293 | GSGQRNPLLLNQQT | 478 | GSGIGSHIPQNQQT | 663 | GSHTLVVSGQNQQT | 848 |
| GMSAHMSSGQNQQT | 294 | GSSGIPVSHQNQQT | 479 | GSGQNQRLHGVDQT | 664 | GSGPWSAGLQNQQT | 849 |
| GHSFVNRSGQNQQT | 295 | GVHSLTPSGQNQQT | 480 | GEVSRVLSGQNQQT | 665 | GSGQHSPHALNQQT | 850 |
| GRAVMDHSGQNQQT | 296 | GVIVLHGSGQNQQT | 481 | GSGQNQQKVSPLLT | 666 | GSGQNQQPNSGSMT | 851 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| GALTVMQSGQNQQT | 297 | GGTRVVDSGQNQQT | 482 | GSGLALERSQNQQT | 667 | GSGLAHLGGQNQQT | 852 |
| GSGQRSPVLPNQQT | 298 | GSGGVTYQSGQNQQT | 483 | GPDRIGSSGQNQQT | 668 | GSSVRYEPKQNQQT | 853 |
| GSGQNGHLSLKQQT | 299 | GSGQNQAGHGPGQT | 484 | GSGQNQDHQNKQQT | 669 | GSGQNQQARPLELT | 854 |
| GSLPRGTSDQNQQT | 300 | GSGQLVTSGPNQQT | 485 | GSGQNQQTALYNNT | 670 | GSGQPRSTGINQQT | 855 |
| GVAGSLVSGQNQQT | 301 | GSGIAAQRTQNQQT | 486 | GSGAVHLTAQNQQT | 671 | GSGQNQANWVKVQT | 856 |
| GRGGIPQSGQNQQT | 302 | GSTPAGVGGQNQQT | 487 | GSLVSTQSGQNQQT | 672 | GSGHLFQSGQNQQT | 857 |
| GSGQYASSIPNQQT | 303 | GSGQNQQTSTGVHS | 488 | GSGVSARMVQNQQT | 673 | GSGQNRGISISQQT | 858 |
| GTDFGRQSSQNQQT | 304 | GSGQIRQLVDNQQT | 489 | GSGQTRMPLANQQT | 674 | GSGTHYDNRQNQQT | 859 |
| GIFMQTPSGQNQQT | 305 | GSLIGMQSGQNQQT | 490 | GSGISSRNMQNQQT | 675 | GSGQNQQTSTTPLP | 860 |
| GSGQNQQTRLVDLT | 306 | GSGQIKGKMDNQQT | 491 | GSGEKVHSGQNQQT | 676 | GSGQVHASQVNQKT | 861 |
| GTREMPLSGQNQQT | 307 | GSGSDMSSWQNQQT | 492 | GSGQNQQKLSSMST | 677 | GSSGHRESGQNQQT | 862 |
| GSRLVHVHGQNQQT | 308 | GRGQNQQHTGLATT | 493 | GSGQNQQTGQHMRV | 678 | GLSAEKSSGQNQQT | 863 |
| GSGRLVPNGPNQQT | 309 | GSGQNQQTLYSSNT | 494 | GSGMIHTTAQNQQT | 679 | GSGQEHRSLANQQT | 864 |
| GSGYLRESPQNQQT | 310 | GSGQTQVLKSNQQT | 495 | GSGQNWPALKGQQT | 680 | GSGQTVVRIANQQT | 865 |
| GARIQNASGQKQQT | 311 | GSRTLSNVGQNQQT | 496 | GASHMSISGQNQQT | 681 | GSGQNVSSVHRQQT | 866 |
| GLSNPMPSGQNQQT | 312 | GSGVQHSLPQNQQT | 497 | GSDQNQQLGYSKQT | 682 | GSGASRMSIQNQQT | 867 |
| GSTVQDTRGQNQQT | 313 | GNYLHQASGQNQQT | 498 | GIPSIRESGQNQQT | 683 | GVAFIGSSGQNQQT | 868 |
| GPFGMPSSGQNQQT | 314 | GSGGTSVHQQNQQT | 499 | GSGIPSVKFQNQQT | 684 | GSGQNQQTVPTRQT | 869 |
| GSGQNHGVLSNQQT | 315 | GMDHSRPSGQNQQT | 500 | GSGQNQQTSVSQNV | 685 | GSGQAAKSSQNQQT | 870 |
| GSGYSMSQAQNQQT | 316 | GSGQNQQSMGTFTT | 501 | GSGQNQQIGESRMT | 686 | GSGQNQQVAIRTST | 871 |
| GSGMLTHTLQNQQT | 317 | GSGQNQQTPLRPPT | 502 | GSGSSSMSFQNQQT | 687 | GSVHMQNAGQNQQT | 872 |
| GRGSPHASRQNQQT | 318 | GSGQNQHHSVSQQT | 503 | GSGKQERAVSKQT | 688 | GSGMRQAGVQNQQT | 873 |
| GLSWPSTSGQNQQT | 319 | GSGQLRSLSTNQQT | 504 | GCTTRLNSGQNQQT | 689 | GSGQNQQVGGKTVT | 874 |

TABLE 1-continued

Exemplary Peptide Sequences

| Peptide Sequence | SEQ ID NO: | Peptide Sequence | SEQ ID NO: | Peptide Sequence | SEQ ID NO: |
|---|---|---|---|---|---|
| GNSMERTSGQNQQT | 320 | GSGSPRQLSQNQQT | 505 | GSGQNQQIISTKIT | 690 | GVHDMRVSGQNQQT | 875 |
| GSGMSPSTLQNQQT | 321 | GSGQNQQTTASSHT | 506 | GSGQNQQKSLNGNT | 691 | GSGQHVSVANNQQT | 876 |
| GSGHGQVLSQNQQT | 322 | GRGQVVSTHQNQQT | 507 | GSGIPAPRLQNQQT | 692 | GSAAMSVRGQNQQT | 877 |
| GRGQIYSTGGNQQT | 323 | GSAQVSMVGQNQQT | 508 | GSGQIRESMGNQQT | 693 | GVSRGGPSGQNQQT | 878 |
| GVVAAHNSGQNQQT | 324 | GSSTLVTIGKNQQT | 509 | GSGQNSGVHFNQQT | 694 | GSGQMVHTIGNQQT | 879 |
| GDSSLRHSGQNQQT | 325 | GFAHQASSGQNQQT | 510 | GSGQNIGHSLPQQT | 695 | GRGGSMAETQNQQT | 880 |
| GSLVSQGAGQNQQT | 326 | GSGQPVLSISNQQT | 511 | GSGERSISVQNQQT | 696 | GSGHTNPTRQNQQT | 881 |
| GSLLQAHSGQNQQT | 327 | GSGQSHRSELNQQT | 512 | GSGLKPNVLQNQQT | 697 | GSGEAARYEQNQQT | 882 |
| GSGHIYVGIQNQQT | 328 | GSSVGSPIGQNQQT | 513 | GSGQVAYAQGNQQT | 698 | GSGQNERHLVLQQT | 883 |
| GHHTTVQSGQNQQT | 329 | GSGMPIRNVQNQQT | 514 | GSGQSSYGSGNQQT | 699 | GSGQNQQSKQQVLT | 884 |
| GSRQSKRNELNQQT | 330 | GSSTRVDSGQNQQT | 515 | GSGQNQAMTHGDQT | 700 | GSGQARAHRGNQQT | 885 |
| GSGQNQQHVSSPRT | 331 | GSGQNQQTAMRSTT | 516 | GSGQNQALVSMGQT | 701 | GSGQNQQPLDTSRT | 886 |
| GSSKELLWGQNQQT | 332 | GSGQNQQHSSSHLT | 517 | GSGQNPSFMRGQQT | 702 | GSGQNQQLANMVTT | 887 |
| GSLSTPSSGQNQQT | 333 | GSRNGHAVGQNQQT | 518 | GSGQNQQSHLRTNT | 703 | GSGQMKDLHRNQQT | 888 |
| GSIGYAGQGQNQQT | 334 | GLGAYQSSGQNQQT | 519 | GYTRLETSGQNQQT | 704 | GSGQNQHLSSFVQT | 889 |
| GSGQNQRVSNSQQT | 335 | GPGLSGHSGQNQQT | 520 | GSGQSYDMRGNQQT | 705 | GSGQNQQPSSRVTT | 890 |
| GSGYASHVQQNQQT | 336 | GSTGIVSSGQNQQT | 521 | GSRTTQDIGQNQQT | 706 | GSGQNQQLAITLGT | 891 |
| GSGEYSRSGQNQQT | 337 | GSRTTQVIGQNQQT | 522 | GSGHPYKAAQNQQT | 707 | GSGQNQQTVGNPAT | 892 |
| GSVSTHSSGQNQQT | 338 | GSGLLHRAQQNQQT | 523 | GRLSNAHGGQNQQT | 708 | GSGQNQGRAHPMQT | 893 |
| GSGQNQHSLGNYQT | 339 | GSGQNAQQAAAQQT | 524 | GSGQNQRAVLNDQT | 709 | GSGQLIASVVNQQT | 894 |
| GSGGLDTRGQNQQT | 340 | GSGQNQQSALRTQT | 525 | GGSHTYGGGQNQQT | 710 | GSSVRSLVGQNQQT | 895 |
| GNILHATSGQNQQT | 341 | GSGFLSDTRQNQQT | 526 | GSSVNSMIGQNQQT | 711 | GGAGSAHSGQNQQT | 896 |
| GSGQSYTMTQNQQT | 342 | GSGLLYHDQQNQQT | 527 | GNSSMMGSGQNQQT | 712 | GSDQNQQTMSSTRT | 897 |
| GSGQNQHSAPNSQT | 343 | GSGQNQHYSLHKQT | 528 | GNRDRPSSGQNQQT | 713 | GSGQNQQMAGAFRT | 898 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| GSGQNQQTMDHNRT | 344 | GSGHSPLPQQNQQT | 529 | GSGNMHASRQNQQT | 714 | GSLGNLQRGQNQQT | 899 |
| GSNGGVGTGQNQQT | 345 | GNGHSMRPNQNQQT | 530 | GFIFPKVSGQNQQT | 715 | GSGPSISHGQNQQT | 900 |
| GAGSIIPSGQNQQT | 346 | GSGLKWSTLQNQQT | 531 | GSGQNQQLKNSTST | 716 | GSGQNQQSSFNVQT | 901 |
| GSGQTHGGQHNQQT | 347 | GSGQMGRQAVNQQT | 532 | GSGQNQQSQYMPRT | 717 | GSGQNQQTGQATHN | 902 |
| GSNLSFQSGQNQQT | 348 | GSGQNQQTSGVLTL | 533 | GSGQRMADIGNQQT | 718 | VSGSPHSKAQNQQT | 903 |
| GATLQVHSGQNQQT | 349 | GSGQNQQALHNPHT | 534 | GSGQNQSHYPSQQT | 719 | CSGSPHSKAQNQQT | 904 |
| GSGFNQRSEQNQQT | 350 | GSGQNQQVIPNSKT | 535 | GSDGKMHRGQNQQT | 720 | GSGSPHRKAQNQQT | 905 |
| GSGSLRDFDQNQQT | 351 | GSPLQDRVGQNQQT | 536 | GSGSVGFIGQNQQT | 721 | GRGSPHSKAQNQQT | 906 |
| GSGDSITGKQNQQT | 352 | GSGQNQYSSTNPQT | 537 | GLHGMTLSGQNQQT | 722 | GSGSPHSKAQNKQT | 907 |
| GSGQDRNIVQNQQT | 353 | GAMTVTISGQNQQT | 538 | GSDQSKRGDSNQQT | 723 | GSGSPHSKAQTQQT | 908 |
| GSGLSHSHQQNQQT | 354 | GSGQNQQLQTLIRT | 539 | GSLFLATGGQNQQT | 724 | GSGSTHASRQNQQT | 909 |
| GSGQNQQTGMSSVK | 355 | GSGLRQTSQQNQQT | 540 | GSGQNQQPSAFSKT | 725 | GSGSPHKYGQNQQT | 910 |
| GSVTHGISGQNQQT | 356 | GSGQNQQTGLRQQT | 541 | GSGQLPQSGLNQQT | 726 | GSGSPHKFGQNQQT | 911 |
| GVVAHQPSGQNQQT | 357 | GSGQTRQMKDNQQT | 542 | GSGSKQNALQNQQT | 727 | VSGSPHKFGQNQQT | 912 |
| GSGPILGQLQNQQT | 358 | GSGQNHGLQSGQQT | 543 | GSGQRRELSQNQQT | 728 | GSGSPHSKAQNHQT | 913 |
| GSGHVPNSGLNQQT | 359 | GSGQSHRQPENQQT | 544 | GSGQREPKASNQQT | 729 | GSGSPHSKAQHQQT | 914 |
| GDAGVRSSGQNQQT | 360 | GSGQDRHIVQNQQT | 545 | GSGQNQQHPSTQQT | 730 | GSGSPHKTYQNQQT | 915 |
| GSGSQLMSLQNQQT | 361 | GSGQNQQLPHSNLT | 546 | GSQSTLGLGQNQQT | 731 | VSGSPHASRQNQQT | 916 |
| GSGLDYSQRQNQQT | 362 | GSGQLSVPYDNQQT | 547 | GSGQNQQMPGLSST | 732 | GSGSPHKFGKNQQT | 917 |
| GSGQSSGRLINKQT | 363 | GSGRNPQTQPLQQT | 548 | GSGQNQQTVGGKNL | 733 | GSGSPHASRQNQHT | 918 |
| GSSVSPSSGQNQQT | 364 | GSGQPYSTGLNQQT | 549 | GSSREFHSGQNQQT | 734 | GSHSPHKSGQNQQT | 919 |
| GSGQVVGLSGNQQT | 365 | GSGQNQQTHGGLRD | 550 | GSGQNQQTVPSNLV | 735 | GSGQNQQRRMSPST | 920 |
| GSNMGVPLGQNQQT | 366 | GAYGMVSSGQNQQT | 551 | GSGQNAYSSQAQQT | 736 | GSGSPHSKPQNQQT | 921 |
| GSFYPSSTGQNQQT | 367 | GSGIQSSYSQNQQT | 552 | GSGQNKDHSTRRQT | 737 | GSGSPHKFGQKQQT | 922 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| GSGQNQQTRLTDLT | 368 | GPRLSDQSGQNQQT | 553 | GQLGSVGSGQDQQT | 738 | VSGSPHGARQNQQT | 923 |
| GPTNGRSSGQNQQT | 369 | GSGQNQQTHPSPCT | 554 | GSGQHAAPGHNQQT | 739 | GSGSPHSKAQKQQT | 924 |
| GSGLLHGKLQNQQT | 370 | GSGQSFQMHTNQQT | 555 | GSGQNQQTSQSPPT | 740 | GSHSPHKRGQNQQT | 925 |
| GANMGHVSGQNQQT | 371 | GSGQNQQTGNPKHT | 556 | GSGNYRDHEQNQQT | 741 | GSGQNRQRLKGLET | 926 |
| GSGQNQQSGRGDLT | 372 | GFSSAVHSGQNQQT | 557 | GSGQHSNQHVNQQT | 742 | GSGSPHKLGQNQQT | 927 |
| GSHGHYASGQKQQT | 373 | GSGQNQQTSMSNAT | 558 | GSGQTARNGINQQT | 743 | GSGSPHKTSKNQQT | 928 |
| GSGDLRISPQNQQT | 374 | GSGQDMKQHHNQQT | 559 | GSGQNQQHYGSQGT | 744 | GSGSPHKIGQNQQT | 929 |
| GSGMPVILGQNQQT | 375 | GLRLSTPSGQNQQT | 560 | GSGSPQASRQNQQT | 745 | GSGQDSPHVRNQQT | 930 |
| GRGVITSSGQNHQT | 376 | GSGQNQQTSVYMNT | 561 | GSGFSHSMGKNQQT | 746 | GSGSPHKTSQNQQT | 931 |
| GSGHSVSGPQNQQT | 377 | GSGQNQYSQSSMQT | 562 | GSGQSHSLETNQQT | 747 | GSGSPHASRKNQQT | 932 |
| GSRNGHTVGRNQQT | 378 | GSGQNQQSMADHTT | 563 | GTEQTRQSGQNQQT | 748 | GSHSPHKSGQKQQT | 933 |
| GAGVHMVSGQNQQT | 379 | GWERSFVSGQNQQT | 564 | GSGRHLASVQNQQT | 749 | GSGSPHKTSQKQQT | 934 |
| GSGQNHRPSVLQQT | 380 | GLLAGKSSGQNQQT | 565 | GLGSKNHSGQNQQT | 750 | GSGSPHVRGQNKQT | 935 |
| GSGSPRDSIQNQQT | 381 | GKSFVPQSGQNQQT | 566 | GSGQNQQTSHFPSA | 751 | GSGSPHKTTQNQQT | 936 |
| GSGQGIHSSVNQQT | 382 | GSGQMQSAGSNQQT | 567 | GSGQLSGTPQNQQT | 752 | GSGPVRALRQNQQT | 937 |
| GSGQQLSITPNQQT | 383 | GSDQNQRLTSSMQT | 568 | GSGQNQQAPHKKET | 753 | GSGSPHVRGQKQQT | 938 |
| GGYHSQTSGQNQQT | 384 | GESRAVLSGQNQQT | 569 | GSGQNQQTLRGSLE | 754 | CSGSPHKTSQNQQT | 939 |
| CSHSPHKSGQNQQT | 940 | DAGSPHKAQNQQ | 1909 | GSGSPHASRQNQQ | 2019 | GNDSPHKSVQNQQ | 2129 |
| GHDSPHKSGQNQQ | 1800 | GSGSPHSKGQNQQ | 1910 | GSGSPHASRQNKQ | 2020 | GHDSPHKSAQNYQ | 2130 |
| GSGSPHSKAQNQQ | 1801 | DGGSPHSKAQNQQ | 1911 | GSGSPHVKIQNQQ | 2021 | GSASPHSKALNQQ | 2131 |
| GSGSPHSKAQNRH | 1802 | ASGSPHSKAHNQQ | 1912 | GSGSPHSKAKNQQ | 2022 | GHESPHKSAQNRQ | 2132 |
| GSGSPHSKVQNQQ | 1803 | GSGSPHSKAQNTY | 1913 | GSGSPHKKNQNQQ | 2023 | GQDSPHKIGQNQQ | 2133 |
| MSGSPHSKAQNQQ | 1804 | GSGSPHSKSQNQH | 1914 | GSGSPHVRMQNQQ | 2024 | GHDSPHKSGQNHL | 2134 |
| GRGSPHSKAQNQQ | 1805 | GGGSPHSKAQDKQ | 1915 | GSGSPHASRQKQQ | 2025 | GHDSPHKSGQYQH | 2135 |

TABLE 1-continued

Exemplary Peptide Sequences

| Peptide Sequence | SEQ ID NO: | Peptide Sequence | SEQ ID NO: | Peptide Sequence | SEQ ID NO: |
|---|---|---|---|---|---|
| RNGSPHSKAQNQQ | 1806 | GSGSPHSKAQNHL | 1916 | GHSSPHRSGQNQQ | 2026 | GNDSPHKSVQNHQ | 2136 |
| GSGSPHSKARDQQ | 1807 | GSGSPHSKAQIGM | 1917 | GSGSPHTRGQNQQ | 2027 | GHDSPHKSGQNQW | 2137 |
| GSGSPHSKAPNLQ | 1808 | GSGSPHSKALNKQ | 1918 | CSGSPHSKAQNQQ | 2028 | GHDSPHKSVQNQH | 2138 |
| TSGSPHSKAQNQQ | 1809 | GGGSPHSKAQNPQ | 1919 | GSGSPHRKAQNQQ | 2029 | GHDSPHKSGQNQH | 2139 |
| GSGSPHSKAHVRQ | 1810 | GTGSPHSKAPNQL | 1920 | GSGSPHSKAQNKQ | 2030 | GHDSPHKSGQTRQ | 2140 |
| GSGSPHSKAPNQH | 1811 | GSGSPHSKAQLQQ | 1921 | GSGSPHSKAQTQQ | 2031 | GHDSPHKSGQNLH | 2141 |
| ISGSPHSKAQNQQ | 1812 | GGGSPHSKAQYQQ | 1922 | CSGSPHKTSQNQQ | 2032 | GHDSPHKSAQNQE | 2142 |
| GPGSPHSKAHNQQ | 1813 | GGGSPHSKAQHQQ | 1923 | CSHSPHKSGQNQQ | 2033 | GHDSPHKSGQHLQ | 2143 |
| GSGSPHSKTQSQQ | 1814 | GSGSPHSKAQRMS | 1924 | GQSSPHRSGQNQQ | 2034 | GHDSPHKSRLNQP | 2144 |
| ESGSPHSKAQNQQ | 1815 | GSGSPHSKAQGIL | 1925 | GRGSPHASRQNQQ | 2035 | GQDSPHKSGQNQD | 2145 |
| GSGSPHSKAQPAK | 1816 | GSGSPHSKAQDRQ | 1926 | GSGSPHASRKNQQ | 2036 | GHDSPHKSGRNQQ | 2146 |
| SSGSPHSKAQNQQ | 1817 | GSGSPHSKARDWQ | 1927 | GSGSPHASRQNQH | 2037 | GHDSPHKSGQNLL | 2147 |
| GNGSPHSKAQNQQ | 1818 | GSGSPHSKAQNTH | 1928 | GSGSPHKFGKNQQ | 2038 | GHDSPHKSGQLVI | 2148 |
| GSGSPHSKSQTQQ | 1819 | GSGSPHSKAQERS | 1929 | GSGSPHKFGQKQQ | 2039 | GHDSPHKSRQSQQ | 2149 |
| ASGSPHSKAQNQQ | 1820 | GSGSPHSKAQNYQ | 1930 | GSGSPHKFGQNQQ | 2040 | GHDSPHKSGRTQE | 2150 |
| GSGSPHSKAQNLA | 1821 | GSGSPHSKAQRTC | 1931 | GSGSPHKIGQNQQ | 2041 | GHDSPHKSVQTHQ | 2151 |
| GSGSPHSKSQNQL | 1822 | GSGSPHSKAQIGH | 1932 | GSGSPHKLGQNQQ | 2042 | GHDSPHKSGQNQP | 2152 |
| NSGSPHSKAQNQQ | 1823 | GSGSPHSKAQGAI | 1933 | GSGSPHKTSKNQQ | 2043 | GHDSPHKSGQTQQ | 2153 |
| GSGSPHSKAQGQQ | 1824 | GSGSPHSKAQVPP | 1934 | GSGSPHKTSQKQQ | 2044 | GPDSPHKIGQNQQ | 2154 |
| VSGSPHSKAQNQQ | 1825 | GSGSPHSKAQVQQ | 1935 | GSGSPHKTSQNQQ | 2045 | GHDSPHKSVQNQQ | 2155 |
| GSGSPHSKALNRQ | 1826 | GSGSPHSKALMRQ | 1936 | GSGSPHKTTQNQQ | 2046 | GHDSPHKSRQDQH | 2156 |
| LSGSPHSKAQNQQ | 1827 | GSGSPHSKAQYSV | 1937 | GSGSPHKTYQNQQ | 2047 | GPDSPHKSGQKQQ | 2157 |
| GSGSPHSKAHNQQ | 1828 | GSGSPHSKVPNLQ | 1938 | GSGSPHKYGQNQQ | 2048 | GHDSPHKSRQSQH | 2158 |
| GSGSPHSKTQNQQ | 1829 | GSGSPHSKAQAIT | 1939 | GSGSPHKAQHQQ | 2049 | GHDSPHKSVQNQL | 2159 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| GGGSPHSKAQTQQ | 1830 | GSGSPHSKAQKTL | 1940 | GSGSPHSKDQNQQ | 2050 | GYDSPHKSGQYQH | 2160 |
| GSGSPHSKAQNPP | 1831 | GSGSPHSKAQNQW | 1941 | GSGSPHSKPQNQQ | 2051 | GHDSPHKSRQNQQ | 2161 |
| GSGSPHSKAQNLQ | 1832 | GSGSPHSKAQLHH | 1942 | GSGSPHVRGQKQQ | 2052 | GHDSPHKSWVRQQ | 2162 |
| GGGSPHSKAQNQQ | 1833 | GSGSPHSKAQNI | 1943 | GSGSPHVRGQNKQ | 2053 | GHESPHKSGQNQH | 2163 |
| GSGSPHSKAQYQQ | 1834 | MEGSPHSKAQNQQ | 1944 | GSHSPHKRGQNQQ | 2054 | GHDSPHKIGHNQQ | 2164 |
| GGGSPHSKAQNKQ | 1835 | GSGSPHSKAQGHH | 1945 | GSHSPHKSGQKQQ | 2055 | GHDSPHKSNAWQQ | 2165 |
| GSGSPHSKAQDQE | 1836 | GSGSPHSKAQSKV | 1946 | GSHSPHKSGQNQQ | 2056 | GHDSPHKSGQSVP | 2166 |
| KSGSPHSKAQNQQ | 1837 | GSGSPHSKAQLPS | 1947 | VSGSPHASRQNQQ | 2057 | GHESPHKSGQNIQ | 2167 |
| GGGSPHSKAQNQL | 1838 | GSGSPHSKAIGKQ | 1948 | VSGSPHGARQNQQ | 2058 | GHDSPHSVQNHL | 2168 |
| GSGSPHSKAQNHQ | 1839 | GGGSPHSKSQNQQ | 1949 | VSGSPHKFGQNQQ | 2059 | GHDSPHKIGLDQQ | 2169 |
| GSGSPHSKAQDQQ | 1840 | GSGSPHSKAQAIH | 1950 | GSGSPHSKAQYYV | 2060 | ASGSPHSKAQHQQ | 2170 |
| GGGSPHSKSQNQL | 1841 | GSGSPHSKAQHGL | 1951 | GSGSPHSKLRRQQ | 2061 | GHDSPHKRGPDQQ | 2171 |
| GNGSPHSKAQNKQ | 1842 | GSGSPHSKAQFMC | 1952 | GSGSPHSKAGCGQ | 2062 | GMGSPHSKTQNQQ | 2172 |
| GSGSPHSKGHWQQ | 1843 | VSGSPHSKAQGQQ | 1953 | GSGSPHSRAQNQQ | 2063 | GHDSPHKSGESQQ | 2173 |
| GSGSPHSKAPNQQ | 1844 | GGGSPHSKAQNQM | 1954 | GSGSPHSKRLRQQ | 2064 | GHDSPHKHGQNHQ | 2174 |
| GSGSPHSKAQNQL | 1845 | GSGSPHSKAQHLQ | 1955 | GSGSPHSLRRNQQ | 2065 | GTGSPHSKAQNQL | 2175 |
| GSGSPHSKRPEQQ | 1846 | ENGSPHSKAQNQQ | 1956 | GSGSPHSRGRNQQ | 2066 | GHDSPHKSVQNKQ | 2176 |
| GSGSPHSKAQRTM | 1847 | GSGSPHSKTQNHQ | 1957 | GSGSPHSSRRNQQ | 2067 | GQVSPHKSGQNQQ | 2177 |
| GNGSPHSKAQNQH | 1848 | GSGSPHSKAQPAR | 1958 | GSGSPHSKAFRLQ | 2068 | GHDSPHKSGQRQL | 2178 |
| HSGSPHSKAQNQQ | 1849 | GSGSPHSKAQSLQ | 1959 | GSCSPHRKAQNQQ | 2069 | GHDSPHKIGQNQL | 2179 |
| GGGSPHSKALNQQ | 1850 | GSGSPHSKSQSQL | 1960 | GSGSPHFLRQNQQ | 2070 | GHDSPHKSGQIIV | 2180 |
| GSGSPHSKALHQH | 1851 | GSASPHSKAHSQQ | 1961 | GSGSPHSLRFNQQ | 2071 | GYDSPHKSGQKQS | 2181 |
| GTGSPHSKAQNHQ | 1852 | GSGSPHSKAQMPS | 1962 | GSGSPHSKWLLQQ | 2072 | GNGSPHSKAQNQE | 2182 |
| GSGSPHSKAQHRI | 1853 | GSGSPHSKAQGSL | 1963 | GSGSPHSKRRLQQ | 2073 | GDDSPHKSVQNQQ | 2183 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| GSGSPHSKAQYIH | 1854 | GSGSPHSKSQNQQ | 1964 | GSGSPHSKAQRKL | 2074 | GHDSPHKSVQSHQ | 2184 |
| GGGSPHSKAHNQQ | 1855 | GNGSPHSKSQNQQ | 1965 | GSGSPHSKALRRQ | 2075 | GHDSPHKSGQFVV | 2185 |
| GSGSPHSKAQKFE | 1856 | GSGSPHSKAQVPA | 1966 | GSGSPHSKAQRLR | 2076 | GHDSPHKSRQNLQ | 2186 |
| ESGSPHSKAQNHQ | 1857 | GNGSPHSKAQNLQ | 1967 | GSGSPHSKAQRRL | 2077 | GHNSPHKSGQNQE | 2187 |
| GSGSPHSKAQFPS | 1858 | GSGSPHSKAQDKQ | 1968 | GSGSPHSKARRQQ | 2078 | GHDSPHKSGQSQP | 2188 |
| PSGSPHSKAQNQQ | 1859 | GSGSPHSKAHYQQ | 1969 | GSGSPHSKARRLQ | 2079 | GHESPHKSGQNEQ | 2189 |
| GNGSPHSKAQNPL | 1860 | GSGSPHSKAQVPS | 1970 | GSGSPHSKSRRQQ | 2080 | GHDSPHKSGQNQL | 2190 |
| GGGSPHSKAQSQQ | 1861 | GGGSPHSKAQNHQ | 1971 | GLLSPHWKAQNQQ | 2081 | GHDSPHKSAQNLL | 2191 |
| GSGSPHSKAQAIK | 1862 | GSGSPHSKARGEQ | 1972 | GSGSPHSKARLRQ | 2082 | ASGSPHSKAINQQ | 2192 |
| GSGSPHSKGQNRQ | 1863 | GGGSPHSKAQYQH | 1973 | GSGSPHSKASKRQ | 2083 | GNGSPHKRGQNQQ | 2193 |
| GSGSPHSKAQSQQ | 1864 | GSGSPHSKAPGQQ | 1974 | GSGSPHVRRQNQQ | 2084 | GHDSPHKSGQSLQ | 2194 |
| GSVSPHGKAQNQL | 1865 | KNGSPHSKAQNQQ | 1975 | GSGSPHSKAQLYR | 2085 | GHDSPHKSAQNHQ | 2195 |
| ASGSPHSKAQNQL | 1866 | GSGSPHSKRLEQQ | 1976 | GSGSPHSKAQLTV | 2086 | GHDSPHKSGRNRQ | 2196 |
| RSGSPHSKAQNQQ | 1867 | GSGSPHSKAQNQS | 1977 | GHDSPHKRGQHRQ | 2087 | GHDSPHKYGQNEQ | 2197 |
| GSGSPHSKAQYQH | 1868 | GSGSPHSKAQKVI | 1978 | GHDSPHKSGQKQQ | 2088 | GNGSPHSKAPNLQ | 2198 |
| GSGSPHTKAQNPQ | 1869 | GSGSPHSKAQNND | 1979 | GHDSPHKSGLTQQ | 2089 | GHDSPHKSQQNQQ | 2199 |
| GSGSPHSKGQNPP | 1870 | GSGSPHSKAQSVH | 1980 | GDDSPHKSGRNQQ | 2090 | GHDSPHKSVQSKQ | 2200 |
| GSGSPHSKAQHQL | 1871 | GSGSPHSKAQPLG | 1981 | GHDSPHKSGLNQQ | 2091 | GNDSPHIGHNQQ | 2201 |
| GSGSPHSKAQSPP | 1872 | KEGSPHSKAQNQQ | 1982 | GHESPHKAQNHQ | 2092 | GGGSPHSKAQDQQ | 2202 |
| GSGSPHSKAQAKL | 1873 | GSGSPHSKAHNQE | 1983 | GHDSPHKSAQNQW | 2093 | GQDSPHKSGQNPL | 2203 |
| GSGSPHSKTKSQQ | 1874 | GSGSPHSKAQIQQ | 1984 | GHDSPHKSGQNTH | 2094 | ASGSPHSKAQNHQ | 2204 |
| GSGSPHSKAQDRP | 1875 | GSGSPHSKAQVRN | 1985 | GHDSPHKSGRRRQ | 2095 | GHDSPHKSGRDQK | 2205 |
| GIGSPHSKAQNLG | 1876 | GSGSPHSKAPSNQ | 1986 | GHDSPHKSAQNQQ | 2096 | GHDSPHKSVHNQQ | 2206 |
| GSGSPHSKAQAFH | 1877 | GSGSPHSKAQVGH | 1987 | GHDSPHKSGQYQQ | 2097 | GHDSPHKSGQWKR | 2207 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| GSGSPHSKAQKQQ | 1878 | GSGSPHSKAQRDI | 1988 | GNYSPHKIGQNQQ | 2098 | GSGSPHSKAENRQ | 2208 |
| GSGSPHSKAQNAQ | 1879 | GSGSPHSKAQMPN | 1989 | GHDSPHKSRQNDQ | 1990 | GHDSPHKSGQSQQ | 2209 |
| WSGSPHSKAQNQQ | 1880 | AIGSPHSKAQNQQ | 1990 | GHDSPHKSGQIRQ | 2100 | GHDSPHKSRQAQQ | 2210 |
| GSGSPHSKAHNQL | 1881 | GSGSPHSKARGLQ | 1991 | GHDSPHKIGQNQH | 2101 | GHDSPHKSVQNHQ | 2211 |
| GNGSPHSKAQNHQ | 1882 | GSGSPHSKLQKQQ | 1992 | GYDSPHKSGQKQQ | 2102 | GHDSPHKSKQNQQ | 2212 |
| GGGSPHSKAQNLQ | 1883 | GSGSPHSKAPSLQ | 1993 | GHDSPHKSGQSVQ | 2103 | GHDSPHKSAQNQL | 2213 |
| GSGSPHSKAQKLN | 1884 | GSGSPHSKAQRDQ | 1994 | GHESPHKSGRSQQ | 2104 | GHDSPHKSGQTQP | 2214 |
| GGGSPHSKSQNQH | 1885 | GSGSPHSKNRDQQ | 1995 | GHDSPHKSGQNKL | 2105 | GHDSPHKLWINQQ | 2215 |
| GSGSPHSKSQNVQ | 1886 | GSGSPHSKAQAKG | 1996 | GHDSPHKTGQNQQ | 2106 | GPDSPHKSGQNQQ | 2216 |
| GSGSPHSKAQAQQ | 1887 | GSGSPHSKAQSAH | 1997 | GRGSPHKRGQNQQ | 2107 | GHDSPHKSVQKQL | 2217 |
| DSGSPHSKAQNQQ | 1888 | GNGSPHSKSQNQH | 1998 | GSGSPHTKAQNPP | 2108 | GHPSPHWKGQNQQ | 2218 |
| ASGSPHSKAPNQQ | 1889 | GSGSPHSKSQNHQ | 1999 | GQDSPHKSGQHQQ | 2109 | GHDSPHKSGRNQL | 2219 |
| GSGSPHSKAQTPP | 1890 | RSGSPHSKAQDQQ | 2000 | GHDSPHKSGQIQH | 2110 | GSGSPHSKVQDQQ | 2220 |
| IDGSPHSKAQNQQ | 1891 | GSGSPHSKAQSTM | 2001 | GHDSPHKSGPRQQ | 2111 | GHDSPHKMGRNQQ | 2221 |
| GSGSPHNKAQNHQ | 1892 | GSGSPHSKAQREM | 2002 | GHDSPHKSGHTQQ | 2112 | GHDSPHKSGISIQ | 2222 |
| GSGSPHSKAQPPA | 1893 | GGGSPHSKSQNRQ | 2003 | GHDSPHKSGQRQH | 2113 | GHDSPHKSVQNLQ | 2223 |
| GSGSPHSKAQERP | 1894 | GSGSPHSKAQYRA | 2004 | GSGSPHTKAQNQQ | 2114 | GHDSPHKMAHNQQ | 2224 |
| GSGSPHSKAQDLQ | 1895 | GGGSPHSKAQRQQ | 2005 | GHDSPHKSAQSQQ | 2115 | GHDSPHKHGQNQQ | 2225 |
| GGGSPHSKAQNPP | 1896 | GSGSPHSKNQWQQ | 2006 | GHESPHKSGQNQQ | 2116 | GHDSPHKSVQSQQ | 2226 |
| GSGSPHSKAQAMH | 1897 | GSGSPHSKAQRMN | 2007 | GHDSPHKSLQNQQ | 2117 | GHDSPHKSGQTVC | 2227 |
| GSGSPHSKALNQQ | 1898 | GSGSPHAKAQNHQ | 2008 | GHGSPHSKAQNPQ | 2118 | GQDSPHKSGQYQQ | 2228 |
| GSGSPHSKAQHPS | 1899 | GSGSPHSKAGDSQ | 2009 | GHDSPHKSGRNQE | 2119 | GHDSPHKSGQQIM | 2229 |
| GLGSPHSKSQNQQ | 1900 | GSGSPHSKLKSQQ | 2010 | GHDSPHKSGQTQL | 2120 | GHDSPHKSRQNEQ | 2230 |
| GTGSPHSKAQNQQ | 1901 | GSGSPHSKAQKIS | 2011 | GHDSPHKSEKNQQ | 2121 | GHDSPHKSGLNHQ | 2231 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| GSGSPHSKAPGLQ | 1902 | GSGSPHSKAPSMQ | 2012 | GRDSPHKSGQDQQ | 2122 | GYDSPHKSGQNQQ | 2232 |
| GSGSPHSKAQGIR | 1903 | GSGSPHSKASPRQ | 2013 | GHDSPHKTGHNQQ | 2123 | GHDSPHKSGQNLQ | 2233 |
| GSGSPHSKAQAPA | 1904 | GSGSPHSKRMEQQ | 2014 | GYDSPHKSGQTQQ | 2124 | GHDSPHKSRQDQQ | 2234 |
| GSGSPHSKSQSQQ | 1905 | GSGSPHSKAQYQN | 2015 | GHESPHKSGQTQQ | 2125 | GDDSPHKSGQKQL | 2235 |
| GSGSPHSKAQIPP | 1906 | GSGSPHARMQNQQ | 2016 | GHDSPHKSGQSKQ | 2126 | GSGSPHSKAQNQA | 2236 |
| GSGSPHSKAQTQL | 1907 | GSGSPHVKSQNQQ | 2017 | GHDSPHKTGQNQP | 2127 | GDDSPHKSGHNQQ | 2237 |
| GSGSPHSKAQAPS | 1908 | GQDSPHKSGQNQQ | 2018 | GHDSPHKSGQSPQ | 2128 | GHDSPHKSGQMIH | 2238 |
| GHDSPHKSGRNHQ | 2239 | GHDSPHKSVQNRQ | 2240 | GHDSPHKSGQKMN | 2241 | TINGHDSPHKSRLNQP | 2728 |
| TINGSGSPHSKAQNQQ | 2242 | TDRGSGSPHSKAQNQQ | 2404 | TINGSGSPHSKAQSTM | 2566 | TVDGHDSPHKSGQKQQ | 2729 |
| TINGHDSPHKSGQNQQ | 2243 | TINGSGSPHSKAQIPP | 2405 | TVNASGSPHSKAQNQL | 2567 | TINGQDSPHKSGQNQD | 2730 |
| TIIGSGSPHSKAQNRH | 2244 | TVKGSGSPHSKAQDQQ | 2406 | TINGSGSPHSKAQREM | 2568 | TIEGHDSPHKSGRNQQ | 2731 |
| TFPGSGSPHSKVQNQQ | 2245 | NADGSGSPHSKAQNQQ | 2407 | TVHGSGSPHSKAQSQQ | 2569 | TTNGHDSPHKSGQNLL | 2732 |
| TEKMSGSPHSKAQNQQ | 2246 | TDKVSGSPHSKAQNQQ | 2408 | TINGGGSPHSKSQNRQ | 2570 | TINGHDSPHKSGQLVI | 2733 |
| EINGRGSPHSKAQNQQ | 2247 | TITGSGSPHSKAQTQL | 2409 | TINGSGSPHSKAQYRA | 2571 | TVNGHDSPHKSRQSQQ | 2734 |
| TVNRNGSPHSKAQNQQ | 2248 | TINGSGSPHSKAQAPS | 2410 | TINGGGSPHSKAQRQQ | 2572 | TINGHDSPHKSGRTQE | 2735 |
| TVNGSGSPHSKARDQQ | 2249 | NCVGSGSPHSKAQNQQ | 2411 | TEPMSGSPHSKAQNQQ | 2573 | TINGHDSPHKSVQTHQ | 2736 |
| TENGSGSPHSKAPNLQ | 2250 | TIRDAGSPHSKAQNQQ | 2412 | TINGSGSPHSKNQWQQ | 2574 | TSNGHDSPHKSGQNQP | 2737 |
| TEKTSGSPHSKAQNQQ | 2251 | TVKDSGSPHSKAQNQQ | 2413 | ETAGSGSPHSKAQNQQ | 2575 | VINGHDSPHKSGQTQQ | 2738 |
| TINGSGSPHSKAHVRQ | 2252 | NALGSGSPHSKAQNQQ | 2414 | TINGSGSPHSKAQRMN | 2576 | TINGPDSPHKIGQNQQ | 2739 |
| TVNGSGSPHSKAPNQH | 2253 | VINGSGSPHSKGQNQQ | 2415 | NNLGSGSPHSKAQNQQ | 2577 | AVNGHDSPHKSVQNQQ | 2740 |
| TEKISGSPHSKAQNQQ | 2254 | TVNGGGSPHSKAQNQQ | 2416 | TINGSGSPHAKAQNHQ | 2578 | TINGHDSPHKSRQDQH | 2741 |
| TINGPGSPHSKAHNQQ | 2255 | TIQDGGSPHSKAQNQQ | 2417 | TIIKNGSPHSKAQNQQ | 2579 | AINGPDSPHKSGQKQQ | 2742 |
| TVNGSGSPHSKTQSQQ | 2256 | TISGGGSPHSKAQNQQ | 2418 | TINGSGSPHSKAGDSQ | 2580 | TINGHDSPHKSRQSQH | 2743 |
| SINESGSPHSKAQNQQ | 2257 | TSNASGSPHSKAHNQQ | 2419 | TINGSGSPHSKLKSQQ | 2581 | TIYGHDSPHKSVQNQL | 2744 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| TERTSGSPHSKAQNQQ | 2258 | TINGSGSPHSKAQNTY | 2420 | TINGSGSPHSKAQKIS | 2582 | TVNGHDSPHKSGQNLL | 2745 |
| TINGSGSPHSKAQPAK | 2259 | TINGSGSPHSKSQNQH | 2421 | TEYNSGSPHSKAQNQQ | 2422 | TENKSGSPHSKAQNQQ | 2746 |
| TEKSSGSPHSKAQNQQ | 2260 | TINGGGSPHSKAQDKQ | 2422 | TINGSGSPHSKAPSMQ | 2584 | TTNGQDSPHKSGQNQQ | 2747 |
| TSYGNGSPHSKAQNQQ | 2261 | TEFVSGSPHSKAQNQQ | 2423 | AINGSGSPHSKAQNQQ | 2585 | TDKGSGSPHSKAQNQQ | 2748 |
| TEKGSGSPHSKAQNQQ | 2262 | TVNGSGSPHSKAQNHL | 2424 | TINGSGSPHSKASPRQ | 2586 | TIDGHDSPHKSGRNQQ | 2749 |
| TINGSGSPHSKSQTQQ | 2263 | TREISGSPHSKAQNQQ | 2425 | TINGSGSPHSKRMEQQ | 2587 | TINGYDSPHKSGQYQH | 2750 |
| TERISGSPHSKAQNQQ | 2264 | TINGSGSPHSKAQIGM | 2426 | TINGSGSPHSKAQYQN | 2588 | TDNGHDSPHKSRQNQQ | 2751 |
| TERASGSPHSKAQNQQ | 2265 | TIDGSGSPHSKALNKQ | 2427 | TINGSGSPHSKAQYYV | 2589 | TINGHDSPHKSWVRQQ | 2752 |
| ELHGSGSPHSKAQNQQ | 2266 | TIIGGSPHSKAQNPQ | 2428 | TINGSGSPHSKLRRQQ | 2590 | TINGHESPHKSGQNQH | 2753 |
| AINGSGSPHSKAQNLA | 2267 | QGEGSGSPHSKAQNQQ | 2429 | TINGSGSPHSKAGCGQ | 2591 | TVNGHDSPHKIGHNQQ | 2754 |
| TVNGSGSPHSKSQNQL | 2268 | TINGTGSPHSKAPNQL | 2430 | SMNGSGSPHSRAQNQQ | 2592 | TCNGHDSPHKSGRNQQ | 2755 |
| TERNSGSPHSKAQNQQ | 2269 | TVNGSGSPHSKAQLQQ | 2431 | TINGSGSPHSKRLRQQ | 2593 | TINGNGSPHSKAQNHQ | 2756 |
| SVNGNGSPHSKAQNQQ | 2270 | TFNGGGSPHSKAQYQQ | 2432 | TINGSGSPHSLRRNQQ | 2594 | NVVGHDSPHKSGQNQQ | 2757 |
| TFNGSGSPHSKAQGQQ | 2271 | SINGSGSPHSKTQSQQ | 2433 | TINGSGSPHSRGRNQQ | 2595 | TINGHDSPHKSNAWQQ | 2758 |
| TERVSGSPHSKAQNQQ | 2272 | TVNGGGSPHSKAQHQQ | 2434 | TINGSGSPHSSRRNQQ | 2596 | TDAGHDSPHKSGQNQQ | 2759 |
| TINGSGSPHSKALNRQ | 2273 | SEKGSGSPHSKAQNQQ | 2435 | TINGSGSPHSKAFRLQ | 2597 | TEVGHDSPHKSGQNQQ | 2760 |
| TERLSGSPHSKAQNQQ | 2274 | NVNGSGSPHSKAQNQQ | 2436 | TINGSCSPHRKAQNQQ | 2598 | SELGHDSPHKSGQNQQ | 2761 |
| TDNGSGSPHSKAHNQQ | 2275 | GGEGSGSPHSKAQNQQ | 2437 | TINGSGSPHFLRQNQQ | 2599 | TINGHDSPHKSGQSVP | 2762 |
| TFHGSGSPHSKTQNQQ | 2276 | TINGSGSPHSKAQRMS | 2438 | TINGSGSPHSLRFNQQ | 2600 | TINGHESPHKSGQNIQ | 2763 |
| TINGGGSPHSKAQTQQ | 2277 | TINGSGSPHSKAQGIL | 2439 | TINGSGSPHSKWLLQQ | 2601 | TINGHDSPHKSVQNHL | 2764 |
| TSNGSGSPHSKAQNPP | 2278 | EFVGSGSPHSKAQNQQ | 2440 | TINGSGSPHSKRRLQQ | 2602 | TINGHDSPHKIGLDQQ | 2765 |
| TINGSGSPHSKAQNLQ | 2279 | TIIGSGSPHSKAQDRQ | 2441 | TINGSGSPHSKAQRKL | 2603 | TSNASGSPHSKAQHQQ | 2766 |
| TVHGNGSPHSKAQNQQ | 2280 | SDKGSGSPHSKAQNQQ | 2442 | TINGSGSPHSKALRRQ | 2604 | TINGHDSPHKRGPDQQ | 2767 |
| TINGGGSPHSKAQNQQ | 2281 | TEQVSGSPHSKAQNQQ | 2443 | TINGSGSPHSKAQRLR | 2605 | TINGMGSPHSKTQNQQ | 2768 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| TENMSGSPHSKAQNQQ | 2282 | TEHVSGSPHSKAQNQQ | 2444 | YLSGSGSPHSKAQNQQ | 2606 | TIKGHDSPHKSGESQQ | 2769 |
| TENVSGSPHSKAQNQQ | 2283 | TINGSGSPHSKARDWQ | 2445 | TINGSGSPHSKAQRRL | 2607 | TINGHDSPHKHGQNHQ | 2770 |
| TSSGSGSPHSKAQYQQ | 2284 | TENASGSPHSKAQNQQ | 2446 | TINGSGSPHSKARRQQ | 2608 | TVNGTGSPHSKAQNQL | 2771 |
| TIDGGGSPHSKAQNKQ | 2285 | EVQGSGSPHSKAQNQQ | 2447 | TINGSGSPHSKARRLQ | 2609 | TIIGHDSPHKSGQYQH | 2772 |
| TEKVSGSPHSKAQNQQ | 2286 | TINGSGSPHSKAQNTH | 2448 | TINGSGSPHSKSRRQQ | 2610 | TSNGHDSPHKSVQNKQ | 2773 |
| AINGSGSPHSKAQDQE | 2287 | TINGLLSPHWKAQNQQ | 2449 | TINGSGSPHSKAPNLQ | 2611 | IVNGQVSPHKSGQNQQ | 2774 |
| TCNKSGSPHSKAQNQQ | 2288 | TINGSGSPHSKAQERS | 2450 | TINGSGSPHSKARLRQ | 2612 | TVNGHDSPHKSGQRQL | 2775 |
| TINGGGSPHSKAQNQL | 2289 | TSNGSGSPHSKAQNYQ | 2451 | TINGSGSPHSKASKRQ | 2613 | TVNGHDSPHKIGQNQL | 2776 |
| NINGGGSPHSKAQNQQ | 2290 | TEYISGSPHSKAQNQQ | 2452 | TINGSGSPHVRRQNQQ | 2614 | TINGHDSPHKSGQIIV | 2777 |
| TEHLSGSPHSKAQNQQ | 2291 | TINGSGSPHSKAQRTC | 2453 | TINGSGSPHSKAQLYR | 2615 | IGNGHESPHKSGQNQQ | 2778 |
| AEMGSGSPHSKAQNQQ | 2292 | TINGSGSPHSKAQIGH | 2454 | GLSGSGSPHSKAQNQQ | 2616 | EVMGHDSPHKSGQNQQ | 2779 |
| ATNGSGSPHSKAQNHQ | 2293 | NCWGSGSPHSKAQNQQ | 2455 | TINGSGSPHSKAQLTV | 2617 | TINGYDSPHKSGQKQS | 2780 |
| AIKGSGSPHSKAQDQQ | 2294 | TINGSGSPHSKAQGAI | 2456 | TINGHDSPHKRGQHRQ | 2618 | TIHGNGSPHSKAQNQE | 2781 |
| TINGGGSPHSKSQNQL | 2295 | TDVNSGSPHSKAQNQQ | 2457 | MPEGHDSPHKSGQNQQ | 2619 | YQVGHDSPHKSGQNQQ | 2782 |
| TVNGNGSPHSKAQNKQ | 2296 | SDIGSGSPHSKAQNQQ | 2458 | MEGGHDSPHKSGQNQQ | 2620 | TIKGDDSPHKSVQNQQ | 2783 |
| TINGSGSPHSKGHWQQ | 2297 | TINGSGSPHSKAQVPP | 2459 | MEYGHDSPHKSGQNQQ | 2621 | TINGHDSPHKSVQSHQ | 2784 |
| TDKTSGSPHSKAQNQQ | 2298 | TINGSGSPHSKAQVQQ | 2460 | AEWGHDSPHKSGQNQQ | 2622 | TINGHDSPHKSGQFVV | 2785 |
| TFKGSGSPHSKAPNQQ | 2299 | TINGSGSPHSKALMRQ | 2461 | CEWGHDSPHKSGQNQQ | 2623 | TVNGHDSPHKSRQNLQ | 2786 |
| TVNGSGSPHSKAQNQL | 2300 | TINGSGSPHSKAQYSV | 2462 | ANNGQDSPHKSGQNQQ | 2624 | ATNGHNSPHKSGQNQE | 2787 |
| TINGSGSPHSKRPEQQ | 2301 | NSIGSGSPHSKAQNQQ | 2463 | IPEGHDSPHKSGQNQQ | 2625 | AINGHDSPHKSAQNQQ | 2788 |
| TINGSGSPHSKAQRTM | 2302 | TINGSGSPHSKVPNLQ | 2464 | ADMGHDSPHKSGQNQQ | 2626 | TEHGHDSPHKSGQNQQ | 2789 |
| TEKASGSPHSKAQNQQ | 2303 | AINGSGSPHSKAQSQQ | 2465 | IEYGHDSPHKSGQNQQ | 2627 | TIYGHDSPHKSGQSQP | 2790 |
| SDQGSGSPHSKAQNQQ | 2304 | TINGSGSPHSKAQAIT | 2466 | ADYGHDSPHKSGQNQQ | 2628 | TISGHESPHKSGQNEQ | 2791 |
| TEITSGSPHSKAQNQQ | 2305 | TINGSGSPHSKAQKTL | 2467 | IETGHDSPHKSGQNQQ | 2629 | AIIGHDSPHKSAQNQQ | 2792 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| TDKSSGSPHSKAQNQQ | 2306 | TVNGSGSPHSKAQNQW | 2468 | MEWGHDSPHKSGQNQQ | 2630 | AIDGHDSPHKSGQNQL | 2793 |
| TIDGSGSPHSKAQNQQ | 2307 | TINGSGSPHSKAQLHH | 2469 | CEYGHDSPHKSGQNQQ | 2470 | TIMGHDSPHKSVQNQQ | 2631 | | 2794 |
| TVNGNGSPHSKAQNQH | 2308 | TEQTSGSPHSKAQNQQ | 2470 | RINGHDSPHKSGQKQQ | 2471 | EVGGHDSPHKSGQNQQ | 2632 | | 2795 |
| NTNGSGSPHSKAQNQQ | 2309 | TINGSGSPHSKAQNII | 2471 | MEIGHDSPHKSGQNQQ | | TINGHDSPHKSAQNLL | 2633 | | 2796 |
| TETHSGSPHSKAQNQQ | 2310 | NSLGSGSPHSKAQNQQ | 2472 | LEYGHDSPHKSGQNQQ | | TINASGSPHSKAINQQ | 2634 | | 2797 |
| TINGGGSPHSKALNQQ | 2311 | TIPMEGSPHSKAQNQQ | 2473 | ADWGHDSPHKSGQNQQ | | AINGNGSPHKRGQNQQ | 2635 | | 2798 |
| TINGSGSPHSKALHQH | 2312 | TINGSGSPHSKAQGHH | 2474 | IEIGHDSPHKSGQNQQ | | SEMGHDSPHKSGQNQQ | 2636 | | 2799 |
| TINGTGSPHSKAQNHQ | 2313 | TDRTSGSPHSKAQNQQ | 2475 | DIMGHDSPHKSGQNQQ | | AQQGHDSPHKSGQNQQ | 2637 | | 2800 |
| TINGSGSPHSKAQHRI | 2314 | TINGSGSPHSKAQSKV | 2476 | FEQGHDSPHKSGQNQQ | | AINGHDSPHKSGQSLQ | 2638 | | 2801 |
| TINGSGSPHSKAQYIH | 2315 | EVVGSGSPHSKAQNQQ | 2477 | MEFGHDSPHKSGQNQQ | | TINGSGSPHSKAPNQQ | 2639 | | 2802 |
| TENISGSPHSKAQNQQ | 2316 | TINGSGSPHSKAQLPS | 2478 | CDQGHDSPHKSGQNQQ | | CGEGHDSPHKSGQNQQ | 2640 | | 2803 |
| TIIGGGSPHSKAHNQQ | 2317 | TINGSGSPHSKAIGKQ | 2479 | LPEGHDSPHKSGQNQQ | | TVNGHDSPHKSAQNHQ | 2641 | | 2804 |
| TINGSGSPHSKAQKFE | 2318 | TEPTSGSPHSKAQNQQ | 2480 | IENGHDSPHKSGQNQQ | | TVNGHDSPHKSGQTQL | 2642 | | 2805 |
| TSNESGSPHSKAQNHQ | 2319 | TVNGGGSPHSKSQNQQ | 2481 | MESGHDSPHKSGQNQQ | | TNNGHDSPHKSGRNRQ | 2643 | | 2806 |
| TINGSGSPHSKAQFPS | 2320 | TINGSGSPHSKAQAIH | 2482 | AEIGHDSPHKSGQNQQ | | TINGHDSPHKYGQNEQ | 2644 | | 2807 |
| TERPSGSPHSKAQNQQ | 2321 | TINGSGSPHSKAQHGL | 2483 | VEYGHDSPHKSGQNQQ | | TINGNGSPHSKAPNLQ | 2645 | | 2808 |
| TINGNGSPHSKAQNPL | 2322 | SELGSGSPHSKAQNQQ | 2484 | IINGHDSPHKSGLTQQ | | SINGHDSPHKSQQNQQ | 2646 | | 2809 |
| SIKGNGSPHSKAQNQQ | 2323 | TINGSGSPHSKAQFMC | 2485 | TSNGDDSPHKSGRNQQ | | TIGGHDSPHKSGQNQQ | 2647 | | 2810 |
| TERMSGSPHSKAQNQQ | 2324 | TINVSGSPHSKAQGQQ | 2486 | IEVGHDSPHKSGQNQQ | | TINGHDSPHKSVQSKQ | 2648 | | 2811 |
| TERSSGSPHSKAQNQQ | 2325 | TINGGGSPHSKAQNQM | 2487 | MEMGHDSPHKSGQNQQ | | ELVGHDSPHKSGQNQQ | 2649 | | 2812 |
| TELHSGSPHSKAQNQQ | 2326 | TVNGSGSPHSKAQHLQ | 2488 | AEVGHDSPHKSGQNQQ | | ELMGHDSPHKSGQNQQ | 2650 | | 2813 |
| TELTSGSPHSKAQNQQ | 2327 | TIRENGSPHSKAQNQQ | 2489 | MDAGHDSPHKSGQNQQ | | TINGNDSPHKIGHNQQ | 2651 | | 2814 |
| TINGSGSPHSKAHNQQ | 2328 | TINGSGSPHSKTQNHQ | 2490 | VEWGHDSPHKSGQNQQ | | TIKGGGSPHSKAQDQQ | 2652 | | 2815 |
| TINGGGSPHSKAQSQQ | 2329 | TINGSGSPHSKAQPAR | 2491 | AEQGHDSPHKSGQNQQ | | TVNGHDSPHKSGQTQQ | 2653 | | 2816 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| TINGSGSPHSKAQAIK | 2330 | TVNGSGSPHSKAQSLQ | 2492 | LEWGHDSPHKSGQNQQ | 2654 | TINGQDSPHKSGQNPL | 2817 |
| TENTSGSPHSKAQNQQ | 2331 | TINGSGSPHSKSQSQL | 2493 | MELGHDSPHKSGQNQQ | 2655 | TVNASGSPHSKAQNHQ | 2818 |
| TIDGSGSPHSKGQNRQ | 2332 | TINGSASPHSKAHSQQ | 2494 | METGHDSPHKSGQNQQ | 2656 | TINGHDSPHKSGRDQK | 2819 |
| NINGSGSPHSKAQSQQ | 2333 | TWQNSGSPHSKAQNQQ | 2495 | MEAGHDSPHKSGQNQQ | 2657 | TINGHDSPHKSVHNQQ | 2820 |
| TINGSVSPHGKAQNQL | 2334 | TINGSGSPHSKAQDRQ | 2496 | IESGHDSPHKSGQNQQ | 2658 | TINGHDSPHKSGQWKR | 2821 |
| TSNASGSPHSKAQNQL | 2335 | TINGSGSPHSKAQMPS | 2497 | MEVGHDSPHKSGQNQQ | 2659 | TIDGSGSPHSKAENRQ | 2822 |
| TEARSGSPHSKAQNQQ | 2336 | TNNGGGSPHSKAQNLQ | 2498 | CEIGHDSPHKSGQNQQ | 2660 | NEIGHDSPHKSGQNQQ | 2823 |
| TEKNSGSPHSKAQNQQ | 2337 | TINGSGSPHSKAQGSL | 2499 | ATNGHDSPHKSGLNQQ | 2661 | AINGHDSPHKSGQSQQ | 2824 |
| TANGSGSPHSKAQYQQ | 2338 | TEVTSGSPHSKAQNQQ | 2500 | MDGGHDSPHKSGQNQQ | 2662 | IINGHDSPHKSRQAQQ | 2825 |
| TVNGSGSPHSKAQYQH | 2339 | SINGGGSPHSKAQYQQ | 2501 | QEVGHDSPHKSGQNQQ | 2663 | TPNGHDSPHKSGQNQQ | 2826 |
| TINGSGSPHTKAQNPQ | 2340 | TVIGSGSPHSKSQNQQ | 2502 | ADQGHDSPHKSGQNQQ | 2664 | ITNGHDSPHKSGQTQQ | 2827 |
| TINGSGSPHSKGQNPP | 2341 | AVNVSGSPHSKAQNQQ | 2503 | TINGHESPHKSAQNHQ | 2665 | TINGHDSPHKSVQNHQ | 2828 |
| TIIGSGSPHSKAQHQL | 2342 | TVNGNGSPHSKSQNQQ | 2504 | TINGHDSPHKSAQNQW | 2666 | TINGHDSPHKSKQNQQ | 2829 |
| TINGSGSPHSKAQSPP | 2343 | TDRNSGSPHSKAQNQQ | 2505 | NMNGHDSPHKSGQNTH | 2667 | TINGHDSPHKSAQNQL | 2830 |
| TIYGSGSPHSKAQNQQ | 2344 | TINGSGSPHSKAQVPA | 2506 | IEMGHDSPHKSGQNQQ | 2668 | TVNGHDSPHKSGQTQP | 2831 |
| TINGSGSPHSKAQAKL | 2345 | GVLGSGSPHSKAQNQQ | 2507 | TINGHDSPHKSGRRQ | 2669 | TDQGHDSPHKSGQNQQ | 2832 |
| TDKNSGSPHSKAQNQQ | 2346 | TLNGNGSPHSKAQNLQ | 2508 | ISNGHDSPHKSAQNQQ | 2670 | TINGHDSPHKLWINQQ | 2833 |
| TINGSGSPHSKTKSQQ | 2347 | AINGSGSPHSKAQDKQ | 2509 | TGNGHDSPHKSGQYQQ | 2671 | GINGPDSPHKSGQNQQ | 2834 |
| TINGSGSPHSKAQDRP | 2348 | TSNGSGSPHSKAHYQQ | 2510 | TINGNYSPHKIGQNQQ | 2672 | SEIGHDSPHKSGQNQQ | 2835 |
| TINGIGSPHSKAQNLG | 2349 | TINGSGSPHSKAQVPS | 2511 | TINGHDSPHKSRQNDQ | 2673 | TINGHDSPHKSVQKQL | 2836 |
| TINGSGSPHSKAQSQQ | 2350 | TELRSGSPHSKAQNQQ | 2512 | QQQGHDSPHKSGQNQQ | 2674 | TINGHPSPHWKGQNQQ | 2837 |
| TENLSGSPHSKAQNQQ | 2351 | NINGSGSPHSKAQNHQ | 2513 | HDWGHDSPHKSGQNQQ | 2675 | TVNGHDSPHKSGRNQL | 2838 |
| TINGSGSPHSKAQAFH | 2352 | TVNGGGSPHSKAQNHQ | 2514 | IEGGHDSPHKSGQNQQ | 2676 | TIKGSGSPHSKVQDQQ | 2839 |
| TINGSGSPHSKAQKQQ | 2353 | TINGSGSPHSKARGEQ | 2515 | TFNRSGSPHSKAQNQQ | 2677 | SEKGHDSPHKSGQNQQ | 2840 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| TFSGSGSPHSKAQNLQ | 2354 | TINGGGSPHSKAQYQH | 2516 | AINGHDSPHKSGQIRQ | 2678 | WSAGHDSPHKSGQNQQ | 2841 |
| AINGSGSPHSKAQNAQ | 2355 | TEDLSGSPHSKAQNQQ | 2517 | TINGHDSPHKIGQNQH | 2679 | ELAGHDSPHKSGQNQQ | 2842 |
| TESWSGSPHSKAQNQQ | 2356 | TINGSGSPHSKAPGQQ | 2518 | AINGYDSPHKSGQKQQ | 2680 | TINGHDSPHKMGRNQQ | 2843 |
| TTNGSGSPHSKAHNQL | 2357 | TIPKNGSPHSKAQNQQ | 2519 | TESGHDSPHKSGQNQQ | 2681 | TINGHDSPHKSGISIQ | 2844 |
| TVNGNGSPHSKAQNHQ | 2358 | TINGSGSPHSKAQSLQ | 2520 | TINGHDSPHKSGQSVQ | 2682 | TSNGHDSPHKSVQNLQ | 2845 |
| TEDKSGSPHSKAQNQQ | 2359 | TINGSGSPHSKRLEQQ | 2521 | TINGHESPHKSGRSQQ | 2683 | QTQGHDSPHKSGQNQQ | 2846 |
| TESASGSPHSKAQNQQ | 2360 | TERGSGSPHSKAQNQQ | 2522 | TINGHDSPHKSGQNKL | 2684 | TINGHDSPHKMAHNQQ | 2847 |
| TNNGSGSPHSKAQNQQ | 2361 | TVNGSGSPHSKAPNQQ | 2523 | TINGHDSPHKTGQNQQ | 2685 | AINGSGSPHSKAQTQQ | 2848 |
| TSNGGGSPHSKAQNLQ | 2362 | TSNGSGSPHSKAQNQS | 2524 | TINGRGSPHKRGQNQQ | 2686 | TINGHDSPHKHGQNQQ | 2849 |
| TDKMSGSPHSKAQNQQ | 2363 | TINGSGSPHSKAQKVI | 2525 | TINGSGSPHTKAQNPP | 2687 | GADGHDSPHKSGQNQQ | 2850 |
| EVHGSGSPHSKAQNQQ | 2364 | TEGISGSPHSKAQNQQ | 2526 | TINGQDSPHKSGQHQQ | 2688 | VGEGHDSPHKSGQNQQ | 2851 |
| TINGSGSPHSKAQKLN | 2365 | TINGSGSPHSKAQNND | 2527 | SINGHDSPHKSGQIQH | 2689 | ANEGHDSPHKSGQNQQ | 2852 |
| TINGGGSPHSKSQNQH | 2366 | TINGSGSPHSKAQSVH | 2528 | AINGHDSPHKSGPRQQ | 2690 | TEAKSGSPHSKAQNQQ | 2853 |
| TVNGGGSPHSKAQSQQ | 2367 | TINGSGSPHSKAQPLG | 2529 | TVNGHDSPHKSGHTQQ | 2691 | TINGHDSPHKSVQSQQ | 2854 |
| TTNGSGSPHSKAQYQH | 2368 | TINKEGSPHSKAQNQQ | 2530 | SINGHDSPHKSGRQH | 2692 | TIPGSGSPHSKAQNLQ | 2855 |
| TISGSGSPHSKAQYQH | 2369 | TCNASGSPHSKAQNQQ | 2531 | SLNGSGSPHTKAQNQQ | 2693 | TINGHDSPHKSGQTVC | 2856 |
| TESTSGSPHSKAQNQQ | 2370 | AINGSGSPHSKAHNQE | 2532 | AINGHDSPHKSAQSQQ | 2694 | ELRGHDSPHKSGQNQQ | 2857 |
| TINGSGSPHSKSQNVQ | 2371 | TEGLSGSPHSKAQNQQ | 2533 | SIYGHESPHKSGQNQQ | 2695 | CQIGHDSPHKSGQNQQ | 2858 |
| SINGSGSPHSKAQAQQ | 2372 | TRDASGSPHSKAQNQQ | 2534 | TVNGHDSPHKSLQNQQ | 2696 | GVMGHDSPHKSGQNQQ | 2859 |
| TVNGSGSPHSKAQNLQ | 2373 | TSNGSGSPHSKAQNLQ | 2535 | TINGHGSPHSKAQNPQ | 2697 | ACDGHDSPHKSGQNQQ | 2860 |
| TVRDSGSPHSKAQNQQ | 2374 | TGNGSGSPHSKAQIQQ | 2536 | TSNGYDSPHKSGQKQQ | 2698 | TINGQDSPHKSGQYQQ | 2861 |
| TFNASGSPHSKAPNQQ | 2375 | TVNGGGSPHSKAQNLQ | 2537 | TVNGHDSPHKSGRNQE | 2699 | TINGHDSPHKSGQQIM | 2862 |
| TDRMSGSPHSKAQNQQ | 2376 | TDRSSGSPHSKAQNQQ | 2538 | TTNGHDSPHKSGQTQL | 2700 | TINGHDSPHKSRQNEQ | 2863 |
| TINGSGSPHSKAQTPP | 2377 | TINGSGSPHSKAQVRN | 2539 | AINGHDSPHKSEKNQQ | 2701 | ASNGHDSPHKSGLNHQ | 2864 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| TIKGSGSPHSKAQNQQ | 2378 | TINGSGSPHSKAPSNQ | 2540 | IINGRDSPHKSGQDQQ | 2702 | TVNGHDSPHKSGQSQP | 2865 |
| NHIGSGSPHSKAQNQQ | 2379 | TINGSGSPHSKAQVGH | 2541 | TISGHDSPHKTGHNQQ | 2703 | NELGHDSPHKSGQNQQ | 2866 |
| TINGSGSPHSKAQYQH | 2380 | NAIGSGSPHSKAQNQQ | 2542 | SINGYDSPHKSGQTQQ | 2704 | AAEGHDSPHKSGQNQQ | 2867 |
| TIPIDGSPHSKAQNQQ | 2381 | AENGSGSPHSKAQNQQ | 2543 | TINGHESPHKSGQTQQ | 2705 | GQNGHDSPHKSGQNQQ | 2868 |
| TINGSGSPHSKAQGQQ | 2382 | TINGSGSPHSKAQRDI | 2544 | TINGHDSPHKSGQSKQ | 2706 | NEFGHDSPHKSGQNQQ | 2869 |
| TFNGSGSPHNKAQNHQ | 2383 | TINGSGSPHSKAQMPN | 2545 | AIIGHESPHKSGQNQQ | 2707 | TSIGYDSPHKSGQNQQ | 2870 |
| ESDGSGSPHSKAQNQQ | 2384 | TVNGSGSPHSKSQNQQ | 2546 | TINGHDSPHKTGQNQP | 2708 | TDNGHDSPHKSGQNLQ | 2871 |
| TINGSGSPHSKAQPPA | 2385 | TIPAIGSPHSKAQNQQ | 2547 | AINGHDSPHKSGQSPQ | 2709 | TITGHDSPHKSRQDQQ | 2872 |
| TINGSGSPHSKAQERP | 2386 | TINGSGSPHSKARGLQ | 2548 | TIKGNDSPHKSVQNQQ | 2710 | AEHGHDSPHKSGQNQQ | 2873 |
| TIKGSGSPHSKAQDLQ | 2387 | TELGSGSPHSKAQNQQ | 2549 | TEFGHDSPHKSGQNQQ | 2711 | TINGDDSPHKSGQKQL | 2874 |
| TDLKSGSPHSKAQNQQ | 2388 | AETGSGSPHSKAQNQQ | 2550 | TINGHDSPHKSAQNYQ | 2712 | EILGHDSPHKSGQNQQ | 2875 |
| TINGGGSPHSKAQNPP | 2389 | TINGSGSPHSKLQKQQ | 2551 | TFNGSASPHSKALNQQ | 2713 | TIHGSGSPHSKAQNQA | 2876 |
| TINGSGSPHSKAQAMH | 2390 | TINGSGSPHSKAPSLQ | 2552 | TINGHESPHKSAQNRQ | 2714 | AINGDDSPHKSGHNQQ | 2877 |
| TVPNSGSPHSKAQNQQ | 2391 | TINGSGSPHSKAQRDQ | 2553 | TTNGHDSPHKSGQNQQ | 2715 | TSNGHNSPHKSGQNQE | 2878 |
| TVIGSGSPHSKALNQQ | 2392 | TDVGSGSPHSKAQNQQ | 2554 | TIKGQDSPHKIGQNQQ | 2716 | TINGHDSPHKSGQMIH | 2879 |
| TINGSGSPHSKAQHPS | 2393 | TINGSGSPHSKNRDQQ | 2555 | TVNGHDSPHKSGQNHL | 2717 | NAIGHDSPHKSGQNQQ | 2880 |
| TINGLGSPHSKSQNQQ | 2394 | SINGSGSPHSKAPNLQ | 2556 | SINGHDSPHKSGQYQH | 2718 | VINGHDSPHKSGRNHQ | 2881 |
| TINGTGSPHSKAQNQQ | 2395 | TINGSGSPHSKAQAKG | 2557 | TINGNDSPHKSVQNHQ | 2719 | TITGHDSPHKSVQNRQ | 2882 |
| TINGSGSPHSKAPGLQ | 2396 | TVNGSGSPHSKAQDKQ | 2558 | TITGHDSPHKSGQNQW | 2720 | TINGHDSPHKSGQKMN | 2883 |
| TINGSGSPHSKAQGIR | 2397 | TINGGGSPHSKAQNPQ | 2559 | TNNGHDSPHKSVQNQH | 2721 | TIHGHDSPHKSGQSQQ | 2884 |
| TESHSGSPHSKAQNQQ | 2398 | TINGSGSPHSKAQSAH | 2560 | TIDGHDSPHKSGQNQH | 2722 | TEIGHDSPHKSGQNQQ | 2885 |
| TINGSGSPHSKAQAPA | 2399 | TINGNGSPHSKSQNQH | 2561 | TVNGHDSPHKSGQTRQ | 2723 | TINGHDSPHKSGQYQH | 2886 |
| TINGSGSPHSKSQSQQ | 2400 | TVPTSGSPHSKAQNQQ | 2562 | TVNGHDSPHKSGQNLH | 2724 | NCLGSGSPHSKAQNQQ | 2403 |
| AEHGSGSPHSKAQNQQ | 2401 | TIDGSGSPHSKSQNHQ | 2563 | AISGHDSPHKSGLNQQ | 2725 | AINRSGSPHSKAQDQQ | 2565 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| TEDRSGSPHSKAQNQQ | 2402 | TDVKSGSPHSKAQNQQ | 2564 | AINGHDSPHKSAQNQE | 2726 | TITGHDSPHKSGQHLQ | 2727 |
| GSGSPHSKAQNRHT | 2887 | GSGSPHSKAQSQQT | 2936 | GSGSPHSKAQRMST | 2985 | GSGSPHSKAQNNDQ | 3034 |
| GSGSPHSKVQNQQT | 2888 | ASGSPHSKAQNQLT | 2937 | GSGSPHSKAQGILT | 2986 | GSGSPHSKAQSVHT | 3035 |
| MSGSPHSKAQNQQT | 2889 | RSGSPHSKAQNQQT | 2938 | GSGSPHSKAQDRQT | 2987 | GSGSPHSKAQPLGT | 3036 |
| GSGSPHSKARDQQT | 2890 | GSGSPHSKAQYQHT | 2939 | GSGSPHSKARDWQT | 2988 | GSGSPHSKAHNQET | 3037 |
| GSGSPHSKAPNLQT | 2891 | GSGSPHTKAQNPQS | 2940 | GSGSPHSKAQNTHD | 2989 | GSGSPHSKAQNLQI | 3038 |
| TSGSPHSKAQNQQT | 2892 | GSGSPHSKGQNPPT | 2941 | GSGSPHSKAPNLQI | 2990 | GSGSPHSKAQIQQT | 3039 |
| GSGSPHSKAHVRQT | 2893 | GSGSPHSKAQHQLT | 2942 | GSGSPHSKAQERST | 2991 | GSGSPHSKAQVRNT | 3040 |
| GSGSPHSKAPNQHT | 2894 | GSGSPHSKAQSPPT | 2943 | GSGSPHSKAQNYQT | 2992 | GSGSPHSKAPSNQT | 3041 |
| ISGSPHSKAQNQQT | 2895 | GSGSPHSKAQAKLT | 2944 | GSGSPHSKAQRTCT | 2993 | GSGSPHSKAQVGHT | 3042 |
| GSGSPHSKTQSQQT | 2896 | GSGSPHSKTKSQQT | 2945 | GSGSPHSKAQIGHT | 2994 | GSGSPHSKAQRDIT | 3043 |
| GSGSPHSKAQNQST | 3032 | GSGSPHSKAQDRPT | 2898 | GSGSPHSKAQGAIT | 2946 | GSGSPHSKAQMPNT | 3044 |
| ESGSPHSKAQNQQI | — | GSGSPHSKAQSQQL | 2898 | GSGSPHSKAQVPPT | 2947 | GSGSPHSKARGLQT | 3045 |
| GSGSPHSKAQPAKT | 2899 | GSGSPHSKAQAFHT | — | GSGSPHSKAQVQQI | 2948 | GSGSPHSKLQKQQT | 3046 |
| SSGSPHSKAQNQQT | 2900 | GSGSPHSKAQKQQD | — | GSGSPHSKALMRQT | 2949 | GSGSPHSKAPSLQT | 3047 |
| GSGSPHSKSQTQQN | 2901 | GSGSPHSKAQNAQT | — | GSGSPHSKAQYSVT | 2950 | GSGSPHSKAQRDQT | 3048 |
| ASGSPHSKAQNQQT | 2902 | WSGSPHSKAQNQQT | — | GSGSPHSKVPNLQT | 2951 | GSGSPHSKNRDQQT | 3049 |
| GSGSPHSKAQNLAT | 2903 | GSGSPHSKAHNQLT | — | GSGSPHSKAQSQQI | 2952 | GSGSPHSKAQAKGT | 3050 |
| GSGSPHSKSQNQLT | 2904 | GSGSPHSKAQNQQY | — | GSGSPHSKAQAITT | 3002 | GSGSPHSKAQSAHT | 3051 |
| NSGSPHSKAQNQQT | 2905 | GSGSPHSKAQKLNT | — | GSGSPHSKAQKTLT | 3003 | GSGSPHSKSQNHQT | 3052 |
| GSGSPHSKAQGQQT | 2906 | GSGSPHSKSQNVQT | — | GSGSPHSKAQNQWT | 3004 | RSGSPHSKAQDQQT | 3053 |
| VSGSPHSKAQNQQT | 2907 | GSGSPHSKAQAQQT | — | GSGSPHSKAQLHHT | 3005 | GSGSPHSKAQSTMT | 3054 |
| GSGSPHSKALNRQS | 2908 | GSGSPHSKAQNLQA | — | GSGSPHSKAQNIII | 3006 | GSGSPHSKAQREMT | 3055 |
| LSGSPHSKAQNQQT | 2909 | DSGSPHSKAQNQQT | — | GSGSPHSKAQGHHT | 3007 | GSGSPHSKAQYRAT | 3056 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| GSGSPHSKAHNQQT | 2910 | ASGSPHSKAPNQQT | 2959 | GSGSPHSKAQSKVT | 3008 | GSGSPHSKNQWQQT | 3057 |
| GSGSPHSKTQNQQT | 2911 | GSGSPHSKAQTPPT | 2960 | GSGSPHSKAQLPST | 3009 | GSGSPHSKAQRMNT | 3058 |
| GSGSPHSKAQNPPT | 2912 | GSGSPHSKAQYQHA | 2961 | GSGSPHSKAIGKQT | 3010 | GSGSPHAKAQNHQT | 3059 |
| GSGSPHSKAQNLQT | 2913 | GSGSPHSKAQGQQA | 2962 | GSGSPHSKAQAIHT | 3011 | GSGSPHSKAGDSQT | 3060 |
| GSGSPHSKAQYQQT | 2914 | GSGSPHNKAQNHQT | 2963 | GSGSPHSKAQHGLT | 3012 | GSGSPHSKLKSQQT | 3061 |
| GSGSPHSKAQDQET | 2915 | GSGSPHSKAQPPAT | 2964 | GSGSPHSKAQFMCT | 3013 | GSGSPHSKAQKIST | 3062 |
| KSGSPHSKAQNQQT | 2916 | GSGSPHSKAQERPT | 2965 | VSGSPHSKAQGQQT | 3014 | GSGSPHSKAPSMQT | 3063 |
| GSGSPHSKAQNHQT | 2917 | GSGSPHSKAQDLQT | 2966 | GSGSPHSKAQHLQT | 3015 | GSGSPHSKASPRQT | 3064 |
| GSGSPHSKAQDQQT | 2918 | GSGSPHSKAQAMHT | 2967 | GSGSPHSKTQNH?N | 3016 | GSGSPHSKRMEQQT | 3065 |
| GSGSPHSKGHWQQT | 2919 | GSGSPHSKALNQQT | 2968 | GSGSPHSKAQPART | 3017 | GSGSPHSKAQYQNT | 3066 |
| GSGSPHSKAPNQQT | 2920 | GSGSPHSKAQHPST | 2969 | GSGSPHSKAQSLQT | 3018 | RSGSPHSKAQNQQI | 3067 |
| GSGSPHSKAQNQLI | 2921 | GSGSPHSKAPGLQT | 2970 | GSGSPHSKSQSQLT | 3019 | GSGSPHTKAQNPPT | 3068 |
| GSGSPHSKRPEQQT | 2922 | GSGSPHSKAQGIRT | 2971 | GSGSPHSKAQDRQS | 3020 | GSGSPHTKAQNQQT | 3069 |
| GSGSPHSKAQRTMT | 2923 | GSGSPHSKAQAPAT | 2972 | GSGSPHSKAQMPST | 3021 | ASGSPHSKAQHQQT | 3070 |
| GSGSPHSKAQNQQH | 2924 | GSGSPHSKSQSQQI | 2973 | GSGSPHSKAQGSLT | 3022 | ASGSPHSKAINQQT | 3071 |
| HSGSPHSKAQNQQT | 2925 | GSGSPHSKAQIPPT | 2974 | GSGSPHSKSQNQQT | 3023 | GSGSPHSKAPNQQH | 3072 |
| GSGSPHSKALHQHT | 2926 | GSGSPHSKAQTQLT | 2975 | GSGSPHSKAQVPAT | 3024 | ASGSPHSKAQNHQT | 3073 |
| GSGSPHSKAQHRIT | 2927 | GSGSPHSKAQAPST | 2976 | GSGSPHSKAQDKQT | 3025 | GSGSPHSKAENRQT | 3074 |
| GSGSPHSKAQYIHT | 2928 | GSGSPHSKGQNQQT | 2977 | GSGSPHSKAQHYQQT | 3026 | GSGSPHSKVQDQQT | 3075 |
| GSGSPHSKAQKFET | 2929 | ASGSPHSKAHNQQT | 2978 | GSGSPHSKAQVPST | 3027 | GSGSPHSKAQTQQA | 3076 |
| ESGSPHSKAQNHQT | 2930 | GSGSPHSKAQNTYA | 2979 | GSGSPHSKAQRGEQT | 3028 | GSGSPHSKAQNQAT | 3077 |
| GSGSPHSKAQFPST | 2931 | GSGSPHSKSQNQHI | 2980 | GSGSPHSKAPGQQT | 3029 | GSGSPHSKGQNRQT | 2935 |
| PSGSPHSKAQNQQT | 2932 | GSGSPHSKAQNHLT | 2981 | GSGSPHSKAQSLQI | 3030 | GSGSPHSKAQLQQT | 2984 |
| GSGSPHSKAHNQQR | 2933 | GSGSPHSKAQIGMT | 2982 | GSGSPHSKRLEQQT | 3031 | GSGSPHSKAQKVIT | 3033 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| GSGSPHSKAQAIKT | 2934 | GSGSPHSKALNKQT | 2983 | GHDSPHKHGQNHQT | 3160 | GHDSPHKSGQWKRT | 3202 |
| GHDSPHKSGQIRQT | 3078 | GHDSPHKSGQNQHA | 3119 | LHDSPHKSGQNQQT | 3161 | GHDSPHKSGQSQQI | 3203 |
| GHDSPHKIGQNQHA | 3079 | GHDSPHKSGQTRQT | 3120 | GHDSPHKSVQNKQT | 3162 | GHDSPHKSRQAQQT | 3204 |
| GYDSPHKSGQKQQT | 3080 | GHDSPHKSGQNLHT | 3121 | GQVSPHKSGQNQQT | 3163 | GHDSPHKSVQNHQI | 3205 |
| GHDSPHKSGQNQQT | 3081 | GHDSPHKSGLNQQT | 3122 | GHDSPHKSGQRQLT | 3164 | GHDSPHKSKQNQQA | 3206 |
| GHDSPHKSGQSVQT | 3082 | GHDSPHKSAQNQET | 3123 | GHDSPHKIGQNQLT | 3165 | GHDSPHKSAQNQLN | 3207 |
| GHESPHKSGRSQQT | 3083 | GHDSPHKSGQHLQT | 3124 | GHDSPHKSGQIIVT | 3166 | GHDSPHKSGQTQPT | 3208 |
| GHDSPHKSGQNKLE | 3084 | GHDSPHKSRLNQPT | 3125 | IHDSPHKSGQNQQT | 3167 | FHDSPHKSGQNQQT | 3209 |
| GHDSPHKTGQNQQK | 3085 | GHDSPHKSGQKQQT | 3126 | GYDSPHKSGQKQST | 3127 | GHDSPHKLWINQQT | 3210 |
| GRGSPHKRGQNQQT | 3086 | GQDSPHKSGQNQDT | 3086 | MHDSPHKSGQNQQT | 3127 | GPDSPHKSGQNQQT | 3211 |
| GHDNPHKSGQNQQT | 3087 | GHDSPHKSGRNQQT | 3087 | GDDSPHKSVQNQQT | 3128 | GHDSPHKSVQKQLT | 3212 |
| GQDSPHKSGQHQQA | 3088 | GHDSPHKSGQNLLT | 3088 | GHDSPHKSVQSHQT | 3129 | GHDSPHKSGRNQLA | 3213 |
| GHDSPHKSGQIQHT | 3089 | GHDSPHKSGQLVIT | 3089 | GHDSPHKSGQFVVT | 3130 | VHDSPHKSGQNQQS | 3214 |
| GHDSPHKSGPRQQT | 3090 | GHDSPHKSRQSQQT | 3090 | GHDSPHKSRQNLQT | 3131 | GHDSPHKMGRNQQS | 3215 |
| GHDSPHKSGHTQQT | 3091 | GHDSPHKSGRTQET | 3091 | GHNSPHKSGQNQET | 3132 | GHDSPHKSGISIQT | 3216 |
| GHDSPHKSGQRQHT | 3092 | GHDSPHKSVQTHQT | 3092 | GHDSPHKSAQNQQI | 3133 | VHDSPHKSGQNQQT | 3217 |
| GHDSPHKSAQSQQT | 3093 | GHDSPHKSGQNQPA | 3093 | NHDSPHKSGQNQQT | 3134 | GHDSPHKSVQNLQT | 3218 |
| GHESPHKSGQNQQS | 3094 | KHDSPHKSGQNQQT | 3094 | GHDSPHKSQSQPT | 3135 | GHDSPHKMAHNQQT | 3219 |
| GHDSPHKSLQNQQT | 3095 | GHDSPHKSGQTQQT | 3095 | GHESPHKSGQNEQT | 3136 | GHDSPHKHGQNQQN | 3220 |
| GHDSPHKSGRNQET | 309€ | GPDSPHKIGQNQQS | 3096 | GHDSPHKSAQNQQT | 3137 | GHDSPHKSVQSQQS | 3221 |
| GHDSPHKSGQTQLT | 3097 | GHDSPHKSVQNQQT | 3097 | GHDSPHKSGQNQLT | 3138 | GHDSPHKSGQTVCT | 3222 |
| GHDSPHKSEKNQQT | 3098 | GHDSPHKSRQDQHT | 3098 | GHDSPHKSAQNLLT | 3139 | GQDSPHKSGQYQQI | 3223 |
| GRDSPHKSGQDQQT | 3099 | GPDSPHKSGQKQQT | 3099 | THDSPHKSGQNQQT | 3140 | GHDSPHKSGQQIMT | 3224 |
| GHDSPHKTGHNQQT | 3100 | GHDSPHKSRQSQHT | 3100 | GNGSPHKRGQNQQT | 3141 | GHDSPHKSRQNEQS | 3225 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| AHDSPHKSGQNQLT | 3101 | GHDSPHKSVQNQLT | 3142 | GHDSPHKSGQSLQT | 3184 | GHDSPHKSGLNHQT | 3226 |
| GYDSPHKSGQTQQT | 3102 | AHDSPHKSGQNQQT | 3143 | GHDSPHKSAQNHQT | 3185 | GYDSPHKSGQNQQT | 3227 |
| GHESPHKSGQTQQI | 3103 | GQDSPHKSGQNQQS | 3144 | GHDSPHKSGRNRQT | 3186 | GHDSPHKSGQNLQT | 3228 |
| GHDSPHKSGQSKQA | 3104 | GHDSPHKSGRNQQI | 3145 | EHDSPHKSGQNQQT | 3187 | GHDSPHKSRQDQQT | 3229 |
| GHESPHKSGQNQQT | 3105 | GYDSPHKSGQYQHT | 3146 | GHDSPHKYGQNEQT | 3188 | GDDSPHKSGQKQLT | 3230 |
| GHDSPHKTGQNQPP | 3106 | GHDSPHKSRQNQQT | 3147 | RHDSPHKSGHNQQT | 3189 | GDDSPHKSGHNQQT | 3231 |
| GHDSPHKSGQSPQT | 3107 | GHDSPHKSWVRQQT | 3148 | GHDSPHKSQQNQQT | 3190 | GHDSPHKSGQMIHT | 3232 |
| GNDSPHKSVQNQQT | 3108 | GHESPHKSGQNQHS | 3149 | GHDSPHKSGQNQQI | 3191 | GHDSPHKSGRNHQS | 3233 |
| GHDSPHKSAQNYQT | 3109 | GHDSPHKIGHNQQT | 3150 | QHDSPHKSGQNQQT | 3192 | GHDSPHKSVQNRQT | 3234 |
| AHDSPHKIGQNHQT | 3110 | WHDSPHKSGQNQQT | 3151 | RHDSPHKIVQNQQT | 3193 | GHDSPHKSGQKMNT | 3235 |
| GHESPHKSAQNRQT | 3111 | RHDSPHKSGQNQQT | 3152 | YHDSPHKSGQNQQT | 3194 | GHDSPHKSGQSQQN | 3236 |
| GHDSPHKSGQNQQG | 3112 | GHDSPHKSNAWQQT | 3153 | GHDSPHKSVQSKQT | 3195 | GHDSPHKSGQYQHA | 3237 |
| GQDSPHKIGQNQQT | 3113 | GHDSPHKSGQSVPT | 3154 | GNDSPHKIGHNQQT | 3196 | GHDSPHKSGQNWT | 3117 |
| GHDSPHKSGQNHLT | 3114 | GHESPHKSGQNIQP | 3155 | HHDSPHKSGQNQQT | 3197 | GHDSPHRGPDQQS | 3158 |
| GHDSPHKSGQYQHT | 3115 | GHDSPHKSVQNHLN | 3156 | GHDSPHKSGQTQQI | 3198 | GHDSPHKSGRDQKT | 3200 |
| GNDSPHKSVQNHQT | 3116 | GHDSPHKIGLDQQT | 3157 | GQDSPHKSGQNPLT | 3199 | GHDSPHKSVHNQQN | 3201 |
| GHDSPHKSVQNQHT | 3118 | GHDSPHKSGESQQT | 3159 | KTISKRGSPHSKAQNQQT | 4098 | KGLGGSGSPHSKAQNQQT | 4099 |
| KTINGHDSPHSKAQNLQT | 4100 | KTINGSGSPHSKTCIQQT | 4196 | KEIYGSGSPHSKAQNQQT | 4292 | KTINGSGSPHKRGQKQQT | 4388 |
| KTINGHDSPHSKAQNQQI | 4101 | KTINGSGSPHSKWLTQQT | 4197 | KELSGSGSPHSKAQNQQT | 4293 | KTINGSGSPHKRGQNQET | 4389 |
| KTINGSGSPHFTRQNQQT | 4102 | KTINGSGSPHSKWVVQQT | 4198 | KETIGSGSPHSKAQNQQT | 4294 | KTINGSGSPHKRGQNQLT | 4390 |
| KTINGSGSPHSLPWNQQT | 4103 | KTINGSGSPHSKYRLQQT | 4199 | KEVLGSGSPHSKAQNQQT | 4295 | KTINGSGSPHKRGRNQQT | 4391 |
| KTINGHDSPHSKAQNHQT | 4104 | KTINGSGSPHSKYSKQQT | 4200 | KFALGHDSPHKSGKQQT | 4296 | KTINGSGSPHKSGGNQQT | 4392 |
| KTMNGHDSPHSKAQNQQT | 4105 | KTINGSGSPHSKYSRQQT | 4201 | KIINGHDSPHKSGQNLVL | 4297 | KTINGSGSPHKSGHNQET | 4393 |
| KPYKGSGSPHSKAQNQQT | 4106 | KTINGSGSPHSLKRNQQT | 4202 | KIINGHDSPHKSGQRNYT | 4298 | KTINGSGSPHKSGHNQLT | 4394 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| KRLWGSGSPHSKAQNQQT | 4107 | KTINGSGSPHSLWFNQQT | 4203 | KIINGHDSPHSKAQNQQT | 4299 | KTINGSGSPHKSGHNQQN | 4395 |
| KRMRGSGSPHSKAQNQQT | 4108 | KTINGSGSPHSLWPNQQT | 4204 | KLNPGHDSPHKSGQTQQT | 4300 | KTINGSGSPHKSGLNQLT | 4396 |
| KRTYGSGSPHSKAQNQQT | 4109 | KTINGSGSPHSLWTNQQT | 4205 | KLNRGHDSPHKSGQNQQS | 4301 | KTINGSGSPHKSGPNQQT | 4397 |
| KTINCLRSPHSKAQNQQT | 4110 | KTINGSGSPHSMRRNQQT | 4206 | KLSSGHDSPHKSGQNQQN | 4302 | KTINGSGSPHKSGQGQQT | 4398 |
| KTINFSRSPHSKAQNQQT | 4111 | KTINGSGSPHSPCLNQQT | 4207 | KNINGHDSPHSKAQNQQT | 4303 | KTINGSGSPHKSGQHLQT | 4399 |
| KTINGLRSPHFKAQNQQT | 4112 | KTINGSGSPHSQWQNQQT | 4208 | KNNDGSGSPHSKAQNQQT | 4304 | KTINGSGSPHKSGQHQQT | 4400 |
| KTINGNRSPHNKAQNQQT | 4113 | KTINGSGSPHSRCANQQT | 4209 | KNVMGSGSPHSKAQNQQT | 4305 | KTINGSGSPHKSGQKHQT | 4401 |
| KTINGPRSPHYKAQNQQT | 4114 | KTINGSGSPHSRIRNQQT | 4210 | KPINGHDSPHKSGQNKLS | 4306 | KTINGSGSPHKSGQKQQS | 4402 |
| KTINGQASPHWKAQNQQT | 4115 | KTINGSGSPHSRKSNQQT | 4211 | KPINGHDSPHKSGQNLSS | 4307 | KTINGSGSPHKSGQNEQT | 4403 |
| KTINGRCSPHSKAQNQQT | 4116 | KTINGSGSPHSRLWNQQT | 4212 | KPINGHDSPHSKAQNQQT | 4308 | KTINGSGSPHKSGQNHQT | 4404 |
| KTINGRHSPHSKAQNQQT | 4117 | KTINGSGSPHSRRFNQQT | 4213 | KRINGHDSPHSKAQNQQT | 4309 | KTINGSGSPHKSGQNKQT | 4405 |
| KTINGRKSPHRKAQNQQT | 4118 | KTINGSGSPHSRRPNQQT | 4214 | KSCSGHDSPHKSGQNQQS | 4310 | KTINGSGSPHKSGQNKTS | 4406 |
| KTINGRLSPHWKAQNQQT | 4119 | KTINGSGSPHSRSCNQQT | 4215 | KSINGHDSPHKSGQNLAS | 4311 | KTINGSGSPHKSGQNQEA | 4407 |
| KTINGRLSPHYKAQNQQT | 4120 | KTINGSGSPHSRSKNQQT | 4216 | KSINGHDSPHKSGQNLFL | 4312 | KTINGSGSPHKSGQNQET | 4408 |
| KTINGRPSPHMKAQNQQT | 4121 | KTINGSGSPHSRTKNQQT | 4217 | KSINGHDSPHKSGQNLLM | 4313 | KTINGSGSPHKSGQNQKT | 4409 |
| KTINGRSSPHWKAQNQQT | 4122 | KTINGSGSPHSRWLNQQT | 4218 | KSINGHDSPHKSGQNLLQ | 4314 | KTINGSGSPHKSGQNQQI | 4410 |
| KTINGRWSPHSKAQNQQT | 4123 | KTINGSGSPHSSVCNQQT | 4219 | KSINGHDSPHKSGQNSLG | 4315 | KTINGSGSPHKSGQNQQR | 4411 |
| KTINGSGSPHAPCQNQQT | 4124 | KTINGSGSPHSSWRNQQT | 4220 | KSINGHDSPHKSGQNTLQ | 4316 | KTINGSGSPHKSGQNQRT | 4412 |
| KTINGSGSPHAWAQNQQT | 4125 | KTINGSGSPHSVCQNQQT | 4221 | KSINGHDSPHKSSSNQQT | 4317 | KTINGSGSPHKSGQNQYT | 4413 |
| KTINGSGSPHCMRQNQQT | 4126 | KTINGSGSPHSVLCNQQT | 4222 | KSINGHDSPHKYKLNQQT | 4318 | KTINGSGSPHKSGQRQQT | 4414 |
| KTINGSGSPHFCSQNQQT | 4127 | KTINGSGSPHSVRRNQQT | 4223 | KSINGSGSPHKSGQKQQT | 4319 | KTINGSGSPHKSGQSQQT | 4415 |
| KTINGSGSPHFLFQNQQT | 4128 | KTINGSGSPHSVSCNQQT | 4224 | KSINGSGSPHKSGQNQQT | 4320 | KTINGSGSPHKSGQYQRT | 4416 |
| KTINGSGSPHFWAQNQQT | 4129 | KTINGSGSPHSWALNQQT | 4225 | KSINGSGSPHSKAQGLST | 4321 | KTINGSGSPHKSGRNQQA | 4417 |
| KTINGSGSPHLCAQNQQT | 4130 | KTINGSGSPHSWITNQQT | 4226 | KSINGSGSPHSKAQLLGT | 4322 | KTINGSGSPHKSRHNQQT | 4418 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| KTINGSGSPHLRYQNQQT | 4131 | KTINGSGSPHSWPMNQQT | 4227 | KSINGSGSPHSKTSWQQT | 4323 | KTINGSGSPHKSRQYQQT | 4419 |
| KTINGSGSPHLYYQNQQT | 4132 | KTINGSGSPHSWRSNQQT | 4228 | KSMNGHDSPHSKAQNQQT | 4324 | KTINGSGSPHRKAQAPGT | 4420 |
| KTINGSGSPHPLCQNQQT | 4133 | KTINGSGSPHSYFLNQQT | 4229 | KSTLGSGSPHSKAQNQHT | 4325 | KTINGSGSPHSKAAMKQT | 4421 |
| KTINGSGSPHRIRQNQQT | 4134 | KTINGSGSPHSYTYNQQT | 4230 | KSTLGSGSPHSKAQNQQN | 4326 | KTINGSGSPHSKAGRQQT | 4422 |
| KTINGSGSPHRLFQNQQT | 4135 | KTINGSGSPHSYWQNQQT | 4231 | KSTVGSGSPHSKAQTQQT | 4327 | KTINGSGSPHSKAGRTQT | 4423 |
| KTINGSGSPHSCGQNQQT | 4136 | KTINGSGSPHTLCQNQQT | 4232 | KTCKESGSPHSKAQNQQT | 4328 | KTINGSGSPHSKAKSNQT | 4424 |
| KTINGSGSPHSCLRNQQT | 4137 | KTINGSGSPHWLRQNQQT | 4233 | KTCKGSGSPHSKAQNQQT | 4329 | KTINGSGSPHSKALKTQT | 4425 |
| KTINGSGSPHSCLSNQQT | 4138 | KTINGSGSPHWPSQNQQT | 4234 | KTCKSSGSPHSKAQNQQT | 4330 | KTINGSGSPHSKAPRTQT | 4426 |
| KTINGSGSPHSCRLNQQT | 4139 | KTINGSGSPHYLRQNQQT | 4235 | KTDMGSGSPHSKAQNQQT | 4331 | KTINGSGSPHSKAQAART | 4427 |
| KTINGSGSPHSCSLNQQT | 4140 | KTINGSGSPHYTRQNQQT | 4236 | KTDNGIGSPHSKAQNQQT | 4332 | KTINGSGSPHSKAQAILT | 4428 |
| KTINGSGSPHSKACTLQT | 4141 | KTINGSLSPHLWAQNQQT | 4142 | KTEGGSGSPHSKAQNQQT | 4237 | KTINGSGSPHSKAQCRGT | 4429 |
| KTINGSGSPHSKAFRAQT | 4142 | KTINGSPSPHCQAQNQQT | 4142 | KTEHHSGSPHSKAQNQQT | 4238 | KTINGSGSPHSKAQGLRT | 4430 |
| KTINGSGSPHSKAIRKQT | 4143 | KTINGSRSPHLCAQNQQT | 4143 | KTEKDSGSPHSKAQNQQT | 4239 | KTINGSGSPHSKAQKGVL | 4431 |
| KTINGSGSPHSKAQASRT | 4144 | KTINGSRSPHWRAQNQQT | 4144 | KTELGHDSPHKRGQNQQT | 4240 | KTINGSGSPHSKAQKSNT | 4432 |
| KTINGSGSPHSKAQFELT | 4145 | KTINGSVSPHWLAQNQQT | 4145 | KTESVSGSPHSKAQNQQT | 4241 | KTINGSGSPHSKAQNNKF | 4433 |
| KTINGSGSPHSKAQIVIT | 4146 | KTINGTFSPHRKAQNQQT | 4146 | KTETNSGSPHSKAQNQQT | 4242 | KTINGSGSPHSKAQNRRT | 4434 |
| KTINGSGSPHSKAQLART | 4147 | KTINGWTSPHRKAQNQQT | 4147 | KTETYSGSPHSKAQNQQT | 4243 | KTINGSGSPHSKAQPKQT | 4435 |
| KTINGSGSPHSKAQLQRT | 4148 | KTINRGISPHSKAQNQQT | 4148 | KTEWLSGSPHSKAQNQQT | 4244 | KTINGSGSPHSKAQRAPT | 4436 |
| KTINGSGSPHSKAQNARR | 4149 | KTINTVRSPHSKAQNQQT | 4149 | KTFNGSGSPHKSGQNQQT | 4245 | KTINGSGSPHSKAQREHT | 4437 |
| KTINGSGSPHSKAQNCPR | 4150 | KTKLRSGSPHSKAQNQQT | 4150 | KTGLRHDSPHKSGQKQQT | 4246 | KTINGSGSPHSKAQRFGT | 4438 |
| KTINGSGSPHSKAQNMRR | 4151 | KTRLRSGSPHSKAQNQQT | 4151 | KTGLRHDSPHKSGQNQQS | 4247 | KTINGSGSPHSKAQRPCT | 4439 |
| KTINGSGSPHSKAQNRRV | 4152 | KWLLGSGSPHSKAQNQQT | 4152 | KTGVTHDSPHKSGQKQQT | 4248 | KTINGSGSPHSKAQRQAT | 4440 |
| KTINGSGSPHSKAQPSRT | 4153 | KWSQGSGSPHSKAQNQQT | 4153 | KTIDGHESPHSKAQNQQT | 4249 | KTINGSGSPHSKAQRQPT | 4441 |
| KTINGSGSPHSKAQQVKT | 4154 | KWYLGSGSPHSKAQNQQT | 4154 | KTIEGHDSPHKSGQTQQT | 4250 | KTINGSGSPHSKAQTKLT | 4442 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| KTINGSGSPHSKAQQVRT | 4155 | KYHSGSGSPHSKAQNQQT | 4251 | KTIHGHDSPHSKAQNQQT | 4347 | KTINGSGSPHSKAQTTHT | 4443 |
| KTINGSGSPHSKAQRLKT | 4156 | KYLPGSGSPHSKAQNQQT | 4252 | KTIHGHESPHSKAQNQQT | 4348 | KTINGSGSPHSKAQVQRT | 4444 |
| KTINGSGSPHSKAQRRAT | 4157 | KAINGGGSPHSKTQNQQT | 4253 | KTIIGHDSPHKSGQNRSS | 4349 | KTINGSGSPHSKAQVVRT | 4445 |
| KTINGSGSPHSKAQRRGT | 4158 | KAINGHDSPHKRSPNQQT | 4254 | KTIIGHDSPHKSGQRLGT | 4350 | KTINGSGSPHSKAQWPNT | 4446 |
| KTINGSGSPHSKAQRRRT | 4159 | KAINGHDSPHKSFSPQQT | 4255 | KTIIGSGSPHKSGQNQQT | 4351 | KTINGSGSPHSKAQYPST | 4447 |
| KTINGSGSPHSKAQRTRT | 4160 | KAINGHDSPHKSGENQQP | 4256 | KTIKGHDSPHKSGQNMLF | 4352 | KTINGSGSPHSKARALQT | 4448 |
| KTINGSGSPHSKAQRVHT | 4161 | KAINGHDSPHKSGQLART | 4257 | KTILGSGSPHSKAQNLQT | 4353 | KTINGSGSPHSKARDQHT | 4449 |
| KTINGSGSPHSKAQTYRT | 4162 | KAINGHDSPHKSGQNAFL | 4258 | KTINGCSSPHWKAQNQQT | 4354 | KTINGSGSPHSKARFQQT | 4450 |
| KTINGSGSPHSKAQVRKT | 4163 | KAINGHDSPHKSGQNAYT | 4259 | KTINGGGSTHSKAQNQQT | 4355 | KTINGSGSPHSKARRTQT | 4451 |
| KTINGSGSPHSKARGRQT | 4164 | KAINGHDSPHKSGQNFAS | 4260 | KTINGHDSPHKAGQSQQT | 4356 | KTINGSGSPHSKARSLQT | 4452 |
| KTINGSGSPHSKARLCQT | 4165 | KAINGHDSPHKSGQNLAS | 4261 | KTINGHDSPHKRGQNVPS | 4357 | KTINGSGSPHSKARVIQT | 4453 |
| KTINGSGSPHSKARLKQT | 4166 | KAINGHDSPHKSGQNLGS | 4262 | KTINGHDSPHKRGRSYQT | 4358 | KTINGSGSPHSKAWYLQT | 4454 |
| KTINGSGSPHSKARNSQT | 4167 | KAINGHDSPHKSGQNLKF | 4263 | KTINGHDSPHKTGQNPPT | 4359 | KTINGSGSPHSKGGGQQT | 1455 |
| KTINGSGSPHSKARWVQT | 4168 | KAINGHDSPHKSGQNLLK | 4264 | KTINGHDSPHSKAENQQT | 4360 | KTINGSGSPHSKGSRQQT | 4456 |
| KTINGSGSPHSKAVRWQT | 4169 | KAINGHDSPHKSGQNLSR | 4265 | KTINGHDSPHSKALSLQT | 4361 | KTINGSGSPHSKLQRQQT | 4457 |
| KTINGSGSPHSKAYTRQT | 4170 | KAINGHDSPHKSGQNLSS | 4266 | KTINGHDSPHSKAQGQQT | 4362 | KTINGSGSPHSKMLRQQT | 4458 |
| KTINGSGSPHSKCQSQQT | 4171 | KAINGHDSPHKSGQNSLG | 4267 | KTINGHDSPHSKAQHQQT | 4363 | KTINGSGSPHSKSSIKQT | 4459 |
| KTINGSGSPHSKFLRQQT | 4172 | KAINGHDSPHKSGQNTLQ | 4268 | KTINGHDSPHSKAQIQQT | 4364 | KTINGSGSPHSKVRFQQT | 4460 |
| KTINGSGSPHSKFRFQQT | 4173 | KAINGHDSPHKSGQNTSL | 4269 | KTINGHDSPHSKAQKQQT | 4365 | KTINGSGSPHSVVWNQQT | 4461 |
| KTINGSGSPHSKFRLQQT | 4174 | KAINGHDSPHKSGQRLGT | 4270 | KTINGHDSPHSKAQNLSS | 4366 | KTINGSTSPHKLAQNQQP | 4462 |
| KTINGSGSPHSKFRRQQT | 4175 | KAINGHDSPHKSGQRNYT | 4271 | KTINGHDSPHSKAQNPQT | 4367 | KTINRHDSPHKSGQRPST | 4463 |
| KTINGSGSPHSKGMKQQT | 4176 | KAINGHDSPHKSGQRPST | 4272 | KTINGHDSPHSKAQNQET | 4368 | KTINRIMSPHSKAQNQQT | 4464 |
| KTINGSGSPHSKKLRQQT | 4177 | KAINGHDSPHKSGQRPVT | 4273 | KTINGHDSPHSKAQNQHT | 4369 | KTINTARSPHSKAQNQQT | 4465 |
| KTINGSGSPHSKKRPQQT | 4178 | KAINGHDSPHKSGQVPST | 4274 | KTINGHDSPHSKAQNQLT | 4370 | KTISGHDSPHSKAQNQQT | 4466 |

TABLE 1-continued

Exemplary Peptide Sequences

| Peptide Sequence | SEQ ID NO: | Peptide Sequence | SEQ ID NO: | Peptide Sequence | SEQ ID NO: | Peptide Sequence | SEQ ID NO: |
|---|---|---|---|---|---|---|---|
| KTINGSGSPHSKKSRQQT | 4179 | KAINGHDSPHKSLSNQQT | 4275 | KTINGHDSPHSKAQNQPT | 4371 | KTISGSGSPHKSGQNQQT | 4467 |
| KTINGSGSPHSKLYRQQT | 4180 | KAINGHDSPHKSVLSQQT | 4276 | KTINGHDSPHSKAQNQQA | 4372 | KTITGHDSPHKSGQRLGT | 4468 |
| KTINGSGSPHSKLYWQQT | 4181 | KAINGHDSPHKTLQNQQT | 4277 | KTINGHDSPHSKAQNTGS | 4373 | KTITGSGSPHKSGQNQQT | 4469 |
| KTINGSGSPHSKPRMQQT | 4182 | KAINGHNSPHSKAQNQQT | 4278 | KTINGHDSPHSKAQSQQT | 4374 | KTIYGHDSPHKSGQRLGT | 4470 |
| KTINGSGSPHSKRFPQQT | 4183 | KAINGLDSPHSKAQNQQT | 4279 | KTINGHDSPHSKAQTQQT | 4375 | KTLNGHDSPHKSGQNLFL | 4471 |
| KTINGSGSPHSKRFRQQT | 4184 | KAINGSGSPHKSGQNQQT | 4280 | KTINGHDSPHSKAQYQQT | 4376 | KTLNGHDSPHKSGQNLSS | 4472 |
| KTINGSGSPHSKRPYQQT | 4185 | KAINGSGSPHSKAQGQQT | 4281 | KTINGHDSPHSKARNQQT | 4377 | KTLSFHDSPHKSGQNQQS | 4473 |
| KTINGSGSPHSKRRMQQT | 4186 | KAINGSGSPHSKAQLSGT | 4282 | KTINGHDSPHSKLPGQQT | 4378 | KTSNGSGSPHSKAQNTMT | 4474 |
| KTINGSGSPHSKRSKQQT | 4187 | KAINGSGSPHSKAQNGSL | 4283 | KTINGHDSPHSKSPNQQT | 4379 | KTTNGHDSPHSKAQNQQT | 4475 |
| KTINGSGSPHSKRSRQQT | 4188 | KAINGSGSPHSKAQNSLL | 4284 | KTINGHESPHKSGQNAFL | 4380 | KTVNGGGSPHSKAQNQQT | 4476 |
| KTINGSGSPHSKRTMQQT | 4189 | KAINGSGSPHSKAVGLQT | 4285 | KTINGIGSPHSKAPNEQT | 4381 | KTVNGHDSPHKSGQNVSL | 4477 |
| KTINGSGSPHSKRTRQQT | 4190 | KAINGSGSPHSLLQQT | 4286 | KTINGQDSPHKSGQNLHM | 4382 | KTVNGHDSPHKSGQRPST | 4478 |
| KTINGSGSPHSKRVRQQT | 4191 | KAINGSGSPHSKSLPQQT | 4287 | KTINGRGSPHSKAQIGMT | 4383 | KTVNGHDSPHKSGQTQQA | 4479 |
| KTINGSGSPHSKRYIQQT | 4192 | KAINGSGSPHSKSTFQQT | 4288 | KTINGRGSPHSKAQNQVL | 4384 | KTVNGHESPHSKAQNQQT | 4480 |
| KTINGSGSPHSKRYNQQT | 4193 | KAITGHDSPHSKAQNQQT | 4289 | KTINGRGSPHSKAQSPTT | 4385 | KTVNGSGSPHSKAQGLST | 4481 |
| KTINGSGSPHSKRYPQQT | 4194 | KDVMGSGSPHSKAQNQQT | 4290 | KTINGRGSPHSKATSFQT | 4386 | KTVNGSGSPHSKAQNVTS | 4482 |
| KTINGSGSPHSKRYSQQT | 4195 | KEIVGSGSPHSKAQNQQT | 4291 | KTINGSGSPHFVVQNQQT | 4387 | KTVPASGSPHSKAQNQQT | 4483 |
| NTINGSGSPHSKAHNQQT | 4484 | TTINGGGSPHSKAQNQQT | 4485 | | | | |

TABLE 2A

Exemplary Peptide Sequences

| SEQ ID NO: | Amino Acid Sequence | SEQ ID NO: | Nucleotide Sequence |
|---|---|---|---|
| 941 | SPHSKA | 942 | AGCCCACACAGCAAAGCA |
| 943 | HDSPHKSG | 944 | CACGACAGCCCACACAAAGCGGA |
| 2 | HDSPHK | 3 | CACGACAGCCCACACAAA |

TABLE 2B

Exemplary Peptide Sequences

| Amino Acid Sequence | SEQ ID NO: | Amino Acid Sequence | SEQ ID NO: | Amino Acid Sequence | SEQ ID NO: | Amino Acid Sequence | SEQ ID NO: |
|---|---|---|---|---|---|---|---|
| SPHSKA | 945 | SPHKKN | 954 | SPHKTS | 963 | SPHTRG | 972 |
| SPHKSG | 946 | SPHVRM | 955 | SPHKTT | 964 | SPHVRG | 973 |
| SPHARM | 947 | SPHRKA | 956 | SPHKTY | 965 | SPHKRG | 974 |
| SPHVKS | 948 | SPHKFG | 957 | SPHKYG | 966 | SPHGAR | 975 |
| SPHASR | 949 | SPHKIG | 958 | SPHSKD | 967 | SPHRSG | 976 |
| SPHVKI | 950 | SPHKLG | 959 | SPHSKP | 968 | SPHKSA | 977 |
| SPHKSR | 951 | SPHSKL | 960 | SPHSRA | 969 | SPHSKR | 978 |
| SPHSLR | 952 | SPHSRG | 961 | SPHSSR | 970 | SPHFLR | 979 |
| SPHSKW | 953 | SPHSKS | 962 | SPHWKA | 971 | SPHVRR | 980 |
| STHASR | 985 | SQHKSG | 986 | HDSPHK | 2 | HDSPHSKA | 4486 |

In some embodiments, the peptide comprises an amino acid sequence having the formula [N1]-[N2]-[N3], wherein [N42] comprises the amino acid sequence of SPH and [N43] comprises X4, X5, and X6, wherein at least one of X4, X5, or X6 is a basic amino acid, e.g., a K or R. In some embodiments, position X4 of [N42] is K. In some embodiments, position X5 of [N42] is K.

In some embodiments, [N1] comprises X1, X2, and X3, wherein at least one of X1, X2, or X3 is G. In some embodiments, position X1 of [N1] is G, V, R, D, E, M, T, I, S, A, N, L, K, H, P, W, or C. In some embodiments, position X2 of [N41] is: S, V, L, N, D, H, R, P, G, T, I, A, E, Y, M, or Q. In some embodiments, position X3 of [N41] is: G, C, L, D, E, Y, H, V, A, N, P, or S. In some embodiments, [N1] comprises GS, SG, GH, HD, GQ, QD, VS, CS, GR, RG, QS, SH, MS, RN, TS, IS, GP, ES, SS, GN, AS, NS, LS, GG, KS, GT, PS, RS, GI, WS, DS, ID, GL, DA, DG, ME, EN, KN, KE, AI, NG, PG, TG, SV, IG, LG, AG, EG, SA, YD, HE, HG, RD, ND, PD, MG, QV, DD, HN, HP, GY, GM, GD, or HS. In some embodiments, [N1] comprises GS, SG, GH, or HD. In some embodiments [N1] is or comprises GSG, GHD, GQD, VSG, CSG, GRG, CSH, GQS, GSH, RVG, GSC, GLL, GDD, GHE, GNY, MSG, RNG, TSG, ISG, GPG, ESG, SSG, GNG, ASG, NSG, LSG, GGG, KSG, HSG, GTG, PSG, GSV, RSG, GIG, WSG, DSG, IDG, GLG, DAG, DGG, MEG, ENG, GSA, KNG, KEG, AIG, GYD, GHG, GRD, GND, GPD, GMG, GQV, GHN, GHP, or GHS. In some embodiments, [N1] is or comprises GSG. In some embodiments, [N1] is or comprises GHD. In some embodiments, [N1]-[N2] comprises SGSPH (SEQ ID NO: 4752), HDSPH (SEQ ID NO: 4703), QDSPH (SEQ ID NO: 4753), RGSPH (SEQ ID NO: 4754), SHSPH (SEQ ID NO: 4755), QSSPH (SEQ ID NO: 4756), DDSPH (SEQ ID NO: 4757), HESPH (SEQ ID NO: 4758), NYSPH (SEQ ID NO: 4759), VGSPH (SEQ ID NO: 4760), SCSPH (SEQ ID NO: 4761), LLSPH (SEQ ID NO: 4762), NGSPH (SEQ ID NO: 4763), PGSPH (SEQ ID NO: 4764), GGSPH (SEQ ID NO: 4765), TGSPH (SEQ ID NO: 4766), SVSPH (SEQ ID NO: 4767), IGSPH (SEQ ID NO: 4768), DGSPH (SEQ ID NO: 4769), LGSPH (SEQ ID NO: 4770), AGSPH (SEQ ID NO: 4771), EGSPH (SEQ ID NO: 4772), SASPH (SEQ ID NO: 4773), YDSPH (SEQ ID NO: 4774), HGSPH (SEQ ID NO: 4775), RDSPH (SEQ ID NO: 4776), NDSPH (SEQ ID NO: 4777), PDSPH (SEQ ID NO: 4778), MGSPH (SEQ ID NO: 4779), QVSPH (SEQ ID NO: 4780), HNSPH (SEQ ID NO: 4781), HPSPH (SEQ ID NO: 4782), or HSSPH (SEQ ID NO: 4783); an amino acid sequence comprising any portion of any of the aforesaid amino acid sequences (e.g., any 2, 3, or 4 amino acids, e.g., consecutive amino acids) thereof; an amino acid sequence comprising one, two, or three but no more than four modifications, e.g., substitutions (e.g., conservative substitutions), insertions, or deletions, relative to any of the aforesaid amino acid sequences; or an amino acid sequence comprising one, two, or three but no more than four different amino acids, relative to any one of the aforesaid amino acid sequences. In some embodiments, [N1]-[N2] is or comprises GSGSPH (SEQ ID NO: 4695), GHDSPH (SEQ ID NO: 4784), GQDSPH (SEQ ID NO: 4785), VSGSPH (SEQ ID NO: 4786), CSGSPH (SEQ ID NO: 4787), GRGSPH (SEQ ID NO: 4788), CSHSPH (SEQ ID NO: 4789), GQSSPH (SEQ ID NO: 4790), GSHSPH (SEQ ID NO: 4791), GDDSPH (SEQ ID NO: 4792), GHESPH (SEQ ID NO: 4793), GNYSPH (SEQ ID NO: 4794), RVGSPH (SEQ ID NO: 4795), GSCSPH (SEQ ID NO: 4796), GLLSPH (SEQ ID NO: 4797), MSGSPH (SEQ ID NO: 4798), RNGSPH (SEQ ID NO: 4799), TSGSPH (SEQ ID NO: 4800), ISGSPH (SEQ ID NO: 4801), GPGSPH (SEQ ID NO: 4802), ESGSPH (SEQ ID NO: 4803), SSGSPH (SEQ ID NO: 4804), GNGSPH (SEQ ID NO: 4805), ASGSPH (SEQ ID NO: 4806), NSGSPH (SEQ ID NO: 4807), LSGSPH (SEQ ID NO: 4808), GGGSPH (SEQ ID NO: 4809), KSGSPH (SEQ ID NO: 4810), HSGSPH (SEQ ID NO: 4811), GTGSPH (SEQ ID NO: 4812), PSGSPH (SEQ ID NO: 4813), GSVSPH (SEQ ID NO: 4814), RSGSPH (SEQ ID NO: 4815), GIGSPH (SEQ ID NO: 4816), WSGSPH (SEQ ID NO: 4817), DSGSPH (SEQ ID NO: 4818), IDGSPH (SEQ ID NO: 4819), GLGSPH (SEQ ID NO: 4820), DAGSPH (SEQ ID NO: 4821), DGGSPH (SEQ ID NO: 4822), MEGSPH (SEQ ID NO: 4823), ENGSPH (SEQ ID NO: 4824), GSASPH (SEQ ID NO: 4825), KNGSPH (SEQ ID NO: 4826), KEGSPH (SEQ ID NO: 4827), AIGSPH (SEQ ID NO: 4828), GYDSPH (SEQ ID NO: 4829), GHGSPH (SEQ ID NO: 4830), GRDSPH (SEQ ID NO: 4831), GNDSPH (SEQ ID NO: 4832), GPDSPH (SEQ ID NO: 4833), GMGSPH (SEQ ID NO: 4834), GQVSPH (SEQ ID NO: 4835), GHNSPH (SEQ ID NO: 4836), GHPSPH (SEQ ID NO: 4837), or GHSSPH (SEQ ID NO: 4838), an amino acid sequence comprising any portion of any of the aforesaid amino acid sequences (e.g., any 2, 3, 4, or 5 amino acids, e.g., consecutive amino acids) thereof; an amino acid sequence comprising one, two, or three but no more than four modifications, e.g., substitutions (e.g., conservative substitutions), insertions, or deletions, relative to any of the aforesaid amino acid sequences; or an amino acid sequence comprising one, two, or three but no more than four different amino acids, relative to any one of the aforesaid amino acid sequences. In some embodiments, [N1]-[N2] is or comprises GSGSPH (SEQ ID NO: 4695). In some embodiments, [N1]-[N2] is or comprises GHDSPH (SEQ ID NO: 4784).

In some embodiments, X4, X5, or both of [N3] are K. In some embodiments, X4, X5, or X6 of [N3] is R. In some embodiments, position X4 of [N3] is: A, K, V, S, T, G, F, W, V, N, or R. In some embodiments, position X5 of [N3] is: S, K, T, F, I, L, Y, H, M, or R. In some embodiments, position X6 of [N3] is: G, R, A, M, I, N, T, Y, D, P, V, L, E, W, N, Q, K, or S. In some embodiments, [N3] comprises SK, KA, KS, AR, RM, VK, AS, SR, VK, KR, KK, KN, VR, RS, RK, KT, TS, KF, FG, KI, IG, KL, LG, TT, TY, KY, YG, KD, KP, TR, RG, VR, GA, SL, SS, FL, WK, SA, RA, LR, KW, RR, GK, TK, NK, AK, KV, KG, KH, KM, TG, SE, SV, SW, SN, HG, SQ, LW, MG, MA, or SG. In some embodiments, [N3] comprises SK, KA, KS, or SG. In some embodiments, [N3] is or comprises SKA, KSG, ARM, VKS, ASR, VKI, KKN, VRM, RKA, KTS, KFG, KIG, KLG, KTT, KTY, KYG, SKD, SKP, TRG, VRG, KRG, GAR, KSA, KSR, SKL, SRA, SKR, SLR, SRG, SSR, FLR, SKW, SKS, WKA, VRR, SKV, SKT, SKG, GKA, TKA, NKA, SKL, SKN, AKA, KTG, KSL, KSE, KSV, KSW, KSN, KHG, KSQ, KSK, KLW, WKG, KMG, KMA, or RSG. In some embodiments, [N3] is or comprises SKA. In some embodiments, [N3] is or comprises KSG. In some embodiments, [N2]-[N3] comprises SPHSK (SEQ ID NO: 4701), SPHKS (SEQ ID NO: 4704), SPHAR (SEQ ID NO: 4705), SPHVK (SEQ ID NO: 4706), SPHAS (SEQ ID NO: 4707), SPHKK (SEQ ID NO: 4708), SPHVR (SEQ ID NO: 4709), SPHRK (SEQ ID NO: 4710), SPHKT (SEQ ID NO: 4711), SPHKF (SEQ ID NO: 4712), SPHKI (SEQ ID NO: 4713), SPHKL (SEQ ID NO: 4714), SPHKY (SEQ ID NO: 4715), SPHTR (SEQ ID NO: 4716), SPHKR (SEQ ID NO: 4717), SPHGA (SEQ ID NO: 4718), SPHSR (SEQ ID NO: 4719), SPHSL (SEQ ID NO: 4720), SPHSS (SEQ ID NO: 4721), SPHFL (SEQ ID NO: 4722), SPHWK (SEQ ID NO: 4723), SPHGK (SEQ ID NO: 4724), SPHTK (SEQ ID NO: 4725), SPHNK (SEQ ID NO: 4726), SPHAK (SEQ ID NO: 4727), SPHKH (SEQ ID NO: 4728), SPHKM (SEQ ID NO: 4729), or SPHRS (SEQ ID NO: 4730). In some embodiments [N2]-[N3] comprises SPHSK (SEQ ID NO: 4701) or SPHKS (SEQ ID NO: 4704). In some embodiments, [N2]-[N3] is or comprises (SEQ ID NO: 941), SPHKSG (SEQ ID NO: 946), SPHARM (SEQ ID NO: 947), SPHVKS (SEQ ID NO: 948), SPHASR (SEQ ID NO: 949), SPHVKI (SEQ ID NO: 950), SPHKKN (SEQ ID NO: 954), SPHVRM (SEQ ID NO: 955), SPHRKA (SEQ ID NO: 956), SPHKFG (SEQ ID NO: 957), SPHKIG (SEQ ID NO: 958), SPHKLG (SEQ ID NO: 959), SPHKTS (SEQ ID NO: 963), SPHKTT (SEQ ID NO: 964), SPHKTY (SEQ ID NO: 965), SPHKYG (SEQ ID NO: 966), SPHSKD (SEQ ID NO: 967), SPHSKP (SEQ ID NO: 968), SPHTRG (SEQ ID NO: 972), SPHVRG (SEQ ID NO: 973), SPHKRG (SEQ ID NO: 974), SPHGAR (SEQ ID NO: 975), SPHKSA (SEQ ID NO: 977), SPHKSR (SEQ ID NO: 951), SPHSKL (SEQ ID NO: 960), SPHSRA (SEQ ID NO: 969), SPHSKR (SEQ ID NO: 978), SPHSLR (SEQ ID NO: 952), SPHSRG (SEQ ID NO: 961), SPHSSR (SEQ ID NO: 970), SPHFLR (SEQ ID NO: 979), SPHSKW (SEQ ID NO: 953), SPHSKS (SEQ ID NO: 962), SPHWKA (SEQ ID NO: 971), SPHVRR (SEQ ID NO: 980), SPHSKT (SEQ ID NO: 4731), SPHSKG (SEQ ID NO: 4732), SPHGKA (SEQ ID NO: 4733), SPHNKA (SEQ ID NO: 4734), SPHSKN (SEQ ID NO: 4735), SPHAKA (SEQ ID NO: 4736), SPHSKV (SEQ ID NO: 4737), SPHKTG (SEQ ID NO: 4738), SPHTKA (SEQ ID NO: 4739), SPHKSL (SEQ ID NO: 4740), SPHKSE (SEQ ID NO: 4741), SPHKSV (SEQ ID NO: 4742), SPHKSW (SEQ ID NO: 4743), SPHKSN (SEQ ID NO: 4744), SPHKHG (SEQ ID NO: 4745), SPHKSQ (SEQ ID NO: 4746), SPHKSK (SEQ ID NO: 4747), SPHKLW (SEQ ID NO: 4748), SPHWKG (SEQ ID NO: 4749), SPHKMG (SEQ ID NO: 4750), SPHKMA (SEQ ID NO: 4751), or SPHRSG (SEQ ID NO: 976). In some embodiments, [N2]-[N3]is or comprises SPHSKA (SEQ ID NO: 941). In some embodiments, [N2]-[N3] is or comprises SPHKSG (SEQ ID NO: 946).

In some embodiments, [N1]-[N2]-[N3] comprises comprises SGSPHSK (SEQ ID NO: 4839), HDSPHKS (SEQ ID NO: 4840), SGSPHAR (SEQ ID NO: 4841), SGSPHVK (SEQ ID NO: 4842), QDSPHKS (SEQ ID NO: 4843), SGSPHKK (SEQ ID NO: 4844), SGSPHVR (SEQ ID NO: 4845), SGSPHAS (SEQ ID NO: 4846), SGSPHRK (SEQ ID NO: 4847), SGSPHKT (SEQ ID NO: 4848), SHSPHKS (SEQ ID NO: 4849), QSSPHRS (SEQ ID NO: 4850), RGSPHAS (SEQ ID NO: 4851), RGSPHSK (SEQ ID NO: 4852), SGSPHKF (SEQ ID NO: 4853), SGSPHKI (SEQ ID NO: 4854), SGSPHKL (SEQ ID NO: 4855), SGSPHKY (SEQ ID NO: 4856), SGSPHTR (SEQ ID NO: 4857), SHSPHKR (SEQ ID NO: 4858), SGSPHGA (SEQ ID NO: 4859), HDSPHKR (SEQ ID NO: 4860), DDSPHKS (SEQ ID NO: 4861), HESPHKS (SEQ ID NO: 4862), NYSPHKI (SEQ ID NO: 4863), SGSPHSR (SEQ ID NO: 4864), SGSPHSL (SEQ ID NO: 4865), SGSPHSS (SEQ ID NO: 4866), VGSPHSK (SEQ ID NO: 4867), SCSPHRK (SEQ ID NO: 4868), SGSPHFL (SEQ ID NO: 4869), LLSPHWK (SEQ ID NO: 4870), NGSPHSK (SEQ ID NO: 4871), PGSPHSK (SEQ ID NO: 4872), GGSPHSK (SEQ ID NO: 4873), TGSPHSK (SEQ ID NO: 4874), SVSPHGK (SEQ ID NO: 4875), SGSPHTK (SEQ ID NO: 4876), IGSPHSK (SEQ ID NO: 4877), DGSPHSK (SEQ ID NO: 4878), SGSPHNK (SEQ ID NO: 4879), LGSPHSK (SEQ ID NO: 4880), AGSPHSK (SEQ ID NO: 4881), EGSPHSK (SEQ ID NO: 4882), SASPHSK (SEQ ID NO: 4883), SGSPHAK (SEQ ID NO: 4884), HDSPHKI (SEQ ID NO: 4885), YDSPHKS (SEQ ID NO: 4886), HDSPHKT (SEQ ID NO: 4887), RGSPHKR (SEQ ID NO: 4888), HGSPHSK (SEQ ID NO: 4889), RDSPHKS (SEQ ID NO: 4890), NDSPHKS (SEQ ID NO: 4891), QDSPHKI (SEQ ID NO: 4892), PDSPHKI (SEQ ID NO: 4893), PDSPHKS (SEQ ID NO: 4894), MGSPHSK (SEQ ID NO: 4895), HDSPHKH (SEQ ID NO: 4896), QVSPHKS (SEQ ID NO: 4897), HNSPHKS (SEQ ID NO: 4898), NGSPHKR (SEQ ID NO: 4899), HDSPHKY (SEQ ID NO: 4900), NDSPHKI (SEQ ID NO: 4901), HDSPHKL (SEQ ID NO: 4902), HPSPHWK (SEQ ID NO: 4903), HDSPHKM (SEQ ID NO: 4904), or HSSPHRS (SEQ ID NO: 4905). In some embodiments, [N1]-[N2]-[N3] is GSGSPHSKA (SEQ ID NO: 4697), GHDSPHKSG (SEQ ID NO: 4698), GSGSPHARM (SEQ ID NO: 4906), GSGSPHVKS (SEQ ID NO: 4907), GQDSPHKSG (SEQ ID NO: 4908), GSGSPHASR (SEQ ID NO: 4909), GSGSPHVKI (SEQ ID NO: 4910), GSGSPHKKN (SEQ ID NO: 4911), GSGSPHVRM (SEQ ID NO: 4912), VSGSPHSKA (SEQ ID NO: 4913), CSGSPHSKA (SEQ ID NO: 4914), GSGSPHRKA (SEQ ID NO: 4915), CSGSPHKTS (SEQ ID NO: 4916), CSHSPHKSG (SEQ ID NO: 4917), GQSSPHRSG (SEQ ID NO: 4918), GRGSPHASR (SEQ ID NO: 4919), GRGSPHSKA (SEQ ID NO: 4920), GSGSPHKFG (SEQ ID NO: 4921), GSGSPHKIG (SEQ ID NO: 4922), GSGSPHKLG (SEQ ID NO: 4923), GSGSPHKTS (SEQ ID NO: 4924), GSGSPHKTT (SEQ ID NO: 4925), GSGSPHKTY (SEQ ID NO: 4926), GSGSPHKYG (SEQ ID NO: 4927), GSGSPHSKD (SEQ ID NO: 4928), GSGSPHSKP (SEQ ID NO: 4929), GSGSPHTRG (SEQ ID NO: 4930), GSGSPHVRG (SEQ ID NO: 4931), GSHSPHKRG (SEQ ID NO: 4932), GSHSPHKSG (SEQ ID NO: 4933), VSGSPHASR (SEQ ID NO: 4934), VSGSPHGAR (SEQ ID NO: 4935), VSGSPHKFG (SEQ ID NO: 4936), GHDSPHKRG (SEQ ID NO: 4937), GDDSPHKSG (SEQ ID NO: 4938), GHESPHKSA (SEQ ID NO: 4939), GHDSPHKSA (SEQ ID NO: 4940), GNYSPHKIG (SEQ ID NO: 4941), GHDSPHKSR (SEQ ID NO: 4942), GSGSPHSKL (SEQ ID NO: 4943), GSGSPHSRA (SEQ ID NO: 4944), GSGSPHSKR (SEQ ID NO: 4945, GSGSPHSLR(SEQ ID NO:4946) GSGSPHSRG (SEQ ID NO: 4947), GSGSPHSSR(SEQ ID NO: 4948), RVGSPHSKA (SEQ ID NO: 4949), GSCSPHRKA (SEQ ID NO: 4950), GSGSPHFLR (SEQ ID NO: 4951), GSGSPHSKW (SEQ ID NO: 4952), GSGSPHSKS (SEQ ID NO: 4953), GLLSPHWKA (SEQ ID NO: 4954), GSGSPHVRR (SEQ ID NO: 4955), GSGSPHSKV (SEQ ID NO: 4956), MSGSPHSKA (SEQ ID NO: 4957), RNGSPHSKA (SEQ ID NO: 4958), TSGSPHSKA (SEQ ID NO: 4959), ISGSPHSKA (SEQ ID NO: 4960), GPGSPHSKA (SEQ ID NO: 4961), GSGSPHSKT (SEQ ID NO: 4962), ESGSPHSKA (SEQ ID NO: 4963), SSGSPHSKA (SEQ ID NO: 4964), GNGSPHSKA (SEQ ID NO: 4965), ASGSPHSKA (SEQ ID NO: 4966), NSGSPHSKA (SEQ ID NO: 4967), LSGSPHSKA (SEQ ID NO: 4968), GGGSPHSKA (SEQ ID NO: 4969), KSGSPHSKA (SEQID}KI4970), GGGSPHSKS(SEQ ID NO: 4971), GSGSPHSKG(SEQ ID NO: 4972), HSGSPHSKA (SEQ ID NO: 4973), GTGSPHSKA (SEQ ID NO: 4974), PSGSPHSKA (SEQ ID NO: 4975), GSVSPHGKA (SEQ ID NO: 4976), RSGSPHSKA (SEQ ID NO: 4977), GSGSPHTKA (SEQ ID NO: 4978), GIGSPHSKA (SEQ ID NO: 4979), WSGSPHSKA (SEQ ID NO: 4980), DSGSPHSKA (SEQ ID NO: 4981), IDGSPHSKA (SEQ ID NO: 4982), GSGSPHNKA (SEQ ID NO: 4983), GLGSPHSKS (SEQ ID NO: 4984), DAGSPHSKA (SEQ ID NO: 4985), DGGSPHSKA (SEQ ID NO: 4986), MEGSPHSKA (SEQ ID NO: 4987), ENGSPHSKA (SEQ ID NO: 4988), GSASPHSKA (SEQ ID NO: 4989), GNGSPHSKS (SEQ ID NO: 4990), KNGSPHSKA (SEQ ID NO: 4991), KEGSPHSKA (SEQ ID NO: 4992), AIGSPHSKA (SEQ ID NO: 4993), GSGSPHSKN (SEQ ID NO: 4994), GSGSPHAKA (SEQ ID NO: 4995), GHDSPHKIG (SEQ ID NO: 4996), GYDSPHKSG (SEQ ID NO: 4997), GHESPHKSG (SEQ ID NO: 4998), GHDSPHKTG (SEQ ID NO: 4999), GRGSPHKRG (SEQ ID NO: 5000), GQDSPHKSG (SEQ ID NO: 4908), GHDSPHKSL (SEQ ID NO: 5001), GHGSPHSKA (SEQ ID NO: 5002), GHDSPHKSE (SEQ ID NO: 5003), VSGSPHSKA (SEQ ID NO: 4913), GRDSPHKSG (SEQ ID NO: 5004), GNDSPHKSV (SEQ ID NO: 5005), GQDSPHKIG (SEQ ID NO: 5006), GHDSPHKSV (SEQ ID NO: 5007), GPDSPHKIG (SEQ ID NO: 5008), GPDSPHKSG (SEQ ID NO: 5009), GHDSPHKSW (SEQ ID NO: 5010), GHDSPHKSN (SEQ ID NO: 5011), GMGSPHSKT (SEQ ID NO: 5012), GHDSPHKHG (SEQ ID NO: 5013), GQVSPHKSG (SEQ ID NO: 5014), GDDSPHKSV (SEQ ID NO: 5015), GHNSPHKSG (SEQ ID NO: 5016), GNGSPHKRG (SEQ ID NO: 5017), GHDSPHKYG (SEQ ID NO: 5018), GHDSPHKSQ (SEQ ID NO: 5019), GNDSPHKIG (SEQ ID NO: 5020), GHDSPHKSK (SEQ ID NO: 5021), GHDSPHKLW (SEQ ID NO: 5022), GHPSPHWKG (SEQ ID NO: 5023), GHDSPHKMG (SEQ ID NO: 5024), GHDSPHKMA (SEQ ID NO: 5025), or GHSSPHRSG (SEQ ID NO: 5026); an amino acid sequence comprising any portion of any of the aforesaid amino acid sequences (e.g., any 2, 3, 4, 5, 6, 7, or 8 amino acids, e.g., consecutive amino acids) thereof; an amino acid sequence comprising one, two, or three but no more than four modifications, e.g., substitutions (e.g., conservative substitutions), insertions, or deletions, relative to any of the aforesaid amino acid sequences; or an amino acid sequence comprising one, two, or three but no more than four different amino acids, relative to any one of the aforesaid amino acid sequences. In some embodiments, [N1]-[N2]-[N3] is or comprises GSGSPHSKA (SEQ ID NO: 4697). In some embodiments, [N1]-[N2]-[N3] is or comprises GHDSPHKSG (SEQ ID NO: 4698).

In some embodiments, the peptide comprising an amino acid sequence having the formula [N1]-[N2]-[N3], further comprises [N4] which comprises X7 X8 X9 X10. In some embodiments, position X7 of [N4] is W, Q, K, R, G, L, V, S, P, H, K, I, M, A, E, or F. In some embodiments, position X8 of [N4] is N, Y, C, K, T, H, R, D, V, S, P, G, W, E, F, A, I, M, Q, or L. In some embodiments, position X9 of [N4] is Q, G, K, H, R, T, L, D, A, P, I, F, V, M, W, Y, S, E, N, or Y. In some embodiments, position X10 of [N4] is Q, H, L, R, W, K, A, P, E, M, I, S, G, N, Y, C, V, T, D, or V. In some embodiments [N4] is or comprises QNQQ (SEQ ID NO: 5028), WNQQ (SEQ ID NO: 5029), QYYV (SEQ ID NO: 5030), RRQQ (SEQ ID NO: 5031), QNQQ (SEQ ID NO: 5028), GCGQ (SEQ ID NO: 5032), LRQQ (SEQ ID NO: 5033), RNQQ (SEQ ID NO: 5034), VNQQ (SEQ ID NO: 5035), FRLQ (SEQ ID NO: 5036), FNQQ (SEQ ID NO: 5037), LLQQ (SEQ ID NO: 5038), SNQQ (SEQ ID NO: 5039), RLQQ (SEQ ID NO: 5040), LNQQ (SEQ ID NO: 5041), QRKL (SEQ ID NO: 5042), LRRQ (SEQ ID NO: 5043), QRLR (SEQ ID NO: 5044), QRRL (SEQ ID NO: 5045), RRLQ (SEQ ID NO: 5046), RLRQ (SEQ ID NO: 5047), SKRQ (SEQ ID NO: 5048), QLYR (SEQ ID NO: 5049), QLTV (SEQ ID NO: 5050), QNKQ (SEQ ID NO: 5051), KNQQ (SEQ ID NO: 5052), QKQQ (SEQ ID NO: 5053), QTQQ (SEQ ID NO: 5054), QNHQ (SEQ ID NO: 5055), QHQQ (SEQ ID NO: 5056), QNQH (SEQ ID NO: 5057), QHRQ (SEQ ID NO: 5058), LTQQ (SEQ ID NO: 5059), QNQW (SEQ ID NO: 5060), QNTH (SEQ ID NO: 5061), RRRQ (SEQ ID NO: 5062), QYQQ (SEQ ID NO: 5063), QNDQ (SEQ ID NO: 5064), QNRH (SEQ ID NO: 5065), RDQQ (SEQ ID NO: 5066), PNLQ (SEQ ID NO: 5067), HVRQ (SEQ ID NO: 5068), PNQH (SEQ ID NO:

5069), HNQQ (SEQ ID NO: 5070), QSQQ (SEQ ID NO: 5071), QPAK (SEQ ID NO: 5072), QNLA (SEQ ID NO: 5073), QNQL (SEQ ID NO: 5074), QGQQ (SEQ ID NO: 5075), LNRQ (SEQ ID NO: 5076), QNPP (SEQ ID NO: 5077), QNLQ (SEQ ID NO: 5078), QDQE (SEQ ID NO: 5079), QDQQ (SEQ ID NO: 5080), HWQQ (SEQ ID NO: 5081), PNQQ (SEQ ID NO: 5082), PEQQ (SEQ ID NO: 5083), QRTM (SEQ ID NO: 5084), LHQH (SEQ ID NO: 5085), QHRI (SEQ ID NO: 5086), QYIH (SEQ ID NO: 5087), QKFE (SEQ ID NO: 5088), QFPS (SEQ ID NO: 5089), QNPL (SEQ ID NO: 5090), QAIK (SEQ ID NO: 5091), QNRQ (SEQ ID NO: 5092), QYQH (SEQ ID NO: 5093), QNPQ (SEQ ID NO: 5094), QHQL (SEQ ID NO: 5095), QSPP (SEQ ID NO: 5096), QAKL (SEQ ID NO: 5097), KSQQ (SEQ ID NO: 5098), QDRP (SEQ ID NO: 5099), QNLG (SEQ ID NO: 5100), QAFH (SEQ ID NO: 5101), QNAQ (SEQ ID NO: 5102), HNQL (SEQ ID NO: 5103), QKLN (SEQ ID NO: 5104), QNVQ (SEQ ID NO: 5105), QAQQ (SEQ ID NO: 5106), QTPP (SEQ ID NO: 5107), QPPA (SEQ ID NO: 5108), QERP (SEQ ID NO: 5109), QDLQ (SEQ ID NO: 5110), QAMH (SEQ ID NO: 5111), QHPS (SEQ ID NO: 5112), PGLQ (SEQ ID NO: 5113), QGIR (SEQ ID NO: 5114), QAPA (SEQ ID NO: 5115), QIPP (SEQ ID NO: 5116), QTQL (SEQ ID NO: 5117), QAPS (SEQ ID NO: 5118), QNTY (SEQ ID NO: 5119), QDKQ (SEQ ID NO: 5120), QNHL (SEQ ID NO: 5121), QIGM (SEQ ID NO: 5122), LNKQ (SEQ ID NO: 5123), PNQL (SEQ ID NO: 5124), QLQQ (SEQ ID NO: 5125), QRMS (SEQ ID NO: 5126), QGIL (SEQ ID NO: 5127), QDRQ (SEQ ID NO: 5128), RDWQ (SEQ ID NO: 5129), QERS (SEQ ID NO: 5130), QNYQ (SEQ ID NO: 5131), QRTC (SEQ ID NO: 5132), QIGH (SEQ ID NO: 5133), QGAI (SEQ ID NO: 5134), QVPP (SEQ ID NO: 5135), QVQQ (SEQ ID NO: 5136), LMRQ (SEQ ID NO: 5137), QYSV (SEQ ID NO: 5138), QAIT (SEQ ID NO: 5139), QKTL (SEQ ID NO: 5140), QLHH (SEQ ID NO: 5141), QNII (SEQ ID NO: 5142), QGHH (SEQ ID NO: 5143), QSKV (SEQ ID NO: 5144), QLPS (SEQ ID NO: 5145), IGKQ (SEQ ID NO: 5146), QAIH (SEQ ID NO: 5147), QHGL (SEQ ID NO: 5148), QFMC (SEQ ID NO: 5149), QNQM (SEQ ID NO: 5150), QHLQ (SEQ ID NO: 5151), QPAR (SEQ ID NO: 5152), QSLQ (SEQ ID NO: 5153), QSQL (SEQ ID NO: 5154), HSQQ (SEQ ID NO: 5155), QMPS (SEQ ID NO: 5156), QGSL (SEQ ID NO: 5157), QVPA (SEQ ID NO: 5158), HYQQ (SEQ ID NO: 5159), QVPS (SEQ ID NO: 5160), RGEQ (SEQ ID NO: 5161), PGQQ (SEQ ID NO: 5162), LEQQ (SEQ ID NO: 5163), QNQS (SEQ ID NO: 5164), QKVI (SEQ ID NO: 5165), QNND (SEQ ID NO: 5166), QSVH (SEQ ID NO: 5167), QPLG (SEQ ID NO: 5168), HNQE (SEQ ID NO: 5169), QIQQ (SEQ ID NO: 5170), QVRN (SEQ ID NO: 5171), PSNQ (SEQ ID NO: 5172), QVGH (SEQ ID NO: 5173), QRDI (SEQ ID NO: 5174), QMPN (SEQ ID NO: 5175), RGLQ (SEQ ID NO: 5176), PSLQ (SEQ ID NO: 5177), QRDQ (SEQ ID NO: 5178), QAKG (SEQ ID NO: 5179), QSAH (SEQ ID NO: 5180), QSTM (SEQ ID NO: 5181), QREM (SEQ ID NO: 5182), QYRA (SEQ ID NO: 5183), QRQQ (SEQ ID NO: 5184), QWQQ (SEQ ID NO: 5185), QRMN (SEQ ID NO: 5186), GDSQ (SEQ ID NO: 5187), QKIS (SEQ ID NO: 5188), PSMQ (SEQ ID NO: 5189), SPRQ (SEQ ID NO: 5190), MEQQ (SEQ ID NO: 5191), QYQN (SEQ ID NO: 5192), QIRQ (SEQ ID NO: 5193), QSVQ (SEQ ID NO: 5194), RSQQ (SEQ ID NO: 5195), QNKL (SEQ ID NO: 5196), QIQH (SEQ ID NO: 5197), PRQQ (SEQ ID NO: 5198), HTQQ (SEQ ID NO: 5199), QRQH (SEQ ID NO: 5200), RNQE (SEQ ID NO: 5201), QSKQ (SEQ ID NO: 5202), QNQP (SEQ ID NO: 5203), QSPQ (SEQ ID NO: 5204), QTRQ (SEQ ID NO: 5205), QNLH (SEQ ID NO: 5206), QNQE (SEQ ID NO: 5207), LNQP (SEQ ID NO: 5208), QNQD (SEQ ID NO: 5209), QNLL (SEQ ID NO: 5210), QLVI (SEQ ID NO: 5211), RTQE (SEQ ID NO: 5212), QTHQ (SEQ ID NO: 5213), QDQH (SEQ ID NO: 5214), QSQH (SEQ ID NO: 5215), VRQQ (SEQ ID NO: 5216), AWQQ (SEQ ID NO: 5217), QSVP (SEQ ID NO: 5218), QNIQ (SEQ ID NO: 5219), LDQQ (SEQ ID NO: 5220), PDQQ (SEQ ID NO: 5221), ESQQ (SEQ ID NO: 5222), QRQL (SEQ ID NO: 5223), QIIV (SEQ ID NO: 5224), QKQS (SEQ ID NO: 5225), QSHQ (SEQ ID NO: 5226), QFVV (SEQ ID NO: 5227), QSQP (SEQ ID NO: 5228), QNEQ (SEQ ID NO: 5229), INQQ (SEQ ID NO: 5230), RNRQ (SEQ ID NO: 5231), RDQK (SEQ ID NO: 5232), QWKR (SEQ ID NO: 5233), ENRQ (SEQ ID NO: 5234), QTQP (SEQ ID NO: 5235), QKQL (SEQ ID NO: 5236), RNQL (SEQ ID NO: 5237), ISIQ (SEQ ID NO: 5238), QTVC (SEQ ID NO: 5239), QQIM (SEQ ID NO: 5240), LNHQ (SEQ ID NO: 5241), QNQA (SEQ ID NO: 5242), QMIH (SEQ ID NO: 5243), RNHQ (SEQ ID NO: 5244), or QKMN (SEQ ID NO: 5245), or any dipeptide or tripeptide thereof. In some embodiments, [N1]-[N2]-[N3]-[N4] is or comprises: the amino acid sequence of any of SEQ ID NOs: 1800-2241; an amino acid sequence comprising any portion of any of the aforesaid amino acid sequences (e.g., any 2, 3, 4, 5, 6, 7, 8, 9, 10, 11, or 12 amino acids, e.g., consecutive amino acids) thereof; an amino acid sequence comprising one, two, or three but no more than four modifications, e.g., substitutions (e.g., conservative substitutions), insertions, or deletions, relative to any of the aforesaid amino acid sequences; or an amino acid sequence comprising one, two, or three but no more than four different amino acids, relative to any one of the aforesaid amino acid sequences. In some embodiments, [N1]-[N2]-[N3]-[N4] is or comprises GSGSPHSKAQNQQ (SEQ ID NO: 1801). In some embodiments, [N1]-[N2]-[N3]-[N4] is or comprises GHDSPHKSGQNQQ (SEQ ID NO: 1800).

In some embodiments, the peptide comprising an amino acid sequence having the formula [N1]-[N2]-[N3], further comprises [N0], which comprises XA XB and XC. In some embodiments, XA of [N0] is T, S, Y, M, A, C, I, R, L, D, F, V, Q, N, H, E, or G. In some embodiments, XB of [N0] is I, M, P, E, N, D, S, A, T, G, Q, F, V, L, C, H, R, W, or L. In some embodiments, XC of [N0] is N, M, E, G, Y, W, T, I, Q, F, V, A, L, I, P, K, R, H, S, D, or S. In some embodiments, [N0] is or comprises TIN, SMN, TIM, YLS, GLS, MPE, MEG, MEY, AEW, CEW, ANN, IPE, ADM, IEY, ADY, IET, MEW, CEY, RIN, MEI, LEY, ADW, IEI, DIM, FEQ, MEF, CDQ, LPE, IEN, MES, AEI, VEY, IIN, TSN, IEV, MEM, AEV, MDA, VEW, AEQ, LEW, MEL, MET, MEA, IES, MEV, CEI, ATN, MDG, QEV, ADQ, NMN, IEM, ISN, TGN, QQQ, HDW, IEG, TII, TFP, TEK, EIN, TVN, TFN, SIN, TER, TSY, ELH, AIN, SVN, TDN, TFH, TVH, TEN, TSS, TID, TCN, NIN, TEH, AEM, AIK, TDK, TFK, SDQ, TEI, NTN, TET, SIK, TEL, TEA, TAN, TIY, TFS, TES, TTN, TED, TNN, EVH, TIS, TVR, TDR, TIK, NHI, TIP, ESD, TDL, TVP, TVI, AEH, NCL, TVK, NAD, TIT, NCV, TIR, NAL, VIN, TIQ, TEF, TRE, QGE, SEK, NVN, GGE, EFV, SDK, TEQ, EVQ, TEY, NCW, TDV, SDI, NSI, NSL, EVV, TEP, SEL, TWQ, TEV, AVN, GVL, TLN, TEG, TRD, NAI, AEN, AET, ETA, NNL, or any dipeptide thereof. In some embodiments, [N0]-[N1]-[N2]-[N3]-[N4] is or comprises the amino acid sequence of any one of SEQ ID NOs: 2242-2886; an amino acid sequence comprising any portion of any of the aforesaid amino acid sequences (e.g., any 2, 3, 4, 5, 6, 7, 8, 9, 10, 11, 12, 13, 14, or 15 amino acids, e.g., consecutive amino acids) thereof; an amino acid sequence comprising one, two, or three but no more than four modifications, e.g., substitutions (e.g., conservative substitutions), insertions, or deletions, relative to any of the aforesaid amino acid sequences; or an amino acid sequence comprising one, two, or three but no more than four different amino acids, relative to any one of the aforesaid amino acid sequences. In some embodiments, [N0]-[N1]-[N2]-[N3]-[N4] is or comprises TINGSGSPHSKAQNQQ (SEQ ID NO: 2242). In some embodiments, [N0]-[N1]-[N2]-[N3]-[N4] is or comprises TINGHDSPHKSGQNQQ (SEQ ID NO: 2243).

In some embodiments, [N3] is present immediately subsequent to [N2]. In some embodiments, the peptide comprises from N-terminus to C-terminus, [N2]-[N3]. In some embodiments, the peptide comprises from N-terminus to C-terminus, [N1]-[N2]-[N3]. In some embodiments, the peptide comprises from N-terminus to C-terminus, [N1]-[N2]-[N3]-[N4]. In some embodiments, the peptide comprises from N-terminus to C-terminus, [N0]-[N1]-[N2]-[N3]. In some embodiments, the peptide comprises from N-terminus to C-terminus, [N0]-[N1]-[N2]-[N3]-[N4].

In some embodiments, the peptide comprises an amino acid sequence having the formula [A][B](SEQ ID NO: 4694), wherein [A] comprises the amino acid sequence of GSGSPH (SEQ ID NO: 4695) and [B] comprises X1 X2 X3 X4 X5 X6 X7. In some embodiments, position X1 of [B] is S, C, F, or V. In some embodiments, position X2 of [B] is K, L, R, I, E, Y, V, or S. In some embodiments, X3 of [B] is A, R, L, G, I, Y, S, F, or W. In some embodiments X4 of [B] is W, Q, R, G, L, V, S, or F. In some embodiments, position X5 of [B] is N, Y, R, C, K, or L. In some embodiments, position X6 of [B] is Q, G, K, R, T, L, or Y. In some embodiment, position X7 of [B] is Q, L, R, or V. In some embodiments, [B] comprises LLWNQQ (SEQ ID NO: 5247), SKAQYYV (SEQ ID NO: 5248), SKLRRQQ (SEQ ID NO: 5249), SIWQNQQ (SEQ ID NO: 5250), SKAGCGQ (SEQ ID NO: 5251), SRAQNQQ (SEQ ID NO: 5252), SKRLRQQ (SEQ ID NO: 5253), SLRRNQQ (SEQ ID NO: 5254), SRGRNQQ (SEQ ID NO: 5255), SEIVNQQ (SEQ ID NO: 5256), SSRRNQQ (SEQ ID NO: 5257), CLLQNQQ (SEQ ID NO: 5258), SKAFRLQ (SEQ ID NO: 5259), CLAQNQQ (SEQ ID NO: 5260), FLRQNQQ (SEQ ID NO: 5261), SLRFNQQ (SEQ ID NO: 5262), SYLRNQQ (SEQ ID NO: 5263), CSLQNQQ (SEQ ID NO: 5264), VLWQNQQ (SEQ ID NO: 5265), SKWLLQQ (SEQ ID NO: 5266), SLWSNQQ (SEQ ID NO: 5267), SKRRLQQ (SEQ ID NO: 5268), SVYLNQQ (SEQ ID NO: 5269), SLWLNQQ (SEQ ID NO: 5270), SKAQRKL (SEQ ID NO: 5271), SKALRRQ (SEQ ID NO: 5272), SKAQRLR (SEQ ID NO: 5273), SKAQNQQ (SEQ ID NO: 5274), SKAQRRL (SEQ ID NO: 5275), SKARRQQ (SEQ ID NO: 5276), SKARRLQ (SEQ ID NO: 5277), SKSRRQQ (SEQ ID NO: 5278), SKARLRQ (SEQ ID NO: 5279), SKASKRQ (SEQ ID NO: 5280), VRRQNQQ (SEQ ID NO: 5281), SKAQLYR (SEQ ID NO: 5282), SLFRNQQ (SEQ ID NO: 5283), SKAQLTV (SEQ ID NO: 5284), or any dipeptide, tripeptide, tetrapeptide, pentapeptide, or hexapeptide thereof. In some embodiments, [A][B] comprises GSGSPHSLLWNQQ (SEQ ID NO: 5285), GSGSPHSKAQYYV (SEQ ID NO: 2060), GSGSPHSKLRRQQ (SEQ ID NO: 2061), GSGSPHSIWQNQQ (SEQ ID NO: 5286), GSGSPHSKAGCGQ (SEQ ID NO: 2062), GSGSPHSRAQNQQ (SEQ ID NO: 2063), GSGSPHSKRLRQQ (SEQ ID NO: 2064), GSGSPHSLRRNQQ (SEQ ID NO: 2065), GSGSPHSRGRNQQ (SEQ ID NO: 2066), GSGSPHSEIVNQQ (SEQ ID NO: 5287), GSGSPHSSRRNQQ (SEQ ID NO: 2067), GSGSPHCLLQNQQ (SEQ ID NO: 5288), GSGSPHSKAFRLQ (SEQ ID NO: 2068), GSGSPHCLAQNQQ (SEQ ID NO: 5289), GSGSPHFLRQNQQ (SEQ ID NO: 2070), GSGSPHSLRFNQQ (SEQ ID NO: 2071), GSGSPHSYLRNQQ (SEQ ID NO: 5290), GSGSPHCSLQNQQ (SEQ ID NO: 5291), GSGSPHVLWQNQQ (SEQ ID NO: 5292), GSGSPHSKWLLQQ (SEQ ID NO: 2072), GSGSPHSLWSNQQ (SEQ ID NO: 5293), GSGSPHSKRRLQQ (SEQ ID NO: 2073), GSGSPHSVYLNQQ (SEQ ID NO: 5294), GSGSPHSLWLNQQ (SEQ ID NO: 5295), GSGSPHSKAQRKL (SEQ ID NO: 2074), GSGSPHSKALRRQ (SEQ ID NO: 2075), GSGSPHSKAQRLR (SEQ ID NO: 2076), GSGSPHSKAQNQQ (SEQ ID NO: 1801), GSGSPHSKAQRRL (SEQ ID NO: 2077), GSGSPHSKARRQQ (SEQ ID NO: 2078), GSGSPHSKARRLQ (SEQ ID NO: 2079), GSGSPHSKSRRQQ (SEQ ID NO: 2080), GSGSPHSKARLRQ (SEQ ID NO: 2082), GSGSPHSKASKRQ (SEQ ID NO: 2083), GSGSPHVRRQNQQ (SEQ ID NO: 2084), GSGSPHSKAQLYR (SEQ ID NO: 2085), GSGSPHSLFRNQQ (SEQ ID NO: 5296), GSGSPHSKAQLTV (SEQ ID NO: 2086), or any portion thereof, e.g., any 2, 3, 4, 5, 6, 7, 8, 9, 10, 11, or 12 amino acids, e.g., consecutive amino acids, thereof. In some embodiments, [B] is present immediately subsequent to [A]. In some embodiments, the peptide comprises from N-terminus to C-terminus, [A][B].

In some embodiments, the peptide comprises an amino acid sequence having the formula [A][B](SEQ ID NO: 4699), wherein [A] comprises X1 X2 X3 X4 X5 X6 and [B] comprises SPHKSG (SEQ ID NO: 946). In some embodiments, position X1 of [A] is T, M, A, C, I, R, L, D, F, V, Q, N, or H. In some embodiments, position X2 of [A] is I, P, E, N, D, S, A, T, M, or Q. In some embodiments, position X3 of [A] is N, E, G, Y, W, M, T, I, K, Q, F, S, V, A, or L. In some embodiments, position X4 of [A] is G, D, R, or E. In some embodiments, position X5 of [A] is H, Q, N, or D. In some embodiments, position X6 of [A] is D or R. In some embodiments, [A] comprises TINGHD (SEQ ID NO: 5297), MPEGHD (SEQ ID NO: 5298), MEGGHD (SEQ ID NO: 5299), MEYGHD (SEQ ID NO: 5300), AEWGHD (SEQ ID NO: 5301), CEWGHD (SEQ ID NO: 5302), ANNGQD (SEQ ID NO: 5303), IPEGHD (SEQ ID NO: 5304), ADMGHD (SEQ ID NO: 5305), IEYGHD (SEQ ID NO: 5306), ADYGHD (SEQ ID NO: 5307), IETGHD (SEQ ID NO: 5308), MEWGHD (SEQ ID NO: 5309), CEYGHD (SEQ ID NO: 5310), RINGHD (SEQ ID NO: 5311), MEIGHD (SEQ ID NO: 5312), LEYGHD (SEQ ID NO: 5313), ADWGHD (SEQ ID NO: 5314), IEIGHD (SEQ ID NO: 5315), TIKDND (SEQ ID NO: 5316), DIMGHD (SEQ ID NO: 5317), FEQGHD (SEQ ID NO: 5318), MEFGHD (SEQ ID NO: 5319), CDQGHD (SEQ ID NO: 5320), LPEGHD (SEQ ID NO: 5321), IENGHD (SEQ ID NO: 5322), MESGHD (SEQ ID NO: 5323), AEIGHD (SEQ ID NO: 5324), VEYGHD (SEQ ID NO: 5325), TSNGDD (SEQ ID NO: 5326), IEVGHD (SEQ ID NO: 5327), MEMGHD (SEQ ID NO: 5328), AEVGHD (SEQ ID NO: 5329), MDAGHD (SEQ ID NO: 5330), VEWGHD (SEQ ID NO: 5331), AEQGHD (SEQ ID NO: 5332), LEWGHD (SEQ ID NO: 5333), MELGHD (SEQ ID NO: 5334), METGHD (SEQ ID NO: 5335), MEAGHD (SEQ ID NO: 5336), TINRQR (SEQ ID NO: 5337), IESGHD (SEQ ID NO: 5338), TAKDHD (SEQ ID NO: 5339), MEVGHD (SEQ ID NO: 5340), CEIGHD (SEQ ID NO: 5341), ATNGHD (SEQ ID NO: 5342), MDGGHD (SEQ ID NO: 5343), QEVGHD (SEQ ID NO: 5344), ADQGHD (SEQ ID NO: 5345), NMNGHD (SEQ ID NO: 5346), TPWEHD (SEQ ID NO: 5347), IEMGHD (SEQ ID NO: 5348), TANEHD (SEQ ID NO: 5349), QQQGHD (SEQ ID NO: 5350), TPQDHD (SEQ ID NO: 5351), HDWGHD (SEQ ID NO: 5352), IEGGHD (SEQ ID NO: 5353), or any dipeptide, tripeptide, tetrapeptide, or pentapeptide thereof. In some embodiments, [A][B]comprises TINGHDSPHKR (SEQ ID NO: 5354), MPEGHDSPHKS (SEQ ID NO: 5355), MEGGHDSPHKS (SEQ ID NO: 5356), MEYGHDSPHKS (SEQ ID NO: 5357), AEWGHDSPHKS (SEQ ID NO: 5358), CEWGHDSPHKS (SEQ ID NO: 5359), ANNGQDSPHKS (SEQ ID NO: 5360), IPEGHDSPHKS (SEQ ID NO: 5361), ADMGHDSPHKS (SEQ ID NO: 5362), IEYGHDSPHKS (SEQ ID NO: 5363), ADYGHDSPHKS (SEQ ID NO: 5364), IETGHDSPHKS (SEQ ID NO: 5365), MEWGHDSPHKS (SEQ ID NO: 5366), CEYGHDSPHKS (SEQ ID NO: 5367), RINGHDSPHKS (SEQ ID NO: 5368), MEIGHDSPHKS (SEQ ID NO: 5369), LEYGHDSPHKS (SEQ ID NO: 5370), ADWGHDSPHKS (SEQ ID NO: 5371), IEIGHDSPHKS (SEQ ID NO: 5372), TIKDNDSPHKS (SEQ ID NO: 5373), DIMGHDSPHKS (SEQ ID NO: 5374), FEQGHDSPHKS (SEQ ID NO: 5375), MEFGHDSPHKS (SEQ ID NO: 5376), CDQGHDSPHKS (SEQ ID NO: 5377), LPEGHDSPHKS (SEQ ID NO: 5378), IENGHDSPHKS (SEQ ID NO: 5379), MESGHDSPHKS (SEQ ID NO: 5380), AEIGHDSPHKS (SEQ ID NO: 5381), VEYGHDSPHKS (SEQ ID NO: 5382), TSNGDDSPHKS (SEQ ID NO: 5383), IEVGHDSPHKS (SEQ ID NO: 5384), MEMGHDSPHKS (SEQ ID NO: 5385), AEVGHDSPHKS (SEQ ID NO: 5386), MDAGHDSPHKS (SEQ ID NO: 5387), VEWGHDSPHKS (SEQ ID NO: 5388), AEQGHDSPHKS (SEQ ID NO: 5389), LEWGHDSPHKS (SEQ ID NO: 5390), MELGHDSPHKS (SEQ ID NO: 5391), METGHDSPHKS (SEQ ID NO: 5392), MEAGHDSPHKS (SEQ ID NO: 5393), TINRQRSPHKS (SEQ ID NO: 5394), IESGHDSPHKS (SEQ ID NO: 5395), TAKDHDSPHKS (SEQ ID NO: 5396), MEVGHDSPHKS (SEQ ID NO: 5397), CEIGHDSPHKS (SEQ ID NO: 5398), ATNGHDSPHKS (SEQ ID NO: 5399), MDGGHDSPHKS (SEQ ID NO: 5400), QEVGHDSPHKS (SEQ ID NO: 5401), ADQGHDSPHKS (SEQ ID NO: 5402), NMNGHDSPHKS (SEQ ID NO: 5403), TPWEHDSPHKS (SEQ ID NO: 5404), IEMGHDSPHKS (SEQ ID NO: 5405), TANEHDSPHKS (SEQ ID NO: 5406), TINGHDSPHKS (SEQ ID NO: 5407), QQQGHDSPHKS (SEQ ID NO: 5408), TPQDHDSPHKS (SEQ ID NO: 5409), HDWGHDSPHKS (SEQ ID NO: 5410), IEGGHDSPHKS (SEQ ID NO: 5411), or any portion thereof, e.g., any 2, 3, 4, 5, 6, 7, 8, 9, 10, 11, or 12 amino acids, e.g., consecutive amino acids, thereof. In some embodiments, [B] is present immediately subsequent to [A]. In some embodiments, the peptide comprises from N-terminus to C-terminus, [A][B].

In some embodiments, the peptide comprises an amino acid sequence comprising at least 3, 4, 5, 6, 7, 8, 9, 10, 11, 12, 13, 14, 15, 16, or 17 consecutive amino acids from any one of the sequences provided in Tables 1, 2A, 2B, 13-19. In some embodiments, the peptide comprises an amino acid sequence comprising at least 3, 4, or 5 consecutive amino acids from any one of SEQ ID NOs: 945-980 or 985-986. In some embodiments, the peptide comprises an amino acid sequence comprising at least 3, 4, 5, 6, 7, 8, 9, 10, 11, 12, or 13 consecutive amino acids from any one of SEQ ID NOs: 2, 200, 201, 941, 943, 204, 208, 404, or 903-909.

In some embodiments, the 3 consecutive amino acids comprise SPH. In some embodiments, the 4 consecutive amino acids comprise SPHS (SEQ ID NO: 4700). In some embodiments, the 5 consecutive amino acids comprise SPHSK (SEQ ID NO: 4701). In some embodiments, the 6 consecutive amino acids comprise SPHSKA (SEQ ID NO: 941).

In some embodiments, 3 consecutive amino acids comprise HDS. In some embodiments, the 4 consecutive amino acids comprise HDSP (SEQ ID NO: 4702). In some embodiments, the 5 consecutive amino acids comprise HDSPH (SEQ ID NO: 4703). In some embodiments, the 6 consecutive amino acids comprise HDSPHK (SEQ ID NO: 2).

In some embodiments, the 3 consecutive amino acids comprise SPH. In some embodiments, the 4 consecutive amino acids comprise SPHK (SEQ ID NO: 6398). In some embodiments, the 5 consecutive amino acids comprise SPHKY (SEQ ID NO: 4715). In some embodiments, the 6 consecutive amino acids comprise SPHKYG (SEQ ID NO: 966).

In some embodiments, the peptide comprises an amino acid sequence comprising at least one, two, or three but no more than four modifications, e.g., substitutions (e.g., conservative substitutions), insertions, or deletions, relative to the amino acid sequence of any one of the sequences provided in Tables 1, 2A, 2B, 13-19. In some embodiments, the peptide comprises an amino acid sequence comprising at least one, two, or three but no more than four different amino acids, relative to the amino acid sequence of any one of the sequences provided in Tables 1, 2A, 2B, 13-19. In some embodiments, the peptide comprises an amino acid sequence comprising at least one, two, or three but no more than four modifications, e.g., substitutions (e.g., conservative substitutions), insertions, or deletions, relative to the amino acid sequence of any one of SEQ ID NOs: 945-980 or 985-986. In some embodiments, the peptide comprises an amino acid sequence comprising at least one, two, or three but no more than four different amino acids, relative to the amino acid sequence of any one of SEQ ID NOs: 945-980 or 985-986. In some embodiments, the peptide comprises an amino acid sequence comprising at least one, two, or three but no more than four modifications, e.g., substitutions (e.g., conservative substitutions), insertions, or deletions, relative to the amino acid sequence of any one of SEQ ID NOs: 2, 200, 201, 941, 943, 204, 208, 404, or 903-909. In some embodiments, the peptide comprises an amino acid sequence comprising at least one, two, or three but no more than four different amino acids relative to the amino acid sequence of any one of SEQ ID NOs: 2, 200, 201, 941, 943, 204, 208, 404, or 903-909. In some embodiments, the peptide comprises an amino acid sequence comprising at least one, two, or three but no more than four modifications, e.g., substitutions (e.g., conservative substitutions), insertions, or deletions, relative to the amino acid sequence of SEQ ID NO: 3589. In some embodiments, the peptide comprises an amino acid sequence comprising at least one, two, or three but no more than four different amino acids relative to the amino acid sequence of SEQ ID NO: 3589. In some embodiments, the peptide comprises an amino acid sequence comprising at least one, two, or three but no more than four modifications, e.g., substitutions (e.g., conservative substitutions), insertions, or deletions, relative to the amino acid sequence of SEQ ID NO: 1754. In some embodiments, the peptide comprises an amino acid sequence comprising at least one, two, or three but no more than four different amino acids relative to the amino acid sequence of SEQ ID NO: 1754.

In some embodiments, the peptide comprises an amino acid sequence comprising at least one, two, or three but no more than four modifications, e.g., substitutions (e.g., conservative substitutions), insertions, or deletions, relative to the amino acid sequence of SPHSKA (SEQ ID NO: 941). In some embodiments, the peptide comprises an amino acid sequence comprising at least one, two, or three but no more than four different amino acids relative to the amino acid sequence of SPHSKA (SEQ ID NO: 941).

In some embodiments, the peptide comprises an amino acid sequence comprising at least one, two, or three but no more than four modifications, e.g., substitutions (e.g., conservative substitutions), insertions, or deletions, relative to the amino acid sequence of HDSPHK (SEQ ID NO: 2). In some embodiments, the peptide comprises an amino acid sequence comprising at least one, two, or three but no more than four different amino acids relative to the amino acid sequence of HDSPHK (SEQ ID NO: 2).

In some embodiments, the peptide comprises an amino acid sequence comprising at least one, two, or three but no more than four modifications, e.g., substitutions (e.g., conservative substitutions), insertions, or deletions, relative to the amino acid sequence of SPHKYG (SEQ ID NO: 966). In some embodiments, the peptide comprises an amino acid sequence comprising at least one, two, or three but no more than four different amino acids relative to the amino acid sequence of SPHKYG (SEQ ID NO: 966).

In some embodiments, the peptide comprises the amino acid sequence of any of the sequences provided in Tables 1, 2A, 2B, 13-19. In some embodiments, the peptide comprises the amino acid sequence of any of SEQ ID NOs: 945-980 or 985-986. In some embodiments, the peptide comprises the amino acid sequence of any of SEQ ID NOs: 2, 200, 201, 941, 943, 204, 208, 404, or 903-909. In some embodiments, the peptide comprises the amino acid sequence of SEQ ID NO: 941. In some embodiments, the peptide comprises the amino acid sequence of SEQ ID NO: 943. In some embodiments, the peptide comprises the amino acid sequence of SEQ ID NO: 2. In some embodiments, the peptide comprises the amino acid sequence of SEQ ID NO: 3589. In some embodiments, the peptide comprises the amino acid sequence of SEQ ID NO: 1754. In some embodiments, the peptide comprises the amino acid sequence of SEQ ID NO: 3241. In some embodiments, the peptide comprises the amino acid sequence of SEQ ID NO: 4100. In some embodiments, the peptide comprises the amino acid sequence of SEQ ID NO: 4062. In some embodiments, the peptide comprises the amino acid sequence of SEQ ID NO: 4486.

In some embodiments, the peptide comprises an amino acid sequence encoded by a nucleotide sequence described herein, e.g., a nucleotide sequence of Table 2A. In some embodiments, the peptide comprises an amino acid sequence encoded by a nucleotide sequence comprising at least one, two, three, four, five, six, or seven modifications, e.g., substitutions (e.g., conservative substitutions), insertions, or deletions, but no more than ten modifications, e.g., substitutions (e.g., conservative substitutions), insertions, or deletions, relative to the nucleotide sequence of SEQ ID NO: 942. In some embodiments, the peptide comprises an amino acid sequence encoded by a nucleotide sequence comprising at least one, two, three, four, five, six, or seven, but no more than ten different nucleotides, relative to the nucleotide sequence of SEQ ID NO: 942. In some embodiments, the peptide comprises an amino acid sequence encoded by the nucleotide sequence of SEQ ID NO: 942, or a nucleotide sequence substantially identical (e.g., having at least 70%, 75%, 80%, 85%, 90%, 92%, 95%, 97%, 98%, or 99% sequence identity) thereto. In some embodiments, the peptide comprises an amino acid sequence encoded by a nucleotide sequence comprising at least one, two, three, four, five, six, or seven modifications, e.g., substitutions (e.g., conservative substitutions), insertions, or deletions, but no more than ten modifications, e.g., substitutions (e.g., conservative substitutions), insertions, or deletions, relative to the nucleotide sequence of SEQ ID NO: 944. In some embodiments, the peptide comprises an amino acid sequence encoded by a nucleotide sequence comprising at least one, two, three, four, five, six, or seven, but no more than ten different nucleotides, relative to the nucleotide sequence of SEQ ID NO: 944. In some embodiments, the peptide comprises an amino acid sequence encoded by the nucleotide sequence of SEQ ID NO: 944, or a nucleotide sequence substantially identical (e.g., having at least 70%, 75%, 80%, 85%, 90%, 92%, 95%, 97%, 98%, or 99% sequence identity) thereto.

In some embodiments, the nucleotide sequence encoding a peptide described herein comprises a nucleotide sequence described herein, e.g., as described in Table 2A. In some embodiments, the nucleotide sequence encoding a peptide described herein is codon optimized. In some embodiments, the nucleotide sequence encoding a peptide described herein is isolated, e.g., recombinant.

In some embodiments the nucleotide sequence encoding a peptide described herein comprises the nucleotide sequence of SEQ ID NO: 942, or a nucleotide sequence comprising at least one, two, three, four, five, six, or seven modifications, e.g., substitutions (e.g., conservative substitutions), insertions, or deletions, but no more than ten modifications, e.g., substitutions (e.g., conservative substitutions), insertions, or deletions, relative to the nucleotide sequence of SEQ ID NO: 942. In some embodiments, the nucleotide sequence encoding a peptide described herein comprises a nucleotide sequence comprising at least one, two, three, four, five, six, or seven, but no more than ten different nucleotides, relative to the nucleotide sequence of SEQ ID NO: 942. In some embodiments the nucleic acid sequence encoding a peptide described herein comprises a nucleotide sequence comprising the nucleotide sequence of SEQ ID NO: 942, or a nucleotide sequence substantially identical (e.g., having at least 70%, 75%, 80%, 85%, 90%, 92%, 95%, 97%, 98%, or 99% sequence identity) thereto.

In some embodiments, the nucleic acid encoding a peptide described herein comprises the nucleotide sequence of SEQ ID NO: 3, or a nucleotide sequence comprising at least one, two, three, four, five, six, or seven modifications, e.g., substitutions (e.g., conservative substitutions), insertions, or deletions, but no more than ten modifications, e.g., substitutions (e.g., conservative substitutions), insertions, or deletions, relative to the nucleotide sequence of SEQ ID NO: 3. In some embodiments, the nucleotide sequence encoding a peptide described herein comprises a nucleotide sequence comprising at least one, two, three, four, five, six, or seven, but no more than ten different nucleotides, relative to the nucleotide sequence of SEQ ID NO: 3. In some embodiments the nucleic acid encoding a peptide described herein comprises a nucleotide sequence comprising the nucleotide sequence of SEQ ID NO: 3, or a nucleotide sequence substantially identical (e.g., having at least 70%, 75%, 80%, 85%, 90%, 92%, 95%, 97%, 98%, or 99% sequence identity) thereto.

In some embodiments, the nucleic acid encoding a peptide described herein comprises the nucleotide sequence of SEQ ID NO: 944, or a nucleotide sequence comprising at least one, two, three, four, five, six, or seven modifications, e.g., substitutions (e.g., conservative substitutions), insertions, or deletions, but no more than ten modifications, e.g., substitutions (e.g., conservative substitutions), insertions, or deletions, relative to the nucleotide sequence of SEQ ID NO: 944. In some embodiments, the nucleotide sequence encoding a peptide described herein comprises a nucleotide sequence comprising at least one, two, three, four, five, six, or seven, but no more than ten different nucleotides, relative to the nucleotide sequence of SEQ ID NO: 944. In some embodiments the nucleic acid encoding a peptide described herein comprises a nucleotide sequence comprising the nucleotide sequence of SEQ ID NO: 944, or a nucleotide sequence substantially identical (e.g., having at least 70%, 75%, 80%, 85%, 90%, 92%, 95%, 97%, 98%, or 99% sequence identity) thereto.

In some embodiments, a peptide described herein is fused or coupled, e.g., conjugated, to an active agent. In some embodiments, the active agent is a therapeutic agent. In some embodiments, the agent is a therapeutic agent. In some embodiments, the active agent comprises a therapeutic protein, an antibody molecule, an enzyme, one or more components of a genome editing system, an Fc polypeptide fused or coupled (e.g., covalently or non covalently) to a therapeutic agent, and/or an RNAi agent (e.g., a dsRNA, antisense oligonucleotide (ASO), siRNA, shRNA, pre-miRNA, pri-miRNA, miRNA, stRNA, lncRNA, piRNA, or snoRNA). In some embodiments, the therapeutic agent is an antibody. In some embodiments, the peptide is fused or coupled, e.g., conjugated (e.g., directly or indirectly) to the Fc region of the antibody, e.g., at the C-terminus of the Fc region or the N-terminus of the Fc region. In some embodiments, the therapeutic agent is an RNAi agent. In some embodiments, the RNAi agent is a siRNA or an ASO. In some embodiments, the ASO or siRNA comprises at least one (e.g., one or more or all) modified nucleotides. In some embodiments, the peptide is fused or coupled, e.g., conjugated (e.g., directly or indirectly via a linker), to at least one strand of the RNAi agent. In some embodiments, the peptide is conjugated, e.g., directly or indirectly via a linker, to the C-terminus of at least one strand of the RNAi agent. In some embodiments, the peptide is conjugated, e.g., directly or indirectly via a linker, to an internal nucleotide of at least one strand of the RNAi agent. In some embodiments, the at least one strand is the sense strand. In some embodiments, the therapeutic agent modulates, e.g., inhibits, decreases, or increases, expression of, a CNS related gene, mRNA, and/or protein.

In some embodiments, the active agent is a diagnostic agent. In some embodiments, the diagnostic agent is or comprises an imaging agent (e.g., a protein or small molecule compound coupled to a detectable moiety). In some embodiments, the imaging agent comprises a PET or MRI ligand, or an antibody molecule coupled to a detectable moiety. In some embodiments, the detectable moiety is or comprises a radiolabel, a fluorophore, a chromophore, or an affinity tag. In some embodiments, the radiolabel is or comprises tc99m, iodine-123, a spin label, iodine-131, indium-111, fluorine-19, carbon-13, nitrogen-15, oxygen-17, gadolinium, manganese, or iron. In some embodiments, the active agent is a small molecule. In some embodiments, the active agent is a ribonucleic acid complex (e.g., a Cas9/gRNA complex), a plasmid, a closed-end DNA, a circ-RNA, or an mRNA.

In some embodiments, at least 1-5, e.g., at least 1, 2, 3, 4, or 5, peptides are fused or coupled, e.g., conjugated, to an active agent, e.g., a therapeutic agent or a diagnostic agent. In some embodiments, the at least 1-5, e.g., at least 1, 2, 3, 4, or 5, peptides comprise the same amino acid sequence. In some embodiments, the at least 1-5, e.g., at least 1, 2, 3, 4, or 5, peptides comprise different amino acid sequences. In some embodiments, the at least 1-5, e.g., at least 1, 2, 3, 4, or 5, peptides are present in tandem (e.g., connected directly or indirectly via a linker) or in a multimeric configuration. In some embodiments, the peptide comprises an amino acid sequence of at least 3, 4, 5, 6, 7, 8, 9, 10, 11, 12, 15, 20, 25, 30, or 35 amino acids in length.

In some embodiments, the peptide covalently linked, e.g., directly or indirectly via a linker, to the active agent. In some embodiments, the peptide is conjugated to the active agent via a linker. In some embodiments, the linker is a cleavable linker or a non-cleavable linker. In some embodiments, the cleavable linker is a pH sensitive linker or an enzyme sensitive linker. In some embodiments, the pH sensitive linker comprises a hydrazine/hydrazone linker or a disulfide linker. In some embodiments, the enzyme sensitive linker comprises a peptide based linker, e.g., a peptide linker sensitive to a protease (e.g., a lysosomal protease); or a beta-glucuronide linker. In some embodiments, the non-cleavable linker is a linker comprising a thioether group or a maleimidocaproyl group. In some embodiments, the peptide and the active agent are fused or coupled post-translationally, e.g., using click chemistry. In some embodiments, the peptide and the active agent are fused or couple via chemically induced dimerization. In some embodiments, the peptide is present N-terminal relative to the active agent. In some embodiments, the peptide is present C-terminal relative to the active agent.

In some embodiments, the peptide is present or coupled to a carrier. In some embodiments, the carrier comprises an exosome, a microvesicle, or a lipid nanoparticle (LNP). In some embodiments, the carrier comprises a therapeutic agent (e.g., an RNAi agent (e.g., an dsRNA, a siRNA, a shRNA, a pre-miRNA, a pri-miRNA, a miRNA, a stRNA, a lncRNA, a piRNA, an antisense oligonucleotide agent (ASO), or a snoRNA), an mRNA, a ribonucleoprotein complex (e.g., a Cas9/gRNA complex), or a circRNA). In some embodiments, the peptide is present on the surface of the carrier. In some embodiments, at least 10%, 20%, 30%, 40%, 50%, 60%, 70%, or 80% of the surface of the carrier comprises at least 1-5, e.g., at least 1, 2, 3, 4, or 5 peptides described herein.

The present disclosure also provides a nucleic acid or polynucleotide encoding any of the peptides described herein and AAV capsid variants, AAV particles, vectors, and cells comprising the same.

AAV Capsid Variant

In some embodiments, an AAV particle described herein comprises an AAV capsid variant, e.g., an AAV capsid variant described herein (e.g., an AAV capsid variant comprising a peptide described herein). In some embodiments, an AAV capsid variant comprises a peptide as set forth in any of Tables 1, 2A, 2B, 13-19.

In some embodiments, an AAV capsid variant described herein comprises an amino acid sequence having the formula [N1]-[N2]-[N3], wherein [N2] comprises the amino acid sequence of SPH and [N3] comprises X4, X5, and X6, wherein at least one of X4, X5, or X6 is a basic amino acid, e.g., a K or R. In some embodiments, position X4 of [N2] is K. In some embodiments, position X5 of [N2] is K.

In some embodiments, [N1] comprises X1, X2, and X3, wherein at least one of X1, X2, or X3 is G. In some embodiments, position X1 of [N1] is G, V, R, D, E, M, T, I, S, A, N, L, K, H, P, W, or C. In some embodiments, position X2 of [N1] is: S, V, L, N, D, H, R, P, G, T, I, A, E, Y, M, or Q. In some embodiments, position X3 of [N1] is: G, C, L, D, E, Y, H, V, A, N, P, or S. In some embodiments, [N1] comprises GS, SG, GH, HD, GQ, QD, VS, CS, GR, RG, QS, SH, MS, RN, TS, IS, GP, ES, SS, GN, AS, NS, LS, GG, KS, GT, PS, RS, GI, WS, DS, ID, GL, DA, DG, ME, EN, KN, KE, AI, NG, PG, TG, SV, IG, LG, AG, EG, SA, YD, HE, HG, RD, ND, PD, MG, QV, DD, HN, HP, GY, GM, GD, or HS. In some embodiments, [N1] comprises GS, SG, GH, or HD. In some embodiments [N1] is or comprises GSG, GHD, GQD, VSG, CSG, CSH, GQS, GRG, GSH, RVG, GSC, GLL, GDD, GHE, GNY, MSG, RNG, TSG, ISG, GPG, ESG, SSG, GNG, ASG, NSG, LSG, GGG, KSG, HSG, GTG, PSG, GSV, RSG, GIG, WSG, DSG, IDG, GLG, DAG, DGG, MEG, ENG, GSA, KNG, KEG, AIG, GYD, GHG, GRD, GND, GPD, GMG, GQV, GHN, GHP, or GHS. In some embodiments, [N1] is or comprises GSG. In some embodiments, [N1] is or comprises GHD. In some embodiments, [N1]-[N2] comprises SGSPH (SEQ ID NO: 4752), HDSPH (SEQ ID NO: 4703), QDSPH (SEQ ID NO: 4753), RGSPH (SEQ ID NO: 4754), SHSPH (SEQ ID NO: 4755), QSSPH (SEQ ID NO: 4756), DDSPH (SEQ ID NO: 4757), HESPH (SEQ ID NO: 4758), NYSPH (SEQ ID NO: 4759), VGSPH (SEQ ID NO: 4760), SCSPH (SEQ ID NO: 4761), LLSPH (SEQ ID NO: 4762), NGSPH (SEQ ID NO: 4763), PGSPH (SEQ ID NO: 4764), GGSPH (SEQ ID NO: 4765), TGSPH (SEQ ID NO: 4766), SVSPH (SEQ ID NO: 4767), IGSPH (SEQ ID NO: 4768), DGSPH (SEQ ID NO: 4769), LGSPH (SEQ ID NO: 4770), AGSPH (SEQ ID NO: 4771), EGSPH (SEQ ID NO: 4772), SASPH (SEQ ID NO: 4773), YDSPH (SEQ ID NO: 4774), HGSPH (SEQ ID NO: 4775), RDSPH (SEQ ID NO: 4776), NDSPH (SEQ ID NO: 4777), PDSPH (SEQ ID NO: 4778), MGSPH (SEQ ID NO: 4779), QVSPH (SEQ ID NO: 4780), HNSPH (SEQ ID NO: 4781), HPSPH (SEQ ID NO: 4782), or HSSPH (SEQ ID NO: 4783); an amino acid sequence comprising any portion of any of the aforesaid amino acid sequences (e.g., any 2, 3, or 4 amino acids, e.g., consecutive amino acids) thereof; an amino acid sequence comprising one, two, or three but no more than four modifications, e.g., substitutions (e.g., conservative substitutions), insertions, or deletions, relative to any of the aforesaid amino acid sequences; or an amino acid sequence comprising one, two, or three but no more than four different amino acids, relative to any one of the aforesaid amino acid sequences. In some embodiments, [N1]-[N2] is or comprises GSGSPH (SEQ ID NO: 4695), GHDSPH (SEQ ID NO: 4784), GQDSPH (SEQ ID NO: 4785), VSGSPH (SEQ ID NO: 4786), CSGSPH (SEQ ID NO: 4787), GRGSPH (SEQ ID NO: 4788), CSHSPH (SEQ ID NO: 4789), GQSSPH (SEQ ID NO: 4790), GSHSPH (SEQ ID NO: 4791), GDDSPH (SEQ ID NO: 4792), GHESPH (SEQ ID NO: 4793), GNYSPH (SEQ ID NO: 4794), RVGSPH (SEQ ID NO: 4795), GSCSPH (SEQ ID NO: 4796), GLLSPH (SEQ ID NO: 4797), MSGSPH (SEQ ID NO: 4798), RNGSPH (SEQ ID NO: 4799), TSGSPH (SEQ ID NO: 4800), ISGSPH (SEQ ID NO: 4801), GPGSPH (SEQ ID NO: 4802), ESGSPH (SEQ ID NO: 4803), SSGSPH (SEQ ID NO: 4804), GNGSPH (SEQ ID NO: 4805), ASGSPH (SEQ ID NO: 4806), NSGSPH (SEQ ID NO: 4807), LSGSPH (SEQ ID NO: 4808), GGGSPH (SEQ ID NO: 4809), KSGSPH (SEQ ID NO: 4810), HSGSPH (SEQ ID NO: 4811), GTGSPH (SEQ ID NO: 4812), PSGSPH (SEQ ID NO: 4813), GSVSPH (SEQ ID NO: 4814), RSGSPH (SEQ ID NO: 4815), GIGSPH (SEQ ID NO: 4816), WSGSPH (SEQ ID NO: 4817), DSGSPH (SEQ ID NO: 4818), IDGSPH (SEQ ID NO: 4819), GLGSPH (SEQ ID NO: 4820), DAGSPH (SEQ ID NO: 4821), DGGSPH (SEQ ID NO: 4822), MEGSPH (SEQ ID NO: 4823), ENGSPH (SEQ ID NO: 4824), GSASPH (SEQ ID NO: 4825), KNGSPH (SEQ ID NO: 4826), KEGSPH (SEQ ID NO: 4827), AIGSPH (SEQ ID NO: 4828), GYDSPH (SEQ ID NO: 4829), GHGSPH (SEQ ID NO: 4830), GRDSPH (SEQ ID NO: 4831), GNDSPH (SEQ ID NO: 4832), GPDSPH (SEQ ID NO: 4833), GMGSPH (SEQ ID NO: 4834), GQVSPH (SEQ ID NO: 4835), GHNSPH (SEQ ID NO: 4836), GHPSPH (SEQ ID NO: 4837), or GHSSPH (SEQ ID NO: 4838); an amino acid sequence comprising any portion of any of the aforesaid amino acid sequences (e.g., any 2, 3, 4, or 5 amino acids, e.g., consecutive amino acids) thereof; an amino acid sequence comprising one, two, or three but no more than four modifications, e.g., substitutions (e.g., conservative substitutions), insertions, or deletions, relative to any of the aforesaid amino acid sequences; or an amino acid sequence comprising one, two, or three but no more than four different amino acids, relative to any one of the aforesaid amino acid sequences. In some embodiments, [N1]-[N2] is or comprises GSGSPH (SEQ ID NO: 4695). In some embodiments, [N1]-[N2] is or comprises GHDSPH (SEQ ID NO: 4784).

In some embodiments, X4, X5, or both of [N3] are K. In some embodiments, X4, X5, or X6 of [N3] is R. In some embodiments, position X4 of [N3] is: A, K, V, S, T, G, F, W, V, N, or R. In some embodiments, position X5 of [N3] is: S, K, T, F, I, L, Y, H, M, or R. In some embodiments, position X6 of [N3] is: G, R, A, M, I, N, T, Y, D, P, V, L, E, W, N, Q, K, or S. In some embodiments, [N3] comprises SK, KA, KS, AR, RM, VK, AS, SR, VK, KR, KK, KN, VR, RS, RK, KT, TS, KF, FG, KI, IG, KL, LG, TT, TY, KY, YG, KD, KP, TR, RG, VR, GA, SL, SS, FL, WK, SA, RA, LR, KW, RR, GK, TK, NK, AK, KV, KG, KH, KM, TG, SE, SV, SW, SN, HG, SQ, LW, MG, MA, or SG. In some embodiments, [N3] comprises SK, KA, KS, or SG. In some embodiments, [N3] is or comprises SKA, KSG, ARM, VKS, ASR, VKI, KKN, VRM, RKA, KTS, KFG, KIG, KLG, KTT, KTY, KYG, SKD, SKP, TRG, VRG, KRG, GAR, KSA, KSR, SKL, SRA, SKR, SLR, SRG, SSR, FLR, SKW, SKS, WKA, VRR, SKV, SKT, SKG, GKA, TKA, NKA, SKL, SKN, AKA, KTG, KSL, KSE, KSV, KSW, KSN, KHG, KSQ, KSK, KLW, WKG, KMG, KMA, or RSG. In some embodiments, [N3] is or comprises SKA. In some embodiments, [N3] is or comprises KSG. In some embodiments, [N2]-[N3] comprises SPHSK (SEQ ID NO: 4701), SPHKS (SEQ ID NO: 4704), SPHAR (SEQ ID NO: 4705), SPHVK (SEQ ID NO: 4706), SPHAS (SEQ ID NO: 4707), SPHKK (SEQ ID NO: 4708), SPHVR (SEQ ID NO: 4709), SPHRK (SEQ ID NO: 4710), SPHKT (SEQ ID NO: 4711), SPHKF (SEQ ID NO: 4712), SPHKI (SEQ ID NO: 4713), SPHKL (SEQ ID NO: 4714), SPHKY (SEQ ID NO: 4715), SPHTR (SEQ ID NO: 4716), SPHKR (SEQ ID NO: 4717), SPHGA (SEQ ID NO: 4718), SPHSR (SEQ ID NO: 4719), SPHSL (SEQ ID NO: 4720), SPHSS (SEQ ID NO: 4721), SPHFL (SEQ ID NO: 4722), SPHWK (SEQ ID NO: 4723), SPHGK (SEQ ID NO: 4724), SPHTK (SEQ ID NO: 4725), SPHNK (SEQ ID NO: 4726), SPHAK (SEQ ID NO: 4727), SPHKH (SEQ ID NO: 4728), SPHKM (SEQ ID NO: 4729), or SPHRS (4730). In some embodiments [N2]-[N3] comprises SPHSK (SEQ ID NO: 4701) or SPHKS (SEQ ID NO: 4704). In some embodiments, [N2]-[N3] is or comprises SPHSKA (SEQ ID NO: 941), SPHKSG (SEQ ID NO: 946), SPHARM (SEQ ID NO: 947), SPHVKS (SEQ ID NO: 948), SPHASR (SEQ ID NO: 949), SPHVKI (SEQ ID NO: 950), SPHKKN (SEQ ID NO: 954), SPHVRM (SEQ ID NO: 955), SPHRKA (SEQ ID NO: 956), SPHKFG (SEQ ID NO: 957), SPHKIG (SEQ ID NO: 958), SPHKLG (SEQ ID NO: 959), SPHKTS (SEQ ID NO: 963), SPHKTT (SEQ ID NO: 964), SPHKTY (SEQ ID NO: 965), SPHKYG (SEQ ID NO: 966), SPHSKD (SEQ ID NO: 967), SPHSKP (SEQ ID NO: 968), SPHTRG (SEQ ID NO: 972), SPHVRG (SEQ ID NO: 973), SPHKRG (SEQ ID NO: 974), SPHGAR (SEQ ID NO: 975), SPHKSA (SEQ ID NO: 977), SPHKSR (SEQ ID NO: 951), SPHSKL (SEQ ID NO:

960), SPHSRA (SEQ ID NO: 969), SPHSKR (SEQ ID NO: 978), SPHSLR (SEQ ID NO: 952), SPHSRG (SEQ ID NO: 961), SPHSSR (SEQ ID NO: 970), SPHFLR (SEQ ID NO: 979), SPHSKW (SEQ ID NO: 953), SPHSKS (SEQ ID NO: 962), SPHWKA (SEQ ID NO: 971), SPHVRR (SEQ ID NO: 980), SPHSKT (SEQ ID NO: 4731), SPHSKG (SEQ ID NO: 4732), SPHGKA (SEQ ID NO: 4733), SPHNKA (SEQ ID NO: 4734), SPHSKN (SEQ ID NO: 4735), SPHAKA (SEQ ID NO: 4736), SPHSKV (SEQ ID NO: 4737), SPHKTG (SEQ ID NO: 4738), SPHTKA (SEQ ID NO: 4739), SPHKSL (SEQ ID NO: 4740), SPHKSE (SEQ ID NO: 4741), SPHKSV (SEQ ID NO: 4742), SPHKSW (SEQ ID NO: 4743), SPHKSN (SEQ ID NO: 4744), SPHKHG (SEQ ID NO: 4745), SPHKSQ (SEQ ID NO: 4746), SPHKSK (SEQ ID NO: 4747), SPHKLW (SEQ ID NO: 4748), SPHWKG (SEQ ID NO: 4749), SPHKMG (SEQ ID NO: 4750), SPHKMA (SEQ ID NO: 4751), or SPHRSG (SEQ ID NO: 976). In some embodiments, [N2]-[N3] is SPHSKA (SEQ ID NO: 941). In some embodiments, [N2]-[N3] is or comprises SPHKSG (SEQ ID NO: 946).

In some embodiments, [N1]-[N2]-[N3] comprises SGSPHSK (SEQ ID NO: 4839), HDSPHKS (SEQ ID NO: 4840), SGSPHAR (SEQ ID NO: 4841), SGSPHVK (SEQ ID NO: 4842), QDSPHKS (SEQ ID NO: 4843), SGSPHKK (SEQ ID NO: 4844), SGSPHVR (SEQ ID NO: 4845), SGSPHAS (SEQ ID NO: 4846), SGSPHRK (SEQ ID NO: 4847), SGSPHKT (SEQ ID NO: 4848), SHSPHKS (SEQ ID NO: 4849), QSSPHRS (SEQ ID NO: 4850), RGSPHAS (SEQ ID NO: 4851), RGSPHSK (SEQ ID NO: 4852), SGSPHKF (SEQ ID NO: 4853), SGSPHKI (SEQ ID NO: 4854), SGSPHKL (SEQ ID NO: 4855), SGSPHKY (SEQ ID NO: 4856), SGSPHTR (SEQ ID NO: 4857), SHSPHKR (SEQ ID NO: 4858), SGSPHGA (SEQ ID NO: 4859), HDSPHKR (SEQ ID NO: 4860), DDSPHKS (SEQ ID NO: 4861), HESPHKS (SEQ ID NO: 4862), NYSPHKI (SEQ ID NO: 4863), SGSPHSR (SEQ ID NO: 4864), SGSPHSL (SEQ ID NO: 4865), SGSPHSS (SEQ ID NO: 4866), VGSPHSK (SEQ ID NO: 4867), SCSPHRK (SEQ ID NO: 4868), SGSPHFL (SEQ ID NO: 4869), LLSPHWK (SEQ ID NO: 4870), NGSPHSK (SEQ ID NO: 4871), PGSPHSK (SEQ ID NO: 4872), GGSPHSK (SEQ ID NO: 4873), TGSPHSK (SEQ ID NO: 4874), SVSPHGK (SEQ ID NO: 4875), SGSPHTK (SEQ ID NO: 4876), IGSPHSK (SEQ ID NO: 4877), DGSPHSK (SEQ ID NO: 4878), SGSPHNK (SEQ ID NO: 4879), LGSPHSK (SEQ ID NO: 4880), AGSPHSK (SEQ ID NO: 4881), EGSPHSK (SEQ ID NO: 4882), SASPHSK (SEQ ID NO: 4883), SGSPHAK (SEQ ID NO: 4884), HDSPHKI (SEQ ID NO: 4885), YDSPHKS (SEQ ID NO: 4886), HDSPHKT (SEQ ID NO: 4887), RGSPHKR (SEQ ID NO: 4888), HGSPHSK (SEQ ID NO: 4889), RDSPHKS (SEQ ID NO: 4890), NDSPHKS (SEQ ID NO: 4891), QDSPHKI (SEQ ID NO: 4892), PDSPHKI (SEQ ID NO: 4893), PDSPHKS (SEQ ID NO: 4894), MGSPHSK (SEQ ID NO: 4895), HDSPHKH (SEQ ID NO: 4896), QVSPHKS (SEQ ID NO: 4897), HNSPHKS (SEQ ID NO: 4898), NGSPHKR (SEQ ID NO: 4899), HDSPHKY (SEQ ID NO: 4900), NDSPHKI (SEQ ID NO: 4901), HDSPHKL (SEQ ID NO: 4902), HPSPHWK (SEQ ID NO: 4903), HDSPHKM (SEQ ID NO: 4904), or HSSPHRS (SEQ ID NO: 4905). In some embodiments, [N1]-[N2]-[N3] is GSGSPHSKA (SEQ ID NO: 4697), GHDSPHKSG (SEQ ID NO: 4698), GSGSPHARM (SEQ ID NO: 4906), GSGSPHVKS (SEQ ID NO: 4907), GQDSPHKSG (SEQ ID NO: 4908), GSGSPHASR (SEQ ID NO: 4909), GSGSPHVKI (SEQ ID NO: 4910), GSGSPHKKN (SEQ ID NO: 4911), GSGSPHVRM (SEQ ID NO: 4912), VSGSPHSKA (SEQ ID NO: 4913), CSGSPHSKA (SEQ ID NO: 4914), GSGSPHRKA (SEQ ID NO: 4915), CSGSPHKTS (SEQ ID NO: 4916), CSHSPHKSG (SEQ ID NO: 4917), GQSSPHRSG (SEQ ID NO: 4918), GRGSPHASR (SEQ ID NO: 4919), GRGSPHSKA (SEQ ID NO: 4920), GSGSPHKFG (SEQ ID NO: 4921), GSGSPHKIG (SEQ ID NO: 4922), GSGSPHKLG (SEQ ID NO: 4923), GSGSPHKTS (SEQ ID NO: 4924), GSGSPHKTT (SEQ ID NO: 4925), GSGSPHKTY (SEQ ID NO: 4926), GSGSPHKYG (SEQ ID NO: 4927), GSGSPHSKD (SEQ ID NO: 4928), GSGSPHSKP (SEQ ID NO: 4929), GSGSPHTRG (SEQ ID NO: 4930), GSGSPHVRG (SEQ ID NO: 4931), GSHSPHKRG (SEQ ID NO: 4932), GSHSPHKSG (SEQ ID NO: 4933), VSGSPHASR (SEQ ID NO: 4934), VSGSPHGAR (SEQ ID NO: 4935), VSGSPHKFG (SEQ ID NO: 4936), GHDSPHKRG (SEQ ID NO: 4937), GDDSPHKSG (SEQ ID NO: 4938), GHESPHKSA (SEQ ID NO: 4939), GHDSPHKSA (SEQ ID NO: 4940), GNYSPHKIG (SEQ ID NO: 4941), GHDSPHKSR (SEQ ID NO: 4942), GSGSPHSKL (SEQ ID NO: 4943), GSGSPHSRA (SEQ ID NO: 4944), GSGSPHSKR (SEQ ID NO: 4945), GSGSPHSLR (SEQ ID NO: 4946), GSGSPHSRG (SEQ ID NO: 4947), GSGSPHSSR (SEQ ID NO: 4948), RVGSPHSKA (SEQ ID NO: 4949), GSCSPHRKA (SEQ ID NO: 4950), GSGSPHFLR (SEQ ID NO: 4951), GSGSPHSKW (SEQ ID NO: 4952), GSGSPHSKS (SEQ ID NO: 4953), GLLSPHWKA (SEQ ID NO: 4954), GSGSPHVRR (SEQ ID NO: 4955), GSGSPHSKV (SEQ ID NO: 4956), MSGSPHSKA (SEQ ID NO: 4957), RNGSPHSKA (SEQ ID NO: 4958), TSGSPHSKA (SEQ ID NO: 4959), ISGSPHSKA (SEQ ID NO: 4960), GPGSPHSKA (SEQ ID NO: 4961), GSGSPHSKT (SEQ ID NO: 4962), ESGSPHSKA (SEQ ID NO: 4963), SSGSPHSKA (SEQ ID NO: 4964), GNGSPHSKA (SEQ ID NO: 4965), ASGSPHSKA (SEQ ID NO: 4966), NSGSPHSKA (SEQ ID NO: 4967), LSGSPHSKA (SEQ ID NO: 4968), GGGSPHSKA (SEQ ID NO: 4969), KSGSPHSKA (SEQ ID NO: 4970), GGGSPHSKS (SEQ ID NO: 4971), GSGSPHSKG (SEQ ID NO: 4972), HSGSPHSKA (SEQ ID NO: 4973), GTGSPHSKA (SEQ ID NO: 4974), PSGSPHSKA (SEQ ID NO: 4975), GSVSPHGKA (SEQ ID NO: 4976), RSGSPHSKA (SEQ ID NO: 4977), GSGSPHTKA (SEQ ID NO: 4978), GIGSPHSKA (SEQ ID NO: 4979), WSGSPHSKA (SEQ ID NO: 4980), DSGSPHSKA (SEQ ID NO: 4981), IDGSPHSKA (SEQ ID NO: 4982), GSGSPHNKA (SEQ ID NO: 4983), GLGSPHSKS (SEQ ID NO: 4984), DAGSPHSKA (SEQ ID NO: 4985), DGGSPHSKA (SEQ ID NO: 4986), MEGSPHSKA (SEQ ID NO: 4987), ENGSPHSKA (SEQ ID NO: 4988), GSASPHSKA (SEQ ID NO: 4989), GNGSPHSKS (SEQ ID NO: 4990), KNGSPHSKA (SEQ ID NO: 4991), KEGSPHSKA (SEQ ID NO: 4992), AIGSPHSKA (SEQ ID NO: 4993), GSGSPHSKN (SEQ ID NO: 4994), GSGSPHAKA (SEQ ID NO: 4995), GHDSPHKIG (SEQ ID NO: 4996), GYDSPHKSG (SEQ ID NO: 4997), GHESPHKSG (SEQ ID NO: 4998), GHDSPHKTG (SEQ ID NO: 4999), GRGSPHKRG (SEQ ID NO: 5000), GQDSPHKSG (SEQ ID NO: 4908), GHDSPHKSL (SEQ ID NO: 5001), GHGSPHSKA (SEQ ID NO: 5002), GHDSPHKSE (SEQ ID NO: 5003), VSGSPHSKA (SEQ ID NO: 4913), GRDSPHKSG (SEQ ID NO: 5004), GNDSPHKSV (SEQ ID NO: 5005), GQDSPHKIG (SEQ ID NO: 5006), GHDSPHKSV (SEQ ID NO: 5007), GPDSPHKIG (SEQ ID NO: 5008), GPDSPHKSG (SEQ ID NO: 5009), GHDSPHKSW (SEQ ID NO: 5010), GHDSPHKSN (SEQ ID NO: 5011), GMGSPHSKT (SEQ ID NO: 5012), GHDSPHKHG (SEQ ID NO: 5013), GQVSPHKSG (SEQ ID NO: 5014), GDDSPHKSV (SEQ ID NO: 5015), GHNSPHKSG (SEQ ID NO: 5016), GNGSPHKRG (SEQ ID NO: 5017), GHDSPHKYG (SEQ ID NO: 5018), GHDSPHKSQ (SEQ ID NO: 5019), GNDSPHKIG (SEQ ID NO: 5020), GHDSPHKSK (SEQ ID NO: 5021), GHDSPHKLW (SEQ ID NO: 5022), GHPSPHWKG (SEQ ID NO: 5023), GHDSPHKMG (SEQ ID NO: 5024), GHDSPHKMA (SEQ ID NO: 5025), or (SEQ ID NO: 5026); an amino acid sequence comprising any portion of any of the aforesaid amino acid sequences (e.g., any 2, 3, 4, 5, 6, 7, or 8 amino acids, e.g., consecutive amino acids) thereof; an amino acid sequence comprising one, two, or three but no more than four modifications, e.g., substitutions (e.g., conservative substitutions), insertions, or deletions, relative to any of the aforesaid amino acid sequences; or an amino acid sequence comprising one, two, or three but no more than four different amino acids, relative to any one of the aforesaid amino acid sequences. In some embodiments, [N1]-[N2]-[N3] is or comprises GSGSPHSKA (SEQ ID NO: 4697). In some embodiments, [N1]-[N2]-[N3] is or comprises GHDSPHKSG (SEQ ID NO: 4698).

In some embodiments, the AAV capsid variant comprising an amino acid sequence having the formula [N1]-[N2]-[N3], further comprises [N4], wherein [N4] comprises X7 X8 X9 X10. In some embodiments, position X7 of [N4] is W, Q, K, R, G, L, V, S, P, H, K, I, M, A, E, or F. In some embodiments, position X8 of [N4] is N, Y, C, K, T, H, R, D, V, S, P, G, W, E, F, A, I, M, Q, or L. In some embodiments, position X9 of [N4] is Q, G, K, H, R, T, L, D, A, P, I, F, V, M, W, Y, S, E, N, or Y. In some embodiments, position X10 of [N4] is Q, H, L, R, W, K, A, P, E, M, I, S, G, N, Y, C, V, T, D, or V. In some embodiments [N4] comprises QNQQ (SEQ ID NO: 5028), WNQQ (SEQ ID NO: 5029), QYYV (SEQ ID NO: 5030), RRQQ (SEQ ID NO: 5031), GCGQ (SEQ ID NO: 5032), LRQQ (SEQ ID NO: 5033), RNQQ (SEQ ID NO: 5034), VNQQ (SEQ ID NO: 5035), FRLQ (SEQ ID NO: 5036), FNQQ (SEQ ID NO: 5037), LLQQ (SEQ ID NO: 5038), SNQQ (SEQ ID NO: 5039), RLQQ (SEQ ID NO: 5040), LNQQ (SEQ ID NO: 5041), QRKL (SEQ ID NO: 5042), LRRQ (SEQ ID NO: 5043), QRLR (SEQ ID NO: 5044), QRRL (SEQ ID NO: 5045), RRLQ (SEQ ID NO: 5046), RLRQ (SEQ ID NO: 5047), SKRQ (SEQ ID NO: 5048), QLYR (SEQ ID NO: 5049), QLTV (SEQ ID NO: 5050), QNKQ (SEQ ID NO: 5051), KNQQ (SEQ ID NO: 5052), QKQQ (SEQ ID NO: 5053), QTQQ (SEQ ID NO: 5054), QNHQ (SEQ ID NO: 5055), QHQQ (SEQ ID NO: 5056), QNQH (SEQ ID NO: 5057), QHRQ (SEQ ID NO: 5058), LTQQ (SEQ ID NO: 5059), QNQW (SEQ ID NO: 5060), QNTH (SEQ ID NO: 5061), RRRQ (SEQ ID NO: 5062), QYQQ (SEQ ID NO: 5063), QNDQ (SEQ ID NO: 5064), QNRH (SEQ ID NO: 5065), RDQQ (SEQ ID NO: 5066), PNLQ (SEQ ID NO: 5067), HVRQ (SEQ ID NO: 5068), PNQH (SEQ ID NO: 5069), HNQQ (SEQ ID NO: 5070), QSQQ (SEQ ID NO: 5071), QPAK (SEQ ID NO: 5072), QNLA (SEQ ID NO: 5073), QNQL (SEQ ID NO: 5074), QGQQ (SEQ ID NO: 5075), LNRQ (SEQ ID NO: 5076), QNPP (SEQ ID NO: 5077), QNLQ (SEQ ID NO: 5078), QDQE (SEQ ID NO: 5079), QDQQ (SEQ ID NO: 5080), HWQQ (SEQ ID NO: 5081), PNQQ (SEQ ID NO: 5082), PEQQ (SEQ ID NO: 5083), QRTM (SEQ ID NO: 5084), LHQH (SEQ ID NO: 5085), QHRI (SEQ ID NO: 5086), QYIH (SEQ ID NO: 5087), QKFE (SEQ ID NO: 5088), QFPS (SEQ ID NO: 5089), QNPL (SEQ ID NO: 5090), QAIK (SEQ ID NO: 5091), QNRQ (SEQ ID NO: 5092), QYQH (SEQ ID NO: 5093), QNPQ (SEQ ID NO: 5094), QHQL (SEQ ID NO: 5095), QSPP (SEQ ID NO: 5096), QAKL (SEQ ID NO: 5097), KSQQ (SEQ ID NO: 5098), QDRP (SEQ ID NO: 5099), QNLG (SEQ ID NO: 5100), QAFH (SEQ ID NO: 5101), QNAQ (SEQ ID NO: 5102), HNQL (SEQ ID NO: 5103), QKLN (SEQ ID NO: 5104), QNVQ (SEQ ID NO: 5105), QAQQ (SEQ ID NO: 5106), QTPP (SEQ ID NO: 5107), QPPA (SEQ ID NO: 5108), QERP (SEQ ID NO: 5109), QDLQ (SEQ ID NO: 5110), QAMH (SEQ ID NO: 5111), QHPS (SEQ ID NO: 5112), PGLQ (SEQ ID NO: 5113), QGIR (SEQ ID NO: 5114), QAPA (SEQ ID NO: 5115), QIPP (SEQ ID NO: 5116), QTQL (SEQ ID NO: 5117), QAPS (SEQ ID NO: 5118), QNTY (SEQ ID NO: 5119), QDKQ (SEQ ID NO: 5120), QNHL (SEQ ID NO: 5121), QIGM (SEQ ID NO: 5122), LNKQ (SEQ ID NO: 5123), PNQL (SEQ ID NO: 5124), QLQQ (SEQ ID NO: 5125), QRMS (SEQ ID NO: 5126), QGIL (SEQ ID NO: 5127), QDRQ (SEQ ID NO: 5128), RDWQ (SEQ ID NO: 5129), QERS (SEQ ID NO: 5130), QNYQ (SEQ ID NO: 5131), QRTC (SEQ ID NO: 5132), QIGH (SEQ ID NO: 5133), QGAI (SEQ ID NO: 5134), QVPP (SEQ ID NO: 5135), QVQQ (SEQ ID NO: 5136), LMRQ (SEQ ID NO: 5137), QYSV (SEQ ID NO: 518), QAIT (SEQ ID NO: 5139), QKTL (SEQ ID NO: 5140), QLHH (SEQ ID NO: 5141), QNII (SEQ ID NO: 5142), QGHH (SEQ ID NO: 5143), QSKV (SEQ ID NO: 5144), QLPS (SEQ ID NO: 5145), IGKQ (SEQ ID NO: 5146), QAIH (SEQ ID NO: 5147), QHGL (SEQ ID NO: 5148), QFMC (SEQ ID NO: 5149), QNQM (SEQ ID NO: 5150), QHLQ (SEQ ID NO: 5151), QPAR (SEQ ID NO: 5152), QSLQ (SEQ ID NO: 5153), QSQL (SEQ ID NO: 5154), HSQQ (SEQ ID NO: 5155), QMPS (SEQ ID NO: 5156), QGSL (SEQ ID NO: 5157), QVPA (SEQ ID NO: 5158), HYQQ (SEQ ID NO: 5159), QVPS (SEQ ID NO: 5160), RGEQ (SEQ ID NO: 5161), PGQQ (SEQ ID NO: 5162), LEQQ (SEQ ID NO: 5163), QNQS (SEQ ID NO: 5164), QKVI (SEQ ID NO: 5165), QNND (SEQ ID NO: 5166), QSVH (SEQ ID NO: 5167), QPLG (SEQ ID NO: 5168), HNQE (SEQ ID NO: 5169), QIQQ (SEQ ID NO: 5170), QVRN (SEQ ID NO: 5171), PSNQ (SEQ ID NO: 5172), QVGH (SEQ ID NO: 5173), QRDI (SEQ ID NO: 5174), QMPN (SEQ ID NO: 5175), RGLQ (SEQ ID NO: 5176), PSLQ (SEQ ID NO: 5177), QRDQ (SEQ ID NO: 5178), QAKG (SEQ ID NO: 5179), QSAH (SEQ ID NO: 5180), QSTM (SEQ ID NO: 5181), QREM (SEQ ID NO: 5182), QYRA (SEQ ID NO: 5183), QRQQ (SEQ ID NO: 5184), QWQQ (SEQ ID NO: 5185), QRMN (SEQ ID NO: 5186), GDSQ (SEQ ID NO: 5187), QKIS (SEQ ID NO: 5188), PSMQ (SEQ ID NO: 5189), SPRQ (SEQ ID NO: 5190), MEQQ (SEQ ID NO: 5191), QYQN (SEQ ID NO: 5192), QIRQ (SEQ ID NO: 5193), QSVQ (SEQ ID NO: 5194), RSQQ (SEQ ID NO: 5195), QNKL (SEQ ID NO: 5196), QIQH (SEQ ID NO: 5197), PRQQ (SEQ ID NO: 5198), HTQQ (SEQ ID NO: 5199), QRQH (SEQ ID NO: 5200), RNQE (SEQ ID NO: 5201), QSKQ (SEQ ID NO: 5202), QNQP (SEQ ID NO: 5203), QSPQ (SEQ ID NO: 5204), QTRQ (SEQ ID NO: 5205), QNLH (SEQ ID NO: 5206), QNQE (SEQ ID NO: 5207), LNQP (SEQ ID NO: 5208), QNQD (SEQ ID NO: 5209), QNLL (SEQ ID NO: 5210), QLVI (SEQ ID NO: 5211), RTQE (SEQ ID NO: 5212), QTHQ (SEQ ID NO: 5213), QDQH (SEQ ID NO: 5214), QSQH (SEQ ID NO: 5215), VRQQ (SEQ ID NO: 5216), AWQQ (SEQ ID NO: 5217), QSVP (SEQ ID NO: 5218), QNIQ (SEQ ID NO: 5219), LDQQ (SEQ ID NO: 5220), PDQQ (SEQ ID NO: 5221), ESQQ (SEQ ID NO: 5222), QRQL (SEQ ID NO: 5223), QIIV (SEQ ID NO: 5224), QKQS (SEQ ID NO: 5225), QSHQ (SEQ ID NO: 5226), QFVV (SEQ ID NO: 5227), QSQP (SEQ ID NO: 5228), QNEQ (SEQ ID NO: 5229), INQQ (SEQ ID NO: 5230), RNRQ (SEQ ID NO: 5231), RDQK (SEQ ID NO: 5232), QWKR (SEQ ID NO: 5233), ENRQ (SEQ ID NO:

5234), QTQP (SEQ ID NO: 5235), QKQL (SEQ ID NO: 5236), RNQL (SEQ ID NO: 5237), ISIQ (SEQ ID NO: 5238), QTVC (SEQ ID NO: 5239), QQIM (SEQ ID NO: 5240), LNHQ (SEQ ID NO: 5241), QNQA (SEQ ID NO: 5242), QMIH (SEQ ID NO: 5243), RNHQ (SEQ ID NO: 5244), or QKMN (SEQ ID NO: 5245), or any dipeptide or tripeptide thereof. In some embodiments, [N1]-[N2]-[N3]-[N4] is or comprises: the amino acid sequence of any of SEQ ID NOs: 1800-2241; an amino acid sequence comprising any portion of any of the aforesaid amino acid sequences (e.g., any 2, 3, 4, 5, 6, 7, 8, 9, 10, 11, or 12 amino acids, e.g., consecutive amino acids) thereof; an amino acid sequence comprising one, two, or three but no more than four modifications, e.g., substitutions (e.g., conservative substitutions), insertions, or deletions, relative to any of the aforesaid amino acid sequences; or an amino acid sequence comprising one, two, or three but no more than four different amino acids, relative to any one of the aforesaid amino acid sequences. In some embodiments, [N1]-[N2]-[N3]-[N4] is or comprises GSGSPHSKAQNQQ (SEQ ID NO: 1801). In some embodiments, [N1]-[N2]-[N3]-[N4] is or comprises GHDSPHKSGQNQQ (SEQ ID NO: 1800).

In some embodiments, the AAV capsid variant comprising an amino acid sequence having the formula [N1]-[N2]-[N3], further comprises [N0], wherein [N0] comprises XA XB and XC. In some embodiments, XA of [N0] is T, S, Y, M, A, C, I, R, L, D, F, V, Q, N, H, E, or G. In some embodiments, XB of [N0] is I, M, P, E, N, D, S, A, T, G, Q, F, V, L, C, H, R, W, or L. In some embodiments, XC of [N0] is N, M, E, G, Y, W, T, I, Q, F, V, A, L, I, P, K, R, H, S, D, or S. In some embodiments, [N0] comprises TIN, SMN, TIM, YLS, GLS, MPE, MEG, MEY, AEW, CEW, ANN, IPE, ADM, IEY, ADY, IET, MEW, CEY, RIN, MEI, LEY, ADW, IEI, DIM, FEQ, MEF, CDQ, LPE, IEN, MES, AEI, VEY, IIN, TSN, IEV, MEM, AEV, MDA, VEW, AEQ, LEW, MEL, MET, MEA, IES, MEV, CEI, ATN, MDG, QEV, ADQ, NMN, IEM, ISN, TGN, QQQ, HDW, IEG, TII, TFP, TEK, EIN, TVN, TFN, SIN, TER, TSY, ELH, AIN, SVN, TDN, TFH, TVH, TEN, TSS, TID, TCN, NIN, TEH, AEM, AIK, TDK, TFK, SDQ, TEI, NTN, TET, SIK, TEL, TEA, TAN, TIY, TFS, TES, TTN, TED, TNN, EVH, TIS, TVR, TDR, TIK, NHI, TIP, ESD, TDL, TVP, TVI, AEH, NCL, TVK, NAD, TIT, NCV, TIR, NAL, VIN, TIQ, TEF, TRE, QGE, SEK, NVN, GGE, EFV, SDK, TEQ, EVQ, TEY, NCW, TDV, SDI, NSI, NSL, EVV, TEP, SEL, TWQ, TEV, AVN, GVL, TLN, TEG, TRD, NAI, AEN, AET, ETA, NNL, or any dipeptide thereof. In some embodiments, [N0]-[N1]-[N2]-[N3]-[N4] is or comprises the amino acid sequence of any one of SEQ ID NOs: 2242-2886; an amino acid sequence comprising any portion of any of the aforesaid amino acid sequences (e.g., any 2, 3, 4, 5, 6, 7, 8, 9, 10, 11, 12, 13, 14, or 15 amino acids, e.g., consecutive amino acids) thereof; an amino acid sequence comprising one, two, or three but no more than four modifications, e.g., substitutions (e.g., conservative substitutions), insertions, or deletions, relative to any of the aforesaid amino acid sequences; or an amino acid sequence comprising one, two, or three but no more than four different amino acids, relative to any one of the aforesaid amino acid sequences. In some embodiments, [N0]-[N1]-[N2]-[N3]-[N4] is or comprises TINGSGSPHSKAQNQQ (SEQ ID NO: 2242). In some embodiments, [N0]-[N1]-[N2]-[N3]-[N4] is or comprises TINGHDSPHKSGQNQQ (SEQ ID NO: 2243).

In some embodiments, [N1]-[N2]-[N3] is present in loop IV of the AAV capsid variant. In some embodiments [N0] and [N4] are present in loop IV of the AAV capsid variant. In some embodiments, [N0]-[N1]-[N2]-[N3]-[N4] is present in loop IV of the AAV capsid variant. In some embodiments, [N0] is present immediately subsequent to position 449, relative to a reference sequence numbered according to the amino acid sequence of SEQ ID NO: 138. In some embodiments, wherein [N0] is present immediately subsequent to position 449, relative to a reference sequence numbered according to the amino acid sequence of SEQ ID NO: 981 or 982. In some embodiments, [N0] replaces positions 450, 451, and 452 (e.g., amino acids T450, I451, and N452), relative to a reference sequence numbered according to SEQ ID NO: 138, 981, or 982. wherein [N0] is present immediately subsequent to position 449 and wherein [N0] replaces positions 450-452 (e.g., T450, I451, and N452), relative to a reference sequence numbered according to SEQ ID NO: 138, 981, or 982. In some embodiments, [N1] is present immediately subsequent to position 452, relative to a reference sequence numbered according to the amino acid sequence of SEQ ID NO: 138, 981 or 982. In some embodiments, wherein [N1] replaces positions 453-455 (e.g., G453, S454, and G455), relative to a reference sequence numbered according to SEQ ID NO: 138, 981, or 982. In some embodiments, [N1] is present immediately subsequent to position 452 and wherein [N1] replaces positions 453-455 (e.g., G453, S454, and G455), relative to a reference sequence numbered according to SEQ ID NO: 138, 981, or 982. In some embodiments, [N2] is present immediately subsequent to position 455, relative to a reference sequence numbered according to the amino acid sequence of SEQ ID NO: 138, 981, or 982. In some embodiments, [N2]-[N3] is present immediately subsequent to position 455, relative to a reference sequence numbered according to the amino acid sequence of SEQ ID NO: 138, 981, or 982. In some embodiments [N1]-[N2]-[N3] is present immediately subsequent to position 452, numbered relative to SEQ ID NO: 138, 981, or 982. In some embodiments, [N1]-[N2]-[N3] replaces positions 453-455 (e.g., G453, S454, and G455), relative to a reference sequence numbered according to SEQ ID NO: 138, 981, or 982. In some embodiments, [N1] is present immediately subsequent to position 452 and wherein [N1]-[N2]-[N3] replaces positions 453-455 (e.g., G453, S454, and G455), relative to a reference sequence numbered according to SEQ ID NO: 138, 981, or 982. In some embodiments, [N4] is present immediately subsequent to position 455, relative to a reference sequence numbered according to the amino acid sequence of SEQ ID NO: 138. In some embodiments, [N4] replaces positions 456-459 (e.g., Q456, N457, Q458, and Q459), relative to a reference sequence numbered according to the amino acid sequence of SEQ ID NO: 138. In some embodiments, [N4] is present immediately subsequent to position 455, and [N4] replaces positions 456-459 (e.g., Q456, N457, Q458, and Q459), relative to a reference sequence numbered according to the amino acid sequence of SEQ ID NO: 138. In some embodiments, [N2]-[N3]-[N4] replaces positions 456-459 (e.g., Q456, N457, Q458, and Q459), relative to a reference sequence numbered according to the amino acid sequence of SEQ ID NO: 138. In some embodiments, [N2]-[N3]-[N4] is present immediately subsequent to position 455, and wherein [N2]-[N3]-[N4] replaces positions 456-459 (e.g., Q456, N457, Q458, and Q459), relative to a reference sequence numbered according to the amino acid sequence of SEQ ID NO: 138. In some embodiments, [N1]-[N2]-[N3]-[N4] replaces positions 453-459 (e.g., G453, S454, G455, Q456, N457, Q458, and Q459), relative to a reference sequence numbered according to the amino acid sequence of SEQ ID NO: 138. In some embodiments, [N1]-[N2]-[N3]-[N4] is present immediately subsequent to position 452, and wherein [N1]-[N2]-[N3]-[N4] replaces positions 453-459 (e.g., G453, S454, G455, Q456, N457, Q458, and Q459), relative to a reference sequence numbered according to the amino acid sequence of SEQ ID NO: 138. In some embodiments, [N0]-[N1]-[N2]-[N3]-[N4] replaces positions 450-456 (e.g., T450, I451, N452, G453, S454, G455, Q456, N457, Q458, and Q459), relative to a reference sequence numbered according to the amino acid sequence of SEQ ID NO: 138. In some embodiments, [N0]-[N1]-[N2]-[N3]-[N4] is present immediately subsequent to position 449, and wherein [N0]-[N1]-[N2]-[N3]-[N4] replaces positions 450-456 (e.g., T450, I451, N452, G453, S454, G455, Q456, N457, Q458, and Q459), relative to a reference sequence numbered according to the amino acid sequence of SEQ ID NO: 138.

In some embodiments, [N3] is present immediately subsequent to [N2].

In some embodiments, the AAV capsid variant comprises from N-terminus to C-terminus, [N2]-[N3]. In some embodiments, the AAV capsid variant comprises from N-terminus to C-terminus, [N1]-[N2]-[N3]. In some embodiments, the AAV capsid variant comprises from N-terminus to C-terminus, [N1]-[N2]-[N3]-[N4]. In some embodiments, the AAV capsid variant comprises from N-terminus to C-terminus, [N0]-[N1]-[N2]-[N3]. In some embodiments, the AAV capsid variant comprises from N-terminus to C-terminus, [N0]-[N1]-[N2]-[N3]-[N4].

In some embodiments, an AAV capsid variant described herein comprises an amino acid sequence having the formula [A][B](SEQ ID NO: 4694), wherein [A] comprises the amino acid sequence of GSGSPH (SEQ ID NO: 4695) and [B] comprises X1 X2 X3 X4 X5 X6 X7. In some embodiments, position X1 of [B] is S, C, F, or V. In some embodiments, position X2 of [B] is K, L, R, I, E, Y, V, or S. In some embodiments, X3 of [B] is A, R, L, G, I, Y, S, F, or W. In some embodiments X4 of [B] is W, Q, R, G, L, V, S, or F. In some embodiments, position X5 of [B] is N, Y, R, C, K, or L. In some embodiments, position X6 of [B] is Q, G, K, R, T, L, or Y. In some embodiment, position X7 of [B] is Q, L, R, or V. In some embodiments, [B] comprises S LLWNQQ (SEQ ID NO: 5247), SKAQYYV (SEQ ID NO: 5248), SKLRRQQ (SEQ ID NO: 5249), SIWQNQQ (SEQ ID NO: 5250), SKAGCGQ (SEQ ID NO: 5251), SRAQNQQ (SEQ ID NO: 5252), SKRLRQQ (SEQ ID NO: 5253), SLRRNQQ (SEQ ID NO: 5254), SRGRNQQ (SEQ ID NO: 5255), SEIVNQQ (SEQ ID NO: 5256), SSRRNQQ (SEQ ID NO: 5257), CLLQNQQ (SEQ ID NO: 5258), SKAFRLQ (SEQ ID NO: 5259), CLAQNQQ (SEQ ID NO: 5260), FLRQNQQ (SEQ ID NO: 5261), SLRFNQQ (SEQ ID NO: 5262), SYLRNQQ (SEQ ID NO: 5263), CSLQNQQ (SEQ ID NO: 5264), VLWQNQQ (SEQ ID NO: 5265), SKWLLQQ (SEQ ID NO: 5266), SLWSNQQ (SEQ ID NO: 5267), SKRRLQQ (SEQ ID NO: 5268), SVYLNQQ (SEQ ID NO: 5269), SLWLNQQ (SEQ ID NO: 5270), SKAQRKL (SEQ ID NO: 5271), SKALRRQ (SEQ ID NO: 5272), SKAQRLR (SEQ ID NO: 5273), SKAQNQQ (SEQ ID NO: 5274), SKAQRRL (SEQ ID NO: 5275), SKARRQQ (SEQ ID NO: 5276), SKARRLQ (SEQ ID NO: 5277), SKSRRQQ (SEQ ID NO: 5278), SKARLRQ (SEQ ID NO: 5279), SKASKRQ (SEQ ID NO: 5280), VRRQNQQ (SEQ ID NO: 5281), SKAQLYR (SEQ ID NO: 5282), SLFRNQQ (SEQ ID NO: 5283), SKAQLTV (SEQ ID NO: 5284), or any dipeptide, tripeptide, tetrapeptide, pentapeptide, or hexapeptide thereof. In some embodiments, [A][B] comprises GSGSPHSLLWNQQ (SEQ ID NO: 5285), GSGSPHSKAQYYV (SEQ ID NO: 2060), GSGSPHSKLRRQQ (SEQ ID NO: 2061), GSGSPHSIWQNQQ (SEQ ID NO: 5286), GSGSPHSKAGCGQ (SEQ ID NO: 2062), GSGSPHSRAQNQQ (SEQ ID NO: 2063), GSGSPHSKRLRQQ (SEQ ID NO: 2064), GSGSPHSLRRNQQ (SEQ ID NO: 2065), GSGSPHSRGRNQQ (SEQ ID NO: 2066), GSGSPHSEIVNQQ (SEQ ID NO: 5287), GSGSPHSSRRNQQ (SEQ ID NO: 2067), GSGSPHCLLQNQQ (SEQ ID NO: 5288), GSGSPHSKAFRLQ (SEQ ID NO: 2068), GSGSPHCLAQNQQ (SEQ ID NO: 5289), GSGSPHFLRQNQQ (SEQ ID NO: 2070), GSGSPHSLRFNQQ (SEQ ID NO: 2071), GSGSPHSYLRNQQ (SEQ ID NO: 5290), GSGSPHCSLQNQQ (SEQ ID NO: 5291), GSGSPHVLWQNQQ (SEQ ID NO: 5292), GSGSPHSKWLLQQ (SEQ ID NO: 2072), GSGSPHSLWSNQQ (SEQ ID NO: 5293), GSGSPHSKRRLQQ (SEQ ID NO: 2073), GSGSPHSVYLNQQ (SEQ ID NO: 5294), GSGSPHSLWLNQQ (SEQ ID NO: 5295), GSGSPHSKAQRKL (SEQ ID NO: 2074), GSGSPHSKALRRQ (SEQ ID NO: 2075), GSGSPHSKAQRLR (SEQ ID NO: 2076), GSGSPHSKAQNQQ (SEQ ID NO: 1801), GSGSPHSKAQRRL (SEQ ID NO: 2077), GSGSPHSKARRQQ (SEQ ID NO: 2078), GSGSPHSKARRLQ (SEQ ID NO: 2079), GSGSPHSKSRRQQ (SEQ ID NO: 2080), GSGSPHSKARLRQ (SEQ ID NO: 2082), GSGSPHSKASKRQ (SEQ ID NO: 2083), GSGSPHVRRQNQQ (SEQ ID NO: 2084), GSGSPHSKAQLYR (SEQ ID NO: 2085), GSGSPHSLFRNQQ (SEQ ID NO: 5296), GSGSPHSKAQLTV (SEQ ID NO: 2086), or any portion thereof, e.g., any 2, 3, 4, 5, 6, 7, 8, 9, 10, 11, or 12 amino acids, e.g., consecutive amino acids, thereof.

In some embodiments, [A][B] is present in loop IV of the AAV capsid variant. In some embodiments, [A] is present immediately subsequent to position 452, relative to a reference sequence numbered according to the amino acid sequence of SEQ ID NO: 138. In some embodiments, [A] replaces positions 453-455 (e.g., G453, S454, G455), relative to a reference sequence numbered according to the amino acid sequence of SEQ ID NO: 138. In some embodiments, [A] is present immediately subsequent to position 452, and wherein [A] replaces positions 453-455 (e.g., G453, S454, G455), relative to a reference sequence numbered according to the amino acid sequence of SEQ ID NO: 138. In some embodiments, [B] is present immediately subsequent to [A]. In some embodiments, [B] replaces positions 456-459 (e.g., Q456, N457, Q458, Q459), relative to a reference sequence numbered according to the amino acid sequence of SEQ ID NO: 138. In some embodiments, [A][B] replaces positions 453-459 (e.g., G453, S454, G455, Q456, N457, Q458, Q459), relative to a reference sequence numbered according to the amino acid sequence of SEQ ID NO: 138. In some embodiments, [A][B] is present immediately subsequent to position 452, and wherein [A][B] replaces positions 453-459 (e.g., G453, S454, G455, Q456, N457, Q458, Q459), relative to a reference sequence numbered according to the amino acid sequence of SEQ ID NO: 138. In some embodiments, the AAV capsid variant comprises from N-terminus to C-terminus, [A][B].

In some embodiments, an AAV capsid variant described herein comprises an amino acid sequence having the formula [A][B](SEQ ID NO: 4699), wherein [A] comprises X1 X2 X3 X4 X5 X6 and [B] comprises SPHKSG (SEQ ID NO: 946). In some embodiments, position X1 of [A] is T, M, A, C, I, R, L, D, F, V, Q, N, or H. In some embodiments, position X2 of [A] is I, P, E, N, D, S, A, T, M, or Q. In some embodiments, position X3 of [A] is N, E, G, Y, W, M, T, I, K, Q, F, S, V, A, or L. In some embodiments, position X4 of [A] is G, D, R, or E. In some embodiments, position X5 of [A] is H, Q, N, or D. In some embodiments, position X6 of

[A] is D or R. In some embodiments, [A] comprises TINGHD (SEQ ID NO: 5297), MPEGHD (SEQ ID NO: 5298), MEGGHD (SEQ ID NO: 5299), MEYGHD (SEQ ID NO: 5300), AEWGHD (SEQ ID NO: 5301), CEWGHD (SEQ ID NO: 5302), ANNGQD (SEQ ID NO: 5303), IPEGHD (SEQ ID NO: 5304), ADMGHD (SEQ ID NO: 5305), IEYGHD (SEQ ID NO: 5306), ADYGHD (SEQ ID NO: 5307), IETGHD (SEQ ID NO: 5308), MEWGHD (SEQ ID NO: 5309), CEYGHD (SEQ ID NO: 5310), RINGHD (SEQ ID NO: 5311), MEIGHD (SEQ ID NO: 5312), LEYGHD (SEQ ID NO: 5313), ADWGHD (SEQ ID NO: 5314), IEIGHD (SEQ ID NO: 5315), TIKDND (SEQ ID NO: 5316), DIMGHD (SEQ ID NO: 5317), FEQGHD (SEQ ID NO: 5318), MEFGHD (SEQ ID NO: 5319), CDQGHD (SEQ ID NO: 5320), LPEGHD (SEQ ID NO: 5321), IENGHD (SEQ ID NO: 5322), MESGHD (SEQ ID NO: 5323), AEIGHD (SEQ ID NO: 5324), VEYGHD (SEQ ID NO: 5325), TSNGDD (SEQ ID NO: 5326), IEVGHD (SEQ ID NO: 5327), MEMGHD (SEQ ID NO: 5328), AEVGHD (SEQ ID NO: 5329), MDAGHD (SEQ ID NO: 5330), VEWGHD (SEQ ID NO: 5331), AEQGHD (SEQ ID NO: 5332), LEWGHD (SEQ ID NO: 5333), MELGHD (SEQ ID NO: 5334), METGHD (SEQ ID NO: 5335), MEAGHD (SEQ ID NO: 5336), TINRQR (SEQ ID NO: 5337), IESGHD (SEQ ID NO: 5338), TAKDHD (SEQ ID NO: 5339), MEVGHD (SEQ ID NO: 5340), CEIGHD (SEQ ID NO: 5341), ATNGHD (SEQ ID NO: 5342), MDGGHD (SEQ ID NO: 5343), QEVGHD (SEQ ID NO: 5344), ADQGHD (SEQ ID NO: 5345), NMNGHD (SEQ ID NO: 5346), TPWEHD (SEQ ID NO: 5347), IEMGHD (SEQ ID NO: 5348), TANEHD (SEQ ID NO: 5349), QQQGHD (SEQ ID NO: 5350), TPQDHD (SEQ ID NO: 5351), HDWGHD (SEQ ID NO: 5352), IEGGHD (SEQ ID NO: 5353), or any dipeptide, tripeptide, tetrapeptide, or pentapeptide thereof. In some embodiments, [A][B] comprises TINGHDSPHKR (SEQ ID NO: 5354), MPEGHDSPHKS (SEQ ID NO: 5355), MEGGHDSPHKS (SEQ ID NO: 5356), MEYGHDSPHKS (SEQ ID NO: 5357), AEWGHDSPHKS (SEQ ID NO: 5358), CEWGHDSPHKS (SEQ ID NO: 5359), ANNGQDSPHKS (SEQ ID NO: 5360), IPEGHDSPHKS (SEQ ID NO: 5361), ADMGHDSPHKS (SEQ ID NO: 5362), IEYGHDSPHKS (SEQ ID NO: 5363), ADYGHDSPHKS (SEQ ID NO: 5364), IETGHDSPHKS (SEQ ID NO: 5365), MEWGHDSPHKS (SEQ ID NO: 5366), CEYGHDSPHKS (SEQ ID NO: 5367), RINGHDSPHKS (SEQ ID NO: 5368), MEIGHDSPHKS (SEQ ID NO: 5369), LEYGHDSPHKS (SEQ ID NO: 5370), ADWGHDSPHKS (SEQ ID NO: 5371), IEIGHDSPHKS (SEQ ID NO: 5372), TIKDNDSPHKS (SEQ ID NO: 5373), DIMGHDSPHKS (SEQ ID NO: 5374), FEQGHDSPHKS (SEQ ID NO: 5375), MEFGHDSPHKS (SEQ ID NO: 5376), CDQGHDSPHKS (SEQ ID NO: 5377), LPEGHDSPHKS (SEQ ID NO: 5378), IENGHDSPHKS (SEQ ID NO: 5379), MESGHDSPHKS (SEQ ID NO: 5380), AEIGHDSPHKS (SEQ ID NO: 5381), VEYGHDSPHKS (SEQ ID NO: 5382), TSNGDDSPHKS (SEQ ID NO: 5383), IEVGHDSPHKS (SEQ ID NO: 5384), MEMGHDSPHKS (SEQ ID NO: 5385), AEVGHDSPHKS (SEQ ID NO: 5386), MDAGHDSPHKS (SEQ ID NO: 5387), VEWGHDSPHKS (SEQ ID NO: 5388), AEQGHDSPHKS (SEQ ID NO: 5389), LEWGHDSPHKS (SEQ ID NO: 5390), MELGHDSPHKS (SEQ ID NO: 5391), METGHDSPHKS (SEQ ID NO: 5392), MEAGHDSPHKS (SEQ ID NO: 5393), TINRQRSPHKS (SEQ ID NO: 5394), IESGHDSPHKS (SEQ ID NO: 5395), TAKDHDSPHKS (SEQ ID NO: 5396), MEVGHDSPHKS (SEQ ID NO: 5397), CEIGHDSPHKS (SEQ ID NO: 5398), ATNGHDSPHKS (SEQ ID NO: 5399), MDGGHDSPHKS (SEQ ID NO: 5400), QEVGHDSPHKS (SEQ ID NO: 5401), ADQGHDSPHKS (SEQ ID NO: 5402), NMNGHDSPHKS (SEQ ID NO: 5403), TPWEHDSPHKS (SEQ ID NO: 5404), IEMGHDSPHKS (SEQ ID NO: 5405), TANEHDSPHKS (SEQ ID NO: 5406), TINGHDSPHKS (SEQ ID NO: 5407), QQQGHDSPHKS (SEQ ID NO: 5408), TPQDHDSPHKS (SEQ ID NO: 5409), HDWGHDSPHKS (SEQ ID NO: 5410), IEGGHDSPHKS (SEQ ID NO: 5411), or any portion thereof, e.g., any 2, 3, 4, 5, 6, 7, 8, 9, 10, 11, or 12 amino acids, e.g., consecutive amino acids, thereof.

In some embodiments, [A][B] is present in loop IV of the AAV capsid variant. In some embodiments, [A] is present immediately subsequent to position 449, relative to a reference sequence numbered according to the amino acid sequence of SEQ ID NO: 138. In some embodiments, [A] replaces positions 450-455 (e.g., T450, I451, N452, G453, S454, G455), relative to a reference sequence numbered according to the amino acid sequence of SEQ ID NO: 138. In some embodiments, [A] is present immediately subsequent to position 449, and wherein [A] replaces positions 450-455 (e.g., T450, I451, N452, G453, S454, G455), relative to a reference sequence numbered according to the amino acid sequence of SEQ ID NO: 138. In some embodiments, [B] is present immediately subsequent to [A]. In some embodiments, [A][B] replaces positions 450-455 (e.g., T450, I451, N452, G453, S454, G455), relative to a reference sequence numbered according to the amino acid sequence of SEQ ID NO: 138. In some embodiments, [A][B] is present immediately subsequent to position 449, and wherein [A][B] replaces positions 450-455 (e.g., T450, I451, N452, G453, S454, G455), relative to a reference sequence numbered according to the amino acid sequence of SEQ ID NO: 138. In some embodiments, the peptide comprises from N-terminus to C-terminus, [A][B].

In some embodiments, an AAV capsid variant described herein comprises an amino acid sequence comprising at least 3, 4, 5, 6, 7, 8, 9, 10, 11, 12, 13, 16, or 17 consecutive amino acids from any one of the sequences provided in Tables 1, 2A, 2B, 13-19. In some embodiments, the AAV capsid variant comprises an amino acid sequence comprising at least 3, 4, or 5 consecutive amino acids from any one of SEQ ID NOs: 945-980 or 985-986. In some embodiments, the AAV capsid variant comprises an amino acid sequence comprising at least 3, 4, 5, 6, 7, 8, 9, 10, 11, 12, or 13 consecutive amino acids from any one of SEQ ID NOs: 2, 200, 201, 941, 943, 204, 208, 404, or 903-909. In some embodiments, the amino acid sequence is present in loop IV. In some embodiments, the amino acid sequence is present immediately subsequent to position 448, 452, 453, 455, relative to a reference sequence numbered according to the amino acid sequence of SEQ ID NO: 138, 981, or 982. In some embodiments, the amino acid sequence is present immediately subsequent to position 455, numbered according to SEQ ID NO: 982. In some embodiments, the amino acid sequence is present immediately subsequent to position 455, numbered according to SEQ ID NO: 138. In some embodiments, the amino acid sequence is present immediately subsequent to position 453, numbered according to SEQ ID NO: 981. In some embodiments, the amino acid sequence is present immediately subsequent to position 453, numbered according to SEQ ID NO: 138. In some embodiments, the amino acid sequence replaces 1, 2, 3, 4, 5, 6, 7, 8, 9, 10, 11, or all of positions 499 (e.g., K499), 450 (e.g., T450), 451 (e.g., I451), 452 (e.g., N452), 453 (e.g., G453), 454 (e.g., S454), 455 (e.g., G455), 456 (e.g., Q456), 457 (e.g., N457), 458 (e.g., Q458), 459 (e.g., Q459), and 460

(e.g., T460), numbered according to SEQ ID NO: 138. In some embodiments, the AAV capsid variant comprises one or more amino acid substitutions at positions 499 (e.g., K499), 450 (e.g., T450), 451 (e.g., I451), 452 (e.g., N452), 453 (e.g., G453), 454 (e.g., S454), 455 (e.g., G455), 456 (e.g., Q456), 457 (e.g., N457), 458 (e.g., Q458), 459 (e.g., Q459), and/or 460 (e.g., T460), numbered according to SEQ ID NO: 138.

In some embodiments, the 3 consecutive amino acids comprise SPH. In some embodiments, the 4 consecutive amino acids comprise SPHS (SEQ ID NO: 4700). In some embodiments, the 5 consecutive amino acids comprise SPHSK (SEQ ID NO: 4701). In some embodiments, the 6 consecutive amino acids comprise SPHSKA (SEQ ID NO: 941).

In some embodiments, 3 consecutive amino acids comprise HDS. In some embodiments, the 4 consecutive amino acids comprise HDSP (SEQ ID NO: 4702). In some embodiments, the 5 consecutive amino acids comprise HDSPH (SEQ ID NO: 4703). In some embodiments, the 6 consecutive amino acids comprise HDSPHK (SEQ ID NO: 2).

In some embodiments, an AAV capsid variant described herein comprises an amino acid sequence comprising at least one, two, or three but no more than four modifications, e.g., substitutions (e.g., conservative substitutions), insertions, or deletions, relative to the amino acid sequence of any one of the sequences provided in Tables 1, 2A, 2B, 13-19. In some embodiments, the AAV capsid variant comprises an amino acid sequence comprising at least one, two, or three but no more than four different amino acids, relative to the amino acid sequence of any one of the sequences provided in Tables 1, 2A, 2B, 13-19. In some embodiments, the AAV capsid variant comprises an amino acid sequence comprising at least one, two, or three but no more than four modifications, e.g., substitutions (e.g., conservative substitutions), insertions, or deletions, relative to the amino acid sequence of any one of SEQ ID NOs: 945-980 or 985-986. In some embodiments, the AAV capsid variant comprises an amino acid sequence comprising at least one, two, or three but no more than four different amino acids, relative to the amino acid sequence of any one of SEQ ID NOs: 945-980 or 985-986. In some embodiments, the AAV capsid variant comprises an amino acid sequence comprising at least one, two, or three but no more than four modifications, e.g., substitutions (e.g., conservative substitutions), insertions, or deletions, relative to the amino acid sequence of any one of SEQ ID NOs: 2, 200, 201, 941, 943, 204, 208, 404, or 903-909. In some embodiments, the AAV capsid variant comprises an amino acid sequence comprising at least one, two, or three but no more than four different amino acids, from the amino acid sequence of any one of SEQ ID NOs: 2, 200, 201, 941, 943, 204, 208, 404, or 903-909. In some embodiments, the amino acid sequence is present in loop IV. In some embodiments, the amino acid sequence is present immediately subsequent to position 448, 452, 453, 455, relative to a reference sequence numbered according to the amino acid sequence of SEQ ID NO: 138, 981, or 982. In some embodiments, the amino acid sequence is present immediately subsequent to position 455, numbered according to SEQ ID NO: 982. In some embodiments, the amino acid sequence is present immediately subsequent to position 455, numbered according to SEQ ID NO: 138. In some embodiments, the amino acid sequence is present immediately subsequent to position 453, numbered according to SEQ ID NO: 981. In some embodiments, the amino acid sequence is present immediately subsequent to position 453, numbered according to SEQ ID NO: 138. In some embodiments, the amino acid sequence replaces 1, 2, 3, 4, 5, 6, 7, 8, 9, 10, 11, or all of positions 499 (e.g., K499), 450 (e.g., T450), 451 (e.g., I451), 452 (e.g., N452), 453 (e.g., G453), 454 (e.g., S454), 455 (e.g., G455), 456 (e.g., Q456), 457 (e.g., N457), 458 (e.g., Q458), 459 (e.g., Q459), and 460 (e.g., T460), numbered according to SEQ ID NO: 138.

In some embodiments, the AAV capsid variant comprises an amino acid sequence comprising at least one, two, or three but no more than four modifications, e.g., substitutions (e.g., conservative substitutions), insertions, or deletions, relative to the amino acid sequence of SPHSKA (SEQ ID NO: 941). In some embodiments, the AAV capsid variant comprises an amino acid sequence comprising at least one, two, or three, but no more than four different amino acids from the amino acid sequence of SPHSKA (SEQ ID NO: 941).

In some embodiments, the AAV capsid variant comprises an amino acid sequence comprising at least one, two, or three but no more than four modifications, e.g., substitutions (e.g., conservative substitutions), insertions, or deletions, relative to the amino acid sequence of HDSPHK (SEQ ID NO: 2). In some embodiments, the AAV capsid variant comprises an amino acid sequence comprising at least one, two, or three, but no more than four different amino acids that relative to the amino acid sequence of HDSPHK (SEQ ID NO: 2).

In some embodiments, the AAV capsid variant, comprises the amino acid sequence of any of the sequences provided in Tables 1, 2A, 2B, 13-19. In some embodiments, the peptide comprises the amino acid sequence of any of SEQ ID NOs: 945-980 or 985-986. In some embodiments, the AAV capsid variant comprises the amino acid sequence of any of SEQ ID NOs: 2, 200, 201, 941, 943, 204, 208, 404, or 903-909. In some embodiments, the AAV capsid variant comprises the amino acid sequence of SEQ ID NO: 941. In some embodiments, the AAV capsid variant comprises the amino acid sequence of SEQ ID NO: 2. In some embodiments, the AAV capsid variant comprises the amino acid sequence of SEQ ID NO: 943. In some embodiments, the AAV capsid variant comprises the amino acid sequence of SEQ ID NO: 3589. In some embodiments, the AAV capsid variant comprises the amino acid sequence of SEQ ID NO: 1754. In some embodiments, the amino acid sequence is present in loop IV. In some embodiments, the amino acid sequence is present immediately subsequent to position 448, relative to a reference sequence numbered according to the amino acid sequence of SEQ ID NO: 138. In some embodiments, the amino acid sequence replaces positions 449-460 (e.g., K449, T450, I451, N452, G453, S454, G455, Q456, N457, Q458, Q459, and T460), numbered relative to SEQ ID NO: 138. In some embodiments, the amino acid sequence is present immediately subsequent to position 448 and replaces positions 449-460 (e.g., K449, T450, I451, N452, G453, S454, G455, Q456, N457, Q458, Q459, and T460), numbered relative to SEQ ID NO: 138. In some embodiments, the amino acid sequence is present immediately subsequent to position 449, relative to a reference sequence numbered according to the amino acid sequence of SEQ ID NO: 138. In some embodiments, the amino acid sequence replaces positions 450-460 (e.g., T450, I451, N452, G453, S454, G455, Q456, N457, Q458, Q459, and T460), numbered relative to SEQ ID NO: 138. In some embodiments, the amino acid sequence is present immediately subsequent to position 449, and replaces positions 450-460 (e.g., T450, I451, N452, G453, S454, G455, Q456, N457, Q458, Q459, and T460), numbered relative to SEQ ID NO: 138. In some embodiments, the amino acid sequence is present immediately subsequent to position 450, relative to a reference sequence numbered according to the amino acid sequence of SEQ ID NO: 138. In some embodiments, the amino acid sequence replaces positions 451-460 (e.g., I451, N452, G453, S454, G455, Q456, N457, Q458, Q459, and T460), numbered relative to SEQ ID NO: 138. In some embodiments, the amino acid sequence is present immediately subsequent to position 450 and replaces positions 451-460 (e.g., I451, N452, G453, S454, G455, Q456, N457, Q458, Q459, and T460), numbered relative to SEQ ID NO: 138. In some embodiments, the amino acid sequence is present immediately subsequent to position 451, relative to a reference sequence numbered according to the amino acid sequence of SEQ ID NO: 138. In some embodiments, the amino acid sequence replaces positions 452-460 (e.g., N452, G453, S454, G455, Q456, N457, Q458, Q459, and T460), numbered relative to SEQ ID NO: 138. In some embodiments, the amino acid sequence is present immediately subsequent to position 451 and replaces positions 452-460 (e.g., N452, G453, S454, G455, Q456, N457, Q458, Q459, and T460), numbered relative to SEQ ID NO: 138. In some embodiments, the amino acid sequence is present immediately subsequent to position 452, relative to a reference sequence numbered according to the amino acid sequence of SEQ ID NO: 138. In some embodiments, the amino acid sequence replaces positions 453-460 (e.g., G453, S454, G455, Q456, N457, Q458, Q459, and T460), numbered relative to SEQ ID NO: 138. In some embodiments, the amino acid sequence is present immediately subsequent to position 452, and replaces positions 453-460 (e.g., G453, S454, G455, Q456, N457, Q458, Q459, and T460), numbered relative to SEQ ID NO: 138. In some embodiments, the amino acid sequence is present immediately subsequent to position 453, relative to a reference sequence numbered according to the amino acid sequence of SEQ ID NO: 138. In some embodiments, the amino acid sequence replaces positions 454 and 455 (e.g., S454 and G455), numbered according to SEQ ID NO: 138. In some embodiments, the amino acid sequence is present immediately subsequent to position 453, and replaces positions 454 and 455 (e.g., S454 and G455), numbered according to SEQ ID NO: 138. In some embodiments, the amino acid sequence replaces positions 454-460 (e.g., S454, G455, Q456, N457, Q458, Q459, and T460), numbered relative to SEQ ID NO: 138. In some embodiments, the amino acid sequence is present immediately subsequent to position 453, and replaces positions 454-460 (e.g., S454, G455, Q456, N457, Q458, Q459, and T460), numbered relative to SEQ ID NO: 138. In some embodiments, the amino acid sequence is present immediately subsequent to position 454, relative to a reference sequence numbered according to the amino acid sequence of SEQ ID NO: 138. In some embodiments, the amino acid sequence is present immediately subsequent to position 454, relative to a reference sequence numbered according to the amino acid sequence of SEQ ID NO: 981. In some embodiments, the amino acid sequence replaces positions 455-460 (e.g., positions G455, Q456, N457, Q458, Q459, and T460), numbered relative to SEQ ID NO: 138. In some embodiments, the amino acid sequence is present immediately subsequent to positions 454, and replaces positions 455-460 (e.g., positions G455, Q456, N457, Q458, Q459, and T460), numbered relative to SEQ ID NO: 138. In some embodiments, the amino acid sequence is present immediately subsequent to position 455, relative to a reference sequence numbered according to the amino acid sequence of SEQ ID NO: 138. In some embodiments, the amino acid sequence is present immediately subsequent to position 455, relative to a reference sequence numbered according to the amino acid sequence of SEQ ID NO: 982. In some embodiments, the amino acid sequence replaces positions 456-460 (e.g., Q456, N457, Q458, Q459, and T460), numbered relative to SEQ ID NO: 138. In some embodiments, the amino acid sequence is present immediately subsequent to position 455, and replaces positions 456-460 (e.g., Q456, N457, Q458, Q459, and T460), numbered relative to SEQ ID NO: 138.

In some embodiments, the AAV capsid variant (e.g., an AAV capsid variant described herein), comprises an amino acid sequence encoded by the nucleotide sequence of SEQ ID NO: 942 or 944, or a nucleotide sequence substantially identical (e.g., having at least 70%, 75%, 80%, 85%, 90%, 92%, 95%, 97%, 98%, or 99% sequence identity) thereto. In some embodiments, the AAV capsid variant described herein, comprises an amino acid sequence encoded by the nucleotide sequence of SEQ ID NO: 3 or 942, or a nucleotide sequence comprising at least one, two, three, four, five, six, or seven modifications, e.g., substitutions (e.g., conservative substitutions), insertions, or deletions, but no more than ten modifications, e.g., substitutions (e.g., conservative substitutions), insertions, or deletions, relative to the nucleotide sequence of SEQ ID NO: 3 or 942. In some embodiments, the AAV capsid variant comprises an amino acid sequence encoded by a nucleotide sequence comprising at least one, two, three, four, five, six, or seven, but no more than ten different nucleotides relative to the nucleotide sequence of SEQ ID NO: 3 or 942.

In some embodiments, the nucleotide sequence encoding the AAV capsid variant (e.g., an AAV capsid variant described herein), comprises the nucleotide sequence of SEQ ID NO: 942, or a nucleotide sequence substantially identical (e.g., having at least 70%, 75%, 80%, 85%, 90%, 92%, 95%, 97%, 98%, or 99% sequence identity) thereto. In some embodiments, the nucleic acid sequence encoding the AAV capsid variant comprises a nucleotide sequence comprising at least one, two, three, four, five, six, or seven modifications, e.g., substitutions (e.g., conservative substitutions), insertions, or deletions, but no more than ten modifications, e.g., substitutions (e.g., conservative substitutions), insertions, or deletions, relative to the nucleotide sequences of SEQ ID NO: 942. In some embodiments, the nucleotide sequence encoding an AAV capsid variant described herein comprises a nucleotide sequence comprising at least one, two, three, four, five, six, or seven, but no more than ten different nucleotides, relative to the nucleotide sequence of SEQ ID NO: 942.

In some embodiments, the nucleotide sequence encoding the AAV capsid variant (e.g., an AAV capsid variant described herein), comprises the nucleotide sequence of SEQ ID NO: 3, or a nucleotide sequence substantially identical (e.g., having at least 70%, 75%, 80%, 85%, 90%, 92%, 95%, 97%, 98%, or 99% sequence identity) thereto. In some embodiments, the nucleic acid sequence encoding the AAV capsid variant comprises a nucleotide sequence comprising at least one, two, three, four, five, six, or seven modifications, e.g., substitutions (e.g., conservative substitutions), insertions, or deletions, but no more than ten modifications, e.g., substitutions (e.g., conservative substitutions), insertions, or deletions, relative to the nucleotide sequences of SEQ ID NO: 3. In some embodiments, the nucleotide sequence encoding an AAV capsid variant described herein comprises a nucleotide sequence comprising at least one, two, three, four, five, six, or seven, but no more than ten different nucleotides relative to the nucleotide sequence of SEQ ID NO: 3.

In some embodiments, an AAV capsid variant described herein comprises the amino acid sequence of SPHSKA (SEQ ID NO: 941), wherein the amino acid sequence is present immediately subsequent to position 455, relative to a reference sequence numbered according to the amino acid sequence of SEQ ID NO: 138. In some embodiments, an AAV capsid variant described herein comprises the amino acid sequence of SPHSKA (SEQ ID NO: 941), wherein the amino acid sequence is present immediately subsequent to position 455, relative to a reference sequence numbered according to the amino acid sequence of SEQ ID NO: 981.

In some embodiments, an AAV capsid variant described herein comprises the amino acid sequence of HDSPHK (SEQ ID NO: 2), wherein the amino acid sequence is present immediately subsequent to position 453, relative to a reference sequence numbered according to the amino acid sequence of SEQ ID NO: 138. In some embodiments, an AAV capsid variant described herein comprises the amino acid sequence of HDSPHK (SEQ ID NO: 2), wherein the amino acid sequence is present immediately subsequent to position 453, relative to a reference sequence numbered according to the amino acid sequence of SEQ ID NO: 982.

In some embodiments, an AAV capsid variant described herein comprises (i) the amino acid sequence of HDSPHSKA (SEQ ID NO: 4486), which is present immediately subsequent to position 453; and (ii) a deletion of amino acids SG at position 454 and 455; wherein (i) and (ii) are numbered according to SEQ ID NO: 138.

In some embodiments, an AAV capsid variant described herein comprises an amino acid other than S at position 454 and/or an amino acid other than G at position 455, numbered according to SEQ ID NO: 138. In some embodiments, the AAV capsid variant comprises the amino acid H at position 454 and the amino acid D at position 455, numbered according to SEQ ID NO: 138. In some embodiments, the AAV capsid variant further comprises the amino acid sequence of SPHSKA (SEQ ID NO: 941). In some embodiments, the AAV capsid variant comprises: (i) the amino acid H at position 454 and the amino acid D at position 455, and (ii) the amino acid sequence SPHSKA (SEQ ID NO: 941), wherein the amino acid sequence of SPHKSG (SEQ ID NO: 946) is present immediately subsequent to position 455, wherein (i) and (ii) are numbered according to SEQ ID NO: 138.

In some embodiments, an AAV capsid variant described herein comprises a modification, e.g., substitution, relative to SEQ ID NO: 138. In some embodiments, the AAV capsid variant comprises a modification, e.g., substitution, at position S454 and/or G455, numbered relative to SEQ ID NO: 138. In some embodiments, the AAV capsid variant comprises a S454H substitution and/or G455D substitution, numbered relative to SEQ ID NO: 138. In some embodiments, the AAV capsid variant comprises a S454H substitution and a G455D substitution, numbered relative to SEQ ID NO: 138. In some embodiments, the AAV capsid variant further comprises the amino acid sequence of SPHSKA (SEQ ID NO: 941). In some embodiments, the AAV capsid variant comprises: (i) a S454H substitution and a G455D substitution, and (ii) the amino acid sequence SPHKSG (SEQ ID NO: 946), wherein the amino acid sequence of SPHSKA (SEQ ID NO: 941) is present immediately subsequent to position 455, wherein (i) and (ii) are numbered according to SEQ ID NO: 138.

In some embodiments, the AAV capsid variant further comprises one, two, or all of an amino acid other than T at position 450 (e.g., S, Y, or G), an amino acid other than I at position 451 (e.g., M or L), and/or an amino acid other than N at position 452 (e.g., S), relative to a reference sequence numbered according to the amino acid sequence of SEQ ID NO: 138. In some embodiments, the AAV capsid variant further comprises an S at position 450 and an M at position 451, relative to a reference sequence numbered according to the amino acid sequence of SEQ ID NO: 138. In some embodiments, the AAV capsid variant further comprises a Y at position 450, an L at position 451, and an S at position 452, relative to a reference sequence numbered according to the amino acid sequence of SEQ ID NO: 138. In some embodiments, the AAV capsid variant further comprises a G at position 450, an L at position 451, and an S at position 452, relative to a reference sequence numbered according to the amino acid sequence of SEQ ID NO: 138.

In some embodiments, the AAV capsid variant further comprises one, two, three, four, or all of an amino acid other than Q at position 456 (e.g., R or L), N at position 457 (e.g., H, K, or R), Q at position 458 (e.g., R or T), Q at position 459 (H), and/or T at position 460 (N or S), relative to a reference sequence numbered according to the amino acid sequence of SEQ ID NO: 138. In some embodiments, the AAV capsid variant further comprises an R at position 456, relative to a reference sequence numbered according to the amino acid sequence of SEQ ID NO: 138. In some embodiments, the AAV capsid variant further comprises an L at position 456, relative to a reference sequence numbered according to the amino acid sequence of SEQ ID NO: 138. In some embodiments, the AAV capsid variant further comprises an H at position 457 and an R at position 458, relative to a reference sequence numbered according to the amino acid sequence of SEQ ID NO: 138. In some embodiments, the AAV capsid variant further comprises a K at position 457 and an N at position 460, relative to a reference sequence numbered according to the amino acid sequence of SEQ ID NO: 138. In some embodiments, the AAV capsid variant further comprises a T at position 458, an H at position 459, and an S at position 460, relative to a reference sequence numbered according to the amino acid sequence of SEQ ID NO: 138. In some embodiments, the AAV capsid variant further comprises an R at position 456, an R at position 457, and an R at position 458, relative to a reference sequence numbered according to the amino acid sequence of SEQ ID NO: 138.

In some embodiments, an AAV capsid variant described herein comprises an amino acid other than I at position 451, an amino acid other than N at position 452, and an amino acid other than G at position 453, numbered according to SEQ ID NO: 138 or 981. In some embodiments, the AAV capsid variant comprises E at position 451, R at position 452, and V at position 453, numbered according to SEQ ID NO: 138 or 981. In some embodiments, the AAV capsid variant comprises the substitutions I451E, N452R, and G453V, numbered according to SEQ ID NO: 138 or 981.

In some embodiments, the AAV capsid variant comprises the amino acid sequence of SPHSKA (SEQ ID NO: 941), wherein the amino acid sequence is present immediately subsequent to position 455 and wherein the AAV capsid variant comprises the E at position 451, R at position 452, and V at position 453, numbered according to the amino acid sequence of SEQ ID NO: 138 or 981. In some embodiments, the AAV capsid variant comprises the substitutions I451E, N452R, and G453V, and further comprises the amino acid sequence of SPHSKA (SEQ ID NO: 941), wherein the amino acid sequence is present immediately subsequent to position 455, all numbered according to SEQ ID NO: 138 or 981. In some embodiments, the AAV capsid variant comprises the amino acid sequence of ERVSGSPHSKA (SEQ ID NO: 6399), and wherein the amino acid sequence is present immediately subsequent to position 449 and replaces positions 450-455, numbered according to SEQ ID NO: 138. In some embodiments, the AAV capsid variant comprises the amino acid sequence of KTERVSGSPHSKAQNQQT (SEQ ID NO: 3589), wherein the amino acid sequence is present immediately subsequent to position 448 and replaces positions 449-460, numbered according to SEQ ID NO: 138.

In some embodiments, an AAV capsid variant described herein comprises an amino acid other than T at position 450, an amino acid other than I at position 451, and an amino acid other than N at position 452, numbered according to SEQ ID NO: 138 or 982. In some embodiments, the AAV capsid variant comprises A at position 450, E at position 451, and I at position 452, numbered according to SEQ ID NO: 138 or 982. In some embodiments, the AAV capsid variant comprises the substitutions T450A, I451E, and N452I, numbered according to SEQ ID NO: 138 or 982.

In some embodiments, the AAV capsid variant comprises the amino acid sequence of HDSPHK (SEQ ID NO: 2), which is present immediately subsequent to positions 453, and further comprises A at position 450, E at position 451, and I at position 452, all numbered according to SEQ ID NO: 138 or 982. In some embodiments, the AAV capsid variant comprises the substitutions T450A, I451E, and N452I, and further comprises the amino acid sequence HDSPHK (SEQ ID NO: 2) present immediately subsequent to position 453, all numbered according to SEQ ID NO: 138 or 982. In some embodiments, the AAV capsid variant comprises the amino acid sequence of AEIGHDSPHKSG (SEQ ID NO: 6400), wherein the amino acid sequence is present immediately subsequent to position 449 and replaces positions 450-455, numbered according to SEQ ID NO: 138. In some embodiments, the AAV capsid variant comprises the amino acid sequence of KAEIGHDSPHKSGQNQQT (SEQ ID NO: 1754), wherein the amino acid sequence is present immediately subsequent to position 448 and replaces positions 449-460, numbered according to SEQ ID NO: 138.

In some embodiments, the AAV capsid variant, further comprises a substitution at position K449, e.g., a K449R substitution, numbered according to SEQ ID NO: 138. In some embodiments, the AAV capsid variant, further comprises an amino acid other than K at position 449 (e.g., R), relative to a reference sequence numbered according to the amino acid sequence of SEQ ID NO: 138. In some embodiments, the AAV capsid variant comprises an R at position 449, relative to a reference sequence numbered according to the amino acid sequence of SEQ ID NO: 138. In some embodiments, the AAV capsid variant further comprises a modification, e.g., an insertion, substitution, and/or deletion in loop I, II, VI, and/or VIII.

In some embodiments, the AAV capsid variant, further comprises an amino acid sequence comprising at least one, two or three modifications, e.g., substitutions (e.g., conservative substitutions), insertions, or deletions, but not more than 30, 20 or 10 modifications, e.g., substitutions (e.g., conservative substitutions), insertions, or deletions, of the amino acid sequence of SEQ ID NO: 138. In some embodiments, the AAV capsid variant, further comprises an amino acid sequence comprising at least one, two or three, but not more than 30, 20 or 10 amino acids that differ from the amino acid sequence of SEQ ID NO: 138. In some embodiments, the AAV capsid variant further comprises the amino acid sequence of SEQ ID NO: 138, or an amino acid sequence with at least 70% (e.g., at least about 80, 85, 90, 95, 96, 97, 98, or 99%) sequence identity thereto.

In some embodiments, the AAV capsid variant further comprises (a) a VP1 protein comprising the amino acid sequence of SEQ ID NO: 138, 981, or 982; (b) a VP2 protein comprising the amino acid sequence of positions 138-736 of SEQ ID NO: 138 or positions 138-742 of SEQ ID NO: 981 or 982; (c) a VP3 protein comprising the amino acid sequence of positions 203-736 of SEQ ID NO: 138 or positions 203-742 of SEQ ID NO: 981 or 982; or (d) an amino acid sequence with at least 70% (e.g., at least about 80, 85, 90, 95, 96, 97, 98, or 99%) sequence identity to any of the amino acid sequences in (a)-(c), an amino acid sequence comprising at least one, two or three, but not more than 30, 20 or 10 different amino acids relative to any of the amino acid sequences in (a)-(c), or an amino acid sequence comprising at least one, two or three modifications, e.g., substitutions (e.g., conservative substitutions), insertions, or deletions, but not more than 30, 20 or 10 modifications, e.g., substitutions (e.g., conservative substitutions), insertions, or deletions, relative to any of the amino acid sequences in (a)-(c).

In some embodiments, the AAV capsid variant further comprises an amino acid sequence encoded by the nucleotide sequence of SEQ ID NO: 137, or a sequence with at least 70% (e.g., at least about 80, 85, 90, 95, 96, 97, 98, or 99%) sequence identity thereto. In some embodiments, the AAV capsid variant further comprises an amino acid sequence encoded by a nucleotide sequence comprising at least one, two or three modifications, e.g., substitutions (e.g., conservative substitutions), insertions, or deletions, but not more than 30, 20 or 10 modifications, e.g., substitutions (e.g., conservative substitutions), insertions, or deletions, relative to the nucleotide sequence of SEQ ID NO: 137. In some embodiments, the AAV capsid variant further comprises an amino acid sequence encoded by a nucleotide sequence comprising at least one, two or three, but not more than 30, 20 or 10 different nucleotides, relative to the amino acid sequence of SEQ ID NO: 137.

In some embodiments, the nucleotide sequence encoding the AAV capsid variant further comprises the nucleotide sequence of SEQ ID NO: 137, or a sequence with at least 70% (e.g., at least about 80, 85, 90, 95, 96, 97, 98, or 99%) sequence identity thereto. In some embodiments, the nucleotide sequence encoding the AAV capsid variant further comprises a nucleotide sequence comprising at least one, two or three modifications, e.g., substitutions (e.g., conservative substitutions), insertions, or deletions, but not more than 30, 20 or 10 modifications, e.g., substitutions (e.g., conservative substitutions), insertions, or deletions, relative to the nucleotide sequence of SEQ ID NO: 137. In some embodiments, the nucleotide sequence encoding the AAV capsid variant further comprises a nucleotide sequence comprising at least one, two or three, but not more than 30, 20 or 10 different nucleotides, relative to the amino acid sequence of SEQ ID NO: 137.

In some embodiments, an AAV capsid variant of the present disclosure comprises an amino acid sequence as described herein, e.g., an amino acid sequence of an AAV capsid variant of TTM-001 or TTM-002, e.g., as described in Tables 3 and 4. In some embodiments, an AAV capsid variant of the present disclosure comprises an amino acid sequence as described herein, e.g., an amino acid sequence of an AAV capsid variant of TTM-003, TTM-004, TTM-005, TTM-006, TTM-007, TTM-008, TTM-009, TTM-010, TTM-011, TTM-012, TTM-013, TTM-014, TTM-015, TTM-016, TTM-017, TTM-018, TTM-019, TTM-020, TTM-021, TTM-022, TTM-023, TTM-024, TTM-025, or TTM-026, e.g., as described in Table 4.

In some embodiments, an AAV capsid variant described herein comprises a VP1, VP2, and/or VP3 protein comprising an amino acid sequence described herein, e.g., an amino acid sequence of an AAV capsid variant of TTM-001 or TTM-002, e.g., as described in Tables 3 and 4. In some embodiments, an AAV capsid variant described herein comprises a VP1, VP2, and/or VP3 protein comprising an amino acid sequence described herein, e.g., an amino acid sequence of an AAV capsid variant of TTM-003, TTM-004, TTM-005, TTM-006, TTM-007, TTM-008, TTM-009, TTM-010, TTM-011, TTM-012, TTM-013, TTM-014, TTM-015, TTM-016, TTM-017, TTM-018, TTM-019, TTM-020, TTM-021, TTM-022, TTM-023, TTM-024, TTM-025, or TTM-026, e.g., as described in Table 4.

In some embodiments, an AAV capsid variant described herein comprises an amino acid sequence encoded by a nucleotide sequence as described herein, e.g., a nucleotide sequence of an AAV capsid variant of TTM-001 or TTM-002, e.g., as described in Tables 3 and 5. In some embodiments, an AAV capsid variant described herein comprises an amino acid sequence encoded by a nucleotide sequence as described herein, e.g., a nucleotide sequence of an AAV capsid variant of TTM-003, TTM-004, TTM-005, TTM-006, TTM-007, TTM-008, TTM-009, TTM-010, TTM-011, TTM-012, TTM-013, TTM-014, TTM-015, TTM-016, TTM-017, TTM-018, TTM-019, TTM-020, TTM-021, TTM-022, TTM-023, TTM-024, TTM-025, or TTM-026, e.g., as described in Table 5.

In some embodiments, a polynucleotide or nucleic acid encoding an AAV capsid variant, of the present disclosure comprises a nucleotide sequence described herein, e.g., a nucleotide sequence of an AAV capsid variant of TTM-001 or TTM-002, e.g., as described in Tables 3 and 5. In some embodiments, a polynucleotide or nucleic acid encoding an AAV capsid variant, of the present disclosure comprises a nucleotide sequence described herein, e.g., a nucleotide sequence of an AAV capsid variant of TTM-003, TTM-004, TTM-005, TTM-006, TTM-007, TTM-008, TTM-009, TTM-010, TTM-011, TTM-012, TTM-013, TTM-014, TTM-015, TTM-016, TTM-017, TTM-018, TTM-019, TTM-020, TTM-021, TTM-022, TTM-023, TTM-024, TTM-025, or TTM-026, e.g., as described in Table 5.

TABLE 3

Exemplary full length capsid sequences

| Name | VP1 DNA SEQ ID NO: | VP1 (amino acid) SEQ ID NO: | Peptide (amino acid) SEQ ID NO: | Peptide DNA SEQ ID NO: |
|---|---|---|---|---|
| TTM-001 | 983 | 981 | 941 | 942 |
| TTM-002 | 984 | 982 | 2 | 3 |

TABLE 4

Exemplary full length capsid amino acid sequences

| Name and Annotation | SEQ ID NO: | Amino Acid Sequence |
|---|---|---|
| TTM-001 6mer peptide underlined, starts at position 456 (immediately subsequent to position 455); 742 aa | 981 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVEMIPQYGYLTLNDGSQAVGRS SFYCLEYFPSQMLRTGNNFQFSYEFENVPFHSSYAHSQSLDRLMNPLIDQYLYYLS KTINGSGSSPHSKAQNQQTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAFNKDK LNSFITQYSTGQVSVEIEWELQKENSKRWNPEIQYTSNYYKSNNVEFAVNTEGVYS EPRPIGTRYLTRNL |
| TTM-002 6mer peptide underlined, starts at position 454 (immediately subsequent to position 453); 742 aa | 982 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVEMIPQYGYLTLNDGSQAVGRS SFYCLEYFPSQMLRTGNNFQFSYEFENVPFHSSYAHSQSLDRLMNPLIDQYLYYLS KTINGHDSPHKSGQNQQTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAFNKDK LNSFITQYSTGQVSVEIEWELQKENSKRWNPEIQYTSNYYKSNNVEFAVNTEGVYS EPRPIGTRYLTRNL |
| TTM-003 6mer peptide underlined, starts at position 456 (immediately subsequent to position 455); | 36 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVEMIPQYGYLTLNDGSQAVGRS SFYCLEYFPSQMLRTGNNFQFSYEFENVPFHSSYAHSQSLDRLMNPLIDQYLYYLS |

| Name and Annotation | SEQ ID NO: | Amino Acid Sequence |
| --- | --- | --- |
| modifications at positions 451, 452, and 453 underlined; 742 aa | | KTERVSGSPHSKAQNQQTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAFNKDK LNSFITQYSTGQVSVEIEWELQKENSKRWNPEIQYTSNYYKSNNVEFAVNTEGVYS EPRPIGTRYLTRNL |
| TTM-004 6mer peptide underlined, starts at position 454 (immediately subsequent to position 453); modifications at positions 450, 451, and 452 underlined; 742 aa | 37 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLIDQYLYYLS KAEIGHDSPHKSGQNQQTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAFNKDK LNSLITQYSTGQVSVEIEWELQKENSKRWNPEIQYTSNYYKSNNVEFAVNTEGVYS EPRPIGTRYLTRNL |
| TTM-005 6mer peptide underlined, starts at position 456 (immediately subsequent to position 455); modifications at positions 452, 464, and 465 underlined; 742 aa | 38 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLIDQYLYYLS KTIIGSGSPHSKAQNRHTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAFNKDK LNSFITQYSTGQVSVEIEWELQKENSKRWNPEIQYTSNYYKSNNVEFAVNTEGVYS EPRPIGTRYLTRNL |
| TTM-006 6mer peptide underlined, starts at position 456 (immediately subsequent to position 455); modifications at positions 451, 452, and 453 underlined; 742 aa | 39 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLIDQYLYYLS KTEKMSGSPHSKAQNQQTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAFNKDK LNSFITQYSTGQVSVEIEWELQKENSKRWNPEIQYTSNYYKSNNVEFAVNTEGVYS EPRPIGTRYLTRNL |
| TTM-007 6mer peptide underlined, starts at position 456 (immediately subsequent to position 455); modifications at positions 450 and 454 underlined; 742 aa | 40 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLIDQYLYYLS KEINGRGSPHSKAQNQQTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAFNKDK LNSFITQYSTGQVSVEIEWELQKENSKRWNPEIQYTSNYYKSNNVEFAVNTEGVYS EPRPIGTRYLTRNL |
| TTM-008 6mer peptide underlined, starts at position 456 (immediately subsequent to position 455); | 41 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVEMIPQYGYLTLNDGSQAVGRS SFYCLEYFPSQMLRTGNNFQFSYEFENVPFHSSYAHSQSLDRLMNPLIDQYLYYLS |

TABLE 4-continued

Exemplary full length capsid amino acid sequences

| Name and Annotation | SEQ ID NO: | Amino Acid Sequence |
|---|---|---|
| modifications at positions 451, 462, and 464 underlined; 742 aa | | KTFNGSGSPHSKAPNLQTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAFNKDK LNSFITQYSTGQVSVEIEWELQKENSKRWNPEIQYTSNYYKSNNVEFAVNTEGVYS EPRPIGTRYLTRNL |
| TTM-009 6mer peptide underlined, starts at position 456 (immediately subsequent to position 455); modifications at positions 451, 452, and 453 underlined; 742 aa | 42 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLIDQYLYYLS KTEKTSGSPHSKAQNQQTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAFNKDK LNSFITQYSTGQVSVEIEWELQKENSKRWNPEIQYTSNYYKSNNVEFAVNTEGVYS EPRPIGTRYLTRNL |
| TTM-010 6mer peptide underlined, starts at position 456 (immediately subsequent to position 455); modifications at positions 451, 454, and 455 underlined; 742 aa | 43 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLIDQYLYYLS KTMNGHDSPHSKAQNQQTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAFNKDK LNSFITQYSTGQVSVEIEWELQKENSKRWNPEIQYTSNYYKSNNVEFAVNTEGVYS EPRPIGTRYLTRNL |
| TTM-011 6mer peptide underlined, starts at position 456 (immediately subsequent to position 455); modifications at positions 452, 454, and 455 underlined; 742 aa | 44 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLIDQYLYYLS KTIDGHDSPHSKAQNQQTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAFNKDK LNSFITQYSTGQVSVEIEWELQKENSKRWNPEIQYTSNYYKSNNVEFAVNTEGVYS EPRPIGTRYLTRNL |
| TTM-012 6mer peptide underlined, starts at position 456 (immediately subsequent to position 455); modifications at positions 452, 454, and 455 underlined; 742 aa | 45 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLIDQYLYYLS KTNNGHDSPHSKAQNQQTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAFNKDK LNSFITQYSTGQVSVEIEWELQKENSKRWNPEIQYTSNYYKSNNVEFAVNTEGVYS EPRPIGTRYLTRNL |
| TTM-013 6mer peptide underlined, starts at position 456 (immediately subsequent to position 455); | 46 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVEMIPQYGYLTLNDGSQAVGRS SFYCLEYFPSQMLRTGNNFQFSYEFENVPFHSSYAHSQSLDRLMNPLIDQYLYYLS |

TABLE 4-continued

Exemplary full length capsid amino acid sequences

| Name and Annotation | SEQ ID NO: | Amino Acid Sequence |
|---|---|---|
| modifications at positions 451, 452, and 453 underlined; 742 aa | | KTQRKSGSPHSKAQNQQTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAFNKDK LNSFITQYSTGQVSVEIEWELQKENSKRWNPEIQYTSNYYKSNNVEFAVNTEGVYS EPRPIGTRYLTRNL |
| TTM-014 6mer peptide underlined, starts at position 456 (immediately subsequent to position 455); modifications at positions 463, 464, and 465 underlined; 742 aa | 47 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVEMIPQYGYLTLNDGSQAVGRS SFYCLEYFPSQMLRTGNNFQFSYEFENVPFHSSYAHSQSLDRLMNPLIDQYLYYLS KTINGSGSPHSKAQARKTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAFNKDK LNSFITQYSTGQVSVEIEWELQKENSKRWNPEIQYTSNYYKSNNVEFAVNTEGVYS EPRPIGTRYLTRNL |
| TTM-015 6mer peptide underlined, starts at position 456 (immediately subsequent to position 455); modifications at positions 450 and 452 underlined; 742 aa | 48 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLIDQYLYYLS KYIVIGSGSPHSKAQNQQTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAENKDK LNSFITQYSTGQVSVEIEWELQKENSKRWNPEIQYTSNYYKSNNVEFAVNTEGVYS EPRPIGTRYLTRNL |
| TTM-016 6mer peptide underlined, starts at position 456 (immediately subsequent to position 455); modifications at positions 452, 453, and 454 underlined; 742 aa | 49 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLIDQYLYYLS KTISKRGSPHSKAQNQQTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAFNKDK LNSFITQYSTGQVSVEIEWELQKENSKRWNPEIQYTSNYYKSNNVEFAVNTEGVYS EPRPIGTRYLTRNL |
| TTM-017 6mer peptide underlined, starts at position 456 (immediately subsequent to position 455); modifications at positions 450, 451, and 452 underlined; 742 aa | 50 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLIDQYLYYLS KGLGGSGSPHSKAQNQQTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAENKDK LNSFITQYSTGQVSVEIEWELQKENSKRWNPEIQYTSNYYKSNNVEFAVNTEGVYS EPRPIGTRYLTRNL |
| TTM-018 6mer peptide underlined, starts at position 456 (immediately subsequent to position 455); | 51 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLIDQYLYYLS |

TABLE 4-continued

Exemplary full length capsid amino acid sequences

| Name and Annotation | SEQ ID NO: | Amino Acid Sequence |
|---|---|---|
| modifications at positions 454, 455, and 464 underlined; 742 aa | | KTINGHDSPHSKAQN<u>L</u>QTLKFSVAGPSNMAVQGRNYIPGPSYRQQRVSTTVTQNNN SEFAWPGASSWALNGR<u>N</u>SLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAFNKDK LNSFITQYSTGQVSVEIEWELQKENSKRWNPEIQYTSNYYKSNNVEFAVNTEGVYS EPRPIGTRYLTRNL |
| TTM-019 6mer peptide underlined, starts at position 456 (immediately subsequent to position 455); modifications at positions 451, 454, and 455 underlined; 742 aa | 52 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLIDQYLYYLS KTV<u>N</u>GHDSPHSKAQN<u>QQ</u>TLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAENKDK LNSFITQYSTGQVSVEIEWELQKENSKRWNPEIQYTSNYYKSNNVEFAVNTEGVYS EPRPIGTRYLTRNL |
| TTM-020 6mer peptide underlined, starts at position 456 (immediately subsequent to position 455); modifications at positions 454, 455, and 462 underlined; 742 aa | 53 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLIDQYLYYLS KTINGHDSPHSKALNQQTLKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAENKDK LNSFITQYSTGQVSVEIEWELQKENSKRWNPEIQYTSNYYKSNNVEFAVNTEGVYS EPRPIGTRYLTRNL |
| TTM-021 6mer peptide underlined, starts at position 456 (immediately subsequent to position 455); modifications at positions 454, 455, and 466 underlined; 742 aa | 54 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLIDQYLYYLS KTINGHDSPHSKAQNQQ<u>S</u>LKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAFNKDK LNSFITQYSTGQVSVEIEWELQKENSKRWNPEIQYTSNYYKSNNVEFAVNTEGVYS EPRPIGTRYLTRNL |
| TTM-022 6mer peptide underlined, starts at position 456 (immediately subsequent to position 455); modifications at positions 454, 455, and 466 underlined; 742 aa | 55 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVFMIPQYGYLTLNDGSQAVGRS SFYCLEYFPSQMLRTGNNFQFSYEFENVPFHSSYAHSQSLDRLMNPLIDQYLYYLS KTINGHDSPHSKAQNQQ<u>I</u>LKFSVAGPSNMAVQGRNYIPGPSYRQQRVSTTVTQNNN SEFAWPGASSWALNGRNSLMNPGPAMASHKEGEDRFFPLSGSLIFGKQGTGRDNVD ADKVMITNEEEIKTTNPVATESYGQVATNHQSAQAQAQTGWVQNQGILPGMVWQDR DVYLQGPIWAKIPHTDGNFHPSPLMGGFGMKHPPPQILIKNTPVPADPPTAENKDK LNSFITQYSTGQVSVEIEWELQKENSKRWNPEIQYTSNYYKSNNVEFAVNTEGVYS EPRPIGTRYLTRNL |
| TTM-023 6mer peptide underlined, starts at position 456 (immediately subsequent to position 455); | 56 | MAADGYLPDWLEDNLSEGIREWWALKPGAPQPKANQQHQDNARGLVLPGYKYLGPG NGLDKGEPVNAADAAALEHDKAYDQQLKAGDNPYLKYNHADAEFQERLKEDTSFGG NLGRAVFQAKKRLLEPLGLVEEAAKTAPGKKRPVEQSPQEPDSSAGIGKSGAQPAK KRLNFGQTGDTESVPDPQPIGEPPAAPSGVGSLTMASGGGAPVADNNEGADGVGSS SGNWHCDSQWLGDRVITTSTRTWALPTYNNHLYKQISNSTSGGSSNDNAYFGYSTP WGYFDFNRFHCHFSPRDWQRLINNNWGFRPKRLNFKLFNIQVKEVTDNNGVKTIAN NLTSTVQVFTDSDYQLPYVLGSAHEGCLPPFPADVEMIPQYGYLTLNDGSQAVGRS SFYCLEYFPSQMLRTGNNFQFSYEFENVPFHSSYAHSQSLDRLMNPLIDQYLYYLS |

TABLE 4-continued

Exemplary full length capsid amino acid sequences

| Name and Annotation | SEQ ID NO: | Amino Acid Sequence |
|---|---|---|
| 742 aa | | KTINGSGSPHFTRQNQQTLKFSVAGPSNMAVQGRNYIPGPSYRQQRVSTTVTQNNN<br>SEFAWPGASSWALNGRNSLMNPGPAMASHKEGEDRFFPLSGSLIFGKQGTGRDNVD<br>ADKVMITNEEEIKTTNPVATESYGQVATNHQSAQAQAQTGWVQNQGILPGMVWQDR<br>DVYLQGPIWAKIPHTDGNFHPSPLMGGFGMKHPPPQILIKNTPVPADPPTAFNKDK<br>LNSFITQYSTGQVSVEIEWELQKENSKRWNPEIQYTSNYYKSNNVEFAVNTEGVYS<br>EPRPIGTRYLTRNL |
| TTM-024<br>6mer peptide underlined, starts at position 456 (immediately subsequent to position 455); modifications at positions 451, 454, and 455 underlined;<br>742 aa | 57 | MAADGYLPDWLEDNLSEGIREWWALKPGAPQPKANQQHQDNARGLVLPGYKYLGPG<br>NGLDKGEPVNAADAAALEHDKAYDQQLKAGDNPYLKYNHADAEFQERLKEDTSFGG<br>NLGRAVFQAKKRLLEPLGLVEEAAKTAPGKKRPVEQSPQEPDSSAGIGKSGAQPAK<br>KRLNFGQTGDTESVPDPQPIGEPPAAPSGVGSLTMASGGGAPVADNNEGADGVGSS<br>SGNWHCDSQWLGDRVITTSTRTWALPTYNNHLYKQISNSTSGGSSNDNAYFGYSTP<br>WGYFDFNRFHCHFSPRDWQRLINNNWGFRPKRLNFKLFNIQVKEVTDNNGVKTIAN<br>NLTSTVQVFTDSDYQLPYVLGSAHEGCLPPFPADVFMIPQYGYLTLNDGSQAVGRS<br>SFYCLEYFPSQMLRTGNNFQFSYEFENVPFHSSYAHSQSLDRLMNPLIDQYLYYLS<br>KTSNGHDSPHSKAQNQQTLKFSVAGPSNMAVQGRNYIPGPSYRQQRVSTTVTQNNN<br>SEFAWPGASSWALNGRNSLMNPGPAMASHKEGEDRFFPLSGSLIFGKQGTGRDNVD<br>ADKVMITNEEEIKTTNPVATESYGQVATNHQSAQAQAQTGWVQNQGILPGMVWQDR<br>DVYLQGPIWAKIPHTDGNFHPSPLMGGFGMKHPPPQILIKNTPVPADPPTAFNKDK<br>LNSFITQYSTGQVSVEIEWELQKENSKRWNPEIQYTSNYYKSNNVEFAVNTEGVYS<br>EPRPIGTRYLTRNL |
| TTM-025<br>6mer peptide underlined, starts at position 456 (immediately subsequent to position 455); modification at position 462 underlined;<br>742 aa | 58 | MAADGYLPDWLEDNLSEGIREWWALKPGAPQPKANQQHQDNARGLVLPGYKYLGPG<br>NGLDKGEPVNAADAAALEHDKAYDQQLKAGDNPYLKYNHADAEFQERLKEDTSFGG<br>NLGRAVFQAKKRLLEPLGLVEEAAKTAPGKKRPVEQSPQEPDSSAGIGKSGAQPAK<br>KRLNFGQTGDTESVPDPQPIGEPPAAPSGVGSLTMASGGGAPVADNNEGADGVGSS<br>SGNWHCDSQWLGDRVITTSTRTWALPTYNNHLYKQISNSTSGGSSNDNAYFGYSTP<br>WGYFDFNRFHCHFSPRDWQRLINNNWGFRPKRLNFKLFNIQVKEVTDNNGVKTIAN<br>NLTSTVQVFTDSDYQLPYVLGSAHEGCLPPFPADVFMIPQYGYLTLNDGSQAVGRS<br>SFYCLEYFPSQMLRTGNNFQFSYEFENVPFHSSYAHSQSLDRLMNPLIDQYLYYLS<br>KTINGSGSPHSLPWNQQTLKFSVAGPSNMAVQGRNYIPGPSYRQQRVSTTVTQNNN<br>SEFAWPGASSWALNGRNSLMNPGPAMASHKEGEDRFFPLSGSLIFGKQGTGRDNVD<br>ADKVMITNEEEIKTTNPVATESYGQVATNHQSAQAQAQTGWVQNQGILPGMVWQDR<br>DVYLQGPIWAKIPHTDGNFHPSPLMGGFGMKHPPPQILIKNTPVPADPPTAFNKDK<br>LNSFITQYSTGQVSVEIEWELQKENSKRWNPEIQYTSNYYKSNNVEFAVNTEGVYS<br>EPRPIGTRYLTRNL |
| TTM-026<br>6mer peptide underlined, starts at position 456 (immediately subsequent to position 455); modification at positions 454, 455, and 464 underlined;<br>742 aa | 59 | MAADGYLPDWLEDNLSEGIREWWALKPGAPQPKANQQHQDNARGLVLPGYKYLGPG<br>NGLDKGEPVNAADAAALEHDKAYDQQLKAGDNPYLKYNHADAEFQERLKEDTSFGG<br>NLGRAVFQAKKRLLEPLGLVEEAAKTAPGKKRPVEQSPQEPDSSAGIGKSGAQPAK<br>KRLNFGQTGDTESVPDPQPIGEPPAAPSGVGSLTMASGGGAPVADNNEGADGVGSS<br>SGNWHCDSQWLGDRVITTSTRTWALPTYNNHLYKQISNSTSGGSSNDNAYFGYSTP<br>WGYFDFNRFHCHFSPRDWQRLINNNWGFRPKRLNFKLFNIQVKEVTDNNGVKTIAN<br>NLTSTVQVFTDSDYQLPYVLGSAHEGCLPPFPADVFMIPQYGYLTLNDGSQAVGRS<br>SFYCLEYFPSQMLRTGNNFQFSYEFENVPFHSSYAHSQSLDRLMNPLIDQYLYYLS<br>KTINGHDSPHSKAQNHQTLKFSVAGPSNMAVQGRNYIPGPSYRQQRVSTTVTQNNN<br>SEFAWPGASSWALNGRNSLMNPGPAMASHKEGEDRFFPLSGSLIFGKQGTGRDNVD<br>ADKVMITNEEEIKTTNPVATESYGQVATNHQSAQAQAQTGWVQNQGILPGMVWQDR<br>DVYLQGPIWAKIPHTDGNFHPSPLMGGFGMKHPPPQILIKNTPVPADPPTAFNKDK<br>LNSFITQYSTGQVSVEIEWELQKENSKRWNPEIQYTSNYYKSNNVEFAVNTEGVYS<br>EPRPIGTRYLTRNL |

TABLE 5

Exemplary full length capsid nucleic acid sequences

| Name and Annotation | SEQ ID NO: | NT Sequence |
|---|---|---|
| TTM-001<br>9mer peptide underlined | 983 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCCTCAGGTGTGGGATCTCTTACAATGGCTTCAG<br>GTGGTGGCGCACCAGTGGCAGACAATAACGAAGGTGCCGATGGAGTGGGTAGTTCC |

TABLE 5-continued

Exemplary full length capsid nucleic acid sequences

| Name and Annotation | SEQ ID NO: | NT Sequence |
|---|---|---|
| | | TCGGGAAATTGGCATTGCGATTCCCAATGGCTGGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGACCAATACTTGTAtTActTgagt<br>AAaACaATTAACGGAAGCGGAAGCCCACACAGCAAAGCACAAAACCAACAGACCtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACGcGgTAttTAACgaGgAActTaTAA |
| TTM-002<br>7mer peptide<br>underlined | 984 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGACCAATACTTGTAtTActTgagt<br>AAaACaATTAACGGACACGACAGCCCACACAAAAGCGGACAAAACCAACAGACCtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACGcGgTAttTAACgaGgAActTaTAA |
| TTM-023 | 12 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA |

TABLE 5-continued

Exemplary full length capsid nucleic acid sequences

| Name and Annotation | SEQ ID NO: | NT Sequence |
|---|---|---|
| | | CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGACGGAGCGTGTGTCTGGTTCTCCGCATTCTAAGGCGCAGAATCAGCAGACGtT<br>gAAgTTttcgTaGCtGGtCCtAGCAAcATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-004 | 13 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGGCGGAGATTGGTCATGATTCTCCGCATAAGTCTGGTCAGAATCAGCAGACGtT<br>gAAgTTttcgTaGCtGGtCCtAGCAAcATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTAATCACCCAGTATTCTACTGGCCAAGTCAGCGTGGAGATCGAGTG |

TABLE 5-continued

Exemplary full length capsid nucleic acid sequences

| Name and Annotation | SEQ ID NO: | NT Sequence |
|---|---|---|
| | | GGAGCTGCAGAAGGAAAACAGCAAGCGCTGGAACCCGGAGATCCAGTACACTTCCA ACTATTACAAGTCTAATAATGTTGAATTTGCTGTTAATACTGAAGGTGTATATAGT GAACCCCGCCCCATTGGCACgcGgTAttTAACgaGgAActTa |
| TTM-005 | 14 | ATGGCTGCCGATGGTTATCTTCCAGattggcTCGAGGACAACCTTAGTGAAGGAAT TCGCGAGTGGTGGGCTTTGAAACCTGGAGCCCCTCAACCCAAGGCAAATCAACAAC ATCAAGACAACGCTCGAGGTCTTGTGCTTCCGGGTTACAAATACCTTGGACCCGGC AACGGACTCGACAAGGGGGAGCCGGTCAACGCAGCAGACGCGGCGGCCCTCGAGCA CGACAAGGCCTACGACCAGCAGCTCAAGGCCGGAGACAACCCGTACCTCAAGTACA ACCACGCCGACGCCGAGTTCCAGGAGCGGCTCAAAGAAGATACGTCTTTTGGGGGC AACCTCGGGCGAGCAGTCTTCCAGGCCAAAAAGAGGCTTCTTGAACCTCTTGGTCT GGTTGAGGAAGCGGCTAAGACGGCTCCTGGAAAGAAGAGGCCTGTAGAGCAGTCTC CTCAGGAACCGGACTCCTCCGCGGGTATTGGCAAATCGGGTGCACAGCCCGCTAAA AAGAGACTCAATTTCGGTCAGACTGGCGACACAGAGTCAGTCCCAGACCCTCAACC AATCGGAGAACCTCCCGCAGCCCCCTCAGGTGTGGGATCTCTTACAATGGCTTCAG GTGGTGGCGCACCAGTGGCAGACAATAACGAAGGTGCCGATGGAGTGGGTAGTTCC TCGGGAAATTGGCATTGCGATTCCCAATGGCTGGGGGACAGAGTCATCACCACCAG CACCCGAACCTGGGCCCTGCCCACCTACAACAATCACCTCTACAAGCAAATCTCCA ACAGCACATCTGGAGGATCTTCAAATGACAACGCCTACTTCGGCTACAGCACCCCC TGGGGGTATTTTGACTTCAACAGATTCCACTGCCACTTCTCACCACGTGACTGGCA GCGACTCATCAACAACAACTGGGGATTCCGGCCTAAGCGACTCAACTTCAAGCTCT TCAACATTCAGGTCAAAGAGGTTACGGACAACAATGGAGTCAAGACCATCGCCAAT AACCTTACCAGCACGGTCCAGGTCTTCACGGACTCAGACTATCAGCTCCCGTACGT GCTCGGGTCGGCTCACGAGGGCTGCCTCCCGCCGTTCCCAGCGGACGTTTTCATGA TTCCTCAGTACGGGTATCTGACGCTTAATGATGGAAGCCAGGCCGTGGGTCGTTCG TCCTTTTACTGCCTGGAATATTTCCCGTCGCAAATGCTAAGAACGGGTAACAACTT CCAGTTCAGCTACGAGTTTGAGAACGTACCTTTCCATAGCAGCTACGCTCACAGCC AAAGCCTGGACCGACTAATGAATCCACTCATCGAtCAgTAtcTGTAtTActTgagt AAGACGATTATTGGTTCTGGTTCTCCGCATTCTAAGGCGCAGAATCGTCATACGtT gAAgTTttcgGTaGCtGGtCCtAGCAACATGGCTGTCCAGGGAAGAAACTACATAC CTGGACCCAGCTACCGACAACAACGTGTCTCAACCACTGTGACTCAAAACAACAAC AGCGAATTTGCTTGGCCTGGAGCTTCTTCTTGGGCTCTCAATGGACGTAATAGCTT GATGAATCCTGGACCTGCTATGGCCAGCCACAAAGAAGGAGAGGACCGTTTCTTTC CTTTGTCTGGATCTTTAATTTTTGGCAAACAAGGAACTGGAAGAGACAACGTGGAT GCGGACAAAGTCATGATAACCAACGAAGAAGAAATTAAAACTACTAACCCGGTAGC AACGGAGTCCTATGGACAAGtggccacaaaccaccagagtGCCCAAGCACAGGCGC AGaccggctgggttcaaaaccaAGGAATACTTCCGGGTATGGTTTGGCAGGACAGA GATGTGTACCTGCAAGGACCCATTTGGGCCAAAATTCCTCACACGGACGGCAACTT TCACCCTTCTCCGCTGATGGGAGGGTTTGGAATGAAGCACCCGCCTCCTCAGATCC TCATCAAAAACACACCTGTACCTGCGGATCCTCCAACGGCCTTCAACAAGGACAAG CTGAACTCTTTCATCACCCAGTATTCTACTGGCCAAGTCAGCGTGGAGATCGAGTG GGAGCTGCAGAAGGAAAACAGCAAGCGCTGGAACCCGGAGATCCAGTACACTTCCA ACTATTACAAGTCTAATAATGTTGAATTTGCTGTTAATACTGAAGGTGTATATAGT GAACCCCGCCCCATTGGCACgcGgTAttTAACgaGgAActTa |
| TTM-006 | 15 | ATGGCTGCCGATGGTTATCTTCCAGattggcTCGAGGACAACCTTAGTGAAGGAAT TCGCGAGTGGTGGGCTTTGAAACCTGGAGCCCCTCAACCCAAGGCAAATCAACAAC ATCAAGACAACGCTCGAGGTCTTGTGCTTCCGGGTTACAAATACCTTGGACCCGGC AACGGACTCGACAAGGGGGAGCCGGTCAACGCAGCAGACGCGGCGGCCCTCGAGCA CGACAAGGCCTACGACCAGCAGCTCAAGGCCGGAGACAACCCGTACCTCAAGTACA ACCACGCCGACGCCGAGTTCCAGGAGCGGCTCAAAGAAGATACGTCTTTTGGGGGC AACCTCGGGCGAGCAGTCTTCCAGGCCAAAAAGAGGCTTCTTGAACCTCTTGGTCT GGTTGAGGAAGCGGCTAAGACGGCTCCTGGAAAGAAGAGGCCTGTAGAGCAGTCTC CTCAGGAACCGGACTCCTCCGCGGGTATTGGCAAATCGGGTGCACAGCCCGCTAAA AAGAGACTCAATTTCGGTCAGACTGGCGACACAGAGTCAGTCCCAGACCCTCAACC AATCGGAGAACCTCCCGCAGCCCCCTCAGGTGTGGGATCTCTTACAATGGCTTCAG GTGGTGGCGCACCAGTGGCAGACAATAACGAAGGTGCCGATGGAGTGGGTAGTTCC TCGGGAAATTGGCATTGCGATTCCCAATGGCTGGGGGACAGAGTCATCACCACCAG CACCCGAACCTGGGCCCTGCCCACCTACAACAATCACCTCTACAAGCAAATCTCCA ACAGCACATCTGGAGGATCTTCAAATGACAACGCCTACTTCGGCTACAGCACCCCC TGGGGGTATTTTGACTTCAACAGATTCCACTGCCACTTCTCACCACGTGACTGGCA GCGACTCATCAACAACAACTGGGGATTCCGGCCTAAGCGACTCAACTTCAAGCTCT TCAACATTCAGGTCAAAGAGGTTACGGACAACAATGGAGTCAAGACCATCGCCAAT AACCTTACCAGCACGGTCCAGGTCTTCACGGACTCAGACTATCAGCTCCCGTACGT GCTCGGGTCGGCTCACGAGGGCTGCCTCCCGCCGTTCCCAGCGGACGTTTTCATGA TTCCTCAGTACGGGTATCTGACGCTTAATGATGGAAGCCAGGCCGTGGGTCGTTCG TCCTTTTACTGCCTGGAATATTTCCCGTCGCAAATGCTAAGAACGGGTAACAACTT CCAGTTCAGCTACGAGTTTGAGAACGTACCTTTCCATAGCAGCTACGCTCACAGCC AAAGCCTGGACCGACTAATGAATCCACTCATCGAtCAgTAtcTGTAtTActTgagt AAGACGGAGAAGATGTCTGGTTCTCCGCATTCTAAGGCGCAGAATCAGCAGACGtT gAAgTTttcgGTaGCtGGtCCtAGCAACATGGCTGTCCAGGGAAGAAACTACATAC CTGGACCCAGCTACCGACAACAACGTGTCTCAACCACTGTGACTCAAAACAACAAC AGCGAATTTGCTTGGCCTGGAGCTTCTTCTTGGGCTCTCAATGGACGTAATAGCTT GATGAATCCTGGACCTGCTATGGCCAGCCACAAAGAAGGAGAGGACCGTTTCTTTC |

TABLE 5-continued

Exemplary full length capsid nucleic acid sequences

| Name and Annotation | SEQ ID NO: | NT Sequence |
|---|---|---|
| | | CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-007 | 16 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGGAGATTAATGGTCGTGGTTCTCCGCATTCTAAGGCGCAGAATCAGCAGACGtT<br>gAAgTTTtcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-008 | 17 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG |

TABLE 5-continued

Exemplary full length capsid nucleic acid sequences

| Name and Annotation | SEQ ID NO: | NT Sequence |
|---|---|---|
| | | TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGACGTTTAATGGTTCTGGTTCTCCGCATTCTAAGGCGCCGAATCTGCAGACGtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-009 | 18 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGACGGAGAAGACGTCTGGTTCTCCGCATTCTAAGGCGCAGAATCAGCAGACGtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-010 | 19 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGGACAGAGTCATCACCACCAG |

TABLE 5-continued

Exemplary full length capsid nucleic acid sequences

| Name and Annotation | SEQ ID NO: | NT Sequence |
|---|---|---|
| | | CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGACGATGAATGGTCATGATTCTCCGCATTCTAAGGCGCAGAATCAGCAGACGtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACGcGgTAttTAACgaGgAActTa |
| TTM-011 | 20 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGACGATTGATGGTCATGATTCTCCGCATTCTAAGGCGCAGAATCAGCAGACGtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACGcGgTAttTAACgaGgAActTa |
| TTM-012 | 21 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA |

TABLE 5-continued

Exemplary full length capsid nucleic acid sequences

| Name and Annotation | SEQ ID NO: | NT Sequence |
|---|---|---|
| | | ACCACGCCGACGCCGAGTTCCAGGAGCGGCTCAAAGAAGATACGTCTTTTGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGACGAATAATGGTCATGATTCTCCGCATTCTAAGGCGCAGAATCAGCAGACGtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACGcGgTAttTAACgaGgAActTa |
| TTM-013 | 22 | ATGGCTGCCGATGGTTATCTTCCAGATtggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGAGACAACCCGTACCTCAAGTACA<br>ACCACGCCGACGCCGAGTTCCAGGAGCGGCTCAAAGAAGATACGTCTTTTGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGACGCAGTAGTCTGGTTCTCCGCATTCTAAGGCGCAGAATCAGCAGACGtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA |

TABLE 5-continued

Exemplary full length capsid nucleic acid sequences

| Name and Annotation | SEQ ID NO: | NT Sequence |
|---|---|---|
| | | ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-014 | 23 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTATcTGTAtTActTgagt<br>AAGACGATTAATGGTTCTGGTTCTCCGCATTCTAAGGCGCAGGCGCGTAAGACGtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCAGTGG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-015 | 24 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTATcTGTAtTActTgagt<br>AAGTATATTGTGGGTTCTGGTTCTCCGCATTCTAAGGCGCAGAATCAGCAGACGtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT |

TABLE 5-continued

Exemplary full length capsid nucleic acid sequences

| Name and Annotation | SEQ ID NO: | NT Sequence |
|---|---|---|
| | | GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-016 | 25 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCA<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGACGATTTCTAAGCGTGGTTCTCCGCATTCTAAGGCGCAGAATCAGCAGACGtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-017 | 26 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT |

TABLE 5-continued

Exemplary full length capsid nucleic acid sequences

| Name and Annotation | SEQ ID NO: | NT Sequence |
|---|---|---|
| | | CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGGGTCTGGGTGGTTCTGGTTCTCCGCATTCTAAGGCGCAGAATCAGCAGACGtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-018 | 27 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGACGATTAATGGTCATGATTCTCCGCATTCTAAGGCGCAGAATCTGCAGACGtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-019 | 28 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGACAGAGTCATCACCACCAG<br>CACCCGAACCTGGGCCCTGCCCACCTACAACAATCACCTCTACAAGCAAATCTCCA |

TABLE 5-continued

Exemplary full length capsid nucleic acid sequences

| Name and Annotation | SEQ ID NO: | NT Sequence |
|---|---|---|
| | | ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGACGGTGAATGGTCATGATTCTCCGCATTCTAAGGCGCTGAATCAGCAGACGtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-020 | 29 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGACGATTAATGGTCATGATTCTCCGCATTCTAAGGCGCTGAATCAGCAGACGtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-021 | 30 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC |

TABLE 5-continued

Exemplary full length capsid nucleic acid sequences

| Name and Annotation | SEQ ID NO: | NT Sequence |
|---|---|---|
| | | AACCTCGGGCGAGCAGTCTTCCAGGCCAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGACGATTAATGGTCATGATTCTCCGCATTCTAAGGCGCAGAATCAGCAGTCTtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-022 | 31 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGCAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGACGATTAATGGTCATGATTCTCCGCATTCTAAGGCGCAGAATCAGCAGATTtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA |

TABLE 5-continued

Exemplary full length capsid nucleic acid sequences

| Name and Annotation | SEQ ID NO: | NT Sequence |
|---|---|---|
| | | GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-023 | 32 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGACGATTAATGGTTCTGGTTCTCCGCATTTTACGCGTCAGAATCAGCAGACGtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-024 | 33 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGACGTCTAATGGTCATGATTCTCCGCATTCTAAGGCGCAGAATCAGCAGACGtT |

TABLE 5-continued

Exemplary full length capsid nucleic acid sequences

| Name and Annotation | SEQ ID NO: | NT Sequence |
|---|---|---|
| | | gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-025 | 34 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT<br>TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGCTAATGAATCCACTCATCGAtCAgTAtcTGTAtTActTgagt<br>AAGACGATTAATGGTTCTGGTTCTCCGCATTCTCTGCCGTGGAATCAGCAGACGtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |
| TTM-026 | 35 | ATGGCTGCCGATGGTTATCTTCCAGattggcTCGAGGACAACCTTAGTGAAGGAAT<br>TCGCGAGTGGTGGGCTTTGAAACCTGGAGCCCCTCAACCCAAGGCAAATCAACAAC<br>ATCAAGACAACGCTCGAGGTCTTGTGCTTCCGGGTTACAAATACCTTGGACCCGGC<br>AACGGACTCGACAAGGGGGAGCCGGTCAACGCAGCAGACGCGGCGGCCCTCGAGCA<br>CGACAAGGCCTACGACCAGCAGCTCAAGGCCGGAGACAACCCGTACCTCAAGTACA<br>ACCACGCCGACGCCGAGTTCCAGGAGCGGCTCAAAGAAGATACGTCTTTTGGGGGC<br>AACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGAGCAGTCTC<br>CTCAGGAACCGGACTCCTCCGCGGGTATTGGCAAATCGGGTGCACAGCCCGCTAAA<br>AAGAGACTCAATTTCGGTCAGACTGGCGACACAGAGTCAGTCCCAGACCCTCAACC<br>AATCGGAGAACCTCCCGCAGCCCCTCAGGTGTGGGATCTCTTACAATGGCTTCAG<br>GTGGTGGCGCACCAGTGGCAGACAATAACGAAGGTGCCGATGGAGTGGGTAGTTCC<br>TCGGGAAATTGGCATTGCGATTCCCAATGGCTGGGGACAGAGTCATCACCACCAG<br>CACCCGAACCTGGGCCCTGCCCACCTACAACAATCACCTCTACAAGCAAATCTCCA<br>ACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCA<br>GCGACTCATCAACAACAACTGGGGATTCCGGCCTAAGCGACTCAACTTCAAGCTCT |

TABLE 5-continued

Exemplary full length capsid nucleic acid sequences

| Name and Annotation | SEQ ID NO: | NT Sequence |
|---|---|---|
| | | TCAACATTCAGGTCAAAGAGGTTACGGACAACAATGGAGTCAAGACCATCGCCAAT<br>AACCTTACCAGCACGGTCCAGGTCTTCACGGACTCAGACTATCAGCTCCCGTACGT<br>GCTCGGGTCGGCTCACGAGGGCTGCCTCCCGCCGTTCCCAGCGGACGTTTTCATGA<br>TTCCTCAGTACGGGTATCTGACGCTTAATGATGGAAGCCAGGCCGTGGGTCGTTCG<br>TCCTTTTACTGCCTGGAATATTTCCCGTCGCAAATGCTAAGAACGGGTAACAACTT<br>CCAGTTCAGCTACGAGTTTGAGAACGTACCTTTCCATAGCAGCTACGCTCACAGCC<br>AAAGCCTGGACCGACTAATGAATCCACTCATCGAtCAgTAtcTGTAtTActTgagt<br>AAGACGATTAATGGTCATGATTCTCCGCATTCTAAGGCGCAGAATCATCAGACGtT<br>gAAgTTttcgGTaGCtGGtCCtAGCAACATGGCTGTCCAGGGAAGAAACTACATAC<br>CTGGACCCAGCTACCGACAACAACGTGTCTCAACCACTGTGACTCAAAACAACAAC<br>AGCGAATTTGCTTGGCCTGGAGCTTCTTCTTGGGCTCTCAATGGACGTAATAGCTT<br>GATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGAT<br>GCGGACAAAGTCATGATAACCAACGAAGAAGAAATTAAAACTACTAACCCGGTAGC<br>AACGGAGTCCTATGGACAAGtggccacaaaccaccagagtGCCCAAGCACAGGCGC<br>AGaccggctgggttcaaaaccaAGGAATACTTCCGGGTATGGTTTGGCAGGACAGA<br>GATGTGTACCTGCAAGGACCCATTTGGGCCAAAATTCCTCACACGGACGGCAACTT<br>TCACCCTTCTCCGCTGATGGGAGGGTTTGGAATGAAGCACCCGCCTCCTCAGATCC<br>TCATCAAAAACACACCTGTACCTGCGGATCCTCCAACGGCCTTCAACAAGGACAAG<br>CTGAACTCTTTCATCACCCAGTATTCTACTGGCCAAGTCAGCGTGGAGATCGAGTG<br>GGAGCTGCAGAAGGAAAACAGCAAGCGCTGGAACCCGGAGATCCAGTACACTTCCA<br>ACTATTACAAGTCTAATAATGTTGAATTTGCTGTTAATACTGAAGGTGTATATAGT<br>GAACCCCGCCCCATTGGCACgcGgTAttTAACgaGgAActTa |

In some embodiments, the polynucleotide encoding an AAV capsid variant, described herein comprises the nucleotide sequence of SEQ ID NO: 983 or 984, or a nucleotide sequence with at least 70% (e.g., at least about 80, 85, 90, 95, 96, 97, 98, or 99%) sequence identity thereto.

In some embodiments, the polynucleotide encoding an AAV capsid variant, described herein comprises the nucleotide sequence of any one of SEQ ID NOs: 12-35, or a nucleotide sequence with at least 70% (e.g., at least about 80, 85, 90, 95, 96, 97, 98, or 99%) sequence identity thereto.

In some embodiments, the polynucleotide encoding an AAV capsid variant described herein comprises the nucleotide sequence of SEQ ID NO: 983, or a nucleotide sequence with at least 70% (e.g., at least about 80, 85, 90, 95, 96, 97, 98, or 99%) sequence identity thereto. In some embodiments, the nucleotide sequence encoding an AAV capsid variant described herein, comprises a nucleotide sequence comprising at least one, two or three modifications, e.g., substitutions (e.g., conservative substitutions), insertions, or deletions, but not more than 30, 20 or 10 modifications, e.g., substitutions (e.g., conservative substitutions), insertions, or deletions, relative to the nucleotide sequence of SEQ ID NO: 983. In some embodiments, the nucleotide sequence encoding an AAV capsid variant described herein, comprises a nucleotide sequence comprising at least one, two or three, but not more than 30, 20 or 10 different nucleotides relative to the amino acid sequence of SEQ ID NO: 983. In some embodiments, the nucleic acid sequence encoding an AAV capsid variant described herein is codon optimized.

In some embodiments, the polynucleotide encoding an AAV capsid variant described herein comprises the nucleotide sequence of SEQ ID NO: 984, or a nucleotide sequence with at least 70% (e.g., at least about 80, 85, 90, 95, 96, 97, 98, or 99%) sequence identity thereto. In some embodiments, the nucleotide sequence encoding an AAV capsid variant described herein, comprises a nucleotide sequence comprising at least one, two or three modifications, e.g., substitutions (e.g., conservative substitutions), insertions, or deletions, but not more than 30, 20 or 10 modifications, e.g., substitutions (e.g., conservative substitutions), insertions, or deletions, relative to the nucleotide sequence of SEQ ID NO: 984. In some embodiments, the nucleotide sequence encoding an AAV capsid variant described herein, comprises a nucleotide sequence comprising at least one, two or three, but not more than 30, 20 or 10 different nucleotides, relative to the amino acid sequence of SEQ ID NO: 984. In some embodiments, the nucleic acid sequence encoding an AAV capsid variant described herein is codon optimized.

In some embodiments, an AAV capsid variant described herein comprises the amino acid sequence of any one of SEQ ID NOs: 36-59, 981, or 982, or an amino acid sequence with at least 70% (e.g., at least about 80, 85, 90, 95, 96, 97, 98, or 99%) sequence identity thereto. In some embodiments, an AAV capsid variant described herein comprises an amino acid sequence comprising at least one, two, or three modifications, e.g., substitutions (e.g., conservative substitutions), insertions, or deletions, but not more than 30, 20 or 10 modifications, e.g., substitutions (e.g., conservative substitutions), insertions, or deletions, relative to the amino acid sequence of SEQ ID NO: 36-59, 981, or 982. In some embodiments, the AAV capsid variant, comprises an amino acid sequence comprising at least one, two or three, but not more than 30, 20 or 10 different amino acids, relative to the amino acid sequence of SEQ ID NO: 36-59, 981, or 982.

In some embodiments, an AAV capsid variant described herein, comprises the amino acid sequence of SEQ ID NO: 981, or an amino acid sequence with at least 70% (e.g., at least about 80, 85, 90, 95, 96, 97, 98, or 99%) sequence identity thereto. In some embodiments, an AAV capsid variant described herein comprises an amino acid sequence comprising at least one, two, or three modifications, e.g., substitutions (e.g., conservative substitutions), insertions, or deletions, but not more than 30, 20 or 10 modifications, e.g., substitutions (e.g., conservative substitutions), insertions, or deletions, relative to the amino acid sequence of SEQ ID NO: 981. In some embodiments, an AAV capsid variant described herein comprises an amino acid sequence comprising at least one, two or three, but not more than 30, 20 or 10 different amino acids, relative to the amino acid sequence of SEQ ID NO: 981.

In some embodiments, an AAV capsid variant described herein comprises the amino acid sequence of SEQ ID NO: 982, or an amino acid sequence with at least 70% (e.g., at least about 80, 85, 90, 95, 96, 97, 98, or 99%) sequence identity thereto. In some embodiments, an AAV capsid variant described herein comprises an amino acid sequence comprising at least one, two, or three modifications, e.g., substitutions (e.g., conservative substitutions), insertions, or deletions, but not more than 30, 20 or 10 modifications, e.g., substitutions (e.g., conservative substitutions), insertions, or deletions, relative to the amino acid sequence of SEQ ID NO: 982. In some embodiments, the AAV capsid variant, comprises an amino acid sequence comprising at least one, two or three, but not more than 30, 20 or 10 different amino acids, relative to the amino acid sequence of SEQ ID NO: 982.

In some embodiments, an AAV capsid variant described herein comprises the amino acid sequence of SEQ ID NO: 36, or an amino acid sequence with at least 70% (e.g., at least about 80, 85, 90, 95, 96, 97, 98, or 99%) sequence identity thereto. In some embodiments, an AAV capsid variant described herein comprises an amino acid sequence comprising at least one, two, or three modifications, e.g., substitutions (e.g., conservative substitutions), insertions, or deletions, but not more than 30, 20 or 10 modifications, e.g., substitutions (e.g., conservative substitutions), insertions, or deletions, relative to the amino acid sequence of SEQ ID NO: 36. In some embodiments, the AAV capsid variant, comprises an amino acid sequence comprising at least one, two or three, but not more than 30, 20 or 10 different amino acids, relative to the amino acid sequence of SEQ ID NO: 36.

In some embodiments, an AAV capsid variant described herein comprises the amino acid sequence of SEQ ID NO: 39, or an amino acid sequence with at least 70% (e.g., at least about 80, 85, 90, 95, 96, 97, 98, or 99%) sequence identity thereto. In some embodiments, an AAV capsid variant described herein comprises an amino acid sequence comprising at least one, two, or three modifications, e.g., substitutions (e.g., conservative substitutions), insertions, or deletions, but not more than 30, 20 or 10 modifications, e.g., substitutions (e.g., conservative substitutions), insertions, or deletions, relative to the amino acid sequence of SEQ ID NO: 39. In some embodiments, the AAV capsid variant, comprises an amino acid sequence comprising at least one, two or three, but not more than 30, 20 or 10 different amino acids, relative to the amino acid sequence of SEQ ID NO: 39.

In some embodiments, an AAV capsid variant described herein comprises the amino acid sequence of SEQ ID NO: 51, or an amino acid sequence with at least 70% (e.g., at least about 80, 85, 90, 95, 96, 97, 98, or 99%) sequence identity thereto. In some embodiments, an AAV capsid variant described herein comprises an amino acid sequence comprising at least one, two, or three modifications, e.g., substitutions (e.g., conservative substitutions), insertions, or deletions, but not more than 30, 20 or 10 modifications, e.g., substitutions (e.g., conservative substitutions), insertions, or deletions, relative to the amino acid sequence of SEQ ID NO: 51. In some embodiments, the AAV capsid variant, comprises an amino acid sequence comprising at least one, two or three, but not more than 30, 20 or 10 different amino acids, relative to the amino acid sequence of SEQ ID NO: 51.

In some embodiments, an AAV capsid variant described herein comprises the amino acid sequence of SEQ ID NO: 52, or an amino acid sequence with at least 70% (e.g., at least about 80, 85, 90, 95, 96, 97, 98, or 99%) sequence identity thereto. In some embodiments, an AAV capsid variant described herein comprises an amino acid sequence comprising at least one, two, or three modifications, e.g., substitutions (e.g., conservative substitutions), insertions, or deletions, but not more than 30, 20 or 10 modifications, e.g., substitutions (e.g., conservative substitutions), insertions, or deletions, relative to the amino acid sequence of SEQ ID NO: 52. In some embodiments, the AAV capsid variant, comprises an amino acid sequence comprising at least one, two or three, but not more than 30, 20 or 10 different amino acids, relative to the amino acid sequence of SEQ ID NO: 52.

In some embodiments, an AAV capsid variant described herein comprises an amino acid sequence encoded by the nucleotide sequence of SEQ ID NO: 983 or 984, or a nucleotide sequence with at least 70% (e.g., at least about 80, 85, 90, 95, 96, 97, 98, or 99%) sequence identity thereto. In some embodiments, an AAV capsid variant described herein comprises an amino acid sequence encoded by a nucleotide sequence comprising at least one, two or three, but not more than 30, 20 or 10 different nucleotides, relative to the amino acid sequence of SEQ ID NO: 983 or 984. In some embodiments, an AAV capsid variant described herein comprises an amino acid sequence encoded by a nucleotide sequence comprising at least one, two or three modifications, e.g., substitutions, insertions, or deletions, but not more than 30, 20 or 10 modifications, e.g., substitutions, insertions, or deletions, relative to the nucleotide sequence of SEQ ID NO: 983 or 984.

In some embodiments, an AAV capsid variant described herein comprises an amino acid sequence encoded by the nucleotide sequence of any one of SEQ ID NOs: 12-35, or a nucleotide sequence with at least 70% (e.g., at least about 80, 85, 90, 95, 96, 97, 98, or 99%) sequence identity thereto. In some embodiments, an AAV capsid variant described herein comprises an amino acid sequence encoded by a nucleotide sequence comprising at least one, two or three, but not more than 30, 20 or 10 different nucleotides, relative to the amino acid sequence of any one of SEQ ID NOs: 12-35. In some embodiments, an AAV capsid variant described herein comprises an amino acid sequence encoded by a nucleotide sequence comprising at least one, two or three modifications, e.g., substitutions, insertions, or deletions, but not more than 30, 20 or 10 modifications, e.g., substitutions, insertions, or deletions, relative to the nucleotide sequence of any one of SEQ ID NOs: 12-35.

In some embodiments, an AAV capsid variant described herein comprises a VP1, VP2, VP3 protein, or a combination thereof. In some embodiments, an AAV capsid variant comprises the amino acid sequence corresponding to positions 138-742, e.g., a VP2, of SEQ ID NO: 981 or 982, or a sequence with at least 70% (e.g., at least about 80, 85, 90, 95, 96, 97, 98, or 99%) sequence identity thereto. In some embodiments, the AAV capsid protein comprises the amino acid sequence corresponding to positions 203-742, e.g., a VP3, of SEQ ID NO: 981 or 982, or a sequence with at least 70% (e.g., at least about 80, 85, 90, 95, 96, 97, 98, or 99%) sequence identity thereto. In some embodiments, the AAV capsid variant comprises the amino acid sequence corresponding to positions 1-742, e.g., a VP1, of SEQ ID NO: 981 or 982, or an amino acid sequence with at least 70% (e.g., at least about 80, 85, 90, 95, 96, 97, 98, or 99%) sequence identity thereto.

In some embodiments, an AAV capsid variant described herein comprises a VP1, VP2, VP3 protein, or a combination thereof. In some embodiments, an AAV capsid variant comprises the amino acid sequence corresponding to positions 138-742, e.g., a VP2, of any one of SEQ ID NOs: 36-59, or a sequence with at least 70% (e.g., at least about 80, 85, 90, 95, 96, 97, 98, or 99%) sequence identity thereto. In some embodiments, the AAV capsid protein comprises the amino acid sequence corresponding to positions 203-742, e.g., a VP3, of any one of SEQ ID NOs: 36-59, or a sequence with at least 70% (e.g., at least about 80, 85, 90, 95, 96, 97, 98, or 99%) sequence identity thereto. In some embodiments, the AAV capsid variant comprises the amino acid sequence corresponding to positions 1-742, e.g., a VP1, of any one of SEQ ID NOs: 36-59, or an amino acid sequence with at least 70% (e.g., at least about 80, 85, 90, 95, 96, 97, 98, or 99%) sequence identity thereto.

In some embodiments, an AAV capsid variant, described herein has an increased tropism for a CNS cell or tissue, e.g., a brain cell, brain tissue, spinal cord cell, or spinal cord tissue, relative to the tropism of a reference sequence comprising the amino acid sequence of SEQ ID NO: 138.

In some embodiments, an AAV capsid variant described herein transduces a brain region, e.g., a midbrain region (e.g., the hippocampus, or thalamus) or the brain stem. In some embodiments, the level of transduction is at least 5, 10, 15, 20, 25, 30, 35, 40, 45, 50, 55, 60, or 65-fold greater as compared to a reference sequence of SEQ ID NO: 138. In some embodiments, the level of transduction is at least 30, 35, 40, 45, 50, 55, 60, or 65-fold greater as compared to a reference sequence of SEQ ID NO: 138.

In some embodiments, an AAV capsid variant described herein is enriched at least about 3, 4, 5, 6, 7, 8, 9, or 10-fold in the brain compared to a reference sequence of SEQ ID NO: 138. In some embodiments, an AAV capsid variant described herein is enriched at least about 20, 25, 30, 35, 40, 45, 50, 55, 60, 65, 70, 75, 80 or 85-fold in the brain compared to a reference sequence of SEQ ID NO: 138.

In some embodiments, an AAV capsid variant described herein is enriched in the brain of at least two to three species, e.g., a non-human primate and rodent (e.g., mouse) species, compared to a reference sequence of SEQ ID NO: 138. In some embodiments, an AAV capsid variant described herein is enriched at least about 10, 15, 20, 25, 30, 35, 40, 45, 50, 55, 60, 65, 70, 75, 80, 85, 90, 95, or 100-fold in the brain of at least two to three species, e.g., a non-human primate and rodent (e.g., mouse) species, compared to a reference sequence of SEQ ID NO: 138. In some embodiments, the at least two to three species are *Macaca fascicularis, Chlorocebus sabaeus, Callithrix jacchus*, and/or mouse (e.g., BALB/c mice, C57B1/6 mice, and/or CD-1 outbred mice).

In some embodiments, an AAV capsid variant described herein is enriched at least about 2, 2.5, 3, 3.5, 4, 4.5, 5, 5.5, 6, 6.5, 7, 7.5, or 8-fold, in the brain compared to a reference sequence of SEQ ID NO: 981. In some embodiments, an AAV capsid variant described herein is enriched about 2, 2.5, 3, 3.5, 4, 4.5, 5, or 5.5-fold, in the brain compared to a reference sequence of SEQ ID NO: 982.

In some embodiments, an AAV capsid variant described herein delivers an increased level of viral genomes to a brain region. In some embodiments, the level of viral genomes is increased by at least 20, 25, 30, 35, 40, 45, or 50-fold, as compared to a reference sequence of SEQ ID NO: 138. In some embodiments, the brain region comprises a midbrain region (e.g., the hippocampus or thalamus) and/or the brainstem.

In some embodiments, an AAV capsid variant described herein delivers an increased level of a payload to a brain region. In some embodiments, the level of the payload is increased by at least 20, 25, 30, 35, 40, 45, 50, 55, 60, 65, or 70-fold, as compared to a reference sequence of SEQ ID NO: 138. In some embodiments, the brain region comprises a midbrain region (e.g., the hippocampus or thalamus) and/or the brainstem.

In some embodiments, an AAV capsid variant described herein is enriched at least about 5, 10, 15, 20, 25, 30, or 35-fold, in the spinal cord compared to a reference sequence of SEQ ID NO: 138.

In some embodiments, an AAV capsid variant described herein shows preferential transduction in a brain region relative to the transduction in the dorsal root ganglia (DRG). In some embodiments, the AAV capsid variant shows preferential transduction in a brain region relative to the transduction in the liver. In some embodiments, the AAV capsid variant shows preferential transduction in a brain region relative to the transduction in the liver and the DRG. In some embodiments, the AAV capsid variant shows preferential transduction in a brain region relative to the transduction in the heart. In some embodiments, the AAV capsid variant shows preferential transduction in a brain region relative to the transduction in the heart and DRG. In some embodiments, the AAV capsid variant shows preferential transduction in a brain region relative to the transduction in the heart, DRG, and liver. In some embodiments, the AAV capsid variant shows preferential transduction in a brain region and/or a heart region relative to the transduction in the liver and DRG.

In some embodiments, an AAV capsid variant described herein is capable of transducing non-neuronal cells, e.g., glial cells (e.g., oligodendrocytes or astrocytes). In some embodiments, the AAV capsid variant described herein is capable of transducing neuronal cells and non-neuronal cells, e.g., glial cells (e.g., oligodendrocytes or astrocytes). In some embodiments, the non-neuronal cells are glial cells, oligodendrocytes (e.g., Olig2 positive oligodendrocytes), or astrocytes (e.g., Olig2 positive astrocytes). In some embodiments, the AAV capsid variant is capable of transducing Olig2 positive cells, e.g., Olig2 positive astrocytes or Olig2 positive oligodendrocytes.

In some embodiments, an AAV capsid polypeptide, e.g., an AAV capsid variant, described herein has an increased tropism for a muscle cell or tissue, e.g., a heart or quadriceps cell or tissue, relative to the tropism of a reference sequence comprising the amino acid sequence of SEQ ID NO: 138. In some embodiments, the AAV capsid variant is enriched at least about 4, 5, 8, 12, 17, 18, 20, 26, 27, 28, 30, or 36-fold, in the muscle compared to a reference sequence of SEQ ID NO: 138. In some embodiments, the muscle region comprises a quadriceps muscle, heart muscle, and/or a diaphragm muscle region. In some embodiments, the muscle region comprises a heart muscle region, e.g., a heart atrium muscle region or a heart ventricle muscle region.

In some embodiments, an AAV capsid polypeptide, e.g., an AAV capsid variant, described herein has an increased tropism for a heart cell or heart tissue. In some embodiments, the AAV capsid variant is enriched at least about 4, 5, 8, 10, 11, 12, 13, 14, 18, 19, 20, 21, 22, 24, 25, 27, 31, 33, or 34-fold, in the heart compared to a reference sequence of SEQ ID NO: 138.

In some embodiments, an AAV capsid variant described herein has increased tropism for a liver cell or tissue, relative to the tropism of a reference sequence comprising the amino acid sequence of SEQ ID NO: 138. In some embodiments, the AAV capsid variant is enriched at least about 10, 15, 20, 25, 30, 35, 40, 45, 50, 55, 60, 65, 70, 75, 80, 85, 90, 95, 100, 105, 110, 115, 120, 125, 130, 135, 140, 150, 160, 170, 180, 190, or 200-fold, in the liver compared to a reference sequence of SEQ ID NO: 138. In some embodiments, the AAV capsid variant has reduced tropism for a CNS cell or tissue, e.g., a brain cell, brain tissue, spinal cord cell, or spinal cord tissue, relative to the tropism of a reference sequence comprising the amino acid sequence of SEQ ID NO: 138. In some embodiments, the AAV capsid variant shows preferential transduction in a liver region relative to the transduction in the brain and/or dorsal root ganglia (DRG). In some embodiments, the AAV capsid variant shows preferential transduction in a liver region relative to the transduction in the heart and/or muscle (e.g., quadriceps).

In some embodiments, an AAV capsid variant of the present disclosure has decreased tropism for the liver. In some embodiments, an AAV capsid variant comprises a modification, e.g., substitution (e.g., conservative substitution), insertion, or deletion, that results in reduced tropism (e.g., de-targeting) and/or activity in the liver. In some embodiments, the reduced tropism in the liver is compared to an otherwise similar capsid that does not comprise the modification, e.g., a wild-type capsid. In some embodiments, an AAV capsid variant described herein comprises a modification, e.g., substitution (e.g., conservative substitution), insertion, or deletion that results in one or more of the following properties: (1) reduced tropism in the liver; (2) reduced, e.g., de-targeted, expression in the liver; (3) reduced activity in the liver; and/or (4) reduced binding to galactose. In some embodiments, the reduction in any one, or all of properties (1)-(3) is compared to an otherwise similar AAV capsid variant that does not comprise the modification. Exemplary modifications are provided in WO 2018/119330; Pulicherla et al. (2011) *Mol. Ther.* 19(6): 1070-1078; Adachi et al. (2014) *Nature Communications* 5(3075), DOI: 10.1038/ncomms4075; and Bell et al. (2012) *J. Virol.* 86(13): 7326-33; the contents of which are hereby incorporated by reference in their entirety. In some embodiments, the AAV capsid variant comprises a modification e.g., substitution (e.g., conservative substitution), insertion, or deletion, at position N470 (e.g., N470A), D271 (e.g., D271A), N272 (e.g., N297A), Y446 (e.g., Y446A), N498 (e.g., N498Y or N498I), W503 (e.g., W530R or W530A), L620 (e.g., L620F), or a combination thereof, relative to a reference sequence numbered according to SEQ ID NO: 138. In some embodiments, the AAV capsid variant comprises one, two, three, four, five or all of an amino acid other than N at position 470 (e.g., A), an amino acid other than D at position 271 (e.g., A), an amino acid other than N at position 272 (e.g., A), an amino acid other than Y at position 446 (e.g., A), and amino acid other than N at position 498/(e.g., Y or I), and amino acid other than W at position 503 (e.g., R or A), and amino acid other than L at position 620 (e.g., F), relative to a reference sequence numbered according to SEQ ID NO: 138. In some embodiments, the AAV capsid variant comprises a modification e.g., substitution (e.g., conservative substitution), insertion, or deletion, at position N470 (e.g., N470A), D271 (e.g., D271A), N272 (e.g., N297A), Y446 (e.g., Y446A), and W503 (e.g., W530R or W530A), relative to a reference sequence numbered according to SEQ ID NO: 138. In some embodiments, the AAV capsid variant comprises a modification e.g., substitution (e.g., conservative substitution), insertion, or deletion, at N498 (e.g., N498Y) and L620 (e.g., L620F).

In some embodiments, an AAV capsid variant comprised herein comprises a modification as described in Adachi et al. (2014) *Nature Communications* 5(3075), DOI: 10.1038/ncomms4075, the contents of which are hereby incorporated by reference in its entirety. Exemplary modifications that alter or do not alter tissue transduction in at least the brain, liver, heart, lung, and/or kidney can be found in Supplementary Data 2 showing the AAV Barcode-Seq data obtained with AAV9-AA-VBCLib of Adachi et al. (supra), the contents of which are hereby incorporated by reference in its entirety.

In some embodiments, an AAV capsid variant of the present disclosure is isolated, e.g., recombinant. In some embodiments, a polynucleotide encoding an AAV capsid polypeptide, e.g., an AAV capsid variant, of the present disclosure is isolated, e.g., recombinant.

Also provided herein are polynucleotide sequences encoding any of the AAV capsid variants described above and AAV particles, vectors, and cells comprising the same.

AAV Serotypes and Capsids

In some embodiments, an AAV particle of the present disclosure may comprise a capsid protein or variant thereof any natural or recombinant AAV serotype. AAV serotypes may differ in characteristics such as, but not limited to, packaging, tropism, transduction and immunogenic profiles. While not wishing to be bound by theory, it is believed in some embodiments, that the AAV capsid protein, e.g., an AAV capsid variant, can modulate, e.g., direct, AAV particle tropism to a particular tissue.

In some embodiments, an AAV capsid variant described herein allows for blood brain barrier penetration following intravenous administration. In some embodiments, the AAV capsid variant allows for blood brain barrier penetration following intravenous administration, focused ultrasound (FUS), e.g., coupled with the intravenous administration of microbubbles (FUS-MB), or MRI-guided FUS coupled with intravenous administration. In some embodiments the AAV capsid variant allows for increased distribution to a brain region. In some embodiments, the brain region comprises a frontal cortex, sensory cortex, motor cortex, caudate, dentate nucleus, cerebellar cortex, cerebral cortex, brain stem, hippocampus, thalamus, putamen, or a combination thereof. In some embodiments, the AAV capsid variant allows for preferential transduction in a brain region relative to the transduction in the dorsal root ganglia (DRG). In some embodiments, the AAV capsid variant allows for transduction in a non-neuronal cell, e.g., a glial cell (e.g., an astrocyte, an oligodendrocyte, or a combination thereof).

In some embodiments, an AAV capsid variant allows for increased distribution to a spinal cord region. In some embodiments, the spinal region comprises a cervical spinal cord region, thoracic spinal cord region, and/or lumbar spinal cord region.

In some embodiments, the AAV capsid variant, is suitable for intramuscular administration and/or transduction of muscle fibers. In some embodiments the AAV capsid variant, allows for increased distribution to a muscle region. In some embodiments, the muscle region comprises a heart muscle, quadriceps muscle, a diaphragm muscle region, or a combination thereof. In some embodiments, the muscle region comprises a heart muscle region, e.g., a heart atrium muscle region or a heart ventricle muscle region.

In some embodiments, the initiation codon for translation of the AAV VP1 capsid protein, e.g., a capsid variant, described herein may be CTG, TTG, or GTG as described in U.S. Pat. No. 8,163,543, the contents of which are herein incorporated by reference in its entirety. The present disclosure refers to structural capsid proteins (including VP1, VP2 and VP3) which are encoded by capsid (Cap) genes. These capsid proteins form an outer protein structural shell (e.g., capsid) of a viral vector such as AAV. VP capsid proteins synthesized from Cap polynucleotides generally include a methionine as the first amino acid in the peptide sequence (Met1), which is associated with the start codon (AUG or ATG) in the corresponding Cap nucleotide sequence. However, it is common for a first-methionine (Met1) residue or generally any first amino acid (AA1) to be cleaved off after or during polypeptide synthesis by protein processing enzymes such as Met-aminopeptidases. This "Met/AA-clipping" process often correlates with a corresponding acetylation of the second amino acid in the polypeptide sequence (e.g., alanine, valine, serine, threonine, etc.). Met-clipping commonly occurs with VP1 and VP3 capsid proteins but can also occur with VP2 capsid proteins.

Where the Met/AA-clipping is incomplete, a mixture of one or more (one, two or three) VP capsid proteins comprising the viral capsid may be produced, some of which may include a Met1/AA1 amino acid (Met+/AA+) and some of which may lack a Met1/AA1 amino acid as a result of Met/AA-clipping (Met−/AA−). For further discussion regarding Met/AA-clipping in capsid proteins, see Jin, et al. Direct Liquid Chromatography/Mass Spectrometry Analysis for Complete Characterization of Recombinant Adeno-Associated Virus Capsid Proteins. *Hum Gene Ther Methods.* 2017 Oct. 28(5):255-267; Hwang, et al. N-Terminal Acetylation of Cellular Proteins Creates Specific Degradation Signals. *Science.* 2010 Feb. 19. 327(5968): 973-977; the contents of which are each incorporated herein by reference in its entirety.

According to the present disclosure, references to capsid proteins, e.g., AAV capsid variants, is not limited to either clipped (Met−/AA−) or unclipped (Met+/AA+) and may, in context, refer to independent capsid proteins, viral capsids comprised of a mixture of capsid proteins, and/or polynucleotide sequences (or fragments thereof) which encode, describe, produce or result in capsid proteins of the present disclosure. A direct reference to a capsid protein or capsid polypeptide (such as VP1, VP2 or VP2) may also comprise VP capsid proteins which include a Met1/AA1 amino acid (Met+/AA+) as well as corresponding VP capsid proteins which lack the Met1/AA1 amino acid as a result of Met/AA-clipping (Met−/AA−).

Further according to the present disclosure, a reference to a specific SEQ ID NO: (whether a protein or nucleic acid) which comprises or encodes, respectively, one or more capsid proteins which include a Met1/AA1 amino acid (Met+/AA+) should be understood to teach the VP capsid proteins which lack the Met1/AA1 amino acid as upon review of the sequence, it is readily apparent any sequence which merely lacks the first listed amino acid (whether or not Met1/AA1).

As a non-limiting example, reference to a VP1 polypeptide sequence which is 736 amino acids in length, and which includes a "Met1" amino acid (Met+) encoded by the AUG/ATG start codon may also be understood to teach a VP1 polypeptide sequence which is 735 amino acids in length, and which does not include the "Met1" amino acid (Met−) of the 736 amino acid Met+ sequence. As a second non-limiting example, reference to a VP1 polypeptide sequence which is 736 amino acids in length, and which includes an "AA1" amino acid (AA1+) encoded by any NNN initiator codon may also be understood to teach a VP1 polypeptide sequence which is 735 amino acids in length, and which does not include the "AA1" amino acid (AA1−) of the 736 amino acid AA1+ sequence.

References to viral capsids formed from VP capsid proteins (such as reference to specific AAV capsid serotypes), can incorporate VP capsid proteins which include a Met1/AA1 amino acid (Met+/AA1+), corresponding VP capsid proteins which lack the Met1/AA1 amino acid as a result of Met/AA1-clipping (Met−/AA1−), and combinations thereof (Met+/AA1+ and Met−/AA1−).

As a non-limiting example, an AAV capsid serotype can include VP1 (Met+/AA1+), VP1 (Met−/AA1−), or a combination of VP1 (Met+/AA1+) and VP1 (Met−/AA1−). An AAV capsid serotype can also include VP3 (Met+/AA1+), VP3 (Met−/AA1−), or a combination of VP3 (Met+/AA1+) and VP3 (Met−/AA1−); and can also include similar optional combinations of VP2 (Met+/AA1) and VP2 (Met−/AA1−).

Additional AAV Sequences

In some embodiments, the AAV capsid variant, comprises immediately subsequent to position 448, 449, 452, 453, 455, numbered relative to SEQ ID NO: 138 or corresponding to equivalent positions in any other AAV serotype (e.g., AAV1, AAV2, AAV3, AAV3b, AAV4, AAV5, AAV6, AAV7, AAV8, AAVrh8, AAVrh10, AAVrh32.33, AAVrh74, SEQ ID NO: 1, SEQ ID NO: 11, PHP.N, PHP.B, or an AAV serotype as provided in Table 6 of WO 2021/230987 (the contents of which are hereby incorporated by reference in their entirety)), at least 3, 4, 5, 6, 7, 8, 9, 10, 11, 12, or 13 consecutive amino acids of any of amino acid sequence provided in Tables 1, 2A, 2B, 13-19. In some embodiments, the at least 3, 4, 5, 6, 7, 8, 9, 10, 11, 12, or 13 consecutive amino acids of any of amino acid sequence provided in Tables 1, 2A, 2B, 13-19 replaces at least one, two, three, four, five, six, seven, eight, nine, ten, or all of positions K449, T450, I451, N452, G453, 5454, G455, Q456, N457, Q458, and/or Q459, numbered according to SEQ ID NO: 138 or corresponding to equivalent positions in any other AAV serotype (e.g., AAV1, AAV2, AAV3, AAV3b, AAV4, AAV5, AAV6, AAV7, AAV8, AAVrh8, AAVrh10, AAVrh32.33, AAVrh74, SEQ ID NO: 1, SEQ ID NO: 11, PHP.N, PHP.B, or an AAV serotype as provided in Table 6 of WO 2021/230987 (the contents of which are hereby incorporated by reference in their entirety). In some embodiments, the at least 3, 4, 5, 6, 7, 8, 9, 10, 11, 12, or 13 consecutive amino acids of any of amino acid sequence provided in Tables 1, 2A, 2B, 13-19 replaces positions S454, G455, or both positions S454 and G455, numbered according to SEQ ID NO: 138 or corresponding to equivalent positions in any other AAV serotype (e.g., AAV1, AAV2, AAV3, AAV3b, AAV4, AAV5, AAV6, AAV7, AAV8, AAVrh8, AAVrh10, AAVrh32.33, AAVrh74, SEQ ID NO: 1, SEQ ID NO: 11, PHP.N, PHP.B, or an AAV serotype as provided in Table 6 of WO 2021/230987 (the contents of which are hereby incorporated by reference in their entirety).

In some embodiments, the AAV capsid variant comprises an amino acid other than the wild-type, e.g., native, amino acid, at one, two, three, four, five, six, seven, eight, nine or all of positions T450, 1451, N452, G453, S454, G455, Q456, N457, Q458, and/or Q459, numbered according to SEQ ID NO: 138 or corresponding to equivalent positions in any other AAV serotype (e.g., AAV1, AAV2, AAV3, AAV3b, AAV4, AAV5, AAV6, AAV7, AAV8, AAVrh8, AAVrh10, AAVrh32.33, AAVrh74, SEQ ID NO: 1, SEQ ID NO: 11, PHP.N, PHP.B, or an AAV serotype as provided in Table 6 of WO 2021/230987 (the contents of which are hereby incorporated by reference in their entirety). In some embodiments, the AAV capsid variant comprises an amino acid other than the wild-type, e.g., native, amino acid, at position S454, G455, or both positions S454 and G455, numbered according to SEQ ID NO: 138 or corresponding to equivalent positions in any other AAV serotype (e.g., AAV1, AAV2, AAV3, AAV3b, AAV4, AAV5, AAV6, AAV7, AAV8, AAVrh8, AAVrh10, AAVrh32.33, AAVrh74, SEQ ID NO: 1, SEQ ID NO: 11, PHP.N, PHP.B, or an AAV serotype as provided in Table 6 of WO 2021/230987 (the contents of which are hereby incorporated by reference in their entirety)). In some embodiments, the AAV capsid variant comprises a modification, e.g., substitution, at one, two, three, four, five, six, seven, eight, nine, ten or all of positions K449, T450, I451, N452, G453, S454, G455, Q456, N457, Q458, and/or Q459, numbered according to SEQ ID NO: 138 or corresponding to equivalent positions in any other AAV serotype (e.g., AAV1, AAV2, AAV3, AAV3b, AAV4, AAV5, AAV6, AAV7, AAV8, AAVrh8, AAVrh10, AAVrh32.33, AAVrh74, SEQ ID NO: 1, SEQ ID NO: 11, PHP.N, PHP.B, or an AAV serotype as provided in Table 6 of WO 2021/230987 (the contents of which are hereby incorporated by reference in their entirety). In some embodiments, the AAV capsid variant comprises a modification, e.g., substitution, at position S454, G455, or both positions S454 and G455, numbered according to SEQ ID NO: 138 or corresponding to equivalent positions in any other AAV serotype (e.g., AAV1, AAV2, AAV3, AAV3b, AAV4, AAV5, AAV6, AAV7, AAV8, AAVrh8, AAVrh10, AAVrh32.33, AAVrh74, SEQ ID NO: 1, SEQ ID NO: 11, PHP.N, PHP.B, or an AAV serotype as provided in Table 6 of WO 2021/230987 (the contents of which are hereby incorporated by reference in their entirety).

In some embodiments, an AAV capsid polypeptide or AAV capsid variant described herein may comprise a VOY101 capsid polypeptide, an AAVPHP.B (PHP.B) capsid polypeptide, a AAVPHP.N (PHP.N) capsid polypeptide, an AAV1 capsid polypeptide, an AAV2 capsid polypeptide, an AAV5 capsid polypeptide, an AAV9 capsid polypeptide, an AAV9 K449R capsid polypeptide, an AAVrh10 capsid polypeptide, or a functional variant thereof. In some embodiments, the AAV capsid polypeptide, e.g., AAV capsid variant, comprises an amino acid sequence of any of the AAV capsid polypeptides in Table 6, or an amino acid sequence substantially identical (e.g., having at least 70%, 75%, 80%, 85%, 90%, 92%, 95%, 97%, 98%, or 99% sequence identity) thereto. In some embodiments, the nucleotide sequence encoding the AAV capsid polypeptide comprises any one of the nucleotide sequences in Table 6, or a nucleotide sequence substantially identical (e.g., having at least 70%, 75%, 80%, 85%, 90%, 92%, 95%, 97%, 98%, or 99% sequence identity) thereto.

In some embodiments, an AAV capsid polypeptide or an AAV capsid variant described herein comprises the amino acid sequence of SEQ ID NO: 138 or an amino acid sequence substantially identical (e.g., having at least 70%, 75%, 80%, 85%, 90%, 92%, 95%, 97%, 98%, or 99% sequence identity) thereto. In some embodiments the AAV capsid polypeptide or the AAV capsid variant, comprises an amino acid sequence comprising at least one, two, or three modifications, e.g., substitutions (e.g., conservative substitutions), but no more than 30, 20, or 10 modifications, e.g., substitutions (e.g., conservative substitutions), relative to the amino acid sequence of SEQ ID NO: 138. In some embodiments, the AAV capsid polypeptide or the AAV capsid variant, comprises an amino acid sequence encoded by the nucleotide sequence of SEQ ID NO: 137 or a nucleotide sequence substantially identical (e.g., having at least 70%, 75%, 80%, 85%, 90%, 92%, 95%, 97%, 98%, or 99% sequence identity) thereto. In some embodiments, the nucleotide sequence encoding the AAV capsid polypeptide or the AAV capsid variant comprises the nucleotide sequence of SEQ ID NO: 137 or a nucleotide sequence substantially identical (e.g., having at least 70%, 75%, 80%, 85%, 90%, 92%, 95%, 97%, 98%, or 99% sequence identity) thereto. In some embodiments, the AAV capsid polypeptide or the AAV capsid variant, comprises substitution at position K449, e.g., a K449R substitution, numbered according to SEQ ID NO: 138.

In some embodiments, the AAV capsid polypeptide or the AAV capsid variant, comprises a peptide comprising the amino acid sequence of TLAVPFK (SEQ ID NO: 4680). In some embodiments, the peptide is present immediately subsequent to position 588, relative to a reference sequence numbered according to SEQ ID NO: 138. In some embodiments, the capsid polypeptide comprises the amino acid substitutions of A587D and Q588G, numbered according to SEQ ID NO: 138.

In some embodiments, the AAV capsid polypeptide or the AAV capsid variant comprises the amino acid substitution of K449R, numbered according to SEQ ID NO: 138; and a peptide comprising the amino acid sequence of TLAVPFK (SEQ ID NO: 4680), wherein the peptide is present immediately subsequent to position 588, relative to a reference sequence numbered according to SEQ ID NO: 138.

In some embodiments, the AAV capsid polypeptide or the AAV capsid variant comprises the amino acid substitution of K449R, numbered according to SEQ ID NO: 138; an peptide comprising the amino acid sequence of TLAVPFK (SEQ ID NO: 4680), wherein the insert is present immediately subsequent to position 588, relative to a reference sequence numbered according to SEQ ID NO: 138; and the amino acid substitutions of A587D and Q588G, numbered according to SEQ ID NO: 138.

In some embodiments, the AAV capsid polypeptide or the AAV capsid variant comprises a peptide comprising the amino acid sequence of TLAVPFK (SEQ ID NO: 4680), wherein the insert is present immediately subsequent to position 588, relative to a reference sequence numbered according to SEQ ID NO: 138; and the amino acid substitutions of A587D and Q588G, numbered according to SEQ ID NO: 138.

In some embodiments, the AAV capsid polypeptide or the AAV capsid variant comprises the amino acid sequence of SEQ ID NO: 11 or an amino acid sequence substantially identical (e.g., having at least 70%, 75%, 80%, 85%, 90%, 92%, 95%, 97%, 98%, or 99% sequence identity) thereto. In some embodiments the AAV capsid polypeptide or the AAV capsid variant, comprises an amino acid sequence comprising at least one, two, or three modifications, e.g., substitutions (e.g., conservative substitutions), but no more than 30, 20, or 10 modifications, e.g., substitutions (conservative substitutions), relative to the amino acid sequence of SEQ ID NO: 11, optionally wherein position 449 is not R.

In some embodiments, the AAV capsid polypeptide or AAV capsid variant, comprises the amino acid sequence of SEQ ID NO: 1 or an amino acid sequence substantially identical (e.g., having at least 70%, 75%, 80%, 85%, 90%, 92%, 95%, 97%, 98%, or 99% sequence identity) thereto. In some embodiments the AAV capsid polypeptide or the AAV capsid variant, comprises an amino acid sequence comprising at least one, two, or three modifications, e.g., substitutions (e.g., conservative substitutions), but no more than 30, 20, or 10 modifications, e.g., substitutions (e.g., conservative substitutions), relative to the amino acid sequence of SEQ ID NO: 1.

TABLE 6

| | AAV Sequences | |
|---|---|---|
| Serotype | SEQ ID NO: | Sequence |
| VQY101 | 1 | MAADGYLPDWLEDNLSEGIREWWALKPGAPQPKANQQHQDNARGLVLPGYKYLGPGNGLD<br>KGEPVNAADAAALEHDKAYDQQLKAGDNPYLKYNHADAEFQERLKEDTSFGGNLGRAVFQ<br>AKKRLLEPLGLVEEAAKTAPGKKRPVEQSPQEPDSSAGIGKSGAQPAKKRLNFGQTGDTE<br>SVPDPQPIGEPPAAPSGVGSLTMASGGGAPVADNNEGADGVGSSSGNWHCDSQWLGDRVI<br>TTSTRTWALPTYNNHLYKQISNSTSGGSSNDNAYFGYSTPWGYFDFNRFHCHFSPRDWQR<br>LINNNWGFRPKRLNFKLFNIQVKEVTDNNGVKTIANNLTSTVQVFTDSDYQLPYVLGSAH<br>EGCLPPFPADVFMIPQYGYLTLNDGSQAVGRSSFYCLEYFPSQMLRTGNNFQFSYEFENV<br>PFHSSYAHSQSLDRLMNPLIDQYLYYLSKTINGSGQNQQTLKFSVAGPSNMAVQGRNYIP<br>GPSYRQQRVSTTVTQNNNSEFAWPGASSWALNGRNSLMNPGPAMASHKEGEDRFFPLSGS<br>LIFGKQGTGRDNVDADKVMITNEEEIKTTNPVATESYGQVATNHQSDGTLAVPFKAQAQT<br>GWVQNQGILPGMVWQDRDVYLQGPIWAKIPHTDGNFHPSPLMGGFGMKHPPPQILIKNTP<br>VPADPPTAFNKDKLNSFITQYSTGQVSVEIEWELQKENSKRWNPEIQYTSNYYKSNNVEF<br>AVNTEGVYSEPRPIGTRYLTRNL |
| AAV9/hu.14<br>K449R | 11 | MAADGYLPDWLEDNLSEGIREWWALKPGAPQPKANQQHQDNARGLVLPGYKYLGPGNGLD<br>KGEPVNAADAAALEHDKAYDQQLKAGDNPYLKYNHADAEFQERLKEDTSFGGNLGRAVFQ<br>AKKRLLEPLGLVEEAAKTAPGKKRPVEQSPQEPDSSAGIGKSGAQPAKKRLNFGQTGDTE<br>SVPDPQPIGEPPAAPSGVGSLTMASGGGAPVADNNEGADGVGSSSGNWHCDSQWLGDRVI<br>TTSTRTWALPTYNNHLYKQISNSTSGGSSNDNAYFGYSTPWGYFDFNRFHCHFSPRDWQR<br>LINNNWGFRPKRLNFKLFNIQVKEVTDNNGVKTIANNLTSTVQVFTDSDYQLPYVLGSAH<br>EGCLPPFPADVEMIPQYGYLTLNDGSQAVGRSSFYCLEYFPSQMLRTGNNFQFSYEFENV<br>PFHSSYAHSQSLDRLMNPLIDQYLYYLSRTINGSGQNQQTLKFSVAGPSNMAVQGRNYIP<br>GPSYRQQRVSTTVTQNNNSEFAWPGASSWALNGRNSLMNPGPAMASHKEGEDRFFPLSGS<br>LIFGKQGTGRDNVDADKVMITNEEEIKTTNPVATESYGQVATNHQSAQAQAQTGWVQNQG<br>ILPGMVWQDRDVYLQGPIWAKIPHTDGNFHPSPLMGGFGMKHPPPQILIKNTPVPADPPT<br>AFNKDKLNSFITQYSTGQVSVEIEWELQKENSKRWNPEIQYTSNYYKSNNVEFAVNTEGV<br>YSEPRPIGTRYLTRNL |
| AAV9/hu.14 WT (amino acid) | 138 | MAADGYLPDWLEDNLSEGIREWWALKPGAPQPKANQQHODNARGLVLPGYKYLGPGNGLD<br>KGEPVNAADAAALEHDKAYDQQLKAGDNPYLKYNHADAEFQERLKEDTSFGGNLGRAVFQ<br>AKKRLLEPLGLVEEAAKTAPGKKRPVEQSPQEPDSSAGIGKSGAQPAKKRLNFGQTGDTE<br>SVPDPQPIGEPPAAPSGVGSLTMASGGGAPVADNNEGADGVGSSSGNWHCDSQWLGDRVI<br>TTSTRTWALPTYNNHLYKQISNSTSGGSSNDNAYFGYSTPWGYFDFNRFHCHFSPRDWQR<br>LINNNWGFRPKRLNFKLFNIQVKEVTDNNGVKTIANNLTSTVQVFTDSDYQLPYVLGSAH<br>EGCLPPFPADVFMIPQYGYLTLNDGSQAVGRSSFYCLEYFPSQMLRTGNNFQFSYEFENV<br>PFHSSYAHSQSLDRLMNPLIDQYLYYLSKTINGSGQNQQTLKFSVAGPSNMAVQGRNYIP<br>GPSYRQQRVSTTVTQNNNSEFAWPGASSWALNGRNSLMNPGPAMASHKEGEDRFFPLSGS<br>LIFGKQGTGRDNVDADKVMITNEEEIKTTNPVATESYGQVATNHQSAQAQAQTGWVQNQG<br>ILPGMVWQDRDVYLQGPIWAKIPHTDGNFHPSPLMGGFGMKHPPPQILIKNTPVPADPPT<br>AFNKDKLNSFITQYSTGQVSVEIEWELQKENSKRWNPEIQYTSNYYKSNNVEFAVNTEGV<br>YSEPRPIGTRYLTRNL |
| AAV9/hu.14 WT (DNA) | 137 | ATGGCTGCCGATGGTTATCTTCCAGATTGGCTCGAGGACAACCTTAGTGAAGGAATTCGC<br>GAGTGGTGGGCTTTGAAACCTGGAGCCCCTCAACCCAAGGCAAATCAACAACATCAAGAC<br>AACGCTCGAGGTCTTGTGCTTCCGGGTTACAAATACCTTGGACCCGGCAACGGACTCGAC<br>AAGGGGGAGCCGGTCAACGCAGCAGACGCGGCGGCCCTCGAGCACGACAAGGCCTACGAC<br>CAGCAGCTCAAGGCCGGAGACAACCCGTACCTCAAGTACAACCACGCCGACGCCGAGTTC<br>CAGGAGCGGCTCAAAGAAGATACGTCTTTTGGGGGCAACCTCGGGCGAGCAGTCTTCCAG<br>GCCAAAAAGAGGCTTCTTGAACCTCTTGGTCTGGTTGAGGAAGCGGCTAAGACGGCTCCT<br>GGAAAGAAGAGGCCTGTAGAGCAGTCTCCTCAGGAACCGGACTCCTCCGCGGGTATTGGC<br>AAATCGGGTGCACAGCCCGCTAAAAAGAGACTCAATTTCGGTCAGACTGGCGACACAGAG<br>TCAGTCCCAGACCCTCAACCAATCGGAGAACCTCCCGCAGCCCCCTCAGGTGTGGGATCT<br>CTTACAATGGCTTCAGGTGGTGGCGCACCAGTGGCAGACAATAACGAAGGTGCCGATGGA<br>GTGGGTAGTTCCTCGGGAAATTGGCATTGCGATTCCCAATGGCTGGGGGACAGAGTCATC<br>ACCACCAGCACCCGAACCTGGGCCCTGCCCACCTACAACAATCACCTCTACAAGCAAATC<br>TCCAACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCAGCGA<br>CTCATCAACAACAACTGGGGATTCCGGCCTAAGCGACTCAACTTCAAGCTCTTCAACATT<br>CAGGTCAAAGAGGTTACGGACAACAATGGAGTCAAGACCATCGCCAATAACCTTACCAGC<br>ACGGTCCAGGTCTTCACGGACTCAGACTATCAGCTCCCGTACGTGCTCGGGTCGGCTCAC<br>GAGGGCTGCCTCCCGCCGTTCCCAGCGGACGTTTTCATGATTCCTCAGTACGGGTATCTG<br>ACGCTTAATGATGGAAGCCAGGCCGTGGGTCGTTCGTCCTTTTACTGCCTGGAATATTTC<br>CCGTCGCAAATGCTAAGAACGGGTAACAACTTCCAGTTCAGCTACGAGTTTGAGAACGTA<br>CCTTTCCATAGCAGCTACGCTCACAGCCAAAGCCTGGACCGACTAATGAATCCACTCATC<br>GACCAATACTTGTACTATCTCTCAAAGACTATTAACGGTTCTGGACAGAATCAACAAACG<br>CTAAAATTCAGTGTGGCCGGACCCAGCAACATGGCTGTCCAGGGAAGAAACTACATACCT<br>GGACCCAGCTACCGACAACAACGTGTCTCAACCACTGTGACTCAAAACAACAACAGCGAA<br>TTTGCTTGGCCTGGAGCTTCTTCTTGGGCTCTCAATGGACGTAATAGCTTGATGAATCCT<br>GGACCTGCTATGGCCAGCCACAAAGAAGGAGAGGACCGTTTCTTTCCTTTGTCTGGATCT<br>TTAATTTTTGGCAAACAAGGAACTGGAAGAGACAACGTGGATGCGGACAAAGTCATGATA<br>ACCAACGAAGAAGAAATTAAAACTACTAACCCCGTAGCAACGGAGTCCTATGGACAAGTG<br>GCCACAAACCACCAGAGTGCCCAAGCACAGGCGCAGACCGGCTGGGTTCAAAACCAAGGA<br>ATACTTCCGGGTATGGTTTGGCAGGACAGAGATGTGTACCTGCAAGGACCCATTTGGGCC<br>AAAATTCCTCACACGGACGGCAACTTTCACCCTTCTCCGCTGATGGGAGGGTTTGGAATG TABLE 6-continued AAV Sequences

| Serotype | SEQ ID NO: | Sequence |
|---|---|---|
| | | AAGCACCCGCCTCCTCAGATCCTCATCAAAAACACACCTGTACCTGCGGATCCTCCAACG<br>GCCTTCAACAAGGACAAGCTGAACTCTTTCATCACCCAGTATTCTACTGGCCAAGTCAGC<br>GTGGAGATCGAGTGGGAGCTGCAGAAGGAAAACAGCAAGCGCTGGAACCCGGAGATCCAG<br>TACACTTCCAACTATTACAAGTCTAATAATGTTGAATTTGCTGTTAATACTGAAGGTGTA<br>TATAGTGAACCCCGCCCCATTGGCACCAGATACCTGACTCGTAATCTGTAA |

Viral Genome of the AAV Particle

In some embodiments, an AAV particle as described herein comprising an AAV capsid variant described herein, may be used for the delivery of a viral genome to a tissue (e.g., CNS, DRG, and/or muscle). In some embodiments, an AAV particle comprising an AAV capsid variant described herein can be used for delivery of a viral genome to a tissue or cell, e.g., CNS, DRG, or muscle cell or tissue. In some embodiments, an AAV particle of the present disclosure is a recombinant AAV particle. In some embodiments, an AAV particle of the present disclosure is an isolated AAV particle.

The viral genome may encode any payload, such as but not limited to a polypeptide (e.g., a therapeutic polypeptide), an antibody, an enzyme, an RNAi agent and/or components of a gene editing system. In one embodiment, the AAV particles described herein are used to deliver a payload to cells of the CNS, after intravenous delivery. In another embodiment, the AAV particles described herein are used to deliver a payload to cells of the DRG, after intravenous delivery. In some embodiments, the AAV particles described herein are used to deliver a payload to cells of a muscle, e.g., a heart muscle, after intravenous delivery.

In some embodiments, a viral genome of an AAV particle comprising an AAV capsid variant, as described herein, comprises a nucleotide sequence comprising a transgene encoding a payload. In some embodiments, the viral genome comprises an inverted terminal repeat sequence (ITR). In some embodiments, the viral genome comprises two ITR sequences, one at the 5' end of the viral genome (e.g., 5' relative to the encoded payload) and one at the 3' end of the viral genome (e.g., 3' relative to the encoded payload). In some embodiments, a viral genome of an AAV particle, e.g., an AAV particle comprising an AAV capsid variant described herein, may comprise a regulatory element (e.g., promoter), untranslated regions (UTR), a miR binding site, a polyadenylation sequence (polyA), a filler or stuffer sequence, an intron, and/or a linker sequence, e.g., for enhancing transgene expression.

In some embodiments, the viral genome components are selected and/or engineered for expression of the payload in a target tissue (e.g., CNS, muscle, or DRG).

Viral Genome Component: Inverted Terminal Repeats (ITRs)

In some embodiments, the AAV particle comprising an AAV capsid variant described herein comprises a viral genome comprising an ITR and a transgene encoding a payload. In some embodiments, the viral genome comprises two ITRs. In some embodiments, the two ITRs flank the nucleotide sequence encoding the payload at the 5' and 3' ends. In some embodiments, the ITRs function as origins of replication comprising recognition sites for replication. In some embodiments, the ITRs comprise sequence regions which can be complementary and symmetrically arranged. In some embodiments, the ITRs incorporated into viral genomes as described herein may be comprised of naturally occurring polynucleotide sequences or recombinantly derived polynucleotide sequences.

In some embodiments, the ITR may be from the same serotype as the capsid polypeptide, e.g., capsid variant, selected from any of the known serotypes, or a variant thereof. In some embodiments, the ITR may be of a different serotype than the capsid. In some embodiments, the viral genome comprises two ITR sequence regions, wherein the ITRs are of the same serotype as one another. In some embodiments, the viral genome comprises two ITR sequence regions, wherein the ITRs are of different serotypes. Non-limiting examples include zero, one or both of the ITRs having the same serotype as the capsid. In one embodiment both ITRs of the viral genome of the AAV particle are AAV2 ITRs.

Independently, each ITR may be about 100 to about 150 nucleotides in length. An ITR may be about 100-105 nucleotides in length, 106-110 nucleotides in length, 111-115 nucleotides in length, 116-120 nucleotides in length, 121-125 nucleotides in length, 126-130 nucleotides in length, 131-135 nucleotides in length, 136-140 nucleotides in length, 141-145 nucleotides in length or 146-150 nucleotides in length. In one embodiment, the ITRs are 140-142 nucleotides in length. Non-limiting examples of ITR length are 102, 105, 130, 140, 141, 142, 145 nucleotides in length.

Viral Genome Component: Promoters

In some embodiments, viral genome of an AAV particle described herein comprises at least one element to enhance the payload target specificity and expression (See e.g., Powell et al. Viral Expression Cassette Elements to Enhance Transgene Target Specificity and Expression in Gene Therapy, 2015; the contents of which are herein incorporated by reference in their entirety). Non-limiting examples of elements to enhance payload target specificity and expression include promoters, endogenous miRNAs, post-transcriptional regulatory elements (PREs), polyadenylation (Poly A) signal sequences and upstream enhancers (USEs), CMV enhancers and introns.

In some embodiments, an AAV particle comprising an AAV capsid variant described herein comprises a viral genome comprising a nucleic acid comprising a transgene encoding a payload, wherein the transgene is operably linked to a promoter. In some embodiments, the promoter is a species specific promoter, an inducible promoter, a tissue-specific promoter, or a cell cycle-specific promoter (e.g., a promoter as described in Parr et al., Nat. Med. 3:1145-9 (1997); the contents of which are herein incorporated by reference in their entirety).

In some embodiments, the Promoter may be naturally occurring or non-naturally occurring. Non-limiting examples of promoters include those derived from viruses, plants, mammals, or humans. In some embodiments, the promoters may be those derived from human cells or systems. In some embodiments, the promoter may be truncated or mutated, e.g., a promoter variant.

In some embodiments, the promoter is a ubiquitous promoter, e.g., capable of expression in multiple tissues. In some embodiments the promoter is an human elongation factor 1α-subunit (EF1α) promoter, the cytomegalovirus (CMV) immediate-early enhancer and/or promoter, the chicken β-actin (CBA) promoter and its derivative CAG, β glucuronidase (GUSB) promoter, or ubiquitin C (UBC) promoter. In some embodiments, the promoter is a cell or tissue specific promoter, e.g., capable of expression in tissues or cells of the central or peripheral nervous systems, targeted regions within (e.g., frontal cortex), and/or sub-sets of cells therein (e.g., excitatory neurons). In some embodiments, the promoter is a cell-type specific promoters capable of expression of a payload in excitatory neurons (e.g., glutamatergic), inhibitory neurons (e.g., GABA-ergic), neurons of the sympathetic or parasympathetic nervous system, sensory neurons, neurons of the dorsal root ganglia, motor neurons, or supportive cells of the nervous systems such as microglia, glial cells, astrocytes, oligodendrocytes, and/or Schwann cells.

In some embodiments, the promoter is a liver specific promoter (e.g., hAAT, TBG), skeletal muscle specific promoter (e.g., desmin, MCK, C512), B cell promoter, monocyte promoter, leukocyte promoter, macrophage promoter, pancreatic acinar cell promoter, endothelial cell promoter, lung tissue promoter, and/or cardiac or cardiovascular promoter (e.g., αMHC, cTnT, and CMV-MLC2k).

In some embodiments, the promoter is a tissue-specific promoter for payload expression in a tissue or cell of the central nervous system. In some embodiments, the promoter is a synapsin (Syn) promoter, glutamate vesicular transporter (VGLUT) promoter, vesicular GABA transporter (VGAT) promoter, parvalbumin (PV) promoter, sodium channel $Na_v$ 1.8 promoter, tyrosine hydroxylase (TH) promoter, choline acetyltransferase (ChaT) promoter, methyl-CpG binding protein 2 (MeCP2) promoter, $Ca^{2+}$/calmodulin-dependent protein kinase II (CaMKII) promoter, metabotropic glutamate receptor 2 (mGluR2) promoter, neurofilament light (NFL) or heavy (NFH) promoter, neuron-specific enolase (NSE) promoter, β-globin minigene nβ2 promoter, preproenkephalin (PPE) promoter, enkephalin (Enk) promoter, and excitatory amino acid transporter 2 (EAAT2) promoter, or a fragment thereof. In some embodiments, the promoter is a cell-type specific promoter capable of expression in an astrocyte, e.g., a glial fibrillary acidic protein (GFAP) promoter and a EAAT2 promoter, or a fragment thereof. In some embodiments, the promoter is a cell-type specific promoter capable of expression in an oligodendrocyte, e.g., a myelin basic protein (MBP) promoter or a fragment thereof.

In some embodiments, the promoter is a GFAP promoter. In some embodiments, the promoter is a synapsin (syn or syn1) promoter, or a fragment thereof.

In some embodiments, the promoter comprises an insulin promoter or a fragment thereof.

In some embodiments, the promoter of the viral genome described herein (e.g., comprised within an AAV particle comprising an AAV capsid variant described herein) comprises an EF-1α promoter or variant thereof, e.g., as provided in Table 8. In some embodiments, the EF-1α promoter comprises the nucleotide sequence of any one of SEQ ID NOs: 987, 988, 990, 991, 995, 996, 998-1007 or any one of the sequences provided in Table 8, a nucleotide sequence comprising at least one, two, or three but no more than four modifications, e.g., substitutions, relative to the nucleotide sequence of SEQ ID NOs: 987, 988, 990, 991, 995, 996, 998-1007 or any one of the sequences provided in Table 8, or a nucleotide sequence with at least 70% (e.g., 80, 85%, 90%, 95%, 96%, 97%, 98%, or 99%) sequence identity to any one of SEQ ID NOs: 987, 988, 990, 991, 995, 996, 998-1007 or any one of the sequences provided in Table 8.

TABLE 8

Exemplary Promoter Variants

| Description | Sequences | SEQ ID NO: |
|---|---|---|
| EF1a Promoter (intron underlined) | CGTGAGGCTCCGGTGCCCGTCAGTGGGCAGAGCGCACATCGCCCACAGTCCCCGA GAAGTTGGGGGGAGGGGTCGGCAATTGAACCGGTGCCTAGAGAAGGTGGCGCGGG GTAAACTGGGAAAGTGATGTCGTGTACTGGCTCCGCCTTTTTCCCGAGGGTGGGG GAGAACCGTATATAAGTGCAGTAGTCGCCGTGAACGTTCTTTTTCGCAACGGGTT TGCCGCCAGAACACAGGTAAGTGCCGTGTGTGGTTCCCGCGGGCCTGGCCTCTTT ACGGGTTATGGCCCTTGCGTGCCTTGAATTACTTCCACCTGGCTGCAGTACGTGA TTCTTGATCCCGAGCTTCGGGTTGGAAGTGGGTGGGAGAGTTCGAGGCCTTGCGC TTAAGGAGCCCCTTCGCCTCGTGCTTGAGTTGAGGCCTGGCCTGGGCGCTGGGGC CGCCGCGTGCGAATCTGGTGGCACCTTCGCGCCTGTCTCGCTGCTTTCGATAAGT CTCTAGCCATTTAAAATTTTTGATGACCTGCTGCGACGCTTTTTTTCTGGCAAGA TAGTCTTGTAAATGCGGGCCAAGATCTGCACACTGGTATTTCGGTTTTTGGGGCC GCGGGCGGCGACGGGGCCCGTGCGTCCCAGCGCACATGTTCGGCGAGGCGGGGCC TGCGAGCGCGGCCACCGAGAATCGGACGGGGGTAGTCTCAAGCTGGCCGGCCTGC TCTGGTGCCTGGCCTCGCGCCGCCGTGTATCGCCCCGCCCTGGGCGGCAAGGCTG GCCCGGTCGGCACCAGTTGCGTGAGCGGAAAGATGGCCGCTTCCCGGCCCTGCTG CAGGGAGCTCAAAATGGAGGACGCGGCGCTCGGGAGAGCGGGCGGGTGAGTCACC CACACAAAGGAAAAGGGCCTTTCCGTCCTCAGCCGTCGCTTCATGTGACTCCACG GAGTACCGGGCGCCGTCCAGGCACCTCGATTAGTTCTCGAGCTTTTGGAGTACGT CGTCTTTAGGTTGGGGGGAGGGGTTTTATGCGATGGAGTTTCCCCACACTGAGTG GGTGGAGACTGAAGTTAGGCCAGCTTGGCACTTGATGTAATTCTCCTTGGAATTT GCCCTTTTTGAGTTTGGATCTTGGTTCATTCTCAAGCCTCAGACAGTGGTTCAAA GTTTTTTTCTTCCATTTCAGGTGTCGTGA | 987 |
| miniEF1a | GCCCGTCAGTGGGCAGAGCGCACATCGCCCACAGTCCCCGAGAAGTTGGGGGGAG GGGTCGGCAATTGAACCGGTGCCTAGAGAAGGTGGCGCGGGTAAACTGGGAAAG TGATGTCGTGTACTGGCTCCGCCTTTTTCCCGAGGGTGGGGGAGAACCGTATATA AGTGCAGTAGTCGCCGTGAACGTTCTTTTTCGCAACGGGTTTGCCGCCAGAACAC GCGTAAG | 988 |

TABLE 8-continued

Exemplary Promoter Variants

| Description | Sequences | SEQ ID NO: |
|---|---|---|
| Promoter Variant 1 | GCATG | |
| Promoter Variant 2 | GGTGGAGAAGAGCATG | 990 |
| Promoter Variant 3 | GTCATCACTGAGGTGGAGAAGAGCATG | 991 |
| Promoter Variant 4 | CGTGAG | |
| Promoter Variant 5 | GT | |
| Promoter Variant 6 | GCTCCGGT | |
| Promoter Variant 19 | GCCCGTCAGTGGGCAGAGCGCACATCGCCCACAGTCCCCGAGAAGTTGGGGGGAG GGGTCGGCAATTGAACCGGTGCCTAGAGAAGGTGGCGCGGGGTAAACTGGGAAAG TGATGTCGTGTACTGGCTCCGCCTTTTTCCCGAGGGTGGGGGAGAACCGTATATA AGTGCAGTAGTCGCCGTGAACGTTCTTTTTCGCAACGGGTTTGCCGCCAGAACAC AG | 995 |
| Promoter Variant 20 | GCCCGTCAGTGGGCAGAGCGCACATCGCCCACAGTCCCCGAGAAGTTGGGGGGAG GGGTCGGCAATTGAACCGGTGCCTAGAGAAGGTGGCGCGGGGTAAACTGGGAAAG TGATGTCGTGTACTGGCTCCGCCTTTTTCCCGAGGGTGGGGGAGAACCGTATATA AGTGCAGTAGTCGCCGTGAACGTTCTTTTTCGCAACGGGTTTGCCGCCAGAACAC GC | 996 |
| Promoter Variant 7 | GTAAG | |
| Promoter Variant 8 | GTGCCCGTCAGTGGGCAGAGCGCACATCGCCCACAGTCCCCGAGAAGTTGGGGGG AGGGGTCGGCAATTGAACCGGTGCCTAGAGAAGGTGGCGCGGGGTAAACTGGGAA AGTGATGTCGTGTACTGGCTCCGCCTTTTTCCCGAGGGTGGGGGAGAACCGTATA TAAGTGCAGTAGTCGCCGTGAACGTTCTTTTTCGCAACGGGTTTGCCGCCAGAAC ACGCGTAAG | 998 |
| Promoter Variant 9 | GCTCCGGTGCCCGTCAGTGGGCAGAGCGCACATCGCCCACAGTCCCCGAGAAGTT GGGGGGAGGGGTCGGCAATTGAACCGGTGCCTAGAGAAGGTGGCGCGGGGTAAAC TGGGAAAGTGATGTCGTGTACTGGCTCCGCCTTTTTCCCGAGGGTGGGGGAGAAC CGTATATAAGTGCAGTAGTCGCCGTGAACGTTCTTTTTCGCAACGGGTTTGCCGC CAGAACACGCGTAAG | 999 |
| Promoter Variant 10 | CGTGAGGCTCCGGTGCCCGTCAGTGGGCAGAGCGCACATCGCCCACAGTCCCCGA GAAGTTGGGGGGAGGGGTCGGCAATTGAACCGGTGCCTAGAGAAGGTGGCGCGGG GTAAACTGGGAAAGTGATGTCGTGTACTGGCTCCGCCTTTTTCCCGAGGGTGGGG GAGAACCGTATATAAGTGCAGTAGTCGCCGTGAACGTTCTTTTTCGCAACGGGTT TGCCGCCAGAACACGCGTAAG | 1000 |
| Promoter Variant 11 | CGTGAGGCTCCGGTGCCCGTCAGTGGGCAGAGCGCACATCGCCCACAGTCCCCGA GAAGTTGGGGGGAGGGGTCGGCAATTGAACCGGTGCCTAGAGAAGGTGGCGCGGG GTAAACTGGGAAAGTGATGTCGTGTACTGGCTCCGCCTTTTTCCCGAGGGTGGGG GAGAACCGTATATAAGTGCAGTAGTCGCCGTGAACGTTCTTTTTCGCAACGGGTT TGCCGCCAGAACACAG | 1001 |
| Promoter Variant 12 | GCATGCGTGAGGCTCCGGTGCCCGTCAGTGGGCAGAGCGCACATCGCCCACAGTC CCCGAGAAGTTGGGGGGAGGGGTCGGCAATTGAACCGGTGCCTAGAGAAGGTGGC GCGGGGTAAACTGGGAAAGTGATGTCGTGTACTGGCTCCGCCTTTTTCCCGAGGG TGGGGGAGAACCGTATATAAGTGCAGTAGTCGCCGTGAACGTTCTTTTTCGCAAC GGGTTTGCCGCCAGAACACGCGTAAG | 1002 |
| Promoter Variant 13 | GCATGCGTGAGGCTCCGGTGCCCGTCAGTGGGCAGAGCGCACATCGCCCACAGTC CCCGAGAAGTTGGGGGGAGGGGTCGGCAATTGAACCGGTGCCTAGAGAAGGTGGC GCGGGGTAAACTGGGAAAGTGATGTCGTGTACTGGCTCCGCCTTTTTCCCGAGGG TGGGGGAGAACCGTATATAAGTGCAGTAGTCGCCGTGAACGTTCTTTTTCGCAAC GGGTTTGCCGCCAGAACACAG | 1003 |
| Promoter Variant 14 | GGTGGAGAAGAGCATGCGTGAGGCTCCGGTGCCCGTCAGTGGGCAGAGCGCACAT CGCCCACAGTCCCCGAGAAGTTGGGGGGAGGGGTCGGCAATTGAACCGGTGCCTA GAGAAGGTGGCGCGGGGTAAACTGGGAAAGTGATGTCGTGTACTGGCTCCGCCTT TTTCCCGAGGGTGGGGGAGAACCGTATATAAGTGCAGTAGTCGCCGTGAACGTTC TTTTTCGCAACGGGTTTGCCGCCAGAACACGCGTAAG | 1004 |

TABLE 8-continued

Exemplary Promoter Variants

| Description | Sequences | SEQ ID NO: |
|---|---|---|
| Promoter Variant 15 | GGTGGAGAAGAGCATGCGTGAGGCTCCGGTGCCCGTCAGTGGGCAGAGCGCACAT CGCCCACAGTCCCCGAGAAGTTGGGGGGAGGGGTCGGCAATTGAACCGGTGCCTA GAGAAGGTGGCGCGGGGTAAACTGGGAAAGTGATGTCGTGTACTGGCTCCGCCTT TTTCCCGAGGGTGGGGGAGAACCGTATATAAGTGCAGTAGTCGCCGTGAACGTTC TTTTTCGCAACGGGTTTGCCGCCAGAACACAG | 1005 |
| Promoter Variant 16 | GTCATCACTGAGGTGGAGAAGAGCATGCGTGAGGCTCCGGTGCCCGTCAGTGGGC AGAGCGCACATCGCCCACAGTCCCCGAGAAGITGGGGGGAGGGGTCGGCAATTGA ACCGGTGCCTAGAGAAGGTGGCGCGGGGTAAACTGGGAAAGTGATGTCGTGTACT GGCTCCGCCTTTTTCCCGAGGGTGGGGGAGAACCGTATATAAGTGCAGTAGTCGC CGTGAACGTTCTTTTTCGCAACGGGTTTGCCGCCAGAACACGCGTAAG | 1006 |
| Promoter Variant 18 | GTCATCACTGAGGTGGAGAAGAGCATGCGTGAGGCTCCGGTGCCCGTCAGTGGGC AGAGCGCACATCGCCCACAGTCCCCGAGAAGTTGGGGGGAGGGGTCGGCAATTGA ACCGGTGCCTAGAGAAGGTGGCGCGGGGTAAACTGGGAAAGTGATGTCGTGTACT GGCTCCGCCTTTTTCCCGAGGGTGGGGGAGAACCGTATATAAGTGCAGTAGTCGC CGTGAACGTTCTTTTTCGCAACGGGTTTGCCGCCAGAACACAG | 1007 |

Viral Genome Component: Untranslated Regions (UTRs)

In some embodiments, wild type untranslated regions (UTRs) of a gene are transcribed but not translated. Generally, the 5' UTR starts at the transcription start site and ends at the start codon and the 3' UTR starts immediately following the stop codon and continues until the termination signal for transcription.

Features typically found in abundantly expressed genes of specific target organs (e.g., CNS tissue, muscle, or DRG) may be engineered into UTRs to enhance stability and protein production. As a non-limiting example, a 5' UTR from mRNA normally expressed in the brain (e.g., huntingtin) may be used in the viral genomes of the AAV particles described herein to enhance expression in neuronal cells or other cells of the central nervous system.

While not wishing to be bound by theory, wild-type 5' untranslated regions (UTRs) include features which play roles in translation initiation. Kozak sequences, which are commonly known to be involved in the process by which the ribosome initiates translation of many genes, are usually included in 5' UTRs. Kozak sequences have the consensus CCR(A/G)CCAUGG, where R is a purine (adenine or guanine) three bases upstream of the start codon (ATG), which is followed by another 'G'.

In one embodiment, the 5'UTR in the viral genome includes a Kozak sequence.

In one embodiment, the 5'UTR in the viral genome does not include a Kozak sequence.

While not wishing to be bound by theory, wild-type 3' UTRs are known to have stretches of Adenosines and Uridines embedded therein. These AU rich signatures are particularly prevalent in genes with high rates of turnover. Based on their sequence features and functional properties, the AU rich elements (AREs) can be separated into three classes (Chen et al, 1995, the contents of which are herein incorporated by reference in its entirety): Class I AREs, such as, but not limited to, c-Myc and MyoD, contain several dispersed copies of an AUUUA motif within U-rich regions. Class II AREs, such as, but not limited to, GM-CSF and TNF-a, possess two or more overlapping UUAUUUA(U/A)(U/A) nonamers. Class III ARES, such as, but not limited to, c-Jun and Myogenin, are less well defined. These U rich regions do not contain an AUUUA motif Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of a polynucleotide. When engineering specific polynucleotides, e.g., payload regions of viral genomes, one or more copies of an ARE can be introduced to make polynucleotides less stable and thereby curtail translation and decrease production of the resultant protein. Likewise, AREs can be identified and removed or mutated to increase the intracellular stability and thus increase translation and production of the resultant protein.

In one embodiment, the 3' UTR of the viral genome may include an oligo(dT) sequence for templated addition of a poly-A tail.

In one embodiment, the viral genome may include at least one miRNA seed, binding site or full sequence. microRNAs (or miRNA or miR) are 19-25 nucleotide noncoding RNAs that bind to the sites of nucleic acid targets and downregulate gene expression either by reducing nucleic acid molecule stability or by inhibiting translation. In some embodiments, a microRNA sequence comprises a seed region, e.g., a sequence in the region of positions 2-8 of the mature microRNA, which has Watson-Crick sequence fully or partially complementarity to the miRNA target sequence of the nucleic acid.

In one embodiment, the viral genome may be engineered to include, alter or remove at least one miRNA binding site, full sequence or seed region.

Any UTR from any gene known in the art may be incorporated into the viral genome of the AAV particle. These UTRs, or portions thereof, may be placed in the same orientation as in the gene from which they were selected or they may be altered in orientation or location. In one embodiment, the UTR used in the viral genome of the AAV particle may be inverted, shortened, lengthened, made with one or more other 5' UTRs or 3' UTRs known in the art. As used herein, the term "altered" as it relates to a UTR, means that the UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides.

In one embodiment, the viral genome of the AAV particle comprises at least one artificial UTR which is not a variant of a wild type UTR.

In one embodiment, the viral genome of the AAV particle comprises UTRs which have been selected from a family of transcripts whose proteins share a common function, structure, feature or property.

Viral Genome Component: Polyadenylation Sequence

The viral genome of the AAV particle described herein (e.g., an AAV particle comprising an AAV capsid variant, described herein) may comprise a polyadenylation sequence. In some embodiments, the viral genome of the AAV particle (e.g., an AAV particle comprising an AAV capsid variant, described herein) comprises a polyadenylation sequence between the 3' end of the nucleotide sequence encoding the payload and the 5' end of the 3'ITR.

Viral Genome Component: Introns

In some embodiments, the viral genome of the AAV particle as described herein (e.g., an AAV particle comprising an AAV capsid variant), comprises an element to enhance the payload target specificity and expression (See e.g., Powell et al. *Viral Expression Cassette Elements to Enhance Transgene Target Specificity and Expression in Gene Therapy*, Discov. Med, 2015, 19(102): 49-57; the contents of which are herein incorporated by reference in their entirety), such as an intron. Non-limiting examples of introns include, MVM (67-97 bps), FIX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

Viral Genome Component: Stuffer Sequences

In some embodiments, the viral genome of an AAV particle described herein (e.g., an AAV particle comprising an AAV capsid polypeptide, e.g., an AAV capsid variant), comprises an element to improve packaging efficiency and expression, such as a stuffer or filler sequence. Non-limiting examples of stuffer sequences include albumin and/or alpha-1 antitrypsin. Any known viral, mammalian, or plant sequence may be manipulated for use as a stuffer sequence.

In one embodiment, the stuffer or filler sequence may be from about 100-3500 nucleotides in length. The stuffer sequence may have a length of about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900 or 3000 nucleotides.

Viral Genome Component: miRNA

In one embodiment, the viral genome comprises a sequence encoding a miRNA to reduce the expression of the payload in a tissue or cell, e.g., the DRG (dorsal root ganglion), or neurons of other ganglia, such as those of the sympathetic or parasympathetic nervous system. In some embodiments, a miRNA, e.g., a miR183, a miR182, and/or miR96, may be encoded in the viral genome to modulate, e.g., reduce the expression, of the viral genome in a DRG neuron. As another non-limiting example, a miR-122 miRNA may be encoded in the viral genome to modulate, e.g., reduce, the expression of the viral genome in the liver. In some embodiments, a miRNA, e.g., a miR-142-3p, may be encoded in the viral genome to modulate, e.g., reduce, the expression, of the viral genome in a cell or tissue of the hematopoietic lineage, including for example immune cells (e.g., antigen presenting cells or APC, including dendritic cells (DCs), macrophages, and B-lymphocytes). In some embodiments, a miRNA, e.g., a miR-1, may be encoded in the viral genome to modulate, e.g., reduce, the expression, of the viral genome in a cell or tissue of the heart.

Viral Genome Component: miR Binding Site

Tissue- or cell-specific expression of the AAV viral particles disclosed herein can be enhanced by introducing tissue- or cell-specific regulatory sequences, e.g., promoters, enhancers, microRNA binding sites, e.g., a detargeting site. Without wishing to be bound by theory, it is believed that an encoded miR binding site can modulate, e.g., prevent, suppress, or otherwise inhibit, the expression of a gene of interest on the viral genome disclosed herein, based on the expression of the corresponding endogenous microRNA (miRNA) or a corresponding controlled exogenous miRNA in a tissue or cell, e.g., a non-targeting cell or tissue. In some embodiments, a miR binding site modulates, e.g., reduces, expression of the payload encoded by a viral genome of an AAV particle described herein in a cell or tissue where the corresponding mRNA is expressed.

In some embodiments, the viral genome of an AAV particle described herein comprises a nucleotide sequence encoding a microRNA binding site, e.g., a detargeting site. In some embodiments, the viral genome of an AAV particle described herein comprises a nucleotide sequence encoding a miR binding site, a microRNA binding site series (miR BSs), or a reverse complement thereof.

In some embodiments, the nucleotide sequence encoding the miR binding site series or the miR binding site is located in the 3'-UTR region of the viral genome (e.g., 3' relative to the nucleotide sequence encoding a payload), e.g., before the polyA sequence, 5'-UTR region of the viral genome (e.g., 5' relative to the nucleotide sequence encoding a payload), or both.

In some embodiments, the encoded miR binding site series comprise at least 1-5 copies, e.g., at least 1-3, 2-4, 3-5, 1, 2, 3, 4, 5 or more copies of a miR binding site (miR BS). In some embodiments, all copies are identical, e.g., comprise the same miR binding site. In some embodiments, the miR binding sites within the encoded miR binding site series are continuous and not separated by a spacer. In some embodiments, the miR binding sites within an encoded miR binding site series are separated by a spacer, e.g., a non-coding sequence. In some embodiments, the spacer is about 1 to 6 nucleotides or about 5 to 10 nucleotides, e.g., about 7-8 nucleotides, nucleotides in length. In some embodiments, the spacer coding sequence or reverse complement thereof comprises one or more of (i) GGAT; (ii) CACGTG; (iii) GCATGC, or a repeat of one or more of (i)-(iii). In some embodiments, the spacer comprises the nucleotide sequence of GATAGTTA, or a nucleotide sequence having at least one, two, or three modifications, e.g., substitutions (e.g., conservative substitutions), insertions, or deletions, but no more than four modifications, e.g., substitutions (e.g., conservative substitutions), insertions, or deletions relative to the nucleotide sequence of GATAGTTA.

In some embodiments, the encoded miR binding site series comprise at least 1-5 copies, e.g., at least 1-3, 2-4, 3-5, 1, 2, 3, 4, 5 or more copies of a miR binding site (miR BS). In some embodiments, at least 1, 2, 3, 4, 5, or all of the copies are different, e.g., comprise a different miR binding site. In some embodiments, the miR binding sites within the encoded miR binding site series are continuous and not separated by a spacer. In some embodiments, the miR binding sites within an encoded miR binding site series are separated by a spacer, e.g., a non-coding sequence. In some embodiments, the spacer is about 1 to 6 nucleotides or about 5 to 10 nucleotides, e.g., about 7-8 nucleotides, in length. In some embodiments, the spacer comprises one or more of (i) GGAT; (ii) CACGTG; (iii) GCATGC, or a repeat of one or more of (i)-(iii). In some embodiments, the spacer comprises the nucleotide sequence of GATAGTTA, or a nucleotide sequence having at least one, two, or three modifications, e.g., substitutions (e.g., conservative substitutions), insertions, but no more than four modifications, e.g., substitutions (e.g., conservative substitutions), insertions, or deletions relative to the nucleotide sequence of GATAGTTA.

In some embodiments, the encoded miR binding site is substantially identical (e.g., at least 70%, 75%, 80%, 85%, 90%, 95%, 99% or 100% identical), to the miR in the host cell. In some embodiments, the encoded miR binding site comprises at least 1, 2, 3, 4, or 5 mismatches or no more than 6, 7, 8, 9, or 10 mismatches to a miR in the host cell. In some embodiments, the mismatched nucleotides are contiguous. In some embodiments, the mismatched nucleotides are non-contiguous. In some embodiments, the mismatched nucleotides occur outside the seed region-binding sequence of the miR binding site, such as at one or both ends of the miR binding site. In some embodiments, the miR binding site is 100% identical to the miR in the host cell.

In some embodiments, the nucleotide sequence encoding the miR binding site is substantially complementary (e.g., at least 70%, 75%, 80%, 85%, 90%, 95%, 99% or 100% complementary), to the miR in the host cell. In some embodiments, to complementary sequence of the nucleotide sequence encoding the miR binding site comprises at least 1, 2, 3, 4, or 5 mismatches or no more than 6, 7, 8, 9, or 10 mismatches to a miR in the host cell. In some embodiments, the mismatched nucleotides are contiguous. In some embodiments, the mismatched nucleotides are non-contiguous. In some embodiments, the mismatched nucleotides occur outside the seed region-binding sequence of the miR binding site, such as at one or both ends of the miR binding site. In some embodiments, the encoded miR binding site is 100% complementary to the miR in the host cell.

In some embodiments, an encoded miR binding site or sequence region is at least about 10 to about 125 nucleotides in length, e.g., at least about 10 to 50 nucleotides, 10 to 100 nucleotides, 50 to 100 nucleotides, 50 to 125 nucleotides, or 100 to 125 nucleotides in length. In some embodiments, an encoded miR binding site or sequence region is at least about 7 to about 28 nucleotides in length, e.g., at least about 8-28 nucleotides, 7-28 nucleotides, 8-18 nucleotides, 12-28 nucleotides, 20-26 nucleotides, 22 nucleotides, 24 nucleotides, or 26 nucleotides in length, and optionally comprises at least one consecutive region (e.g., 7 or 8 nucleotides) complementary (e.g., fully or partially complementary) to the seed sequence of a miRNA (e.g., a miR122, a miR142, a miR183, or a miR1).

In some embodiments, the encoded miR binding site is complementary (e.g., fully or partially complementary) to a miR expressed in liver or hepatocytes, such as miR122. In some embodiments, the encoded miR binding site or encoded miR binding site series comprises a miR122 binding site sequence. In some embodiments, the encoded miR122 binding site comprises the nucleotide sequence of ACAAACACCATTGTCACACACTCCA (SEQ ID NO: 4673), or a nucleotide sequence having at least 50%, 55%, 60%, 65%, 70%, 75%, 80%, 85%, 90%, at least 95%, at least 99%, or 100% sequence identity, or having at least one, two, three, four, five, six, or seven modifications, e.g., substitutions (e.g., conservative substitutions), insertions, or deletions, but no more than ten modifications, e.g., insertions, deletions, or substitutions (e.g., conservative substitutions), relative to the nucleotide sequence of SEQ ID NO: 4673, e.g., wherein the modification can result in a mismatch between the encoded miR binding site and the corresponding miRNA. In some embodiments, the viral genome comprises at least 2, 3, 4, or 5 copies of the encoded miR122 binding site, e.g., an encoded miR122 binding site series, optionally wherein the encoded miR122 binding site series comprises the nucleotide sequence of:

(SEQ ID NO: 4674)
ACAAACACCATTGTCACACTCCACACAAACACCATTGTCACACTCCACA
CAAACACCATTGTCACACTCCA, or a nucleotide sequence having at least 50%, 55%, 60%, 65%, 70%, 75%, 80%, 85%, 90%, at least 95%, at least 99%, or 100% sequence identity, or having at least one, two, three, four, five, six, or seven modifications, e.g., substitutions (e.g., conservative substitutions), insertions, or deletions, but no more than ten modifications, e.g., substitutions (e.g., conservative substitutions), insertions, or deletions, relative to the nucleotide sequence of SEQ ID NO: 4674, e.g., wherein the modification can result in a mismatch between the encoded miR binding site and the corresponding miRNA. In some embodiments, at least two of the encoded miR122 binding sites are connected directly, e.g., without a spacer. In other embodiments, at least two of the encoded miR122 binding sites are separated by a spacer, e.g., 1, 2, 3, 4, 5, 6, 7, 8, 9, or 10 nucleotides in length, which is located between two or more consecutive encoded miR122 binding site sequences. In embodiments, the spacer is about 1 to 6 nucleotides or about 5 to 10 nucleotides, e.g., about 7-8, in length. In some embodiments, the spacer coding sequence or reverse complement thereof comprises one or more of (i) GGAT; (ii) CACGTG; (iii) GCATGC, or a repeat of one or more of (i)-(iii). In some embodiments, an encoded miR binding site series comprises at least 3-5 copies (e.g., 4 copies) of a miR122 binding site, with or without a spacer, wherein the spacer is about 1 to 6 nucleotides or about 5 to 10 nucleotides, e.g., about 7-8 nucleotides or about 8 nucleotides, in length. In some embodiments, the spacer comprises the nucleotide sequence of GATAGTTA, or a nucleotide sequence having at least one, two, or three modifications, e.g., substitutions (e.g., conservative substitutions), insertions, or deletions, but no more than four modifications, e.g., substitutions (e.g., conservative substitutions), insertions, or deletions relative to the nucleotide sequence of GATAGTTA.

In some embodiments, the encoded miR binding site is complementary (e.g., fully or partially complementary) to a miR expressed in the heart. In embodiments, the encoded miR binding site or encoded miR binding site series comprises a miR-1 binding site. In some embodiments, the encoded miR-1 binding site comprises the nucleotide sequence of ATACATACTTCTTTACATTCCA (SEQ ID NO: 4679), a nucleotide sequence having at least 50%, 55%, 60%, 65%, 70%, 75%, 80%, 85%, 90%, at least 95%, at least 99%, or 100% sequence identity, or having at least one, two, three, four, five, six, or seven modifications, e.g., substitutions (e.g., conservative substitutions), insertions, or deletions, but no more than ten modifications, e.g., substitutions (e.g., conservative substitutions), insertions, or deletions, relative to the nucleotide sequence of SEQ ID NO: 4679, e.g., wherein the modification can result in a mismatch between the encoded miR binding site and the corresponding miRNA. In some embodiments, the viral genome comprises at least 2, 3, 4, or 5 copies of the encoded miR-1 binding site, e.g., an encoded miR-1 binding site series. In some embodiments, the at least 2, 3, 4, or 5 copies (e.g., 2 or 3 copies) of the encoded miR-1 binding site are continuous (e.g., not separated by a spacer) or separated by a spacer. In some embodiments, the spacer is about 1 to 6 nucleotides or about 5 to 10 nucleotides, e.g., about 7-8 nucleotides or about 8 nucleotides, in length. In some embodiments, the spacer sequence comprises one or more of (i) GGAT; (ii) CACGTG; (iii) GCATGC, or a repeat of one or more of (i)-(iii). In some embodiments, the spacer comprises the nucleotide sequence of GATAGTTA, or a nucleotide sequence having at least one, two, or three modifications, e.g., substitutions (e.g., conservative substitutions), insertions, or deletions, but no more than four modifications, e.g., substitutions (e.g., conservative substitutions), insertions, or deletions, relative to the nucleotide sequence of GATAGTTA.

In some embodiments, the encoded miR binding site is complementary (e.g., fully or partially complementary) to a miR expressed in hematopoietic lineage, including immune cells (e.g., antigen presenting cells or APC, including dendritic cells (DCs), macrophages, and B-lymphocytes). In some embodiments, the encoded miR binding site complementary to a miR expressed in hematopoietic lineage comprises a nucleotide sequence disclosed, e.g., in US 2018/0066279, the contents of which are incorporated by reference herein in its entirety.

In embodiments, the encoded miR binding site or encoded miR binding site series comprises a miR-142-3p binding site sequence. In some embodiments, the encoded miR-142-3p binding site comprises the nucleotide sequence of TCCATAAAGTAGGAAACACTACA (SEQ ID NO: 4675), a nucleotide sequence having at least 50%, 55%, 60%, 65%, 70%, 75%, 80%, 85%, 90%, at least 95%, at least 99%, or 100% sequence identity, or having at least one, two, three, four, five, six, or seven modifications, e.g., substitutions (e.g., conservative substitutions), insertions, or deletions, but no more than ten modifications, e.g., substitutions (e.g., conservative substitutions), insertions, or deletions, relative to the nucleotide sequence of SEQ ID NO: 4675, e.g., wherein the modification can result in a mismatch between the encoded miR binding site and the corresponding miRNA. In some embodiments, the viral genome comprises at least 2, 3, 4, or 5 copies of the encoded miR-142-3p binding site, e.g., an encoded miR-142-3p binding site series. In some embodiments, the at least 2, 3, 4, or 5 copies (e.g., 2 or 3 copies) of the encoded miR-142-3p binding site are continuous (e.g., not separated by a spacer) or separated by a spacer. In some embodiments, the spacer is about 1 to 6 nucleotides or about 5 to 10 nucleotides, e.g., about 7-8 nucleotides or about 8 nucleotides, in length. In some embodiments, the spacer sequence comprises one or more of (i) GGAT; (ii) CACGTG; (iii) GCATGC, or a repeat of one or more of (i)-(iii). In some embodiments, the spacer comprises the nucleotide sequence of GATAGTTA, or a nucleotide sequence having at least one, two, or three modifications, e.g., substitutions (e.g., conservative substitutions), insertions, or deletions, but no more than four modifications, e.g., substitutions (e.g., conservative substitutions), insertions, or deletions, relative to the nucleotide sequence of GATAGTTA.

In some embodiments, the encoded miR binding site is complementary (e.g., fully complementary or partially complementary) to a miR expressed in a DRG (dorsal root ganglion) neuron, e.g., a miR183, a miR182, and/or miR96 binding site. In some embodiments, the encoded miR binding site is complementary to a miR expressed in expressed in a DRG neuron comprises a nucleotide sequence disclosed, e.g., in WO2020/132455, the contents of which are incorporated by reference herein in its entirety.

In some embodiments, the encoded miR binding site or encoded miR binding site series comprises a miR183 binding site sequence. In some embodiments, the encoded miR183 binding site comprises the nucleotide sequence of AGTGAATTCTACCA<u>GTGCCAT</u>A (SEQ ID NO: 4676), or a nucleotide sequence having at least 50%, 55%, 60%, 65%, 70%, 75%, 80%, 85%, 90%, at least 95%, at least 99%, or 100% sequence identity, or having at least one, two, three, four, five, six, or seven modifications, e.g., substitutions (e.g., conservative substitutions), insertions, or deletions, but no more than ten modifications, e.g., substitutions (e.g., conservative substitutions), insertions, or deletions, relative to the nucleotide sequence of SEQ ID NO: 4676, e.g., wherein the modification can result in a mismatch between the encoded miR binding site and the corresponding miRNA. In some embodiments, the sequence complementary to the seed sequence corresponds to the double underlined of the encoded miR-183 binding site sequence. In some embodiments, the viral genome comprises at least comprises at least 2, 3, 4, or 5 copies (e.g., at least 2 or 3 copies) of the encoded miR183 binding site, e.g., an encoded miR183 binding site. In some embodiments, the at least 2, 3, 4, or 5 copies (e.g., 2 or 3 copies) of the encoded miR183 binding site are continuous (e.g., not separated by a spacer) or separated by a spacer. In some embodiments, the spacer is about 1 to 6 nucleotides or about 5 to 10 nucleotides, e.g., about 7-8 nucleotides or about 8 nucleotides, in length. In some embodiments, the spacer comprises the nucleotide sequence of GATAGTTA, or a nucleotide sequence having at least one, two, or three modifications, e.g., substitutions (e.g., conservative substitutions), insertions, or deletions, but no more than four modifications, e.g., substitutions (e.g., conservative substitutions), insertions, or deletions, relative to the nucleotide sequence of GATAGTTA. In some embodiments, the spacer sequence comprises one or more of (i) GGAT; (ii) CACGTG; (iii) GCATGC, or a repeat of one or more of (i)-(iii).

In some embodiments, the encoded miR binding site or the encoded miR binding site series comprises a miR182 binding site sequence. In some embodiments, the encoded miR182 binding site comprises, the nucleotide sequence of AGTGTGAGTTCTACCATTGCCAAA (SEQ ID NO: 4677), a sequence having at least 50%, 55%, 60%, 65%, 70%, 75%, 80%, 85%, 90%, at least 95%, at least 99%, or 100% sequence identity, or having at least one, two, three, four, five, six, or seven modifications, e.g., substitutions (e.g., conservative substitutions), insertions, or deletions, but no more than ten modifications, e.g., substitutions (e.g., conservative substitutions), insertions, or deletions, relative to the nucleotide sequence of SEQ ID NO: 4677, e.g., wherein the modification can result in a mismatch between the encoded miR binding site and the corresponding miRNA. In some embodiments, the viral genome comprises at least 2, 3, 4, or 5 copies of the encoded miR182 binding site, e.g., an encoded miR182 binding site series. In some embodiments, the at least 2, 3, 4, or 5 copies (e.g., 2 or 3 copies) of the encoded miR182 binding site are continuous (e.g., not separated by a spacer) or separated by a spacer. In some embodiments, the spacer is about 1 to 6 nucleotides or about 5 to 10 nucleotides, e.g., about 7-8 nucleotides or about 8 nucleotides, in length. In some embodiments, the spacer comprises the nucleotide sequence of GATAGTTA, or a nucleotide sequence having at least one, two, or three modifications, e.g., substitutions (e.g., conservative substitutions), insertions, or deletions, but no more than four modifications, e.g., substitutions (e.g., conservative substitutions), insertions, or deletions, relative to the nucleotide sequence of GATAGTTA. In some embodiments, the spacer sequence comprises one or more of (i) GGAT; (ii) CACGTG; (iii) GCATGC, or a repeat of one or more of (i)-(iii).

In certain embodiments, the encoded miR binding site or the encoded miR binding site series comprises a miR96 binding site sequence. In some embodiments, the encoded miR96 binding site comprises the nucleotide sequence of AGCAAAAATGTGCTAGTGCCAAA (SEQ ID NO: 4678), a sequence having at least 50%, 55%, 60%, 65%, 70%, 75%, 80%, 85%, 90%, at least 95%, at least 99%, or 100% sequence identity, or having at least one, two, three, four, five, six, or seven modifications, e.g., substitutions (e.g., conservative substitutions), insertions, or deletions, but no more than ten modifications, e.g., substitutions (e.g., conservative substitutions), insertions, or deletions, relative to the nucleotide sequence of SEQ ID NO: 4678, e.g., wherein the modification can result in a mismatch between the encoded miR binding site and the corresponding miRNA. In some embodiments, the viral genome comprises at least 2, 3, 4, or 5 copies of the encoded miR96 binding site, e.g., an encoded miR96 binding site series. In some embodiments, the at least 2, 3, 4, or 5 copies (e.g., 2 or 3 copies) of the encoded miR96 binding site are continuous (e.g., not separated by a spacer) or separated by a spacer. In some embodiments, the spacer is about 1 to 6 nucleotides or about 5 to 10 nucleotides, e.g., about 7-8 nucleotides or about 8 nucleotides, in length. In some embodiments, the spacer comprises the nucleotide sequence of GATAGTTA, or a nucleotide sequence having at least one, two, or three modifications, e.g., substitutions (e.g., conservative substitutions), insertions, or deletions, but no more than four modifications, e.g., substitutions (e.g., conservative substitutions), insertions, or deletions, relative to the nucleotide sequence of GATAGTTA. In some embodiments, the spacer sequence comprises one or more of (i) GGAT; (ii) CACGTG; (iii) GCATGC, or a repeat of one or more of (i)-(iii).

In some embodiments, the encoded miR binding site series comprises a miR122 binding site, a miR-1, a miR142 binding site, a miR183 binding site, a miR182 binding site, a miR 96 binding site, or a combination thereof. In some embodiments, the encoded miR binding site series comprises at least 2, 3, 4, or 5 copies of a miR122 binding site, a miR142 binding site, a miR183 binding site, a miR182 binding site, a miR 96 binding site, or a combination thereof. In some embodiments, at least two of the encoded miR binding sites are connected directly, e.g., without a spacer. In other embodiments, at least two of the encoded miR binding sites are separated by a spacer, e.g., 1, 2, 3, 4, 5, 6, 7, 8, 9, or 10 nucleotides in length, which is located between two or more consecutive encoded miR binding site sequences. In embodiments, the spacer is at least about 5 to 10 nucleotides, e.g., about 7-8 nucleotides or about 8 nucleotides, in length. In some embodiments, the spacer coding sequence or reverse complement thereof comprises one or more of (i) GGAT; (ii) CACGTG; (iii) GCATGC, or a repeat of one or more of (i)-(iii). In some embodiments, the spacer comprises the nucleotide sequence of GATAGTTA, or a nucleotide sequence having at least one, two, or three modifications, e.g., substitutions (e.g., conservative substitutions), insertions, or deletions, but no more than four modifications, e.g., substitutions (e.g., conservative substitutions), insertions, or deletions, relative to the nucleotide sequence of GATAGTTA.

In some embodiments, an encoded miR binding site series comprises at least 2-5 copies (e.g., 2 or 3 copies) of a combination of at least two, three, four, five, or all of a miR-1, miR122 binding site, a miR142 binding site, a miR183 binding site, a miR182 binding site, a miR96 binding site, wherein each of the miR binding sites within the series are continuous (e.g., not separated by a spacer) or are separated by a spacer. In some embodiments, the spacer is about 1 to 6 nucleotides or about 5 to 10 nucleotides, e.g., about 7-8 nucleotides or about 8 nucleotides, in length. In some embodiments, the spacer sequence comprises one or more of (i) GGAT; (ii) CACGTG; (iii) GCATGC, or a repeat of one or more of (i)-(iii). In some embodiments, the spacer comprises the nucleotide sequence of GATAGTTA, or a nucleotide sequence having at least one, two, or three modifications, e.g., substitutions (e.g., conservative substitutions), insertions, or deletions, but no more than four modifications, e.g., substitutions (e.g., conservative substitutions), insertions, or deletions, relative to the nucleotide sequence of GATAGTTA.

In some embodiments, an encoded miR binding site series comprises at least 2-5 copies (e.g., 2 or 3 copies) of a combination of a miR-122 binding site and a miR-1 binding site, wherein each of the miR binding sites within the series are continuous (e.g., not separated by a spacer) or are separated by a spacer. In some embodiments, the spacer is about 1 to 6 nucleotides or about 5 to 10 nucleotides, e.g., about 7-8 nucleotides or about 8 nucleotides, in length. In some embodiments, the spacer sequence comprises one or more of (i) GGAT; (ii) CACGTG; (iii) GCATGC, or a repeat of one or more of (i)-(iii). In some embodiments, the spacer comprises the nucleotide sequence of GATAGTTA, or a nucleotide sequence having at least one, two, or three modifications, e.g., substitutions (e.g., conservative substitutions), insertions, or deletions, but no more than four modifications, e.g., substitutions (e.g., conservative substitutions), insertions, or deletions, relative to the nucleotide sequence of GATAGTTA.

Genome Size

In one embodiment, the AAV particle described herein (e.g., an AAV particle comprising an AAV capsid variant), may comprise a single-stranded or double-stranded viral genome. The size of the viral genome may be small, medium, large or the maximum size. As described above, the viral genome may comprise a promoter and a polyA tail.

In one embodiment, the viral genome may be a small single stranded viral genome. A small single stranded viral genome may be 2.1 to 3.5 kb in size such as, but not limited to, about 2.1, 2.2, 2.3, 2.4, 2.5, 2.6, 2.7, 2.8, 2.9, 3.0, 3.1, 3.2, 3.3, 3.4, and 3.5 kb in size.

In one embodiment, the viral genome may be a small double stranded viral genome. A small double stranded viral genome may be 1.3 to 1.7 kb in size such as, but not limited to, about 1.3, 1.4, 1.5, 1.6, and 1.7 kb in size.

In one embodiment, the viral genome may be a medium single stranded viral genome. A medium single stranded viral genome may be 3.6 to 4.3 kb in size such as, but not limited to, about 3.6, 3.7, 3.8, 3.9, 4.0, 4.1, 4.2 and 4.3 kb in size.

In one embodiment, the viral genome may be a medium double stranded viral genome. A medium double stranded viral genome may be 1.8 to 2.1 kb in size such as, but not limited to, about 1.8, 1.9, 2.0, and 2.1 kb in size.

In one embodiment, the viral genome may be a large single stranded viral genome. A large single stranded viral genome may be 4.4 to 6.0 kb in size such as, but not limited to, about 4.4, 4.5, 4.6, 4.7, 4.8, 4.9, 5.0, 5.1, 5.2, 5.3, 5.4, 5.5, 5.6, 5.7, 5.8, 5.9 and 6.0 kb in size.

In one embodiment, the viral genome may be a large double stranded viral genome. A large double stranded viral genome may be 2.2 to 3.0 kb in size such as, but not limited to, about 2.2, 2.3, 2.4, 2.5, 2.6, 2.7, 2.8, 2.9 and 3.0 kb in size.

Payloads

In some embodiments, an AAV particle of the present disclosure (e.g. an AAV particle comprising an AAV capsid variant described herein) comprises a viral genome comprising a nucleic acid encoding a payload. In some embodiments, the encoded payload is an RNAi agent or a polypeptide. A payload of the present disclosure may be, but is not limited to, a peptide, a polypeptide, a protein, an antibody, an RNAi agent, etc.

In some embodiments, the nucleotide sequence encoding a payload may comprise a combination of coding and non-coding nucleic acid sequences. In some embodiments, the nucleotide sequence encoding the payload may encode a coding or non-coding RNA.

In some embodiments, the AAV particles described herein, e.g., an AAV particle comprising an AAV capsid variant, comprises a nucleic acid encoding a payload. In some embodiments, the encoded payload comprises a therapeutic protein, an antibody, an enzyme, one or more components of a genome editing system, and/or an RNAi agent (e.g., a dsRNA, siRNA, shRNA, pre-miRNA, pri-miRNA, miRNA, stRNA, lncRNA, piRNA, or snoRNA). In some embodiments, the encoded payload modulates, e.g., increases or decreases, the presence, level, and/or activity of a gene, mRNA, protein, or a combination thereof, e.g., in a cell or a tissue.

Polypeptides

In some embodiments, the encoded payload of AAV particle comprising an AAV capsid polypeptide, e.g., an AAV capsid variant, described herein comprises a polypeptide, protein, or peptide, e.g., a polypeptide, protein, or peptide described herein. The nucleic acid encoding the payload, may encode a product of any known gene and/or a recombinant version thereof. In some embodiments, the nucleic acid encoding the payload may encode at least one allele of apolipoprotein E (APOE) such as, but not limited to ApoE2, ApoE3 and/or ApoE4. In one embodiment, the nucleic acid encoding the payload encodes ApoE2 (cys112, cys158) protein or a fragment or variant thereof. In one embodiment, the nucleic acid encoding the payload encodes an ApoE3 (cys112, arg158) protein or fragment or variant thereof. In one embodiment, the nucleic acid encoding the payload encodes ApoE4 (arg112, arg158). As another non-limiting example, the encoded payload comprises an aromatic L-amin acid decarboxylase (AADC) protein. As another non-limiting example, the encoded payload comprises an antibody, or a fragment thereof. As another non-limiting example, the encoded payload comprises a human survival of motor neuron (SMN) 1 or SMN2 protein, or fragments or variants thereof. As another non-limiting example, the encoded payload region comprises a glucocerebrosidase (GBA1) protein, or a fragment or variant thereof. As another non-limiting example, the encoded payload comprises a granulin precursor or progranulin (GRN) protein, or a fragment or variant thereof. As another non-limiting example, the encoded payload comprises an aspartoacylase (ASPA) protein, or a fragment or variant thereof. As another non-limiting example, the encoded payload comprises a tripeptidyl peptidase I (CLN2) protein, or a fragment or variant thereof. As another non-limiting example, the encoded payload comprises a beta-galactosidase (GLB1) protein, or a fragment or variant thereof. As another non-limiting example, the encoded payload comprises a N-sulphoglucosamine sulphohydrolase (SGSH) protein, or a fragment or variant thereof. As another non-limiting example, the encoded payload comprises an N-acetyl-alpha-glucosaminidase (NAGLU) protein, or a fragment or variant thereof. As another non-limiting example, the encoded payload comprises a iduronate 2-sulfatase (IDS) protein, or a fragment or variant thereof. As another non-limiting example, the encoded payload comprises an intracellular cholesterol transporter (NPC1) protein, or a fragment or variant thereof. As another non-limiting example, the encoded payload comprises a gigaxonin (GAN) protein, or a fragment or variant thereof. The AAV viral genomes encoding polypeptides described herein may be useful in the fields of human disease, viruses, infections veterinary applications and a variety of in vivo and in vitro settings.

Amino acid sequences of a payload polypeptide encoded by a viral genome described herein, may be translated as a whole polypeptide, a plurality of polypeptides or fragments of polypeptides, which independently may be encoded by one or more nucleic acids, fragments of nucleic acids or variants of any of the aforementioned.

Antibodies and Antibody Binding Fragments

In some embodiments, the encoded payload of AAV particle comprising an AAV capsid variant described herein comprises an antibody or antibody binding fragment. In some embodiments, the antibody may be a full antibody, a fragment, or any functional variant thereof. As non-limiting examples, an antibody may be a native antibody (e.g., with two heavy and two light chains), a heavy chain variable region, a light chain variable region, a heavy chain constant region, a light chain constant region, Fab, Fab', F(ab')$_2$, Fv, or scFv fragments, a diabody, a linear antibody, a single-chain antibody, a multi-specific antibody, an intrabody, one or more heavy chain complementarity determining regions (CDR), one or more light chain CDRs, a bi-specific antibody, a monoclonal antibody, a polyclonal antibody, a humanized antibody, an antibody mimetic, an antibody variant, a miniaturized antibody, a unibody, a maxibody, and/or a chimeric antigen receptor. The encoded antibody or antibody binding fragment may be useful in the treatment of a neurological disease, a neurodegenerative disorder, a muscular disease, a neuromuscular disorder, a neuro-oncological disorder, or any disorder associated with the central and/or peripheral nervous systems.

In some embodiments, the viral genome of the AAV particle (e.g., an AAV particle comprising an AAV capsid variant described herein) may comprise a nucleic acid which has been engineered to enable or enhance the expression of an antibody, or antibody binding fragment thereof.

In some embodiments, the encoded antibody of the payload of an AAV particle comprising an AAV capsid variant, described herein comprises at least one immunoglobulin variable domain sequence. An antibody may include, for example, full-length, mature antibodies and antigen-binding fragments of an antibody. For example, an antibody can include a heavy (H) chain variable domain sequence (VH), and a light (L) chain variable domain sequence (VL). In another example, an antibody includes two heavy (H) chain variable domain sequences and two light (L) chain variable domain sequence, thereby forming two antigen binding sites, such as Fab, Fab', F(ab')2, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments, e.g., an antibody binding fragments, retain the ability to selectively bind with their respective antigen or receptor.

In some embodiments, the antibody binding fragment comprises at least one portion of an intact antibody, or recombinant variants thereof, and refers to the antigen binding domain, for example, an antigenic determining variable region of an intact antibody, that is sufficient to confer recognition and specific binding of the antibody fragment to a target, such as an antigen. Examples of antigen binding fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) Science 242:423-426; and Huston et al. (1988) Proc. Natl. Acad. Sci. USA 85:5879-5883); and (viii) a single domain antibody. These antibody fragments are obtained using conventional techniques known to those with skill in the art, and the fragments are screened for utility in the same manner as are intact antibodies. An antibody fragment can also be incorporated into single domain antibodies, maxibodies, minibodies, nanobodies, intrabodies, diabodies, triabodies, tetrabodies, v-NAR and bis-scFv (see, for example, Hollinger and Hudson, Nature Biotechnology 23:1126-1136, 2005).

In some embodiments, the encoded antibody of the payload of an AAV particle described herein comprises a multispecific antibody, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In some embodiments, the first and second epitopes are on the same antigen, e.g., the same protein (or subunit of a multimeric protein). In some embodiments, the first and second epitopes overlap. In some embodiments, the first and second epitopes do not overlap. In some embodiments, the first and second epitopes are on different antigens, e.g., the different proteins (or different subunits of a multimeric protein). In some embodiments, a multispecific antibody comprises a third, fourth or fifth immunoglobulin variable domain. In some embodiments, a multispecific antibody is a bispecific antibody, a trispecific antibody, or tetraspecific antibody.

In some embodiments, an encoded multispecific antibody of the payload of an AAV particle described herein is an encoded bispecific antibody. A bispecific antibody has specificity for no more than two antigens. A bispecific antibody is characterized by a first immunoglobulin variable domain sequence which has binding specificity for a first epitope and a second immunoglobulin variable domain sequence that has binding specificity for a second epitope. In some embodiments, the first and second epitopes are on the same antigen, e.g., the same protein (or subunit of a multimeric protein). In some embodiments, the first and second epitopes overlap. In some embodiments, the first and second epitopes do not overlap. In some embodiments, the first and second epitopes are on different antigens, e.g., the different proteins (or different subunits of a multimeric protein).

An antibody or an antibody binding fragment encoded by a viral genome of an AAV particle described herein, may be, but is not limited to, an antibody or antibody fragment that binds to β3-amyloid, APOE, tau, SOD1, TDP-43, huntingtin, and/or synuclein. In some embodiments, the encoded payload comprises an antibody or antibody fragment that binds to a neuro-oncology related target, e.g., HER2, EGFR (e.g., EGFRvIII). In some embodiments, the encoded payload comprises an antibody that binds to HER2/neu. In some embodiments, the encoded payload comprises an antibody that binds to β3-amyloid. In some embodiments, the encoded payload comprises an antibody that binds to tau.

Gene Editing System

In some embodiments, the encoded payload of AAV particle comprising an AAV capsid variant described herein comprises a gene editing system or one or more components thereof. In some embodiments, the gene editing system comprises nucleic acid sequences that encode proteins having enzymatic activity to (i) selectively induce double or single stranded breaks in a DNA or RNA sequence, or (ii) substitute, insert or delete a particular base or set of bases of a DNA or RNA sequence in the absence of a double or single stranded break in the DNA or RNA. In some embodiments, the gene editing system includes, but is not limited to a CRISPR-Cas system (including different Cas or Cas-related nucleases), a Zinc finger nuclease, a meganuclease, a TALEN or a base editors. In some embodiments, the gene editing system comprises a chromosomal integration of a transgene, e.g., introduced by a parvovirus vector in the absence of an exogenous nuclease or an enzymatic entity.

RNAi Agents

In some embodiments, the encoded payload of AAV particle comprising an AAV capsid variant described herein comprises an RNAi agent, e.g., an RNAi agent described herein. In some embodiments, the encoded payload of a viral genome of an AAV particle comprising an AAV capsid variant described herein comprises a dsRNA, a siRNA, a shRNA, a pre-miRNA, a pri-miRNA, a miRNA, a stRNA, a lncRNA, a piRNA, or a snoRNA. In some embodiments, the encoded payload comprises an RNAi agent for inhibiting expression of a SOD1, MAPT, APOE, HTT, C9ORF72, TDP-43, APP, BACE, SNCA, ATXN1, ATXN3, ATXN7, SCN1A-SCN5A, or SCN8A-SCN11A gene, protein, and/or mRNA. In some embodiments, the RNAi agent encoded by a viral genome described herein inhibits SOD1, MAPT, APOE, HTT, C9ORF72, TDP-43, APP, BACE, SNCA, ATXN1, ATXN3, ATXN7, SCN1A-SCN5A, or SCN8A-SCN11A.

An AAV particle comprising an AAV capsid variant described herein may comprise a viral genome encoding an RNAi agent, which targets the mRNA of a gene to modulate, e.g., interfere with gene expression and/or protein production.

In some embodiments, the RNAi agent may target a gene at the location of a single-nucleotide polymorphism (SNP) or variant within the nucleotide sequence of the gene.

The RNAi agent may be an siRNA duplex, wherein the siRNA duplex contains an antisense strand (guide strand) and a sense strand (passenger strand) hybridized together forming a duplex structure, wherein the antisense strand is complementary to the nucleic acid sequence of the targeted gene, and wherein the sense strand is homologous to the nucleic acid sequence of the targeted gene. In some aspects, the 5' end of the antisense strand has a 5' phosphate group and the 3' end of the sense strand contains a 3' hydroxyl group. In other aspects, there are none, one or 2 nucleotide overhangs at the 3' end of each strand.

Each strand of an siRNA duplex targeting a gene of interest may be about 19 to 25, 19 to 24 or 19 to 21 nucleotides in length, preferably about 19 nucleotides, 20 nucleotides, 21 nucleotides, 22 nucleotides, 23 nucleotides, 24 nucleotides, or 25 nucleotides in length.

In one embodiment, an siRNA or dsRNA includes at least two sequences that are complementary to each other. The dsRNA includes a sense strand having a first sequence and an antisense strand having a second sequence. The antisense strand includes a nucleotide sequence that is substantially complementary to at least part of an mRNA encoding the target gene, and the region of complementarity is 30 nucleotides or less, and at least 15 nucleotides in length. Generally, the dsRNA is 19 to 25, 19 to 24 or 19 to 21 nucleotides in length. In some embodiments, the dsRNA is from about 15 to about 25 nucleotides in length, and in other embodiments the dsRNA is from about 25 to about 30 nucleotides in length. In some embodiments, the dsRNA is about 15 nucleotides in length, 16 nucleotides in length, 17 nucleotides in length, 18 nucleotides in length, 19 nucleotides, 20 nucleotides, 21 nucleotides, 22 nucleotides, 23 nucleotides, 24 nucleotides, 25 nucleotides in length, 26 nucleotides in length, 27 nucleotides in length, 28 nucleotides in length, 29 nucleotides in length, or 30 nucleotides in length.

In some embodiments, the encoded RNAi agent is an siRNA.

In some embodiments, the RNAi agent, e.g., an RNAi agent described herein inhibits the expression of the gene, mRNA, and/or protein by at least 10%, at least 20%, at least 25%, at least 30%, at least 35% or at least 40% or more, such as when assayed by a method known in the art. In some embodiments, the RNAi agent inhibits expression of a gene, mRNA, and protein by 50-100%, e.g., by 30%, 40%, 50%, 60%, 70%, 80%, 85%, 90%, 95% and 100%.

In some embodiments, the AAV particle described herein, comprising a viral genome encoding an RNAi agent targeting a gene of interest is administered to a subject in need for treating and/or ameliorating a disease, e.g., a neurological disorder of any disease associated with the central or peripheral nervous systems.

Design of siRNA

An AAV particle described herein (e.g., an AAV particle comprising an AAV capsid variant described herein) may comprise a viral genome encoding a siRNA molecule (e.g., siRNA duplex or encoded dsRNA) that target a gene of interest and suppress target gene expression, mRNA expression, and protein production. In some aspects, the siRNA molecules are designed and used to knock out target gene variants in cells, e.g., transcripts that are identified in neurological disease. In some aspects, the siRNA molecules are designed and used to knock down target gene variants in cells.

Some guidelines for designing siRNAs (for insertion into a viral genome of the AAV particles described herein) have been proposed in the art. These guidelines generally recommend generating a 19-nucleotide duplexed region, symmetric 2-3 nucleotide 3' overhangs, 5-phosphate and 3-hydroxyl groups targeting a region in the gene to be silenced. Other rules that may govern siRNA sequence preference include, but are not limited to, (i) A/U at the 5' end of the antisense strand; (ii) G/C at the 5' end of the sense strand; (iii) at least five A/U residues in the 5' terminal one-third of the antisense strand; and (iv) the absence of any GC stretch of more than 9 nucleotides in length. In accordance with such considerations, together with the specific sequence of a target gene, highly effective siRNA molecules essential for suppressing mammalian target gene expression may be readily designed.

In one embodiment, the sense and/or antisense strand is designed based on the method and rules outlined in European Patent Publication No. EP1752536, the contents of which are herein incorporated by reference in their entirety. As a non-limiting example, the 3'-terminal base of the sequence is adenine, thymine or uracil. As a non-limiting example, the 5'-terminal base of the sequence is guanine or cytosine. As a non-limiting example, the 3'-terminal sequence comprises seven bases rich in one or more bases of adenine, thymine and uracil.

In one embodiment, an siRNA molecule comprises a sense strand and a complementary antisense strand in which both strands are hybridized together to form a duplex structure. The antisense strand has sufficient complementarity to the target mRNA sequence to direct target-specific RNAi, e.g., the siRNA molecule has a sequence sufficient to trigger the destruction of the target mRNA by the RNAi machinery or process.

In some embodiments, the antisense strand and target mRNA sequences have 100% complementarity. The antisense strand may be complementary to any part of the target mRNA sequence. Neither the identity of the sense sequence nor the homology of the antisense sequence need be 100% complementary to the target.

In other embodiments, the antisense strand and target mRNA sequences comprise at least one mismatch. As a non-limiting example, the antisense strand and the target mRNA sequence have at least 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementary.

The siRNA molecule may have a length from about 10-50 or more nucleotides, e.g., each strand comprising 10-50 nucleotides (or nucleotide analogs). Preferably, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementary to a target region. In one embodiment, the siRNA molecule has a length from about 19 to 25, 19 to 24 or 19 to 21 nucleotides.

In some embodiments, the siRNA molecule can be a synthetic RNA duplex comprising about 19 nucleotides to about 25 nucleotides, and two overhanging nucleotides at the 3'-end.

The siRNA molecule may comprise an antisense sequence and a sense sequence, or a fragment or variant thereof. As a non-limiting example, the antisense sequence and the sense sequence have at least 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementary.

The sense and antisense sequences may be completely complementary across a substantial portion of their length. In other embodiments, the sense sequence and antisense sequence may be at least 70, 80, 90, 95 or 99% complementary across independently at least 50, 60, 70, 80, 85, 90, 95, or 99% of the length of the strands.

In some embodiments, the sense and antisense strands of a siRNA duplex are linked by a short spacer sequence leading to the expression of a stem-loop structure termed short hairpin RNA (shRNA). The hairpin is recognized and cleaved by Dicer, thus generating mature siRNA molecules.

In some embodiments, the siRNA molecules, as well as associated spacer and/or flanking regions once designed, can be encoded by the viral genome of the AAV particles described herein, for delivery to a cell.

Molecular Scaffold

In some embodiments, the siRNA molecules may be encoded in a modulatory polynucleotide which also comprises a molecular scaffold.

In some embodiments, the modulatory polynucleotide which comprises the payload (e.g., siRNA, miRNA or other RNAi agent described herein) includes a molecular scaffold which comprises a 5' flanking sequence, a loop region, and/or a 3' flanking region. In some embodiments a 5' or 3' flanking region may be of any length and may a wild type microRNA sequence or a portion thereof, or may be completely artificial. A 3' flanking sequence may mirror the 5' flanking sequence in size and origin. Either flanking sequence may be absent. In one embodiment, both the 5' and 3' flanking sequences are absent. The 3' flanking sequence may optionally contain one or more CNNC motifs, where "N" represents any nucleotide. In some embodiments, the loop comprises at least one UGUG motif. In some embodiments, the UGUG motif is located at the 5' terminus of the loop. In some embodiments the 5' and 3' flanking sequences are the same sequence. In some embodiments they differ by 2%, 3%, 4%, 5%, 10%, 20% or more than 30% when aligned to each other.

In some embodiments, modulatory polynucleotide comprises a stem loop structure. In some embodiments, the modulatory polynucleotide comprises in 5' to 3' order: a 5' flanking sequence, a guide strand sequence, a loop region, a passenger strand sequence, and a 3' flanking sequence. In some embodiments, the modulatory polynucleotide comprises in 5' to 3' order: a 5' flanking sequence, a passenger strand sequence, a loop region, a guide strand sequence, and a 3' flanking sequence.

In one embodiment, the molecular scaffold comprises a dual-function targeting modulatory polynucleotide.

In one embodiment, the molecular scaffold may comprise one or more linkers known in the art. The linkers may separate regions or one molecular scaffold from another. As a non-limiting example, the molecular scaffold may be polycistronic.

In one embodiment, the modulatory polynucleotide is designed using at least one of the following properties: loop variant, seed mismatch/bulge/wobble variant, stem mismatch, loop variant and basal stem mismatch variant, seed mismatch and basal stem mismatch variant, stem mismatch and basal stem mismatch variant, seed wobble and basal stem wobble variant, or a stem sequence variant.

AAV Production

Viral production disclosed herein describes processes and methods for producing AAV particles (with enhanced, improved and/or increased tropism for a target tissue), e.g., an AAV particle comprising an AAV capsid variant that may be used to contact a target cell to deliver a payload.

In some embodiments, disclosed herein is a method of making AAV particle of the present disclosure, e.g., an AAV particle comprising an AAV capsid variant the method comprising: (i) providing a host cell comprising a viral genome described herein and (ii) incubating the host cell under conditions suitable to enclose the viral genome in an AAV capsid variant, e.g., an AAV capsid variant described herein (e.g., an AAV capsid variant listed in Tables 3, 4, or 5), thereby making the AAV particle. In some embodiments, the method comprises prior to step (i), introducing a first nucleic acid comprising the viral genome into a cell. In some embodiments, the host cell comprises a second nucleic acid encoding the AAV capsid variant. In some embodiments, the second nucleic acid is introduced into the host cell prior to, concurrently with, or after the first nucleic acid molecule. In some embodiments, the AAV particle described herein is an isolated AAV particle. In some embodiments, the AAV particle described herein is a recombinant AAV particle.

Any method known in the art may be used for the preparation of AAV particles. In some embodiments, AAV particles are produced in mammalian cells (e.g., HEK293). In another embodiment, AAV particles are produced in insect cells (e.g., Sf9).

Methods of making AAV particles are well known in the art and are described in e.g., U.S. Pat. Nos. U.S. Pat. Nos. 6,204,059, 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508, 5,064,764, 6,194,191, 6,566,118, 8,137,948; or International Publication Nos. WO1996039530, WO1998010088, WO1999014354, WO1999015685, WO1999047691, WO2000055342, WO2000075353 and WO2001023597; Methods In Molecular Biology, ed. Richard, Humana Press, NJ (1995); O'Reilly et al., Baculovirus Expression Vectors, A Laboratory Manual, Oxford Univ. Press (1994); Samulski et al., J. Vir. 63:3822-8 (1989); Kajigaya et al., Proc. Nat'l. Acad. Sci. USA 88: 4646-50 (1991); Ruffing et al., J. Vir. 66:6922-30 (1992); Kimbauer et al., Vir., 219:37-44 (1996); Zhao et al., Vir.272:382-93 (2000); the contents of each of which are herein incorporated by reference in their entirety. In some embodiments, the AAV particles are made using the methods described in International Patent Publication WO2015191508, the contents of which are herein incorporated by reference in their entirety.

Therapeutic Applications

The present disclosure provides a method for treating a disease, disorder and/or condition in a subject, including a human subject, comprising administering to the subject an AAV particle described herein, e.g., an AAV particle comprising an AAV capsid variant (e.g., an AAV capsid variant described herein), or administering to the subject any of the described compositions, including a pharmaceutical composition, described herein.

In some embodiments, the AAV particle (e.g., an AAV particle comprising an AAV capsid variant) is administered to a subject prophylactically, to prevent on-set of disease. In another embodiment, the AAV particle (e.g., an AAV particle comprising an AAV capsid variant) is administered to treat (e.g., lessen the effects of) a disease or symptoms thereof. In yet another embodiment, the AAV particle (e.g., an AAV particle comprising an AAV capsid variant) is administered to cure (eliminate) a disease. In another embodiment, the AAV particle (e.g., an AAV particle comprising an AAV capsid variant) of the present disclosure is administered to prevent or slow progression of disease. In yet another embodiment, the AAV particle (e.g., an AAV particle comprising an AAV capsid variant) of the present disclosure are used to reverse the deleterious effects of a disease. Disease status and/or progression may be determined or monitored by standard methods known in the art.

In some embodiments, the AAV particle of the disclosure (e.g., an AAV particle comprising an AAV capsid variant) is useful for treatment, prophylaxis, palliation or amelioration of a genetic disorder, e.g., an autosomal dominant genetic disorder, an autosomal recessive disorder, X-linked dominant genetic disorder, an X-linked recessive genetic disorder, or a Y-linked genetic disorder. In some embodiments, the genetic disorder is a monogenetic disorder or a polygenic disorder. In some embodiments, treatment of a genetic disorder, e.g., a monogenic disorder, comprises the use of an AAV particle described herein (e.g., an AAV particle comprising an AAV capsid variant described herein) for a gene replacement therapy.

In some embodiments, provided herein is method for treating a neurological disorder and/or neurodegenerative disorder in a subject, comprising administering to the subject an effective amount of a pharmaceutical composition described herein or an AAV particle, e.g., a plurality of particles, comprising an AAV capsid variant described herein. In some embodiments, treatment of a neurological disorder and/or neurodegenerative disorder comprises prevention of said neurological disorder and/or neurological disorder.

In some embodiments, the AAV particle (e.g., an AAV particle comprising an AAV capsid variant) of the disclosure is useful for the treatment, prophylaxis, palliation or amelioration of neurological diseases and/or disorders. In some embodiments, the AAV particle of the disclosure (e.g., an AAV particle comprising an AAV capsid variant) is useful for the treatment, prophylaxis, palliation or amelioration of tauopathy.

In some embodiments, the AAV particle of the disclosure (e.g., an AAV particle comprising an AAV capsid variant) is for the treatment, prophylaxis, palliation or amelioration of Alzheimer's Disease. In some embodiments, treatment of Alzheimer's Disease comprises the use of an AAV particle described herein (e.g., an AAV particle comprising an AAV capsid variant described herein) for a gene replacement therapy. In some embodiments, the payload encoded by an AAV particle comprising a capsid variant described herein comprises an ApoE2 protein, ApoE4 protein, an ApoE3 protein, BDNF protein, CYP46A1 protein, Klotho protein, fractalkine (FKN) protein, neprilysin protein (NEP), CD74 protein, caveolin-1, or a combination or variant thereof. In some embodiments, treatment of Alzheimer's Disease comprises the use of an AAV particle described herein (e.g., an AAV particle comprising an AAV capsid variant described herein) for a reduction in the expression of a tau gene and/or protein, a synuclein gene and/or protein, or a combination or variant thereof. In some embodiments, the payload encoded by an AAV particle comprising a capsid variant described herein comprises an antibody that binds to tau or synuclein, an RNAi agent for inhibiting tau or synuclein, a gene editing system (e.g., a CRISPR-Cas system) for altering tau or synuclein expression, or a combination thereof.

In some embodiments, the AAV particle of the disclosure (e.g., an AAV particle comprising an AAV capsid variant) is useful the treatment, prophylaxis, palliation or amelioration of Friedreich's ataxia, or any disease stemming from a loss or partial loss of frataxin protein.

In some embodiments, the AAV particle of the disclosure (e.g., an AAV particle comprising an AAV capsid variant) is for the treatment, prophylaxis, palliation or amelioration of frontal temporal dementia. In some embodiments, treatment of frontal temporal dementia comprises the use of an AAV particle described herein (e.g., an AAV particle comprising an AAV capsid variant described herein) for a gene replacement therapy. In some embodiments, the payload encoded by an AAV particle comprising a capsid variant described herein comprises a progranulin protein or variant thereof.

In some embodiments, the AAV particle of the disclosure (e.g., an AAV particle comprising an AAV capsid variant) is useful for the treatment, prophylaxis, palliation or amelioration of Parkinson's Disease. In some embodiments, treatment of Parkinson's disease comprises the use of an AAV particle described herein (e.g., an AAV particle comprising an AAV capsid variant described herein) for a gene replacement therapy. In some embodiments, the payload encoded by an AAV particle comprising a capsid variant described herein comprises an AADC protein, GAD protein, GDNF protein, TH-GCH1 protein, GBA protein, AIMP2-DX2 protein, or a combination or variant thereof. In some embodiments, treatment of Parkinson's disease comprises the use of an AAV particle described herein (e.g., an AAV particle comprising an AAV capsid variant described herein) for a gene knock-down therapy or a gene editing therapy (e.g., knock-out, repression, or correction). In some embodiments, the payload encoded by an AAV particle comprising a capsid variant described herein comprises a modulator, e.g., an RNAi agent or a CRISPR-Cas system, for altering expression of an alpha-synuclein gene, mRNA, and/or protein, or variant thereof. In some embodiments, the AAV particle of the disclosure (e.g., an AAV particle comprising an AAV capsid variant) is useful for the treatment, prophylaxis, palliation or amelioration of an AADC deficiency. In some embodiments, treatment of AADC deficiency comprises the use of an AAV particle described herein (e.g., an AAV particle comprising an AAV capsid variant described herein) for a gene replacement therapy. In some embodiments, the payload encoded by an AAV particle comprising a capsid variant described herein comprises an AADC protein or variant thereof.

In some embodiments, the AAV particle of the disclosure (e.g., an AAV particle comprising an AAV capsid variant) is useful for the treatment, prophylaxis, palliation or amelioration of Amyotrophic lateral sclerosis. In some embodiments, treatment of ALS comprises the use of an AAV particle described herein (e.g., an AAV particle comprising an AAV capsid variant described herein) for a gene replacement therapy. In some embodiments, the payload encoded by an AAV particle comprising a capsid variant described herein comprises a TDP-43 protein, UPF1 protein, C9orf72 protein, CCNF protein, HSF1 protein, Factor H protein, NGF protein, ADAR2 protein, GDNF protein, VEGF protein, HGF protein, NRTN protein, AIMP2-DX2 protein, or a combination or variant thereof. In some embodiments, treatment of ALS comprises the use of an AAV particle described herein (e.g., an AAV particle comprising an AAV capsid variant described herein) for a gene knock-down therapy or a gene editing therapy (e.g., knock-out, repression, or correction). In some embodiments, the payload encoded by an AAV particle comprising a capsid variant described herein comprises a modulator, e.g., an RNAi agent or a CRISPR-Cas system, for altering expression of a SOD1 or C90RF72 gene, mRNA, and/or protein, or a combination or variant thereof.

In some embodiments, the AAV particle of the disclosure (e.g., an AAV particle comprising an AAV capsid variant) is useful for the treatment, prophylaxis, palliation or amelioration of Huntington's Disease. In some embodiments, treatment of ALS comprises the use of an AAV particle described herein (e.g., an AAV particle comprising an AAV capsid variant described herein) for a gene knock-down (e.g., knock-out) therapy or a gene editing therapy (e.g., knock-out, repression, or correction). In some embodiments, the payload encoded by an AAV particle comprising a capsid variant described herein comprises a modulator, e.g., an RNAi agent or a CRISPR-Cas system, for altering expression of an HTT gene, mRNA, and/or protein, or a variant thereof.

In some embodiments, the AAV particle of the disclosure (e.g., an AAV particle comprising an AAV capsid variant) is useful for the treatment, prophylaxis, palliation or amelioration of spinal muscular atrophy. In some embodiments, treatment of spinal muscular atrophy comprises the use of an AAV particle described herein (e.g., an AAV particle comprising an AAV capsid variant described herein) for a gene replacement therapy. In some embodiments, the payload encoded by an AAV particle comprising a capsid variant described herein comprises an SMN1 protein, an SMN2 protein, or a combination or variant thereof.

In some embodiments, the AAV particle of the disclosure (e.g., an AAV particle comprising an AAV capsid variant) is useful for the treatment, prophylaxis, palliation or amelioration of multiple system atrophy. In some embodiments, treatment of multiple system atrophy comprises the use of an AAV particle described herein (e.g., an AAV particle comprising an AAV capsid variant described herein) for a gene replacement therapy.

In some embodiments, the AAV particle of the disclosure (e.g., an AAV particle comprising an AAV capsid variant) is useful for the treatment, prophylaxis, palliation or amelioration of Gaucher disease (GD) (e.g., Type 1 GD, Type 2 GD, or Type 3 GD). In some embodiments, the AAV particle of the disclosure (e.g., an AAV particle comprising an AAV capsid variant) is useful for the treatment, prophylaxis, palliation or amelioration of Parkinson's disease associated with a GBA mutation. In some embodiments, the AAV particle of the disclosure (e.g., an AAV particle comprising an AAV capsid variant) is useful for the treatment, prophylaxis, palliation or amelioration of dementia with Lewy Bodies (DLB).

In some embodiments, the AAV particle of the disclosure (e.g., an AAV particle comprising an AAV capsid variant) is useful for treatment, prophylaxis, palliation or amelioration of a leukodystrophy, e.g., Alexander disease, autosomal dominant leukodystrophy with autonomic diseases (ADLD), Canavan disease, cerebrotendinous xanthomatosis (CTX), metachromatic leukodystrophy (MLD), Pelizaeus-Merzbacher disease, or Refsum disease. In some embodiments, treatment of MLD comprises the use of an AAV particle described herein (e.g., an AAV particle comprising an AAV capsid variant described herein) for a gene replacement therapy. In some embodiments, the payload encoded by an AAV particle comprising a capsid variant described herein comprises an ARSA protein or variant thereof. In some embodiments, treatment of ALD comprises the use of an AAV particle described herein (e.g., an AAV particle comprising an AAV capsid variant described herein) for a gene replacement therapy. In some embodiments, the payload encoded by an AAV particle comprising a capsid variant described herein comprises an ABCD-1 protein or variant thereof.

In some embodiments, the AAV particle of the disclosure (e.g., an AAV particle comprising an AAV capsid variant) is useful for the treatment, prophylaxis, palliation, or amelioration of megalencephalic leukoencephalopathy (MLC). In some embodiments, treatment of MLC comprises the use of an AAV particle described herein (e.g., an AAV particle comprising an AAV capsid variant described herein) for a gene replacement therapy. In some embodiments, the payload encoded by an AAV particle comprising a capsid variant described herein comprises an MLC1 protein or variant thereof.

In some embodiments, the AAV particle of the disclosure (e.g., an AAV particle comprising an AAV capsid variant) is useful for the treatment, prophylaxis, palliation, or amelioration of Krabbe disease. In some embodiments, treatment of Krabbe disease comprises the use of an AAV particle described herein (e.g., an AAV particle comprising an AAV capsid variant described herein) for a gene replacement therapy. In some embodiments, the payload encoded by an AAV particle comprising a capsid variant described herein comprises a GALC protein or variant thereof.

In some embodiments, the AAV particle of the disclosure (e.g., an AAV particle comprising an AAV capsid variant) is useful for the treatment, prophylaxis, palliation, or amelioration of Mucopolysaccharidosis, e.g., a Type I (MPS I), Type II (MPS II), Type IIIA (MPS IIIA), Type IIIB (MPS IIIB), or Type IIIC (MPS IIIC). In some embodiments, treatment of Mucopolysaccharidosis comprises the use of an AAV particle described herein (e.g., an AAV particle comprising an AAV capsid variant described herein) for a gene replacement therapy or a gene editing therapy (e.g., enhancement or correction). In some embodiments, the payload encoded or corrected by an AAV particle comprising a capsid variant described herein comprises an IDUA protein, IDS protein, SGSH protein, NAGLU protein, HGSNAT protein, or a combination or variant thereof.

In some embodiments, the AAV particle of the disclosure (e.g., an AAV particle comprising an AAV capsid variant) is useful for the treatment, prophylaxis, palliation, or amelioration of Batten/NCL. In some embodiments, treatment of Batten/NCL comprises the use of an AAV particle described herein (e.g., an AAV particle comprising an AAV capsid variant described herein) for a gene replacement therapy. In some embodiments, the payload encoded by an AAV particle comprising a capsid variant described herein comprises a CLN1 protein, CLN2 protein, CLN3 protein, CLN5 protein, CLN6 protein, CLN7 protein, CLN8 protein, or a combination or variant thereof.

In some embodiments, the AAV particle of the disclosure (e.g., an AAV particle comprising an AAV capsid variant) is useful for the treatment, prophylaxis, palliation or amelioration of Rett Syndrome. In some embodiments, treatment of Rett Syndrome comprises the use of an AAV particle described herein (e.g., an AAV particle comprising an AAV capsid variant described herein) for a gene replacement therapy. In some embodiments, the payload encoded by an AAV particle comprising a capsid variant described herein comprises an MeCP2 protein or variant thereof.

In some embodiments, the AAV particle of the disclosure (e.g., an AAV particle comprising an AAV capsid variant) is useful for the treatment, prophylaxis, palliation, or amelioration of Angelman Syndrome. In some embodiments, treatment of Angelman Syndrome comprises the use of an AAV particle described herein (e.g., an AAV particle comprising an AAV capsid variant described herein) for a gene replacement therapy. In some embodiments, the payload encoded by an AAV particle comprising a capsid variant described herein comprises a UBE3A protein or variant thereof.

In some embodiments, the AAV particle of the disclosure (e.g., an AAV particle comprising an AAV capsid variant) is useful for the treatment, prophylaxis, palliation, or amelioration of Fragile X Syndrome. In some embodiments, treatment of Fragile X Syndrome comprises the use of an AAV particle described herein (e.g., an AAV particle comprising an AAV capsid variant described herein) for a gene replacement therapy. In some embodiments, the payload encoded by an AAV particle comprising a capsid variant described herein comprises a Reelin protein, a DgkK protein, a FMR1 protein, or a combination or variant thereof.

In some embodiments, the AAV particle of the disclosure (e.g., an AAV particle comprising an AAV capsid variant) is useful for the treatment, prophylaxis, palliation, or amelioration of Canavan Disease. In some embodiments, treatment of Canavan Disease comprises the use of an AAV particle described herein (e.g., an AAV particle comprising an AAV capsid variant described herein) for a gene replacement therapy. In some embodiments, the payload encoded by an AAV particle comprising a capsid variant described herein comprises an ASPA protein or variant thereof.

In some embodiments, the AAV particle of the disclosure (e.g., an AAV particle comprising an AAV capsid variant) is useful for the treatment, prophylaxis, palliation, or amelioration of a Gangliosidosis, e.g., a GM1 Gangliosidosis or a GM2 Gangliosidosis (e.g., Tay Sachs Sandhoff). In some embodiments, treatment of a Gangliosidosis, e.g., a GM1 Gangliosidosis or a GM2 Gangliosidosis (e.g., Tay Sachs Sandhoff), comprises the use of an AAV particle described herein (e.g., an AAV particle comprising an AAV capsid variant described herein) for a gene replacement therapy. In some embodiments, the payload encoded by an AAV particle comprising a capsid variant described herein comprises a GLB1 protein, a HEXA protein, a HEXB protein, a GM2A protein, or a combination or variant thereof.

In some embodiments, the AAV particle of the disclosure (e.g., an AAV particle comprising an AAV capsid variant) is useful for the treatment, prophylaxis, palliation, or amelioration of GM3 Synthase Deficiency. In some embodiments, treatment of GM3 Synthase Deficiency comprises the use of an AAV particle described herein (e.g., an AAV particle comprising an AAV capsid variant described herein) for a gene replacement therapy. In some embodiments, the payload encoded by an AAV particle comprising a capsid variant described herein comprises an ST3GAL5 protein or variant thereof.

In some embodiments, the AAV particle of the disclosure (e.g., an AAV particle comprising an AAV capsid variant) is useful for the treatment, prophylaxis, palliation, or amelioration of a Niemann-Pick disorder, e.g., a Niemann-Pick A or a Niemann-Pick C1 (NPC-1). In some embodiments, treatment of a Niemann-Pick disorder, e.g., a Niemann-Pick A or a Niemann-Pick C1 (NPC-1) comprises the use of an AAV particle described herein (e.g., an AAV particle comprising an AAV capsid variant described herein) for a gene replacement therapy. In some embodiments, the payload encoded by an AAV particle comprising a capsid variant described herein comprises an ASM protein, an NPC1 protein, or variant thereof.

In some embodiments, the AAV particle of the disclosure (e.g., an AAV particle comprising an AAV capsid variant) is useful for the treatment, prophylaxis, palliation, or amelioration of Schwannoma (e.g., Neuroma). In some embodiments, treatment of Schwannoma (e.g., Neuroma) comprises the use of an AAV particle described herein (e.g., an AAV particle comprising an AAV capsid variant described herein) for a gene replacement therapy. In some embodiments, the payload encoded by an AAV particle comprising a capsid variant described herein comprises a Caspase-1 protein or variant thereof.

In some embodiments, the AAV particle of the disclosure (e.g., an AAV particle comprising an AAV capsid variant) is useful for the treatment, prophylaxis, palliation, or amelioration of a Tuberous Sclerosis, e.g., Tuberous Sclerosis Type 1 or Tuberous Sclerosis Type 2. In some embodiments, treatment of Tuberous Sclerosis, e.g., Tuberous Sclerosis Type 1 or Tuberous Sclerosis Type 2 comprises the use of an AAV particle described herein (e.g., an AAV particle comprising an AAV capsid variant described herein) for a gene replacement therapy. In some embodiments, the payload encoded by an AAV particle comprising a capsid variant described herein comprises a TSC1 protein, a TSC2 protein, or variant thereof.

In some embodiments, the AAV particle of the disclosure (e.g., an AAV particle comprising an AAV capsid variant) is useful for the treatment, prophylaxis, palliation, or amelioration of a CDKL5 Deficiency. In some embodiments, treatment of a CDKL5 Deficiency comprises the use of an AAV particle described herein (e.g., an AAV particle comprising an AAV capsid variant described herein) for a gene replacement therapy. In some embodiments, the payload encoded by an AAV particle comprising a capsid variant described herein comprises a CDKL5 protein or variant thereof.

In some embodiments, the AAV particle of the disclosure (e.g., an AAV particle comprising an AAV capsid variant) is useful for the treatment, prophylaxis, palliation, or amelioration of a Charcot-Marie-Tooth disorder, e.g., a Charcot-Marie-Tooth Type 1x (CMT1X) disorder, a Charcot-Marie-Tooth Type 2A (CMT2A) disorder, or a Charcot-Marie-Tooth Type 4J (CMT4J) disorder. In some embodiments, treatment of a Charcot-Marie-Tooth disorder, e.g., a Charcot-Marie-Tooth Type 1X (CMT1X) disorder, a Charcot-Marie-Tooth Type 2A (CMT2A) disorder, or a Charcot-Marie-Tooth Type 4J (CMT4J) disorder, comprises the use of an AAV particle described herein (e.g., an AAV particle comprising an AAV capsid variant described herein) for a gene replacement therapy. In some embodiments, the payload encoded by an AAV particle comprising a capsid variant described herein comprises a GJB1 protein, a MFN2 protein, a FIG4 protein, or variant thereof.

In some embodiments, the AAV particle of the disclosure (e.g., an AAV particle comprising an AAV capsid variant) is useful for the treatment, prophylaxis, palliation, or amelioration of an Aspartylglucosaminuria (AGU). In some embodiments, treatment of an AGU comprises the use of an AAV particle described herein (e.g., an AAV particle comprising an AAV capsid variant described herein) for a gene replacement therapy. In some embodiments, the payload encoded by an AAV particle comprising a capsid variant described herein comprises an AGA protein or variant thereof.

In some embodiments, the AAV particle of the disclosure (e.g., an AAV particle comprising an AAV capsid variant) is useful for the treatment, prophylaxis, palliation, or amelioration of a Leigh Syndrome. In some embodiments, treatment of a Leigh Syndrome comprises the use of an AAV particle described herein (e.g., an AAV particle comprising an AAV capsid variant described herein) for a gene replacement therapy. In some embodiments, the payload encoded by an AAV particle comprising a capsid variant described herein comprises a SURF1 protein or variant thereof.

In some embodiments, the AAV particle of the disclosure (e.g., an AAV particle comprising an AAV capsid variant) is useful for the treatment, prophylaxis, palliation, or amelioration of epilepsy. In some embodiments, treatment of epilepsy comprises the use of an AAV particle described herein (e.g., an AAV particle comprising an AAV capsid variant described herein) for a gene replacement therapy. In some embodiments, the payload encoded by an AAV particle comprising a capsid variant described herein comprises an NPY/Y2 protein, a Galanin protein, a Dynorphin protein, an AIMP2-DX2 protein, an SLC6A1 protein, an SLC13A5 protein, a KCNQ2 protein, or variant thereof.

In some embodiments, the AAV particle of the disclosure (e.g., an AAV particle comprising an AAV capsid variant) is useful for the treatment, prophylaxis, palliation, or amelioration of a Dravet Syndrome. In some embodiments, treatment of Dravet Syndrome comprises the use of an AAV particle described herein (e.g., an AAV particle comprising an AAV capsid variant described herein) for a gene replacement therapy. In some embodiments, the payload encoded by an AAV particle comprising a capsid variant described herein comprises an SCN1a protein, or variant thereof.

In some embodiments, the AAV particle of the disclosure (e.g., an AAV particle comprising an AAV capsid variant) is useful for the treatment, prophylaxis, palliation, or amelioration of a Duchenne muscular dystrophy (DMD). In some embodiments, treatment of DMD comprises the use of an AAV particle described herein (e.g., an AAV particle comprising an AAV capsid variant described herein) for a gene replacement therapy or enhancement (e.g., correction of exon-skipping), or a gene editing therapy (e.g., enhancement or correction). In some embodiments, the payload encoded or corrected by an AAV particle comprising a capsid variant described herein comprises a Dystrophin gene and/or protein, a Utrophin gene and/or protein, or a GALGT2 gene and/or protein, or a Follistatin gene and/or protein, or a combination or variant thereof.

In some embodiments, the AAV particle of the disclosure (e.g., an AAV particle comprising an AAV capsid variant) is useful for the treatment, prophylaxis, palliation, or amelioration of Pompe Disease. In some embodiments, treatment of Pompe Disease comprises the use of an AAV particle described herein (e.g., an AAV particle comprising an AAV capsid variant described herein) for a gene replacement therapy. In some embodiments, the payload encoded by an AAV particle comprising a capsid variant described herein comprises a GAA protein, or variant thereof.

In some embodiments, the AAV particle of the disclosure (e.g., an AAV particle comprising an AAV capsid variant) is useful for the treatment, prophylaxis, palliation, or amelioration of Limb-Girdle Muscular Dystrophy (LGMD2A). In some embodiments, treatment of LGMD2A comprises the use of an AAV particle described herein (e.g., an AAV particle comprising an AAV capsid variant described herein) for a gene replacement therapy. In some embodiments, the payload encoded by an AAV particle comprising a capsid variant described herein comprises a CAPN-3 protein, DYSF protein, a SGCG protein, a SGCA protein, a SGCB protein, a FKRP protein, a ANO5 protein, or a combination or variant thereof.

In some embodiments, the AAV particle of the disclosure (e.g., an AAV particle comprising an AAV capsid variant) is useful for the treatment, prophylaxis, palliation or amelioration of chronic or neuropathic pain.

In some embodiments, the AAV particle of the disclosure (e.g., an AAV particle comprising AAV capsid variant) is useful for treatment, prophylaxis, palliation or amelioration of a disease associated with the central nervous system.

In some embodiments, the AAV particle of the disclosure (e.g., an AAV particle comprising an AAV capsid variant) is useful for treatment, prophylaxis, palliation or amelioration of a disease associated with the peripheral nervous system.

In some embodiments, provided herein is a method for treating a neuro-oncological disorder in a subject, comprising administering to the subject an effective amount of a pharmaceutical composition described herein or an AAV particle, e.g., a plurality of particles, comprising an AAV capsid variant described herein. In some embodiments, treatment of a neuro-oncological disorder comprises prevention of said neuro-oncological disorder. In some embodiments, a neuro-oncological disorder comprises a cancer of a primary CNS origin (e.g., a CNS cell, a tissue, or a region), or a metastatic cancer in a CNS cell, tissue, or region. Examples of primary CNS cancers could be gliomas (which may include glioblastoma (also known as glioblastoma multiforme), astrocytomas, oligodendrogliomas, and ependymomas, and mixed gliomas), meningiomas, medulloblastomas, neuromas, and primary CNS lymphoma (in the brain, spinal cord, or meninges), among others. Examples of metastatic cancers include those originating in another tissue or organ, e.g., breast, lung, lymphoma, leukemia, melanoma (skin cancer), colon, kidney, prostate, or other types that metastasize to brain.

In some embodiments, the AAV particle of the disclosure (e.g., an AAV particle comprising an AAV capsid variant) is useful for the treatment, prophylaxis, palliation or amelioration of a disease associated with expression of HER2, e.g., a disease associated with overexpression of HER2. In some embodiments, the AAV particle of the disclosure (e.g., an AAV particle comprising an AAV capsid variant) is useful for the treatment, prophylaxis, palliation or amelioration of a HER2-positive cancer. In some embodiments, the HER2-positive cancer is a HER2-positive solid tumor. Additionally, or alternatively, the HER2-positive cancer may be a locally advanced or metastatic HER2-positive cancer. In some instances, the HER2-positive cancer is a HER2-positive breast cancer or a HER2-positive gastric cancer. In some embodiments, the HER2-positive cancer is selected from the group consisting of a HER2-positive gastroesophageal junction cancer, a HER2-positive colorectal cancer, a HER2-positive lung cancer (e.g., a HER2-positive non-small cell lung carcinoma), a HER2-positive pancreatic cancer, a HER2-positive colorectal cancer, a HER2-positive bladder cancer, a HER2-positive salivary duct cancer, a HER2-positive ovarian cancer (e.g., a HER2-positive epithelial ovarian cancer), or a HER2-positive endometrial cancer. In some instances, the HER2-positive cancer is prostate cancer. In some embodiments, the HER2-positive cancer has metastasized to the central nervous system (CNS). In some instances, the metastasized HER2-cancer has formed CNS neoplasms.

In some embodiments, the AAV particle of the present disclosure (e.g., an AAV particle comprising an AAV capsid polypeptide, e.g., an AAV capsid variant) is administered to a subject having at least one of the diseases or symptoms described herein. In some embodiments, an AAV particle of the present disclosure is administered to a subject having or diagnosed with having a disease or disorder described herein.

In some embodiments, provided herein is a method for treating a muscular disorder and/or neuromuscular disorder in a subject, comprising administering to the subject an effective amount of a pharmaceutical composition described herein or an AAV particle, e.g., a plurality of particles, comprising an AAV capsid variant described herein. In some embodiments, treatment of a muscular disorder and/or neuromuscular disorder comprises prevention of said muscular disorder and/or neuromuscular disorder.

In some embodiments, the AAV particle of the disclosure (e.g., an AAV particle comprising an AAV capsid variant) is useful for treatment, prophylaxis, palliation or amelioration of a cardiac disease or heart disease and/or method of improving (e.g., enhancing) cardiac function in a subject. In some embodiments, the cardiac disease is a cardiomyopathy (e.g., arrhythmogenic right ventricular cardiomyopathy, dilated cardiomyopathy, or hypertrophic cardiomyopathy), congestive heart failure, tachycardia (e.g., catecholaminergic polymorphic ventricular tachycardia), ischemic heart disease, and/or myocardial infarction. In some embodiments, the cardiac disease is a disease associated with expression, e.g., aberrant expression, of LAMP2B, MYBPC3, TNNI3, LMNA, BAG3, DWORF, PKP2, Cx43, TAZ, CASQ2, SERCA2a, I-1c, S100A1 and/or ARC, S100A1, ASCL1, miR133, Mydelta3, Sav, or a combination or variant thereof. In some embodiments, treatment of a cardiac disorder described herein comprises the use of an AAV particle described herein (e.g., an AAV particle comprising an AAV capsid variant described herein) for a gene replacement therapy.

In some embodiments, the cardiac disease is a genetic disorder, e.g., an autosomal dominant genetic disorder, an autosomal recessive disorder, or an X-linked recessive genetic disorder. In some embodiments, the cardiomyopathy is a genetic disorder, e.g., a genetic disorder associated with an abnormality (e.g., mutation, insertion, rearrangement and/or deletion) in a gene chosen from TTN, LMNA, MYH7, MYH6, SCN5A, TNNT2, RBM20, TNNI3, MYL2, MYL3, PKP2, DSP, DSG2, DSC2, JUP, or a combination thereof. In some embodiments, the cardiac disorder is a dilated cardiomyopathy, e.g., a dilated cardiomyopathy associated with an abnormality (e.g., mutation, insertion, rearrangement and/or deletion) in a gene chosen from TTN, LMNA, MIH7, BAG3, MIPN, TNNT2, SCN5A, RBN20, TNPO, LAMA4, VCL, LDB3, TCAP, PSEN1/2, ACTN2, CRYAB, TPM1, ABCC9, ACTC1, PDLIM3, ILK, TNNC1, TNNI3, PLN, DES, SGCD, CSRP3, MIH6, EYA4, ANKRD1, DMD, GATADI, TAZ/G4.5, or combination thereof. In some embodiments, the cardiac disorder is a hypertrophic cardiomyopathy, e.g., a hypertrophic cardiomyopathy associated with an abnormality (e.g., mutation, insertion, rearrangement and/or deletion) in a gene chosen from MYH7, TNNT2, TNNI3, TPM1, MYL2, MYL3, ACTC1, CSRP3, TTN, ACTN2, MYH6, TCAP, TNNC1, or a combination thereof. In some embodiments, the cardiac disorder is an arrhythmogenic ventricular cardiomyopathy, e.g., an arrhythmogenic ventricular cardiomyopathy associated with an abnormality (e.g., mutation, insertion, rearrangement and/or deletion) in a gene chosen from PKP2, DSG2, DSP, RYR2, DSC2, TGFB3, TMEM43, DES, TTN, LMNA, or a combination thereof.

In some embodiments, the AAV particle of the present disclosure (e.g., an AAV particle comprising an AAV capsid polypeptide, e.g., an AAV capsid variant) is administered to a subject having at least one of the diseases or symptoms described herein. In some embodiments, an AAV particle of the present disclosure is administered to a subject having or diagnosed with having a disease or disorder described herein.

Any neurological disease or disorder, neurodegenerative disorder, muscular disorder, neuromuscular disorder, and/or neuro-oncological disorder may be treated with the AAV particles of the disclosure, or pharmaceutical compositions thereof.

Pharmaceutical Composition and Formulations

According to the present disclosure, an AAV particle comprising an AAV capsid variant described herein may be prepared as a pharmaceutical composition. In some embodiments, the pharmaceutical composition comprises at least one active ingredients. In some embodiments, the pharmaceutical composition comprises a pharmaceutically acceptable excipient.

In some embodiments, an AAV particle of the present disclosure (e.g., an AAV particle comprising an AAV capsid polypeptide, e.g., an AAV capsid variant) can be formulated using an excipient to: (1) increase stability; (2) increase cell transfection or transduction; (3) permit the sustained or delayed expression of the payload; (4) alter the biodistribution (e.g., target the viral particle to specific tissues or cell types); (5) increase the translation of encoded protein; (6) alter the release profile of encoded protein; and/or (7) allow for regulatable expression of the payload. Formulations of the present disclosure can include, without limitation, saline, liposomes, lipid nanoparticles, polymers, peptides, proteins, cells transfected with viral vectors (e.g., for transfer or transplantation into a subject) and combinations thereof.

In some embodiments, the relative amount of the active ingredient (e.g. an AAV particle comprising an AAV capsid variant described herein), a pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, the pharmaceutical composition comprising an AAV particle described herein may comprise an AAV capsid variant and a viral genome encoding a payload, e.g., a payload described herein, with or without a pharmaceutically acceptable excipient.

The present disclosure also provides in some embodiments, a pharmaceutical composition suitable for administration to a subject, e.g., a human. In some embodiments, the pharmaceutical composition is administered to a subject, e.g., a human.

Administration

In some embodiments, an AAV particle disclosed herein (e.g., an AAV particle comprising an AAV capsid variant) may be administered to a subject by a delivery route, e.g., a localized delivery route or a systemic delivery route.

In some embodiments, an AAV particle described herein (e.g., an AAV particle comprising an AAV capsid variant) may be administered via such a route that it is able to cross the blood-brain barrier, vascular barrier, or other epithelial barrier. In some embodiments, an AAV particle of the present disclosure (e.g., an AAV particle comprising an AAV capsid variant) may be administered in any suitable form, either as a liquid solution or suspension, as a solid form suitable for liquid solution or suspension in a liquid solution. In some embodiments, an AAV particle (e.g., an AAV particle comprising an AAV capsid variant) may be formulated with any appropriate and pharmaceutically acceptable excipient.

In some embodiments, the AAV particle described herein (e.g., an AAV particle comprising an AAV capsid variant) is administered intramuscularly, intravenously, intracerebrally, intrathecally, intratumorally, intracerebroventricularly, via intraparenchymal administration, or via intra-cisterna magna injection (ICM). In some embodiments, the AAV particle described herein (e.g., an AAV particle comprising an AAV capsid variant) is administered intravenously. In some embodiments, the AAV particle described herein (e.g., an AAV particle comprising an AAV capsid variant) is administered via intra-cisterna magna injection (ICM). In some embodiments, the AAV particle described herein (e.g., an AAV particle comprising an AAV capsid variant) is administered intratumorally. In some embodiments, the AAV particle described herein (e.g., an AAV particle comprising an AAV capsid variant) is administered intraarterially.

In some embodiments, an AAV particle of the present disclosure (e.g., an AAV particle comprising an AAV capsid variant) may be delivered to a subject via a single route administration. In some embodiments, an AAV particle of the present disclosure may be delivered to a subject via a multi-site route of administration. In some embodiments, a subject may be administered at 2, 3, 4, 5, or more than 5 sites.

In some embodiments, an AAV particle of the present disclosure (e.g., an AAV particle comprising an AAV capsid variant) is administered via a bolus infusion. In some embodiments, an AAV particle of the present disclosure is administered via sustained delivery over a period of minutes, hours, or days. In some embodiments, the infusion rate may be changed depending on the subject, distribution, formulation, and/or another delivery parameter. In some embodiments, an AAV particle of the present disclosure is administered using a controlled release. In some embodiments, an AAV particle of the present disclosure is administered using a sustained release, e.g., a release profile that conforms to a release rate over a specific period of time.

In some embodiments, an AAV particle (e.g., an AAV particle comprising an AAV capsid variant) may be delivered by more than one route of administration. As non-limiting examples of combination administrations, an AAV particle may be delivered by intrathecal and intracerebroventricular, or by intravenous and intraparenchymal administration.

Intravenous Administration

In some embodiments, an AAV particle described herein (e.g., an AAV particle comprising an AAV capsid variant) may be administered to a subject by systemic administration. In some embodiments, the systemic administration is intravenous administration. In another embodiment, the systemic administration is intraarterial administration. In some embodiments, an AAV particle of the present disclosure may be administered to a subject by intravenous administration. In some embodiments, the intravenous administration may be achieved by subcutaneous delivery. In some embodiments, the AAV particle is administered to the subject via focused ultrasound (FUS), e.g., coupled with the intravenous administration of microbubbles (FUS-MB) or MRI-guided FUS coupled with intravenous administration, e.g., as described in Terstappen et al. (Nat Rev Drug Discovery, doi.org/10.1038/s41573-021-00139-y (2021)), the contents of which are incorporated herein by reference in its entirety. In some embodiments, the AAV particle is administered to the subject intravenously. In some embodiments, the subject is a human.

Administration to the CNS

In some embodiments, an AAV particle described herein (e.g., an AAV particle comprising an AAV capsid variant) may be delivered by direct injection into the brain. As a non-limiting example, the brain delivery may be by intrahippocampal administration. In some embodiments, an AAV particle of the present disclosure may be administered to a subject by intraparenchymal administration. In some embodiments, the intraparenchymal administration is to tissue of the central nervous system. In some embodiments, an AAV particle of the present disclosure may be administered to a subject by intracranial delivery (See, e.g., U.S. Pat. No. 8,119,611; the content of which is incorporated herein by reference in its entirety). In some embodiments, an AAV particle described herein may be delivered by injection into the CSF pathway. Non-limiting examples of delivery to the CSF pathway include intrathecal and intracerebroventricular administration. In some embodiments, an AAV particle described herein may be administered via intracisternal magna (ICM) injection.

In some embodiments, an AAV particle of the present disclosure (e.g., an AAV particle comprising an AAV capsid variant) may be delivered to the brain by systemic delivery. As a non-limiting example, the systemic delivery may be by intravascular administration. As a non-limiting example, the systemic or intravascular administration may be intravenous.

In some embodiments, an AAV particle (e.g., an AAV particle comprising an AAV capsid variant) of the present disclosure may be delivered by an intraocular delivery route. A non-limiting example of an intraocular administration includes an intravitreal injection.

Intramuscular Administration

In some embodiments, an AAV particle described herein (e.g., an AAV particle comprising an AAV capsid variant) may be delivered by intramuscular administration. Without wishing to be bound by theory, it is believed in some embodiments, that the multi-nucleated nature of muscle cells provides an advantage to gene transduction subsequent to AAV delivery. In some embodiments, cells of the muscle are capable of expressing recombinant proteins with the appropriate post-translational modifications. Without wishing to be bound by theory, it is believed in some embodiments, the enrichment of muscle tissue with vascular structures allows for transfer to the blood stream and whole-body delivery. Examples of intramuscular administration include systemic (e.g., intravenous), subcutaneous or directly into the muscle. In some embodiments, more than one injection is administered. In some embodiments, an AAV particle of the present disclosure may be delivered by an intramuscular delivery route. (See, e.g., U.S. Pat. No. 6,506,379; the content of which is incorporated herein by reference in its entirety). Non-limiting examples of intramuscular administration include an intravenous injection or a subcutaneous injection.

In some embodiments, an AAV particle of the present disclosure (e.g., an AAV particle comprising an AAV capsid variant) is administered to a subject and transduces the muscle of a subject. As a non-limiting example, an AAV particle is administered by intramuscular administration. In some embodiments, an AAV particle of the present disclosure may be administered to a subject by subcutaneous administration. In some embodiments, the intramuscular administration is via systemic delivery. In some embodiments, the intramuscular administration is via intravenous delivery. In some embodiments, the intramuscular administration is via direct injection to the muscle.

In some embodiments, the muscle is transduced by administration, e.g., intramuscular administration. In some embodiments, an intramuscular delivery comprises administration at one site. In some embodiments, an intramuscular delivery comprises administration at more than one site. In some embodiments, an intramuscular delivery comprises administration at two, three, four, or more sites. In some embodiments, intramuscular delivery is combined with at least one other method of administration.

In some embodiments, an AAV particle pf the present disclosure (e.g., an AAV particle comprising an AAV capsid variant) may be administered to a subject by peripheral injections. Non-limiting examples of peripheral injections include intraperitoneal, intramuscular, intravenous, conjunctival, or joint injection. It was disclosed in the art that the peripheral administration of AAV vectors can be transported to the central nervous system, for example, to the motor neurons (e.g., U. S. Patent Publication Nos.

US20100240739 and US20100130594; the content of each of which is incorporated herein by reference in their entirety).

In some embodiments, an AAV particle of the present disclosure (e.g., an AAV particle comprising an AAV capsid variant) may be administered to a subject by intraparenchymal administration. In some embodiments, the intraparenchymal administration is to muscle tissue. In some embodiments, an AAV particle of the present disclosure is delivered as described in Bright et al 2015 (Neurobiol Aging. 36(2): 693-709), the contents of which are herein incorporated by reference in their entirety. In some embodiments, an AAV particle of the present disclosure is administered to the gastrocnemius muscle of a subject. In some embodiments, an AAV particle of the present disclosure is administered to the bicep femorii of the subject. In some embodiments, an AAV particles of the present disclosure is administered to the tibialis anterior muscles. In some embodiments, an AAV particle of the present disclosure is administered to the soleus muscle.

Depot Administration

In some embodiments, a pharmaceutical composition and/or an AAV particle of the present disclosure (e.g., an AAV particle comprising an AAV capsid variant) are formulated in depots for extended release. Generally, specific organs or tissues are targeted for administration.

In some embodiments, a pharmaceutical composition and/or an AAV particle of the present disclosure (e.g., an AAV particle comprising an AAV capsid variant) are spatially retained within or proximal to target tissues. Provided are methods of providing a pharmaceutical composition, an AAV particle, to target tissues of mammalian subjects by contacting target tissues (which comprise one or more target cells) with the pharmaceutical composition and/or the AAV particle, under conditions such that they are substantially retained in target tissues, e.g., such that at least 10, 20, 30, 40, 50, 60, 70, 80, 85, 90, 95, 96, 97, 98, 99, 99.9, 99.99 or greater than 99.99% of the composition is retained in the target tissues. In some embodiments, retention is determined by measuring the amount of pharmaceutical composition and/or AAV particle, that enter a target cell or a plurality of target cells. For example, at least 1%, 5%, 10%, 20%, 30%, 40%, 50%, 60%, 70%, 80%, 85%, 90%, 95%, 96%, 97%, 98%, 99%, 99.9%, 99.99%, or greater than 99.99% of a pharmaceutical composition and/or an AAV particle, administered to a subject are present intracellularly at a period of time following administration. For example, intramuscular injection to a subject may be performed using aqueous compositions comprising a pharmaceutical composition and/or an AAV particle of the present disclosure and a transfection reagent, and retention is determined by measuring the amount of the pharmaceutical composition and/or the AAV particle, present in the muscle cell or plurality of muscle cells.

In some embodiments, disclosed herein are methods of providing a pharmaceutical composition and/or an AAV particle of the present disclosure (e.g., an AAV particle comprising an AAV capsid variant) to a tissue of a subject, by contacting the tissue (comprising a cell, e.g., a plurality of cells) with the pharmaceutical composition and/or the AAV particle under conditions such that they are substantially retained in the tissue. In some embodiments, a pharmaceutical composition and/or AAV particle described herein comprise a sufficient amount of an active ingredient such that the effect of interest is produced in at least one cell. In some embodiments, a pharmaceutical composition and/or an AAV particle generally comprise one or more cell penetration agents. In some embodiments, the disclosure provides a naked formulations (such as without cell penetration agents or other agents), with or without pharmaceutically acceptable carriers.

Methods of Treatment

Provided in the present disclosure are methods for introducing (e.g., delivering) an AAV particle of the present disclosure (e.g., an AAV particle comprising an AAV capsid variant) into cells. In some embodiments, the method comprises introducing into said cells an AAV particle or vector described herein in an amount sufficient to modulate, e.g., increase, the production of a target gene, mRNA, and/or protein. In some embodiments, the method comprises introducing into said cells an AAV particle or vector described herein in an amount sufficient to modulate, e.g., decrease, expression of a target gene, mRNA, and/or protein. In some aspects, the cells may be neurons such as but not limited to, motor, hippocampal, entorhinal, thalamic, cortical, sensory, sympathetic, or parasympathetic neurons, and glial cells such as astrocytes, microglia, and/or oligodendrocytes. In other aspects, the cells may be a muscle cell, e.g., a cell of a diaphragm, a quadriceps, or a heart (e.g., a heart atrium or a heart ventricle). In other embodiments, the cells may be a muscle cell (e.g., a cell of a diaphragm, a quadriceps, or a heart (e.g., a heart atrium or a heart ventricle)) or a liver cell. In some embodiments, the cell may be a heart cell (e.g., a cell of a heart atrium or a cell of a heart ventricle).

Disclosed in the present disclosure are methods for treating a neurological disease/disorder or a neurodegenerative disorder, a muscular or neuromuscular disorder, or a neurooncological disorder associated with aberrant, e.g., insufficient or increased, function/presence of a protein, e.g., a target protein in a subject in need of treatment.

In some embodiments, the method comprises administering to the subject a therapeutically effective amount of a composition comprising AAV particles of the present disclosure. As a non-limiting example, the AAV particles can increase target gene expression, increase target protein production, and thus reduce one or more symptoms of neurological disease in the subject such that the subject is therapeutically treated.

In other embodiments, the method comprises administering to the subject a therapeutically effective amount of a composition comprising AAV particles (e.g., an AAV particle comprising an AAV capsid polypeptide, e.g., an AAV capsid variant) comprising a viral genome with a nucleic acid sequence encoding one or more siRNA molecules. As a non-limiting example, the siRNA molecules can silence target gene expression, inhibit target protein production, and reduce one or more symptoms of neurological disease in the subject such that the subject is therapeutically treated.

In some embodiments, the composition comprising the AAV particles of the present disclosure (e.g., an AAV particle comprising an AAV capsid variant described herein) is administered to the central nervous system of the subject via systemic administration. In some embodiments, the systemic administration is intravenous (IV) injection. In some embodiments, the AAV particle described herein or a pharmaceutical composition comprising an AAV particle described herein is administered by focused ultrasound (FUS), e.g., coupled with the intravenous administration of microbubbles (FUS-MB) or MRI-guided FUS coupled with intravenous administration.

In some embodiments, the composition comprising the AAV particle of the present disclosure (e.g., an AAV particle comprising an AAV capsid variant) is administered to the central nervous system of the subject via intraventricular administration. In some embodiments, the composition comprising the AAV particle of the present disclosure (e.g., an AAV particle comprising an AAV capsid variant) is administered via intra-cisterna magna injection (ICM).

In some embodiments, the composition comprising an AAV particle of the present disclosure (e.g., an AAV particle comprising an AAV capsid variant) is administered to the central nervous system of the subject via intraventricular injection and intravenous injection.

In some embodiments, the composition comprising the AAV particle of the present disclosure (e.g., an AAV particle comprising an AAV capsid variant) is administered to the central nervous system of the subject via ICM injection and intravenous injection at a specific dose per subject. As a non-limiting example, the AAV particles are administered via ICM injection at a dose of $1\times10^4$ VG per subject. As a non-limiting example, the AAV particles are administered via IV injection at a dose of $2\times10^{13}$ VG per subject.

In some embodiments, the composition comprising the AAV particle of the present disclosure (e.g., an AAV particle comprising an AAV capsid variant) is administered to the central nervous system of the subject. In other embodiments, the composition comprising the AAV particles of the present disclosure is administered to a CNS tissue of a subject (e.g., putamen, hippocampus, thalamus, or cortex of the subject).

In some embodiments, the composition comprising the AAV particle of the present disclosure (e.g., an AAV particle comprising an AAV capsid variant) is administered to the central nervous system of the subject via intraparenchymal injection. Non-limiting examples of intraparenchymal injections include intraputamenal, intracortical, intrathalamic, intrastriatal, intrahippocampal or into the entorhinal cortex.

In some embodiments, the composition comprising the AAV particle of the present disclosure (e.g., an AAV particle comprising an AAV capsid variant) is administered to the central nervous system of the subject via intraparenchymal injection and intravenous injection.

In some embodiments, the composition comprising the AAV particle of the present disclosure (e.g., an AAV particle comprising an AAV capsid variant) is administered to the central nervous system of the subject via intraventricular injection, intraparenchymal injection and intravenous injection.

In some embodiments, the composition comprising an AAV particle (e.g., an AAV particle comprising an AAV capsid variant) of a plurality of particles of the present disclosure is administered to a muscle of the subject via intravenous injection. In some embodiments, the composition comprising an AAV particle of a plurality of particles of the present disclosure is administered to a muscle of the subject via intramuscular injection.

In some embodiments, an AAV particle of the present disclosure (e.g., an AAV particle comprising an AAV capsid variant) may be delivered into specific types of cells, including, but not limited to, thalamic, hippocampal, entorhinal, cortical, motor, sensory, excitatory, inhibitory, sympathetic, or parasympathetic neurons; glial cells including oligodendrocytes, astrocytes and microglia; and/or other cells surrounding neurons such as T cells. In some embodiments, an AAV particle of the present disclosure may be delivered into a muscle cell, e.g., a cell of the quadriceps, diaphragm, liver, and/or heart (e.g., heart atrium or heart ventricle).

In some embodiments, an AAV particle (e.g., an AAV particle comprising an AAV capsid polypeptide, e.g., an AAV capsid variant), e.g., a plurality of particles, of the present disclosure may be delivered to a cell or region of the midbrain. In some embodiments, an AAV particle (e.g., an AAV particle comprising an AAV capsid polypeptide, e.g., an AAV capsid variant), e.g., a plurality of particles, of the present disclosure may be delivered to a cell or region of the brains stem.

In some embodiments, an AAV particle (e.g., an AAV particle comprising an AAV capsid polypeptide, e.g., an AAV capsid variant), e.g., a plurality of particles, of the present disclosure may be delivered to neurons in the putamen, hippocampus, thalamus and/or cortex.

In some embodiments, an AAV particle (e.g., an AAV particle comprising an AAV capsid variant), e.g., a plurality of particles, of the present disclosure may be used as a therapy for a genetic disorder, e.g., an autosomal dominant genetic disorder, an autosomal recessive disorder, X-linked dominant genetic disorder, an X-linked recessive genetic disorder, or a Y-linked genetic disorder. In some embodiments, the genetic disorder is a monogenetic disorder or a polygenic disorder. In some embodiments, treatment of a genetic disorder, e.g., a monogenic disorder, comprises the use of an AAV particle described herein (e.g., an AAV particle comprising an AAV capsid variant described herein) for a gene replacement therapy.

In some embodiments, an AAV particle (e.g., an AAV particle comprising an AAV capsid variant), e.g., a plurality of particles, of the present disclosure may be used as a therapy for a neurological disease.

In some embodiments, an AAV particle (e.g., an AAV particle comprising an AAV capsid variant), e.g., a plurality of particles, of the present disclosure may be used as a therapy for tauopathies.

In some embodiments, an AAV particle (e.g., an AAV particle comprising an AAV capsid variant), e.g., a plurality of particles, of the present disclosure may be used as a therapy for Alzheimer's Disease.

In some embodiments, an AAV particle (e.g., an AAV particle comprising an AAV capsid variant), e.g., a plurality of particles, of the present disclosure may be used as a therapy for Amyotrophic Lateral Sclerosis.

In some embodiments, an AAV particle (e.g., an AAV particle comprising an AAV capsid variant), e.g., a plurality of particles, of the present disclosure may be used as a therapy for Huntington's Disease.

In some embodiments, an AAV particle (e.g., an AAV particle comprising an AAV capsid variant), e.g., a plurality of particles, of the present disclosure may be used as a therapy for Parkinson's Disease.

In some embodiments, an AAV particle (e.g., an AAV particle comprising an AAV capsid variant), e.g., a plurality of particles, of the present disclosure may be used as a therapy for Gaucher disease (GD) (e.g., Type 1 GD, Type 2 GD, or Type 3 GD). In some embodiments, an AAV particle (e.g., an AAV particle comprising an AAV capsid variant), e.g., a plurality of particles, of the present disclosure may be used as a therapy for Parkinson's disease associated with a GBA mutation. In some embodiments, an AAV particle (e.g., an AAV particle comprising an AAV capsid variant), e.g., a plurality of particles, of the present disclosure may be used as a therapy for dementia with Lewy Bodies (DLB).

In some embodiments, an AAV particle (e.g., an AAV particle comprising an AAV capsid variant), e.g., a plurality of particles, of the present disclosure may be used as a therapy for spinal muscular atrophy.

In some embodiments, an AAV particle (e.g., an AAV particle comprising an AAV capsid variant), e.g., a plurality of particles, of the present disclosure may be used as a therapy for a leukodystrophy, e.g., Alexander disease, autosomal dominant leukodystrophy with autonomic diseases (ADLD), Canavan disease, cerebrotendinous xanthomatosis (CTX), metachromatic leukodystrophy (MLD), Pelizaeus-Merzbacher disease, or Refsum disease.

In some embodiments, an AAV particle (e.g., an AAV particle comprising an AAV capsid variant), e.g., a plurality of particles, of the present disclosure may be used as a therapy for Friedreich's Ataxia.

In some embodiments, an AAV particle (e.g., an AAV particle comprising an AAV capsid variant), e.g., a plurality of particles, of the present disclosure may be used as a therapy for chronic or neuropathic pain.

In some embodiments, an AAV particle (e.g., an AAV particle comprising an AAV capsid variant), e.g., a plurality of particles, of the present disclosure may be used as a therapy for a muscular disorder or a neuromuscular disorder.

In some embodiments, an AAV particle (e.g., an AAV particle comprising an AAV capsid variant), e.g., a plurality of particles, of the present disclosure may be used as a therapy for a cardiac disease or heart disease and/or method of improving (e.g., enhancing) cardiac function in a subject. In some embodiments, the cardiac disease is a cardiomyopathy (e.g., arrhythmogenic right ventricular cardiomyopathy, dilated cardiomyopathy, or hypertrophic cardiomyopathy), congestive heart failure, tachycardia (e.g., catecholaminergic polymorphic ventricular tachycardia), ischemic heart disease, and/or myocardial infarction.

In some embodiments, an AAV particle (e.g., an AAV particle comprising an AAV capsid variant), e.g., a plurality of particles, of the present disclosure may be used as a therapy for a disease associated with expression of HER2, e.g., a disease associated with overexpression of HER2. In some embodiments, the AAV particle of the disclosure (e.g., an AAV particle comprising an AAV capsid variant) is useful for the treatment, prophylaxis, palliation or amelioration of a HER2-positive cancer. In some embodiments, the HER2-positive cancer is a HER2-positive solid tumor. Additionally, or alternatively, the HER2-positive cancer may be a locally advanced or metastatic HER2-positive cancer. In some instances, the HER2-positive cancer is a HER2-positive breast cancer or a HER2-positive gastric cancer. In some embodiments, the HER2-positive cancer is selected from the group consisting of a HER2-positive gastroesophageal junction cancer, a HER2-positive colorectal cancer, a HER2-positive lung cancer (e.g., a HER2-positive non-small cell lung carcinoma), a HER2-positive pancreatic cancer, a HER2-positive colorectal cancer, a HER2-positive bladder cancer, a HER2-positive salivary duct cancer, a HER2-positive ovarian cancer (e.g., a HER2-positive epithelial ovarian cancer), or a HER2-positive endometrial cancer. In some instances, the HER2-positive cancer is prostate cancer. In some embodiments, the HER2-positive cancer has metastasized to the central nervous system (CNS). In some instances, the metastasized HER2-cancer has formed CNS neoplasms.

In some embodiments, an AAV particle (e.g., an AAV particle comprising an AAV capsid variant) e.g., a plurality of particles, of the present disclosure may be used as a therapy for a neuro-oncological disorder. In some embodiments, the neuro-oncological disorder is a cancer of primary CNS origin (e.g., a cancer of a CNS cell and/or CNS tissue). In some embodiments, the neuro-oncological disorder is metastatic cancer in a CNS cell, CNS region, and/or a CNS tissue. Examples of primary CNS cancers could be gliomas (which may include glioblastoma (also known as glioblastoma multiforme), astrocytomas, oligodendrogliomas, and ependymomas, and mixed gliomas), meningiomas, medulloblastomas, neuromas, and primary CNS lymphoma (in the brain, spinal cord, or meninges), among others. Examples of metastatic cancers include those originating in another tissue or organ, e.g., breast, lung, lymphoma, leukemia, melanoma (skin cancer), colon, kidney, prostate, or other types that metastasize to brain.

In some embodiments, administration of the AAV particle described herein (e.g., an AAV particle comprising an AAV capsid polypeptide, e.g., an AAV capsid variant) to a subject may increase target gene, mRNA, and/or protein levels in a subject, relative to a control, e.g., the gene, mRNA, and/or mRNA levels in the subject prior to receiving AAV particle. The target gene, mRNA, and/or protein levels may be increased by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS, or a muscle, a region of a muscle, or a cell of a muscle, of a subject. In some embodiments, cell of the CNS comprises an astrocyte, microglia, cortical neuron, hippocampal neuron, DRG and/or sympathetic neuron, sensory neuron, oligodendrocyte, motor neuron, or combination thereof. As a non-limiting example, the AAV particles may increase the gene, mRNA, and/or protein levels of a target protein by fold increases over baseline. In some embodiments, AAV particles lead to 5-6 times higher levels of a target gene, mRNA, or protein.

In some embodiments, administration of the AAV particle described herein (e.g., an AAV particle comprising an AAV capsid polypeptide, e.g., an AAV capsid variant), e.g., an AAV particle comprising a nucleic acid encoding a siRNA molecule, to a subject may decrease target gene, mRNA, and/or protein levels in a subject, relative to a control, e.g., the gene, mRNA, and/or mRNA levels in the subject prior to receiving AAV particle. The target gene, mRNA, and/or protein levels may be decreased by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS, or a muscle, a region of a muscle, or a cell of a muscle, of a subject. In some embodiments, cell of the CNS comprises an astrocyte, microglia, cortical neuron, hippocampal neuron, DRG and/or sympathetic neuron, sensory neuron, oligodendrocyte, motor neuron, or combination thereof. As a non-limiting example, the AAV particles may decrease the gene, mRNA, and/or protein levels of a target protein by fold decreases over baseline.

In some embodiments, the AAV particles of the present disclosure (e.g., an AAV particle comprising an AAV capsid polypeptide, e.g., an AAV capsid variant) may be used to increase target protein and reduce symptoms of neurological disease in a subject. In some embodiments, the AAV particles of the present disclosure (e.g., an AAV particle comprising an AAV capsid polypeptide, e.g., an AAV capsid variant) may be used to decrease target protein and reduce symptoms of neurological disease in a subject.

In some embodiments, the AAV particles of the present disclosure (e.g., an AAV particle comprising an AAV capsid polypeptide, e.g., an AAV capsid variant) may be used to reduce the decline of functional capacity and activities of daily living as measured by a standard evaluation system such as, but not limited to, the total functional capacity (TFC) scale.

In some embodiments, the AAV particles of the present disclosure (e.g., an AAV particle comprising an AAV capsid polypeptide, e.g., an AAV capsid variant) may be used to improve performance on any assessment used to measure symptoms of neurological disease. Such assessments include, but are not limited to ADAS-cog (Alzheimer Disease Assessment Scale-cognitive), MMSE (Mini-Mental State Examination), GDS (Geriatric Depression Scale), FAQ (Functional Activities Questionnaire), ADL (Activities of Daily Living), GPCOG (General Practitioner Assessment of Cognition), Mini-Cog, AMTS (Abbreviated Mental Test Score), Clock-drawing test, 6-CIT (6-item Cognitive Impairment Test), TYM (Test Your Memory), MoCa (Montreal Cognitive Assessment), ACE-R (Addenbrookes Cognitive Assessment), MIS (Memory Impairment Screen), BADLS (Bristol Activities of Daily Living Scale), Barthel Index, Functional Independence Measure, Instrumental Activities of Daily Living, IQCODE (Informant Questionnaire on Cognitive Decline in the Elderly), Neuropsychiatric Inventory, The Cohen-Mansfield Agitation Inventory, BEHAVE-AD, EuroQol, Short Form-36 and/or MBR Caregiver Strain Instrument, or any of the other tests as described in Sheehan B (Ther Adv Neurol Disord. 5(6):349-358 (2012)), the contents of which are herein incorporated by reference in their entirety.

In some embodiments, the present composition is administered as a solo therapeutic or as combination therapeutic for the treatment of a neurological disease/disorder or a neurodegenerative disorder, a muscular disorder or neuromuscular disorder, and/or a neuro-oncological disorder.

The AAV particles (e.g., an AAV particle comprising an AAV capsid variant) encoding the target protein may be used in combination with one or more other therapeutic agents. In some embodiments, compositions can be administered concurrently with, prior to, or subsequent to, additional therapeutic or medical procedures. In general, each agent will be administered at a dose and/or on a time schedule determined for that agent.

Therapeutic agents that may be used in combination with the AAV particles of the present disclosure (e.g., an AAV particle comprising an AAV capsid variant) can be small molecule compounds which are antioxidants, anti-inflammatory agents, anti-apoptosis agents, calcium regulators, anti-glutamatergic agents, structural protein inhibitors, compounds involved in muscle function, and compounds involved in metal ion regulation. As a non-limiting example, the combination therapy may be in combination with one or more neuroprotective agents such as small molecule compounds, growth factors and hormones which have been tested for their neuroprotective effect on motor neuron degeneration.

Compounds tested for treating neurological disease which may be used in combination with the AAV particles described herein include, but are not limited to, cholinesterase inhibitors (donepezil, rivastigmine, galantamine), NMDA receptor antagonists such as memantine, anti-psychotics, anti-depressants, anti-convulsants (e.g., sodium valproate and levetiracetam for myoclonus), secretase inhibitors, amyloid aggregation inhibitors, copper or zinc modulators, BACE inhibitors, inhibitors of tau aggregation, such as Methylene blue, phenothiazines, anthraquinones, n-phenylamines or rhodamines, microtubule stabilizers such as NAP, taxol or paclitaxel, kinase or phosphatase inhibitors such as those targeting GSK3β (lithium) or PP2A, immunization with Aβ peptides or tau phospho-epitopes, anti-tau or anti-amyloid antibodies, dopamine-depleting agents (e.g., tetrabenazine for chorea), benzodiazepines (e.g., clonazepam for myoclonus, chorea, dystonia, rigidity, and/or spasticity), amino acid precursors of dopamine (e.g., levodopa for rigidity), skeletal muscle relaxants (e.g., baclofen, tizanidine for rigidity and/or spasticity), inhibitors for acetylcholine release at the neuromuscular junction to cause muscle paralysis (e.g., botulinum toxin for bruxism and/or dystonia), atypical neuroleptics (e.g., olanzapine and quetiapine for psychosis and/or irritability, risperidone, sulpiride and haloperidol for psychosis, chorea and/or irritability, clozapine for treatment-resistant psychosis, aripiprazole for psychosis with prominent negative symptoms), selective serotonin reuptake inhibitors (SSRIs) (e.g., citalopram, fluoxetine, paroxetine, sertraline, mirtazapine, venlafaxine for depression, anxiety, obsessive compulsive behavior and/or irritability), hypnotics (e.g., xopiclone and/or zolpidem for altered sleep-wake cycle), anticonvulsants (e.g., sodium valproate and carbamazepine for mania or hypomania) and mood stabilizers (e.g., lithium for mania or hypomania).

Neurotrophic factors may be used in combination therapy with the AAV particles of the present disclosure (e.g., an AAV particle comprising an AAV capsid variant) for treating neurological disease. Generally, a neurotrophic factor is defined as a substance that promotes survival, growth, differentiation, proliferation and/or maturation of a neuron, or stimulates increased activity of a neuron. In some embodiments, the present methods further comprise delivery of one or more trophic factors into the subject in need of treatment. Trophic factors may include, but are not limited to, IGF-I, GDNF, BDNF, CTNF, VEGF, Colivelin, Xaliproden, Thyrotrophin-releasing hormone and ADNF, and variants thereof.

In one aspect, the AAV particle described herein (e.g., an AAV particle comprising an AAV capsid variant) may be co-administered with AAV particles expressing neurotrophic factors such as AAV-IGF-I (See e.g., Vincent et al., *Neuromolecular medicine*, 2004, 6, 79-85; the contents of which are incorporated herein by reference in their entirety) and AAV-GDNF (See e.g., Wang et al., *J Neurosci.*, 2002, 22, 6920-6928; the contents of which are incorporated herein by reference in their entirety).

In some embodiments, administration of the AAV particles (e.g., an AAV particle comprising an AAV capsid variant) to a subject will modulate, e.g., increase or decrease, the expression of a target protein in a subject and the modulation, e.g., increase or decrease of the presence, level, activity, and/or expression of the target protein will reduce the effects and/or symptoms of a neurological disease/disorder or a neurodegenerative disorder, a muscular disorder or neuromuscular disorder, and/or a neuro-oncological disorder in a subject.

Definitions

Unless defined otherwise, all technical and scientific terms used herein have the same meaning as commonly understood by one of ordinary skill in the art to which the invention pertains.

Articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" and "consisting essentially thereof" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

Adeno-associated virus: As used herein, the term "adeno-associated virus" or "AAV" refers to members of the dependovirus genus or a variant, e.g., a functional variant, thereof. In some embodiments, the AAV is wildtype, or naturally occurring. In some embodiments, the AAV is recombinant.

AAV Particle: As used herein, an "AAV particle" refers to a particle or a virion comprising an AAV capsid, e.g., an AAV capsid variant, and a polynucleotide, e.g., a viral genome or a vector genome. In some embodiments, the viral genome of the AAV particle comprises at least one payload region and at least one ITR. In some embodiments, an AAV particle of the disclosure is an AAV particle comprising an AAV variant. In some embodiments, the AAV particle is capable of delivering a nucleic acid, e.g., a payload region, encoding a payload to cells, typically, mammalian, e.g., human, cells. In some embodiments, an AAV particle of the present disclosure may be produced recombinantly. In some embodiments, an AAV particle may be derived from any serotype, described herein or known in the art, including combinations of serotypes (e.g., "pseudotyped" AAV) or from various genomes (e.g., single stranded or self-complementary). In some embodiments, the AAV particle may be replication defective and/or targeted. It is to be understood that reference to the AAV particle of the disclosure also includes pharmaceutical compositions thereof, even if not explicitly recited.

Administering: As used herein, the term "administering" refers to providing a pharmaceutical agent or composition to a subject.

Amelioration: As used herein, the term "amelioration" or "ameliorating" refers to a lessening of severity of at least one indicator of a condition or disease. For example, in the context of neurodegeneration disorder, amelioration includes the reduction of neuron loss.

Amplicon: As used herein, "amplicon" may refer to any piece of RNA or DNA formed as the product of amplification events, e.g. PCR. In some embodiments, full-length capsid amplicons may be used as templates for next generation sequencing (NGS) library generation. Full-length capsid amplicons may be used for cloning into a DNA library for any number of additional rounds of AAV selection as described herein.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically engineered animal, or a clone.

Antisense strand: As used herein, the term "the antisense strand" or "the first strand" or "the guide strand" of a siRNA molecule refers to a strand that is substantially complementary to a section of about 10-50 nucleotides, e.g., about 15-30, 16-25, 18-23 or 19-22 nucleotides of the mRNA of a gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biopanning: As used herein, the term "biopanning" refers to an AAV capsid library selection process comprising administration of an AAV particle with enhanced tissue- and/or cell type-specific transduction to a cell and/or subject; extraction of nucleotides encoded by said AAV particle from said transduced tissue- and/or cell type-specific; and, use of the extracted nucleotides for cloning into a nucleotide library for the generation of AAV particles for subsequent rounds of the same.

Capsid: As used herein, the term "capsid" refers to the exterior, e.g., a protein shell, of a virus particle, e.g., an AAV particle, that is substantially (e.g., >50%, >60%, >70%, >80%, >90%, >95%, >99%, or 100%) protein. In some embodiments, the capsid is an AAV capsid comprising an AAV capsid protein described herein, e.g., a VP1, VP2, and/or VP3 polypeptide. The AAV capsid protein can be a wild-type AAV capsid protein or a variant, e.g., a structural and/or functional variant from a wild-type or a reference capsid protein, referred to herein as an "AAV capsid variant." In some embodiments, the AAV capsid variant described herein has the ability to enclose, e.g., encapsulate, a viral genome and/or is capable of entry into a cell, e.g., a mammalian cell. In some embodiments, the AAV capsid variant described herein may have modified tropism compared to that of a wild-type AAV capsid, e.g., the corresponding wild-type capsid.

Complementary and substantially complementary: As used herein, the term "complementary" refers to the ability of polynucleotides to form base pairs with one another. Base pairs are typically formed by hydrogen bonds between nucleotide units in antiparallel polynucleotide strands.

Complementary polynucleotide strands can form base pairs in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenine. However, when a U is denoted in the context of the present disclosure, the ability to substitute a T is implied, unless otherwise stated. Perfect complementarity or 100% complementarity refers to the situation in which each nucleotide unit of one polynucleotide strand can form a hydrogen bond with a nucleotide unit of a second polynucleotide strand. Less than perfect complementarity refers to the situation in which some, but not all, nucleotide units of two strands can form hydrogen bond with each other. For example, for two 20-mers, if only two base pairs on each strand can form a hydrogen bond with each other, the polynucleotide strands exhibit 10% complementarity. In the same example, if 18 base pairs on each strand can form hydrogen bonds with each other, the polynucleotide strands exhibit 90% complementarity. The term "complementary" as used herein can encompass fully complementary, partially complementary, or substantially complementary. As used herein, the term "substantially complementary" means that the siRNA has a sequence (e.g., in the antisense strand) which is sufficient to bind the desired target mRNA, and to trigger the RNA silencing of the target mRNA. "Fully complementary", "perfect complementarity", or "100% complementarity" refers to the situation in which each nucleotide unit of one polynucleotide or oligonucleotide strand can base-pair with a nucleotide unit of a second polynucleotide or oligonucleotide strand.

Control Elements: As used herein, "control elements", "regulatory control elements" or "regulatory sequences" refers to promoter regions, polyadenylation signals, transcription termination sequences, upstream regulatory domains, origins of replication, internal ribosome entry sites ("IRES"), enhancers, and the like, which provide for the replication, transcription and translation of a coding sequence in a recipient cell. Not all of these control elements need always be present as long as the selected coding sequence is capable of being replicated, transcribed and/or translated in an appropriate host cell.

Delivery: As used herein, "delivery" refers to the act or manner of delivering an AAV particle, a compound, substance, entity, moiety, cargo or payload.

Element: As used herein, the term "element" refers to a distinct portion of an entity. In some embodiments, an element may be a polynucleotide sequence with a specific purpose, incorporated into a longer polynucleotide sequence.

Encapsulate: As used herein, the term "encapsulate" means to enclose, surround or encase. As an example, a capsid protein, e.g., an AAV capsid variant, often encapsulates a viral genome. In some embodiments, encapsulate within a capsid, e.g., an AAV capsid variant, encompasses 100% coverage by a capsid, as well as less than 100% coverage, e.g., 95%, 90%, 85%, 80%, 70%, 60% or less. For example, gaps or discontinuities may be present in the capsid so long as the viral genome is retained in the capsid, e.g., prior to entry into a cell.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Formulation: As used herein, a "formulation" includes at least one AAV particle (active ingredient) and an excipient, and/or an inactive ingredient.

Fragment: A "fragment," as used herein, refers to a portion. For example, an antibody fragment may comprise a CDR, or a heavy chain variable region, or a scFv, etc.

Homology: As used herein, the term "homology" refers to the overall relatedness between polymeric molecules, e.g. between polynucleotide molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the disclosure, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the disclosure, two protein sequences are considered to be homologous if the proteins are at least about 50%, 60%, 70%, 80%, or 90% identical for at least one stretch of at least about 20 amino acids.

Identity: As used herein, the term "identity" refers to the overall relatedness between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; the contents of each of which are incorporated herein by reference in their entirety. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically, a reduction in the level of an mRNA results in a reduction in the level of a polypeptide translated therefrom. The level of expression may be determined using standard techniques for measuring mRNA or protein.

Inverted terminal repeat: As used herein, the term "inverted terminal repeat" or "ITR" refers to a cis-regulatory element for the packaging of polynucleotide sequences into viral capsids.

Isolated: As used herein, the term "isolated" refers to a substance or entity that is altered or removed from the natural state, e.g., altered or removed from at least some of component with which it is associated in the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell. Such polynucleotides could be part of a vector and/or such polynucleotides or polypeptides could be part of a composition, and still be isolated in that such vector or composition is not part of the environment in which it is found in nature. In some embodiments, an isolated nucleic acid is recombinant, e.g., incorporated into a vector.

Library: As used herein, the term "library" refers to a diverse collection of linear polypeptides, polynucleotides, viral particles, or viral vectors. As examples, a library may be a DNA library or an AAV capsid library.

Molecular scaffold: As used herein a "molecular scaffold" is a framework or starting molecule that forms the sequence or structural basis against which to design or make a subsequent molecule.

Neurological disease: As used herein, a "neurological disease" is any disease associated with the central or peripheral nervous system and components thereof (e.g., neurons).

Orthogonal evolution: As used herein, the term "orthogonal evolution" refers to a method wherein AAV particles are administered for a first round of AAV selection as described herein across a set of any number of cell- and/or subject-types that may be from different species and/or strains, and wherein any number of additional, i.e., subsequent, AAV selection rounds are performed either across a set of any number of cell- and/or subject-types that may be from different species and/or strains, or across a set of any number of cell- and/or subject-types that may be from the same species and/or strain.

Open reading frame: As used herein, "open reading frame" or "ORF" refers to a sequence which does not contain a stop codon in a given reading frame.

Particle: As used herein, a "particle" is a virus comprised of at least two components, a protein capsid and a polynucleotide sequence enclosed within the capsid.

Payload region: As used herein, a "payload region" is any nucleic acid sequence (e.g., within the viral genome) which encodes one or more "payloads" of the disclosure. As non-limiting examples, a payload region may be a nucleic acid sequence within the viral genome of an AAV particle, which encodes a payload, wherein the payload is an RNAi agent or a polypeptide. Payloads of the present disclosure may be, but are not limited to, peptides, polypeptides, proteins, antibodies, RNAi agents, etc.

Polypeptide: As used herein, "polypeptide" means a polymer of amino acid residues (natural or unnatural) linked together most often by peptide bonds. The term, as used herein, refers to proteins, polypeptides, and peptides of any size, structure, or function. In some instances, the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. They may also comprise single chain or multichain polypeptides and may be associated or linked. The term polypeptide may also apply to amino acid polymers in which one or more amino acid residues are an artificial chemical analogue of a corresponding naturally occurring amino acid.

Polypeptide variant: The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. In some embodiments, a variant comprises a sequence having at least about 50%, at least about 80%, or at least about 90%, identical (homologous) to a native or a reference sequence.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Preventing: As used herein, the term "preventing" or "prevention" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease.

Region: As used herein, the term "region" refers to a zone or general area. In some embodiments, when referring to a protein or protein module, a region may comprise a linear sequence of amino acids along the protein or protein module or may comprise a three-dimensional area, an epitope and/or a cluster of epitopes. In some embodiments, regions comprise terminal regions. As used herein, the term "terminal region" refers to regions located at the ends or termini of a given agent. When referring to proteins, terminal regions may comprise N- and/or C-termini.

In some embodiments, when referring to a polynucleotide, a region may comprise a linear sequence of nucleic acids along the polynucleotide or may comprise a three-dimensional area, secondary structure, or tertiary structure. In some embodiments, regions comprise terminal regions. As used herein, the term "terminal region" refers to regions located at the ends or termini of a given agent. When referring to polynucleotides, terminal regions may comprise 5' and/or 3' termini.

RNA or RNA molecule: As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally, e.g., by DNA replication and transcription of DNA, respectively; or be chemically synthesized. DNA and RNA can be single-stranded (i.e., ssRNA or ssDNA, respectively) or multi-stranded (e.g., double stranded, i.e., dsRNA and dsDNA, respectively). The term "mRNA" or "messenger RNA", as used herein, refers to a single stranded RNA that encodes the amino acid sequence of one or more polypeptide chains.

RNA interfering or RNAi: As used herein, the term "RNA interfering" or "RNAi" refers to a sequence specific regulatory mechanism mediated by RNA molecules which results in the inhibition or interfering or "silencing" of the expression of a corresponding protein-coding gene. RNAi has been observed in many types of organisms, including plants, animals and fungi. RNAi occurs in cells naturally to remove foreign RNAs (e.g., viral RNAs). Natural RNAi proceeds via fragments cleaved from free dsRNA which direct the degradative mechanism to other similar RNA sequences. RNAi is controlled by the RNA-induced silencing complex (RISC) and is initiated by short/small dsRNA molecules in cell cytoplasm, where they interact with the catalytic RISC component argonaute. The dsRNA molecules can be introduced into cells exogenously. Exogenous dsRNA initiates RNAi by activating the ribonuclease protein Dicer, which binds and cleaves dsRNAs to produce double-stranded fragments of 21-25 base pairs with a few unpaired overhang bases on each end. These short double stranded fragments are called small interfering RNAs (siRNAs).

RNAi agent: As used herein, the term "RNAi agent" refers to an RNA molecule, or its derivative, that can induce inhibition, interfering, or "silencing" of the expression of a target gene and/or its protein product. An RNAi agent may knock-out (virtually eliminate or eliminate) expression, or knock-down (lessen or decrease) expression. The RNAi agent may be, but is not limited to, dsRNA, siRNA, shRNA, pre-miRNA, pri-miRNA, miRNA, stRNA, lncRNA, piRNA, or snoRNA.

miR binding site: As used herein, a "miR binding site" comprises a nucleic acid sequence (whether RNA or DNA, e.g., differ by "U" of RNA or "T" in DNA) that is capable of binding, or binds, in whole or in part to a microRNA (miR) through complete or partial hybridization. Typically, such binding occurs between the miR and the miR binding site in the reverse complement orientation. In some embodiments, the miR binding site is transcribed from the AAV vector genome encoding the miR binding site.

In some embodiments, a miR binding site may be encoded or transcribed in series. Such a "miR binding site series" or "miR BSs" may include two or more miR binding sites having the same or different nucleic acid sequence.

Spacer: As used here, a "spacer" is generally any selected nucleic acid sequence of, e.g., 1, 2, 3, 4, 5, 6, 7, 8, 9, or 10 nucleotides in length, which is located between two or more consecutive miR binding site sequences. Spacers may also be more than 10 nucleotides in length, e.g., 20, 30, 40, or 50 or more than 50 nucleotides.

Sample: As used herein, the term "sample" or "biological sample" refers to a subset of its tissues, cells, nucleic acids, or component parts (e.g. body fluids, including but not limited to blood, serum, mucus, lymphatic fluid, synovial fluid, cerebrospinal fluid, saliva, amniotic fluid, amniotic cord blood, urine, vaginal fluid and semen).

Self-complementary viral particle: As used herein, a "self-complementary viral particle" is a particle comprised of at least two components, a protein capsid and a self-complementary viral genome enclosed within the capsid.

Sense Strand: As used herein, the term "the sense strand" or "the second strand" or "the passenger strand" of a siRNA molecule refers to a strand that is complementary to the antisense strand or first strand. The antisense and sense strands of a siRNA molecule are hybridized to form a duplex structure. As used herein, a "siRNA duplex" includes a siRNA strand having sufficient complementarity to a section of about 10-50 nucleotides of the mRNA of the gene targeted for silencing and a siRNA strand having sufficient complementarity to form a duplex with the other siRNA strand.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Short interfering RNA or siRNA: As used herein, the terms "short interfering RNA," "small interfering RNA" or "siRNA" refer to an RNA molecule (or RNA analog) comprising between about 5-60 nucleotides (or nucleotide analogs) which is capable of directing or mediating RNAi. Preferably, a siRNA molecule comprises between about 15-30 nucleotides or nucleotide analogs, such as between about 16-25 nucleotides (or nucleotide analogs), between about 18-23 nucleotides (or nucleotide analogs), between about 19-22 nucleotides (or nucleotide analogs) (e.g., 19, 20, 21 or 22 nucleotides or nucleotide analogs), between about 19-25 nucleotides (or nucleotide analogs), and between about 19-24 nucleotides (or nucleotide analogs). The term "short" siRNA refers to a siRNA comprising 5-23 nucleotides, preferably 21 nucleotides (or nucleotide analogs), for example, 19, 20, 21 or 22 nucleotides. The term "long" siRNA refers to a siRNA comprising 24-60 nucleotides, preferably about 24-25 nucleotides, for example, 23, 24, 25 or 26 nucleotides. Short siRNAs may, in some instances, include fewer than 19 nucleotides, e.g., 16, 17 or 18 nucleotides, or as few as 5 nucleotides, provided that the shorter siRNA retains the ability to mediate RNAi. Likewise, long siRNAs may, in some instances, include more than 26 nucleotides, e.g., 27, 28, 29, 30, 35, 40, 45, 50, 55, or even 60 nucleotides, provided that the longer siRNA retains the ability to mediate RNAi or translational repression absent further processing, e.g., enzymatic processing, to a short siRNA. siRNAs can be single stranded RNA molecules (ss-siRNAs) or double stranded RNA molecules (ds-siRNAs) comprising a sense strand and an antisense strand which hybridized to form a duplex structure called an siRNA duplex.

Subject: As used herein, the term "subject" or "patient" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target Cells: As used herein, "target cells" or "target tissue" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition. In some embodiments, a therapeutically effective amount is provided in a single dose.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Conservative amino acid substitution: As used herein, a "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Variant: As used herein, the term "variant" refers to a polypeptide or polynucleotide that has an amino acid or a nucleotide sequence that is substantially identical, e.g., having at least 70%, 75%, 80%, 85%, 90%, 95% or 99% sequence identity to a reference sequence. In some embodiments, the variant is a functional variant.

Functional Variant: As used herein, the term "functional variant" refers to a polypeptide variant or a polynucleotide variant that has at least one activity of the reference sequence.

Insertional Variant: "Insertional variants" when referring to polypeptides are those with one or more amino acids inserted, e.g., immediately adjacent or subsequent, to a position in an amino acid sequence. "Immediately adjacent" or "immediately subsequent" to an amino acid means connected to either the alpha-carboxy or alpha-amino functional group of the amino acid.

Deletional Variant: "Deletional variants" when referring to polypeptides, are those with one or more amino acids in deleted from a reference protein.

Vector: As used herein, the term "vector" refers to any molecule or moiety which transports, transduces or otherwise acts as a carrier of a heterologous molecule. In some embodiments, vectors may be plasmids. In some embodiments, vectors may be viruses. An AAV particle is an example of a vector. Vectors of the present disclosure may be produced recombinantly and may be based on and/or may comprise adeno-associated virus (AAV) parent or reference sequences. The heterologous molecule may be a polynucleotide and/or a polypeptide.

Viral Genome: As used herein, the terms "viral genome" or "vector genome" refer to the nucleic acid sequence(s) encapsulated in an AAV particle. A viral genome comprises a nucleic acid sequence with at least one payload region encoding a payload and at least one ITR.

Equivalents and Scope

The disclosures of each and every patent, patent application, and publication cited herein are hereby incorporated herein by reference in their entirety. While this invention has been disclosed with reference to certain embodiments, it is apparent that further embodiments and variations of this invention may be devised by others skilled in the art without departing from the true spirit and scope of the invention. The appended claims are intended to be construed to include all such embodiments and equivalent variations.

The present disclosure is further illustrated by the following non-limiting examples.

EXAMPLES

Example 1. High-throughput Screen of TRACER AAV Library in NHP and Mice

A TRACER based method as described in WO2020072683, WO 2021/202651, and WO2021230987, the contents of which are herein incorporated by reference in their entirety, was used to generate the AAV capsid variants described herein. An orthogonal evolution approach was combined with a high throughput screening by NGS. Briefly, the library of AAV capsid variants was generated using a sliding window approach, where 6 amino acid sequences were inserted into 8 different positions across loop IV of AAV9, including immediately subsequent to positions 453, 454, 455, 456, 457, 458, 459, and 460, relative to a reference sequence numbered according to SEQ ID NO: 138. The initial library was passed twice through non-human primates (NHP, 2-4 years of age). After the second passage (e.g., 28 days post injection into two NHPs), RNA was extracted from six brain regions. Following RNA recovery and RT-PCR amplification, a systematic NGS enrichment analysis was performed to calculate fold enrichment relative to an AAV9 wild-type control. Following these two passages, approximately 21195 variants were identified with an average fold change greater than wild-type. Of the 21195 variants, 1558 demonstrated a fold-change of greater than 6 compared to wild-type and were detected across all brain regions investigated. Of these 1558, approximately 1470 variants were selected for constructing a synthetic library and a third passage through two NHPs. Within the 1470 variants selected for further characterization and investigation, there was a relatively even distribution for each insertion position of the sliding window used to generate the initial library.

After creation of the synthetic library with the sub-selected variants, the synthetic library was screened (passage 3) in two NHPs (2-4 years of age) and two strains of mice, BALB/c (n=3, 6-8 weeks of age) and C57B1/6 mice (n=3, 6-8 weeks of age), in a first cross-species evolution screen. The animals were injected intravenously with the synthetic library. After a period in vivo, (e.g., 28-days) RNA was extracted from nervous tissue, e.g., brain, spinal cord, and DRG of the NHPs and the brains of mice. Following RNA recovery and RT-PCR amplification, a systematic NGS enrichment analysis was performed, and the peptides comprised within the variants were identified and the capsid enrichment ratio for each variant compared to the wild-type AAV9 control was calculated (fold enrichment relative to wild-type AAV9) (Table 9). Values above 1 indicate an increase in expression relative to AAV9. All animals were dosed intravenously at 2-3 VG/kg across the screen.

As shown in Table 9, approximately 700 variants demonstrated an increase in expression relative to AAV9, and several variants demonstrated a greater than 10-fold enrichment relative to AAV9 in the brain of NHPs. Further, the variants demonstrating the greatest fold enrichment in the brain also demonstrated the greatest fold enrichment in the spinal cord relative to AAV9 in NHPs. These variants also demonstrated de-targeting in the DRG (data not shown). For instance, the variant comprising GSGSPHSKAQNQQT (SEQ ID NO: 200) demonstrated a 76.6 fold enrichment in the brain, a 29.4 fold enrichment in the spinal cord, and 0.4 fold enrichment in the DRG of NHPs relative to AAV9; and GHDSPHKSGQNQQT (SEQ ID NO: 201) demonstrated a 62.6 fold enrichment in the brain, a 15.6 fold enrichment in the spinal cord, and 0.0 fold enrichment in the DRG of NHPs relative to AAV9. Also, across the peptides comprised within the AAV capsid variants with the greatest fold-enrichment in the NHP brain relative wild-type AAV9, it was observed that each of these peptides comprised an SPH motif in the same position (e.g., immediately subsequent to position 455, relative to a reference sequence numbered according to the amino acid sequence of SEQ ID NO: 138), regardless of the insertion position within the variant capsid, as well as a positive amino acid (e.g., K or R) in one of the next three residues subsequent to the SPH motif.

Those variants with the greatest fold enrichment in the brains of NHPs also had the greatest fold enrichment in the brains of both mouse species. Also, when comparing the fold enrichment relative to wild-type for each variant between the two species of mice investigated (C57B1/6 and BALB/c mice), they were highly correlated ($R^2$=0.8591).

TABLE 9

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57B1/6) | Fold enrichment over AAV9 in the brain of Mice (BALB/c) |
|---|---|---|---|---|---|
| GSGSPHSKAQNQQT | 200 | 73.615 | 29.402 | 25.293 | 41.304 |
| GHDSPHKSGQNQQT | 201 | 62.612 | 15.641 | 63.993 | 49.760 |
| GSGSPHARMQNQQT | 202 | 56.138 | 22.690 | 7.795 | 4.164 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGSPHVKSQNQQT | 203 | 37.551 | 13.649 | 8.069 | 15.861 |
| GQDSPHKSGQNQQT | 204 | 24.569 | 3.548 | 57.344 | 42.615 |
| GSGSPHASRQNQQT | 205 | 18.265 | 7.804 | 28.028 | 36.577 |
| GSGSPHASRQNKQT | 206 | 17.520 | 35.029 | 13.096 | 18.114 |
| GSGSPHVKIQNQQT | 207 | 16.854 | 9.068 | 2.173 | 2.227 |
| GSGSPHSKAKNQQT | 208 | 14.458 | 0.049 | 21.494 | 23.556 |
| GSGSPHKKNQNQQT | 209 | 12.991 | 0.379 | 25.958 | 7.415 |
| GSGSPHVRMQNQQT | 210 | 11.574 | 6.764 | 9.121 | 10.076 |
| GSGSPHASRQKQQT | 211 | 11.417 | 0.005 | 7.413 | 12.400 |
| GHSSPHRSGQNQQT | 212 | 10.357 | 1.887 | 23.197 | 25.442 |
| GMRTYHLSGQNQQT | 213 | 9.241 | 1.939 | 2.033 | 1.586 |
| GSGSPHTRGQNQQT | 214 | 7.092 | 3.815 | 10.801 | 6.240 |
| GSGIIPVSSQNQQT | 215 | 6.352 | 0.000 | 0.642 | 0.253 |
| GSEYGHKSGQNQQT | 216 | 6.308 | 2.750 | 5.198 | 5.332 |
| GRGQNVSSVHRQQT | 217 | 5.404 | 0.000 | 1.206 | 0.691 |
| GSSHRFYGGQNQQT | 218 | 4.732 | 0.000 | 0.787 | 0.110 |
| GYFVAAWSGQNQQT | 219 | 4.488 | 0.000 | 0.071 | 0.175 |
| GSVLHSHAAQNQQT | 220 | 4.150 | 6.448 | 0.675 | 0.423 |
| GSGDLVVSTQNQQT | 221 | 3.874 | 1.177 | 0.411 | 0.273 |
| GSYGMAASGQNQQT | 222 | 3.817 | 10.052 | 1.274 | 0.829 |
| GLNHFGASGQNQQT | 223 | 3.802 | 3.188 | 0.774 | 0.579 |
| GSTGSHSAGQNQHT | 224 | 3.717 | 0.285 | 1.190 | 0.850 |
| GLAGHTVSGQNQQT | 225 | 3.632 | 0.229 | 0.972 | 0.202 |
| GIILGASSGQNQQT | 226 | 3.630 | 4.868 | 1.378 | 0.865 |
| GSGVSTYNIQNQQT | 227 | 3.609 | 2.912 | 0.769 | 0.520 |
| GSLVSVQTGQNQQT | 228 | 3.534 | 6.043 | 0.903 | 0.469 |
| GQSSPHRSGQNQQT | 229 | 3.496 | 2.142 | 12.352 | 19.366 |
| GREYGHKSGQNQQT | 230 | 3.453 | 0.000 | 1.422 | 0.959 |
| GHTLTLSSGQNQQT | 231 | 3.405 | 5.648 | 0.648 | 0.606 |
| GSITLIPSGQNQQT | 232 | 3.361 | 3.917 | 0.326 | 0.435 |
| GSNGFTALGQNQQT | 233 | 3.361 | 2.663 | 0.830 | 0.332 |
| GSGHSSHSVQNQQT | 234 | 3.339 | 3.318 | 0.942 | 0.424 |
| GSGIPQRSGKNQQT | 235 | 3.331 | 0.000 | 1.418 | 1.685 |
| GSGDTLHMLQNQQT | 236 | 3.317 | 1.174 | 0.393 | 0.482 |
| GERHTVLSGQNQQT | 237 | 3.289 | 3.008 | 1.027 | 0.607 |
| GSGMPQSHIQNQQT | 238 | 3.289 | 11.609 | 0.514 | 0.334 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGQLSGIGGNQQT | 239 | 3.266 | 0.287 | 0.993 | 0.626 |
| GSGQNRKPASFAQT | 240 | 3.204 | 0.000 | 0.892 | 1.061 |
| GSGSVSQLGQNQQT | 241 | 3.184 | 2.307 | 0.596 | 0.375 |
| GSDFLGTHGQNQQT | 242 | 3.171 | 0.348 | 1.038 | 0.750 |
| GQIVQNPSGQNQQT | 243 | 3.133 | 0.406 | 1.446 | 0.635 |
| GSGTQIPSQQNQQT | 244 | 3.112 | 1.224 | 0.470 | 0.151 |
| GSGQNQQSAREGLT | 245 | 3.111 | 5.632 | 1.221 | 1.104 |
| GSGLGMSTGQNQQT | 246 | 3.110 | 5.499 | 0.458 | 0.660 |
| GSGLPVLSGQNQQT | 247 | 3.100 | 4.149 | 0.631 | 0.210 |
| GSGHSIRTDQNQQT | 248 | 3.074 | 15.600 | 0.229 | 0.148 |
| GSGQSVQTVVNQQT | 249 | 3.057 | 5.441 | 0.582 | 0.240 |
| GSGQNRAQSRFQQT | 250 | 3.043 | 0.000 | 0.619 | 1.788 |
| GGGDLGRSSQNQQT | 251 | 3.036 | 4.830 | 0.916 | 0.539 |
| GGGTKMDSGQNQQT | 252 | 3.034 | 0.000 | 0.733 | 0.297 |
| GSGSPHPSRQNQQT | 253 | 3.017 | 1.993 | 1.869 | 0.975 |
| GSGQFTNAGMNQQT | 254 | 2.969 | 0.936 | 0.565 | 0.418 |
| GGRNGHTVGQNQQT | 255 | 2.965 | 3.732 | 1.105 | 1.003 |
| GSGFGPQTGQNQQT | 256 | 2.964 | 2.861 | 1.280 | 0.849 |
| GRTDSHTSGQNQQT | 257 | 2.913 | 1.510 | 1.299 | 0.704 |
| GYEVLGSSGQNQQT | 258 | 2.891 | 0.000 | 2.459 | 0.319 |
| GSVHLSVTGQNQQT | 259 | 2.882 | 1.157 | 0.741 | 0.282 |
| GFMSYKGSGQNQQT | 260 | 2.865 | 0.209 | 1.808 | 0.569 |
| GNIAGSVSGQNQQT | 261 | 2.849 | 1.187 | 0.446 | 0.257 |
| GSGSHRDVSQNQQT | 262 | 2.843 | 4.022 | 0.626 | 0.550 |
| GGLGSMSSGQNQQT | 263 | 2.812 | 1.405 | 1.802 | 0.822 |
| GSGHLPQSAQNQQT | 264 | 2.803 | 7.828 | 0.826 | 0.496 |
| GGVLVGGSGQNQQT | 265 | 2.778 | 0.178 | 1.527 | 0.688 |
| GTHPYTSSGQNQQT | 266 | 2.775 | 1.684 | 0.758 | 0.471 |
| GSGQNQQLKENRST | 267 | 2.765 | 0.062 | 1.149 | 1.118 |
| GSGQNQQTSPHNHT | 268 | 2.761 | 3.132 | 1.524 | 0.845 |
| GSGTLYPQSQNQQT | 269 | 2.761 | 5.558 | 0.324 | 0.160 |
| GSGQNQQSNWITKT | 270 | 2.711 | 0.000 | 0.540 | 0.634 |
| GSGYTSLFLQNQQT | 271 | 2.710 | 0.010 | 0.490 | 1.044 |
| GSGVMTHVLQNQQT | 272 | 2.692 | 0.347 | 0.370 | 0.533 |
| GSVSDVRAGQNQQT | 273 | 2.661 | 1.647 | 0.267 | 0.747 |
| GSGQSHMATLNQQT | 274 | 2.657 | 0.724 | 1.173 | 0.504 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGLSVHLAQNQQT | 275 | 2.657 | 1.234 | 0.806 | 0.508 |
| GSGLSHATQQNQQT | 276 | 2.640 | 7.819 | 1.111 | 0.638 |
| GSGLSVQSGQNQQT | 277 | 2.637 | 2.929 | 1.695 | 1.005 |
| GSGHMTYREKNQQT | 278 | 2.633 | 5.267 | 1.257 | 0.540 |
| GSKGVPTPGQNQQT | 279 | 2.625 | 1.292 | 1.452 | 0.459 |
| GSGLLPLSSQNQQT | 280 | 2.612 | 1.130 | 0.501 | 0.293 |
| GNGLYAVSGQNQQT | 281 | 2.611 | 9.148 | 0.322 | 0.213 |
| GFNGSPSSGQNQQT | 282 | 2.609 | 12.197 | 2.338 | 0.924 |
| GSGQIRHSDQNQQT | 283 | 2.600 | 12.884 | 1.170 | 0.320 |
| GGQVAPSSGQNQQT | 284 | 2.581 | 2.427 | 1.433 | 0.709 |
| GSFSMHTHGQNQQT | 285 | 2.535 | 0.118 | 1.027 | 0.693 |
| GSGQNQQVIQGSNT | 286 | 2.521 | 8.778 | 0.935 | 0.810 |
| GRVLHSHAGQNQQT | 287 | 2.513 | 0.826 | 1.294 | 0.908 |
| GSGQNQQTSLQDQT | 288 | 2.505 | 0.500 | 0.315 | 0.968 |
| GSGLGRAPVQNQQT | 289 | 2.503 | 2.214 | 0.841 | 0.383 |
| GNGFSSASGQNQQT | 290 | 2.493 | 0.772 | 0.240 | 0.182 |
| GSGQMASRESNQQT | 291 | 2.492 | 0.300 | 0.341 | 0.288 |
| GPGLPNHSGQNQQT | 292 | 2.486 | 1.992 | 1.197 | 0.659 |
| GNIQWQGSGQNQQT | 293 | 2.468 | 6.266 | 1.182 | 0.837 |
| GMSAHMSSGQNQQT | 294 | 2.456 | 5.255 | 1.310 | 0.947 |
| GHSFVNRSGQNQQT | 295 | 2.447 | 11.148 | 1.305 | 0.756 |
| GRAVMDHSGQNQQT | 296 | 2.408 | 3.209 | 0.728 | 0.283 |
| GALTVMQSGQNQQT | 297 | 2.381 | 0.430 | 0.246 | 0.199 |
| GSGQRSPVLPNQQT | 298 | 2.369 | 6.230 | 0.434 | 0.526 |
| GSGQNGHLSLKQQT | 299 | 2.362 | 1.896 | 0.718 | 0.270 |
| GSLPRGTSDQNQQT | 300 | 2.362 | 0.000 | 0.453 | 0.495 |
| GVAGSLVSGQNQQT | 301 | 2.358 | 7.670 | 1.321 | 1.160 |
| GRGGIPQSGQNQQT | 302 | 2.352 | 8.683 | 1.639 | 1.181 |
| GSGQYASSIPNQQT | 303 | 2.346 | 3.321 | 1.022 | 0.489 |
| GTDFGRQSSQNQQT | 304 | 2.346 | 3.196 | 1.021 | 0.797 |
| GIFMQTPSGQNQQT | 305 | 2.344 | 6.198 | 0.938 | 0.252 |
| GSGQNQQTRLVDLT | 306 | 2.342 | 9.348 | 1.268 | 0.490 |
| GTREMPLSGQNQQT | 307 | 2.339 | 2.830 | 1.436 | 0.538 |
| GSRLVHVHGQNQQT | 308 | 2.334 | 1.174 | 1.277 | 0.934 |
| GSGRLVPNGPNQQT | 309 | 2.314 | 3.925 | 0.639 | 0.411 |
| GSGYLRESPQNQQT | 310 | 2.311 | 0.878 | 0.331 | 0.677 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GARIQNASGQKQQT | 311 | 2.300 | 2.103 | 1.220 | 1.039 |
| GLSNPMPSGQNQQT | 312 | 2.280 | 6.033 | 1.190 | 0.829 |
| GSTVQDTRGQNQQT | 313 | 2.270 | 4.979 | 0.576 | 0.473 |
| GPFGMPSSGQNQQT | 314 | 2.260 | 2.700 | 0.727 | 0.560 |
| GSGQNHGVLSNQQT | 315 | 2.254 | 1.603 | 1.113 | 0.701 |
| GSGYSMSQAQNQQT | 316 | 2.250 | 4.479 | 0.519 | 0.329 |
| GSGMLTHTLQNQQT | 317 | 2.246 | 2.272 | 0.496 | 0.199 |
| GRGSPHASRQNQQT | 318 | 2.241 | 0.000 | 5.050 | 5.856 |
| GLSWPSTSGQNQQT | 319 | 2.238 | 0.000 | 0.910 | 0.610 |
| GNSMERTSGQNQQT | 320 | 2.221 | 4.177 | 1.047 | 0.935 |
| GSGMSPSTLQNQQT | 321 | 2.216 | 3.053 | 0.318 | 0.153 |
| GSGHGQVLSQNQQT | 322 | 2.213 | 12.133 | 1.880 | 0.661 |
| GRGQIYSTGGNQQT | 323 | 2.210 | 11.629 | 1.329 | 0.743 |
| GVVAAHNSGQNQQT | 324 | 2.202 | 1.301 | 1.196 | 1.336 |
| GDSSLRHSGQNQQT | 325 | 2.194 | 0.000 | 0.662 | 0.412 |
| GSLVSQGAGQNQQT | 326 | 2.188 | 4.414 | 1.436 | 1.246 |
| GSLLQAHSGQNQQT | 327 | 2.182 | 1.008 | 0.575 | 0.748 |
| GSGHIYVGIQNQQT | 328 | 2.178 | 6.428 | 0.989 | 0.337 |
| GHHTTVQSGQNQQT | 329 | 2.177 | 6.245 | 0.851 | 0.755 |
| GSRQSKRNELNQQT | 330 | 2.177 | 0.000 | 1.325 | 0.232 |
| GSGQNQQHVSSPRT | 331 | 2.176 | 1.279 | 1.847 | 0.938 |
| GSSKELLWGQNQQT | 332 | 2.163 | 0.000 | 0.506 | 0.883 |
| GSLSTPSSGQNQQT | 333 | 2.159 | 1.279 | 1.094 | 0.669 |
| GSIGYAGQGQNQQT | 334 | 2.157 | 4.951 | 1.604 | 0.712 |
| GSGQNQRVSNSQQT | 335 | 2.146 | 0.492 | 1.086 | 0.985 |
| GSGYASHVQQNQQT | 336 | 2.146 | 3.038 | 1.157 | 0.758 |
| GSGEYSRSGQNQQT | 337 | 2.145 | 0.745 | 0.617 | 0.205 |
| GSVSTHSSGQNQQT | 338 | 2.145 | 3.446 | 1.198 | 0.918 |
| GSGQNQHSLGNYQT | 339 | 2.143 | 1.896 | 1.077 | 0.606 |
| GSGGLDTRGQNQQT | 340 | 2.139 | 6.216 | 0.236 | 0.197 |
| GNILHATSGQNQQT | 341 | 2.136 | 0.125 | 1.159 | 0.424 |
| GSGQSYTMTQNQQT | 342 | 2.136 | 6.755 | 0.297 | 0.231 |
| GSGQNQHSAPNSQT | 343 | 2.134 | 4.143 | 1.187 | 0.731 |
| GSGQNQQTMDHNRT | 344 | 2.130 | 4.944 | 0.642 | 0.440 |
| GSNGGVGTGQNQQT | 345 | 2.130 | 0.788 | 1.191 | 1.087 |
| GAGSIIPSGQNQQT | 346 | 2.129 | 7.164 | 0.595 | 0.249 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGQTHGGQHNQQT | 347 | 2.125 | 12.251 | 1.448 | 1.098 |
| GSNLSFQSGQNQQT | 348 | 2.122 | 5.853 | 1.087 | 0.719 |
| GATLQVHSGQNQQT | 349 | 2.122 | 2.219 | 0.623 | 0.545 |
| GSGFNQRSEQNQQT | 350 | 2.121 | 4.491 | 1.770 | 0.758 |
| GSGSLRDFDQNQQT | 351 | 2.120 | 6.846 | 0.586 | 0.272 |
| GSGDSITGKQNQQT | 352 | 2.112 | 1.295 | 0.793 | 0.306 |
| GSGQDRNIVQNQQT | 353 | 2.112 | 0.229 | 0.454 | 0.632 |
| GSGLSHSHQQNQQT | 354 | 2.109 | 5.852 | 1.256 | 0.592 |
| GSGQNQQTGMSSVK | 355 | 2.109 | 4.544 | 1.451 | 0.679 |
| GSVTHGISGQNQQT | 356 | 2.105 | 4.542 | 1.135 | 0.789 |
| GVVAHQPSGQNQQT | 357 | 2.103 | 0.152 | 0.910 | 2.267 |
| GSGPILGQLQNQQT | 358 | 2.097 | 2.058 | 0.470 | 0.123 |
| GSGHVPNSGLNQQT | 359 | 2.091 | 0.653 | 1.636 | 1.154 |
| GDAGVRSSGQNQQT | 360 | 2.068 | 3.918 | 1.033 | 1.193 |
| GSGSQLMSLQNQQT | 361 | 2.065 | 3.559 | 0.563 | 0.172 |
| GSGLDYSQRQNQQT | 362 | 2.056 | 0.837 | 0.484 | 0.217 |
| GSGQSSGRLINKQT | 363 | 2.055 | 28.135 | 0.543 | 0.277 |
| GSSVSPSSGQNQQT | 364 | 2.054 | 0.579 | 1.064 | 0.787 |
| GSGQVVGLSGNQQT | 365 | 2.052 | 7.212 | 0.785 | 0.881 |
| GSNMGVPLGQNQQT | 366 | 2.049 | 2.448 | 0.334 | 0.420 |
| GSFYPSSTGQNQQT | 367 | 2.047 | 2.374 | 0.420 | 0.277 |
| GSGQNQQTRLTDLT | 368 | 2.046 | 8.470 | 0.910 | 0.776 |
| GPTNGRSSGQNQQT | 369 | 2.034 | 8.903 | 0.936 | 1.308 |
| GSGLLHGKLQNQQT | 370 | 2.032 | 2.521 | 1.068 | 0.917 |
| GANMGHVSGQNQQT | 371 | 2.020 | 0.810 | 1.302 | 1.138 |
| GSGQNQQSGRGDLT | 372 | 2.019 | 6.919 | 0.524 | 1.152 |
| GSHGHYASGQKQQT | 373 | 2.016 | 0.000 | 0.895 | 0.685 |
| GSGDLRISPQNQQT | 374 | 2.012 | 16.207 | 0.620 | 0.237 |
| GSGMPVILGQNQQT | 375 | 2.005 | 0.150 | 0.840 | 0.287 |
| GRGVITSSGQNHQT | 376 | 2.004 | 0.864 | 1.656 | 0.669 |
| GSGHSVSGPQNQQT | 377 | 1.993 | 6.259 | 1.370 | 0.619 |
| GSRNGHTVGRNQQT | 378 | 1.993 | 0.000 | 1.162 | 0.367 |
| GAGVHMVSGQNQQT | 379 | 1.987 | 6.488 | 1.055 | 0.791 |
| GSGQNHRPSVLQQT | 380 | 1.983 | 5.582 | 0.433 | 0.582 |
| GSGSPRDSIQNQQT | 381 | 1.981 | 4.914 | 0.171 | 0.446 |
| GSGQGIHSSVNQQT | 382 | 1.981 | 4.873 | 0.632 | 0.634 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGQQLSITPNQQT | 383 | 1.979 | 10.280 | 0.845 | 0.201 |
| GGYHSQTSGQNQQT | 384 | 1.978 | 2.642 | 1.740 | 1.525 |
| GSLHHDNHGQNQQT | 385 | 1.976 | 0.980 | 0.968 | 0.463 |
| GIMARDSSGQNQQT | 386 | 1.972 | 3.486 | 1.320 | 0.904 |
| GVVHITNSGQNQQT | 387 | 1.969 | 0.504 | 0.794 | 0.846 |
| GSGQNQHSAPFNQT | 388 | 1.969 | 0.499 | 0.759 | 0.870 |
| GSGQTSGLKQNQQT | 389 | 1.968 | 3.927 | 0.394 | 0.334 |
| GSGQNQQTSLSNTA | 390 | 1.959 | 1.186 | 1.567 | 1.182 |
| GSGQNQAVHNKSQT | 391 | 1.956 | 3.791 | 1.465 | 1.083 |
| GVHTHLPSGQNQQT | 392 | 1.952 | 1.364 | 1.414 | 0.796 |
| GHLTMHNSGQNHQT | 393 | 1.938 | 1.798 | 1.030 | 0.586 |
| GSGSSSRPYQNQQT | 394 | 1.934 | 3.823 | 0.962 | 0.496 |
| GILLATPSGQNQQT | 395 | 1.931 | 8.205 | 1.341 | 0.288 |
| GSGQNAGSFPNQQT | 396 | 1.928 | 12.575 | 1.091 | 0.286 |
| GSRDGHTVGQNQQT | 397 | 1.928 | 7.089 | 0.495 | 0.661 |
| GSLLISTSGQNQQT | 398 | 1.919 | 5.763 | 1.488 | 0.808 |
| GSGAMPSHGQNQQT | 399 | 1.915 | 0.000 | 1.142 | 0.912 |
| GALVSPISGQNQQT | 400 | 1.912 | 1.051 | 0.640 | 0.347 |
| GSLSSHGVGQNQQT | 401 | 1.911 | 7.498 | 1.218 | 0.804 |
| GSGQNQQASLAMRT | 402 | 1.910 | 3.577 | 2.066 | 1.638 |
| GPGLGSHSGQNQQT | 403 | 1.906 | 14.563 | 0.880 | 1.195 |
| GHDSQHKSGQNQQT | 404 | 1.904 | 6.988 | 1.154 | 0.869 |
| GSGLTLSATQNQQT | 405 | 1.901 | 0.193 | 0.708 | 0.340 |
| GSGQVVAHVGNQQT | 406 | 1.901 | 0.833 | 0.800 | 0.321 |
| GSGLRTMTTQNQQT | 407 | 1.900 | 8.939 | 0.838 | 0.594 |
| GSGQVGRLLQNQQT | 408 | 1.899 | 1.762 | 0.773 | 0.748 |
| GSGQLSHQSVNQQT | 409 | 1.898 | 4.032 | 0.720 | 0.695 |
| GSGDRYQTLQNQQT | 410 | 1.897 | 1.075 | 0.645 | 0.318 |
| GSGQNQQLKSSAQT | 411 | 1.891 | 1.197 | 0.908 | 0.716 |
| GSGQNQYSIPVAQT | 412 | 1.891 | 1.194 | 0.511 | 0.297 |
| GSGERLHLTQNQQT | 413 | 1.885 | 1.456 | 0.387 | 0.245 |
| GSGHNQQVRTAPNT | 414 | 1.885 | 1.022 | 1.006 | 0.580 |
| GGLSHVMSGQNQQT | 415 | 1.875 | 0.403 | 0.885 | 0.378 |
| GSGQSHRDVLNQQT | 416 | 1.872 | 15.082 | 0.138 | 0.280 |
| GSGQNLAGRMDQQT | 417 | 1.864 | 0.085 | 0.362 | 0.295 |
| GSGQNQQTNRGNPM | 418 | 1.860 | 3.402 | 1.349 | 1.098 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGQSYQRDHNQQT | 419 | 1.859 | 8.013 | 0.779 | 0.323 |
| GSLLSAGMGQNQHT | 420 | 1.856 | 6.168 | 0.589 | 0.342 |
| GSGQNQQTAIYRNI | 421 | 1.854 | 2.207 | 0.818 | 1.437 |
| GSGQNQQTSGTTNC | 422 | 1.854 | 8.161 | 1.040 | 0.806 |
| GMTSHSVSGQNQQT | 423 | 1.850 | 2.732 | 0.220 | 0.154 |
| GSSQSTGYQPNQQT | 424 | 1.847 | 3.388 | 0.522 | 0.577 |
| GSLKPTTLGQNQQT | 425 | 1.840 | 0.476 | 0.175 | 0.220 |
| GRMFSLGSGQNQQT | 426 | 1.836 | 8.429 | 1.630 | 1.174 |
| GSGQNQQTALGVKC | 427 | 1.835 | 1.343 | 1.378 | 1.014 |
| GAMVSHSSGQNQQT | 428 | 1.833 | 8.999 | 0.739 | 0.868 |
| GSGQNQQRNSDSVT | 429 | 1.829 | 0.000 | 1.238 | 0.842 |
| GSGQSMTLHLNQQT | 430 | 1.827 | 0.991 | 0.721 | 0.248 |
| GSGQVHQAEVNQQT | 431 | 1.825 | 0.152 | 0.436 | 0.287 |
| GSGQNQSQNHLQQT | 432 | 1.825 | 0.600 | 1.063 | 0.772 |
| GSLLTTASGQNQQT | 433 | 1.822 | 0.780 | 0.938 | 0.635 |
| GSGLIRTAAQNQQT | 434 | 1.822 | 8.339 | 0.808 | 0.998 |
| GSGQNQQTVSRQST | 435 | 1.820 | 0.472 | 1.330 | 0.796 |
| GSGQYANHGINQQT | 436 | 1.820 | 5.717 | 0.906 | 0.701 |
| GSRSTGPSGQNQQT | 437 | 1.819 | 2.479 | 0.440 | 0.466 |
| GRGVQQKLQQNQQT | 438 | 1.817 | 0.000 | 1.974 | 0.823 |
| GSGQNQQVHLSTGT | 439 | 1.811 | 0.266 | 1.011 | 0.455 |
| GSGQNQQLSAKSST | 440 | 1.809 | 1.567 | 1.224 | 1.115 |
| GSGYKAARPQNQQT | 441 | 1.803 | 0.000 | 1.418 | 0.337 |
| GSAGISPSGQNQQT | 442 | 1.797 | 1.812 | 0.784 | 0.622 |
| GSGQNRAHAFLQQT | 443 | 1.795 | 0.000 | 1.200 | 1.271 |
| GSGLSGITMQNQQT | 444 | 1.792 | 14.796 | 0.862 | 0.496 |
| GPGSAHSSGQNQQT | 445 | 1.785 | 4.392 | 1.099 | 0.872 |
| GSSHTQALGQNQQT | 446 | 1.784 | 0.143 | 0.882 | 0.874 |
| GSGVHGVSSQNQQT | 447 | 1.781 | 4.519 | 1.504 | 0.951 |
| GSSGRDMGGQNQQT | 448 | 1.778 | 2.177 | 1.052 | 0.595 |
| GERAFPTSGQNQQT | 449 | 1.775 | 6.515 | 0.972 | 0.362 |
| GGRIVSLSGQNQQT | 450 | 1.766 | 4.936 | 1.161 | 0.847 |
| GSGQNSYSHTSQQT | 451 | 1.765 | 2.262 | 1.130 | 0.658 |
| GLGYPGSSGQNQQT | 452 | 1.763 | 7.090 | 0.929 | 0.577 |
| GSGPQSHTGQNQQT | 453 | 1.757 | 9.490 | 0.958 | 0.447 |
| GSGQNQQLSRDAST | 454 | 1.754 | 3.716 | 1.877 | 0.611 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGQILHSVPNQQT | 455 | 1.752 | 1.316 | 0.398 | 0.240 |
| GSGFHTDSRQNQQT | 456 | 1.748 | 4.384 | 7.344 | 0.575 |
| GSGQSHSLATNQQT | 457 | 1.745 | 2.711 | 1.021 | 0.343 |
| GSGQNQQTLSKPWT | 458 | 1.743 | 0.253 | 0.845 | 0.733 |
| GSGHAAISQQNQQT | 459 | 1.742 | 2.373 | 1.211 | 0.520 |
| GSGQNQQQIGGNST | 460 | 1.741 | 6.169 | 0.877 | 0.576 |
| GGGPMAGSGQNQQT | 461 | 1.735 | 2.815 | 1.049 | 0.372 |
| GMRMEYQSGQNQQT | 462 | 1.729 | 3.695 | 0.644 | 0.632 |
| GSGQNQQGTLLHQT | 463 | 1.728 | 2.065 | 1.347 | 1.303 |
| GSGQNQRSSGGVQT | 464 | 1.723 | 2.056 | 1.805 | 1.165 |
| GSGQNQRGALATQT | 465 | 1.722 | 1.117 | 0.899 | 0.891 |
| GSGTVHAATQNQQT | 466 | 1.721 | 1.676 | 0.563 | 0.476 |
| GSRMTQQFGQNQQT | 467 | 1.720 | 25.798 | 1.233 | 0.976 |
| GSSSPGASGQNQQT | 468 | 1.717 | 1.244 | 1.378 | 0.660 |
| GHPSPHVSGQNQQT | 469 | 1.713 | 0.416 | 0.551 | 0.488 |
| GSGSHHASRQNQQT | 470 | 1.712 | 0.451 | 3.073 | 0.584 |
| GAVGHSYSGQNQQT | 471 | 1.706 | 0.808 | 0.306 | 0.536 |
| GSRSQYDIGQNQQT | 472 | 1.706 | 0.112 | 0.528 | 0.193 |
| GSGQGPQERGNQQT | 473 | 1.702 | 1.269 | 0.846 | 0.313 |
| GSIAHVGTGQNQQT | 474 | 1.696 | 1.264 | 0.837 | 1.045 |
| GSGQNQQKQNHGNT | 475 | 1.695 | 5.349 | 1.538 | 1.340 |
| GSGQNQQALGSQRT | 476 | 1.695 | 1.934 | 1.419 | 0.562 |
| GSGAITHMPQNQQT | 477 | 1.695 | 1.681 | 0.647 | 0.411 |
| GSGQRNPLLLNQQT | 478 | 1.693 | 0.144 | 0.662 | 0.740 |
| GSSGIPVSHQNQQT | 479 | 1.690 | 3.384 | 0.820 | 0.333 |
| GVHSLTPSGQNQQT | 480 | 1.687 | 4.104 | 0.475 | 0.215 |
| GVIVLHGSGQNQQT | 481 | 1.682 | 14.166 | 1.074 | 1.098 |
| GGTRVVDSGQNQQT | 482 | 1.676 | 9.735 | 0.676 | 0.370 |
| GSGGVTYQSQNQQT | 483 | 1.673 | 7.283 | 0.649 | 0.181 |
| GSGQNQAGHGPGQT | 484 | 1.670 | 2.861 | 1.040 | 0.887 |
| GSGQLVTSGPNQQT | 485 | 1.669 | 5.271 | 0.964 | 0.433 |
| GSGIAAQRTQNQQT | 486 | 1.665 | 2.691 | 1.062 | 0.754 |
| GSTPAGVGGQNQQT | 487 | 1.663 | 2.733 | 0.593 | 0.477 |
| GSGQNQQTSTGVHS | 488 | 1.660 | 8.271 | 1.039 | 1.075 |
| GSGQIRQLVDNQQT | 489 | 1.657 | 5.529 | 0.314 | 0.272 |
| GSLIGMQSGQNQQT | 490 | 1.656 | 6.783 | 0.797 | 0.392 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGQIKGKMDNQQT | 491 | 1.654 | 2.601 | 1.065 | 1.012 |
| GSGSDMSSWQNQQT | 492 | 1.651 | 0.175 | 0.281 | 0.303 |
| GRGQNQQHTGLATT | 493 | 1.650 | 6.174 | 1.134 | 0.691 |
| GSGQNQQTLYSSNT | 494 | 1.642 | 1.044 | 0.664 | 0.368 |
| GSGQTQVLKSNQQT | 495 | 1.640 | 3.031 | 1.599 | 0.975 |
| GSRTLSNVGQNQQT | 496 | 1.640 | 3.219 | 0.617 | 0.542 |
| GSGVQHSLPQNQQT | 497 | 1.639 | 0.764 | 0.440 | 0.387 |
| GNYLHQASGQNQQT | 498 | 1.635 | 1.454 | 0.816 | 0.181 |
| GSGGTSVHQQNQQT | 499 | 1.629 | 0.000 | 0.585 | 0.195 |
| GMDHSRPSGQNQQT | 500 | 1.627 | 3.976 | 0.918 | 0.648 |
| GSGQNQQSMGTFTT | 501 | 1.625 | 0.000 | 1.792 | 0.399 |
| GSGQNQQTPLRPPT | 502 | 1.624 | 0.352 | 0.874 | 0.472 |
| GSGQNQHHSVSQQT | 503 | 1.623 | 3.700 | 0.605 | 0.334 |
| GSGQLRSLSTNQQT | 504 | 1.622 | 6.855 | 1.310 | 0.382 |
| GSGSPRQLSQNQQT | 505 | 1.621 | 0.873 | 0.520 | 0.273 |
| GSGQNQQTTASSHT | 506 | 1.618 | 7.404 | 0.745 | 0.678 |
| GRGQVVSTHQNQQT | 507 | 1.607 | 3.318 | 0.931 | 0.561 |
| GSAQVSMVGQNQQT | 508 | 1.601 | 1.332 | 0.500 | 0.285 |
| GSSTLVTIGKNQQT | 509 | 1.592 | 4.316 | 0.917 | 0.819 |
| GFAHQASSGQNQQT | 510 | 1.587 | 1.852 | 1.638 | 1.080 |
| GSGQPVLSISNQQT | 511 | 1.586 | 2.695 | 0.390 | 0.282 |
| GSGQSHRSELNQQT | 512 | 1.585 | 11.974 | 0.668 | 0.256 |
| GSSVGSPIGQNQQT | 513 | 1.584 | 3.574 | 1.059 | 0.706 |
| GSGMPIRNVQNQQT | 514 | 1.584 | 0.138 | 0.684 | 0.631 |
| GSSTRVDSGQNQQT | 515 | 1.584 | 2.774 | 0.704 | 0.660 |
| GSGQNQQTAMRSTT | 516 | 1.581 | 2.588 | 0.656 | 0.665 |
| GSGQNQQHSSSHLT | 517 | 1.581 | 2.782 | 1.091 | 0.859 |
| GSRNGHAVGQNQQT | 518 | 1.574 | 2.688 | 0.434 | 0.939 |
| GLGAYQSSGQNQQT | 519 | 1.574 | 0.696 | 1.407 | 0.688 |
| GPGLSGHSGQNQQT | 520 | 1.571 | 1.603 | 1.154 | 1.297 |
| GSTGIVSSGQNQQT | 521 | 1.570 | 0.927 | 2.141 | 1.046 |
| GSRTTQVIGQNQQT | 522 | 1.570 | 1.838 | 0.773 | 0.564 |
| GSGLLHRAQQNQQT | 523 | 1.569 | 0.724 | 1.583 | 0.646 |
| GSGQNAQQAAAQQT | 524 | 1.568 | 4.239 | 0.937 | 0.604 |
| GSGQNQQSALRTQT | 525 | 1.568 | 1.913 | 1.581 | 1.421 |
| GSGFLSDTRQNQQT | 526 | 1.566 | 45.953 | 0.473 | 0.575 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGLLYHDQQNQQT | 527 | 1.565 | 2.760 | 0.405 | 0.107 |
| GSGQNQHYSLHKQT | 528 | 1.563 | 3.399 | 1.485 | 1.273 |
| GSGHSPLPQQNQQT | 529 | 1.562 | 0.556 | 0.387 | 0.247 |
| GNGHSMRPNQNQQT | 530 | 1.560 | 2.341 | 0.693 | 0.376 |
| GSGLKWSTLQNQQT | 531 | 1.556 | 0.000 | 1.134 | 2.442 |
| GSGQMGRQAVNQQT | 532 | 1.554 | 1.529 | 0.535 | 0.411 |
| GSGQNQQTSGVLTL | 533 | 1.553 | 0.000 | 1.104 | 0.782 |
| GSGQNQQALHNPHT | 534 | 1.553 | 0.664 | 0.638 | 0.213 |
| GSGQNQQVIPNSKT | 535 | 1.548 | 1.036 | 0.844 | 0.376 |
| GSPLQDRVGQNQQT | 536 | 1.548 | 0.753 | 0.469 | 0.391 |
| GSGQNQYSSTNPQT | 537 | 1.542 | 2.251 | 0.544 | 0.535 |
| GAMTVTISGQNQQT | 538 | 1.542 | 6.249 | 0.443 | 0.257 |
| GSGQNQQLQTLIRT | 539 | 1.538 | 1.425 | 0.813 | 0.514 |
| GSGLRQTSQQNQQT | 540 | 1.537 | 2.067 | 0.978 | 0.705 |
| GSGQNQQTGLRQQT | 541 | 1.533 | 2.120 | 1.217 | 1.103 |
| GSGQTRQMKDNQQT | 542 | 1.530 | 11.079 | 0.841 | 0.214 |
| GSGQNHGLQSGQQT | 543 | 1.530 | 4.960 | 0.938 | 0.779 |
| GSGQSHRQPENQQT | 544 | 1.529 | 2.153 | 0.209 | 0.159 |
| GSGQDRHIVQNQQT | 545 | 1.527 | 11.068 | 0.285 | 0.162 |
| GSGQNQQLPHSNLT | 546 | 1.521 | 1.838 | 0.442 | 0.283 |
| GSGQLSVPYDNQQT | 547 | 1.521 | 0.000 | 0.622 | 0.111 |
| GSGRNPQTQPLQQT | 548 | 1.519 | 0.040 | 0.733 | 0.573 |
| GSGQPYSTGLNQQT | 549 | 1.519 | 1.403 | 0.612 | 0.376 |
| GSGQNQQTHGGLRD | 550 | 1.519 | 6.487 | 1.913 | 1.298 |
| GAYGMVSSGQNQQT | 551 | 1.518 | 3.469 | 0.732 | 0.773 |
| GSGIQSSYSQNQQT | 552 | 1.517 | 15.978 | 1.032 | 0.684 |
| GPRLSDQSGQNQQT | 553 | 1.511 | 0.364 | 0.640 | 0.579 |
| GSGQNQQTHPSPCT | 554 | 1.510 | 1.003 | 1.120 | 0.546 |
| GSGQSFQMHTNQQT | 555 | 1.504 | 9.770 | 0.503 | 0.325 |
| GSGQNQQTGNPKHT | 556 | 1.504 | 5.973 | 1.391 | 1.139 |
| GFSSAVHSGQNQQT | 557 | 1.502 | 1.234 | 0.218 | 0.210 |
| GSGQNQQTSMSNAT | 558 | 1.501 | 6.766 | 1.605 | 0.745 |
| GSGQDMKQHHNQQT | 559 | 1.501 | 1.638 | 0.358 | 0.239 |
| GLRLSTPSGQNQQT | 560 | 1.498 | 4.334 | 0.804 | 0.522 |
| GSGQNQQTSVYMNT | 561 | 1.498 | 0.613 | 0.640 | 0.983 |
| GSGQNQYSQSSMQT | 562 | 1.494 | 4.278 | 0.375 | 0.309 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGQNQQSMADHTT | 563 | 1.494 | 1.728 | 0.428 | 0.215 |
| GWERSFVSGQNQQT | 564 | 1.492 | 0.943 | 0.490 | 0.538 |
| GLLAGKSSGQNQQT | 565 | 1.491 | 2.981 | 0.999 | 0.946 |
| GKSFVPQSGQNQQT | 566 | 1.489 | 2.502 | 1.798 | 0.430 |
| GSGQMQSAGSNQQT | 567 | 1.482 | 0.116 | 1.034 | 1.128 |
| GSDQNQRLTSSMQT | 568 | 1.479 | 0.164 | 0.875 | 0.670 |
| GESRAVLSGQNQQT | 569 | 1.476 | 0.938 | 0.789 | 0.368 |
| GSVFGVPSGQNQQT | 570 | 1.474 | 1.248 | 0.685 | 0.213 |
| GSGLPDRNLQNQQT | 571 | 1.471 | 7.306 | 1.136 | 0.611 |
| GSGTHNSAIQNQQT | 572 | 1.469 | 0.570 | 0.762 | 0.574 |
| GSGMIIASMQNQQT | 573 | 1.469 | 6.722 | 1.135 | 0.415 |
| GGITWTDSGQNQQT | 574 | 1.462 | 4.535 | 1.472 | 0.468 |
| GSGQNQQASGRQQT | 575 | 1.458 | 3.179 | 0.943 | 0.991 |
| GSGQNQQPHLKSLT | 576 | 1.457 | 5.016 | 1.096 | 0.740 |
| GPPQHMTSGQNQQT | 577 | 1.457 | 1.547 | 0.509 | 0.677 |
| GSGQNQQASLPSRT | 578 | 1.456 | 0.389 | 0.930 | 0.673 |
| GSGQIVSTQTNQQT | 579 | 1.456 | 1.103 | 0.453 | 0.512 |
| GSGKGHSAGQNQQT | 580 | 1.453 | 0.936 | 1.035 | 1.173 |
| GSGQNTRLQLGQQT | 581 | 1.452 | 1.747 | 0.181 | 0.234 |
| GSVGSRPVGQNQQT | 582 | 1.442 | 11.363 | 1.182 | 0.716 |
| GSSHTLALGQNQQT | 583 | 1.441 | 7.071 | 0.851 | 0.406 |
| GMYEYSQSGQNQQT | 584 | 1.438 | 0.000 | 1.410 | 0.448 |
| GNGQNQQHSILHGT | 585 | 1.435 | 0.000 | 0.777 | 0.415 |
| GSGYNQPHLQNQQT | 586 | 1.435 | 4.512 | 0.711 | 0.395 |
| GPLVNASSGQNQQT | 587 | 1.434 | 5.239 | 0.831 | 0.343 |
| GSGQNQQVLTTART | 588 | 1.434 | 4.142 | 1.071 | 0.948 |
| GSGQNQHSVHNDQT | 589 | 1.428 | 0.000 | 0.521 | 0.515 |
| GAGLIMHSGQNQQT | 590 | 1.425 | 1.408 | 0.565 | 0.511 |
| GMGRHSASGQNQQT | 591 | 1.417 | 6.500 | 0.470 | 0.389 |
| GSHSQSGHGQNQQT | 592 | 1.413 | 1.240 | 0.696 | 0.318 |
| GSSTTIVSGQNHQT | 593 | 1.411 | 0.000 | 0.993 | 0.672 |
| GRHLVTASGQNQQT | 594 | 1.411 | 2.885 | 0.648 | 0.404 |
| GSGQNQQHANLNQT | 595 | 1.410 | 0.094 | 0.416 | 0.544 |
| GSGSTHSKAQNQQT | 596 | 1.410 | 0.515 | 0.921 | 0.801 |
| GSGQNKQMLSGNTT | 597 | 1.410 | 2.219 | 1.074 | 0.404 |
| GSGQVHNPTQNQQT | 598 | 1.410 | 2.488 | 1.021 | 0.542 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGQNQQIPHVHQT | 599 | 1.409 | 0.768 | 0.576 | 0.218 |
| GSLHAGLSGQNQQT | 600 | 1.408 | 1.739 | 1.286 | 0.936 |
| GPAQHGTSGQNQQT | 601 | 1.407 | 0.866 | 1.030 | 0.615 |
| GEKAVTSSGQNQQT | 602 | 1.402 | 0.998 | 0.558 | 0.327 |
| GSGQNQQTMANGQR | 603 | 1.394 | 0.216 | 1.169 | 1.230 |
| GSGSPHSKDQNQQT | 604 | 1.394 | 0.000 | 2.041 | 4.680 |
| GSFSMGYGGQNQQT | 605 | 1.393 | 18.476 | 1.908 | 1.030 |
| GSGTHLVSLQNQQT | 606 | 1.392 | 0.000 | 0.715 | 1.167 |
| GSGQMQPHVQNQQT | 607 | 1.389 | 9.381 | 0.387 | 0.153 |
| GSGQNQQVAGLNNT | 608 | 1.386 | 3.218 | 0.449 | 0.492 |
| GSSQNQQHDMRLRT | 609 | 1.386 | 2.645 | 0.669 | 0.552 |
| GPASLPISGQNQQT | 610 | 1.386 | 9.008 | 0.312 | 0.155 |
| GSGQNQQPPLATRT | 611 | 1.386 | 2.295 | 0.593 | 0.287 |
| GSSRVPVSGQNQQT | 612 | 1.385 | 13.191 | 0.870 | 0.485 |
| GSGQNQQTNLGHTT | 613 | 1.383 | 1.523 | 1.343 | 1.281 |
| GSGQNQQLVSRVQT | 614 | 1.381 | 1.195 | 0.656 | 0.466 |
| GPNSYPVSGQKQQT | 615 | 1.381 | 4.040 | 0.736 | 0.834 |
| GHAHYQASGQNQQT | 616 | 1.377 | 7.299 | 0.803 | 0.745 |
| GSGQALLSTGNQQT | 617 | 1.377 | 0.847 | 0.536 | 0.370 |
| GSGQLPRQMTNQQT | 618 | 1.376 | 3.550 | 0.400 | 0.562 |
| GSGFPKSTEQNQQT | 619 | 1.376 | 2.058 | 0.610 | 0.194 |
| GSRETSLSGQNQQT | 620 | 1.373 | 5.193 | 1.364 | 0.203 |
| GSGQNQQGTGVSHT | 621 | 1.371 | 4.295 | 1.417 | 0.749 |
| GSRTVPVYGQNQQT | 622 | 1.371 | 0.363 | 1.226 | 0.969 |
| GSNAQSAHGQNQQT | 623 | 1.371 | 0.888 | 0.976 | 0.245 |
| GAFHLAASGQNQQT | 624 | 1.369 | 18.165 | 0.994 | 0.775 |
| GSGQYRSSSDNQQT | 625 | 1.369 | 6.209 | 0.681 | 0.409 |
| GSGQVYISTPNQQT | 626 | 1.367 | 0.000 | 0.859 | 0.282 |
| GSGVSTQLLQNQQT | 627 | 1.367 | 2.467 | 0.928 | 0.509 |
| GSGQLGLSVTNQQT | 628 | 1.364 | 6.906 | 1.395 | 0.376 |
| GSGSNMRLSQNQQT | 629 | 1.363 | 0.588 | 0.962 | 0.730 |
| GSGQNLHSGLPQQT | 630 | 1.363 | 1.594 | 1.054 | 0.592 |
| GSSHTLALGQNKQT | 631 | 1.362 | 2.160 | 0.838 | 0.643 |
| GSGQNQHSLPAHRT | 632 | 1.361 | 0.700 | 0.911 | 0.742 |
| GSGQNQGTVYPNQT | 633 | 1.358 | 7.648 | 0.835 | 0.815 |
| GSGQNQQPSLRQST | 634 | 1.356 | 2.905 | 1.315 | 0.554 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGQNARLKDNQQT | 635 | 1.354 | 2.395 | 0.580 | 0.938 |
| GHAGSTGSGQNQQT | 636 | 1.352 | 2.829 | 1.332 | 1.233 |
| GSGQALSSSGNQQT | 637 | 1.351 | 6.860 | 0.894 | 0.931 |
| GSGASESHRQNQQT | 638 | 1.350 | 0.850 | 0.325 | 0.313 |
| GVGVITSSGQNQQT | 639 | 1.348 | 0.918 | 1.296 | 0.777 |
| GSLYGQSLGQNQQT | 640 | 1.348 | 11.248 | 0.894 | 0.843 |
| GSGQMSDVHGNQQT | 641 | 1.346 | 7.172 | 0.408 | 0.548 |
| GSGQNQQHSSKATT | 642 | 1.345 | 12.248 | 1.350 | 1.401 |
| GSGQNQQTSVSQQT | 643 | 1.342 | 1.614 | 1.030 | 0.913 |
| GSGQKMWKLDNQQT | 644 | 1.341 | 0.000 | 0.990 | 1.418 |
| GSGQNVSMQVNQQT | 645 | 1.341 | 0.000 | 0.357 | 0.251 |
| GSGQNQRATLSNQT | 646 | 1.339 | 1.084 | 0.947 | 0.723 |
| GSGQASSKSANQQT | 647 | 1.339 | 1.138 | 0.500 | 0.175 |
| GSGKNQTPIPKGQT | 648 | 1.339 | 5.077 | 1.306 | 1.154 |
| GSGQNQQTRQEGST | 649 | 1.339 | 0.000 | 0.645 | 0.718 |
| GASSLATSGQNQQT | 650 | 1.337 | 0.703 | 0.423 | 0.217 |
| GSGQRGSLTENQQT | 651 | 1.337 | 2.482 | 0.300 | 0.567 |
| GSEQTRQRGQNQQT | 652 | 1.333 | 2.172 | 0.574 | 0.815 |
| GSGQNQQTLTASKE | 653 | 1.333 | 1.152 | 0.981 | 1.172 |
| GSGTSGKTGKNQQT | 654 | 1.333 | 4.033 | 0.358 | 0.676 |
| GQLVTFTSGQNQQT | 655 | 1.331 | 11.282 | 0.819 | 0.294 |
| GSGQNQQSANKILT | 656 | 1.331 | 3.789 | 0.894 | 1.236 |
| GSGQNQQHSSHTT | 657 | 1.328 | 2.158 | 0.957 | 0.452 |
| GSGQNQKGMQPNQT | 658 | 1.326 | 3.139 | 0.775 | 1.059 |
| GSGQLVSGLYNQQT | 659 | 1.325 | 0.000 | 0.842 | 0.733 |
| GSSVGVPSGQNQQT | 660 | 1.322 | 4.867 | 0.336 | 1.157 |
| GSGQNQQWDSRRQT | 661 | 1.321 | 0.531 | 1.059 | 0.825 |
| GSEQTRQSGQNQQT | 662 | 1.321 | 0.514 | 0.734 | 0.900 |
| GSGIGSHIPQNQQT | 663 | 1.319 | 0.173 | 0.822 | 0.597 |
| GSGQNQRLHGVDQT | 664 | 1.318 | 4.655 | 0.459 | 0.341 |
| GEVSRVLSGQNQQT | 665 | 1.318 | 0.437 | 1.150 | 0.440 |
| GSGQNQQKVSPLLT | 666 | 1.314 | 1.602 | 0.755 | 0.806 |
| GSGLALERSQNQQT | 667 | 1.311 | 0.486 | 0.618 | 0.096 |
| GPDRIGSSGQNQQT | 668 | 1.308 | 0.426 | 0.654 | 0.342 |
| GSGQNQDHQNKQQT | 669 | 1.308 | 1.470 | 0.510 | 0.761 |
| GSGQNQQTALYNNT | 670 | 1.307 | 0.862 | 0.660 | 0.726 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGAVHLTAQNQQT | 671 | 1.306 | 1.668 | 0.541 | 0.466 |
| GSLVSTQSGQNQQT | 672 | 1.305 | 1.293 | 1.282 | 0.650 |
| GSGVSARMVQNQQT | 673 | 1.299 | 0.624 | 0.870 | 0.697 |
| GSGQTRMPLANQQT | 674 | 1.296 | 0.790 | 0.447 | 0.273 |
| GSGISSRNMQNQQT | 675 | 1.291 | 6.328 | 1.671 | 0.560 |
| GSGEKVHSGQNQQT | 676 | 1.289 | 0.062 | 0.862 | 0.671 |
| GSGQNQQKLSSMST | 677 | 1.286 | 1.586 | 1.160 | 1.052 |
| GSGQNQQTGQHMRV | 678 | 1.286 | 4.161 | 1.839 | 1.635 |
| GSGMIHTTAQNQQT | 679 | 1.285 | 0.105 | 0.678 | 0.276 |
| GSGQNWPALKGQQT | 680 | 1.284 | 2.031 | 1.101 | 1.222 |
| GASHMSISGQNQQT | 681 | 1.284 | 0.462 | 0.404 | 0.374 |
| GSDQNQQLGYSKQT | 682 | 1.283 | 0.000 | 0.853 | 0.660 |
| GIPSIRESGQNQQT | 683 | 1.282 | 0.166 | 0.484 | 0.254 |
| GSGIPSVKFQNQQT | 684 | 1.281 | 0.061 | 0.364 | 0.561 |
| GSGQNQQTSVSQNV | 685 | 1.281 | 0.750 | 0.788 | 0.715 |
| GSGQNQQIGESRMT | 686 | 1.279 | 0.103 | 0.890 | 0.453 |
| GSGSSSMSFQNQQT | 687 | 1.279 | 0.540 | 0.466 | 0.095 |
| GSGQKQERAVSKQT | 688 | 1.277 | 0.000 | 1.174 | 0.732 |
| GCTTRLNSGQNQQT | 689 | 1.276 | 0.000 | 0.184 | 0.618 |
| GSGQNQQIISTKIT | 690 | 1.275 | 0.000 | 0.951 | 0.710 |
| GSGQNQQKSLNGNT | 691 | 1.275 | 8.573 | 0.586 | 0.851 |
| GSGIPAPRLQNQQT | 692 | 1.273 | 4.162 | 0.583 | 0.396 |
| GSGQIRESMGNQQT | 693 | 1.270 | 1.676 | 0.833 | 0.523 |
| GSGQNSGVHFNQQT | 694 | 1.268 | 0.587 | 0.871 | 0.377 |
| GSGQNIGHSLPQQT | 695 | 1.264 | 6.183 | 0.740 | 0.478 |
| GSGERSISVQNQQT | 696 | 1.264 | 1.619 | 0.598 | 0.173 |
| GSGLKPNVLQNQQT | 697 | 1.263 | 0.975 | 0.701 | 0.268 |
| GSGQVAYAQGNQQT | 698 | 1.259 | 1.309 | 0.734 | 0.313 |
| GSGQSSYGSGNQQT | 699 | 1.257 | 1.686 | 1.161 | 0.456 |
| GSGQNQAMTHGDQT | 700 | 1.257 | 1.878 | 0.357 | 0.259 |
| GSGQNQALVSMGQT | 701 | 1.255 | 1.876 | 0.987 | 0.560 |
| GSGQNPSFMRGQQT | 702 | 1.252 | 1.454 | 1.293 | 1.094 |
| GSGQNQQSHLRINT | 703 | 1.251 | 4.583 | 1.022 | 0.718 |
| GYTRLETSGQNQQT | 704 | 1.250 | 1.323 | 0.841 | 0.297 |
| GSGQSYDMRGNQQT | 705 | 1.248 | 0.567 | 0.588 | 0.368 |
| GSRTTQDIGQNQQT | 706 | 1.247 | 0.000 | 0.685 | 0.280 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGHPYKAAQNQQT | 707 | 1.246 | 0.000 | 0.872 | 0.507 |
| GRLSNAHGGQNQQT | 708 | 1.245 | 0.839 | 1.036 | 0.725 |
| GSGQNQRAVLNDQT | 709 | 1.242 | 3.023 | 0.556 | 0.259 |
| GGSHTYGGGQNQQT | 710 | 1.241 | 13.065 | 0.982 | 0.730 |
| GSSVNSMIGQNQQT | 711 | 1.239 | 0.000 | 0.976 | 0.580 |
| GNSSMMGSGQNQQT | 712 | 1.239 | 3.856 | 0.656 | 0.364 |
| GNRDRPSSGQNQQT | 713 | 1.239 | 3.947 | 0.298 | 0.178 |
| GSGNMHASRQNQQT | 714 | 1.238 | 3.878 | 0.782 | 0.687 |
| GFIFPKVSGQNQQT | 715 | 1.237 | 0.000 | 1.764 | 0.692 |
| GSGQNQQLKNSTST | 716 | 1.235 | 1.703 | 1.063 | 0.538 |
| GSGQNQQSQYMPRT | 717 | 1.234 | 0.401 | 0.549 | 0.520 |
| GSGQRMADIGNQQT | 718 | 1.233 | 2.539 | 0.352 | 0.427 |
| GSGQNQSHYPSQQT | 719 | 1.228 | 4.315 | 0.644 | 0.402 |
| GSDGKMHRGQNQQT | 720 | 1.227 | 0.000 | 1.826 | 0.776 |
| GSGSVGFIGQNQQT | 721 | 1.227 | 8.261 | 0.689 | 0.445 |
| GLHGMTLSGQNQQT | 722 | 1.226 | 3.552 | 0.470 | 0.338 |
| GSDQSKRGDSNQQT | 723 | 1.225 | 0.639 | 0.479 | 0.267 |
| GSLFLATGGQNQQT | 724 | 1.220 | 0.000 | 0.775 | 0.485 |
| GSGQNQQPSAFSKT | 725 | 1.220 | 4.906 | 1.309 | 0.754 |
| GSGQLPQSGLNQQT | 726 | 1.218 | 1.504 | 0.641 | 0.318 |
| GSGSKQNALQNQQT | 727 | 1.216 | 2.010 | 0.941 | 0.594 |
| GSGQRRELSQNQQT | 728 | 1.215 | 1.791 | 0.622 | 0.396 |
| GSGQREPKASNQQT | 729 | 1.214 | 2.793 | 0.399 | 0.520 |
| GSGQNQQHPSTQQT | 730 | 1.205 | 1.552 | 1.017 | 0.680 |
| GSQSTLGLGQNQQT | 731 | 1.204 | 3.246 | 0.594 | 0.400 |
| GSGQNQQMPGLSST | 732 | 1.204 | 1.887 | 0.234 | 0.181 |
| GSGQNQQTVGGKNL | 733 | 1.203 | 0.128 | 0.777 | 1.051 |
| GSSREFHSGQNQQT | 734 | 1.203 | 1.591 | 0.688 | 0.474 |
| GSGQNQQTVPSNLV | 735 | 1.201 | 0.791 | 0.434 | 0.281 |
| GSGQNAYSSQAQQT | 736 | 1.201 | 12.096 | 0.629 | 0.216 |
| GSGQNKDHSTRRQT | 737 | 1.197 | 0.000 | 0.384 | 0.477 |
| GQLGSVGSGQDQQT | 738 | 1.196 | 0.000 | 1.020 | 0.437 |
| GSGQHAAPGHNQQT | 739 | 1.195 | 5.999 | 0.600 | 0.199 |
| GSGQNQQTSQSPPT | 740 | 1.194 | 1.208 | 0.851 | 0.478 |
| GSGNYRDHEQNQQT | 741 | 1.193 | 7.389 | 0.287 | 0.222 |
| GSGQHSNQHVNQQT | 742 | 1.192 | 1.453 | 0.955 | 0.558 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGQTARNGINQQT | 743 | 1.192 | 2.030 | 1.002 | 0.472 |
| GSGQNQQHYGSQGT | 744 | 1.189 | 0.453 | 1.345 | 0.379 |
| GSGSPQASRQNQQT | 745 | 1.189 | 6.782 | 0.923 | 0.542 |
| GSGFSHSMGKNQQT | 746 | 1.188 | 9.809 | 1.381 | 0.611 |
| GSGQSHSLETNQQT | 747 | 1.188 | 1.319 | 0.520 | 0.363 |
| GTEQTRQSGQNQQT | 748 | 1.188 | 0.132 | 0.756 | 0.756 |
| GSGRHLASVQNQQT | 749 | 1.187 | 1.024 | 0.654 | 0.606 |
| GLGSKNHSGQNQQT | 750 | 1.187 | 5.046 | 0.825 | 0.224 |
| GSGQNQQTSHFPSA | 751 | 1.185 | 0.325 | 0.969 | 0.907 |
| GSGQLSGTPQNQQT | 752 | 1.185 | 1.382 | 1.025 | 0.643 |
| GSGQNQQAPHKKET | 753 | 1.180 | 0.598 | 0.994 | 0.689 |
| GSGQNQQTLRGSLE | 754 | 1.179 | 1.812 | 0.853 | 0.354 |
| GSIAMTSHGQNQQT | 755 | 1.178 | 1.435 | 0.551 | 0.438 |
| GSPGVSPSGQNQQT | 756 | 1.178 | 3.006 | 0.853 | 1.160 |
| GSGQNQQTGSSSRV | 757 | 1.176 | 0.580 | 0.995 | 1.128 |
| GSGQHLPLLGNQQT | 758 | 1.175 | 1.739 | 0.519 | 0.347 |
| GSDHSRGGQNQQT | 759 | 1.174 | 0.504 | 0.818 | 0.331 |
| GSGIVTKLGQNQQT | 760 | 1.174 | 10.571 | 0.599 | 0.242 |
| GSGQDVTKTGNQQT | 761 | 1.173 | 4.523 | 0.531 | 0.035 |
| GSGQNQQSHGRIGT | 762 | 1.173 | 5.117 | 0.607 | 0.455 |
| GSGQNQQINHRSPT | 763 | 1.173 | 0.748 | 0.259 | 0.220 |
| GSGDDSRVGQNQQT | 764 | 1.172 | 0.191 | 0.466 | 0.156 |
| GSGQSTLKRINQQT | 765 | 1.168 | 13.442 | 0.534 | 1.184 |
| GSGSQHSKAQNQQT | 766 | 1.168 | 0.312 | 0.638 | 0.916 |
| GSGQNQQHASSNNT | 767 | 1.166 | 7.155 | 0.789 | 0.896 |
| GSRTYQVSGQNQQT | 768 | 1.164 | 1.853 | 0.638 | 0.641 |
| GSGQNQGLLSSPQT | 769 | 1.164 | 0.000 | 0.707 | 0.417 |
| GSGGGLQHNQNQQT | 770 | 1.163 | 4.098 | 1.137 | 0.778 |
| GSGQNQQTTAATRM | 771 | 1.163 | 3.925 | 0.947 | 1.005 |
| GSGQNQRASILVQT | 772 | 1.162 | 3.632 | 0.531 | 0.569 |
| GSGQNLGLLGAQQT | 773 | 1.161 | 1.458 | 0.524 | 0.226 |
| GSLDLGRSGQNQQT | 774 | 1.160 | 3.283 | 1.002 | 0.505 |
| GNSQVKVSGQNQQT | 775 | 1.158 | 4.930 | 1.422 | 0.728 |
| GSSGSHQYGQNQQT | 776 | 1.155 | 0.000 | 1.129 | 0.794 |
| GSGQNQQQRDGTLT | 777 | 1.152 | 0.387 | 0.760 | 0.730 |
| GRGQHVSVANNQQT | 778 | 1.152 | 1.896 | 1.032 | 0.589 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GDSSSRISGQNQQT | 779 | 1.151 | 3.787 | 0.916 | 0.348 |
| GSGQNQQHSLSSQT | 780 | 1.150 | 3.844 | 0.700 | 0.730 |
| GSLMDVHRGQNQQT | 781 | 1.150 | 0.387 | 1.009 | 0.238 |
| GSIQYQSSGQNQQT | 782 | 1.147 | 2.601 | 1.074 | 1.191 |
| GLGSKNPSGQNQQT | 783 | 1.147 | 1.629 | 1.184 | 0.424 |
| GSGQLVLTLQNQQT | 784 | 1.143 | 0.000 | 0.336 | 0.336 |
| GSGQNQQTSQPLPG | 785 | 1.141 | 0.080 | 0.748 | 0.530 |
| GSGQNQQNLGKLNT | 786 | 1.141 | 0.000 | 0.919 | 0.687 |
| GTTAHQPSGQNQQT | 787 | 1.138 | 0.211 | 0.726 | 0.275 |
| GSGQNRAQIGTQQT | 788 | 1.138 | 0.469 | 0.776 | 0.654 |
| GSGQYVHVSSNQQT | 789 | 1.137 | 1.803 | 0.739 | 0.366 |
| GSGQNQQTAHAFNI | 790 | 1.132 | 3.404 | 0.699 | 0.729 |
| GSGQNQRTMVATQT | 791 | 1.130 | 1.122 | 0.649 | 0.554 |
| GSGQNPIRGAMQQT | 792 | 1.126 | 1.327 | 1.296 | 0.427 |
| GSGYVITGSQNQQT | 793 | 1.125 | 6.271 | 0.971 | 0.248 |
| GRGPKQSNIQNQQT | 794 | 1.125 | 0.737 | 0.771 | 2.490 |
| GSGQNQQTMLGKPC | 795 | 1.125 | 0.047 | 1.090 | 0.992 |
| GSGQNQQVGSTVRT | 796 | 1.124 | 2.040 | 0.918 | 0.614 |
| GNVTTQKSGQNQQT | 797 | 1.122 | 2.546 | 1.215 | 0.922 |
| GSGNPVSHLQNQQT | 798 | 1.121 | 1.037 | 0.583 | 0.310 |
| GSLSHMESGQNQQT | 799 | 1.120 | 0.829 | 0.489 | 0.265 |
| GRAPTNLSGQNQQT | 800 | 1.118 | 0.687 | 0.757 | 0.169 |
| GSGQNQQTVMTARA | 801 | 1.117 | 1.535 | 0.995 | 0.843 |
| GSGMPASRLQNQQT | 802 | 1.117 | 1.689 | 0.790 | 0.372 |
| GVVRNHQSGQNQQT | 803 | 1.116 | 5.801 | 0.899 | 0.868 |
| GSGQNQHSVQVRQT | 804 | 1.116 | 1.909 | 0.782 | 0.916 |
| GSGQNTGHLTMQQT | 805 | 1.114 | 0.078 | 1.026 | 0.595 |
| GSGQNQQYAGKILT | 806 | 1.112 | 0.300 | 1.078 | 0.431 |
| GSGNPHVRNQNQQT | 807 | 1.112 | 0.873 | 0.732 | 0.755 |
| GSGQNGGSSNRQQT | 808 | 1.109 | 2.594 | 1.255 | 0.844 |
| GSGQRLSQGVNHQT | 809 | 1.108 | 3.394 | 0.931 | 1.141 |
| GSGQNAHAKEGQQT | 810 | 1.108 | 0.000 | 0.875 | 1.179 |
| GSSPAPNSGQNQQT | 811 | 1.106 | 2.229 | 0.719 | 0.368 |
| GLAHKTSSGQNQQT | 812 | 1.106 | 0.915 | 0.427 | 0.690 |
| GSGQNQQTPGAHKT | 813 | 1.105 | 3.827 | 0.957 | 0.277 |
| GSGQNQQSLSGSFT | 814 | 1.105 | 0.735 | 0.745 | 0.883 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGQNQQSTGTSRT | 815 | 1.103 | 4.054 | 1.209 | 0.935 |
| GSGQNQQTVQSNLV | 816 | 1.103 | 2.350 | 0.577 | 0.698 |
| GSGQNQQLGSRQCT | 817 | 1.102 | 0.183 | 0.987 | 0.407 |
| GSGQNQYLRLELQT | 818 | 1.101 | 0.000 | 0.416 | 0.839 |
| GSGQNQQTSPRLQT | 819 | 1.100 | 0.795 | 1.156 | 1.091 |
| GSGQNQQTTSSNMT | 820 | 1.099 | 0.569 | 0.638 | 0.698 |
| GTASTYNSGQNQQT | 821 | 1.099 | 2.560 | 0.250 | 0.625 |
| GSGQNQQTMPQHKI | 822 | 1.097 | 2.394 | 0.479 | 0.197 |
| GSGQSHLHTGNQQT | 823 | 1.096 | 2.584 | 0.721 | 0.295 |
| GVKGVGHSGQNQQT | 824 | 1.096 | 2.485 | 0.994 | 0.783 |
| GSGKVTKQSQNQQT | 825 | 1.095 | 0.000 | 0.928 | 1.035 |
| GSGQNQQTALEKSL | 826 | 1.092 | 0.000 | 0.625 | 0.702 |
| GSGYKDTYGQNQQT | 827 | 1.091 | 0.854 | 0.717 | 0.448 |
| GSGQNQQSGTFLST | 828 | 1.090 | 5.673 | 1.021 | 0.742 |
| GSGQNTGQHMMQQT | 829 | 1.090 | 1.058 | 1.147 | 0.917 |
| GSGKNQQRPGLDQT | 830 | 1.089 | 1.557 | 0.583 | 0.385 |
| GSGQSREISLNQQT | 831 | 1.088 | 6.954 | 0.594 | 0.282 |
| GTPTSPSSGQNQQT | 832 | 1.086 | 4.558 | 0.833 | 0.662 |
| GKPAGGLSGQNQQT | 833 | 1.085 | 2.805 | 0.708 | 0.739 |
| GSGQNHRSADMQQT | 834 | 1.084 | 12.001 | 0.417 | 0.212 |
| GSGQNQQTLPSLSL | 835 | 1.084 | 1.758 | 0.527 | 0.175 |
| GSPYMGATGQNQQT | 836 | 1.083 | 5.364 | 0.918 | 0.254 |
| GSGHAKAVGQNQQT | 837 | 1.081 | 4.357 | 0.703 | 0.824 |
| GHMKGVTSGQNQQT | 838 | 1.081 | 2.814 | 0.807 | 0.413 |
| GSGQNQKILTLDQT | 839 | 1.080 | 0.371 | 0.291 | 0.314 |
| GSGQNQQTKVGHSA | 840 | 1.079 | 1.256 | 0.669 | 1.019 |
| GIARTTISGQNQQT | 841 | 1.078 | 1.783 | 0.819 | 0.330 |
| GSGQNQQTSVGFRT | 842 | 1.077 | 3.737 | 0.648 | 0.534 |
| GSGQNQQTMIANIR | 843 | 1.076 | 0.000 | 0.379 | 0.458 |
| GDMTRSSGQNQQT | 844 | 1.075 | 0.802 | 1.145 | 1.038 |
| GSGHMSDLRQNQQT | 845 | 1.073 | 4.291 | 0.555 | 0.328 |
| GRGAVMASGQNQQT | 846 | 1.072 | 0.923 | 0.783 | 0.605 |
| GSGQNQQLSGKSVT | 847 | 1.070 | 1.524 | 1.276 | 0.930 |
| GSHTLVVSGQNQQT | 848 | 1.069 | 1.535 | 0.671 | 0.748 |
| GSGPWSAGLQNQQT | 849 | 1.067 | 0.947 | 0.700 | 0.539 |
| GSGQHSPHALNQQT | 850 | 1.064 | 1.412 | 0.885 | 0.573 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGQNQQPNSGSMT | 851 | 1.064 | 0.925 | 0.588 | 0.339 |
| GSGLAHLGGQNQQT | 852 | 1.064 | 2.191 | 0.749 | 0.794 |
| GSSVRYEPKQNQQT | 853 | 1.063 | 1.564 | 0.450 | 0.501 |
| GSGQNQQARPLELT | 854 | 1.061 | 0.059 | 0.389 | 0.252 |
| GSGQPRSTGINQQT | 855 | 1.061 | 0.693 | 0.650 | 0.542 |
| GSGQNQANWVKVQT | 856 | 1.059 | 0.126 | 0.683 | 0.532 |
| GSGHLFQSGQNQQT | 857 | 1.057 | 0.615 | 0.751 | 0.386 |
| GSGQNRGISISQQT | 858 | 1.057 | 2.166 | 0.686 | 0.566 |
| GSGTHYDNRQNQQT | 859 | 1.054 | 0.072 | 0.612 | 0.486 |
| GSGQNQQTSTTPLP | 860 | 1.052 | 2.823 | 0.828 | 0.741 |
| GSGQVHASQVNQKT | 861 | 1.049 | 0.503 | 0.855 | 0.767 |
| GSSGHRESGQNQQT | 862 | 1.048 | 4.398 | 0.641 | 0.691 |
| GLSAEKSSGQNQQT | 863 | 1.047 | 7.203 | 0.629 | 0.303 |
| GSGQEHRSLANQQT | 864 | 1.046 | 0.000 | 0.507 | 0.344 |
| GSGQTVVRIANQQT | 865 | 1.046 | 4.156 | 0.661 | 0.390 |
| GSGQNVSSVHRQQT | 866 | 1.045 | 0.712 | 0.383 | 0.271 |
| GSGASRMSIQNQQT | 867 | 1.045 | 0.111 | 0.801 | 0.417 |
| GVAFIGSSGQNQQT | 868 | 1.043 | 0.000 | 0.744 | 0.648 |
| GSGQNQQTVPTRQT | 869 | 1.040 | 1.207 | 0.629 | 0.138 |
| GSGQAAKSSQNQQT | 870 | 1.036 | 0.681 | 0.778 | 0.737 |
| GSGQNQQVAIRTST | 871 | 1.035 | 2.447 | 0.963 | 0.370 |
| GSVHMQNAGQNQQT | 872 | 1.034 | 3.608 | 1.004 | 0.625 |
| GSGMRQAGVQNQQT | 873 | 1.032 | 0.811 | 0.736 | 0.775 |
| GSGQNQQVGGKTVT | 874 | 1.032 | 6.195 | 1.094 | 0.821 |
| GVHDMRVSGQNQQT | 875 | 1.032 | 8.083 | 1.171 | 0.818 |
| GSGQHVSVANNQQT | 876 | 1.029 | 5.734 | 0.974 | 0.577 |
| GSAAMSVRGQNQQT | 877 | 1.029 | 2.386 | 0.202 | 0.287 |
| GVSRGGPSGQNQQT | 878 | 1.028 | 1.611 | 0.750 | 0.591 |
| GSGQMVHTIGNQQT | 879 | 1.026 | 1.328 | 0.406 | 0.430 |
| GRGGSMAETQNQQT | 880 | 1.024 | 2.853 | 0.799 | 0.669 |
| GSGHTNPTRQNQQT | 881 | 1.021 | 0.688 | 0.726 | 0.807 |
| GSGEAARYEQNQQT | 882 | 1.020 | 0.000 | 0.107 | 0.125 |
| GSGQNERHLVLQQT | 883 | 1.019 | 5.354 | 0.416 | 0.150 |
| GSGQNQQSKQQVLT | 884 | 1.019 | 1.494 | 1.428 | 1.256 |
| GSGQARAHRGNQQT | 885 | 1.017 | 0.000 | 0.254 | 0.386 |
| GSGQNQQPLDTSRT | 886 | 1.015 | 0.775 | 0.491 | 0.376 |

TABLE 9-continued

NGS fold-enrichment of AAV capsid variants in NHPs and mice

| Peptide Sequence | SEQ ID NO: | Fold enrichment over AAV9 in the brain of NHPs | Fold enrichment over AAV9 in the spinal cord of NHPs | Fold enrichment over AAV9 in the brain of Mice (C57Bl/6) | Fold enrichment over AAV9 in the brain of Mice (BALB/c) |
|---|---|---|---|---|---|
| GSGQNQQLANMVTT | 887 | 1.014 | 1.739 | 1.253 | 0.987 |
| GSGQMKDLHRNQQT | 888 | 1.014 | 1.068 | 0.587 | 0.506 |
| GSGQNQHLSSFVQT | 889 | 1.013 | 0.110 | 1.090 | 0.364 |
| GSGQNQQPSSRVTT | 890 | 1.012 | 2.179 | 0.784 | 0.504 |
| GSGQNQQLAITLGT | 891 | 1.011 | 0.000 | 0.877 | 0.143 |
| GSGQNQQTVGNPAT | 892 | 1.008 | 3.014 | 0.856 | 0.395 |
| GSGQNQGRAHPMQT | 893 | 1.007 | 2.364 | 0.684 | 0.453 |
| GSGQLIASVVNQQT | 894 | 1.005 | 0.086 | 0.197 | 0.359 |
| GSSVRSLVGQNQQT | 895 | 1.004 | 3.840 | 0.412 | 0.608 |
| GGAGSAHSGQNQQT | 896 | 1.003 | 6.108 | 0.474 | 1.092 |
| GSDQNQQTMSSTRT | 897 | 1.003 | 2.428 | 1.306 | 0.835 |
| GSGQNQQMAGAFRT | 898 | 1.003 | 1.784 | 1.307 | 0.762 |
| GSLGNLQRGQNQQT | 899 | 1.003 | 0.895 | 0.947 | 0.385 |
| GSGPSISHGQNQQT | 900 | 1.000 | 0.000 | 0.614 | 0.665 |
| GSGQNQQT | 6406 | 1.000 | 1.000 | 1.000 | 1.000 |
| GSGQNQQSSFNVQT | 901 | 0.998 | 0.000 | 1.307 | 0.675 |
| GSGQNQQTGQATHN | 902 | 0.996 | 2.199 | 0.877 | 0.527 |

A second cross-species evolution screen was performed using an AAV capsid variant library with a modification in loop IV introduced as described above and passaging it once through NHPs (passage 1) and then subsequently injected it into two different strains of mice (passage 2), C571B1/6 and BALB/c. The fold-enrichment for each variant in the brain of each mouse species was calculated by systematic NGS enrichment analysis following RNA recovery and RT-PCR amplification. The fold enrichment values in the second passage in mice were compared to those fold enrichment values from the second pass that was performed in NHPs as described above. As shown in Table 10, when comparing the second pass fold enrichment values in the mice versus NHPs, 12 variants were identified that had a fold-enrichment value greater than 10 in all three animal groups. Further, 10 of these 12 variants comprised the SPH motif and a positive residue in one of the next three subsequent residues (Table 10).

TABLE 10

NGS fold-enrichment of AAV capsid variants from a second passage (P2) in NHPs or mice (C57Bl/6 or BALB/c) following a first passage in NHPs

| Peptide Sequence | SEQ ID NO: | Fold enrichment over AAV9 in NHP P2 | Fold enrichment over AAV9 in BALB/c P2 | Fold enrichment over AAV9 in C57Bl/6 P2 |
|---|---|---|---|---|
| VSGSPHSKAQNQQT | 903 | 99.76 | 92.99 | 34.29 |
| CSGSPHSKAQNQQT | 904 | 85.1 | 66.74 | 22.19 |
| GSGSPHSKAQNQQT | 200 | 56.33 | 44.58 | 14.48 |
| GSGSPHRKAQNQQT | 905 | 46.39 | 42.47 | 14.11 |
| GRGSPHSKAQNQQT | 906 | 43.68 | 59.65 | 28.13 |
| GHDSPHKSGQNQQT | 201 | 33.96 | 59.14 | 27.15 |
| GSGSPHSKAKNQQT | 208 | 31.27 | 41.51 | 14 |
| GSGSPHSKAQNKQT | 907 | 29.52 | 44.1 | 13.69 |

TABLE 10-continued

NGS fold-enrichment of AAV capsid variants from a second passage (P2) in NHPs or mice (C57Bl/6 or BALB/c) following a first passage in NHPs

| Peptide Sequence | SEQ ID NO: | Fold enrichment over AAV9 in NHP P2 | Fold enrichment over AAV9 in BALB/c P2 | Fold enrichment over AAV9 in C57Bl/6 P2 |
|---|---|---|---|---|
| GSGSPHSKAQTQQT | 908 | 24.27 | 41.75 | 18 |
| GQDSPHKSGQNQQT | 204 | 22.7 | 32.37 | 16.02 |
| GSGSTHASRQNQQT | 909 | 11.04 | 23.71 | 10.67 |
| GHDSQHKSGQNQQT | 404 | 10.36 | 21.3 | 13.55 |

Following the second passage in mice, a synthetic library was generated using those variants that demonstrated a fold-change in enrichment relative to wild-type AAV9 that was above 10 in the brain of either strain of mice, as measured by systematic NGS enrichment analysis following RNA recovery and RT-PCR amplification. There were approximately 500 variants in this synthetic library. This synthetic library was then injected back into both strains of mice (C57Bl/6 and BALB/c; passage 3). RNA was recovered from the mouse brains, RT-PCR amplification was performed, and fold-enrichment relative to wild-type AAV9 was calculated by NGS analysis, which is provided in Table 11. As shown in Table 11, the variants with the greatest fold-enrichment in the brain in each strain, were highly correlated across strains ($R^2$=0.8458).

TABLE 11

NGS fold-enrichment of AAV capsid variants in the brain from a third passage (P3) in mice (C57Bl/6 or BALB/c) following a first and second passage in mice

| Peptide Sequence | SEQ ID NO: | Fold enrichment over AAV9 in BALB/c | Fold enrichment over AAV9 in C57Bl/6 | Average |
|---|---|---|---|---|
| GSGSPHKYGQNQQT | 910 | 150.445 | 103.488 | 126.966 |
| GSGSPHKFGQNQQT | 911 | 73.364 | 60.304 | 66.834 |
| GHDSPHKSGQNQQT | 201 | 82.460 | 51.125 | 66.792 |
| GSGSPHSKAQNQQT | 200 | 60.312 | 65.853 | 63.083 |
| VSGSPHKFGQNQQT | 912 | 60.186 | 59.142 | 59.664 |
| GSGSPHSKAQNHQT | 913 | 63.486 | 51.647 | 57.566 |
| VSGSPHSKAQNQQT | 903 | 73.555 | 37.429 | 55.492 |
| GQDSPHKSGQNQQT | 204 | 63.898 | 43.752 | 53.825 |
| GSGSPHSKAQHQQT | 914 | 45.309 | 45.600 | 45.454 |
| GSGSPHKTYQNQQT | 915 | 50.283 | 35.460 | 42.871 |
| GSGSPHSKAQTQQT | 908 | 43.120 | 39.098 | 41.109 |
| VSGSPHASRQNQQT | 916 | 46.572 | 32.480 | 39.526 |
| GSGSPHSKAQNKQT | 907 | 39.848 | 35.596 | 37.722 |
| GSGSPHKFGKNQQT | 917 | 31.948 | 34.899 | 33.423 |
| GSGSPHASRQNQHT | 918 | 28.145 | 30.928 | 29.537 |
| GSHSPHKSGQNQQT | 919 | 22.948 | 35.412 | 29.180 |
| GSGQNQQRRMSPST | 920 | 4.576 | 53.520 | 29.048 |
| GSGSPHASRQNQQT | 205 | 28.866 | 29.139 | 29.003 |
| GSGSPHSKPQNQQT | 921 | 26.958 | 28.599 | 27.779 |
| GSGSPHKFGQKQQT | 922 | 39.597 | 14.927 | 27.262 |
| VSGSPHGARQNQQT | 923 | 30.985 | 22.634 | 26.810 |

TABLE 11-continued

NGS fold-enrichment of AAV capsid variants in the brain from a third passage
(P3) in mice (C57Bl/6 or BALB/c) following a first and second passage in mice

| Peptide Sequence | SEQ ID NO: | Fold enrichment over AAV9 in BALB/c | Fold enrichment over AAV9 in C57Bl/6 | Average |
|---|---|---|---|---|
| GSGSPHSKAQKQQT | 924 | 25.052 | 27.459 | 26.256 |
| GHSSPHRSGQNQQT | 212 | 16.982 | 35.081 | 26.032 |
| GSGSPHSKAKNQQT | 208 | 21.069 | 25.711 | 23.390 |
| GSHSPHKRGQNQQT | 925 | 24.054 | 20.262 | 22.158 |
| GRGSPHSKAQNQQT | 906 | 20.939 | 22.720 | 21.830 |
| GQSSPHRSGQNQQT | 229 | 9.916 | 26.608 | 18.262 |
| GSGQNRQRLKGLET | 926 | 3.937 | 31.022 | 17.480 |
| GSGSPHKLGQNQQT | 927 | 18.905 | 14.732 | 16.818 |
| GSGSPHKTSKNQQT | 928 | 14.654 | 17.606 | 16.130 |
| GSGSPHKIGQNQQT | 929 | 16.999 | 14.794 | 15.897 |
| GSGSPHKKNQNQQT | 209 | 25.633 | 5.605 | 15.619 |
| GSGSPHASRQNKQT | 206 | 10.738 | 20.347 | 15.542 |
| GSGSPHTRGQNQQT | 214 | 16.899 | 13.869 | 15.384 |
| GSGQDSPHVRNQQT | 930 | 15.340 | 14.646 | 14.993 |
| GSGSPHKTSQNQQT | 931 | 20.428 | 8.818 | 14.623 |
| GSGSPHASRKNQQT | 932 | 13.799 | 12.749 | 13.274 |
| GSGSPHASRQKQQT | 211 | 13.624 | 11.188 | 12.406 |
| GSHSPHKSGQKQQT | 933 | 6.700 | 17.736 | 12.218 |
| GSGSPHKTSQKQQT | 934 | 12.621 | 11.720 | 12.170 |
| GSGSPHVRGQNKQT | 935 | 13.174 | 11.017 | 12.095 |
| GSGSPHKTTQNQQT | 936 | 9.722 | 13.381 | 11.552 |
| CSGSPHSKAQNQQT | 904 | 11.772 | 9.447 | 10.610 |
| GSGPVRALRQNQQT | 937 | 3.369 | 17.431 | 10.400 |
| GSGSPHVRGQKQQT | 938 | 7.573 | 12.498 | 10.036 |
| GSGSPHRKAQNQQT | 905 | 12.308 | 7.349 | 9.828 |
| GRGSPHASRQNQQT | 318 | 11.903 | 6.780 | 9.342 |
| CSGSPHKTSQNQQT | 939 | 11.167 | 6.631 | 8.899 |
| CSHSPHKSGQNQQT | 940 | 11.356 | 6.304 | 8.830 |
| GSGSPHSKDQNQQT | 604 | 3.492 | 10.236 | 6.864 |

Taken together, these results demonstrate that after 3 rounds of screening of this AAV9 variant library with loop IV modifications in NHP and mice, many AAV capsid variants outperformed the wild-type AAV9, for example, in penetration of the blood brain barrier (BBB) and spinal cord expression. These capsid variants were able to cross-species, evidenced by expression and tropism in the NHP brain/spinal cord as well as in the brain of two different mouse species.

Example 2. Individual Capsid Characterization in Mice

The goal of these experiments was to determine the transduction level, tropism, ability to cross the blood brain barrier, and overall spatial distribution in the central nervous system (CNS) of 2 capsid variants selected from the study described in Example 1 relative to AAV9 following intravenous injection in mice. The 2 capsid variants were TTM- 001 (SEQ ID NO: 981 (amino acid) and 983 (DNA), comprising SEQ ID NO: 941) and TTM-002 (SEQ ID NO: 982 (amino acid) and 984 (DNA), comprising SEQ ID NO: 2), as outlined in Table 3 above. The amino acid and DNA sequences of TTM-001 and TTM-002 are provided, e.g., in Tables 4 and 5, respectively.

AAV particles were generated with each of these capsid variants encapsulating a luciferase-EGFP transgene driven by a CMV/chicken beta actin promoter in a single stranded viral genome. Each capsid variant and AAV9 control were tested by intravenously administering by tail vein injection, the AAV particle formulation at 5e1 1 VG/dose (2.5E13 vg/kg) to three female BALB/c mice. The in-life period was 28 days and then various CNS and peripheral tissues were collected for measuring transgene mRNA, transgene protein, and viral DNA (biodistribution).

At 28 days post-injection of the AAV particles encapsulated in the TTM-001 capsid variant (AAV_TTM-001), mice were injected with luciferin and their brains were harvested for IVIS imaging. Robust luciferase signal was observed in mice injected with AAV particles encapsulated in the TTM-001 capsid variant, and this was greatly increased relative to AAV particles encapsulated in the wild-type AAV9 control capsid.

The brains isolated from mice injected with the AAV particles encapsulated in the TTM-001 capsid variant (AAV_TTM-001) or the TTM-002 capsid variant (AAV_TTM-002) were assayed by qPCR for the presence of transgene RNA as a measure of transgene expression, and the presence of viral DNA as a measure of viral genome levels. Data were provided as fold over AAV9 (Table 12). As shown in Table 12, when compared to the wild-type AAV9 capsid control, TTM-001 and TTM-002 demonstrated a 30-fold and 66-fold increase, respectively, in transgene mRNA levels and expression in the brain, indicative of enhanced payload delivery. This correlated with a 32-fold (TTM-001) and 47-fold (TTM-002) increase, respectively, in viral genome (DNA) concentrations in the brain relative to the AAV9 capsid control, which is indicative of enhanced CNS tropism and transduction (Table 12).

TABLE 12

Transgene mRNA and viral genome levels (DNA) in mice relative to the AAV9 control

| Measure | Tissue | AAV9 | TTM-001 | TTM-002 |
|---|---|---|---|---|
| mRNA (transgene expression) | Brain | 1.0 | 30.4503 | 66.2161 |
| DNA (viral genome quantification) | Brain | 1.0 | 32.0315 | 47.2810 |
| mRNA (transgene expression) | Liver | 1.0 | 1.2356 | 0.2016 |
| DNA (viral genome quantification) | Liver | 1.0 | 0.4802 | 0.0277 |

The brain tissues and spinal cords of the mice were also subjected to anti-GFP immunohistochemistry staining to evaluate overall CNS tropism and biodistribution. Immunohistochemical staining correlated with the qPCR analysis, as TTM-001 and TTM-002 showed significantly stronger staining and payload expression in the brain and spinal cord, as compared to the AAV9 control. More specifically, TTM-001 and TTM-02 demonstrated localization and strong payload expression and transduction in the mid-brain region, with increased staining observed in the hippocampus and thalamus, as well as in the brain stem, compared to AAV9. Less staining was observed in the cortical regions of the brain compared to the midbrain. However, staining in these cortical regions was stronger for TTM-001 and TTM-002 compared to the AAV9 control. It also appeared that the TTM-001 and TTM-002 capsid variants were able to transduce non-neuronal cells, including glial cells and oligodendrocytes. With respect to the spinal cord, staining and payload expression for TTM-01 and TTM-002 were localized to the ventral horns of the grey matter.

Peripheral tissues were also isolated from the mice intravenously injected with the AAV particles encapsulated in the TTM-001 capsid variant or the TTM-002 capsid variant for analysis by qPCR and/or GFP immunohistochemical staining. Transgene mRNA levels and viral genome DNA levels were quantified in the liver by qPCR and the fold over AAV9 was calculated for each capsid variant (Table 12). TTM-001 resulted in similar levels of payload expression (mRNA levels) as compared to wild-type AAV9, but only half as much viral genome DNA was quantified in the liver compared to AAV9. TTM-002 demonstrated greatly reduced mRNA and viral genome DNA levels in the liver compared to AAV9. GFP immunohistochemical staining of the spleen, heart, skeletal muscle, kidneys, and lungs of mice injected with AAV particles encapsulated in the TTM-001 capsid variant or the TTM-002 capsid variant showed similar levels of payload expression as compared to those mice injected with AAV particles encapsulated in the wild-type AAV9 control capsid.

Taken together, these data demonstrate that TTM-001 and TTM-002 are enhanced CNS tropic capsids in mice that can infect non-neuronal cells. Additionally, these capsid variants were able to successfully penetrate the blood brain barrier following intravenous injection.

Example 3. Maturation of TTM-001 and TTM-002 Capsid in Mice

This Example describes maturation of the TTM-001 (SEQ ID NO: 981 (amino acid) and 983 (DNA), comprising SEQ ID NO: 941) and TTM-002 (SEQ ID NO: 982 (amino acid) and 984 (DNA), comprising SEQ ID NO: 2) capsid variants to further enhance their transduction and biodistribution in the central nervous system and evolve the AAV capsid variants to provide further cross-species compatibility. Two approaches were used to mature the TTM-001 and TTM-002 capsid sequences in order to randomize and mutate within and around the peptide insert comprised within loop IV of the capsid variant. As many of the AAV capsid variants that demonstrated the greatest fold-enrichment in the NHP brain relative wild-type AAV9 comprised an SPH motif in the same position (e.g., immediately subsequent to position 455, relative to a reference sequence numbered according to the amino acid sequence of SEQ ID NO: 138) (see Example 1), the SPH motif was not mutated in either approach to mature the TTM-001 and TTM-002 capsid variants. In the first maturation approach, sets of three contiguous amino acids were randomized across the mutagenesis region in the TTM-001 and TTM-002 sequences, which spanned from position 450 to position 466, numbered according to SEQ ID NO: 981 and 982. In the second maturation approach, mutagenic primers were used to introduce point mutations at a low frequency, scattered across the mutagenesis region in the TTM-001 and TTM-002 sequences ranging from position 449 to position 466, numbered according to SEQ ID NO: 981 and 982. AAV capsid variants arising from each maturation approach for TTM-001 were pooled together and AAV capsid variants arising from each maturation approach for TTM-002 were also pooled together, for subsequent testing and characterization in mice.

The library of pooled matured AAV capsid variants generated from TTM-001 or library of pooled matured AAV capsid variants generated from the TTM-002 matured AAV capsid variant each were intravenously injected into the tail vein of three female CD-1 Outbred mice (Charles River) at a dose of $1.0 \times 10^{12}$ VG/dose. After 14-days in life, the brains of the mice were isolated and RNA was extracted. Following RNA recovery and RT-PCR amplification, a systematic NGS enrichment analysis was performed to calculate the fold enrichment ratio relative to the corresponding TTM-001 or TTM-002 control, and the peptides comprised within the variants were identified. The data for the TTM-001 matured capsid variants is provided in Table 13 and the data for the TTM-002 matured capsid variants is provided in Table 14.

As shown in Table 13, approximately 714 TTM-001 matured capsid variants demonstrated at least a 2-fold increase in expression relative to the non-matured TTM-001 control, and several variants demonstrated greater than a four-fold enrichment relative to the non-matured TTM-001 control. Also, across the peptides comprised within the TTM-001 matured capsid variants with the greatest fold-enrichment relative to the non-matured TTM-001 capsid in the brain, it was observed that the modifications in the variant sequences appeared in the region C-terminal to the SPH motif present within the capsid variant. This indicates that modifications that appeared to improve TTM-001 capsid tropism in the CNS of mice were skewed to the C-terminal portion of the peptide insertion in loop IV of the sequence. Additionally, a number of these C-terminal modifications were the incorporation of an arginine (R) or leucine (L) residue.

TABLE 13

NGS fold-enrichment of TTM-001 matured AAV capsid variants in the brain of CD-1 Outbred mice

| Peptide Sequence | SEQ ID NO: | Fold enrichment over TTM-001 |
|---|---|---|
| KTINGSGSPHSLLWNQQT | 1008 | 7.983 |
| KTINGSGSPHSKAQYYVT | 1009 | 6.283 |
| KTINGSGSPHSKLRRQQT | 1010 | 6.231 |
| KTINGSGSPHSIWQNQQT | 1011 | 5.883 |
| KTINGSSSPHCTAQNQQT | 1012 | 5.607 |
| KTINGSGSPHSKAGCGQT | 1013 | 5.341 |
| KSMNGSGSPHSRAQNQQT | 1014 | 5.145 |
| KTINGSGSPHSKRLRQQT | 1015 | 5.034 |
| KTINGSGSPHSLRRNQQT | 1016 | 4.985 |
| KTINGSGSPHSRGRNQQT | 1017 | 4.961 |
| KTINGSGSPHSEIVNQQT | 1018 | 4.931 |
| KTINGSGSPHSSRRNQQT | 1019 | 4.920 |
| KTINGSGSPHCLLQNQQT | 1020 | 4.898 |
| KTIMRVGSPHSKAQNQQT | 1021 | 4.875 |
| KTINGSGSPHSKAFRLQT | 1022 | 4.849 |

TABLE 13-continued

NGS fold-enrichment of TTM-001 matured AAV capsid variants in the brain of CD-1 Outbred mice

| Peptide Sequence | SEQ ID NO: | Fold enrichment over TTM-001 |
|---|---|---|
| KTINGSGSPHCLAQNQQT | 1023 | 4.847 |
| KTINGSCSPHRKAQNQQT | 1024 | 4.801 |
| KTINGSGSPHFLRQNQQT | 1025 | 4.777 |
| KTINGSGSPHSLRFNQQT | 1026 | 4.765 |
| KTINGSGSPHSYLRNQQT | 1027 | 4.566 |
| KTINGSGSPHCSLQNQQT | 1028 | 4.540 |
| KTINGSGSPHVLWQNQQT | 1029 | 4.533 |
| KTINGSGSPHSKWLLQQT | 1030 | 4.521 |
| KTINGSGSPHSLWSNQQT | 1031 | 4.467 |
| KTINGSGSPHSKRRLQQT | 1032 | 4.451 |
| KTINGSGSPHSVYLNQQT | 1033 | 4.426 |
| KTINGSGSPHSLWLNQQT | 1034 | 4.412 |
| KTINGSGSPHSKAQRKLT | 1035 | 4.339 |
| KTINGSGSPHSKALRRQT | 1036 | 4.330 |
| KTINGSGSPHSKAQRLRT | 1037 | 4.322 |
| KYLSGSGSPHSKAQNQQT | 1038 | 4.264 |
| KTINGSGSPHSKAQRRLT | 1039 | 4.227 |
| KTINGSGSPHSKARRQQT | 1040 | 4.218 |
| KTINGSGSPHSKARRLQT | 1041 | 4.210 |
| KTINGSGSPHSKSRRQQT | 1042 | 4.175 |
| KTINGLLSPHWKAQNQQT | 1043 | 4.173 |
| KTINGSGSPHSKARLRQT | 1044 | 4.155 |
| KTINGSGSPHSKASKRQT | 1045 | 4.117 |
| KTINGSGSPHVRRQNQQT | 1046 | 4.114 |
| KTINGSGSPHSKAQLYRT | 1047 | 4.108 |
| KGLSGSGSPHSKAQNQQT | 1048 | 4.056 |
| KTINGSGSPHSLFRNQQT | 1049 | 4.037 |
| KTINGSGSPHSKAQLTVT | 1050 | 4.026 |
| KTINGSRSPHTRAQNQQT | 1051 | 3.989 |
| KTINGSGSPHSKAKLRQT | 1052 | 3.976 |
| KTINGSGSPHSKLIRQQT | 1053 | 3.968 |
| KTINGSGSPHSKALRFQT | 1054 | 3.894 |
| KTINGSGSPHSKRTFQQT | 1055 | 3.879 |
| KTINGSGSPHSKAQKRLT | 1056 | 3.872 |
| KTINGSGSPHLWSQNQQT | 1057 | 3.857 |
| KTINGSGSPHLLWQNQQT | 1058 | 3.855 |

TABLE 13-continued NGS fold-enrichment of TTM-001 matured AAV capsid variants in the brain of CD-1 Outbred mice

| Peptide Sequence | SEQ ID NO: | Fold enrichment over TTM-001 |
|---|---|---|
| KTINGSGSPHSRLRNQQT | 1059 | 3.851 |
| KTINGSGSPHSKRAAQQT | 1060 | 3.838 |
| KTINGSGSPHSKRSWQQT | 1061 | 3.838 |
| KTINGSGSPHSKAQLRRT | 1062 | 3.825 |
| KTINGSGSPHYLVQNQQT | 1063 | 3.819 |
| KTINGSGSPHSKLFRQQT | 1064 | 3.806 |
| KTINGSGSPHSKRAMQQT | 1065 | 3.801 |
| KTINGSGSPHSKTLRQQT | 1066 | 3.788 |
| KTINGSGSPHSRSRNQQT | 1067 | 3.784 |
| KTINGSGSPHRRRQNQQT | 1068 | 3.754 |
| KTINGSGSPHSKTCLQQT | 1069 | 3.717 |
| KTINGSGSPHSKSRWQQT | 1070 | 3.698 |
| KTINGSGSPHRFRQNQQT | 1071 | 3.698 |
| KTINGLRSPHRKAQNQQT | 1072 | 3.676 |
| KTRSRSGSPHSKAQNQQT | 1073 | 3.669 |
| KTINGSGSPHSKAQLVVT | 1074 | 3.654 |
| KTINGSGSPHSRKLNQQT | 1075 | 3.646 |
| KTINGSGSPHSLLCNQQT | 1076 | 3.644 |
| KTINGKRSPHSKAQNQQT | 1077 | 3.611 |
| KTINGSRSPHLFAQNQQT | 1078 | 3.601 |
| KSINGSGSPHSKAHDQQT | 1079 | 3.592 |
| KTINGSGSPHSKAQRSRT | 1080 | 3.585 |
| KTINGSGSPHSTWLNQQT | 1081 | 3.583 |
| KTINGSGSPHSKASRRQT | 1082 | 3.577 |
| KTINGSGSPHSKRSMQQT | 1083 | 3.561 |
| KTINGSGSPHSCLQNQQT | 1084 | 3.559 |
| KTINGSGSPHSKRLWQQT | 1085 | 3.529 |
| KTINGSGSPHSWLSNQQT | 1086 | 3.495 |
| KTINGSGSPHLRRQNQQT | 1087 | 3.493 |
| KTINGSGSPHSKARRSQT | 1088 | 3.493 |
| KTINGSGSPHSKHLRQQT | 1089 | 3.438 |
| KTINGSGSPHSCSQNQQT | 1090 | 3.428 |
| KTINGSGSPHSKSFRQQT | 1091 | 3.426 |
| KTINGSGSPHLCLQNQQT | 1092 | 3.425 |
| KTINGSGSPHSKAQTSRT | 1093 | 3.421 |
| KTINGSGSPHSLCSNQQT | 1094 | 3.413 |
| KTINGSRSPHLRAQNQQT | 1095 | 3.410 |
| KTINGSGSPHSKAQVSKT | 1096 | 3.406 |
| KTINGSGSPHSKAQRHVT | 1097 | 3.404 |
| KTINGSSSPHLCAQNQQT | 1098 | 3.402 |
| KTINGSGSPHSFLRNQQT | 1099 | 3.384 |
| KTINGSGSPHSFVLNQQT | 1100 | 3.382 |
| KTINGSGSPHSKMRAQQT | 1101 | 3.382 |
| KTINGSGSPHRPRQNQQT | 1102 | 3.380 |
| KTINGSGSPHSKCLLQQT | 1103 | 3.374 |
| KTINGSGSPHSKAQSRRT | 1104 | 3.372 |
| KTINGSGSPHSRWQNQQT | 1105 | 3.372 |
| KYSVGSGSPHSKAQNQQT | 1106 | 3.365 |
| KTINGSGSPHSKRFLQQT | 1107 | 3.359 |
| KTINGSGSPHSLFLNQQT | 1108 | 3.358 |
| KTINGSGSPHSKAYLRQT | 1109 | 3.356 |
| KTINGSGSPHSKRNGQQT | 1110 | 3.350 |
| KTINGSGSPHTRRQNQQT | 1111 | 3.350 |
| KTINGSGSPHSKPRLQQT | 1112 | 3.337 |
| KTINFLRSPHSKAQNQQT | 1113 | 3.331 |
| KTINGSGSPHLLCQNQQT | 1114 | 3.328 |
| KTINGSGSPHSKARIVQT | 1115 | 3.287 |
| KTINGSKSPHFKAQNQQT | 1116 | 3.285 |
| KTINGSGSPHSKAQIRLT | 1117 | 3.279 |
| KTINGSSSPHWVAQNQQT | 1118 | 3.277 |
| KTINGSGSPHSKATRRQT | 1119 | 3.277 |
| KTINGSLSPHSCAQNQQT | 1120 | 3.268 |
| KTINGSGSPHSLYLNQQT | 1121 | 3.264 |
| KTINGSGSPHSKVGRQQT | 1122 | 3.255 |
| KTINGSGSPHSRRLNQQT | 1123 | 3.251 |
| KTINGSGSPHSKAQHSRT | 1124 | 3.227 |
| KTINGSGSPHSKAFPRQT | 1125 | 3.220 |
| KTINGSPSPHRRAQNQQT | 1126 | 3.216 |
| KTINGSGSPHSKRNLQQT | 1127 | 3.210 |
| KTINGSGSPHSKPTRQQT | 1128 | 3.201 |
| KTINGSGSPHSKLWLQQT | 1129 | 3.199 |
| KTINGSGSPHWLAQNQQT | 1130 | 3.192 |

TABLE 13-continued

NGS fold-enrichment of TTM-001 matured AAV capsid variants in the brain of CD-1 Outbred mice

| Peptide Sequence | SEQ ID NO: | Fold enrichment over TTM-001 |
|---|---|---|
| KTINGSGSPHRTRQNQQT | 1131 | 3.190 |
| KTINGSGSPHSKLNKQQT | 1132 | 3.181 |
| KTINGSGSPHSSLWNQQT | 1133 | 3.179 |
| KTINGSGSPHSKAQITLT | 1134 | 3.177 |
| KTINGSGSPHSKFLFQQT | 1135 | 3.173 |
| KTINGSGSPHSKRTPQQT | 1136 | 3.169 |
| KTINGSGSPHSKAQNSRR | 1137 | 3.168 |
| KTINGSGSPHSRLKNQQT | 1138 | 3.156 |
| KTINGSGSPHSCLLNQQT | 1139 | 3.127 |
| KTINGSGSPHTLYQNQQT | 1140 | 3.117 |
| KTINGSGSPHSKYPSQQT | 1141 | 3.114 |
| KTINGSGSPHSKLRNQQT | 1142 | 3.112 |
| KTINGSGSPHLNWQNQQT | 1143 | 3.112 |
| KTINGVVSPHRKAQNQQT | 1144 | 3.106 |
| KTINGSGSPHSYRPNQQT | 1145 | 3.095 |
| KTINGSTSPHRRAQNQQT | 1146 | 3.089 |
| KTINGSCSPHPLAQNQQT | 1147 | 3.086 |
| KTINGSGSPHSKAFARQT | 1148 | 3.082 |
| KTINGSGSPHSKALRYQT | 1149 | 3.076 |
| KTINGSKSPHRLAQNQQT | 1150 | 3.073 |
| KTINMRVSPHSKAQNQQT | 1151 | 3.073 |
| KTINGSGSPHMYLQNQQT | 1152 | 3.061 |
| KTINGSGSPHSKLARQQT | 1153 | 3.054 |
| KTINGSGSPHSKARPYQT | 1154 | 3.050 |
| KTINGSGSPHSKRVPQQT | 1155 | 3.048 |
| KTINGSGSPHLSWQNQQT | 1156 | 3.047 |
| KTINGRSSPHGKAQNQQT | 1157 | 3.035 |
| KTINGSGSPHLWTQNQQT | 1158 | 3.034 |
| KTINGLLSPHRKAQNQQT | 1159 | 3.026 |
| KTINGSGSPHRLRQNQQT | 1160 | 2.998 |
| KTINGSCSPHSGAQNQQT | 1161 | 2.994 |
| KTINGSGSPHSKAQRRST | 1162 | 2.993 |
| KTINGSGSPHSKLCSQQT | 1163 | 2.989 |
| KTINGSGSPHSKAQLLKT | 1164 | 2.985 |
| KTINGRKSPHSKAQNQQT | 1165 | 2.985 |
| KTINGSGSPHLLYQNQQT | 1166 | 2.983 |
| KTINGSGSPHSKLLRQQT | 1167 | 2.981 |
| KTINGSGSPHSLRHNQQT | 1168 | 2.980 |
| KTINGSGSPHSSKRNQQT | 1169 | 2.978 |
| KTINGSGSPHSKARSRQT | 1170 | 2.972 |
| KTINGRSSPHRKAQNQQT | 1171 | 2.965 |
| KTINGSKSPHRTAQNQQT | 1172 | 2.950 |
| KTINGMRSPHVKAQNQQT | 1173 | 2.937 |
| KTINGSGSPHSKRMSQQT | 1174 | 2.931 |
| KTINGSGSPHSKVPKQQT | 1175 | 2.924 |
| KTINLIRSPHSKAQNQQT | 1176 | 2.920 |
| KTINGSGSPHPFLQNQQT | 1177 | 2.916 |
| KTINGSGSPHSKARLWQT | 1178 | 2.914 |
| KTINGSGSPHSRTRNQQT | 1179 | 2.912 |
| KTINGSGSPHSKRSNQQT | 1180 | 2.886 |
| KTINGSLSPHSWAQNQQT | 1181 | 2.885 |
| KTINGSRSPHYKAQNQQT | 1182 | 2.879 |
| KTINRHSSPHSKAQNQQT | 1183 | 2.877 |
| KTINGSGSPHSKRRNQQT | 1184 | 2.877 |
| KTINGSGSPHSKAKHLQT | 1185 | 2.870 |
| KTINGSGSPHSKRTYQQT | 1186 | 2.870 |
| KTINGVLSPHRKAQNQQT | 1187 | 2.868 |
| KTINGSGSPHSFITNQQT | 1188 | 2.868 |
| KTINGSGSPHSTRLNQQT | 1189 | 2.860 |
| KTINGSGSPHSKRTSQQT | 1190 | 2.857 |
| KTINGSGSPHSRRSNQQT | 1191 | 2.851 |
| KTINGHLSPHRKAQNQQT | 1192 | 2.851 |
| KTINGSGSPHSKAQFSRT | 1193 | 2.847 |
| KTINGSGSPHSKAQTFRT | 1194 | 2.847 |
| KTINGSGSPHSKPLRQQT | 1195 | 2.844 |
| KTINGSGSPHSKASCRQT | 1196 | 2.840 |
| KTINGSGSPHSKILWQQT | 1197 | 2.838 |
| KTINGSGSPHSKALKRQT | 1198 | 2.836 |
| KTINGSGSPHSKAHRSQT | 1199 | 2.819 |
| KTINGSGSPHSMLYNQQT | 1200 | 2.808 |
| KTINGSGSPHSKCTLQQT | 1201 | 2.808 |
| KTINGSGSPHSKAQNRMR | 1202 | 2.804 |

TABLE 13-continued

NGS fold-enrichment of TTM-001 matured AAV capsid variants in the brain of CD-1 Outbred mice

| Peptide Sequence | SEQ ID NO: | Fold enrichment over TTM-001 |
|---|---|---|
| KTINGSGSPHSKLVRQQT | 1203 | 2.801 |
| KTINGSGSPHSKRILQQT | 1204 | 2.801 |
| KTINGSGSPHSKAQWLRT | 1205 | 2.795 |
| KTINGSGSPHSLTCNQQT | 1206 | 2.795 |
| KTINGIRSPHTKAQNQQT | 1207 | 2.793 |
| KTINGSGSPHSKAQRWLT | 1208 | 2.788 |
| KTINGSGSPHSKAQLSIT | 1209 | 2.784 |
| KTINGSGSPHIYRQNQQT | 1210 | 2.782 |
| KTINGSGSPHSLRSNQQT | 1211 | 2.778 |
| KTINGSGSPHSKVKPQQT | 1212 | 2.778 |
| KTINGSGSPHSKATRHQT | 1213 | 2.777 |
| KTINGSLSPHLCAQNQQT | 1214 | 2.775 |
| KTINGSGSPHSKACASQT | 1215 | 2.775 |
| KWSPGSGSPHSKAQNQQT | 1216 | 2.764 |
| KTINGYLSPHRKAQNQQT | 1217 | 2.762 |
| KTINGSGSPHSKVIRQQT | 1218 | 2.760 |
| KTINGSGSPHFLLQNQQT | 1219 | 2.758 |
| KTINGSGSPHSKARSKQT | 1220 | 2.758 |
| KTINGVPSPHWKAQNQQT | 1221 | 2.758 |
| KTINGSGSPHSKATRNQT | 1222 | 2.756 |
| KTINGSGSPHSKACSAQT | 1223 | 2.754 |
| KTINGSGSPHSKARYVQT | 1224 | 2.749 |
| KTINGSRSPHARAQNQQT | 1225 | 2.745 |
| KTINGSGSPHSKAQHLRT | 1226 | 2.741 |
| KTINGSGSPHSKAKSRQT | 1227 | 2.739 |
| KTINGSGSPHSKIGRQQT | 1228 | 2.739 |
| KTINGLASPHRKAQNQQT | 1229 | 2.737 |
| KTINGSGSPHSKARTRQT | 1230 | 2.737 |
| KTINGSGSPHSKSIRQQT | 1231 | 2.728 |
| KTINGSGSPHSKRLYQQT | 1232 | 2.721 |
| KTINGLPSPHRKAQNQQT | 1233 | 2.719 |
| KTINGSLSPHRRAQNQQT | 1234 | 2.717 |
| KTINGKTSPHGKAQNQQT | 1235 | 2.717 |
| KTINGSRSPHRLAQNQQT | 1236 | 2.698 |
| KTINGSGSPHSLTWNQQT | 1237 | 2.698 |
| KTINGSKSPHRKAQNQQT | 1238 | 2.696 |
| KTINGSGSPHSKAQLRKT | 1239 | 2.689 |
| KTINGSGSPHSKSRHQQT | 1240 | 2.685 |
| KTINRRLSPHSKAQNQQT | 1241 | 2.678 |
| KTINGSGSPHSRRVNQQT | 1242 | 2.676 |
| KTINGSGSPHSHWQNQQT | 1243 | 2.676 |
| KTTHCSGSPHSKAQNQQT | 1244 | 2.672 |
| KTINGSGSPHSWLQNQQT | 1245 | 2.665 |
| KTINGSTSPHYLAQNQQT | 1246 | 2.665 |
| KTINGLTSPHRKAQNQQT | 1247 | 2.663 |
| KTINGSGSPHSKRLLQQT | 1248 | 2.659 |
| KTINGSGSPHSKLCVQQT | 1249 | 2.659 |
| KTINGFLSPHRKAQNQQT | 1250 | 2.654 |
| KTINGSGSPHSKMRPQQT | 1251 | 2.652 |
| KTINGSGSPHSKQTRQQT | 1252 | 2.650 |
| KTINGSGSPHSYLINQQT | 1253 | 2.650 |
| KTINGSGSPHSKALRSQT | 1254 | 2.648 |
| KTINGMLSPHRKAQNQQT | 1255 | 2.646 |
| KTINGSGSPHSKCLTQQT | 1256 | 2.644 |
| KTINGSGSPHSKAQLTLT | 1257 | 2.641 |
| KTINGHSSPHRKAQNQQT | 1258 | 2.639 |
| KTINGSGSPHLTWQNQQT | 1259 | 2.637 |
| KTINGSGSPHSKAQYCLT | 1260 | 2.628 |
| KTINGSGSPHSFLVNQQT | 1261 | 2.624 |
| KTINMSRSPHSKAQNQQT | 1262 | 2.622 |
| KTINGSGSPHSKAQLHRT | 1263 | 2.618 |
| KTINGSGSPHLYMQNQQT | 1264 | 2.615 |
| KTINGSRSPHRRAQNQQT | 1265 | 2.615 |
| KTINGSGSPHSKAQNRRS | 1266 | 2.613 |
| KTINLRFSPHSKAQNQQT | 1267 | 2.611 |
| KTINGSGSPHSKAQRLWT | 1268 | 2.611 |
| KTINGSGSPHSKGRAQQT | 1269 | 2.607 |
| KTINGSGSPHSLSCNQQT | 1270 | 2.605 |
| KTINGLVSPHCKAQNQQT | 1271 | 2.605 |
| KTINGSSSPHLWAQNQQT | 1272 | 2.605 |
| KTINGSGSPHSKAHRLQT | 1273 | 2.603 |
| KTINGSGSPHPYAQNQQT | 1274 | 2.598 |

TABLE 13-continued

NGS fold-enrichment of TTM-001 matured AAV capsid variants in the brain of CD-1 Outbred mice

| Peptide Sequence | SEQ ID NO: | Fold enrichment over TTM-001 |
|---|---|---|
| KTINGSGSPHSTRPNQQT | 1275 | 2.598 |
| KTINGRSSPHPKAQNQQT | 1276 | 2.596 |
| KTINGSGSPHSKAQSWRT | 1277 | 2.596 |
| KTINGQRSPHVKAQNQQT | 1278 | 2.596 |
| KTINGSGSPHSKAQFVRT | 1279 | 2.596 |
| KTINGSGSPHSKCLNQQT | 1280 | 2.594 |
| KTINGSGSPHSSLCNQQT | 1281 | 2.592 |
| KTINGQRSPHSKAQNQQT | 1282 | 2.590 |
| KTINGSGSPHSLSWNQQT | 1283 | 2.588 |
| KTINGSGSPHSSRKNQQT | 1284 | 2.585 |
| KTINGSGSPHSKRTLQQT | 1285 | 2.583 |
| KTINGSLSPHCLAQNQQT | 1286 | 2.577 |
| KTINGSGSPHSKAQSSRT | 1287 | 2.575 |
| KTINGSGSPHLKRQNQQT | 1288 | 2.564 |
| KTINGSGSPHSKARMGQT | 1289 | 2.564 |
| KTINGSGSPHSKAQVKLT | 1290 | 2.564 |
| KTINGSGSPHSKLPRQQT | 1291 | 2.562 |
| KTINGSGSPHSKLCLQQT | 1292 | 2.562 |
| KTINGSGSPHSPLWNQQT | 1293 | 2.562 |
| KTINGSVSPHSWAQNQQT | 1294 | 2.562 |
| KTIRSKGSPHSKAQNQQT | 1295 | 2.559 |
| KTINGSRSPHSWAQNQQT | 1296 | 2.559 |
| KTINGSGSPHSKILRQQT | 1297 | 2.557 |
| KTINGRQSPHVKAQNQQT | 1298 | 2.557 |
| KTINGSGSPHSKAQSIKT | 1299 | 2.555 |
| KTINGSGSPHSKAQASKT | 1300 | 2.546 |
| KTINGSGSPHSRLFNQQT | 1301 | 2.542 |
| KTINGSGSPHIYLQNQQT | 1302 | 2.542 |
| KTINGSGSPHSRVRNQQT | 1303 | 2.540 |
| KTINGSGSPHSKAVRAQT | 1304 | 2.538 |
| KTINGSGSPHSKPARQQT | 1305 | 2.538 |
| KTINGSGSPHSRYSNQQT | 1306 | 2.536 |
| KTINGSRSPHRSAQNQQT | 1307 | 2.536 |
| KTINGSLSPHIYAQNQQT | 1308 | 2.536 |
| KTINGSGSPHSKPVRQQT | 1309 | 2.529 |
| KTINGMRSPHGKAQNQQT | 1310 | 2.527 |
| KTINGSGSPHSKARITQT | 1311 | 2.525 |
| KTINGSGSPHSWSLNQQT | 1312 | 2.523 |
| KTINTSRSPHSKAQNQQT | 1313 | 2.520 |
| KTINGSGSPHSKAFTRQT | 1314 | 2.518 |
| KTINGSGSPHSKAVRNQT | 1315 | 2.516 |
| KTINGSGSPHSKAQTNRT | 1316 | 2.510 |
| KTINGSGSPHSKANRMQT | 1317 | 2.508 |
| KTINGSGSPHSKAQLVLT | 1318 | 2.508 |
| KTINGSGSPHSKATRQQT | 1319 | 2.505 |
| KTINGSGSPHSKARGTQT | 1320 | 2.505 |
| KTINGSGSPHSKAQWSVT | 1321 | 2.501 |
| KTINGSGSPHSKAWLIQT | 1322 | 2.499 |
| KTINGSGSPHSKAFRPQT | 1323 | 2.499 |
| KTINGSGSPHRRSQNQQT | 1324 | 2.497 |
| KTINGSGSPHSKGIRQQT | 1325 | 2.497 |
| KTINGSGSPHCTLQNQQT | 1326 | 2.497 |
| KPLPGSGSPHSKAQNQQT | 1327 | 2.495 |
| KTINGSGSPHLVCQNQQT | 1328 | 2.493 |
| KTINGSGSPHSKARGYQT | 1329 | 2.492 |
| KTINGRISPHGKAQNQQT | 1330 | 2.492 |
| KTINGSSSPHWLAQNQQT | 1331 | 2.490 |
| KTINGSGSPHSKARMAQT | 1332 | 2.488 |
| KPLDGSGSPHSKAQNQQT | 1333 | 2.488 |
| KPLRGSGSPHSKAQNQQT | 1334 | 2.486 |
| KTINGSGSPHSKAQNAKL | 1335 | 2.486 |
| KTINGSGSPHSKLSKQQT | 1336 | 2.482 |
| KTINGSGSPHSKARNGQT | 1337 | 2.482 |
| KTINGSGSPHSKAQRRQT | 1338 | 2.479 |
| KTINGSGSPHSKWPGQQT | 1339 | 2.477 |
| KTINGSGSPHAFLQNQQT | 1340 | 2.475 |
| KTINGILSPHRKAQNQQT | 1341 | 2.475 |
| KTINGSGSPHSWGSNQQT | 1342 | 2.473 |
| KTINGSGSPHSSCLNQQT | 1343 | 2.471 |
| KTINGSGSPHSKAQSVKT | 1344 | 2.464 |
| KTINGSGSPHSLRYNQQT | 1345 | 2.462 |
| KTINGSGSPHSKARKLQT | 1346 | 2.458 |

TABLE 13-continued

NGS fold-enrichment of TTM-001 matured AAV capsid variants in the brain of CD-1 Outbred mice

| Peptide Sequence | SEQ ID NO: | Fold enrichment over TTM-001 |
|---|---|---|
| KHRSGSGSPHSKAQNQQT | 1347 | 2.456 |
| KTINGSGSPHSKWSLQQT | 1348 | 2.453 |
| KTINGSGSPHSKAQTMRT | 1349 | 2.453 |
| KTINGSGSPHSKTIRQQT | 1350 | 2.453 |
| KTINGKLSPHMKAQNQQT | 1351 | 2.449 |
| KTINGSGSPHSKARPFQT | 1352 | 2.443 |
| KTINGSGSPHSKPRVQQT | 1353 | 2.441 |
| KTINGSGSPHSKAQVVLT | 1354 | 2.438 |
| KTRRSSGSPHSKAQNQQT | 1355 | 2.438 |
| KTINGSGSPHSKPSRQQT | 1356 | 2.438 |
| KTINGSGSPHSVYRNQQT | 1357 | 2.432 |
| KTINGSGSPHSKTCSQQT | 1358 | 2.430 |
| KTINGSPSPHRKAQNQQT | 1359 | 2.430 |
| KTINGRSSPHFKAQNQQT | 1360 | 2.428 |
| KTINGSGSPHSKAQMVRT | 1361 | 2.426 |
| KTINGSRSPHCSAQNQQT | 1362 | 2.426 |
| KTINGSCSPHLRAQNQQT | 1363 | 2.423 |
| KTINGSGSPHSKAQCLFT | 1364 | 2.421 |
| KTINGRPSPHVKAQNQQT | 1365 | 2.419 |
| KTINGSGSPHSMFPNQQT | 1366 | 2.419 |
| KTINGMKSPHSKAQNQQT | 1367 | 2.413 |
| KTINGSGSPHSKVRAQQT | 1368 | 2.412 |
| KGLVGSGSPHSKAQNQQT | 1369 | 2.412 |
| KTINGSRSPHVRAQNQQT | 1370 | 2.412 |
| KTIRLRGSPHSKAQNQQT | 1371 | 2.408 |
| KPRLGSGSPHSKAQNQQT | 1372 | 2.406 |
| KTINGSGSPHSKAWYPQT | 1373 | 2.406 |
| KTINGSCSPHVRAQNQQT | 1374 | 2.406 |
| KTINGSGSPHSKRNVQQT | 1375 | 2.404 |
| KTINGSGSPHSKRGLQQT | 1376 | 2.402 |
| KTINGSGSPHSKRLAQQT | 1377 | 2.397 |
| KTINGSGSPHSKVTRQQT | 1378 | 2.397 |
| KTINGSGSPHTWLQNQQT | 1379 | 2.397 |
| KTINGSGSPHSKQRSQQT | 1380 | 2.395 |
| KTINGSGSPHSKAQRCST | 1381 | 2.393 |
| KTINGSPSPHYLAQNQQT | 1382 | 2.391 |
| KTINGRRSPHLKAQNQQT | 1383 | 2.391 |
| KTINGSGSPHWSLQNQQT | 1384 | 2.389 |
| KTINGVTSPHWKAQNQQT | 1385 | 2.387 |
| KTINGSGSPHSKAQTTRT | 1386 | 2.385 |
| KTINGSGSPHSKAQLFKT | 1387 | 2.385 |
| KTINGSGSPHSKARSYQT | 1388 | 2.382 |
| KTINGSGSPHSKLSRQQT | 1389 | 2.380 |
| KTINGSGSPHLVFQNQQT | 1390 | 2.376 |
| KTINGSGSPHSKAQLVKT | 1391 | 2.376 |
| KTINGSGSPHSKAQTGRT | 1392 | 2.371 |
| KTINGSGSPHSKARYSQT | 1393 | 2.369 |
| KTINGRHSPHLKAQNQQT | 1394 | 2.369 |
| KTINGSGSPHSFARNQQT | 1395 | 2.367 |
| KTINGSGSPHSSCQNQQT | 1396 | 2.365 |
| KTINGSGSPHSLFANQQT | 1397 | 2.365 |
| KTINGSGSPHSKRLTQQT | 1398 | 2.363 |
| KTINGSGSPHSKAQTART | 1399 | 2.363 |
| KTINGSGSPHFLNQNQQT | 1400 | 2.359 |
| KTINGSGSPHSKAQLILT | 1401 | 2.358 |
| KEVGGSGSPHSKAQNQQT | 1402 | 2.358 |
| KTINGSRSPHIRAQNQQT | 1403 | 2.356 |
| KTINGSGSPHSSWLNQQT | 1404 | 2.354 |
| KTINGSMSPHLYAQNQQT | 1405 | 2.354 |
| KTINGMSSPHRKAQNQQT | 1406 | 2.352 |
| KTINGSGSPHSKPRPQQT | 1407 | 2.352 |
| KTINGSGSPHSGLWNQQT | 1408 | 2.350 |
| KTINGSGSPHRWAQNQQT | 1409 | 2.350 |
| KTINGSGSPHSKIRLQQT | 1410 | 2.348 |
| KTINGSGSPHSKFSCQQT | 1411 | 2.348 |
| KTINGSGSPHSKSCAQQT | 1412 | 2.348 |
| KTINGSGSPHSKRLMQQT | 1413 | 2.345 |
| KTSRCSGSPHSKAQNQQT | 1414 | 2.345 |
| KTINGSGSPHSFLLNQQT | 1415 | 2.341 |
| KTINGSGSPHCSAQNQQT | 1416 | 2.339 |
| KTINGSGSPHSKAQPSKT | 1417 | 2.339 |
| KTINGSGSPHSYVRNQQT | 1418 | 2.339 |

TABLE 13-continued

NGS fold-enrichment of TTM-001 matured AAV capsid variants in the brain of CD-1 Outbred mice

| Peptide Sequence | SEQ ID NO: | Fold enrichment over TTM-001 |
|---|---|---|
| KTINGSGSPHSKAQQSRT | 1419 | 2.337 |
| KTINGSGSPHSFVVNQQT | 1420 | 2.335 |
| KTINGFRSPHSKAQNQQT | 1421 | 2.333 |
| KTINGSGSPHSKWLVQQT | 1422 | 2.333 |
| KTINGSGSPHSKRTAQQT | 1423 | 2.331 |
| KTINGLFSPHRKAQNQQT | 1424 | 2.331 |
| KTINTIESPHSKAQNQQT | 1425 | 2.331 |
| KRLFGSGSPHSKAQNQQT | 1426 | 2.330 |
| KTINGSGSPHSKAPNHLT | 1427 | 2.324 |
| KTINGSGSPHLFRQNQQT | 1428 | 2.324 |
| KTINGSGSPHSKASRHQT | 1429 | 2.324 |
| KTINGSGSPHSKLSWQQT | 1430 | 2.322 |
| KETAGSGSPHSKAQNQQT | 1431 | 2.320 |
| KTINGHRSPHLKAQNQQT | 1432 | 2.320 |
| KTINGSGSPHSKGCLQQT | 1433 | 2.320 |
| KTINGSGSPHSKAQVLIT | 1434 | 2.317 |
| KTINGSGSPHSKLRSQQT | 1435 | 2.309 |
| KTINGTLSPHRKAQNQQT | 1436 | 2.307 |
| KTINGSGSPHSTWTNQQT | 1437 | 2.307 |
| KTINGSGSPHSKAQCRLT | 1438 | 2.304 |
| KTINNLRSPHSKAQNQQT | 1439 | 2.302 |
| KTINGSGSPHSKARANQT | 1440 | 2.300 |
| KTINGRQSPHTKAQNQQT | 1441 | 2.294 |
| KTINSARSPHSKAQNQQT | 1442 | 2.292 |
| KTINGCSSPHRKAQNQQT | 1443 | 2.291 |
| KTINGSVSPHFMAQNQQT | 1444 | 2.287 |
| KTINGSGSPHSLCQNQQT | 1445 | 2.285 |
| KTINGSLSPHLFAQNQQT | 1446 | 2.285 |
| KTINGSGSPHSKACPLQT | 1447 | 2.285 |
| KTINGRTSPHRKAQNQQT | 1448 | 2.285 |
| KTINGSGSPHSKRATQQT | 1449 | 2.283 |
| KTINGSGSPHSKARIMQT | 1450 | 2.283 |
| KTINGSGSPHVTWQNQQT | 1451 | 2.281 |
| KTINGSGSPHSKRLPQQT | 1452 | 2.279 |
| KTINGSGSPHSKAQGERT | 1453 | 2.279 |
| KTINGSGSPHLYGQNQQT | 1454 | 2.277 |
| KTINGSGSPHLSCQNQQT | 1455 | 2.277 |
| KTINGSGSPHSKAQFTLT | 1456 | 2.277 |
| KTINGSRSPHFKAQNQQT | 1457 | 2.277 |
| KTINGRPSPHSKAQNQQT | 1458 | 2.276 |
| KTINGFSSPHRKAQNQQT | 1459 | 2.276 |
| KTINGRASPHVKAQNQQT | 1460 | 2.272 |
| KTINGSGSPHSKAQNEVH | 1461 | 2.272 |
| KTINGSGSPHSKRSLQQT | 1462 | 2.270 |
| KTINGSGSPHRSRQNQQT | 1463 | 2.270 |
| KPPTGSGSPHSKAQNQQT | 1464 | 2.270 |
| KTINGSGSPHSKAARTQT | 1465 | 2.266 |
| KTINGSGSPHSSWANQQT | 1466 | 2.264 |
| KTINGSGSPHSKAQRHAT | 1467 | 2.264 |
| KTINSPRSPHSKAQNQQT | 1468 | 2.264 |
| KTINGSGSPHSKSERQQT | 1469 | 2.263 |
| KTINGSGSPHALFQNQQT | 1470 | 2.261 |
| KTINGSGSPHSKAQCYVT | 1471 | 2.261 |
| KTINGVASPHRKAQNQQT | 1472 | 2.261 |
| KTINGSGSPHSALWNQQT | 1473 | 2.261 |
| KTINGSGSPHSKSVRQQT | 1474 | 2.259 |
| KTINGSGSPHSHMENQQT | 1475 | 2.259 |
| KTINGSGTPHSKAQNQQT | 1476 | 2.259 |
| KTINGSGSPHSKTGRQQT | 1477 | 2.259 |
| KTINGSGSPHSKAQANRT | 1478 | 2.255 |
| KTINGSGSPHSKARFSQT | 1479 | 2.253 |
| KYLLGSGSPHSKAQNQQT | 1480 | 2.253 |
| KTINGSGSPHCSSQNQQT | 1481 | 2.253 |
| KTINGSMSPHRKAQNQQT | 1482 | 2.251 |
| KTINGNLSPHRKAQNQQT | 1483 | 2.250 |
| KEVAGSGSPHSKAQNQQT | 1484 | 2.250 |
| KTINLSRSPHSKAQNQQT | 1485 | 2.246 |
| KTINGSGSPHSKARQQQT | 1486 | 2.244 |
| KTINGTPSPHRKAQNQQT | 1487 | 2.244 |
| KTINGSGSPHSKFKLQQT | 1488 | 2.244 |
| KTINGSGSPHSKAWLLQT | 1489 | 2.240 |
| KTINGLRSPHSKAQNQQT | 1490 | 2.238 |

TABLE 13-continued

NGS fold-enrichment of TTM-001 matured AAV capsid variants in the brain of CD-1 Outbred mice

| Peptide Sequence | SEQ ID NO: | Fold enrichment over TTM-001 |
|---|---|---|
| KTINGRLSPHRKAQNQQT | 1491 | 2.238 |
| KTINGSPSPHLFAQNQQT | 1492 | 2.238 |
| KDLRGSGSPHSKAQNQQT | 1493 | 2.238 |
| KTINGSGSPHSKAQLAKT | 1494 | 2.238 |
| KTINGSGSPHSKPRSQQT | 1495 | 2.235 |
| KTINGSGSPHSKKMSQQT | 1496 | 2.235 |
| KTINGSGSPHSKAQLIVT | 1497 | 2.235 |
| KTINGSGSPHSKARFTQT | 1498 | 2.233 |
| KTINGSGSPHPLFQNQQT | 1499 | 2.233 |
| KTINGSGSPHSKAQRGMT | 1500 | 2.231 |
| KTINGSGSPHSKAQNLRR | 1501 | 2.231 |
| KTINGSGSPHSKAQFRVT | 1502 | 2.231 |
| KTINGSGSPHSKAFVRQT | 1503 | 2.225 |
| KTINGSGSPHSKARLTQT | 1504 | 2.223 |
| KTINGSGSPHRFKQNQQT | 1505 | 2.223 |
| KTINGSGSPHSKEETQQT | 1506 | 2.223 |
| KTINGSGSPHSKTRAQQT | 1507 | 2.223 |
| KTINGSGSPHSVSWNQQT | 1508 | 2.223 |
| KTINGSGSPHTKWQNQQT | 1509 | 2.222 |
| KTINGSNSPHRKAQNQQT | 1510 | 2.218 |
| KTINGSGSPHSKAQNKRS | 1511 | 2.214 |
| KTINGSGSPHSTRQNQQT | 1512 | 2.212 |
| KTINGTRSPHTKAQNQQT | 1513 | 2.203 |
| KTINGSGSPHVLFQNQQT | 1514 | 2.203 |
| KTINGSVSPHYLAQNQQT | 1515 | 2.203 |
| KTINGALSPHRKAQNQQT | 1516 | 2.203 |
| KTINGSGSPHSKARLYQT | 1517 | 2.201 |
| KTINGSGSPHEHNQNQQT | 1518 | 2.199 |
| KTINGVLSPHWKAQNQQT | 1519 | 2.199 |
| KTINGSGSPHSKASRQQT | 1520 | 2.197 |
| KTINGSGSPHSKRSFQQT | 1521 | 2.197 |
| KTINGSGSPHSKRVSQQT | 1522 | 2.196 |
| KTINGSGSPHSYSRNQQT | 1523 | 2.196 |
| KTINGSGSPHSTVWNQQT | 1524 | 2.196 |
| KTINGSGSPHSVLFNQQT | 1525 | 2.194 |
| KTINGPLSPHCKAQNQQT | 1526 | 2.194 |
| KTINGSGSPHSKRVGQQT | 1527 | 2.190 |
| KTINGSGSPHSKLWSQQT | 1528 | 2.190 |
| KTINGSGSPHSKAQGVRT | 1529 | 2.188 |
| KTINGSVSPHRRAQNQQT | 1530 | 2.186 |
| KTINGSGSPHLRFQNQQT | 1531 | 2.186 |
| KTINGSASPHVFAQNQQT | 1532 | 2.186 |
| KTWVRSGSPHSKAQNQQT | 1533 | 2.186 |
| KTINGSGSPHSKARMQQT | 1534 | 2.184 |
| KTINGSGSPHSKASRGQT | 1535 | 2.182 |
| KTINGSGSPHSKAQVCLT | 1536 | 2.182 |
| KTINGSGSPHSKARGVQT | 1537 | 2.181 |
| KTINGSGSPHGLWQNQQT | 1538 | 2.181 |
| KTINGSGSPHSKAQVWFT | 1539 | 2.181 |
| KTINGSGSPHSKAQVTLT | 1540 | 2.179 |
| KTINGSGSPHSKAQLRIT | 1541 | 2.179 |
| KDSLGSGSPHSKAQNQQT | 1542 | 2.175 |
| KTINGSGSPHSKRASQQT | 1543 | 2.173 |
| KTINGSGSPHSKRINQQT | 1544 | 2.173 |
| KTINGSGSPHSKASKNQT | 1545 | 2.171 |
| KTINGSGSPHSKAQLPWT | 1546 | 2.169 |
| KTINGSGSPHSKLTRQQT | 1547 | 2.169 |
| KTINGSGSPHSKINRQQT | 1548 | 2.169 |
| KTINRVISPHSKAQNQQT | 1549 | 2.169 |
| KTINGSGSPHTLWQNQQT | 1550 | 2.168 |
| KTINGSGSPHSRRQNQQT | 1551 | 2.166 |
| KTINGSGSPHSKGGRQQT | 1552 | 2.164 |
| KTINGSESPHDSAQNQQT | 1553 | 2.164 |
| KTINGSGSPHSRPRNQQT | 1554 | 2.164 |
| KTINGSGSPHSRKQNQQT | 1555 | 2.162 |
| KTINGSGSPHSKAQEELT | 1556 | 2.162 |
| KTINGWRSPHSKAQNQQT | 1557 | 2.160 |
| KTINGSGSPHSLLYNQQT | 1558 | 2.158 |
| KTINGSGSPHSFRLNQQT | 1559 | 2.158 |
| KTINGSGSPHSKAQFLRT | 1560 | 2.156 |
| KTINGSGSPHSKQSRQQT | 1561 | 2.156 |
| KTINGSRSPHSKAQNRQT | 1562 | 2.155 |

TABLE 13-continued

NGS fold-enrichment of TTM-001 matured AAV capsid variants in the brain of CD-1 Outbred mice

| Peptide Sequence | SEQ ID NO: | Fold enrichment over TTM-001 |
|---|---|---|
| KTINGRPSPHIKAQNQQT | 1563 | 2.155 |
| KTINGSGSPHSKRLVQQT | 1564 | 2.151 |
| KGHEGSGSPHSKAQNQQT | 1565 | 2.151 |
| KTINGSGSPHSKAQKRST | 1566 | 2.151 |
| KTINGSGSPHSYLLNQQT | 1567 | 2.147 |
| KTINGSGSPHSKPRGQQT | 1568 | 2.147 |
| KTINGSGSPHSKTRLQQT | 1569 | 2.145 |
| KTINGSGSPHSKSHRQQT | 1570 | 2.145 |
| KEIKGSGSPHSKAQNQQT | 1571 | 2.140 |
| KTINGSGSPHSKARGIQT | 1572 | 2.140 |
| KTINGYRSPHSKAQNQQT | 1573 | 2.140 |
| KTINGSGSPHSKLWTQQT | 1574 | 2.140 |
| KTINGSGSPHSKPWLQQT | 1575 | 2.138 |
| KTINGSGSPHWSVQNQQT | 1576 | 2.138 |
| KTINGSGSPHSKVARQQT | 1577 | 2.136 |
| KTINGSGSPHTLFQNQQT | 1578 | 2.136 |
| KTINGSCSPHLAAQNQQT | 1579 | 2.134 |
| KTINGSGSPHSKTSRQQT | 1580 | 2.132 |
| KTINGSGSPHSKAQNARH | 1581 | 2.127 |
| KTINGSGSPHSKAQLKLT | 1582 | 2.125 |
| KTINGSGSPHSKAQNWRT | 1583 | 2.125 |
| KTINGSGSPHELPQNQQT | 1584 | 2.123 |
| KTINGSGSPHSKNVRQQT | 1585 | 2.123 |
| KTINGSGSPHFMRQNQQT | 1586 | 2.123 |
| KTINGSGSPHGWAQNQQT | 1587 | 2.121 |
| KTINGSGSPHFHLQNQQT | 1588 | 2.121 |
| KTINGSASPHWSAQNQQT | 1589 | 2.121 |
| KTINGSSSPHSWAQNQQT | 1590 | 2.119 |
| KTINGSGSPHSKAHRQQT | 1591 | 2.117 |
| KTINGSGSPHSKQRVQQT | 1592 | 2.117 |
| KTLRRSGSPHSKAQNQQT | 1593 | 2.117 |
| KTINGSGSPHSKGVRQQT | 1594 | 2.115 |
| KTINGSLSPHTWAQNQQT | 1595 | 2.115 |
| KTINGSGSPHSKRALQQT | 1596 | 2.114 |
| KTINGSGSPHCLSQNQQT | 1597 | 2.114 |
| KTINGSGSPHSKAQSLKT | 1598 | 2.110 |
| KTINGSGSPHSFVRNQQT | 1599 | 2.110 |
| KTINGSGSPHSIFSNQQT | 1600 | 2.110 |
| KTINGSGSPHSKVSRQQT | 1601 | 2.108 |
| KTINGSGSPHSKARNKQT | 1602 | 2.108 |
| KTINASGSPHSKAQGQQT | 1603 | 2.108 |
| KTINGSGSPHSKLRMQQT | 1604 | 2.106 |
| KTINGSWSPHMLAQNQQT | 1605 | 2.106 |
| KTINGSGSPHSLFPNQQT | 1606 | 2.106 |
| KPPLGSGSPHSKAQNQQT | 1607 | 2.102 |
| KTINGIASPHRKAQNQQT | 1608 | 2.099 |
| KTINGSCSPHSLAQNQQT | 1609 | 2.099 |
| KTINGRLSPHFKAQNQQT | 1610 | 2.097 |
| KTINGSGSPHSKARMTQT | 1611 | 2.091 |
| KTINGSGSPHSKARLQQT | 1612 | 2.089 |
| KTINGSGSPHSKWVSQQT | 1613 | 2.089 |
| KTINGSGSPHSKKVSQQT | 1614 | 2.088 |
| KTINGSGSPHSKAQSYRT | 1615 | 2.088 |
| KAFNGSGSPHSKAPNQQT | 1616 | 2.088 |
| KTINGSGSPHSKAQYRLT | 1617 | 2.088 |
| KTINGSWSPHLVAQNQQT | 1618 | 2.084 |
| KTINGSGSPHSWTQNQQT | 1619 | 2.084 |
| KTINGSGSPHSKAQSHRT | 1620 | 2.084 |
| KGINGSGSPHGKAQNQQT | 1621 | 2.084 |
| KTINGSGSPHSKAQNRKL | 1622 | 2.084 |
| KTINGRYSPHSKAQNQQT | 1623 | 2.080 |
| KTINGSGSPHSKGRSQQT | 1624 | 2.080 |
| KTINGSGSPHCVAQNQQT | 1625 | 2.080 |
| KTINGSGSPHSKIRPQQT | 1626 | 2.080 |
| KTINGSGSPHSKAQSSKT | 1627 | 2.078 |
| KTINGSGSPHSKRPFQQT | 1628 | 2.076 |
| KTINGSSSPHCLAQNQQT | 1629 | 2.074 |
| KTINGTRSPHAKAQNQQT | 1630 | 2.071 |
| KTINGSGSPHLLFQNQQT | 1631 | 2.069 |
| KTINGRRSPHTKAQNQQT | 1632 | 2.069 |
| KTINGSGSPHSKASKQQT | 1633 | 2.069 |
| KTINGSGSPHSKAQLGRT | 1634 | 2.069 |

TABLE 13-continued

NGS fold-enrichment of TTM-001 matured AAV capsid variants in the brain of CD-1 Outbred mice

| Peptide Sequence | SEQ ID NO: | Fold enrichment over TTM-001 |
|---|---|---|
| KTINGSGSPHSVFLNQQT | 1635 | 2.069 |
| KTINGSGSPHSKSARQQT | 1636 | 2.067 |
| KTINGSGSPHSKLRLQQT | 1637 | 2.065 |
| KTRKSSGSPHSKAQNQQT | 1638 | 2.065 |
| KTINGFRSPHLKAQNQQT | 1639 | 2.063 |
| KTINGSGSPHSKRSIQQT | 1640 | 2.063 |
| KTINGSGSPHSKGRIQQT | 1641 | 2.061 |
| KTINGSRSPHRPAQNQQT | 1642 | 2.061 |
| KTINGSGSPHSKLRPQQT | 1643 | 2.060 |
| KTINGSGSPHMYAQNQQT | 1644 | 2.060 |
| KTINGRTSPHAKAQNQQT | 1645 | 2.060 |
| KTINGSGSPHSKAGRGQT | 1646 | 2.058 |
| KTINGSGSPHSKLMRQQT | 1647 | 2.056 |
| KTINGSGSPHSKANKSQT | 1648 | 2.056 |
| KTINGSGSPHSKAVRQQT | 1649 | 2.052 |
| KTINGSGSPHSKCLSQQT | 1650 | 2.052 |
| KTINGSGSPHSKAQWVLT | 1651 | 2.052 |
| KTINGSGSPHSKAQFWVT | 1652 | 2.050 |
| KTINGSGSPHSKALCRQT | 1653 | 2.048 |
| KEVMGSGSPHSKAQNQQT | 1654 | 2.047 |
| KTINGSGSPHSKNTRQQT | 1655 | 2.047 |
| KTINGSGSPHTWTQNQQT | 1656 | 2.045 |
| KTINGSTSPHWSAQNQQT | 1657 | 2.043 |
| KTINGNVSPHRKAQNQQT | 1658 | 2.043 |
| KTINGSTSPHLFAQNQQT | 1659 | 2.041 |
| KTINGSGSPHSKAQNYRA | 1660 | 2.039 |
| KTINGSGSPHSKARGQQT | 1661 | 2.039 |
| KTINGSGSPHSKAQNRIR | 1662 | 2.039 |
| KTINGSGSPHSKWTLQQT | 1663 | 2.039 |
| KTINGSGSPHSKAQMKCT | 1664 | 2.039 |
| KTINGSGSPHSLWQNQQT | 1665 | 2.037 |
| KTINGSGSPHSKAQLSKT | 1666 | 2.035 |
| KTINLIWSPHSKAQNQQT | 1667 | 2.035 |
| KTINGSGSPHSKRVLQQT | 1668 | 2.035 |
| KTINGSGSPHSKVRVQQT | 1669 | 2.034 |
| KTINSRFSPHSKAQNQQT | 1670 | 2.032 |
| KRSKGSGSPHSKAQNQQT | 1671 | 2.030 |
| KTINGSGSPHRRLQNQQT | 1672 | 2.030 |
| KTINGSGSPHSCAQNQQT | 1673 | 2.030 |
| KTINGPLSPHRKAQNQQT | 1674 | 2.028 |
| KTINGSVSPHLYAQNQQT | 1675 | 2.028 |
| KTINGRISPHLKAQNQQT | 1676 | 2.028 |
| KTINGSHSPHRKAQNQQT | 1677 | 2.028 |
| KTINGSGSPHSKAQVSIT | 1678 | 2.028 |
| KTINGSMSPHRRAQNQQT | 1679 | 2.028 |
| KTINGRQSPHAKAQNQQT | 1680 | 2.026 |
| KTINGSGSPHSKAVWRQT | 1681 | 2.026 |
| KQPLGSGSPHSKAQNQQT | 1682 | 2.024 |
| KTINGSGSPHSKAQNVKL | 1683 | 2.024 |
| KTINGSGSPHSKRGTQQT | 1684 | 2.022 |
| KTINGSVSPHYVAQNQQT | 1685 | 2.022 |
| KTINGSGSPHSKNLRQQT | 1686 | 2.022 |
| KTINGSGSPHSKAQAFRT | 1687 | 2.022 |
| KTINGSGSPHSKCSNQQT | 1688 | 2.020 |
| KELVGSGSPHSKAQNQQT | 1689 | 2.019 |
| KTINGSGSPHSLVFNQQT | 1690 | 2.019 |
| KTINGSGSPHSKAQATRT | 1691 | 2.019 |
| KTINGTSSPHCKAQNQQT | 1692 | 2.017 |
| KTINGSGSPHSKALWRQT | 1693 | 2.015 |
| KTINGSGSPHSKAQFSVT | 1694 | 2.015 |
| KTINGSGSPHSKLYMQQT | 1695 | 2.015 |
| KTINGSLSPHYMAQNQQT | 1696 | 2.015 |
| KTINGSGSPHSKAWLMQT | 1697 | 2.015 |
| KTINGSGSPHSKSLKQQT | 1698 | 2.013 |
| KTINGSGSPHSKAQNTRR | 1699 | 2.013 |
| KTINGSGSPHYLLQNQQT | 1700 | 2.011 |
| KTINGSGSPHTWSQNQQT | 1701 | 2.011 |
| KTINGSGSPHSKTRMQQT | 1702 | 2.011 |
| KTINTRPSPHSKAQNQQT | 1703 | 2.011 |
| KTINGSGSPHSKAQILVT | 1704 | 2.009 |
| KTINGSGSPHSKAQNAKS | 1705 | 2.009 |
| KTINGSGSPHSRTYNQQT | 1706 | 2.009 |

TABLE 13-continued

NGS fold-enrichment of TTM-001 matured AAV capsid variants in the brain of CD-1 Outbred mice

| Peptide Sequence | SEQ ID NO: | Fold enrichment over TTM-001 |
|---|---|---|
| KTINGSGSPHSKKGGQQT | 1707 | 2.009 |
| KTINGYSSPHRKAQNQQT | 1708 | 2.007 |
| KTINGSGSPHWVSQNQQT | 1709 | 2.007 |
| KTINGSGSPHSKARLAQT | 1710 | 2.007 |
| KTINGMCSPHSKAQNQQT | 1711 | 2.006 |
| KTINGSGSPHSKSNKQQT | 1712 | 2.006 |
| KTINGSGSPHSKAQFVLT | 1713 | 2.006 |
| KTINGSISPHFVAQNQQT | 1714 | 2.006 |
| KTINGSGSPHRRMQNQQT | 1715 | 2.004 |
| KTINGSGSPHSKAWILQT | 1716 | 2.004 |
| KTINGSGSPHSKAQGVKT | 1717 | 2.002 |
| KTINGSGSPHSKAQFSLT | 1718 | 2.000 |
| KTINMLRSPHSKAQNQQT | 1719 | 2.000 |
| KTINGSGSPHSKAQLGKT | 1720 | 2.000 |
| KTINGSGSPHSMYLNQQT | 1721 | 2.000 |

As shown in Table 14, approximately 72 TTM-002 matured capsid variants demonstrated at least a 2-fold increase in expression relative to the non-matured TTM-002 control, with a few variants demonstrating greater than a three- to five-fold enrichment relative to the non-matured TTM-002 control. Also, across the peptides comprised within the TTM-002 matured capsid variants with the greatest fold-enrichment relative to the non-matured TTM-002 capsid in the brain, it was observed that the modifications in the variant sequences appeared in the region N-terminal to the SPH motif present within the capsid variant. This indicates that modifications that appeared to improve TTM-002 capsid tropism in the CNS of mice were skewed to the N-terminal portion of the peptide insertion in loop IV of the sequence. Additionally, a number of these N-terminal modifications that were incorporated into the matured TTM-002 capsid variants were negatively charged amino acids (particularly glutamic acid (E)).

TABLE 14

NGS fold-enrichment of TTM-002 matured AAV capsid variants in the brain of CD-1 Outbred mice

| Peptide Sequence | SEQ ID NO: | Fold enrichment over TTM-002 |
|---|---|---|
| KTINGHDSPHVTDQNQQT | 1722 | 5.20 |
| KTINGHDSPHKRGQHRQT | 1723 | 4.20 |
| KMPEGHDSPHKSGQNQQT | 1724 | 3.18 |
| KMEGGHDSPHKSGQNQQT | 1725 | 2.72 |
| KMEYGHDSPHKSGQNQQT | 1726 | 2.71 |
| KAEWGHDSPHKSGQNQQT | 1727 | 2.69 |
| KCEWGHDSPHKSGQNQQT | 1728 | 2.68 |
| KANNGQDSPHKSGQNQQT | 1729 | 2.67 |
| KTINGHDSPHLCGQNQQT | 1730 | 2.59 |
| KIPEGHDSPHKSGQNQQT | 1731 | 2.54 |
| KADMGHDSPHKSGQNQQT | 1732 | 2.48 |
| KTINGHLSPHYFGQNQQT | 1733 | 2.41 |
| KIEYGHDSPHKSGQNQQT | 1734 | 2.41 |
| KADYGHDSPHKSGQNQQT | 1735 | 2.40 |
| KIETGHDSPHKSGQNQQT | 1736 | 2.38 |
| KTINGHDSPHTNGQKQQT | 1737 | 2.38 |
| KMEWGHDSPHKSGQNQQT | 1738 | 2.38 |
| KTINGHDSPHWLLQNQQT | 1739 | 2.37 |
| KCEYGHDSPHKSGQNQQT | 1740 | 2.36 |
| KRINGHDSPHKSGQKQQN | 1741 | 2.34 |
| KMEIGHDSPHKSGQNQQT | 1742 | 2.34 |
| KLEYGHDSPHKSGQNQQT | 1743 | 2.33 |
| KADWGHDSPHKSGQNQQT | 1744 | 2.32 |
| KIEIGHDSPHKSGQNQQT | 1745 | 2.30 |
| KTIKDNDSPHKSGQNQQT | 1746 | 2.27 |
| KDIMGHDSPHKSGQNQQT | 1747 | 2.23 |
| KFEQGHDSPHKSGQNQQT | 1748 | 2.22 |
| KMEFGHDSPHKSGQNQQT | 1749 | 2.21 |
| KCDQGHDSPHKSGQNQQT | 1750 | 2.21 |
| KLPEGHDSPHKSGQNQQT | 1751 | 2.19 |
| KIENGHDSPHKSGQNQQT | 1752 | 2.19 |
| KMESGHDSPHKSGQNQQT | 1753 | 2.18 |
| KAEIGHDSPHKSGQNQQT | 1754 | 2.17 |
| KVEYGHDSPHKSGQNQQT | 1755 | 2.17 |
| KIINGHDSPHKSGLTQQT | 1756 | 2.17 |
| KTSNGDDSPHKSGRNQQT | 1757 | 2.17 |
| KIEVGHDSPHKSGQNQQT | 1758 | 2.16 |
| KMEMGHDSPHKSGQNQQT | 1759 | 2.16 |

TABLE 14-continued NGS fold-enrichment of TTM-002 matured AAV capsid variants in the brain of CD-1 Outbred mice

| Peptide Sequence | SEQ ID NO: | Fold enrichment over TTM-002 |
|---|---|---|
| KAEVGHDSPHKSGQNQQT | 1760 | 2.15 |
| KMDAGHDSPHKSGQNQQT | 1761 | 2.15 |
| KVEWGHDSPHKSGQNQQT | 1762 | 2.15 |
| KAEQGHDSPHKSGQNQQT | 1763 | 2.14 |
| KLEWGHDSPHKSGQNQQT | 1764 | 2.14 |
| KTINGHPSPHYLGQNQQT | 1765 | 2.14 |
| KTINGHLSPHYYGQNQQT | 1766 | 2.13 |
| KMELGHDSPHKSGQNQQT | 1767 | 2.13 |
| KMETGHDSPHKSGQNQQT | 1768 | 2.12 |
| KMEAGHDSPHKSGQNQQT | 1769 | 2.12 |
| KTINGHDSPHLLWQNQQT | 1770 | 2.12 |
| KTINRQRSPHKSGQNQQT | 1771 | 2.11 |
| KIESGHDSPHKSGQNQQT | 1772 | 2.11 |
| KTAKDHDSPHKSGQNQQT | 1773 | 2.11 |
| KMEVGHDSPHKSGQNQQT | 1774 | 2.11 |
| KCEIGHDSPHKSGQNQQT | 1775 | 2.10 |
| KATNGHDSPHKSGLNQQT | 1776 | 2.10 |
| KMDGGHDSPHKSGQNQQT | 1777 | 2.09 |
| KQEVGHDSPHKSGQNQQT | 1778 | 2.07 |
| KADQGHDSPHKSGQNQQT | 1779 | 2.07 |
| KTINGHESPHKSAQNHQT | 1780 | 2.07 |
| KTINGHDSPHKSAQNQWT | 1781 | 2.07 |
| KNMNGHDSPHKSGQNTHS | 1782 | 2.06 |
| KTPWEHDSPHKSGQNQQT | 1783 | 2.05 |
| KTINGHSSPHYFGQNQQT | 1784 | 2.05 |
| KIEMGHDSPHKSGQNQQT | 1785 | 2.05 |
| KTANEHDSPHKSGQNQQT | 1786 | 2.05 |
| KTINGHDSPHKSGRRRQT | 1787 | 2.04 |
| KISNGHDSPHKSAQNQQT | 1788 | 2.03 |
| KTGNGHDSPHKSGQYQQT | 1789 | 2.03 |
| KTINGHYSPHLFGQNQQT | 1790 | 2.02 |
| KTINGNYSPHKIGQNQQT | 1791 | 2.02 |
| KTINGHDSPHKSRQNDQT | 1792 | 2.01 |
| KQQQGHDSPHKSGQNQQT | 1793 | 2.01 |
| KTPQDHDSPHKSGQNQQT | 1794 | 2.00 |
| KHDWGHDSPHKSGQNQQT | 1795 | 2.00 |
| KIEGGHDSPHKSGQNQQT | 1796 | 2.00 |

These data demonstrate that following two maturation approaches, matured TTM-001 and TTM-002 capsid variants with loop IV modifications were generated with significantly enhanced CNS tropism in mice compared to the corresponding non-matured TTM-001 and TTM-002 capsid variants, which already exhibited a significant fold enrichment over AAV9 in the mouse brain.

Example 4. Maturation of TTM-001 and TTM-002 Capsid in NHPs

This Example describes maturation of the AAV9 capsid variants, TTM-001 (SEQ ID NO: 981 (amino acid) and 983 (DNA), comprising SEQ ID NO: 941 (encoded by SEQ ID NO: 942)) and TTM-002 (SEQ ID NO: 982 (amino acid) and 984 (DNA), comprising SEQ ID NO: 2 (encoded by SEQ ID NO: 3)) in NHPs to further enhance their transduction and biodistribution in the central nervous system as well as other tissues, and evolve the AAV capsid variants to provide further cross-species compatibility. Two approaches were used to mature the TTM-001 and TTM-002 capsid sequences in order to randomize and mutate within and around the peptide insert comprised within loop IV of the capsid variant. As many of the AAV capsid variants that demonstrated the greatest fold-enrichment in the NHP brain relative wild-type AAV9 comprised an SPH motif in the same position (e.g., immediately subsequent to position 455, relative to a reference sequence numbered according to the amino acid sequence of SEQ ID NO: 138) (see Example 1), the SPH motif was not mutated in either approach to mature the TTM-001 and TTM-002 capsid variants. In the first maturation approach, sets of three contiguous amino acids were randomized across the mutagenesis region in the TTM-001 and TTM-002 sequences, which spanned from position 450 to position 466, numbered according to SEQ ID NO: 981 and 982. In the second maturation approach, mutagenic primers were used to introduce point mutations at a low frequency, scattered across the mutagenesis region in the TTM-001 and TTM-002 sequences ranging from position 449 to position 466, numbered according to SEQ ID NO: 981 and 982. AAV capsid variants arising from each maturation approach for TTM-001 and TTM-002 were pooled together, for subsequent testing and characterization in NHPs.

The library of pooled matured AAV capsid variants generated using the first maturation approach and the second maturation approach for the TTM-001 and TTM-002 AAV capsid variants were injected into two NHPs. After a period in life, the brains, heart, liver, muscle, and DRG of the NHPs were isolated and RNA was extracted. Following RNA recovery and RT-PCR amplification, a systematic NGS enrichment analysis was performed to calculate the fold enrichment ratio relative to an AAV9 control, and the peptides comprised within the variants were identified.

Following the RNA recovery and NGS analysis from the second maturation approach, approximately 680,000 capsid variants were identified. The 680,000 matured capsid variants were then filtered based on samples with a raw virus count greater than 10 and a coefficient of variance (CV) of less than 1, which was calculated for each peptide across the brain samples taken from the two NHPs. Those that had a CV value <1 were identified, as these were the peptides that were reliably detected in the majority of samples isolated from the brains of the two NHPs. Using this filtering criteria, this led to approximately 64,000 matured capsid variants.

Table 15 provides the peptide sequences of the matured capsid variants having a raw virus count greater than 10, a CV of less than 1 for the brain samples isolated, and that also demonstrated a 50-fold or greater fold-increase in expression in the brain relative to the AAV9 control in both mice and NHPs. The matured variants in Table 15, were also those variants that had a fold-change in expression that was less than 2 relative to the AAV9 control in the liver and the DRG.

Applying these criteria, approximately 350 matured capsid variants were identified that demonstrated high transduction in the brain in NHPs and mice, cross-species compatibility in mice and NHPs, and were de-targeted in the liver and DRG, relative to the AAV9 control. Several variants as shown in Table 15, led to greater than 100-fold increase in expression relative to AAV9 in the NHP and/or mouse brain, with one variant resulting in a greater than 200-fold increase in expression relative to AAV9 in both species.

Fold-change in expression for the TTM-001 and TTM-002 matured variants in Table 15 that showed increased expression in the brain of the NHPs and mice, were also calculated for the DRG, muscle, liver (RNA and DNA), and heart of the NHPs following each maturation approach. As shown in Table 15, many variants were de-targeted in the peripheral tissues with a lower fold-change in expression relative to the AAV9 control, demonstrating CNS-specific tropism and a preferential transduction of the brain and CNS. Some variants demonstrated increased expression to AAV9 in multiple tissues, including the brain and peripheral tissues, demonstrating pan-tropism.

TABLE 15

NGS fold-enrichment of TTM-001 and TTM-002 matured AAV capsid variants in th ebrain of NHPs and mice

| Sequence | SEQ ID NO: | Fold Enrichment relative to AAV9 | | | | | | |
|---|---|---|---|---|---|---|---|---|
| | | Brain (NHP) | DRG (NHP) | Heart (NHP) | Muscle (NHP) | Liver RNA (NHP) | Liver DNA (NHP) | Brain (Mouse) |
| KTIIGSGSPHSKAQNRHT | 3239 | 217.176 | 0.000 | 0.000 | 0.000 | 0.000 | 0.000 | 210.515 |
| KTFPGSGSPHSKVQNQQT | 3240 | 199.720 | 0.000 | 0.000 | 0.000 | 0.000 | 0.967 | 97.703 |
| KTEKMSGSPHSKAQNQQT | 3241 | 169.461 | 0.523 | 0.000 | 0.000 | 0.000 | 0.158 | 109.161 |
| KEINGRGSPHSKAQNQQT | 3527 | 134.390 | 0.239 | 0.000 | 0.000 | 0.000 | 0.232 | 52.311 |
| KTVNRNGSPHSKAQNQQT | 3528 | 133.016 | 0.000 | 0.416 | 0.000 | 0.000 | 0.000 | 85.361 |
| KTVNGSGSPHSKARDQQT | 3242 | 124.789 | 0.123 | 0.039 | 0.312 | 0.569 | 0.454 | 132.137 |
| KTFNGSGSPHSKAPNLQT | 3243 | 121.436 | 0.000 | 0.167 | 0.000 | 0.000 | 0.015 | 168.920 |
| KTEKTSGSPHSKAQNQQT | 3244 | 120.337 | 0.000 | 0.355 | 0.000 | 0.000 | 0.119 | 101.467 |
| KTINGSGSPHSKAHVRQT | 3245 | 119.798 | 0.000 | 0.000 | 0.262 | 0.694 | 1.039 | 165.590 |
| KTVNGSGSPHSKAPNQHT | 3246 | 117.207 | 0.000 | 0.109 | 0.000 | 0.000 | 0.074 | 51.008 |
| KTEKISGSPHSKAQNQQT | 3247 | 116.603 | 0.000 | 0.000 | 0.000 | 0.000 | 0.426 | 102.978 |
| KTINGPGSPHSKAHNQQT | 3529 | 115.742 | 0.146 | 0.000 | 0.235 | 0.000 | 0.513 | 52.508 |
| KTVNGSGSPHSKTQSQQT | 3248 | 115.086 | 0.000 | 0.726 | 0.000 | 0.000 | 0.340 | 63.248 |
| TTINGSGSPHSKAQNQQT | 3249 | 114.856 | 1.340 | 14.856 | 0.827 | 1.281 | 0.957 | 72.058 |
| KSINESGSPHSKAQNQQI | 3250 | 113.833 | 0.000 | 0.000 | 0.000 | 0.000 | 0.000 | 67.649 |
| KTERTSGSPHSKAQNQQT | 3251 | 112.957 | 0.000 | 0.009 | 0.000 | 1.128 | 0.207 | 117.374 |
| KTINGSGSPHSKAQPAKT | 3252 | 111.472 | 0.331 | 0.000 | 1.089 | 0.044 | 1.796 | 215.275 |
| KTEKSSGSPHSKAQNQQT | 3253 | 107.470 | 0.000 | 0.016 | 0.014 | 0.977 | 0.179 | 100.177 |
| KTSYGNGSPHSKAQNQQT | 3530 | 105.937 | 0.000 | 0.000 | 0.000 | 0.000 | 0.114 | 105.894 |
| KTEKGSGSPHSKAQNQQT | 3254 | 105.614 | 0.053 | 0.031 | 0.000 | 0.586 | 0.169 | 84.653 |
| KTINGSGSPHSKSQTQQN | 3255 | 104.474 | 0.000 | 0.131 | 0.000 | 0.084 | 0.038 | 54.021 |
| KTERISGSPHSKAQNQQT | 3256 | 103.692 | 0.000 | 0.000 | 0.000 | 0.062 | 0.370 | 89.637 |

TABLE 15-continued

NGS fold-enrichment of TTM-001 and TTM-002 matured AAV capsid variants in th ebrain of NHPs and mice

| | | Fold Enrichment relative to AAV9 | | | | | | |
|---|---|---|---|---|---|---|---|---|
| Sequence | SEQ ID NO: | Brain (NHP) | DRG (NHP) | Heart (NHP) | Muscle (NHP) | Liver RNA (NHP) | Liver DNA (NHP) | Brain (Mouse) |
| KTERASGSPHSKAQNQQT | 3257 | 103.669 | 0.000 | 0.000 | 0.000 | 0.127 | 0.070 | 115.550 |
| KELHGSGSPHSKAQNQQT | 3258 | 102.680 | 0.000 | 0.000 | 0.000 | 1.634 | 0.592 | 96.554 |
| KAINGSGSPHSKAQNLAT | 3259 | 101.954 | 0.000 | 10.954 | 8.655 | 0.298 | 0.239 | 116.685 |
| KTVNGSGSPHSKSQNQLT | 3260 | 101.327 | 0.000 | 0.035 | 0.000 | 0.000 | 0.025 | 80.716 |
| KTERNSGSPHSKAQNQQT | 3261 | 99.892 | 0.000 | 0.000 | 0.000 | 0.000 | 0.107 | 87.392 |
| KSVNGNGSPHSKAQNQQT | 3531 | 99.385 | 0.000 | 1.329 | 0.000 | 0.359 | 0.079 | 51.016 |
| KTFNGSGSPHSKAQGQQT | 3262 | 99.253 | 0.000 | 0.208 | 0.000 | 0.128 | 0.099 | 81.459 |
| KTINGSGSPHGWVQNQQT | 3532 | 97.122 | 0.000 | 0.000 | 0.000 | 1.240 | 1.975 | 290.720 |
| KTERVSGSPHSKAQNQQT | 3263 | 96.943 | 0.000 | 0.000 | 0.000 | 0.000 | 0.144 | 135.438 |
| KTINGSGSPHSKALNRQS | 3264 | 96.843 | 0.136 | 0.532 | 0.000 | 0.042 | 0.178 | 55.945 |
| KTERLSGSPHSKAQNQQT | 3265 | 95.857 | 0.000 | 0.004 | 0.005 | 0.126 | 0.260 | 102.372 |
| KTDNGSGSPHSKAHNQQT | 3266 | 95.164 | 0.000 | 0.000 | 0.000 | 0.000 | 0.027 | 55.313 |
| KTFHGSGSPHSKTQNQQT | 3267 | 94.714 | 0.000 | 0.210 | 0.120 | 0.000 | 0.000 | 51.119 |
| KTINGGGSPHSKAQTQQI | 3533 | 92.345 | 0.000 | 0.000 | 0.000 | 0.000 | 0.023 | 54.199 |
| KTSNGSGSPHSKAQNPPT | 3268 | 91.528 | 0.000 | 0.000 | 0.000 | 0.000 | 0.039 | 51.541 |
| ETINGSGSPHSKAQNLQT | 3269 | 90.969 | 0.221 | 1.023 | 0.197 | 0.179 | 0.813 | 107.216 |
| KTVHGNGSPHSKAQNQQT | 3534 | 90.073 | 0.000 | 0.000 | 0.000 | 0.000 | 0.304 | 97.003 |
| NTINGSGSPHSKAQNQQT | 3270 | 90.017 | 1.712 | 1.261 | 1.171 | 0.923 | 0.540 | 55.179 |
| KTINGGGSPHSKAQNQQC | 3535 | 89.301 | 0.219 | 0.000 | 0.000 | 0.287 | 0.319 | 53.840 |
| KTENMSGSPHSKAQNQQT | 3271 | 89.247 | 0.000 | 0.000 | 0.000 | 0.000 | 0.260 | 130.568 |
| KTENVSGSPHSKAQNQQT | 3272 | 88.506 | 0.000 | 0.000 | 0.000 | 0.964 | 0.112 | 108.591 |
| KTSSGSGSPHSKAQYQQT | 3273 | 87.304 | 0.000 | 0.000 | 0.000 | 0.000 | 0.299 | 58.143 |
| KTIDGGGSPHSKAQNKQT | 3536 | 85.019 | 0.000 | 0.000 | 0.000 | 0.000 | 0.477 | 55.517 |
| KTEKVSGSPHSKAQNQQT | 3274 | 84.558 | 0.000 | 0.022 | 0.000 | 0.873 | 0.424 | 112.185 |
| KAINGSGSPHSKAQDQET | 3275 | 84.080 | 0.000 | 0.000 | 0.000 | 0.194 | 0.027 | 87.637 |
| KTCNKSGSPHSKAQNQQT | 3276 | 83.992 | 0.000 | 0.000 | 0.165 | 0.283 | 0.000 | 119.496 |
| KTINGGGSPHSKAQNQLI | 3537 | 83.881 | 0.000 | 0.000 | 0.000 | 0.046 | 0.387 | 78.383 |
| KNINGGGSPHSKAQNQQT | 3538 | 83.083 | 0.000 | 0.042 | 0.000 | 0.000 | 0.000 | 75.913 |
| KTEHLSGSPHSKAQNQQT | 3277 | 83.080 | 0.000 | 0.000 | 0.012 | 0.021 | 0.189 | 69.494 |
| KAEMGSGSPHSKAQNQQT | 3278 | 83.049 | 0.000 | 0.020 | 0.000 | 0.768 | 0.112 | 135.019 |
| KATNGSGSPHSKAQNHQT | 3279 | 82.627 | 0.000 | 0.176 | 0.000 | 0.155 | 0.057 | 66.207 |
| KAIKGSGSPHSKAQDQQT | 3280 | 82.258 | 0.000 | 0.000 | 0.000 | 0.108 | 0.000 | 85.178 |
| KTINGGGSPHSKSQNQLT | 3539 | 82.231 | 0.000 | 0.070 | 0.000 | 0.000 | 0.498 | 126.986 |
| KTVNGNGSPHSKAQNKQT | 3540 | 81.481 | 0.000 | 0.000 | 0.000 | 0.000 | 0.122 | 69.455 |
| KTINGSGSPHSKGHWQQT | 3281 | 81.434 | 0.000 | 0.000 | 0.000 | 0.000 | 1.011 | 65.252 |
| KTDKTSGSPHSKAQNQQT | 3282 | 81.430 | 0.000 | 0.000 | 0.000 | 1.362 | 0.291 | 169.515 |

TABLE 15-continued

NGS fold-enrichment of TTM-001 and TTM-002 matured AAV capsid variants in th ebrain of NHPs and mice

| | | Fold Enrichment relative to AAV9 | | | | | | |
|---|---|---|---|---|---|---|---|---|
| Sequence | SEQ ID NO: | Brain (NHP) | DRG (NHP) | Heart (NHP) | Muscle (NHP) | Liver RNA (NHP) | Liver DNA (NHP) | Brain (Mouse) |
| KTFKGSGSPHSKAPNQQT | 3283 | 80.890 | 0.000 | 0.000 | 0.000 | 0.000 | 0.017 | 71.144 |
| KTVNGSGSPHSKAQNQLI | 3284 | 80.509 | 0.000 | 0.000 | 0.000 | 0.000 | 0.166 | 71.156 |
| KTINGSGSPHSKRPEQQT | 3285 | 80.418 | 0.000 | 0.013 | 0.000 | 0.149 | 0.361 | 50.319 |
| KTINGSGSPHSKAQRTMT | 3286 | 80.388 | 0.000 | 0.022 | 0.170 | 1.812 | 1.025 | 100.248 |
| KTEKASGSPHSKAQNQQT | 3287 | 80.285 | 0.000 | 0.041 | 0.000 | 0.000 | 0.261 | 90.390 |
| KSDQGSGSPHSKAQNQQT | 3288 | 80.076 | 0.000 | 0.000 | 0.000 | 0.993 | 0.124 | 151.911 |
| KTEITSGSPHSKAQNQQT | 3289 | 79.620 | 0.000 | 0.163 | 0.000 | 0.332 | 0.074 | 76.686 |
| KTDKSSGSPHSKAQNQQT | 3290 | 79.470 | 0.055 | 0.012 | 0.000 | 1.437 | 0.367 | 141.351 |
| KTIDGSGSPHSKAQNQQH | 3291 | 79.090 | 0.000 | 0.000 | 0.000 | 0.136 | 0.049 | 57.914 |
| KTVNGNGSPHSKAQNQHT | 3541 | 78.849 | 0.000 | 0.000 | 0.000 | 0.000 | 0.045 | 54.086 |
| KNINGSGSPHSKAQNQQT | 3292 | 78.445 | 0.000 | 0.000 | 0.000 | 0.571 | 0.177 | 89.719 |
| KTETHSGSPHSKAQNQQT | 3293 | 77.974 | 0.000 | 0.067 | 0.000 | 0.000 | 0.512 | 57.287 |
| KTINGGGSPHSKALNQQN | 3542 | 77.822 | 0.000 | 0.131 | 0.000 | 0.000 | 0.274 | 69.884 |
| KTINGSGSPHSKALHQHT | 3294 | 77.502 | 0.000 | 0.052 | 0.041 | 0.000 | 0.188 | 68.196 |
| KTINGTGSPHSKAQNHQI | 3543 | 77.089 | 0.171 | 0.000 | 0.000 | 0.000 | 0.166 | 54.281 |
| KTINGSGSPHSKAQHRIT | 3295 | 76.849 | 0.105 | 0.499 | 0.170 | 1.424 | 0.214 | 127.000 |
| KTINGSGSPHSKAQYIHT | 3296 | 76.170 | 0.000 | 0.014 | 0.033 | 1.523 | 0.168 | 59.649 |
| KTENISGSPHSKAQNQQT | 3297 | 76.072 | 0.000 | 0.000 | 0.000 | 0.115 | 0.132 | 83.118 |
| KTIIGGGSPHSKAHNQQT | 3544 | 75.872 | 0.000 | 0.050 | 0.000 | 0.000 | 0.235 | 65.492 |
| KTINGSGSPHSKAQKFET | 3298 | 75.788 | 0.000 | 0.000 | 0.028 | 0.108 | 0.093 | 65.588 |
| KTSNESGSPHSKAQNHQT | 3299 | 75.720 | 0.000 | 0.000 | 0.000 | 0.169 | 0.217 | 70.590 |
| KTINGSGSPHSKAQFPST | 3300 | 75.677 | 0.000 | 0.004 | 0.000 | 0.849 | 0.127 | 119.712 |
| KTERPSGSPHSKAQNQQT | 3301 | 75.669 | 0.000 | 0.029 | 0.000 | 0.000 | 0.156 | 73.894 |
| KTINGNGSPHSKAQNPLT | 3545 | 75.269 | 0.000 | 0.000 | 0.000 | 0.366 | 0.000 | 53.583 |
| KSIKGNGSPHSKAQNQQT | 3546 | 75.196 | 0.000 | 0.000 | 0.000 | 0.000 | 0.000 | 90.251 |
| KTERMSGSPHSKAQNQQT | 3302 | 74.910 | 0.000 | 0.000 | 0.000 | 0.100 | 0.151 | 122.812 |
| KTERSSGSPHSKAQNQQT | 3303 | 74.853 | 0.000 | 0.071 | 0.000 | 1.036 | 0.056 | 125.538 |
| KTELHSGSPHSKAQNQQT | 3304 | 74.620 | 0.000 | 0.000 | 0.000 | 0.021 | 0.089 | 53.124 |
| KTELTSGSPHSKAQNQQT | 3305 | 74.548 | 0.000 | 0.000 | 0.000 | 0.537 | 0.421 | 100.311 |
| KTINGSGSPHSKAHNQQR | 3306 | 74.272 | 0.562 | 0.486 | 0.047 | 0.956 | 0.057 | 107.301 |
| KTINGGGSPHSKAQSQQI | 3547 | 74.264 | 0.000 | 0.000 | 0.000 | 0.000 | 0.235 | 67.651 |
| KTINGSGSPHSKAQAIKT | 3307 | 74.261 | 0.255 | 0.000 | 0.000 | 0.186 | 0.132 | 73.560 |
| KTENTSGSPHSKAQNQQT | 3308 | 74.061 | 0.000 | 0.000 | 0.218 | 0.233 | 0.730 | 96.249 |
| KTIDGSGSPHSKGQNRQT | 3309 | 73.930 | 0.000 | 0.000 | 0.000 | 0.106 | 0.091 | 63.626 |
| KNINGSGSPHSKAQSQQT | 3310 | 73.757 | 0.000 | 0.000 | 0.000 | 0.000 | 0.041 | 57.432 |

TABLE 15-continued

NGS fold-enrichment of TTM-001 and TTM-002 matured AAV capsid variants in th ebrain of NHPs and mice

| Sequence | SEQ ID NO: | Fold Enrichment relative to AAV9 | | | | | | |
|---|---|---|---|---|---|---|---|---|
| | | Brain (NHP) | DRG (NHP) | Heart (NHP) | Muscle (NHP) | Liver RNA (NHP) | Liver DNA (NHP) | Brain (Mouse) |
| KTINGSVSPHGKAQNQLT | 3548 | 73.525 | 0.000 | 0.061 | 0.067 | 0.000 | 0.053 | 51.358 |
| KTSNASGSPHSKAQNQLT | 3311 | 73.501 | 0.000 | 0.000 | 0.297 | 0.000 | 0.313 | 150.401 |
| KTEARSGSPHSKAQNQQT | 3312 | 73.349 | 0.000 | 0.000 | 0.000 | 0.695 | 0.118 | 62.903 |
| KTEKNSGSPHSKAQNQQT | 3313 | 73.347 | 0.000 | 0.000 | 0.044 | 0.159 | 0.021 | 74.393 |
| KTANGSGSPHSKAQYQQT | 3314 | 73.038 | 0.000 | 0.000 | 0.000 | 0.153 | 0.160 | 139.451 |
| KTVNGSGSPHSKAQYQHT | 3315 | 72.847 | 0.000 | 0.000 | 0.000 | 0.000 | 0.130 | 54.158 |
| KTINGSGSPHTKAQNPQS | 3316 | 72.594 | 0.000 | 0.000 | 0.000 | 0.000 | 0.130 | 62.508 |
| KTINGSGSPHSKGQNPPT | 3317 | 72.339 | 0.000 | 0.206 | 0.000 | 0.000 | 0.041 | 134.808 |
| KTIIGSGSPHSKAQHQLT | 3318 | 72.291 | 0.000 | 0.000 | 0.000 | 0.000 | 0.000 | 100.144 |
| KTINGSGSPHSKAQSPPT | 3319 | 71.632 | 0.069 | 0.047 | 0.274 | 0.179 | 0.425 | 97.111 |
| NTIYGSGSPHSKAQNQQT | 3320 | 71.267 | 1.739 | 0.000 | 273.69 | 0.000 | 0.209 | 59.707 |
| KTINGSGSPHSKAQAKLT | 3321 | 71.154 | 0.000 | 0.273 | 0.017 | 1.591 | 0.777 | 130.132 |
| KTDKNSGSPHSKAQNQQT | 3322 | 70.964 | 0.000 | 0.000 | 0.000 | 0.070 | 0.123 | 62.932 |
| KTINGSGSPHSKTKSQQT | 3323 | 70.891 | 0.000 | 0.568 | 0.045 | 0.418 | 0.496 | 83.923 |
| KTINGSGSPHSKAQDRPT | 3324 | 70.831 | 0.132 | 0.006 | 0.000 | 0.039 | 0.379 | 66.800 |
| KTINGIGSPHSKAQNLGT | 3549 | 70.543 | 0.000 | 0.071 | 0.000 | 0.000 | 0.135 | 104.769 |
| KTINGSGSPHSKAQSQQL | 3325 | 70.539 | 0.000 | 0.000 | 0.000 | 0.000 | 0.041 | 51.126 |
| KTENLSGSPHSKAQNQQT | 3326 | 70.303 | 0.070 | 0.000 | 0.000 | 0.395 | 0.470 | 107.385 |
| KTINGSGSPHSKAQAFHT | 3327 | 70.159 | 0.033 | 0.000 | 0.058 | 0.762 | 0.119 | 86.268 |
| KTINGSGSPHSKAQKQQD | 3328 | 70.116 | 0.000 | 0.024 | 0.000 | 0.064 | 0.083 | 110.196 |
| KTFSGSGSPHSKAQNLQT | 3329 | 70.035 | 0.000 | 0.327 | 0.303 | 0.000 | 0.228 | 70.917 |
| KAINGSGSPHSKAQNAQT | 3330 | 69.651 | 0.000 | 0.000 | 0.000 | 0.023 | 0.142 | 72.160 |
| KTESWSGSPHSKAQNQQT | 3331 | 69.144 | 0.000 | 0.000 | 0.000 | 0.000 | 0.019 | 67.699 |
| KTTNGSGSPHSKAHNQLT | 3332 | 69.062 | 0.000 | 0.000 | 0.000 | 0.708 | 0.000 | 65.505 |
| KTVNGNGSPHSKAQNHQT | 3550 | 68.889 | 0.000 | 0.000 | 0.000 | 0.000 | 0.030 | 52.482 |
| KTEDKSGSPHSKAQNQQT | 3333 | 68.813 | 0.000 | 0.000 | 0.000 | 0.000 | 0.000 | 70.071 |
| KTESASGSPHSKAQNQQT | 3334 | 68.651 | 0.000 | 0.000 | 0.000 | 0.274 | 0.084 | 80.500 |
| KTNNGSGSPHSKAQNQQY | 3335 | 68.530 | 0.000 | 0.040 | 0.000 | 0.000 | 0.059 | 82.656 |
| KTSNGGSPHSKAQNLQT | 3551 | 68.311 | 0.000 | 0.052 | 0.000 | 0.000 | 0.000 | 124.871 |
| KTDKMSGSPHSKAQNQQT | 3336 | 68.167 | 0.000 | 0.000 | 0.000 | 0.017 | 0.205 | 88.234 |
| KEVHGSGSPHSKAQNQQT | 3337 | 67.901 | 0.000 | 0.000 | 0.000 | 0.727 | 0.000 | 100.111 |
| KTINGSGSPHSKAQKLNT | 3338 | 67.782 | 0.073 | 0.092 | 0.000 | 1.232 | 0.201 | 68.637 |
| KTINGGGSPHSKSQNQHT | 3552 | 67.773 | 0.000 | 0.057 | 0.000 | 0.000 | 0.220 | 100.748 |
| KTVNGGGSPHSKAQSQQT | 3553 | 67.634 | 0.000 | 0.055 | 0.000 | 0.000 | 0.210 | 160.711 |
| KTTNGSGSPHSKAQYQHT | 3339 | 67.325 | 0.000 | 0.000 | 0.000 | 1.378 | 0.080 | 83.337 |
| KTISGSGSPHSKAQYQHT | 3340 | 66.739 | 0.000 | 0.000 | 0.000 | 0.000 | 0.191 | 59.822 |

TABLE 15-continued

NGS fold-enrichment of TTM-001 and TTM-002 matured AAV capsid variants in the brain of NHPs and mice

| | | Fold Enrichment relative to AAV9 | | | | | | |
|---|---|---|---|---|---|---|---|---|
| Sequence | SEQ ID NO: | Brain (NHP) | DRG (NHP) | Heart (NHP) | Muscle (NHP) | Liver RNA (NHP) | Liver DNA (NHP) | Brain (Mouse) |
| KTESTSGSPHSKAQNQQT | 3341 | 66.649 | 0.000 | 0.009 | 0.000 | 1.688 | 0.176 | 95.861 |
| KTINGSGSPHSKSQNVQT | 3342 | 66.627 | 0.000 | 0.190 | 0.000 | 0.202 | 0.188 | 56.672 |
| KSINGSGSPHSKAQAQQT | 3343 | 66.464 | 0.000 | 0.711 | 0.000 | 0.148 | 0.111 | 78.451 |
| KTVNGSGSPHSKAQNLQA | 3344 | 66.379 | 0.000 | 0.000 | 0.000 | 0.000 | 0.132 | 50.934 |
| KTVRDSGSPHSKAQNQQT | 3345 | 66.056 | 0.000 | 0.025 | 0.000 | 0.129 | 0.461 | 142.600 |
| KTFNASGSPHSKAPNQQT | 3346 | 65.392 | 0.208 | 0.000 | 0.000 | 0.215 | 0.156 | 66.275 |
| KTDRMSGSPHSKAQNQQT | 3347 | 65.143 | 0.000 | 0.000 | 0.000 | 0.332 | 0.103 | 104.890 |
| KTINGSGSPHSKAQTPPT | 3348 | 64.657 | 0.010 | 0.015 | 0.014 | 0.200 | 0.207 | 54.179 |
| ETIKGSGSPHSKAQNQQT | 3349 | 64.609 | 0.000 | 0.000 | 0.144 | 0.000 | 0.024 | 67.201 |
| KNHIGSGSPHSKAQNQQT | 3350 | 64.535 | 0.000 | 0.000 | 0.000 | 1.253 | 0.187 | 70.356 |
| KTINGSGSPHSKAQYQHA | 3351 | 64.435 | 0.000 | 0.000 | 0.024 | 0.993 | 0.097 | 57.278 |
| KTIPIDGSPHSKAQNQQT | 3554 | 64.421 | 0.000 | 0.047 | 0.000 | 0.234 | 0.936 | 76.826 |
| KTINGSGSPHSKAQGQQA | 3352 | 64.128 | 0.000 | 0.185 | 0.000 | 0.063 | 0.195 | 64.116 |
| KTFNGSGSPHNKAQNHQT | 3353 | 64.060 | 0.000 | 0.000 | 0.035 | 0.094 | 0.317 | 67.757 |
| KESDGSGSPHSKAQNQQT | 3354 | 63.766 | 0.000 | 0.000 | 0.000 | 0.567 | 0.146 | 115.231 |
| KTINGSGSPHSKAQPPAT | 3355 | 63.510 | 0.048 | 0.030 | 0.031 | 0.126 | 0.302 | 117.453 |
| KTINGSGSPHSKAQERPT | 3356 | 63.460 | 0.000 | 0.011 | 0.000 | 0.810 | 0.173 | 57.506 |
| KTIKGSGSPHSKAQDLQT | 3357 | 63.260 | 0.000 | 0.000 | 0.000 | 0.000 | 0.218 | 58.576 |
| KTDLKSGSPHSKAQNQQT | 3358 | 63.152 | 0.000 | 0.000 | 0.012 | 0.285 | 0.377 | 62.687 |
| KTINGGGSPHSKAQNPPT | 3555 | 63.041 | 0.000 | 0.082 | 0.000 | 0.000 | 0.057 | 64.045 |
| KTINGSGSPHSKAQAMHT | 3359 | 62.756 | 0.000 | 0.000 | 0.010 | 0.976 | 0.393 | 84.056 |
| KTVPNSGSPHSKAQNQQT | 3360 | 62.540 | 0.000 | 0.000 | 0.011 | 0.202 | 0.161 | 93.793 |
| KTVIGSGSPHSKALNQQT | 3361 | 62.358 | 0.000 | 0.310 | 0.000 | 0.062 | 0.245 | 60.369 |
| KTINGSGSPHSKAQHPST | 3362 | 62.255 | 0.000 | 0.044 | 0.000 | 1.345 | 0.301 | 101.103 |
| KTINGLGSPHSKSQNQQT | 3556 | 62.170 | 0.000 | 0.157 | 0.000 | 0.146 | 0.107 | 64.139 |
| KTINGTGSPHSKAQNQQM | 3557 | 62.151 | 0.000 | 0.000 | 0.000 | 0.000 | 0.000 | 62.376 |
| KTINGSGSPHSKAPGLQT | 3363 | 62.043 | 0.007 | 0.000 | 0.005 | 0.651 | 0.210 | 144.610 |
| KTINGSGSPHSKAQGIRT | 3364 | 61.952 | 0.041 | 0.000 | 0.012 | 0.897 | 0.502 | 155.013 |
| KTESHSGSPHSKAQNQQT | 3365 | 61.947 | 0.000 | 0.000 | 0.000 | 1.480 | 0.106 | 52.506 |
| KTINGSGSPHSKAQAPAT | 3366 | 61.934 | 0.000 | 0.169 | 0.015 | 0.696 | 0.197 | 127.420 |
| KTINGSGSPHSKSQSQQI | 3367 | 61.870 | 0.000 | 0.000 | 0.000 | 0.200 | 0.175 | 64.027 |
| KAEHGSGSPHSKAQNQQT | 3368 | 61.830 | 0.000 | 0.000 | 0.000 | 0.772 | 0.184 | 116.201 |
| KTEDRSGSPHSKAQNQQT | 3369 | 61.756 | 0.000 | 0.000 | 0.000 | 1.004 | 0.408 | 66.887 |
| KNCLGSGSPHSKAQNQQT | 3370 | 61.442 | 0.000 | 0.036 | 0.000 | 1.849 | 0.026 | 82.488 |
| KTDRGSGSPHSKAQNQQT | 3371 | 61.419 | 0.000 | 0.004 | 0.000 | 0.211 | 0.316 | 74.256 |

TABLE 15-continued

NGS fold-enrichment of TTM-001 and TTM-002 matured AAV capsid variants in the brain of NHPs and mice

| | | Fold Enrichment relative to AAV9 | | | | | |
|---|---|---|---|---|---|---|---|
| Sequence | SEQ ID NO: | Brain (NHP) | DRG (NHP) | Heart (NHP) | Muscle (NHP) | Liver RNA (NHP) | Liver DNA (NHP) | Brain (Mouse) |
| KTINGSGSPHSKAQIPPT | 3372 | 61.258 | 0.000 | 0.000 | 0.000 | 0.758 | 0.115 | 87.661 |
| KTVKGSGSPHSKAQDQQT | 3373 | 61.175 | 0.000 | 0.041 | 0.000 | 0.432 | 0.090 | 58.114 |
| KNADGSGSPHSKAQNQQT | 3374 | 60.944 | 0.000 | 0.000 | 0.000 | 1.239 | 0.085 | 104.503 |
| KTDKVSGSPHSKAQNQQT | 3375 | 60.935 | 0.000 | 0.015 | 0.000 | 0.765 | 0.128 | 146.657 |
| KTITGSGSPHSKAQTQLT | 3376 | 60.846 | 0.160 | 8.992 | 0.000 | 0.000 | 0.000 | 55.640 |
| KTINGSGSPHSKAQAPST | 3377 | 60.696 | 0.200 | 0.005 | 0.000 | 0.751 | 0.263 | 115.528 |
| KNCVGSGSPHSKAQNQQT | 3378 | 60.535 | 0.000 | 0.000 | 0.000 | 0.018 | 0.282 | 96.175 |
| KTIRDAGSPHSKAQNQQT | 3558 | 60.346 | 0.000 | 0.000 | 0.000 | 0.141 | 0.251 | 113.179 |
| KTVKDSGSPHSKAQNQQT | 3379 | 60.216 | 0.000 | 0.019 | 0.000 | 0.443 | 0.251 | 87.334 |
| KNALGSGSPHSKAQNQQT | 3380 | 60.014 | 0.000 | 0.003 | 0.000 | 0.682 | 0.213 | 137.222 |
| KVINGSGSPHSKGQNQQT | 3381 | 60.001 | 0.000 | 0.000 | 0.031 | 0.264 | 0.157 | 68.532 |
| KTVNGGGSPHSKAQNQQS | 3559 | 59.871 | 0.062 | 0.020 | 0.000 | 0.080 | 0.185 | 61.847 |
| KTIQDGGSPHSKAQNQQT | 3560 | 59.865 | 0.000 | 0.000 | 0.116 | 1.435 | 0.789 | 87.522 |
| KTISGGGSPHSKAQNQQN | 3561 | 59.801 | 0.000 | 0.000 | 0.000 | 0.722 | 0.039 | 87.761 |
| KTSNASGSPHSKAHNQQT | 3382 | 59.607 | 0.000 | 0.078 | 0.067 | 0.031 | 0.050 | 67.967 |
| KTINGSGSPHSKAQNTYA | 3383 | 59.603 | 0.000 | 0.000 | 0.000 | 0.425 | 0.346 | 101.715 |
| KTINGSGSPHSKSQNQHI | 3384 | 59.438 | 0.000 | 0.099 | 0.000 | 0.111 | 0.108 | 76.025 |
| KTINGGGSPHSKAQDKQT | 3562 | 59.322 | 0.000 | 0.000 | 0.000 | 0.000 | 0.093 | 50.764 |
| KTEFVSGSPHSKAQNQQT | 3385 | 59.306 | 0.000 | 0.000 | 0.000 | 0.196 | 0.276 | 69.788 |
| KTVNGSGSPHSKAQNHLT | 3386 | 59.239 | 0.133 | 0.034 | 0.000 | 0.000 | 0.156 | 70.786 |
| KTREISGSPHSKAQNQQT | 3387 | 59.027 | 0.000 | 0.042 | 0.224 | 0.356 | 0.269 | 51.696 |
| KTINGSGSPHSKAQIGMT | 3388 | 59.013 | 0.081 | 106.528 | 0.000 | 1.003 | 0.248 | 134.585 |
| KTIDGSGSPHSKALNKQT | 3389 | 58.992 | 0.000 | 0.267 | 0.000 | 0.000 | 0.056 | 74.626 |
| KTIIGGGSPHSKAQNPQT | 3563 | 58.924 | 0.000 | 0.202 | 0.000 | 0.000 | 0.126 | 53.992 |
| KQGEGSGSPHSKAQNQQT | 3390 | 58.752 | 0.000 | 0.000 | 0.000 | 0.000 | 0.151 | 135.300 |
| KTINGTGSPHSKAPNQLT | 3564 | 58.738 | 0.000 | 0.000 | 0.000 | 0.229 | 0.035 | 86.939 |
| KTVNGSGSPHSKAQLQQT | 3391 | 58.681 | 0.315 | 0.465 | 0.045 | 0.529 | 0.333 | 81.201 |
| KTFNGGGSPHSKAYYQQT | 3565 | 58.609 | 0.000 | 0.000 | 0.000 | 0.163 | 0.045 | 72.618 |
| KSINGSGSPHSKTQSQQT | 3392 | 58.608 | 0.000 | 3.017 | 0.000 | 0.155 | 0.017 | 71.397 |
| KTVNGGGSPHSKAQHQQT | 3566 | 58.602 | 0.729 | 0.000 | 0.000 | 0.000 | 0.043 | 138.544 |
| KSEKGSGSPHSKAQNQQT | 3393 | 58.566 | 0.000 | 0.010 | 0.011 | 1.601 | 0.059 | 158.931 |
| KNVNGSGSPHSKAQNQQT | 3394 | 58.481 | 0.000 | 0.000 | 0.000 | 0.917 | 0.166 | 53.379 |
| KGGEGSGSPHSKAQNQQT | 3395 | 58.472 | 0.000 | 0.034 | 0.000 | 0.037 | 0.066 | 91.023 |
| KTINGSGSPHSKAQRMST | 3396 | 58.435 | 0.192 | 0.037 | 0.000 | 1.707 | 0.882 | 53.414 |
| KTINGSGSPHSKAQGILT | 3397 | 58.418 | 0.000 | 0.005 | 0.010 | 0.569 | 0.192 | 102.631 |
| KEFVGSGSPHSKAQNQQT | 3398 | 58.374 | 0.000 | 0.046 | 0.000 | 0.088 | 0.326 | 128.675 |

TABLE 15-continued

NGS fold-enrichment of TTM-001 and TTM-002 matured AAV capsid variants in the brain of NHPs and mice

| Sequence | SEQ ID NO: | Brain (NHP) | DRG (NHP) | Heart (NHP) | Muscle (NHP) | Liver RNA (NHP) | Liver DNA (NHP) | Brain (Mouse) |
|---|---|---|---|---|---|---|---|---|
| KTIIGSGSPHSKAQDRQT | 3399 | 58.258 | 1.393 | 0.230 | 0.219 | 0.000 | 0.045 | 53.981 |
| KSDKGSGSPHSKAQNQQT | 3400 | 58.248 | 0.000 | 0.000 | 0.000 | 0.076 | 0.166 | 146.566 |
| KTEQVSGSPHSKAQNQQT | 3401 | 58.247 | 0.000 | 0.000 | 0.000 | 0.000 | 0.081 | 88.487 |
| KTEHVSGSPHSKAQNQQT | 3402 | 58.228 | 0.000 | 0.024 | 0.000 | 0.433 | 0.141 | 71.410 |
| KTINGSGSPHSKARDWQT | 3403 | 58.216 | 0.000 | 0.005 | 0.000 | 0.800 | 0.259 | 120.704 |
| KTENASGSPHSKAQNQQT | 3404 | 58.187 | 0.000 | 0.038 | 0.000 | 0.371 | 0.129 | 88.439 |
| KEVQGSGSPHSKAQNQQT | 3405 | 58.125 | 0.000 | 0.000 | 0.000 | 0.657 | 0.000 | 168.220 |
| KTINGSGSPHSKAQNTHD | 3406 | 58.108 | 0.000 | 0.027 | 0.000 | 0.410 | 0.126 | 81.189 |
| KTINGSGSPHSKAPNLQI | 3407 | 58.022 | 0.000 | 0.044 | 0.000 | 1.548 | 0.243 | 55.714 |
| KTINGSGSPHSKAQERST | 3408 | 58.021 | 0.000 | 0.01 | 0.005 | 0.829 | 0.409 | 87.656 |
| KTSNGSGSPHSKAQNYQT | 3409 | 57.894 | 0.000 | 0.082 | 0.000 | 0.000 | 0.110 | 63.681 |
| KTEYISGSPHSKAQNQQT | 3410 | 57.891 | 0.000 | 0.000 | 0.000 | 0.076 | 0.075 | 57.620 |
| KTINGSGSPHSKAQRTCT | 3411 | 57.863 | 0.000 | 0.140 | 0.129 | 1.855 | 1.716 | 90.146 |
| KTINGSGSPHSKAQIGHT | 3412 | 57.769 | 0.024 | 0.000 | 0.000 | 0.281 | 0.154 | 99.262 |
| KNCWGSGSPHSKAQNQQT | 3413 | 57.756 | 0.000 | 0.000 | 0.000 | 0.000 | 0.092 | 59.888 |
| KTINGSGSPHSKAQGAIT | 3414 | 57.627 | 0.000 | 0.000 | 0.000 | 0.594 | 0.161 | 95.696 |
| KTDVNSGSPHSKAQNQQT | 3415 | 57.593 | 0.000 | 0.000 | 0.000 | 0.000 | 0.331 | 66.127 |
| KSDIGSGSPHSKAQNQQT | 3416 | 57.592 | 0.000 | 0.000 | 0.000 | 0.844 | 0.128 | 107.342 |
| KTINGSGSPHSKAQVPPT | 3417 | 57.316 | 0.000 | 0.012 | 0.000 | 0.257 | 0.200 | 90.220 |
| KTINGSGSPHSKAQVQQI | 3418 | 57.308 | 0.000 | 1.113 | 0.000 | 0.000 | 0.113 | 61.957 |
| KTINGSGSPHSKALMRQT | 3419 | 57.234 | 0.060 | 0.036 | 0.100 | 1.798 | 0.517 | 81.332 |
| KTINGSGSPHSKAQYSVT | 3420 | 57.130 | 0.000 | 0.093 | 0.000 | 1.235 | 0.302 | 60.023 |
| KNSIGSGSPHSKAQNQQT | 3421 | 57.101 | 0.000 | 0.052 | 0.000 | 0.083 | 0.074 | 97.381 |
| KTINGSGSPHSKVPNLQT | 3422 | 57.046 | 0.000 | 0.029 | 0.000 | 0.459 | 0.082 | 50.474 |
| KAINGSGSPHSKAQSQQI | 3423 | 56.976 | 0.000 | 0.000 | 0.000 | 0.000 | 0.000 | 57.052 |
| KTINGSGSPHSKAQAITT | 3424 | 56.924 | 0.000 | 0.000 | 0.000 | 1.239 | 0.438 | 75.250 |
| KTINGSGSPHSKAQKTLT | 3425 | 56.844 | 0.000 | 0.017 | 0.009 | 1.800 | 1.400 | 66.415 |
| KTVNGSGSPHSKAQNQWT | 3426 | 56.823 | 0.000 | 0.000 | 0.299 | 0.000 | 0.219 | 69.906 |
| KTINGSGSPHSKAQLHHT | 3427 | 56.815 | 0.025 | 0.000 | 0.010 | 0.712 | 0.368 | 58.418 |
| KTEQTSGSPHSKAQNQQT | 3428 | 56.683 | 0.000 | 0.045 | 0.000 | 0.792 | 0.430 | 59.360 |
| KTINGSGSPHSKAQNIII | 3429 | 56.630 | 0.000 | 0.062 | 0.123 | 0.099 | 0.056 | 76.742 |
| KNSLGSGSPHSKAQNQQT | 3430 | 56.621 | 0.000 | 0.028 | 0.000 | 0.308 | 0.162 | 101.942 |
| KTIPMEGSPHSKAQNQQT | 3567 | 56.560 | 0.000 | 0.000 | 0.000 | 1.824 | 0.371 | 89.951 |
| KTINGSGSPHSKAQGHHT | 3431 | 56.559 | 0.000 | 0.000 | 0.000 | 0.632 | 0.117 | 71.050 |
| KTDRTSGSPHSKAQNQQT | 3432 | 56.466 | 0.000 | 0.000 | 0.000 | 0.062 | 0.160 | 148.498 |

TABLE 15-continued

NGS fold-enrichment of TTM-001 and TTM-002 matured AAV capsid variants in th ebrain of NHPs and mice

| Sequence | SEQ ID NO: | Fold Enrichment relative to AAV9 | | | | | | |
|---|---|---|---|---|---|---|---|---|
| | | Brain (NHP) | DRG (NHP) | Heart (NHP) | Muscle (NHP) | Liver RNA (NHP) | Liver DNA (NHP) | Brain (Mouse) |
| KTINGSGSPHSKAQSKVT | 3433 | 56.373 | 0.000 | 0.050 | 0.014 | 1.021 | 0.390 | 76.115 |
| KEVVGSGSPHSKAQNQQT | 3434 | 56.371 | 0.000 | 0.000 | 0.000 | 0.000 | 0.323 | 116.964 |
| KTINGSGSPHSKAQLPST | 3435 | 56.238 | 0.005 | 4.258 | 0.001 | 1.040 | 0.185 | 84.918 |
| KTINGSGSPHSKAIGKQT | 3436 | 56.158 | 0.000 | 0.000 | 0.000 | 0.887 | 0.088 | 110.132 |
| KTEPTSGSPHSKAQNQQT | 3437 | 56.134 | 0.000 | 0.000 | 0.000 | 0.061 | 0.527 | 143.397 |
| KTVNGGGSPHSKSQNQQT | 3568 | 56.114 | 0.116 | 0.000 | 0.000 | 0.000 | 0.040 | 170.548 |
| KTINGSGSPHSKAQAIHT | 3438 | 56.047 | 0.000 | 0.000 | 212.32 | 0.887 | 0.890 | 81.908 |
| KTINGSGSPHSKAQHGLT | 3439 | 55.999 | 0.000 | 0.000 | 0.101 | 1.913 | 0.244 | 117.191 |
| KSELGSGSPHSKAQNQQT | 3440 | 55.997 | 0.000 | 0.005 | 0.000 | 0.881 | 0.239 | 120.521 |
| KTINGSGSPHSKAQFMCT | 3441 | 55.916 | 0.000 | 0.000 | 0.000 | 0.078 | 0.448 | 81.959 |
| KTINVSGSPHSKAQGQQT | 3442 | 55.870 | 0.000 | 0.191 | 0.000 | 0.592 | 0.040 | 87.211 |
| KTINGGGSPHSKAQNQMT | 3569 | 55.778 | 0.000 | 0.000 | 0.000 | 0.866 | 0.012 | 73.177 |
| KTVNGSGSPHSKAQHLQT | 3443 | 55.739 | 0.091 | 0.036 | 0.000 | 0.062 | 0.409 | 62.743 |
| KTIRENGSPHSKAQNQQT | 3570 | 55.605 | 0.000 | 0.000 | 0.016 | 0.131 | 0.257 | 95.931 |
| KTINGSGSPHSKTQNHQN | 3444 | 55.551 | 0.000 | 0.048 | 0.000 | 0.000 | 0.099 | 64.846 |
| KTINGSGSPHSKAQPART | 3445 | 55.513 | 0.000 | 0.000 | 0.328 | 1.294 | 0.991 | 127.301 |
| KTVNGSGSPHSKAQSLQT | 3446 | 55.497 | 0.000 | 0.060 | 0.000 | 0.000 | 0.143 | 69.033 |
| KTINGSGSPHSKSQSQLT | 3447 | 55.430 | 0.000 | 0.035 | 0.000 | 0.050 | 0.013 | 125.577 |
| KTINGSASPHSKAHSQQT | 3571 | 55.293 | 0.000 | 0.000 | 0.000 | 0.000 | 0.166 | 66.252 |
| KTWQNSGSPHSKAQNQQT | 3448 | 55.245 | 0.000 | 0.000 | 0.000 | 0.111 | 0.265 | 114.258 |
| KTINGSGSPHSKAQDRQS | 3449 | 55.137 | 1.146 | 0.016 | 0.106 | 0.644 | 0.086 | 55.701 |
| KTINGSGSPHSKAQMPST | 3450 | 54.986 | 1.691 | 0.039 | 0.028 | 0.450 | 0.202 | 114.331 |
| KTNNGGGSPHSKAQNLQT | 3572 | 54.963 | 0.000 | 0.000 | 0.000 | 0.000 | 0.089 | 80.506 |
| KTINGSGSPHSKAQGSLT | 3451 | 54.717 | 0.000 | 0.006 | 0.013 | 0.480 | 0.298 | 142.786 |
| KTEVTSGSPHSKAQNQQT | 3452 | 54.663 | 0.000 | 0.000 | 0.000 | 0.323 | 0.185 | 81.482 |
| KSINGGGSPHSKAQYQQT | 3573 | 54.612 | 0.000 | 0.000 | 0.000 | 0.105 | 0.010 | 65.952 |
| KTVIGSGSPHSKSQNQQT | 3453 | 54.603 | 0.000 | 0.000 | 0.000 | 0.000 | 0.106 | 69.121 |
| KAVNVSGSPHSKAQNQQT | 3454 | 54.586 | 0.000 | 0.000 | 0.000 | 0.000 | 0.023 | 57.835 |
| KTVNGNGSPHSKSQNQQT | 3574 | 54.586 | 0.000 | 0.000 | 0.000 | 0.256 | 0.168 | 95.384 |
| KTDRNSGSPHSKAQNQQT | 3455 | 54.495 | 0.000 | 0.000 | 0.000 | 0.823 | 0.241 | 85.823 |
| KTINGSGSPHSKAQVPAT | 3456 | 54.475 | 0.000 | 0.002 | 0.000 | 0.782 | 0.223 | 137.743 |
| KGVLGSGSPHSKAQNQQT | 3457 | 54.472 | 0.000 | 0.007 | 0.027 | 0.359 | 0.189 | 145.740 |
| KTLNGNGSPHSKAQNLQT | 3575 | 54.458 | 0.668 | 0.000 | 0.000 | 0.161 | 0.172 | 159.134 |
| KAINGSGSPHSKAQDKQT | 3458 | 54.452 | 0.000 | 0.000 | 0.057 | 0.044 | 0.223 | 56.004 |
| KTSNGSGSPHSKAHYQQT | 3459 | 54.414 | 0.000 | 0.251 | 0.000 | 0.249 | 0.204 | 54.162 |
| KTINGSGSPHSKAQVPST | 3460 | 54.366 | 0.000 | 1.001 | 0.000 | 0.202 | 0.139 | 117.223 |

TABLE 15-continued

NGS fold-enrichment of TTM-001 and TTM-002 matured AAV capsid variants in th ebrain of NHPs and mice

| Sequence | SEQ ID NO: | Fold Enrichment relative to AAV9 | | | | | | |
|---|---|---|---|---|---|---|---|---|
| | | Brain (NHP) | DRG (NHP) | Heart (NHP) | Muscle (NHP) | Liver RNA (NHP) | Liver DNA (NHP) | Brain (Mouse) |
| KTINGSGSSHSKAQNQQT | 3576 | 54.292 | 1.709 | 1.870 | 1.287 | 1.075 | 0.458 | 67.731 |
| KTELRSGSPHSKAQNQQT | 3461 | 54.289 | 0.000 | 0.007 | 0.040 | 0.790 | 0.239 | 57.814 |
| KNINGSGSPHSKAQNHQT | 3462 | 54.248 | 0.000 | 0.034 | 0.000 | 0.340 | 0.075 | 74.979 |
| KTVNGGGSPHSKAQNHQT | 3577 | 54.246 | 0.375 | 0.024 | 0.000 | 0.000 | 0.146 | 67.188 |
| KTINGSGSPHSKARGEQT | 3463 | 54.207 | 0.025 | 0.006 | 0.005 | 0.309 | 0.327 | 128.098 |
| KTINGGGSPHSKAQYQHT | 3578 | 54.188 | 0.000 | 0.000 | 0.000 | 0.000 | 0.223 | 82.256 |
| KTEDLSGSPHSKAQNQQT | 3464 | 54.156 | 0.000 | 0.000 | 0.000 | 1.193 | 0.132 | 70.198 |
| KTINGSGSPHSKAPGQQT | 3465 | 54.071 | 0.065 | 0.000 | 0.004 | 0.542 | 0.179 | 73.440 |
| KTIPKNGSPHSKAQNQQT | 3579 | 53.824 | 0.000 | 0.032 | 0.000 | 0.115 | 0.178 | 77.458 |
| KTINGSGSPHSKAQSLQI | 3466 | 53.778 | 0.000 | 0.186 | 0.000 | 0.022 | 0.047 | 51.543 |
| KTINGSGSPHSKRLEQQT | 3467 | 53.512 | 0.000 | 0.118 | 0.003 | 0.161 | 0.292 | 71.704 |
| KTERGSGSPHSKAQNQQT | 3468 | 53.475 | 0.000 | 0.030 | 0.000 | 1.416 | 0.175 | 85.368 |
| KTVNGSGSPHSKAPNQQT | 3469 | 53.444 | 0.833 | 2.206 | 0.006 | 0.156 | 0.178 | 58.080 |
| KTSNGSGSPHSKAQNQST | 3470 | 53.353 | 0.000 | 0.000 | 0.000 | 0.000 | 0.014 | 120.897 |
| KTINGSGSPHSKAQKVIT | 3471 | 53.273 | 0.000 | 0.000 | 0.000 | 0.357 | 0.402 | 95.147 |
| KTEGISGSPHSKAQNQQT | 3472 | 53.270 | 0.000 | 0.000 | 0.000 | 0.000 | 0.010 | 78.303 |
| KTINGSGSPHSKAQNNDQ | 3473 | 53.226 | 0.000 | 0.000 | 0.000 | 0.593 | 0.046 | 59.664 |
| KTINGSGSPHSKAQSVHT | 3474 | 53.226 | 0.000 | 0.004 | 0.000 | 0.446 | 0.217 | 76.110 |
| KTINGSGSPHSKAQPLGT | 3475 | 53.049 | 0.015 | 0.004 | 0.001 | 0.515 | 0.222 | 68.656 |
| KTINKEGSPHSKAQNQQT | 3580 | 53.006 | 0.000 | 0.029 | 0.000 | 0.177 | 0.111 | 64.520 |
| KTCNASGSPHSKAQNQQT | 3476 | 52.998 | 0.000 | 0.011 | 0.000 | 0.897 | 0.141 | 67.934 |
| KAINGSGSPHSKAHNQET | 3477 | 52.973 | 0.000 | 0.030 | 0.000 | 0.035 | 0.058 | 71.809 |
| KTEGLSGSPHSKAQNQQT | 3478 | 52.891 | 0.000 | 0.000 | 0.020 | 0.104 | 0.155 | 104.529 |
| KTRDASGSPHSKAQNQQT | 3479 | 52.861 | 0.000 | 0.000 | 0.010 | 1.062 | 0.402 | 52.089 |
| KTSNGSGSPHSKAQNLQI | 3480 | 52.843 | 0.000 | 0.000 | 1.605 | 0.178 | 0.214 | 74.823 |
| KTGNGSGSPHSKAQIQQT | 3481 | 52.809 | 0.000 | 0.000 | 0.000 | 0.000 | 0.012 | 98.291 |
| KTVNGGGSPHSKAQNLQT | 3581 | 52.788 | 0.000 | 0.031 | 0.000 | 0.000 | 0.165 | 83.215 |
| KTDRSSGSPHSKAQNQQT | 3482 | 52.737 | 0.000 | 0.000 | 0.000 | 0.995 | 0.085 | 123.421 |
| KTINGSGSPHSKAQVRNT | 3483 | 52.735 | 0.000 | 0.101 | 0.011 | 0.230 | 0.423 | 68.893 |
| KTINGSGSPHSKAPSNQT | 3484 | 52.680 | 1.494 | 4.762 | 0.003 | 0.330 | 0.208 | 87.951 |
| KTINGSGSPHSKAQVGHT | 3485 | 52.624 | 0.000 | 0.000 | 0.006 | 0.535 | 0.192 | 106.448 |
| KNAIGSGSPHSKAQNQQT | 3486 | 52.516 | 0.000 | 0.000 | 0.000 | 0.165 | 0.198 | 117.939 |
| KAENGSGSPHSKAQNQQT | 3487 | 52.487 | 0.000 | 0.157 | 0.029 | 0.000 | 0.242 | 120.256 |
| KTINGSGSPHSKAQRDIT | 3488 | 52.415 | 0.098 | 0.000 | 0.008 | 1.784 | 0.605 | 88.122 |
| KTINGSGSPHSKAQMPNT | 3489 | 52.408 | 0.084 | 0.036 | 0.025 | 0.057 | 0.359 | 66.040 |

TABLE 15-continued

NGS fold-enrichment of TTM-001 and TTM-002 matured AAV capsid variants in the brain of NHPs and mice

| Sequence | SEQ ID NO: | Fold Enrichment relative to AAV9 | | | | | | |
|---|---|---|---|---|---|---|---|---|
| | | Brain (NHP) | DRG (NHP) | Heart (NHP) | Muscle (NHP) | Liver RNA (NHP) | Liver DNA (NHP) | Brain (Mouse) |
| KTVNGSGSPHSKSQNQQT | 3490 | 52.395 | 0.033 | 0.077 | 0.013 | 0.105 | 0.175 | 58.000 |
| KTIPAIGSPHSKAQNQQT | 3582 | 52.346 | 0.000 | 0.009 | 0.000 | 0.034 | 0.134 | 51.949 |
| KTINGSGSPHSKARGLQT | 3491 | 52.275 | 0.000 | 0.000 | 0.036 | 1.235 | 1.425 | 169.881 |
| KTELGSGSPHSKAQNQQT | 3492 | 52.232 | 0.000 | 0.007 | 0.006 | 0.532 | 0.088 | 87.314 |
| KAETGSGSPHSKAQNQQT | 3493 | 52.219 | 0.000 | 0.047 | 0.581 | 0.009 | 0.188 | 132.940 |
| KTINGSGSPHSKLQKQQT | 3494 | 52.144 | 0.615 | 0.477 | 1.071 | 1.113 | 0.429 | 61.833 |
| KTINGSGSPHSKAPSLQT | 3495 | 52.137 | 0.041 | 1.614 | 0.002 | 0.902 | 0.222 | 70.363 |
| KTINGSGSPHSKAQRDQT | 3496 | 51.897 | 0.069 | 0.014 | 0.040 | 0.867 | 0.554 | 102.317 |
| KTDVGSGSPHSKAQNQQT | 3497 | 51.849 | 0.000 | 0.007 | 0.000 | 0.385 | 0.560 | 115.774 |
| KTINGSGSPHSKNRDQQT | 3498 | 51.830 | 0.000 | 0.008 | 0.000 | 0.480 | 0.138 | 100.300 |
| KSINGSGSPHSKAPNLQT | 3499 | 51.812 | 0.000 | 0.256 | 0.000 | 0.085 | 0.139 | 59.270 |
| KTINGSGSPHSKAQAKGT | 3500 | 51.727 | 0.048 | 0.016 | 0.000 | 0.271 | 0.525 | 104.917 |
| KTVNGSGSPHSKAQDKQT | 3501 | 51.580 | 0.428 | 0.000 | 0.069 | 0.041 | 0.063 | 69.225 |
| KTINGGGSPHSKAQNPQA | 3583 | 51.574 | 0.000 | 0.000 | 0.000 | 0.192 | 0.000 | 102.792 |
| KTINGSGSPHSKAQSAHT | 3502 | 51.569 | 0.068 | 0.070 | 0.000 | 0.589 | 0.249 | 79.498 |
| KTINGNGSPHSKSQNQHT | 3584 | 51.379 | 0.000 | 0.054 | 0.000 | 0.000 | 0.082 | 56.614 |
| KTVPTSGSPHSKAQNQQT | 3503 | 51.348 | 0.013 | 0.000 | 0.000 | 1.017 | 0.338 | 102.651 |
| KTIDGSGSPHSKSQNHQT | 3504 | 51.307 | 0.000 | 0.000 | 0.000 | 0.000 | 0.269 | 63.174 |
| KTDVKSGSPHSKAQNQQT | 3505 | 51.296 | 0.000 | 0.000 | 0.000 | 0.515 | 0.224 | 53.601 |
| KAINRSGSPHSKAQDQQT | 3506 | 51.262 | 0.000 | 0.000 | 0.000 | 0.000 | 0.036 | 54.631 |
| KTINGSGSPHSKAQSTMT | 3507 | 51.249 | 0.018 | 0.002 | 0.002 | 0.321 | 0.341 | 73.213 |
| KTVNASGSPHSKAQNQLT | 3508 | 51.249 | 0.000 | 0.000 | 0.000 | 0.000 | 0.268 | 99.559 |
| KTINGSGSPHSKAQREMT | 3509 | 51.076 | 0.000 | 24.900 | 143.49 | 1.564 | 0.476 | 70.961 |
| KTVHGSGSPHSKAQSQQT | 3510 | 51.057 | 0.000 | 0.000 | 0.000 | 0.143 | 0.146 | 54.185 |
| KTINGGGSPHSKSQNRQT | 3585 | 51.017 | 0.000 | 0.000 | 0.000 | 0.000 | 0.421 | 149.370 |
| KTINGSGSPHSKAQYRAT | 3511 | 51.008 | 0.000 | 0.158 | 0.000 | 0.690 | 0.120 | 50.650 |
| KTINGGGSPHSKAQRQQT | 3586 | 50.998 | 0.000 | 0.041 | 0.000 | 0.991 | 0.142 | 147.942 |
| KTEPMSGSPHSKAQNQQT | 3512 | 50.960 | 0.203 | 0.000 | 0.000 | 1.816 | 0.415 | 126.322 |
| KTINGSGSPHSKNQWQQT | 3513 | 50.800 | 0.000 | 0.044 | 0.047 | 0.111 | 0.324 | 65.506 |
| KETAGSGSPHSKAQNQQT | 3514 | 50.762 | 0.000 | 0.027 | 0.000 | 1.706 | 0.054 | 212.795 |
| KTINGSGSPHSKAQRMNT | 3515 | 50.686 | 0.000 | 108.747 | 0.019 | 0.943 | 0.264 | 97.975 |
| KNNLGSGSPHSKAQNQQT | 3516 | 50.670 | 0.000 | 0.019 | 0.000 | 0.406 | 0.121 | 102.408 |
| KTINGSGSPHAKAQNHQT | 3517 | 50.667 | 0.211 | 0.140 | 0.051 | 0.101 | 0.090 | 80.603 |
| KTIIKNGSPHSKAQNQQT | 3587 | 50.587 | 0.000 | 0.000 | 0.000 | 0.000 | 0.751 | 75.547 |
| KTINGSGSPHSYHVNQQT | 3588 | 50.486 | 0.000 | 0.056 | 0.059 | 0.528 | 0.275 | 179.489 |
| KTINGSGSPHSKAGDSQT | 3518 | 50.457 | 0.614 | 0.236 | 0.008 | 1.062 | 0.071 | 74.355 |

TABLE 15-continued

NGS fold-enrichment of TTM-001 and TTM-002 matured AAV capsid variants in th ebrain of NHPs and mice

| | | Fold Enrichment relative to AAV9 | | | | | | |
|---|---|---|---|---|---|---|---|---|
| Sequence | SEQ ID NO: | Brain (NHP) | DRG (NHP) | Heart (NHP) | Muscle (NHP) | Liver RNA (NHP) | Liver DNA (NHP) | Brain (Mouse) |
| KTINGSGSPHSKLKSQQT | 3519 | 50.368 | 0.000 | 0.296 | 0.000 | 1.796 | 1.096 | 95.240 |
| KTINGSGSPHSKAQKIST | 3520 | 50.285 | 0.000 | 0.000 | 0.088 | 0.108 | 0.302 | 51.115 |
| KTEYNSGSPHSKAQNQQT | 3521 | 50.256 | 0.000 | 0.000 | 0.000 | 0.000 | 0.009 | 62.679 |
| KTINGSGSPHSKAPSMQT | 3522 | 50.249 | 0.000 | 0.000 | 0.004 | 0.941 | 0.460 | 75.504 |
| EAINGSGSPHSKAQNQQT | 3523 | 50.243 | 0.629 | 0.094 | 0.000 | 0.057 | 1.519 | 117.305 |
| KTINGSGSPHSKASPRQT | 3524 | 50.227 | 0.088 | 0.005 | 0.068 | 1.761 | 0.530 | 67.241 |
| KTINGSGSPHSKRMEQQT | 3525 | 50.177 | 0.000 | 0.000 | 0.000 | 1.327 | 0.208 | 81.769 |
| KTINGSGSPHSKAQYQNT | 3526 | 50.099 | 0.000 | 0.008 | 0.000 | 0.017 | 0.119 | 71.846 |
| KTERVSGSPHSKAQNQQT | 3589 | 96.943 | 0.000 | 0.000 | 0.000 | 0.000 | 0.144 | 135.438 |
| KAEIGHDSPHKSGQNQQT | 1754 | 63.249 | 0.000 | 0.000 | 0.000 | 0.060 | 0.024 | 27.173 |

Table 16 provides the peptide sequence of 341 matured capsid variants, and the fold enrichment of these matured capsid variants relative to the AAV9 control that demonstrated a 75-fold or greater increase in expression in the brain of NHPs relative to the AAV9 control and had a fold-change in expression that was less than 2 relative to the AAV9 control in the liver and the DRG.

TABLE 16

NGS fold-enrichment of TTM-001 and TTM-002 matured AAV capsid variants in the brain of NHPs

| | | Fold Enrichment relative to AAV9 | | | | | | |
|---|---|---|---|---|---|---|---|---|
| Sequence | SEQ ID NO: | Brain (NHP) | DRG (NHP) | Heart (NHP) | Muscle (NHP) | Liver RNA (NHP) | Liver DNA (NHP) | Brain (Mouse) |
| KTFNRSGSPHSKAQNQQI | 3591 | 86.359 | 0.000 | 113.67 | 0.000 | 0.000 | 0.092 | 25.568 |
| KTIIGSGSPHSKAQNRHT | 3239 | 217.176 | 0.000 | 0.000 | 0.000 | 0.000 | 0.000 | 210.515 |
| KTFPGSGSPHSKVQNQQT | 3240 | 199.720 | 0.000 | 0.000 | 0.000 | 0.000 | 0.967 | 97.703 |
| KTEKMSGSPHSKAQNQQT | 3241 | 169.461 | 0.523 | 0.000 | 0.000 | 0.000 | 0.158 | 109.161 |
| KAINGHDSPHKSGQIRQT | 3606 | 108.510 | 0.000 | 23.908 | 0.000 | 0.132 | 0.261 | 8.862 |
| KTINGHDSPHKIGQNQHA | 3607 | 77.321 | 0.000 | 18.836 | 0.028 | 0.220 | 0.132 | 7.578 |
| KEINGRGSPHSKAQNQQT | 3527 | 134.390 | 0.239 | 0.000 | 0.000 | 0.000 | 0.232 | 52.311 |
| KTVNRNGSPHSKAQNQQT | 3528 | 133.016 | 0.000 | 0.416 | 0.000 | 0.000 | 0.000 | 85.361 |
| KAINGYDSPHKSGQKQQT | 3608 | 83.803 | 0.041 | 9.491 | 0.000 | 0.031 | 0.150 | 13.057 |
| KTVNGSGSPHSKARDQQT | 3242 | 124.789 | 0.123 | 0.039 | 0.312 | 0.569 | 0.454 | 132.137 |
| KTESGHDSPHKSGQNQQT | 3609 | 86.513 | 0.000 | 7.414 | 0.000 | 0.000 | 0.038 | 13.163 |
| KTINGHDSPHKSGQSVQT | 3610 | 75.748 | 0.010 | 6.808 | 0.000 | 0.165 | 0.058 | 9.321 |
| KTFNGSGSPHSKAPNLQT | 3243 | 121.436 | 0.000 | 0.167 | 0.000 | 0.000 | 0.015 | 168.920 |
| KTEKTSGSPHSKAQNQQT | 3244 | 120.337 | 0.000 | 0.355 | 0.000 | 0.000 | 0.119 | 101.467 |
| TTINGHDSPHKSGQNQQT | 3611 | 108.963 | 1.512 | 3.445 | 0.869 | 0.659 | 1.109 | 14.788 |
| KTINGHESPHKSGRSQQT | 3612 | 97.106 | 0.000 | 3.329 | 0.022 | 0.000 | 0.181 | 9.378 |

TABLE 16-continued

NGS fold-enrichment of TTM-001 and TTM-002 matured AAV capsid variants in the brain of NHPs

| Sequence | SEQ ID NO: | Fold Enrichment relative to AAV9 | | | | | |
|---|---|---|---|---|---|---|---|
| | | Brain (NHP) | DRG (NHP) | Heart (NHP) | Muscle (NHP) | Liver RNA (NHP) | Liver DNA (NHP) | Brain (Mouse) |
| KTINGSGSPHSKAHVRQT | 3245 | 119.798 | 0.000 | 0.000 | 0.262 | 0.694 | 1.039 | 165.590 |
| KTVNGSGSPHSKAPNQHT | 3246 | 117.207 | 0.000 | 0.109 | 0.000 | 0.000 | 0.074 | 51.008 |
| KTEKISGSPHSKAQNQQT | 3247 | 116.603 | 0.000 | 0.000 | 0.000 | 0.000 | 0.426 | 102.978 |
| KTINGPGSPHSKAHNQQT | 3529 | 115.742 | 0.146 | 0.000 | 0.235 | 0.000 | 0.513 | 52.508 |
| KTINGHDSPHKSGQNKLE | 3613 | 76.204 | 0.000 | 1.430 | 0.000 | 0.015 | 0.031 | 12.419 |
| KTVNGSGSPHSKTQSQQT | 3248 | 115.086 | 0.000 | 0.726 | 0.000 | 0.000 | 0.340 | 63.248 |
| TTINGSGSPHSKAQNQQT | 3249 | 114.856 | 1.340 | 14.856 | 0.827 | 1.281 | 0.957 | 72.058 |
| KSINESGSPHSKAQNQQI | 3250 | 113.833 | 0.000 | 0.000 | 0.000 | 0.000 | 0.000 | 67.649 |
| KTINGHDSPHKTGQNQQK | 3614 | 77.562 | 0.000 | 1.056 | 0.000 | 0.000 | 0.000 | 6.379 |
| KTERTSGSPHSKAQNQQT | 3251 | 112.957 | 0.000 | 0.009 | 0.000 | 1.128 | 0.207 | 117.374 |
| KTINGSGSPHSKAQPAKT | 3252 | 111.472 | 0.331 | 0.000 | 1.089 | 0.044 | 1.796 | 215.275 |
| KTINGRGSPHKRGQNQQT | 3837 | 120.889 | 0.100 | 0.814 | 0.434 | 0.458 | 0.614 | 13.988 |
| KTINGSGSPHTKAQNPPT | 3592 | 147.061 | 0.000 | 0.727 | 0.000 | 0.000 | 0.000 | 34.425 |
| KTEKSSGSPHSKAQNQQT | 3253 | 107.470 | 0.000 | 0.016 | 0.014 | 0.977 | 0.179 | 100.177 |
| KAINGHDNPHKSGQNQQT | 3615 | 88.906 | 0.297 | 0.721 | 0.482 | 0.222 | 0.130 | 9.702 |
| KTSYGNGSPHSKAQNQQT | 3530 | 105.937 | 0.000 | 0.000 | 0.000 | 0.000 | 0.114 | 105.894 |
| KTINGQDSPHKSGQHQQA | 3616 | 85.657 | 1.127 | 0.579 | 0.000 | 0.193 | 0.557 | 5.582 |
| KTEKGSGSPHSKAQNQQT | 3254 | 105.614 | 0.053 | 0.031 | 0.000 | 0.586 | 0.169 | 84.653 |
| KTINGSGSPHSKSQTQQN | 3255 | 104.474 | 0.000 | 0.131 | 0.000 | 0.084 | 0.038 | 54.021 |
| KTERISGSPHSKAQNQQT | 3256 | 103.692 | 0.000 | 0.000 | 0.000 | 0.062 | 0.370 | 89.637 |
| KTERASGSPHSKAQNQQT | 3257 | 103.669 | 0.000 | 0.000 | 0.000 | 0.127 | 0.070 | 115.550 |
| KSINGHDSPHKSGQIQHT | 3617 | 87.598 | 0.000 | 0.480 | 0.000 | 0.714 | 0.347 | 13.872 |
| KELHGSGSPHSKAQNQQT | 3258 | 102.680 | 0.000 | 0.000 | 0.000 | 1.634 | 0.592 | 96.554 |
| KAINGSGSPHSKAQNLAT | 3259 | 101.954 | 0.000 | 10.954 | 8.655 | 0.298 | 0.239 | 116.685 |
| KTVNGSGSPHSKSQNQLT | 3260 | 101.327 | 0.000 | 0.035 | 0.000 | 0.000 | 0.025 | 80.716 |
| KAINGHDSPHKSGPRQQT | 3618 | 145.142 | 0.000 | 0.408 | 0.000 | 0.000 | 0.000 | 8.259 |
| KTVNGHDSPHKSGHTQQT | 3619 | 82.246 | 0.000 | 0.378 | 1.142 | 0.000 | 0.123 | 6.160 |
| KSINGHDSPHKSGQRQHT | 3620 | 80.132 | 0.000 | 0.357 | 0.000 | 0.000 | 0.000 | 9.851 |
| KTERNSGSPHSKAQNQQT | 3261 | 99.892 | 0.000 | 0.000 | 0.000 | 0.000 | 0.107 | 87.392 |
| KSLNGSGSPHTKAQNQQT | 3593 | 81.515 | 0.197 | 0.333 | 0.000 | 0.000 | 0.085 | 45.140 |
| KSVNGNGSPHSKAQNQQT | 3531 | 99.385 | 0.000 | 1.329 | 0.000 | 0.359 | 0.079 | 51.016 |
| KAINGHDSPHKSAQSQQT | 3621 | 95.204 | 0.146 | 0.310 | 0.000 | 0.699 | 0.058 | 14.595 |
| KSIYGHESPHKSGQNQQS | 3622 | 90.947 | 0.817 | 0.310 | 0.000 | 0.000 | 0.243 | 8.064 |
| KTFNGSGSPHSKAQGQQT | 3262 | 99.253 | 0.000 | 0.208 | 0.000 | 0.128 | 0.099 | 81.459 |
| KTVNGHDSPHKSLQNQQT | 3623 | 112.925 | 0.000 | 0.301 | 0.059 | 0.000 | 0.322 | 16.726 |

TABLE 16-continued

NGS fold-enrichment of TTM-001 and TTM-002 matured AAV capsid variants in the brain of NHPs

| | | Fold Enrichment relative to AAV9 | | | | | | |
|---|---|---|---|---|---|---|---|---|
| Sequence | SEQ ID NO: | Brain (NHP) | DRG (NHP) | Heart (NHP) | Muscle (NHP) | Liver RNA (NHP) | Liver DNA (NHP) | Brain (Mouse) |
| KTINGSGSPHGWVQNQQT | 3532 | 97.122 | 0.000 | 0.000 | 0.000 | 1.240 | 1.975 | 290.720 |
| KTINGHGSPHSKAQNPQT | 3838 | 83.478 | 0.000 | 0.288 | 0.219 | 0.000 | 0.260 | 11.001 |
| KTSNGYDSPHKSGQKQQT | 3624 | 77.001 | 0.032 | 0.286 | 0.000 | 0.000 | 0.016 | 8.813 |
| KTVNGHDSPHKSGRNQET | 3625 | 102.695 | 0.000 | 0.286 | 0.000 | 0.000 | 0.027 | 11.958 |
| KTTNGHDSPHKSGQTQLT | 3626 | 115.637 | 0.000 | 0.283 | 0.000 | 0.052 | 0.321 | 17.885 |
| KAINGHDSPHKSEKNQQT | 3627 | 77.103 | 0.000 | 0.274 | 0.000 | 0.000 | 0.000 | 26.868 |
| KTERVSGSPHSKAQNQQT | 3263 | 96.943 | 0.000 | 0.000 | 0.000 | 0.000 | 0.144 | 135.438 |
| KTINGSGSPHSKALNRQS | 3264 | 96.843 | 0.136 | 0.532 | 0.000 | 0.042 | 0.178 | 55.945 |
| KTERLSGSPHSKAQNQQT | 3265 | 95.857 | 0.000 | 0.004 | 0.005 | 0.126 | 0.260 | 102.372 |
| KIINGRDSPHKSGQDQQT | 3628 | 78.773 | 0.000 | 0.254 | 0.000 | 0.000 | 0.156 | 16.132 |
| KTDNGSGSPHSKAHNQQT | 3266 | 95.164 | 0.000 | 0.000 | 0.000 | 0.000 | 0.027 | 55.313 |
| KTFHGSGSPHSKTQNQQT | 3267 | 94.714 | 0.000 | 0.210 | 0.120 | 0.000 | 0.000 | 51.119 |
| KTISGHDSPHKTGHNQQT | 3629 | 92.490 | 0.000 | 0.233 | 0.057 | 0.730 | 0.000 | 8.823 |
| KTVNAHDSPHKSGQNQLT | 3630 | 79.137 | 0.000 | 0.233 | 0.178 | 0.753 | 0.045 | 29.254 |
| KTINGGGSPHSKAQTQQI | 3533 | 92.345 | 0.000 | 0.000 | 0.000 | 0.000 | 0.023 | 54.199 |
| KSINGYDSPHKSGQTQQT | 3631 | 79.227 | 1.817 | 0.226 | 0.000 | 0.000 | 1.148 | 4.497 |
| KTINGHESPHKSGQTQQI | 3632 | 86.089 | 0.000 | 0.222 | 0.000 | 0.000 | 0.024 | 3.989 |
| KTINGHDSPHKSGQSKQA | 3633 | 101.460 | 0.000 | 0.222 | 0.000 | 0.185 | 0.114 | 7.510 |
| KTSNGSGSPHSKAQNPPT | 3268 | 91.528 | 0.000 | 0.000 | 0.000 | 0.000 | 0.039 | 51.541 |
| ETINGSGSPHSKAQNLQT | 3269 | 90.969 | 0.221 | 1.023 | 0.197 | 0.179 | 0.813 | 107.216 |
| KTVHGNGSPHSKAQNQQT | 3534 | 90.073 | 0.000 | 0.000 | 0.000 | 0.000 | 0.304 | 97.003 |
| NTINGSGSPHSKAQNQQT | 3270 | 90.017 | 1.712 | 1.261 | 1.171 | 0.923 | 0.540 | 55.179 |
| KTINGGGSPHSKAQNQQC | 3535 | 89.301 | 0.219 | 0.000 | 0.000 | 0.287 | 0.319 | 53.840 |
| KTENMSGSPHSKAQNQQT | 3271 | 89.247 | 0.000 | 0.000 | 0.000 | 0.000 | 0.260 | 130.568 |
| KTENVSGSPHSKAQNQQT | 3272 | 88.506 | 0.000 | 0.000 | 0.000 | 0.964 | 0.112 | 108.591 |
| KTSSGSGSPHSKAQYQQT | 3273 | 87.304 | 0.000 | 0.000 | 0.000 | 0.000 | 0.299 | 58.143 |
| KTIDGGGSPHSKAQNKQT | 3536 | 85.019 | 0.000 | 0.000 | 0.000 | 0.000 | 0.477 | 55.517 |
| KTEKVSGSPHSKAQNQQT | 3274 | 84.558 | 0.000 | 0.022 | 0.000 | 0.873 | 0.424 | 112.185 |
| KAINGSGSPHSKAQDQET | 3275 | 84.080 | 0.000 | 0.000 | 0.000 | 0.194 | 0.027 | 87.637 |
| KTCNKSGSPHSKAQNQQT | 3276 | 83.992 | 0.000 | 0.000 | 0.165 | 0.283 | 0.000 | 119.496 |
| KTINGGGSPHSKAQNQLI | 3537 | 83.881 | 0.000 | 0.000 | 0.000 | 0.046 | 0.387 | 78.383 |
| KNINGGGSPHSKAQNQQT | 3538 | 83.083 | 0.000 | 0.042 | 0.000 | 0.000 | 0.000 | 75.913 |
| KTEHLSGSPHSKAQNQQT | 3277 | 83.080 | 0.000 | 0.000 | 0.012 | 0.021 | 0.189 | 69.494 |
| KAIIGHESPHKSGQNQQT | 3634 | 88.563 | 0.000 | 0.150 | 0.000 | 0.062 | 0.145 | 8.530 |
| KTINGHDSPHKTGQNQPP | 3635 | 77.357 | 0.000 | 0.149 | 0.000 | 0.000 | 0.096 | 8.865 |
| KAINGHDSPHKSGQSPQT | 3636 | 75.734 | 0.095 | 0.148 | 0.000 | 0.000 | 0.238 | 14.195 |

TABLE 16-continued

NGS fold-enrichment of TTM-001 and TTM-002 matured AAV capsid variants in the brain of NHPs

| Sequence | SEQ ID NO: | Fold Enrichment relative to AAV9 | | | | | | |
|---|---|---|---|---|---|---|---|---|
| | | Brain (NHP) | DRG (NHP) | Heart (NHP) | Muscle (NHP) | Liver RNA (NHP) | Liver DNA (NHP) | Brain (Mouse) |
| KAEMGSGSPHSKAQNQQT | 3278 | 83.049 | 0.000 | 0.020 | 0.000 | 0.768 | 0.112 | 135.019 |
| KATNGSGSPHSKAQNHQT | 3279 | 82.627 | 0.000 | 0.176 | 0.000 | 0.155 | 0.057 | 66.207 |
| KTIKGNDSPHKSVQNQQT | 3637 | 85.986 | 0.000 | 0.135 | 0.000 | 0.263 | 0.000 | 8.603 |
| KAIKGSGSPHSKAQDQQT | 3280 | 82.258 | 0.000 | 0.000 | 0.000 | 0.108 | 0.000 | 85.178 |
| KTINGGGSPHSKSQNQLT | 3539 | 82.231 | 0.000 | 0.070 | 0.000 | 0.000 | 0.498 | 126.986 |
| KTEFGHDSPHKSGQNQQT | 3638 | 77.245 | 0.000 | 0.124 | 0.000 | 0.561 | 0.063 | 16.337 |
| KTINGHDSPHKSAQNYQT | 3639 | 130.375 | 0.000 | 0.124 | 0.000 | 0.097 | 0.123 | 19.443 |
| KTFNGSASPHSKALNQQT | 3839 | 84.258 | 0.000 | 0.122 | 0.000 | 0.104 | 0.037 | 31.855 |
| KTINGCGSPHASGQNQQT | 3840 | 132.540 | 0.000 | 0.121 | 0.042 | 0.000 | 0.059 | 1.857 |
| KTINAHDSPHKIGQNHQT | 3640 | 106.832 | 0.000 | 0.121 | 0.000 | 0.000 | 0.231 | 5.074 |
| KTVNGNGSPHSKAQNKQT | 3540 | 81.481 | 0.000 | 0.000 | 0.000 | 0.000 | 0.122 | 69.455 |
| KTINGHESPHKSAQNRQT | 3641 | 95.531 | 0.000 | 0.113 | 0.000 | 0.130 | 0.082 | 4.815 |
| KTINGSGSPHSKGHWQQT | 3281 | 81.434 | 0.000 | 0.000 | 0.000 | 0.000 | 1.011 | 65.252 |
| KTTNGHDSPHKSGQNQQG | 3642 | 85.113 | 0.000 | 0.107 | 0.000 | 0.000 | 0.017 | 10.555 |
| KTIKGQDSPHKIGQNQQT | 3643 | 110.357 | 0.000 | 0.103 | 0.058 | 0.166 | 0.135 | 11.829 |
| KTDKTSGSPHSKAQNQQT | 3282 | 81.430 | 0.000 | 0.000 | 0.000 | 1.362 | 0.291 | 169.515 |
| KTVNGHDSPHKSGQNHLT | 3644 | 81.516 | 0.000 | 0.100 | 0.017 | 0.000 | 0.028 | 16.096 |
| KTFKGSGSPHSKAPNQQT | 3283 | 80.890 | 0.000 | 0.000 | 0.000 | 0.000 | 0.017 | 71.144 |
| KSINGHDSPHKSGQYQHT | 3645 | 88.195 | 0.000 | 0.099 | 0.000 | 0.000 | 0.149 | 14.485 |
| KTINGNDSPHKSVQNHQT | 3646 | 120.002 | 0.000 | 0.099 | 0.788 | 0.000 | 0.000 | 7.920 |
| KTVNGSGSPHSKAQNQLI | 3284 | 80.509 | 0.000 | 0.000 | 0.000 | 0.000 | 0.166 | 71.156 |
| KTINGSGSPHSKRPEQQT | 3285 | 80.418 | 0.000 | 0.013 | 0.000 | 0.149 | 0.361 | 50.319 |
| KTINGSGSPHSKAQRTMT | 3286 | 80.388 | 0.000 | 0.022 | 0.170 | 1.812 | 1.025 | 100.248 |
| KTITGHDSPHKSGQNQWT | 3647 | 81.658 | 0.000 | 0.090 | 0.000 | 0.936 | 0.000 | 7.744 |
| KTNNGHDSPHKSVQNQHT | 3648 | 115.172 | 0.000 | 0.083 | 0.000 | 0.000 | 0.062 | 7.934 |
| KTEKASGSPHSKAQNQQT | 3287 | 80.285 | 0.000 | 0.041 | 0.000 | 0.000 | 0.261 | 90.390 |
| KTIDGHDSPHKSGQNQHA | 3649 | 91.058 | 0.000 | 0.082 | 0.000 | 0.000 | 0.000 | 10.781 |
| KSDQGSGSPHSKAQNQQT | 3288 | 80.076 | 0.000 | 0.000 | 0.000 | 0.993 | 0.124 | 151.911 |
| KTVNGHDSPHKSGQTRQT | 3650 | 133.276 | 0.251 | 0.080 | 0.093 | 0.034 | 0.129 | 7.174 |
| KTVNGHDSPHKSGQNLHT | 3651 | 88.080 | 0.000 | 0.080 | 0.000 | 0.000 | 0.039 | 11.363 |
| KAISGHDSPHKSGLNQQT | 3652 | 78.846 | 0.000 | 0.079 | 0.000 | 0.000 | 0.015 | 11.045 |
| KTEITSGSPHSKAQNQQT | 3289 | 79.620 | 0.000 | 0.163 | 0.000 | 0.332 | 0.074 | 76.686 |
| KTDKSSGSPHSKAQNQQT | 3290 | 79.470 | 0.055 | 0.012 | 0.000 | 1.437 | 0.367 | 141.351 |
| KAINGHDSPHKSAQNQET | 3653 | 90.402 | 0.000 | 0.073 | 0.000 | 0.746 | 0.000 | 10.674 |
| KTITGHDSPHKSGQHLQT | 3654 | 137.945 | 0.000 | 0.072 | 0.000 | 0.000 | 0.000 | 4.187 |

TABLE 16-continued

NGS fold-enrichment of TTM-001 and TTM-002 matured AAV capsid variants in the brain of NHPs

| Sequence | SEQ ID NO: | Fold Enrichment relative to AAV9 | | | | | | |
|---|---|---|---|---|---|---|---|---|
| | | Brain (NHP) | DRG (NHP) | Heart (NHP) | Muscle (NHP) | Liver RNA (NHP) | Liver DNA (NHP) | Brain (Mouse) |
| KTIDGSGSPHSKAQNQQH | 3291 | 79.090 | 0.000 | 0.000 | 0.000 | 0.136 | 0.049 | 57.914 |
| KTVNGNGSPHSKAQNQHT | 3541 | 78.849 | 0.000 | 0.000 | 0.000 | 0.000 | 0.045 | 54.086 |
| KNINGSGSPHSKAQNQQT | 3292 | 78.445 | 0.000 | 0.000 | 0.000 | 0.571 | 0.177 | 89.719 |
| KTINGHDSPHKSRLNQPT | 3655 | 92.883 | 0.000 | 0.070 | 0.050 | 0.904 | 1.075 | 5.598 |
| KTETHSGSPHSKAQNQQT | 3293 | 77.974 | 0.000 | 0.067 | 0.000 | 0.000 | 0.512 | 57.287 |
| KTVDGHDSPHKSGQKQQT | 3656 | 78.802 | 0.000 | 0.069 | 0.000 | 0.157 | 0.342 | 7.200 |
| KTINGQDSPHKSGQNQDT | 3657 | 82.075 | 0.000 | 0.067 | 0.000 | 0.225 | 0.144 | 9.626 |
| KTINGGGSPHSKALNQQN | 3542 | 77.822 | 0.000 | 0.131 | 0.000 | 0.000 | 0.274 | 69.884 |
| KTIEGHDSPHKSGRNQQT | 3658 | 75.838 | 0.000 | 0.065 | 0.017 | 0.000 | 0.079 | 7.818 |
| KTTNGHDSPHKSGQNLLT | 3659 | 77.738 | 0.130 | 0.064 | 0.185 | 0.424 | 0.326 | 15.192 |
| KTINGHDSPHKSGQLVIT | 3660 | 76.781 | 0.089 | 0.064 | 0.000 | 0.338 | 0.475 | 11.323 |
| KTVNGHDSPHKSRQSQQT | 3661 | 76.458 | 0.000 | 0.063 | 0.000 | 0.000 | 0.021 | 8.136 |
| KTINGSGSPHSKALHQHT | 3294 | 77.502 | 0.000 | 0.052 | 0.041 | 0.000 | 0.188 | 68.196 |
| KTINGHDSPHKSGRTQET | 3662 | 81.599 | 0.000 | 0.062 | 0.000 | 0.000 | 0.137 | 7.270 |
| KTINGHDSPHKSVQTHQT | 3663 | 77.309 | 0.237 | 0.062 | 0.000 | 0.000 | 0.116 | 7.519 |
| KTINGTGSPHSKAQNHQI | 3543 | 77.089 | 0.171 | 0.000 | 0.000 | 0.000 | 0.166 | 54.281 |
| KTINGSGSPHSKAQHRIT | 3295 | 76.849 | 0.105 | 0.499 | 0.170 | 1.424 | 0.214 | 127.000 |
| KTINGSGSPHSKAQYIHT | 3296 | 76.170 | 0.000 | 0.014 | 0.033 | 1.523 | 0.168 | 59.649 |
| KTSNGHDSPHKSGQNQPA | 3664 | 75.834 | 0.000 | 0.056 | 0.000 | 0.000 | 0.000 | 8.501 |
| KTEGKHDSPHKSGQNQQT | 3665 | 98.384 | 0.000 | 0.056 | 0.000 | 0.000 | 0.000 | 10.345 |
| KTENISGSPHSKAQNQQT | 3297 | 76.072 | 0.000 | 0.000 | 0.000 | 0.115 | 0.132 | 83.118 |
| KVINGHDSPHKSGQTQQT | 3666 | 91.665 | 0.000 | 0.055 | 1.526 | 0.311 | 0.000 | 7.391 |
| KTIIGGGSPHSKAHNQQT | 3544 | 75.872 | 0.000 | 0.050 | 0.000 | 0.000 | 0.235 | 65.492 |
| KTINGPDSPHKIGQNQQS | 3667 | 85.726 | 0.000 | 0.055 | 0.171 | 0.000 | 0.063 | 10.055 |
| KTINGSGSPHSKAQKFET | 3298 | 75.788 | 0.000 | 0.000 | 0.028 | 0.108 | 0.093 | 65.588 |
| KTSNESGSPHSKAQNHQT | 3299 | 75.720 | 0.000 | 0.000 | 0.000 | 0.169 | 0.217 | 70.590 |
| KTINGSGSPHSKAQFPST | 3300 | 75.677 | 0.000 | 0.004 | 0.000 | 0.849 | 0.127 | 119.712 |
| KTERPSGSPHSKAQNQQT | 3301 | 75.669 | 0.000 | 0.029 | 0.000 | 0.000 | 0.156 | 73.894 |
| KAVNGHDSPHKSVQNQQT | 3668 | 81.051 | 0.448 | 0.051 | 0.000 | 0.665 | 0.091 | 11.288 |
| KTINGNGSPHSKAQNPLT | 3545 | 75.269 | 0.000 | 0.000 | 0.000 | 0.366 | 0.000 | 53.583 |
| KSIKGNGSPHSKAQNQQT | 3546 | 75.196 | 0.000 | 0.000 | 0.000 | 0.000 | 0.000 | 90.251 |
| KTINGHDSPHKSRQDQHT | 3669 | 75.595 | 0.000 | 0.049 | 0.118 | 0.030 | 0.045 | 8.540 |
| KAINGPDSPHKSGQKQQT | 3670 | 78.213 | 0.464 | 0.047 | 0.000 | 0.323 | 0.162 | 10.395 |
| KTINGHDSPHKSRQSQHT | 3671 | 88.544 | 0.499 | 0.046 | 0.000 | 0.059 | 0.032 | 8.324 |
| KTIYGHDSPHKSVQNQLT | 3672 | 92.381 | 0.000 | 0.043 | 0.000 | 0.103 | 0.016 | 12.323 |
| KTVNGHDSPHKSGQNLLT | 3673 | 83.969 | 0.114 | 0.040 | 0.023 | 0.000 | 0.035 | 18.894 |

TABLE 16-continued

NGS fold-enrichment of TTM-001 and TTM-002 matured AAV capsid variants in the brain of NHPs

| | | Fold Enrichment relative to AAV9 | | | | | | |
|---|---|---|---|---|---|---|---|---|
| Sequence | SEQ ID NO: | Brain (NHP) | DRG (NHP) | Heart (NHP) | Muscle (NHP) | Liver RNA (NHP) | Liver DNA (NHP) | Brain (Mouse) |
| KTESAHDSPHKSGQNQQT | 3674 | 80.810 | 0.000 | 0.039 | 0.000 | 0.000 | 0.000 | 13.338 |
| KTENKSGSPHSKAQNQQT | 3594 | 103.854 | 0.000 | 0.037 | 0.000 | 0.000 | 0.119 | 31.182 |
| KTTNGQDSPHKSGQNQQS | 3675 | 92.419 | 0.000 | 0.037 | 0.043 | 0.000 | 0.079 | 7.592 |
| KTDKGSGSPHSKAQNQQT | 3595 | 94.572 | 0.000 | 0.037 | 0.000 | 0.951 | 0.367 | 47.888 |
| KTIDGHDSPHKSGRNQQI | 3676 | 80.240 | 0.000 | 0.037 | 0.000 | 0.040 | 0.144 | 10.363 |
| KTINGYDSPHKSGQYQHT | 3677 | 81.534 | 0.000 | 0.036 | 0.000 | 0.000 | 0.000 | 10.524 |
| KTDNGHDSPHKSRQNQQT | 3678 | 105.312 | 0.000 | 0.033 | 0.000 | 0.000 | 0.018 | 7.931 |
| KTINGHDSPHKSWVRQQT | 3679 | 125.537 | 0.000 | 0.033 | 0.000 | 0.291 | 0.174 | 11.687 |
| KTINGHESPHKSGQNQHS | 3680 | 92.248 | 0.000 | 0.032 | 0.012 | 0.090 | 0.088 | 9.720 |
| KTVNGHDSPHKIGHNQQT | 3681 | 120.985 | 0.000 | 0.029 | 0.000 | 0.000 | 0.009 | 10.167 |
| KTCNGHDSPHKSGRNQQT | 3682 | 94.616 | 0.000 | 0.025 | 0.000 | 0.000 | 0.128 | 12.496 |
| KTINGNGSPHSKAQNHQA | 3841 | 88.274 | 0.000 | 0.024 | 0.000 | 0.000 | 0.041 | 36.754 |
| KNVVGHDSPHKSGQNQQT | 3683 | 75.330 | 0.000 | 0.024 | 0.000 | 0.063 | 0.049 | 8.077 |
| KTELWHDSPHKSGQNQQT | 3684 | 85.323 | 0.057 | 0.020 | 0.000 | 0.000 | 0.243 | 9.915 |
| KTELRHDSPHKSGQNQQT | 3685 | 98.098 | 0.000 | 0.019 | 0.000 | 0.000 | 0.007 | 6.588 |
| KTINGHDSPHKSNAWQQT | 3686 | 84.825 | 0.000 | 0.016 | 0.000 | 0.000 | 0.132 | 15.788 |
| KTDAGHDSPHKSGQNQQT | 3687 | 88.924 | 0.000 | 0.013 | 0.000 | 1.076 | 0.070 | 18.107 |
| KTEVGHDSPHKSGQNQQT | 3688 | 112.457 | 0.000 | 0.011 | 0.000 | 0.000 | 0.138 | 13.125 |
| KTESRHDSPHKSGQNQQT | 3689 | 81.766 | 0.000 | 0.011 | 0.000 | 0.052 | 0.036 | 6.975 |
| KSELGHDSPHKSGQNQQT | 3690 | 107.059 | 0.000 | 0.005 | 0.000 | 0.000 | 0.055 | 13.285 |
| KTINGHDSPHKSGQSVPT | 3691 | 77.840 | 0.000 | 0.003 | 0.000 | 0.136 | 0.061 | 6.768 |
| KTINGHESPHKSGQNIQP | 3692 | 253.840 | 0.000 | 0.000 | 0.000 | 0.000 | 0.000 | 14.042 |
| KTEMKHDSPHKSGQNQQT | 3693 | 240.075 | 0.000 | 0.000 | 0.000 | 0.000 | 0.000 | 3.183 |
| KTINGHDSPHKSVQNHLN | 3694 | 196.758 | 0.000 | 0.000 | 0.000 | 0.000 | 0.000 | 14.557 |
| KTINGHDSPHKIGLDQQT | 3695 | 165.627 | 0.000 | 0.000 | 0.000 | 1.942 | 0.000 | 5.469 |
| KTSNASGSPHSKAQHQQT | 3596 | 165.206 | 0.000 | 0.000 | 0.000 | 0.000 | 0.082 | 40.558 |
| KTINGHDSPHKRGPDQQS | 3696 | 160.084 | 0.000 | 0.000 | 0.000 | 0.000 | 0.000 | 2.923 |
| KTINGMGSPHSKTQNQQT | 3842 | 158.728 | 0.000 | 0.000 | 0.000 | 0.000 | 0.638 | 47.809 |
| KTIKGHDSPHKSGESQQT | 3697 | 142.264 | 0.000 | 0.000 | 0.000 | 0.000 | 0.218 | 4.176 |
| KTEGWHDSPHKSGQNQQT | 3698 | 142.064 | 0.000 | 0.000 | 0.000 | 0.000 | 0.264 | 11.785 |
| KTINGHDSPHKHGQNHQT | 3699 | 141.405 | 0.191 | 0.000 | 0.000 | 0.000 | 0.000 | 10.214 |
| KTEQLHDSPHKSGQNQQT | 3700 | 138.345 | 0.000 | 0.000 | 0.000 | 0.000 | 0.000 | 12.606 |
| KTVNGTGSPHSKAQNQLT | 3843 | 137.639 | 0.000 | 0.000 | 0.000 | 0.000 | 0.277 | 48.950 |
| KTIIGHDSPHKSGQYQHT | 3701 | 131.825 | 0.000 | 0.000 | 0.000 | 0.000 | 0.211 | 5.762 |
| KTSNGHDSPHKSVQNKQT | 3702 | 130.640 | 0.000 | 0.000 | 0.000 | 0.172 | 0.039 | 11.850 |

TABLE 16-continued

NGS fold-enrichment of TTM-001 and TTM-002 matured AAV capsid variants in the brain of NHPs

| | | Fold Enrichment relative to AAV9 | | | | | | |
|---|---|---|---|---|---|---|---|---|
| Sequence | SEQ ID NO: | Brain (NHP) | DRG (NHP) | Heart (NHP) | Muscle (NHP) | Liver RNA (NHP) | Liver DNA (NHP) | Brain (Mouse) |
| KIVNGQVSPHKSGQNQQT | 3703 | 129.649 | 0.000 | 0.000 | 0.000 | 0.000 | 0.031 | 16.942 |
| KTVNGHDSPHKSGQRQLT | 3704 | 129.641 | 0.000 | 0.000 | 0.000 | 0.000 | 0.487 | 20.145 |
| KTVNGHDSPHKIGQNQLT | 3705 | 128.582 | 0.000 | 0.000 | 0.499 | 0.027 | 0.199 | 20.957 |
| KTINGHDSPHKSGQIIVT | 3706 | 125.245 | 0.000 | 0.000 | 0.151 | 0.000 | 0.379 | 6.808 |
| KTEKIHDSPHKSGQNQQT | 3707 | 125.178 | 0.000 | 0.000 | 0.000 | 0.000 | 0.000 | 17.604 |
| KTENAHDSPHKSGQNQQT | 3708 | 124.477 | 0.000 | 0.000 | 0.000 | 0.000 | 0.062 | 15.805 |
| KIGNGHESPHKSGQNQQT | 3709 | 123.324 | 0.000 | 0.000 | 0.000 | 0.000 | 0.000 | 11.198 |
| KEVMGHDSPHKSGQNQQT | 3710 | 121.107 | 0.000 | 0.000 | 0.000 | 0.000 | 0.000 | 17.191 |
| KTEVKHDSPHKSGQNQQT | 3711 | 119.733 | 0.000 | 0.000 | 0.000 | 0.000 | 0.000 | 5.550 |
| KTINGYDSPHKSGQKQST | 3712 | 119.615 | 0.000 | 0.000 | 0.000 | 0.000 | 0.000 | 7.970 |
| KTIHGNGSPHSKAQNQET | 3844 | 117.388 | 0.000 | 0.000 | 0.000 | 0.000 | 0.000 | 38.874 |
| KYQVGHDSPHKSGQNQQT | 3713 | 112.797 | 0.000 | 0.000 | 0.000 | 0.000 | 0.542 | 9.335 |
| KTEAMHDSPHKSGQNQQT | 3714 | 111.765 | 0.000 | 0.000 | 0.000 | 0.000 | 0.000 | 16.142 |
| KTIKGDDSPHKSVQNQQT | 3715 | 109.397 | 0.000 | 0.000 | 0.000 | 0.000 | 0.000 | 19.125 |
| KTINGHDSPHKSVQSHQT | 3716 | 109.375 | 0.107 | 0.000 | 0.319 | 0.000 | 0.547 | 12.617 |
| KTINGHDSPHKSGQFVVT | 3717 | 108.725 | 0.000 | 0.000 | 0.000 | 0.124 | 0.406 | 10.179 |
| KTVNGHDSPHKSRQNLQT | 3718 | 107.496 | 0.205 | 0.000 | 0.000 | 1.934 | 0.062 | 8.616 |
| KATNGHNSPHKSGQNQET | 3719 | 106.806 | 0.000 | 0.000 | 0.000 | 0.000 | 0.000 | 10.566 |
| KAINGHDSPHKSAQNQQI | 3720 | 106.539 | 0.000 | 0.000 | 0.000 | 0.000 | 0.113 | 21.786 |
| KTEHGHDSPHKSGQNQQT | 3721 | 106.486 | 0.000 | 0.000 | 0.000 | 0.000 | 0.006 | 14.956 |
| KTVENHDSPHKSGQNQQT | 3722 | 106.468 | 0.000 | 0.000 | 0.000 | 0.000 | 0.156 | 9.246 |
| KTIYGHDSPHKSGQSQPT | 3723 | 106.431 | 0.000 | 0.000 | 0.000 | 0.155 | 0.137 | 6.562 |
| KTISGHESPHKSGQNEQT | 3724 | 105.740 | 0.000 | 0.000 | 0.000 | 0.378 | 1.384 | 9.156 |
| KAIIGHDSPHKSAQNQQT | 3725 | 105.292 | 0.000 | 0.000 | 0.000 | 0.000 | 0.553 | 16.793 |
| KAIDGHDSPHKSGQNQLT | 3726 | 104.701 | 0.331 | 0.000 | 0.000 | 0.201 | 0.638 | 16.109 |
| KTIMGHDSPHKSVQNQQT | 3727 | 104.683 | 0.000 | 0.000 | 0.000 | 0.000 | 0.000 | 8.029 |
| KEVGGHDSPHKSGQNQQT | 3728 | 103.896 | 0.000 | 0.000 | 0.000 | 0.000 | 0.000 | 16.899 |
| KTINGHDSPHKSAQNLLT | 3729 | 103.332 | 0.000 | 0.000 | 0.256 | 0.194 | 0.000 | 15.722 |
| KTEFTHDSPHKSGQNQQT | 3730 | 102.052 | 0.062 | 0.000 | 0.000 | 0.439 | 0.047 | 12.527 |
| KTINASGSPHSKAINQQT | 3597 | 101.122 | 0.233 | 0.000 | 0.000 | 0.000 | 0.145 | 47.196 |
| KAINGNGSPHKRGQNQQT | 3845 | 100.925 | 0.000 | 0.000 | 0.000 | 0.000 | 0.159 | 10.011 |
| KSEMGHDSPHKSGQNQQT | 3731 | 100.539 | 0.000 | 0.000 | 0.000 | 0.000 | 0.000 | 18.356 |
| KAQQGHDSPHKSGQNQQT | 3732 | 100.395 | 0.000 | 0.000 | 0.000 | 0.000 | 0.057 | 3.954 |
| KTEVMHDSPHKSGQNQQT | 3733 | 99.473 | 0.000 | 0.000 | 0.000 | 0.000 | 0.000 | 12.400 |
| KAINGHDSPHKSGQSLQT | 3734 | 99.310 | 0.058 | 0.000 | 1.439 | 0.254 | 0.056 | 17.323 |
| KTINGSGSPHSKAPNQQH | 3598 | 99.300 | 0.252 | 0.000 | 0.000 | 0.000 | 0.038 | 39.297 |

TABLE 16-continued

NGS fold-enrichment of TTM-001 and TTM-002 matured AAV capsid variants in the brain of NHPs

| Sequence | SEQ ID NO: | Fold Enrichment relative to AAV9 | | | | | |
|---|---|---|---|---|---|---|---|
| | | Brain (NHP) | DRG (NHP) | Heart (NHP) | Muscle (NHP) | Liver RNA (NHP) | Liver DNA (NHP) | Brain (Mouse) |
| KCGEGHDSPHKSGQNQQT | 3735 | 99.298 | 0.000 | 0.000 | 0.000 | 0.000 | 0.000 | 13.147 |
| KTVNGHDSPHKSAQNHQT | 3736 | 99.257 | 0.000 | 0.000 | 0.078 | 0.000 | 0.027 | 17.639 |
| KTVNGHDSPHKSGQTQLT | 3737 | 98.524 | 0.000 | 0.000 | 0.313 | 0.183 | 0.172 | 14.883 |
| KTNNGHDSPHKSGRNRQT | 3738 | 98.307 | 0.000 | 0.000 | 0.124 | 0.000 | 0.037 | 5.840 |
| KTCNEHDSPHKSGQNQQT | 3739 | 97.092 | 0.000 | 0.000 | 0.000 | 0.000 | 0.000 | 8.364 |
| KTINGHDSPHKYGQNEQT | 3740 | 96.960 | 0.000 | 0.000 | 0.000 | 0.000 | 0.000 | 4.613 |
| KASNRHDSPHKSGHNQQT | 3741 | 96.283 | 0.000 | 0.000 | 0.000 | 0.000 | 0.675 | 8.045 |
| KTINGNGSPHSKAPNLQT | 3846 | 95.963 | 0.000 | 0.000 | 0.000 | 0.000 | 0.247 | 36.341 |
| KTETKHDSPHKSGQNQQT | 3742 | 95.121 | 0.000 | 0.000 | 0.000 | 0.000 | 0.083 | 4.831 |
| KSINGHDSPHKSQQNQQT | 3743 | 94.479 | 0.000 | 0.000 | 0.000 | 0.000 | 1.696 | 9.633 |
| KTIGGHDSPHKSGQNQQI | 3744 | 94.420 | 0.000 | 0.000 | 0.000 | 0.000 | 0.333 | 19.324 |
| KTDPQHDSPHKSGQNQQT | 3745 | 93.931 | 0.000 | 0.000 | 0.000 | 0.906 | 0.019 | 11.749 |
| KTINRHDSPHKIVQNQQT | 3746 | 93.409 | 0.000 | 0.000 | 0.000 | 0.000 | 0.000 | 3.064 |
| KTEQYHDSPHKSGQNQQT | 3747 | 93.065 | 0.000 | 0.000 | 0.000 | 0.000 | 0.047 | 15.190 |
| KTINGHDSPHKSVQSKQT | 3748 | 92.445 | 0.000 | 0.000 | 0.078 | 0.000 | 0.047 | 4.263 |
| KELVGHDSPHKSGQNQQT | 3749 | 92.262 | 0.000 | 0.000 | 0.000 | 0.594 | 0.000 | 14.890 |
| KTENRHDSPHKSGQNQQT | 3750 | 91.675 | 0.000 | 0.000 | 0.000 | 0.000 | 0.000 | 13.282 |
| KELMGHDSPHKSGQNQQT | 3751 | 91.191 | 0.000 | 0.000 | 0.000 | 0.000 | 0.000 | 14.032 |
| KTINGNDSPHKIGHNQQT | 3752 | 91.183 | 0.000 | 0.000 | 0.117 | 0.000 | 0.270 | 11.095 |
| KTIKGGGSPHSKAQDQQT | 3847 | 91.172 | 0.000 | 0.000 | 0.000 | 0.064 | 0.085 | 49.580 |
| KTEGHHDSPHKSGQNQQT | 3753 | 89.922 | 0.000 | 0.000 | 0.000 | 0.000 | 0.000 | 23.929 |
| KTEGYHDSPHKSGQNQQT | 3754 | 89.891 | 0.000 | 0.000 | 0.000 | 0.000 | 0.000 | 15.116 |
| KTVNGHDSPHKSGQTQQI | 3755 | 89.801 | 0.000 | 0.000 | 0.657 | 0.000 | 0.542 | 11.543 |
| KTINGQDSPHKSGQNPLT | 3756 | 89.726 | 0.000 | 0.000 | 0.000 | 0.363 | 0.000 | 15.561 |
| KTVNASGSPHSKAQNHQT | 3599 | 89.467 | 0.091 | 0.000 | 0.000 | 0.045 | 0.252 | 39.024 |
| KTINGHDSPHKSGRDQKT | 3757 | 88.871 | 0.000 | 0.000 | 0.000 | 0.350 | 0.181 | 12.117 |
| KTINGHDSPHKSVHNQQN | 3758 | 88.715 | 0.089 | 0.000 | 0.081 | 0.000 | 0.143 | 10.787 |
| KTINGHDSPHKSGQWKRT | 3759 | 88.633 | 0.000 | 0.000 | 0.000 | 0.202 | 0.094 | 5.186 |
| KTIDGSGSPHSKAENRQT | 3600 | 87.993 | 0.092 | 0.000 | 0.000 | 0.139 | 0.054 | 40.629 |
| KNEIGHDSPHKSGQNQQT | 3760 | 87.758 | 0.000 | 0.000 | 0.000 | 0.000 | 0.055 | 14.110 |
| KAINGHDSPHKSGQSQQI | 3761 | 87.585 | 0.000 | 0.000 | 5.310 | 0.000 | 0.000 | 12.864 |
| KIINGHDSPHKSRQAQQT | 3762 | 86.966 | 0.000 | 0.000 | 0.000 | 0.000 | 0.000 | 9.193 |
| KTPNGHDSPHKSGQNQQI | 3763 | 86.683 | 0.000 | 0.000 | 0.000 | 0.000 | 0.109 | 21.278 |
| KITNGHDSPHKSGQTQQT | 3764 | 86.443 | 0.000 | 0.000 | 0.000 | 0.192 | 0.190 | 17.479 |
| KTINGHDSPHKSVQNHQI | 3765 | 86.395 | 0.000 | 0.000 | 0.000 | 0.000 | 0.000 | 9.148 |

TABLE 16-continued

NGS fold-enrichment of TTM-001 and TTM-002 matured AAV capsid variants in the brain of NHPs

| Sequence | SEQ ID NO: | Fold Enrichment relative to AAV9 | | | | | | |
|---|---|---|---|---|---|---|---|---|
| | | Brain (NHP) | DRG (NHP) | Heart (NHP) | Muscle (NHP) | Liver RNA (NHP) | Liver DNA (NHP) | Brain (Mouse) |
| KTINGHDSPHKSKQNQQA | 3766 | 86.265 | 0.000 | 0.000 | 0.000 | 0.123 | 0.041 | 5.768 |
| KTINGHDSPHKSAQNQLN | 3767 | 86.153 | 0.000 | 0.000 | 0.000 | 0.050 | 0.019 | 15.587 |
| KTDITHDSPHKSGQNQQT | 3768 | 85.876 | 0.000 | 0.000 | 0.000 | 0.000 | 0.013 | 9.076 |
| KTVNGHDSPHKSGQTQPT | 3769 | 85.680 | 0.000 | 0.000 | 1.301 | 1.064 | 0.000 | 8.067 |
| KTEKFHDSPHKSGQNQQT | 3770 | 85.358 | 0.000 | 0.000 | 0.000 | 0.000 | 0.026 | 7.229 |
| KTDQGHDSPHKSGQNQQT | 3771 | 85.267 | 0.000 | 0.000 | 0.000 | 0.000 | 0.000 | 16.042 |
| KTINGHDSPHKLWINQQT | 3772 | 85.132 | 0.000 | 0.000 | 1.154 | 0.000 | 0.017 | 12.704 |
| KGINGPDSPHKSGQNQQT | 3773 | 85.080 | 0.000 | 0.000 | 0.084 | 0.000 | 0.054 | 13.750 |
| KSEIGHDSPHKSGQNQQT | 3774 | 84.789 | 0.000 | 0.000 | 0.000 | 0.000 | 0.013 | 15.955 |
| KTINGHDSPHKSVQKQLT | 3775 | 84.351 | 0.000 | 0.000 | 0.000 | 0.038 | 0.103 | 11.890 |
| KTINGHPSPHWKGQNQQT | 3848 | 84.153 | 0.000 | 0.000 | 0.000 | 0.000 | 0.058 | 3.280 |
| KTVNGHDSPHKSGRNQLA | 3776 | 83.858 | 0.000 | 0.000 | 0.000 | 0.000 | 0.132 | 21.252 |
| KTNNVHDSPHKSGQNQQS | 3777 | 83.697 | 0.000 | 0.000 | 0.000 | 0.176 | 0.000 | 7.117 |
| KTIKGSGSPHSKVQDQQT | 3601 | 83.077 | 0.000 | 0.000 | 0.034 | 0.000 | 0.107 | 21.001 |
| KSEKGHDSPHKSGQNQQT | 3778 | 82.982 | 0.000 | 0.000 | 0.000 | 0.000 | 0.105 | 16.662 |
| KWSAGHDSPHKSGQNQQT | 3779 | 82.949 | 0.000 | 0.000 | 0.000 | 0.000 | 0.211 | 12.499 |
| KELAGHDSPHKSGQNQQT | 3780 | 82.876 | 0.000 | 0.000 | 0.000 | 0.000 | 0.093 | 18.063 |
| KTINGHDSPHKMGRNQQS | 3781 | 82.787 | 0.000 | 0.000 | 0.000 | 0.000 | 0.000 | 6.467 |
| KTDQAHDSPHKSGQNQQT | 3782 | 82.402 | 0.000 | 0.000 | 0.141 | 0.000 | 0.000 | 13.397 |
| KTETQHDSPHKSGQNQQT | 3783 | 82.316 | 0.000 | 0.000 | 0.000 | 0.000 | 0.198 | 10.823 |
| KTEMTHDSPHKSGQNQQT | 3784 | 82.221 | 0.000 | 0.000 | 0.000 | 0.000 | 0.000 | 8.431 |
| KTINGHDSPHKSGISIQT | 3785 | 82.019 | 0.000 | 0.000 | 0.000 | 0.191 | 0.044 | 7.310 |
| KTDAVHDSPHKSGQNQQT | 3786 | 81.968 | 0.000 | 0.000 | 0.000 | 0.297 | 0.107 | 13.596 |
| KTSNGHDSPHKSVQNLQT | 3787 | 81.921 | 0.000 | 0.000 | 0.072 | 0.000 | 0.330 | 11.544 |
| KTEKYHDSPHKSGQNQQT | 3788 | 81.637 | 0.000 | 0.000 | 0.000 | 0.000 | 0.013 | 7.580 |
| KQTQGHDSPHKSGQNQQT | 3789 | 81.581 | 0.000 | 0.000 | 0.000 | 0.000 | 0.133 | 15.225 |
| KTINGHDSPHKMAHNQQT | 3790 | 81.329 | 0.000 | 0.000 | 0.000 | 0.000 | 0.094 | 15.949 |
| KAINGSGSPHSKAQTQQA | 3602 | 81.207 | 0.000 | 0.000 | 0.000 | 0.000 | 0.016 | 40.435 |
| KTINGHDSPHKHGQNQQN | 3791 | 81.065 | 0.000 | 0.000 | 0.000 | 0.000 | 0.000 | 4.110 |
| KGADGHDSPHKSGQNQQT | 3792 | 80.981 | 0.000 | 0.000 | 0.000 | 0.000 | 0.074 | 11.423 |
| KVGEGHDSPHKSGQNQQT | 3793 | 80.775 | 0.084 | 0.000 | 0.000 | 0.000 | 0.019 | 16.378 |
| KANEGHDSPHKSGQNQQT | 3794 | 80.470 | 0.000 | 0.000 | 0.000 | 0.000 | 0.000 | 12.818 |
| KTDTMHDSPHKSGQNQQT | 3795 | 80.364 | 0.000 | 0.000 | 0.000 | 0.000 | 0.000 | 13.166 |
| KTEAKSGSPHSKAQNQQT | 3603 | 80.088 | 0.192 | 0.000 | 0.000 | 0.000 | 0.613 | 47.130 |
| KTINGHDSPHKSVQSQQS | 3796 | 80.000 | 0.000 | 0.000 | 0.000 | 1.055 | 0.082 | 17.620 |
| KTIPGSGSPHSKAQNLQT | 3604 | 79.973 | 0.871 | 0.000 | 0.000 | 0.000 | 0.000 | 32.693 |

TABLE 16-continued

NGS fold-enrichment of TTM-001 and TTM-002 matured AAV capsid variants in the brain of NHPs

| | | Fold Enrichment relative to AAV9 | | | | | | |
|---|---|---|---|---|---|---|---|---|
| Sequence | SEQ ID NO: | Brain (NHP) | DRG (NHP) | Heart (NHP) | Muscle (NHP) | Liver RNA (NHP) | Liver DNA (NHP) | Brain (Mouse) |
| KTCIAHDSPHKSGQNQQT | 3797 | 79.857 | 0.000 | 0.000 | 0.066 | 0.000 | 0.093 | 1.930 |
| KTINGHDSPHKSGQTVCT | 3798 | 79.730 | 0.000 | 0.000 | 0.000 | 0.050 | 0.030 | 7.873 |
| KELRGHDSPHKSGQNQQT | 3799 | 79.596 | 0.000 | 0.000 | 0.000 | 0.000 | 0.006 | 22.001 |
| KCQIGHDSPHKSGQNQQT | 3800 | 79.359 | 0.000 | 0.000 | 0.000 | 0.000 | 0.000 | 2.614 |
| KGVMGHDSPHKSGQNQQT | 3801 | 79.170 | 0.000 | 0.000 | 0.000 | 0.138 | 0.086 | 17.287 |
| KACDGHDSPHKSGQNQQT | 3802 | 78.648 | 0.000 | 0.000 | 0.000 | 0.000 | 0.128 | 17.767 |
| KTINGQDSPHKSGQYQQI | 3803 | 78.585 | 0.000 | 0.000 | 0.000 | 0.286 | 0.672 | 5.664 |
| KTINGHDSPHKSGQQIMT | 3804 | 78.534 | 0.000 | 0.000 | 0.000 | 0.000 | 0.058 | 7.067 |
| KTINGHDSPHKSRQNEQS | 3805 | 78.534 | 0.000 | 0.000 | 0.000 | 0.112 | 0.188 | 13.388 |
| KASNGHDSPHKSGLNHQT | 3806 | 78.451 | 0.000 | 0.000 | 0.000 | 0.000 | 0.000 | 17.975 |
| KTVNGHDSPHKSGQSQPT | 3807 | 78.309 | 0.000 | 0.000 | 0.000 | 0.000 | 0.231 | 10.627 |
| KNELGHDSPHKSGQNQQT | 3808 | 78.135 | 0.000 | 0.000 | 0.000 | 0.000 | 0.182 | 17.457 |
| KTETFHDSPHKSGQNQQT | 3809 | 78.070 | 0.000 | 0.000 | 0.000 | 0.782 | 0.007 | 4.693 |
| KAAEGHDSPHKSGQNQQT | 3810 | 77.793 | 0.000 | 0.000 | 0.000 | 0.000 | 0.060 | 13.552 |
| KGQNGHDSPHKSGQNQQT | 3811 | 77.770 | 0.000 | 0.000 | 0.000 | 0.107 | 0.056 | 13.618 |
| KNEFGHDSPHKSGQNQQT | 3812 | 77.740 | 0.000 | 0.000 | 0.000 | 0.000 | 0.029 | 16.318 |
| KTSIGYDSPHKSGQNQQT | 3813 | 77.730 | 0.000 | 0.000 | 0.000 | 0.057 | 0.178 | 4.831 |
| KTDNGHDSPHKSGQNLQT | 3814 | 77.565 | 0.504 | 0.000 | 0.000 | 0.000 | 0.000 | 16.184 |
| KTEGQHDSPHKSGQNQQT | 3815 | 77.423 | 0.000 | 0.000 | 0.000 | 0.000 | 0.748 | 20.310 |
| KTITGHDSPHKSRQDQQT | 3816 | 77.127 | 0.000 | 0.000 | 0.000 | 0.000 | 0.000 | 6.250 |
| KAEHGHDSPHKSGQNQQT | 3817 | 77.026 | 0.000 | 0.000 | 0.000 | 0.000 | 0.017 | 20.937 |
| KTINGDDSPHKSGQKQLT | 3818 | 76.968 | 0.000 | 0.000 | 0.000 | 0.163 | 0.014 | 15.820 |
| KCDQGHDSPHKSGQNQQT | 3819 | 76.887 | 0.000 | 0.000 | 0.000 | 0.193 | 0.013 | 27.317 |
| KEILGHDSPHKSGQNQQT | 3820 | 76.770 | 0.000 | 0.000 | 0.000 | 0.804 | 0.009 | 10.771 |
| KTIHGSGSPHSKAQNQAT | 3605 | 76.765 | 0.000 | 0.000 | 0.000 | 0.000 | 0.215 | 43.969 |
| KTERNHDSPHKSGQNQQT | 3821 | 76.751 | 0.000 | 0.000 | 0.000 | 0.000 | 0.000 | 14.979 |
| KAINGDDSPHKSGHNQQT | 3822 | 76.578 | 0.000 | 0.000 | 0.000 | 0.032 | 0.059 | 17.755 |
| KTSNGHNSPHKSGQNQET | 3823 | 76.515 | 0.000 | 0.000 | 0.000 | 0.000 | 0.000 | 4.764 |
| KTINGHDSPHKSGQMIHT | 3824 | 76.364 | 0.000 | 0.000 | 0.000 | 0.000 | 0.000 | 9.486 |
| KNAIGHDSPHKSGQNQQT | 3825 | 76.289 | 0.000 | 0.000 | 0.000 | 0.009 | 0.072 | 15.178 |
| KTDKFHDSPHKSGQNQQT | 3826 | 76.204 | 0.000 | 0.000 | 0.000 | 0.000 | 0.000 | 7.096 |
| KTEGFHDSPHKSGQNQQT | 3827 | 76.191 | 0.000 | 0.000 | 0.000 | 0.000 | 0.080 | 13.163 |
| KVINGHDSPHKSGRNHQS | 3828 | 75.961 | 0.000 | 0.000 | 0.000 | 0.000 | 0.000 | 13.568 |
| KTITGHDSPHKSVQNRQT | 3829 | 75.940 | 0.000 | 0.000 | 0.000 | 0.621 | 0.000 | 4.310 |
| KTPDMHDSPHKSGQNQQT | 3830 | 75.871 | 0.659 | 0.000 | 0.000 | 0.000 | 0.048 | 11.277 |

TABLE 16-continued

NGS fold-enrichment of TTM-001 and TTM-002 matured AAV capsid variants in the brain of NHPs

| Sequence | SEQ ID NO: | Fold Enrichment relative to AAV9 | | | | | | |
|---|---|---|---|---|---|---|---|---|
| | | Brain (NHP) | DRG (NHP) | Heart (NHP) | Muscle (NHP) | Liver RNA (NHP) | Liver DNA (NHP) | Brain (Mouse) |
| KTINGHDSPHKSGQKMNT | 3831 | 75.820 | 0.000 | 0.000 | 0.000 | 0.000 | 0.167 | 6.373 |
| KTELQHDSPHKSGQNQQT | 3832 | 75.814 | 0.000 | 0.000 | 0.000 | 0.105 | 0.000 | 11.798 |
| KTIHGHDSPHKSGQSQQN | 3833 | 75.777 | 0.000 | 0.000 | 0.059 | 0.000 | 0.166 | 7.426 |
| KTEIGHDSPHKSGQNQQT | 3834 | 75.525 | 0.000 | 0.000 | 0.016 | 0.012 | 0.000 | 9.593 |
| KTINGHDSPHKSGQYQHA | 3835 | 75.308 | 0.000 | 0.000 | 0.000 | 0.000 | 0.017 | 17.081 |
| KTELYHDSPHKSGQNQQT | 3836 | 75.235 | 0.000 | 0.000 | 0.000 | 0.000 | 0.042 | 10.354 |

Table 17 provides the sequences of 216 matured capsid variants having a CV of less than 1 for the liver RNA samples isolated and a 10-fold or greater increase in expression relative to AAV9 in the liver of NHPs. These matured variants showed preferential transduction of the liver over other tissues as shown by a low value for fold-enrichment relative to AAV9 in the other tissues investigated including the brain, DRG, heart and muscle. As such, Table 17 provides TTM-001 and TTM-002 matured AAV capsid variants with liver-specific tropism. Across the peptides within the matured capsid variants in Table 17, approximately 175 of them comprised the sequence GSGSPH (SEQ ID NO: 4695) and further comprised additional modifications in the C-terminal region of the sequence.

TABLE 17

NGS fold-enrichment of TTM-001 and TTM-002 matured AAV capsid variants in the liver of NHPs

| Sequence | SEQ ID NO: | Fold Enrichment relative to AAV9 | | | | | |
|---|---|---|---|---|---|---|---|
| | | Liver RNA (NHP) | Liver DNA (NHP) | Brain (NHP) | DRG (NHP) | Heart (NHP) | Muscle (NHP) |
| KTQRKSGSPHSKAQNQQT | 4011 | 119.659 | 1.439 | 0.000 | 0.000 | 0.000 | 0.000 |
| KTINGSGSPHSKAQARKT | 4681 | 96.557 | 3.644 | 0.000 | 0.000 | 0.000 | 0.000 |
| KYIVGSGSPHSKAQNQQT | 4682 | 94.721 | 4.480 | 0.000 | 0.000 | 0.000 | 0.000 |
| KTINGSGSPHSMYMNQQT | 4683 | 81.106 | 5.840 | 0.000 | 0.000 | 0.000 | 0.000 |
| KTINGSGSPHSKAFYRQT | 4684 | 77.541 | 3.577 | 0.000 | 0.000 | 0.000 | 0.000 |
| KTINGSGSPHSKLKRQQT | 4685 | 76.103 | 6.884 | 0.000 | 0.000 | 0.000 | 0.000 |
| KTINGSGSPHSKRHRQQT | 4686 | 73.225 | 4.648 | 0.000 | 0.000 | 0.000 | 0.000 |
| KTINGSGSPHSKAQKCIT | 4687 | 69.547 | 1.887 | 0.000 | 0.000 | 0.000 | 0.000 |
| KTINGSGSPHSKWRLQQT | 4688 | 68.083 | 2.037 | 0.000 | 0.000 | 0.000 | 0.000 |
| KTINGSGSPHSRCRNQQT | 4689 | 64.416 | 5.150 | 0.000 | 0.000 | 0.000 | 0.000 |
| KTINGSGSPHSFTCNQQT | 4690 | 63.936 | 2.155 | 0.000 | 0.000 | 0.000 | 271.289 |
| KTINGSGSPHSKFFIQQT | 4691 | 63.255 | 6.916 | 0.000 | 0.000 | 0.000 | 0.000 |
| KTINGSYSPHCLAQNQQT | 4012 | 62.942 | 0.309 | 0.000 | 0.000 | 0.000 | 0.000 |
| KT TABLE 17-continued NGS fold-enrichment of TTM-001 and TTM-002 matured AAV capsid variants in the liver of NHPs

| Sequence | SEQ ID NO: | Fold Enrichment relative to AAV9 | | | | | |
|---|---|---|---|---|---|---|---|
| | | Liver RNA (NHP) | Liver DNA (NHP) | Brain (NHP) | DRG (NHP) | Heart (NHP) | Muscle (NHP) |
| KTINGSGSPHFPWQNQQT | 3853 | 53.587 | 1.731 | 0.000 | 0.000 | 0.000 | 0.000 |
| KTINGSGSPHSKIRRQQT | 3854 | 53.528 | 1.388 | 0.000 | 0.000 | 0.000 | 0.000 |
| KTINGSGSPHVYYQNQQT | 3855 | 53.294 | 2.173 | 0.944 | 0.000 | 0.246 | 5.268 |
| KTINGSGSPHSLYWNQQT | 3856 | 53.262 | 0.000 | 0.000 | 0.000 | 0.000 | 0.000 |
| KTINGSGSPHSKPKRQQT | 3857 | 52.881 | 2.832 | 0.000 | 0.000 | 0.000 | 0.000 |
| KPRWGSGSPHSKAQNQQT | 3858 | 51.637 | 0.386 | 0.000 | 0.000 | 375.537 | 0.000 |
| KTINGSGSPHSKAFSWQT | 3859 | 51.304 | 1.805 | 0.000 | 0.000 | 0.000 | 0.000 |
| KTINGSGSPHSRFWNQQT | 3860 | 51.225 | 6.955 | 0.000 | 0.000 | 0.000 | 0.000 |
| KTINGSGSPHSKAQCLKT | 3861 | 49.565 | 1.453 | 0.000 | 0.000 | 0.000 | 0.000 |
| KTINGSGSPHSRMRNQQT | 3862 | 48.902 | 2.816 | 0.000 | 0.000 | 0.000 | 0.000 |
| KTINGSGSPHSVKKNQQT | 3863 | 48.475 | 3.908 | 0.000 | 0.000 | 0.000 | 0.000 |
| KTINGSGSPHSWAPNQQT | 3864 | 47.897 | 1.789 | 0.000 | 0.000 | 0.000 | 0.000 |
| KTINGSGSPHSLWKNQQT | 3865 | 45.796 | 4.010 | 0.000 | 0.000 | 0.000 | 0.000 |
| KTINGSGSPHSKARWQQT | 3866 | 45.017 | 2.377 | 0.000 | 0.000 | 0.000 | 0.000 |
| KTINGSGSPHSFRPNQQT | 3867 | 44.801 | 9.191 | 0.000 | 0.000 | 0.000 | 0.000 |
| KTINGSGSPHSKKVFQQT | 3868 | 43.747 | 4.480 | 0.000 | 0.000 | 0.000 | 0.000 |
| KTINGSLSPHFWAQNQQT | 4013 | 43.190 | 2.041 | 0.000 | 0.000 | 0.000 | 0.000 |
| KTINGSGSPHSYAFNQQT | 3869 | 43.037 | 1.742 | 0.000 | 0.000 | 0.000 | 0.000 |
| KTINHRISPHSKAQNQQT | 4014 | 42.998 | 1.876 | 0.000 | 0.000 | 0.000 | 0.000 |
| KTINGSGSPHSKACSRQT | 3870 | 42.696 | 2.468 | 0.000 | 0.000 | 0.000 | 0.000 |
| KTRRPSGSPHSKAQNQQT | 4015 | 42.374 | 2.384 | 0.000 | 0.000 | 0.000 | 0.000 |
| KYSAGSGSPHSKAQNQQT | 3871 | 41.310 | 1.824 | 0.000 | 0.000 | 0.000 | 0.000 |
| KTINGAYSPHRKAQNQQT | 4016 | 40.969 | 1.283 | 0.000 | 0.000 | 0.000 | 0.000 |
| KTINGSGSPHSKRLWQQT | 3872 | 40.932 | 4.801 | 0.000 | 0.000 | 0.000 | 0.000 |
| KTINGSGSPHSCSRNQQT | 3873 | 40.372 | 4.293 | 0.000 | 0.000 | 0.000 | 0.000 |
| KTINGSGSPHSRCPNQQT | 3874 | 39.529 | 4.890 | 0.000 | 0.000 | 0.000 | 0.000 |
| KTINGSGSPHSGACNQQT | 3875 | 39.163 | 3.215 | 0.000 | 0.000 | 0.000 | 4733.916 |
| KYYTGSGSPHSKAQNQQT | 3876 | 38.777 | 1.199 | 0.000 | 0.000 | 0.000 | 0.000 |
| KTINGSGSPHSKFRQQQT | 3877 | 38.665 | 3.260 | 0.000 | 0.000 | 0.000 | 0.000 |
| KTINGSGSPHSFPFNQQT | 3878 | 38.584 | 4.693 | 0.000 | 0.000 | 0.000 | 0.000 |
| KTINGSGSPHSFFGNQQT | 3879 | 38.088 | 6.101 | 0.000 | 0.000 | 0.000 | 0.000 |
| KTINGRRSPHGKAQNQQT | 4017 | 37.728 | 3.259 | 0.000 | 0.000 | 0.000 | 0.000 |
| KTINGSGSPHSMCQNQQT | 3880 | 37.209 | 1.348 | 0.000 | 0.000 | 0.000 | 0.000 |
| KTINGSGSPHSKLFWQQT | 3881 | 37.022 | 4.178 | 0.000 | 0.000 | 0.000 | 0.000 |
| KTINGSGSPHSKTRKQQT | 3882 | 36.010 | 2.858 | 0.000 | 0.000 | 0.000 | 0.000 |
| KTINGRTSPHRKAQNQQT | 4018 | 35.792 | 5.682 | 0.000 | 0.000 | 0.000 | 0.000 |

TABLE 17-continued

NGS fold-enrichment of TTM-001 and TTM-002 matured AAV capsid variants in the liver of NHPs

| Sequence | SEQ ID NO: | Fold Enrichment relative to AAV9 | | | | | |
|---|---|---|---|---|---|---|---|
| | | Liver RNA (NHP) | Liver DNA (NHP) | Brain (NHP) | DRG (NHP) | Heart (NHP) | Muscle (NHP) |
| KTINGSGSPHSGKRNQQT | 3883 | 35.120 | 5.396 | 0.000 | 0.000 | 0.000 | 0.000 |
| KTINGSGSPHSKAQNFKR | 3884 | 32.291 | 0.964 | 0.000 | 0.000 | 0.000 | 0.000 |
| KTINGSGSPHFYRQNQQT | 3885 | 31.724 | 9.342 | 0.000 | 0.000 | 0.000 | 0.000 |
| KTINGSRSPHAWAQNQQT | 4019 | 31.146 | 6.838 | 0.000 | 0.000 | 0.000 | 0.000 |
| KTINGSGSPHCRVQNQQT | 3886 | 31.043 | 1.203 | 0.000 | 0.000 | 0.000 | 0.000 |
| KTINGSGSPHYGIQNQQT | 3887 | 30.908 | 1.076 | 0.000 | 0.000 | 0.000 | 0.000 |
| KTINKCLSPHSKAQNQQT | 4020 | 30.667 | 5.097 | 0.000 | 0.000 | 0.000 | 0.000 |
| KTINGSGSPHSKAQRFKT | 3888 | 30.363 | 0.139 | 0.000 | 0.000 | 0.000 | 0.000 |
| KTINGSGSPHVNCQNQQT | 3889 | 30.010 | 6.122 | 0.000 | 0.000 | 0.000 | 0.000 |
| KTINGSGSPHSKPFRQQT | 3890 | 29.842 | 8.700 | 0.000 | 0.000 | 0.000 | 0.000 |
| KTINGSGSPHSLAWNQQT | 3891 | 29.015 | 4.746 | 0.000 | 0.000 | 0.000 | 0.000 |
| KTINGSGSPHSKRSYQQT | 3892 | 28.973 | 2.116 | 0.000 | 0.000 | 0.000 | 0.000 |
| KTINGSSSPHRCAQNQQT | 4021 | 28.887 | 1.829 | 0.000 | 0.000 | 0.000 | 0.000 |
| KTINGSGSPHWSYQNQQT | 3893 | 28.607 | 3.751 | 0.000 | 0.000 | 0.000 | 0.000 |
| KTINCRTSPHSKAQNQQT | 4022 | 28.301 | 1.117 | 0.000 | 0.000 | 0.000 | 0.000 |
| KTINGSGSPHRWLQNQQT | 3894 | 28.147 | 6.882 | 0.000 | 0.000 | 0.000 | 0.000 |
| KTIFDCGSPHSKAQNQQT | 4023 | 27.844 | 1.602 | 0.000 | 0.000 | 0.000 | 0.000 |
| KTINGSGSPHPSCQNQQT | 3895 | 27.796 | 2.790 | 0.000 | 0.000 | 0.000 | 0.000 |
| KTINGSGSPHSSWLNQQT | 3896 | 27.318 | 3.271 | 0.000 | 0.000 | 0.000 | 0.000 |
| KTINSPRSPHSKAQNQQT | 4024 | 27.240 | 1.554 | 0.000 | 0.000 | 0.000 | 0.000 |
| KPRFGSGSPHSKAQNQQT | 3897 | 27.203 | 0.657 | 0.000 | 0.000 | 0.000 | 0.000 |
| KWLTGSGSPHSKAQNQQT | 3898 | 26.975 | 2.388 | 0.364 | 0.000 | 0.000 | 2578.486 |
| KTINGSGSPHSKRRAQQT | 3899 | 26.523 | 5.906 | 0.000 | 0.000 | 0.000 | 0.000 |
| KTINGSGSPHSKAQTCRT | 3900 | 26.472 | 6.369 | 0.000 | 0.000 | 0.000 | 0.000 |
| KTINGLDSPHRSRQNQQT | 4025 | 26.403 | 0.321 | 0.000 | 0.000 | 0.000 | 0.000 |
| KTINGSGSPHSKGCTQQT | 3901 | 26.068 | 0.529 | 0.000 | 0.000 | 0.000 | 0.000 |
| KTRTRSGSPHSKAQNQQT | 4026 | 25.852 | 6.894 | 0.000 | 0.000 | 0.000 | 0.000 |
| KTINGSGSPHVPWQNQQT | 3902 | 25.294 | 3.435 | 0.000 | 0.000 | 0.000 | 0.000 |
| KTINGSGSPHSKRYTQQT | 3903 | 25.267 | 9.412 | 0.000 | 0.000 | 0.000 | 0.000 |
| KTINGSISPHCPAQNQQT | 4027 | 24.932 | 0.556 | 0.000 | 0.000 | 0.000 | 0.000 |
| KTINGSGSPHSGCQNQQT | 3904 | 24.818 | 1.981 | 0.000 | 0.000 | 0.000 | 0.000 |
| KTINGSGSPHSFTPNQQT | 3905 | 24.227 | 1.036 | 0.000 | 0.000 | 0.000 | 0.000 |
| KTINGSGSPHSTTCNQQT | 3906 | 23.771 | 3.315 | 0.000 | 0.000 | 0.000 | 0.000 |
| KTINGSGSPHSKARMYQT | 3907 | 23.424 | 0.313 | 0.000 | 0.000 | 0.000 | 0.000 |
| KTINGLVSPHRKAQNQQT | 4028 | 23.417 | 2.739 | 0.000 | 0.000 | 0.000 | 0.000 |

TABLE 17-continued

NGS fold-enrichment of TTM-001 and TTM-002 matured AAV capsid variants in the liver of NHPs

| | | Fold Enrichment relative to AAV9 | | | | | |
|---|---|---|---|---|---|---|---|
| Sequence | SEQ ID NO: | Liver RNA (NHP) | Liver DNA (NHP) | Brain (NHP) | DRG (NHP) | Heart (NHP) | Muscle (NHP) |
| KTINGSGSPHPKRQNQQT | 3908 | 23.055 | 2.355 | 0.000 | 0.000 | 0.000 | 0.000 |
| KTINGSGSPHSKCFLQQT | 3909 | 22.987 | 1.434 | 0.000 | 0.000 | 0.000 | 0.000 |
| KTINGSGSPHWVPQNQQT | 3910 | 22.907 | 3.219 | 0.000 | 0.000 | 0.000 | 0.000 |
| KTINGSGSPHSFWSNQQT | 3911 | 22.857 | 1.345 | 0.000 | 0.000 | 0.000 | 0.000 |
| KRSYGSGSPHSKAQNQQT | 3912 | 22.474 | 2.841 | 0.000 | 0.000 | 0.000 | 0.000 |
| KYVFGSGSPHSKAQNQQT | 3913 | 22.232 | 2.346 | 0.000 | 0.000 | 0.000 | 0.000 |
| KTINGSGSPHSKFKNQQT | 3914 | 21.951 | 1.074 | 0.000 | 0.000 | 0.000 | 0.000 |
| KTINGSGSPHRIKQNQQT | 3915 | 21.720 | 3.064 | 0.000 | 0.000 | 0.000 | 0.000 |
| KTINGSGSPHSKAPRRQT | 3916 | 21.645 | 3.940 | 0.000 | 0.000 | 0.000 | 0.000 |
| KTINGSGSPHSFRYNQQT | 3917 | 21.097 | 4.148 | 0.000 | 0.000 | 0.000 | 0.000 |
| KTINGSGSPHSKMICQQT | 3918 | 21.036 | 0.144 | 0.000 | 0.000 | 0.000 | 0.000 |
| KTINGSGSPHLRWQNQQT | 3919 | 21.014 | 9.649 | 0.000 | 0.000 | 0.000 | 0.000 |
| KTINGSGSPHLPTQNQQT | 3920 | 20.704 | 3.127 | 0.000 | 0.000 | 0.000 | 0.000 |
| KTINGSGSPHSKWKSQQT | 3921 | 20.390 | 1.239 | 0.000 | 0.000 | 4.904 | 0.163 |
| KTINALRSPHSKAQNQQT | 4029 | 20.053 | 1.655 | 0.000 | 0.000 | 0.000 | 0.000 |
| KTINGSGSPHSYMRNQQT | 3922 | 20.007 | 2.293 | 0.000 | 0.000 | 0.000 | 0.000 |
| KTINGSGSPHSKAARRQT | 3923 | 19.998 | 6.633 | 0.000 | 0.000 | 0.000 | 0.000 |
| KTINGSGSPHLLCQNQQT | 3924 | 19.796 | 3.484 | 0.673 | 0.000 | 0.000 | 1.309 |
| KTINGSGSPHRCCQNQQT | 3925 | 19.084 | 2.213 | 0.000 | 0.000 | 0.000 | 0.000 |
| KTINGSGSPHLCVQNQQT | 3926 | 19.030 | 1.428 | 0.000 | 0.000 | 0.000 | 0.000 |
| KTINGSGSPHSKLTRQQT | 3927 | 19.004 | 2.712 | 0.000 | 0.000 | 0.000 | 0.000 |
| KTICGRGSPHSKAQNQQT | 4030 | 18.923 | 2.171 | 0.000 | 0.000 | 0.000 | 0.000 |
| KTTRKSGSPHSKAQNQQT | 4031 | 18.849 | 2.617 | 0.000 | 0.000 | 0.000 | 0.000 |
| KTINGSGSPHSKLCTQQT | 3928 | 18.674 | 1.269 | 0.000 | 0.000 | 0.000 | 0.000 |
| KKHLGSGSPHSKAQNQQT | 3929 | 18.521 | 0.658 | 0.000 | 0.000 | 0.000 | 0.000 |
| KTINGSGSPHSKIRGQQT | 3930 | 18.150 | 1.584 | 0.000 | 0.000 | 0.000 | 0.000 |
| KTMQRSGSPHSKAQNQQT | 4032 | 18.020 | 3.159 | 0.000 | 0.000 | 0.000 | 0.000 |
| KTINGSGSPHSYLVNQQT | 3931 | 17.766 | 1.267 | 0.000 | 0.000 | 0.000 | 0.000 |
| KTINGSGSPHQGCQNQQT | 3932 | 17.676 | 1.037 | 0.000 | 0.000 | 0.000 | 0.000 |
| KTINGSGSPHMAFQNQQT | 3933 | 17.644 | 0.542 | 0.000 | 0.000 | 0.000 | 0.000 |
| KTINGSGSPHSKACQFQT | 3934 | 17.640 | 8.562 | 0.000 | 0.000 | 0.000 | 9.605 |
| KTINGSGSPHSKWGLQQT | 3935 | 17.543 | 2.639 | 0.000 | 0.000 | 0.000 | 0.000 |
| KTINGSGSPHSKILRQQT | 3936 | 17.419 | 2.546 | 0.000 | 0.000 | 0.000 | 0.000 |
| KTINGSGSPHSFQINQQT | 3937 | 17.418 | 0.269 | 0.308 | 0.000 | 1.568 | 0.000 |
| KTINGSGSPHSKACISQT | 3938 | 17.371 | 0.240 | 0.000 | 0.000 | 0.000 | 0.000 |
| KTINGSGSPHSKAQTHRT | 3939 | 17.290 | 2.917 | 0.000 | 0.000 | 0.000 | 0.000 |

TABLE 17-continued

NGS fold-enrichment of TTM-001 and TTM-002 matured AAV capsid variants in the liver of NHPs

| Sequence | SEQ ID NO: | Fold Enrichment relative to AAV9 | | | | | |
|---|---|---|---|---|---|---|---|
| | | Liver RNA (NHP) | Liver DNA (NHP) | Brain (NHP) | DRG (NHP) | Heart (NHP) | Muscle (NHP) |
| KTIN TABLE 17-continued NGS fold-enrichment of TTM-001 and TTM-002 matured AAV capsid variants in the liver of NHPs

| Sequence | SEQ ID NO: | Fold Enrichment relative to AAV9 | | | | | |
|---|---|---|---|---|---|---|---|
| | | Liver RNA (NHP) | Liver DNA (NHP) | Brain (NHP) | DRG (NHP) | Heart (NHP) | Muscle (NHP) |
| KTINGSGSPHCPAQNQQT | 3967 | 13.359 | 1.409 | 0.000 | 0.000 | 0.000 | 0.000 |
| KTINGSGSPHSMCTNQQT | 3968 | 13.114 | 0.392 | 0.000 | 0.000 | 0.000 | 0.000 |
| KTINGSGSPHSPPDNQQT | 3969 | 12.973 | 0.033 | 0.000 | 0.000 | 0.000 | 0.000 |
| KTINGSGSPHSKRNYQQT | 3970 | 12.781 | 5.528 | 0.000 | 0.000 | 0.000 | 0.000 |
| KTTRCSGSPHSKAQNQQT | 4041 | 12.639 | 8.168 | 0.000 | 0.000 | 0.000 | 0.000 |
| KTKLCSGSPHSKAQNQQT | 4042 | 12.570 | 2.139 | 0.000 | 0.000 | 0.000 | 0.000 |
| KTINLGCSPHSKAQNQQT | 4043 | 12.564 | 0.654 | 0.000 | 0.000 | 0.000 | 0.000 |
| KTINGSGSPHRWTQNQQT | 3971 | 12.490 | 0.844 | 0.000 | 0.000 | 0.000 | 0.000 |
| KTISGHDSPHISGQYQQT | 4044 | 12.395 | 0.420 | 0.000 | 0.000 | 0.074 | 1214.588 |
| KTINGSGSPHSKACRLQT | 3972 | 12.297 | 6.537 | 0.000 | 0.000 | 0.000 | 0.000 |
| KTINGSGSPHPRKQNQQT | 3973 | 12.249 | 3.248 | 0.000 | 0.000 | 0.000 | 0.000 |
| KTINGSGSPHSKCSVQQT | 3974 | 12.246 | 1.465 | 0.000 | 0.000 | 0.000 | 0.000 |
| KTINGSGSPHSKAQYVRT | 3975 | 12.239 | 3.275 | 0.000 | 0.000 | 0.000 | 0.000 |
| KTINGSGSPHSKARISQT | 3976 | 12.142 | 1.565 | 0.000 | 0.000 | 0.000 | 0.000 |
| KTINGRRSPHMKAQNQQT | 4045 | 12.136 | 3.510 | 0.000 | 0.000 | 0.000 | 0.000 |
| KTINGPWSPHRKAQNQQT | 4046 | 12.103 | 0.434 | 0.000 | 0.000 | 0.000 | 0.000 |
| KTINGSGSPHPFVQNQQT | 3977 | 12.091 | 1.286 | 0.000 | 0.000 | 0.000 | 0.000 |
| KTINGSGSPHSKLPKQQT | 3978 | 11.856 | 0.274 | 0.000 | 0.000 | 0.000 | 0.000 |
| KTINSCFSPHSKAQNQQT | 4047 | 11.847 | 1.016 | 0.000 | 0.000 | 0.000 | 0.000 |
| KTINGSGSPHSKSEQQQT | 3979 | 11.785 | 1.769 | 0.000 | 0.000 | 0.000 | 0.000 |
| KTINGSGSPHWVAQNQQT | 3980 | 11.703 | 3.634 | 0.000 | 0.000 | 0.000 | 0.000 |
| KTINGSGSPHSLYQNQQT | 3981 | 11.590 | 1.503 | 0.000 | 0.000 | 0.000 | 0.000 |
| KTINGSGSPHSKVRMQQT | 3982 | 11.572 | 1.835 | 0.000 | 0.000 | 0.000 | 0.000 |
| KTINYTRSPHSKAQNQQT | 3983 | 11.514 | 0.431 | 0.000 | 0.000 | 0.000 | 0.000 |
| KTIKRYGSPHSKAQNQQT | 4048 | 11.461 | 2.022 | 0.000 | 0.000 | 0.000 | 0.000 |
| KTINGSGSPHCALQNQQT | 4693 | 11.404 | 3.867 | 0.000 | 0.000 | 0.000 | 0.000 |
| KTINGSGSPHSSCTNQQT | 3984 | 11.382 | 3.363 | 0.000 | 0.000 | 0.000 | 0.000 |
| KTINGSGSPHSKNSRQQT | 3985 | 11.280 | 1.093 | 0.000 | 0.000 | 0.000 | 0.000 |
| KTINGSGSPHSKRKRQQT | 3986 | 11.215 | 3.027 | 0.000 | 0.000 | 0.000 | 0.000 |
| KTINGSGSPHLCTQNQQT | 3987 | 11.176 | 2.489 | 0.000 | 0.000 | 0.000 | 0.000 |
| KTINGSGSPHSKAQSAKT | 3988 | 11.162 | 4.200 | 0.000 | 0.000 | 0.000 | 0.000 |
| KTINGSGSPHSTCLNQQT | 3989 | 11.132 | 4.762 | 0.000 | 0.000 | 0.000 | 0.000 |
| KTINGSGSPHSYARNQQT | 3990 | 11.131 | 0.996 | 0.000 | 0.000 | 0.000 | 0.000 |
| KTINGSGSPHSKQRPQQT | 3991 | 11.130 | 2.347 | 0.000 | 0.000 | 0.000 | 0.000 |
| KTINGSGSPHSKRVVQQT | 3992 | 11.094 | 1.639 | 0.000 | 0.000 | 0.000 | 0.000 |
| KRFSGSGSPHSKAQNQQT | 3993 | 11.024 | 1.358 | 0.000 | 0.000 | 0.000 | 0.000 |

TABLE 17-continued

NGS fold-enrichment of TTM-001 and TTM-002 matured AAV capsid variants in the liver of NHPs

| Sequence | SEQ ID NO: | Fold Enrichment relative to AAV9 | | | | | |
|---|---|---|---|---|---|---|---|
| | | Liver RNA (NHP) | Liver DNA (NHP) | Brain (NHP) | DRG (NHP) | Heart (NHP) | Muscle (NHP) |
| KTINGSGSPHKSGQNPQT | 3994 | 11.014 | 11.790 | 0.000 | 0.000 | 0.000 | 0.000 |
| KTINRYSSPHSKAQNQQT | 4049 | 10.926 | 1.544 | 0.000 | 0.000 | 0.000 | 0.000 |
| KTTGRSGSPHSKAQNQQT | 4050 | 10.863 | 0.126 | 0.000 | 0.000 | 0.000 | 0.000 |
| KTINGSGSPHSKALRHQT | 3995 | 10.774 | 4.532 | 0.000 | 0.000 | 0.000 | 0.000 |
| KTINGSGSPHSYYSNQQT | 3996 | 10.680 | 2.856 | 0.000 | 0.000 | 0.000 | 0.000 |
| KTINGSGSPHSLTCNQQT | 3997 | 10.658 | 2.214 | 0.490 | 0.000 | 0.163 | 1.398 |
| KTINGSGSPHSCQSNQQT | 3998 | 10.631 | 1.468 | 0.000 | 0.000 | 0.000 | 0.000 |
| KTINGSGSPHSKAQSIKT | 3999 | 10.544 | 1.355 | 0.000 | 0.000 | 0.000 | 0.000 |
| KYSMGSGSPHSKAQNQQT | 4000 | 10.478 | 1.587 | 0.000 | 0.000 | 0.000 | 0.000 |
| KTINGSGSPHSKAKGWQT | 4001 | 10.450 | 1.827 | 0.000 | 0.000 | 0.000 | 0.000 |
| KTIVGSGSPHSKPQNQQT | 4002 | 10.381 | 0.894 | 0.000 | 0.000 | 0.000 | 0.000 |
| KTINGSGSPHFPFQNQQT | 4003 | 10.322 | 3.715 | 0.000 | 0.000 | 0.000 | 0.000 |
| KPFLGSGSPHSKAQNQQT | 4004 | 10.318 | 1.328 | 0.000 | 0.000 | 0.000 | 0.000 |
| KTINGSGSPHSKCTSQQT | 4005 | 10.311 | 5.821 | 0.493 | 0.232 | 1.413 | 2.353 |
| KTINRQFSPHSKAQNQQT | 4051 | 10.275 | 4.480 | 0.000 | 0.000 | 0.000 | 0.000 |
| KTINGSGSPHSVFENQQT | 4006 | 10.218 | 0.224 | 0.000 | 0.000 | 0.000 | 0.000 |
| KTINGSGSPHSKAKKVQT | 4007 | 10.102 | 3.974 | 0.000 | 0.000 | 0.000 | 0.000 |
| KTINGSGSPHSKAQRCST | 4008 | 10.084 | 0.762 | 0.000 | 0.000 | 0.000 | 0.000 |
| KTINGSGSPHSKAQFCLT | 4009 | 10.065 | 3.371 | 0.000 | 0.000 | 0.000 | 0.000 |
| KTINGSGSPHGRYQNQQT | 4010 | 10.028 | 0.778 | 0.000 | 0.000 | 0.000 | 0.000 |

Table 18 provides the peptide sequences of 43 matured capsid variants having a raw virus count greater than 10, a CV of less than 1 for the heart samples isolated, and that also demonstrated a 4-fold or greater fold-increase in expression in the heart relative to the AAV9 control. A number of the matured variants shown in Table 18 also demonstrated increased expression in other tissues isolated from the NHPs, including the brain, muscle, and/or liver, and are therefore pan-tropic.

TABLE 18

NGS fold-enrichment of TTM-001 and TTM-002 matured AAV capsid variants in the heart of NHPs

| Sequence | SEQ ID NO: | Fold Enrichment relative to AAV9 | | | | | | |
|---|---|---|---|---|---|---|---|---|
| | | Heart (NHP) | Brain (NHP) | DRG (NHP) | Muscle (NHP) | Liver RNA (NHP) | Liver DNA (NHP) | Brain (Mouse) |
| KTITGHDSPHSKAQNQQT | 4052 | 34.375 | 230.437 | 4.338 | 1.378 | 19.165 | 5.672 | 0.000 |
| KTINGSGSPHKSGQYQQT | 4053 | 33.208 | 851.414 | 8.704 | 17.754 | 17.342 | 9.915 | 12.911 |
| KTINGSGSPHKSGQDQQT | 4054 | 31.166 | 218.057 | 34.358 | 33.372 | 27.081 | 8.836 | 24.849 |
| KTINGSGSPHKSGQIQQT | 4055 | 27.293 | 201.467 | 48.033 | 12.706 | 17.874 | 13.192 | 10.912 |
| KTINGSGSPHKSGRNQQT | 4056 | 27.283 | 313.826 | 8.723 | 36.593 | 15.252 | 12.352 | 21.595 |

TABLE 18-continued

NGS fold-enrichment of TTM-001 and TTM-002 matured AAV capsid variants in the heart of NHPs

| Sequence | SEQ ID NO: | Fold Enrichment relative to AAV9 | | | | | | |
|---|---|---|---|---|---|---|---|---|
| | | Heart (NHP) | Brain (NHP) | DRG (NHP) | Muscle (NHP) | Liver RNA (NHP) | Liver DNA (NHP) | Brain (Mouse) |
| KTINGSGSPHKSGKNQQT | 4057 | 25.992 | 230.621 | 6.343 | 97.671 | 15.369 | 7.226 | 31.282 |
| KTIYGHDSPHSKAQNQQT | 4058 | 25.673 | 269.879 | 3.694 | 8.391 | 11.895 | 6.197 | 0.000 |
| KTINGSGSPHKSGQNQQS | 4059 | 24.783 | 244.030 | 16.675 | 26.058 | 18.059 | 9.809 | 29.751 |
| KTINGSGSPHKSGQNLQT | 4060 | 24.464 | 392.519 | 15.629 | 0.371 | 29.977 | 18.332 | 30.446 |
| KAINGHDSPHSKAQNQQT | 4061 | 22.460 | 640.466 | 7.358 | 9.986 | 9.358 | 8.490 | 0.000 |
| KTVNGHDSPHSKAQNQQT | 4062 | 21.066 | 614.034 | 3.392 | 30.908 | 21.560 | 11.933 | 121.235 |
| KTIKGHDSPHSKAQNQQT | 4063 | 20.803 | 213.564 | 24.646 | 12.361 | 15.379 | 6.551 | 13.319 |
| KSINGHDSPHSKAQNQQT | 4064 | 20.698 | 246.819 | 7.592 | 28.235 | 11.773 | 6.888 | 280.630 |
| KTINGSGSPHKSGQTQQT | 4065 | 19.925 | 466.459 | 55.454 | 15.485 | 15.473 | 6.446 | 15.179 |
| KTINGSGSPHKSGHNQQT | 4066 | 19.548 | 287.922 | 12.159 | 20.851 | 17.821 | 10.084 | 21.011 |
| KTFNGHDSPHSKAQNQQT | 4067 | 19.301 | 239.922 | 9.109 | 17.215 | 12.193 | 6.413 | 30.747 |
| KTINGSGSPHKSGLNQQT | 4068 | 19.136 | 319.093 | 3.083 | 4.096 | 14.009 | 7.446 | 9.340 |
| KTINGHDSPHSKALNQQT | 4069 | 18.542 | 605.641 | 13.375 | 1.902 | 12.621 | 7.054 | 51.283 |
| KTINGSGSPHKSGQNQLT | 4070 | 18.454 | 317.452 | 33.967 | 28.952 | 18.533 | 8.992 | 36.272 |
| KTLNGHDSPHSKAQNQQT | 4071 | 18.236 | 195.734 | 19.341 | 9.266 | 25.732 | 13.333 | 0.000 |
| KTINGSGSPHKSGQNQHT | 4072 | 14.269 | 313.837 | 7.125 | 39.273 | 29.714 | 7.797 | 25.119 |
| KTIDGHDSPHSKAQNQQT | 4073 | 13.836 | 242.100 | 1.731 | 12.555 | 17.223 | 7.439 | 0.000 |
| KTNNGHDSPHSKAQNQQT | 4074 | 12.872 | 134.488 | 0.504 | 3.877 | 17.044 | 5.982 | 22.358 |
| KTINGSGSPHKSGQKQQT | 4075 | 12.357 | 323.373 | 10.936 | 1172.3 | 12.604 | 7.970 | 48.699 |
| KTINGSGSPHKSGQNRQT | 4076 | 11.563 | 145.363 | 36.865 | 3.855 | 11.403 | 7.667 | 16.860 |
| KTINGSGSPHKSGQNQQN | 4077 | 11.507 | 156.385 | 582.38 | 8.559 | 9.273 | 7.668 | 18.138 |
| KTINGSGSPHKSGQNQQA | 4078 | 11.313 | 135.164 | 12.425 | 12.699 | 9.714 | 6.077 | 17.265 |
| KTINGHDSPHSKAHNQQT | 4079 | 10.024 | 236.106 | 19.495 | 5.258 | 2.406 | 3.316 | 45.691 |
| KTINGHDSPHSKAQNQQT | 4080 | 8.954 | 186.839 | 9.457 | 5.507 | 5.929 | 3.651 | 31.453 |
| KTINGSGSPHKSGQNQQP | 4081 | 8.744 | 261.947 | 43.435 | 10.217 | 6.468 | 4.265 | 19.828 |
| KTINGHDSPHCKAQNQQT | 4082 | 8.417 | 15.165 | 0.887 | 2.368 | 3.328 | 0.771 | 148.172 |
| KTINGHDSPHSKAQNQQS | 4083 | 5.678 | 603.027 | 7.280 | 0.670 | 4.301 | 4.307 | 65.271 |
| KTINGSGSPHKSGQNQQT | 4084 | 5.586 | 115.994 | 28.397 | 4.326 | 5.307 | 3.569 | 24.908 |
| KTINGHDSPDKSGQNQQT | 4085 | 5.569 | 30.854 | 4.934 | 1.112 | 0.671 | 0.781 | 14.499 |
| KPINGHDSPHKSGQNHQS | 4086 | 5.203 | 36.266 | 0.000 | 0.258 | 4.478 | 0.521 | 28.786 |
| KTSNGSGSPHKSGQNQQT | 4087 | 4.746 | 197.282 | 4.177 | 4.466 | 3.972 | 7.425 | 75.623 |
| KTVNGSGSPHKSGQNQQT | 4088 | 4.610 | 200.076 | 2.739 | 2.873 | 2.725 | 3.478 | 43.548 |
| KTINGHDSTHKSGHNQQT | 4089 | 4.369 | 27.630 | 2.883 | 1.302 | 0.421 | 0.176 | 12.973 |
| KTINGHDSPHSKAQNQQN | 4090 | 4.271 | 319.610 | 1.163 | 5.173 | 3.406 | 4.995 | 50.220 |

TABLE 18-continued

NGS fold-enrichment of TTM-001 and TTM-002 matured AAV capsid variants in the heart of NHPs

| Sequence | SEQ ID NO: | Heart (NHP) | Brain (NHP) | DRG (NHP) | Muscle (NHP) | Liver RNA (NHP) | Liver DNA (NHP) | Brain (Mouse) |
|---|---|---|---|---|---|---|---|---|
| KTIYGSGSPHKSGQNQQT | 4091 | 4.140 | 110.329 | 2.603 | 2.545 | 4.488 | 4.110 | 29.293 |
| KTINGLDSQHKSGQNQQT | 4092 | 4.055 | 12.958 | 3.240 | 3.205 | 0.645 | 0.296 | 5.608 |

Table 19 provides the peptide sequences of 14 matured capsid variants having a raw virus count greater than 10, a CV of less than 1 for the muscle samples isolated (e.g., quadriceps), and that also demonstrated a 4-fold or greater fold-increase in expression in the muscle relative to the AAV9 control. A number of the matured variants shown in Table 19 also demonstrated increased expression in other tissues isolated from the NHPs, including the brain, heart, and/or liver, and are therefore pan-tropic.

TABLE 19

NGS fold-enrichment of TTM-001 and TTM-002 matured AAV capsid variants in the muscle (e.g., quadriceps) of NHPs

| Sequence | SEQ ID NO: | Muscle (NHP) | Brain (NHP) | DRG (NHP) | Heart (NHP) | Liver RNA (NHP) | Liver DNA (NHP) | Brain (Mouse) |
|---|---|---|---|---|---|---|---|---|
| KTINGSGSPHKSGRNQQT | 4056 | 36.593 | 313.826 | 8.723 | 27.283 | 15.252 | 12.352 | 21.595 |
| KTIIGHDSPHSKAQNQQT | 4095 | 27.271 | 341.528 | 5.423 | 26.154 | 18.305 | 6.293 | 0.000 |
| KTIYGHDSPHSKAQNQQT | 4058 | 8.391 | 269.879 | 3.694 | 25.673 | 11.895 | 6.197 | 0.000 |
| KTINGSGSPHKSGONQQS | 4059 | 26.058 | 244.030 | 16.675 | 24.783 | 18.059 | 9.809 | 29.751 |
| KTVNGHDSPHSKAQNQQT | 4062 | 30.908 | 614.034 | 3.392 | 21.066 | 21.560 | 11.933 | 121.235 |
| KTIKGHDSPHSKAQNQQT | 4063 | 12.361 | 213.564 | 24.646 | 20.803 | 15.379 | 6.551 | 13.319 |
| KSINGHDSPHSKAQNQQT | 4064 | 28.235 | 246.819 | 7.592 | 20.698 | 11.773 | 6.888 | 280.630 |
| KTINGSGSPHKSGHNQQT | 4066 | 20.851 | 287.922 | 12.159 | 19.548 | 17.821 | 10.084 | 21.011 |
| KTFNGHDSPHSKAQNQQT | 4067 | 17.215 | 239.922 | 9.109 | 19.301 | 12.193 | 6.413 | 30.747 |
| KTSNGHDSPHSKAQNQQT | 4096 | 18.580 | 507.189 | 7.777 | 17.770 | 21.537 | 8.789 | 70.219 |
| KTINGHDSPHSKAQNQQT | 4080 | 5.507 | 186.839 | 9.457 | 8.954 | 5.929 | 3.651 | 31.453 |
| KTINGSGSPHKSGONOQT | 4084 | 4.326 | 115.994 | 28.397 | 5.586 | 5.307 | 3.569 | 24.908 |
| KTINGHDSPHSKAQNQON | 4090 | 5.173 | 319.610 | 1.163 | 4.271 | 3.406 | 4.995 | 50.220 |
| KTINGSGSPHSKAQNRRR | 4097 | 4.237 | 8.348 | 0.291 | 0.636 | 1.597 | 5.396 | 158.853 |

Additional variants were identified following generation and screening in NHPs that had the following properties. TTM-001 and TTM-002 capsid variants comprising the amino acid sequence of SEQ ID NOs: 4253, 4281, 4290-4295, 4304, 4305, 4320, 4328-4335, 4337-4340, 4353, 4355, 4369, 4387, 4421, 4424-4428, 4430, 4432, 4433, 4435, 4436-4449, 4452, 4455, 4476, 4483, or 4484 had a raw virus count 10 or greater, a CV of less than 1 for the brain samples isolated from the NHPs, demonstrated a 50-fold or greater increase in expression in the brain of mice and NHPs relative to AAV9, and demonstrated 2-fold or less expression in the liver and DRG of NHPs relative to AAV9. TTM-001 and TTM-002 capsid variants comprising the amino acid sequence of SEQ ID NOs: 4098-4105, 4254-4280, 4282-4289, 4296-4303, 4306-4327, 4336, 4341-4352, 4354, 4356-4420, 4422, 4423, 4425, 4429, 4431, 4434, 4444, 4450, 4451, 4453, 4454, 4456-4475, 4477-4482, or 4485 had a CV of less than 1 in across the brain samples isolated from the NHPs and demonstrated a 100-fold or greater increase in expression in the brain of NHPs relative to AAV9. TTM-001 and TTM-002 capsid variants comprising the amino acid sequence of SEQ ID NOs: 4102 and 4106-4252 had normalized virus counts of greater than or equal to 0.01, a CV of less than 1 across the liver RNA samples isolated from the NHPs, and demonstrated a 20-fold or greater increase in expression in the liver of NHPs relative to AAV9. TM-001 and TTM-002 capsid variants comprising the amino acid sequence of SEQ ID NO: 4105 had a raw virus count 9.9 or greater, a CV of less than 1 across the muscle samples isolated from the NHPs, and 5-fold or greater increase in expression in the muscle of the NHPs relative to AAV9. TM-001 and TTM-002 capsid variants comprising the amino acid sequence of SEQ ID NO: 4105 also had a raw virus count 9.9 or greater, a CV of less than 1 across the samples isolated from the heart of the NHPs, and 5-fold or greater increase in expression in the heart of the NHPs relative to AAV9.

These data demonstrate that following two maturation approaches, matured TTM-001 and TTM-002 capsid variants (AAV9 capsid variants) with loop IV modifications were generated with significantly enhanced CNS tropism over wild-type AAV9 controls in both NHPs and mice, while also exhibiting de-targeting in peripheral tissues (e.g., the liver and DRG). These resulting matured variants therefore demonstrated cross-species CNS tropism in both NHPs and mice. Matured TTM-001 and TTM-002 capsid variants with liver-specific tropism were also generated with at least 10 times the expression compared to wild-type AAV9 in the liver of NHPs. Several matured variants were also generated with increased expression in the heart and skeletal muscle (e.g., quadriceps) relative to wild-type AAV9 in NHPs.

Example 5. Evaluation of TTM-001 and TTM-002 AAV Capsid Variants in Diverse Primate Species This Example evaluates the tropism and cross-species compatibility of the TTM-001 (SEQ ID NO: 981 (amino acid) and 983 (DNA), comprising SEQ ID NO: 941) and TTM-002 (SEQ ID NO: 982 (amino acid) and 984 (DNA), comprising SEQ ID NO: 2) capsid variants in two diverse primate species, marmosets (*Callithrix jacchus*) and African green monkeys (*Chlorocebus sabaeus*), as compared to their tropism in cynomolgus macaques (*Macaca fascicularis*) provided in Example 1. The cross-species compatibility and tropism of an AAV9 capsid variant comprising the amino acid sequence of SPHKYG (SEQ ID NO: 966) was also investigated in this example. The amino acid and DNA sequences of TTM-001 and TTM-002 are provided, e.g., in Tables 4 and 5, respectively.

To investigate tropism in African green monkeys, AAV particles comprising the TTM-001 capsid variant, the TTM-002 capsid variant, an AAV9 capsid variant comprising SEQ ID NO: 966, or an AAV9 control under the control of a synapsin promoter, were intravenously injected into NHPs (n=2, 3-12 years of age) at a dose of 2E13 vg/kg. After 14-days in life, the brains and tissues (liver, DRG, quadriceps, and heart) of the NHPs were collected and RNA was extracted. Following RNA recovery and RT-PCR amplification, a systematic NGS enrichment analysis was performed to calculate the fold enrichment ratio relative to the AAV9 wild-type control.

To investigate tropism in marmoset monkeys, AAV particles comprising the TTM-001 capsid variant, the TTM-002 capsid variant, an AAV9 capsid variant comprising SEQ ID NO: 966, or an AAV9 control, were intravenously injected into NHPs (n=2, >10 months of age) at a dose of 2E13 vg/kg (8.75E12 vg/mL). After 28-days in life, the brains and tissues (liver quadriceps, and heart) of the NHPs were collected and RNA was extracted. Following RNA recovery and RT-PCR amplification, a systematic NGS enrichment analysis was performed to calculate the fold enrichment ratio relative to the AAV9 wild-type control.

As provided in Table 20 (African green monkeys) and Table 21 (marmosets), both the TTM-001 and TTM-002 capsid variants demonstrated increased CNS tropism in diverse primate species. The TTM-001 capsid variant demonstrated a 73.6-fold increase in expression relative to AAV9 in the brain of cynomolgus macaques (Table 9, Example 1), a 43.5-fold increase in expression relative to AAV9 in the brain of African green monkeys, and a 703.3-fold increase in expression relative to AAV9 in the brain of marmosets. The TTM-002 capsid variant demonstrated a 62.6-fold increase in expression relative to AAV9 in the brain of cynomolgus macaques (Table 9), a 13.8-fold increase in expression relative to AAV9 in the brain of African green monkeys, and a 366.6-fold increase in expression relative to AAV9 in the brain of marmosets. Both TTM-001 and TTM-002 led to a significant increase in expression relative to AAV9 in the heart of both African green monkeys and marmosets (Table 20 and Table 21). The AAV9 capsid variant comprising SEQ ID NO: 966 also demonstrated in increase in expression relative to AAV9 in the brain and heart of both African green monkeys and marmosets. Furthermore, TTM-001, TTM-002, and the AAV9 capsid variant comprising SEQ ID NO: 966, also all led to increased expression in the brain of both BALB/c and C57B1/6 mice (Table 11, Example 1), demonstrating an average fold change in expression relative to AAV9 across both species of mice of 63.1, 66.8, and 126.97, respectively.

TABLE 20

NGS-fold enrichment of TTM-001 (comprises SEQ ID NO: 941), TTM-002 (comprises SEQ ID NO: 2), and an AAV9 capsid variant comprising SEQ ID NO: 966 in African green monkeys

| Sequence | SEQ ID NO: | Fold Enrichment relative to AAV9 Brain | DRG | Heart | Liver DNA | Liver RNA | Muscle |
|---|---|---|---|---|---|---|---|
| SPHSKA | 941 | 43.525 | 1.010 | 184.789 | 0.242 | 1.547 | 1.715 |
| HDSPHK | 2 | 13.779 | 0.678 | 35.991 | 0.084 | 0.087 | 0.144 |
| SPHKYG | 966 | 9.805 | 0.071 | 44.865 | 0.085 | 0.136 | 0.234 |

TABLE 21

NGS-fold enrichment of TTM-001 (comprises SEQ ID NO: 941),
TTM-002 (comprises SEQ ID NO: 2), and an AAV9 capsid
variant comprising SEQ ID NO: 966 in marmosets

| Sequence | SEQ ID NO: | Fold Enrichment relative to AAV9 | | | | |
|---|---|---|---|---|---|---|
| | | Brain | Heart | Liver DNA | Liver RNA | Muscle |
| SPHSKA | 941 | 703.610 | 48.979 | 0.268 | 0.779 | 0.425 |
| HDSPHK | 2 | 366.625 | 18.572 | 0.075 | 0.276 | 0.229 |
| SPHKYG | 966 | 150.209 | 17.232 | 0.045 | 0.014 | 0.146 |

Taken together, these data demonstrate that the AAV9 capsid variants of TTM-001 and TTM-002 demonstrated increased CNS tropism relative to the AAV9 control in the CNS across three diverse primate species and two species of mice, providing evidence of strong cross-species capacity. The AAV9 capsid variant comprising the amino acid sequence of SEQ ID NO: 966 also demonstrated strong CNS expression relative to the AAV9 control in two species of NHPs and two species of mice, also showing strong cross-species capacity.

Example 6. Advanced Maturation of TTM-002 Capsid Variant in Mice

This Example describes additional maturation of the TTM-002 (SEQ ID NO: 982 (amino acid) and 984 (DNA), comprising SEQ ID NO: 2) capsid variant in mice. In order to mature the TTM-002 capsid variant, sets of three contiguous amino acids were randomized across the mutagenesis region in TTM-002 sequence, which spanned from position 450 to position 466, numbered according to SEQ ID NO: 982. Unlike the maturation performed in in Example 3, where the SPH motif that was observed in the AAV capsid variants that demonstrated the greatest fold-enrichment in the NHP brain relative wild-type AAV9 was not disrupted, in the maturation approach used in this Example, the SPH motif was not held constant to further explore the role of this motif in the capsid variant. The matured TTM-002 capsid variants that resulted from the maturation approach were pooled together for subsequent testing and characterization in mice.

The library of matured AAV capsid variants generated from the TTM-002 matured AAV capsid variant were intravenously injected into the tail vein of three CD-1 Outbred mice (Charles River; 6-8 weeks of age) at a dose of $1.0\times10^{12}$ VG/dose. After about 28 days in life, the brains of the mice were isolated, and RNA was extracted. Following RNA recovery and RT-PCR amplification, a systematic NGS enrichment analysis was performed to calculate the fold enrichment ratio relative to the corresponding TTM-002 non-matured control, and the peptides comprised within the variants were identified. Variants were filtered by those with a raw virus count in the sample above 10 and a coefficient of variance (CV) that was greater than 1 (identifies the peptides/variants reliably detected in the majority of the samples isolated from the three mice).

Following the advanced maturation screen and filtering of the variants, 1302 variants demonstrated an increase in expression relative to the non-matured TTM-002 capsid variant in the brain of the outbred mice. Of the 1302 variants with improved tropism relative to the non-matured TTM-002, 1283 comprised the SPH motif in the same position as the non-matured TTM-002 capsid variant (e.g., immediately subsequent to position 455, relative to a reference sequence numbered according to the amino acid sequence of SEQ ID NO: 138 or 982). Mutations in the region of the SPH motif present in the non-matured TTM-002 capsid variant only consistently appear in those variants with a fold change of 0.2 or 0.1 or lower relative to the non-matured TTM-002 control in the brain of the mice. This indicates that the SPH motif may be important to the increased brain tropism that observed for the TTM-002 capsid variant. In instances when the SPH motif was disrupted, the fold change of the matured variants of TTM-002 decreased considerably in relation to the non-matured TTM-002 variant which comprised the SPH motif.

Example 7. Tropism of TTM-002 AAV Capsid Variant

This Example further investigates the tropism and CNS cells transduced by the TTM-002 capsid variant (SEQ ID NO: 982 (amino acid) and 984 (DNA), comprising SEQ ID NO: 2), as outlined in Table 3 above. The amino acid and DNA sequences of TTM-002 are provided, e.g., in Tables 4 and 5, respectively.

AAV particles were generated with the TTM-002 capsid variant encapsulating a GFP transgene (AAV_TTM-002.GFP) or a payload driven by a heterologous CBA constitutive promoter (AAV_TTM-002.Payload).

Two tandem single cell RNA sequencing runs (scRNA-Seq) of mouse cells derived from the midbrain area were performed. In the first run, cells were pooled from two mice at day 28 post treatment with AAV_TTM-002.Payload particles. In the second run we treated with AAV_TTM-002.GFP particles, in the same manner but without xenografts. Orthotopic xenografts of MDA-MB-361-Luc #1 high passage cells grown as tumorspheres (in tumorsphere media; Sigma #C-28070) were injected (250,000 cells/2 μL/mouse) intracranially into 2-month old female SCID CB17 (Mutation: Icr-Prkdcscid/IcrIcoCrl) congenic immunodeficient mice (Charles River Laboratories). The injections were 2.5 mm (lateral), −1 mm (posterior) with respect to bregma, lowered −3 mm ventral and raised+0.5 mm dorsal to a final −2.5 mm ventral position. Two days later, dilutions of the AAV_TTM-002.Payload particles (run 1), or in the case without xenografts, dilutions of AAV_TTM-002.GFP particles (run 2) were prepared. IV injections of 100 μL (2.5e11 VG/animal) of the AAV_TTM-002.payload particles or AAV_TTM-002.GFP particles were administered through the tail veins of mice (n=5 mice per groups). At 7 days post-injection, mice from run 1 were imaged in an AmiHTX (Spectral Imager) for bioluminescence of the human tumor cells due to expression of luciferase in response to intraperitoneal luciferin injections.

At 28 days post-injection with the AAV_TTM-002.payload particles or AAV_TTM-002.GFP particles, two mice from each run were necropsied, brain samples were isolated, and the midbrain was dissected and isolated. The midbrain samples were then exposed to a cold protease inhibitor (Creative Biomart #NATE-0633) and were dissociated at 6 degrees centigrade. For the samples collected from the mice of run 1 (AAV_TTM-002.Payload particles), myelin depletion was performed (Miltenyi, #130-096-731), cells were filtered through a 40 µM mesh to filter out neurons) and loaded on a 10× chromium G chip. scRNA-Seq was performed (10× Genomics) and samples were sequenced on a NextGen500 Sequencing machine (Illumina). For the samples collected from run 2 (AAV_TTM-002.GFP particles and no xenografts), the cells were not myelin depleted or filtered through 40 µM mesh to include neurons. The cells isolated after run 2 were FACS sorted for GFP+/7AAD– (live GFP+ cells). The resultant cells were loaded on a 10× chromium G chip and the scRNA-Seq was run and processed (10× Genomics).

For run 1, the scRNA-Seq data was filtered to include cells with only greater than 1000 genes per cell and less than 5000, and less than 20 percent mitochondrial gene expression. For run 2, the scRNA-Seq data was filtered to include cells with only greater than 200 genes per cell and less than 5000, and less than 20 percent mitochondrial gene expression. The data were normalized, scaled, and integrated into one combined dataset. Clusters were generated with a resolution of 0.3 and each cluster identity was determined using a panel of cell type specific genes (e.g., as described in Brown et al., 2021. "Deep Parallel Characterization of AAV Tropism and AAV-Mediated Transcriptional Changes via Single-Cell RNA Sequencing". Front. Immunol. 12:730825; the contents of which are hereby incorporated by reference in its entirety). The percentage of GFP sorted cells per cluster was calculated as was the percentage of payload expressing genes per cluster as parallel measures of TTM-002 transduction.

For payload expressing cells, endothelial cells had the highest proportion of payload positive cells, followed by astrocytes (Table 22). For GFP+ sorted cells, endothelial cells had the highest proportion of GFP positive cells, and astrocytes were the third highest cell type when sorting by proportion of cells expressing GFP (Table 22). These data indicate TTM-002 transduction exhibits an endothelial and astrocytic tropism. Furthermore, the astrocytic cluster had the second highest level of expression of Olig2 (oligodendrocytes demonstrated the greatest Olig2 expression). IHC staining was performed on brain samples isolated from AAV_TTM-002.GFP infected mice and demonstrated that GFP co-localized with some but not all Olig2+ cells. No co-staining was observed with mylein basic protein (MBP), a marker of oligodendrocytes. Co-staining with GFP was also not observed in NeuN positive cells (neurons), GFAP positive cells (astrocytes), and Iba1 positive cells (microglia). GFP staining was observed throughout the sagittal section of the mouse brain, which was demonstrative of increased staining in the midbrain. The GFP expressing cells observed did not have a bipolar morphology like oligodendrocyte progenitor (OPC) cells and therefore, together with the scRNA-Seq data, these results indicated that at day 28 post AAV treatment, Olig2+ astrocytes in the midbrain are being transduced by AAV particles comprising a TTM-002 capsid, in a cell type specific tropism.

TABLE 22

Quantification of payload positive cells and GFP positive cells

| Cluster Identity | % Payload Cells/Cluster | Cluster Identity | % GFP Cells/Cluster |
| --- | --- | --- | --- |
| Endothelial-2 | 6.58 | Endothelial-2 | 6.58 |
| Astrocyte | 4.50 | Endothelial-1 | 3.45 |
| Pericytes | 4.23 | Vascular and leptomeningeal Cells (VLM) | 2.38 |
| Mature Oligos | 3.85 | Astrocyte | 2.37 |
| Endothelial-1 | 3.09 | Vascular smooth muscle cells (VSC) | 1.03 |
| Committed Oligos | 1.90 | Pericytes | 0.77 |
| Vascular smooth muscle cells (VSC) | 1.72 | Microglia | 0.00 |
| Microglia | 0.40 | Committed Oligos | 0.00 |
| Macrophages | 0.00 | Macrophages | 0.00 |
| Vascular and leptomeningeal cells (VLM) | 0.00 | Oligodendrocytes | 0.00 |
| Oligodendrocytes | 0.00 | Committed Oligos-2 | 0.00 |
| Committed Oligos-2 | 0.00 | Mature Oligos | 0.00 |

Example 8. Individual Capsid Characterization of TTM-002 in NHPs

This example describes the transduction level, tropism, ability to cross the blood brain barrier, and overall spatial distribution in the central nervous system (CNS) and peripheral tissues of the AAV capsid variant TTM-002 (SEQ ID NO: 982 (amino acid) and 984 (DNA), comprising SEQ ID NO: 2), relative to AAV9 following intravenous administration in African green monkeys (Chlorocebus sabaeus).

AAV particles were generated with the TTM-002 capsid variant or the AAV9 capsid control which comprised a self-complementary viral genome encoding an histone H2b protein with an HA tag driven by a ubiquitous CBA promoter. The AAV particles comprising the TTM-002 capsid variant or the AAV9 capsid control were administered to the NHPs (n=2) intravenously at a dose of 1e12 VG/kg or 1e13 VG/kg. The in-life period was 28 days and then various CNS and peripheral tissues were collected for measuring transgene mRNA (expression) by RT-qPCR and viral DNA (biodistribution) by ddPCR.

As shown in Table 23, the TTM-002 capsid variant resulted in increased brain biodistribution in all brain regions investigated as compared to AAV9 at both doses tested. The TTM-002 capsid variant also led to increased transgene expression in the brain relative to AAV9 at both doses tested (Table 24). In the spinal cord, the TTM-002 capsid variant distributed to the cervical spinal cord and the spinal cord ventral horn at a higher level relative to AAV9 (Table 23) and it mediated higher transgene expression than AAV9 in both the full spinal cord and the ventral horn (Table 24). The TTM-002 capsid variant exhibited lower biodistribution (Table 23) and transgene expression (Table 24) in the DRG relative to AAV9, indicating that TTM-002 capsid variant was detargeted in the DRG relative to AAV9. Similar expression and distribution were observed by immunohistochemistry performed on these CNS tissues.

Distribution and transgene expression was also measured in the peripheral tissues of the liver, heart, and quadriceps. In the liver, TTM-002 capsid variant exhibited lower biodistribution (Table 23) and transgene expression (Table 24) relative to AAV9, indicating that TTM-002 capsid variant was detargeted in the liver relative to AAV9. In the heart, the TTM-002 capsid variant exhibited comparable levels of biodistribution relative to AAV9 (Table 23), but increased transgene expression relative to AAV9 (Table 24). In the quadriceps, TTM-002 capsid variant exhibited lower biodistribution (Table 23) and lower transgene expression (Table 24), relative to AAV9. Similar expression and distribution were observed by immunohistochemistry performed on these peripheral tissues.

TABLE 23

Quantification of viral genome copies per diploid genome (biodistribution) by ddPCR following intravenous administration of AAV particles comprising a TTM-002 capsid

| | 1e12 VG/kg | | | 1e13 VG/kg | | |
|---|---|---|---|---|---|---|
| Tissue | AAV9 (VG copies/ diploid genome) | TTM-002 (VG copies/ diploid genome) | TTM-002 relative to AAV9 | AAV9 (VG copies/ diploid genome) | TTM-002 (VG copies/ diploid genome) | TTM-002 relative to AAV9 |
| Putamen | 0.03 | 0.37 | 12.3 | 0.26 | 2.4 | 9.2 |
| Caudate | 0.02 | 0.58 | 29 | 0.14 | 2.1 | 14.7 |
| Thalamus | 0.06 | 0.21 | 3.5 | 0.25 | 1.0 | 4 |
| Hippocampus | 0.03 | 0.29 | 9.7 | 0.16 | 1.56 | 9.8 |
| Substantia Nigra | 0.05 | 0.34 | 6.8 | 0.37 | 1.38 | 3.7 |
| Motor Cortex | 0.03 | 0.56 | 19 | 0.27 | 2.4 | 8.9 |
| Frontal Cortex | 0.04 | 0.67 | 17 | 0.20 | 3.6 | 18 |
| Temporal Cortex | 0.03 | 0.31 | 10 | 0.11 | 2.67 | 24 |
| Cerebral Cortex | 0.008 | 0.08 | 10 | 0.03 | 0.16 | 5.3 |
| Dentate Nucleus | 0.06 | 0.10 | 1.7 | 0.32 | 3.21 | 10 |
| Cervical Spinal Cord | 0.03 | 0.12 | 4 | 0.19 | 0.91 | 4.8 |
| Thoracic Spinal Cord | 0.04 | 0.03 | 0.75 | 0.36 | 0.38 | 1.1 |
| Lumbar Spinal Cord | 0.04 | 0.03 | 0.75 | 0.29 | 0.37 | 1.3 |
| C5 Ventral Horn | 0.04 | 0.25 | 6.3 | 0.29 | 2.2 | 7.6 |
| L5 Ventral Horn | 0.06 | 0.28 | 4.7 | 0.31 | 1.9 | 6.1 |
| Cervical DRG | 0.07 | 0.01 | −7 | 0.81 | 0.36 | −2.3 |
| Thoracic DRG | 0.06 | 0.01 | −6 | 1.31 | 0.43 | −3 |
| Lumbar DRG | 0.07 | 0.01 | −7 | 1.31 | 0.57 | −2.3 |
| Liver | 9.5 | 1.2 | −7.9 | 127 | 7.7 | −16.5 |
| Heart | 0.6 | 0.7 | 1.2 | 5.4 | 5.4 | 1 |
| Quadriceps | 0.2 | 0.06 | −3.3 | 1.7 | 0.6 | −2.8 |

TABLE 24

Quantification of transgene mRNA by RT-qPCR following intravenous administration of AAV particles comprising a TTM-002 capsid

| | 1e12 VG/kg | | | 1e13 VG/kg | | |
|---|---|---|---|---|---|---|
| Tissue | AAV9 (transgene mRNA fold over housekeeping gene) (2-dCT) | TTM-002 (transgene mRNA fold over housekeeping gene) (2-dCT) | TTM-002 relative to AAV9 | AAV9 (transgene mRNA fold over housekeeping gene) (2-dCT) | TTM-002 (transgene mRNA fold over housekeeping gene) (2-dCT) | TTM-002 relative to AAV9 |
| Putamen | 0.02 | 0.3 | 15 | 0.09 | 4.22 | 47 |
| Caudate | 0.02 | 0.8 | 40 | 0.11 | 4.29 | 39 |
| Thalamus | 0.04 | 0.4 | 10 | 0.4 | 5.8 | 14.5 |
| Hippocampus | 0.02 | 0.4 | 20 | 0.1 | 4.3 | 43 |
| Substantia Nigra | 0.1 | 1.2 | 12 | 0.3 | 11.6 | 39 |
| Motor Cortex | 0.08 | 5.00 | 63 | 0.36 | 21.8 | 61 |
| Frontal Cortex | 0.04 | 3.1 | 78 | 0.3 | 27.7 | 92 |
| Temporal Cortex | 0.02 | 0.8 | 40 | 0.1 | 26.9 | 27 |

TABLE 24-continued

Quantification of transgene mRNA by RT-qPCR following intravenous administration of AAV particles comprising a TTM-002 capsid

| | 1e12 VG/kg | | | 1e13 VG/kg | | |
| --- | --- | --- | --- | --- | --- | --- |
| Tissue | AAV9 (transgene mRNA fold over housekeeping gene) (2-dCT) | TTM-002 (transgene mRNA fold over housekeeping gene) (2-dCT) | TTM-002 relative to AAV9 | AAV9 (transgene mRNA fold over housekeeping gene) (2-dCT) | TTM-002 (transgene mRNA fold over housekeeping gene) (2-dCT) | TTM-002 relative to AAV9 |
| Cerebral Cortex | 0.04 | 1.1 | 28 | 0.2 | 17.4 | 87 |
| Dentate Nucleus | 0.3 | 0.9 | 3 | 1.8 | 42.0 | 23 |
| Cervical Spinal Cord | 0.2 | 2.0 | 10 | 0.8 | 20.2 | 25 |
| Thoracic Spinal Cord | 0.13 | 0.25 | 1.9 | 0.7 | 4.8 | 6.9 |
| Lumbar Spinal Cord | 0.4 | 0.5 | 1.3 | 2.2 | 9.2 | 4.2 |
| C5 Ventral Horn | 0.2 | 1.4 | 7 | 1.7 | 33 | 19 |
| L5 Ventral Horn | 1.1 | 3.4 | 3.1 | 12.4 | 102 | 8.2 |
| Cervical DRG | 3.6 | 1.2 | −3 | 63.1 | 15.9 | −4 |
| Thoracic DRG | 1.8 | 1.3 | −1.4 | 43.9 | 15.7 | −2.8 |
| Lumbar DRG | 1.9 | 1.0 | −1.9 | 34.9 | 27.6 | −1.3 |
| Liver | 0.88 | 0.25 | −3.5 | 2.2 | 0.97 | −2.3 |
| Heart | 8.7 | 42 | 4.8 | 110 | 363 | 3.3 |
| Quadriceps | 9.7 | 1.1 | −8.3 | 59 | 21 | −2.8 |

Taken together, these data demonstrate that TTM-002 is an enhanced CNS tropic capsid in NHPs (African green monkeys) that can infect non-neuronal cells. TTM-002 was also detargeted in the DRG and liver relative to AAV9, but showed increased transgene expression in the heart relative to AAV9. Additionally, the TTM-002 capsid variant was able to successfully penetrate the blood brain barrier following intravenous injection.

SEQUENCE LISTING

The patent contains a lengthy sequence listing. A copy of the sequence listing is available in electronic form from the USPTO web site (https://seqdata.uspto.gov/?pageRequest=docDetail&DocID=US12419969B2). An electronic copy of the sequence listing will also be available from the USPTO upon request and payment of the fee set forth in 37 CFR 1.19(b)(3).

We claim:

1. An adeno-associated virus (AAV) capsid variant comprising an amino acid sequence at least 95% identical to amino acids 203-742 of SEQ ID NO: 981, wherein the amino acid sequence comprises SPHSKA (SEQ ID NO: 941) in variable region IV (VR-IV).

2. The AAV capsid variant of claim 1, wherein the amino acid sequence of SPHSKA (SEQ ID NO: 941) is present immediately subsequent to amino acid 455, numbered according to SEQ ID NO: 981.

3. The AAV capsid variant of claim 1, which comprises an amino acid sequence at least 98% identical to amino acids 203-742 of SEQ ID NO: 981.

4. The AAV capsid variant of claim 1, which comprises the amino acid sequence of amino acids 203-742 of SEQ ID NO: 981.

5. An AAV particle comprising the AAV capsid variant of claim 4.

6. A pharmaceutical composition comprising an AAV particle comprising the AAV capsid variant of claim 4, and a pharmaceutically acceptable excipient.

7. The AAV capsid variant of claim 1, which comprises an amino acid sequence at least 95% identical to amino acids 138-742 of SEQ ID NO: 981.

8. The AAV capsid variant of claim 1, which comprises an amino acid sequence at least 98% identical to amino acids 138-742 of SEQ ID NO: 981.

9. The AAV capsid variant of claim 1, which comprises the amino acid sequence of amino acids 138-742 of SEQ ID NO: 981.

10. The AAV capsid variant of claim 1, which comprises an amino acid sequence at least 95% identical to the amino acid sequence of SEQ ID NO: 981.

11. The AAV capsid variant of claim 1, which comprises an amino acid sequence at least 98% identical to the amino acid sequence of SEQ ID NO: 981.

12. A cell comprising the AAV capsid variant of claim 1.

13. The cell of claim 12, which is:
(i) a mammalian cell or an insect cell;
(ii) a cell of a brain region or a spinal cord region; or
(iii) a neuron or an astrocyte.

14. A pharmaceutical composition comprising an AAV particle comprising the AAV capsid variant of claim 1, and a pharmaceutically acceptable excipient.

15. A method of making an AAV particle, comprising:
(i) providing a host cell comprising a viral genome and a polynucleotide encoding the AAV capsid variant of claim 1; and
(ii) incubating the host cell under conditions suitable to enclose the viral genome in the AAV capsid variant; thereby making the AAV particle.

16. A method of delivering a payload to a cell or tissue, comprising administering an effective amount of an AAV particle comprising the AAV capsid variant of claim 1, thereby delivering the payload to the cell or tissue.

17. The method of claim 16, wherein the cell or tissue is present in a subject and the AAV particle is administered intravenously, via intra-cisterna magna injection (ICM), intracerebrally, intrathecally, intracerebroventricularly, via intraparenchymal administration, or intramuscularly to the subject.

18. The method of claim 16, wherein:
(i) the cell is a neuron, a motor neuron, an astrocyte, a glial cell, or an oligodendrocyte; or
(ii) the tissue is a brain tissue or a spinal cord tissue, wherein the brain tissue or the spinal cord tissue is a putamen, substantia nigra, frontal cortex, motor cortex, temporal cortex, caudate, dentate nucleus, brain stem, cerebral cortex, brain stem, hippocampus, thalamus, cervical spinal cord, thoracic spinal cord, or lumbar spinal cord.

19. An adeno-associated virus (AAV) capsid variant comprising the amino acid sequence of SEQ ID NO: 981.

20. An AAV particle comprising the AAV capsid variant of claim 19.

21. A pharmaceutical composition comprising an AAV particle comprising the AAV capsid variant of claim 19, and a pharmaceutically acceptable excipient.

22. A polynucleotide encoding an adeno-associated virus (AAV) capsid variant comprising an amino acid sequence at least 95% identical to amino acids 203-742 of SEQ ID NO: 981, wherein the amino acid sequence comprises SPHSKA (SEQ ID NO: 941) in variable region IV (VR-IV).

23. The polynucleotide of claim 22, which comprises a nucleotide sequence at least 95% identical to the nucleotide sequence of SEQ ID NO: 983.

24. The polynucleotide of claim 22, which comprises the nucleotide sequence of SEQ ID NO: 983.

25. An adeno-associated virus (AAV) particle comprising an AAV capsid variant comprising an amino acid sequence at least 95% identical to amino acids 203-742 of SEQ ID NO: 981, wherein the amino acid sequence comprises SPHSKA (SEQ ID NO: 941) in variable region IV (VR-IV).

26. The AAV particle of claim 25, wherein the AAV capsid variant comprises the amino acid sequence of amino acids 203-742 of SEQ ID NO: 981.

27. The AAV particle of claim 25, wherein the AAV capsid variant comprises an amino acid sequence at least 95% identical to the amino acid sequence of SEQ ID NO: 981.

28. The AAV particle of claim 25, wherein the AAV capsid variant comprises the amino acid sequence of SEQ ID NO: 981.

29. The AAV particle of claim 25, which comprises a nucleotide sequence encoding a protein, an antibody, an enzyme, or an inhibitory RNA.

30. The AAV particle of claim 29, further comprising:
(i) a promoter operably linked to the nucleotide sequence;
(ii) a 5' inverted terminal repeat (ITR) and a 3' ITR;
(iii) an enhancer;
(iv) an intron;
(v) an exon;
(vi) a nucleotide sequence encoding at least one microRNA (miR) binding site; and/or
(vii) a polyadenylation (polyA) sequence.

* * * * *